US011896480B2

(12) United States Patent
Welham et al.

(10) Patent No.: US 11,896,480 B2
(45) Date of Patent: Feb. 13, 2024

(54) BIOENGINEERED VOCAL FOLD MUCOSA FOR FUNCTIONAL VOICE RESTORATION

(71) Applicant: Wisconsin Alumni Research Foundation, Madison, WI (US)

(72) Inventors: Nathan Welham, Madison, WI (US); Changying Ling, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 1431 days.

(21) Appl. No.: 16/218,667

(22) Filed: Dec. 13, 2018

(65) Prior Publication Data

US 2019/0117384 A1 Apr. 25, 2019

Related U.S. Application Data

(62) Division of application No. 15/136,655, filed on Apr. 22, 2016, now Pat. No. 10,188,508.
(Continued)

(51) Int. Cl.
*A61F 2/20* (2006.01)
*A61L 27/24* (2006.01)
(Continued)

(52) U.S. Cl.
CPC ............... *A61F 2/20* (2013.01); *A61L 27/24* (2013.01); *A61L 27/3804* (2013.01); *A61L 27/3813* (2013.01); *A61L 27/3869* (2013.01); *A61L 27/3873* (2013.01); *A61L 27/3886* (2013.01); *A61L 27/3895* (2013.01); *C12N 5/0656* (2013.01); *C12N 5/0688* (2013.01); *C12N 5/0697* (2013.01); *A61L 2430/00* (2013.01); *A61L 2430/30* (2013.01); *C12N 2509/00* (2013.01); *C12N 2533/54* (2013.01); *C12N 2533/90* (2013.01)

(58) Field of Classification Search
CPC ........ A61F 2/20; A61L 27/24; A61L 27/3804; A61L 27/3813; A61L 27/3895; A61L 27/3873; A61L 27/3869; A61L 2430/00; A61L 27/3886; A61L 2430/30; C12N 5/0697; C12N 5/0688; C12N 2509/00; C12N 2533/54; C12N 2533/90
See application file for complete search history.

(56) References Cited

PUBLICATIONS

Thibeault et al., "A method for identification of vocal fold lamina propria fibroblasts in culture". Otolaryngology—Head and Neck Surgery, 139(6), 2008, pp. 816-822 (Year: 2008).*
(Continued)

*Primary Examiner* — Christie Bahena
(74) *Attorney, Agent, or Firm* — Quarles & Brady, LLP

(57) ABSTRACT

An engineered vocal fold mucosa, including an engineered lamina propria layer and an engineered squamous epithelium layer, is disclosed. The engineered lamina propria is made by seeding and culturing human vocal fold fibroblasts within a polymerized collagen scaffold, and the engineered squamous epithelium is made by culturing human vocal fold epithelial cells on the scaffold surface. The resulting engineered vocal fold mucosa is not immunogenic, and is capable of exhibiting the vibratory function and acoustic output of a native vocal fold mucosa. Accordingly, the engineered vocal fold mucosa may be implanted into the larynx to treat voice impairment.

15 Claims, 39 Drawing Sheets
(39 of 39 Drawing Sheet(s) Filed in Color)

Related U.S. Application Data

(60) Provisional application No. 62/152,468, filed on Apr. 24, 2015.

(51) Int. Cl.
*A61L 27/38* (2006.01)
*C12N 5/071* (2010.01)
*C12N 5/077* (2010.01)

(56) References Cited

PUBLICATIONS

Yamaguchi et al., "Reconstruction of the Laryngeal Mucosa: A Three-Dimensional Collagen Gel Matrix Culture". Archives of Otolaryngology—Head and Neck Surgery, 122(6), 1996, pp. 649-654 (Year: 1996).*
Abou Neel, et al., Collagen—emerging collagen based therapies hit the patient. Adv Drug Deliv Rev 65, 429-456 (2013).
Caton, et al., Viscoelasticity of hyaluronan and nonhyaluronan based vocal fold injectables: implications for mucosal versus muscle use. Laryngoscope 117, 516-521 (2007).
Chan, et al., The importance of hyaluronic acid in vocal fold biomechanics. Otolaryngol Head Neck Surg 124, 607-614 (2001).
Chen, et al., Novel isolation and biochemical characterization of immortalized fibroblasts for tissue engineering vocal fold lamina propria. Tissue Eng Part C Methods 15, 201-212 (2009).
Chhetri, et al., Injection of cultured autologous fibroblasts for human vocal fold scars. Laryngoscope 121, 785-792 (2011).
Dongari-Bagtzoglou, et al., Development of a highly reproducible three-dimensional organotypic model of the oral mucosa. Nat Protoc 1, 2012-2018 (2006).
Finkelhor, et al., The effect of viscosity changes in the vocal folds on the range of oscillation. J Voice 1, 320-325 (1988).
Fukahori, et al., Regeneration of Vocal Fold Mucosa Using Tissue-Engineered Structures with Oral Mucosal Cells, PLoS ONE 11(1): e0146151. doi:10.1371/journal.pone.0146151, pp. 1-15 (2016).
Gangatirkar, et al., Establishment of 3D organotypic cultures using human neonatal epidermal cells. Nat Protoc 2, 178-186 (2007).
Gaston, et al., The response of vocal fold fibroblasts and mesenchymal stromal cells to vibration. PLoS One 7, e30965 (2012).
Gray, et al., Biomechanical and histologic observations of vocal fold fibrous proteins. Ann Otol Rhinol Laryngol 109, 77-85 (2000).
Gray, et al., Vocal fold proteoglycans and their influence on biomechanics. Laryngoscope 109, 845-854 (1999).
Hahn, et al., Midmembranous vocal fold lamina propria proteoglycans across selected species. Ann Otol Rhinol Laryngol 114, 451-462 (2005).
Hahn, et al., Quantitative and comparative studies of the vocal fold extracellular matrix. I: Elastic fibers and hyaluronic acid. Ann Otol Rhinol Laryngol 115, 156-164 (2006).
Hahn, et al., Quantitative and comparative studies of the vocal fold extracellular matrix II: collagen. Ann Otol Rhinol Laryngol 115, 225-232 (2006).
Hanson, et al., Characterization of mesenchymal stem cells from human vocal fold fibroblasts. Laryngoscope 120, 546-551 (2010).
Hartnick, et al., Development and maturation of the pediatric human vocal fold lamina propria. Laryngoscope 115, 4-15 (2005).
Hirano, A technique for glottic reconstruction following vertical partial laryngectomy. Auris Nasus Larynx 5, 63-70 (1978).
Kutty, et al., Vibration stimulates vocal mucosa-like matrix expression by hydrogel-encapsulated fibroblasts. J Tissue Eng Regen Med 4, 62-72 (2010).
Langness, et al., Collagen biosynthesis in nonfibroblastic cell lines. Proc Natl Acad Sci USA 71, 50-51 (1974).
Leydon, et al., A meta-analysis of outcomes of hydration intervention on phonation threshold pressure. J Voice 24, 637-643 (2010).
Leydon, et al., Human embryonic stem cell-derived epithelial cells in a novel in vitro model of vocal mucosa. Tissue Eng Part A 19, 2233-2241 (2013).
Long, et al., Epithelial differentiation of adipose-derived stem cells for laryngeal tissue engineering. Laryngoscope 120, 125-131 (2010).
Long, et al., Functional testing of a tissue-engineered vocal fold cover replacement. Otolaryngol Head Neck Surg 142, 438-440 (2010).
Long, et al., In Vivo Vocal Fold Cover Layer Replacement, Laryngoscope 125:406-411 (2015).
Molteni, et al., Auto-crosslinked hyaluronan gel injections in phonosurgery. Otolaryngol Head Neck Surg 142, 547-553 (2010).
Park, et al., Three-dimensional hydrogel model using adipose-derived stem cells for vocal fold augmentation. Tissue Eng Part A 16, 535-543 (2010).
Quinchia Johnson, et al., Tissue regeneration of the vocal fold using bone marrow mesenchymal stem cells and synthetic extracellular matrix injections in rats. Laryngoscope 120, 537-545 (2010).
Shiba, et al., Tissue-Engineered Vocal Fold Mucosa Implantation in Rabbits, Otolaryngology—Head and Neck Surgery, pp. 1-10 (2016).
Shultz, et al., Humanized mice for immune system investigation: progress, promise and challenges. Nat Rev Immunol 12, 786-798 (2012).
Svensson, et al., Injection of human mesenchymal stem cells improves healing of scarred vocal folds: analysis using a xenograft model. Laryngoscope 120, 1370-1375 (2010).
Svensson, et al., Injection of human mesenchymal stem cells improves healing of vocal folds after scar excision—A kenograft analysis. Laryngoscope 121, 2185-2190 (2011).
Titze, et al., Design and validation of a bioreactor for engineering vocal fold tissues under combined tensile and vibrational stresses. J Biomech 37, 1521-1529 (2004).
VonKoskull, et al., Induction of cytokeratin expression in human mesenchymal cells. J Cell Physiol 133, 321-329 (1987).
Wang, et al., Endoscopic diode laser welding of mucosal grafts on the larynx: a new technique. Laryngoscope 105, 49-52 (1995).
Welham, et al., A rat excised larynx model of vocal fold scar. J Speech Lang Hear Res 52, 1008-1020 (2009).
Welham, et al., Proteomic analysis of a decellularized human vocal fold mucosa scaffold using 2D electrophoresis and high-resolution mass spectrometry. Biomaterials 34, 669-676 (2013).
Xu, et al., A biodegradable, acellular xenogeneic scaffold for regeneration of the vocal fold lamina propria. Tissue Eng 13, 551-566 (2007).
Yamaguchi, et al., Reconstruction of the laryngeal mucosa. A three-dimensional collagen gel matrix culture. Arch Otolaryngol Head Neck Surg 122, 649-654 (1996).
Zybailov, et al., Statistical analysis of membrane proteome expression changes in *Saccharomyces cerevisiae*. J Proteome Res 5, 2339-2347 (2006).

* cited by examiner

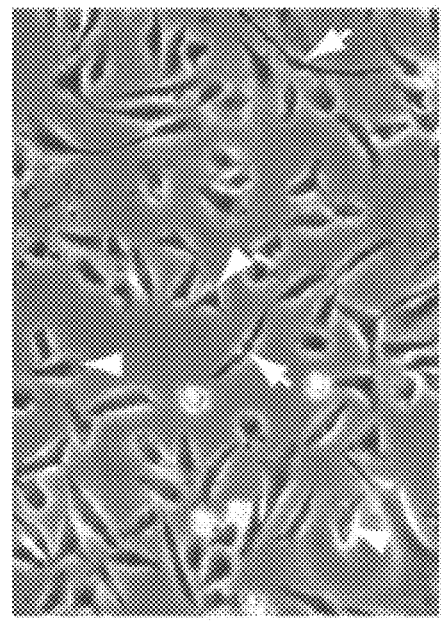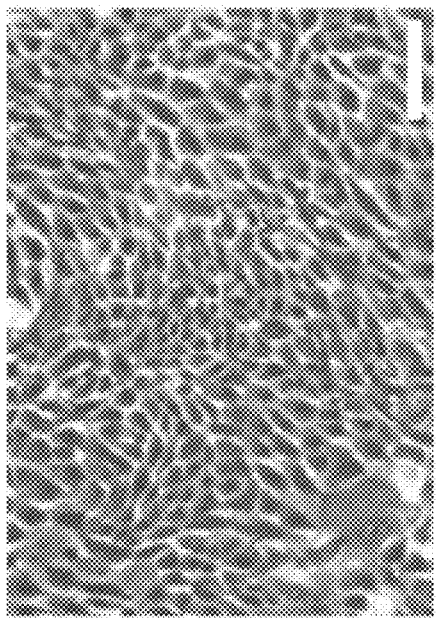
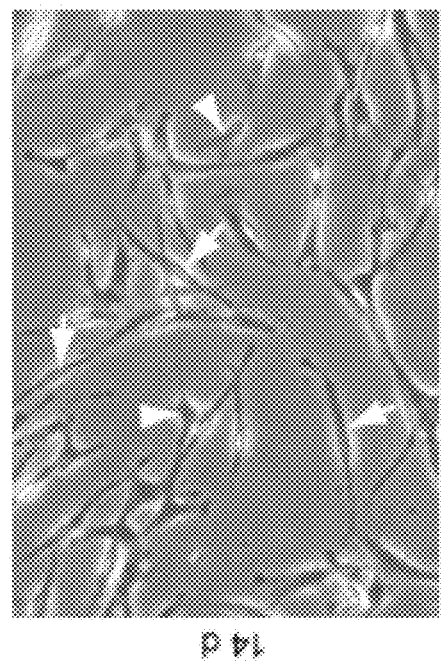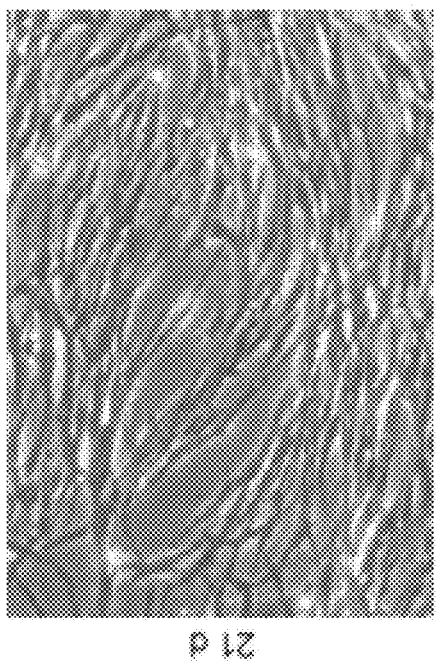
FIG. 1A  FIG. 1B

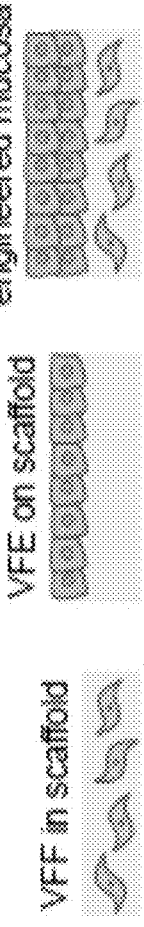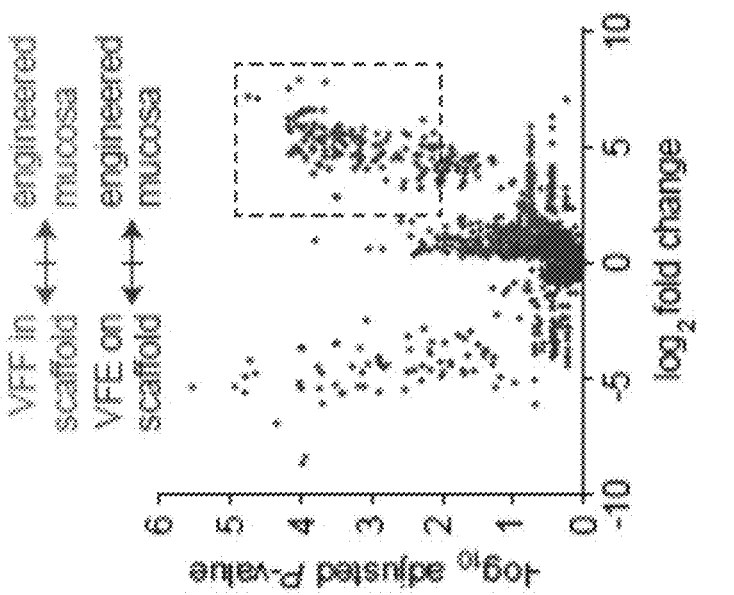
FIG. 6A
FIG. 6B
FIG. 6C

BIOENGINEERED VOCAL FOLD MUCOSA FOR FUNCTIONAL VOICE RESTORATION

CROSS-REFERENCE TO RELATED APPLICATIONS

This application is a divisional of U.S. patent application Ser. No. 15,136,655, filed Apr. 22, 2016, which claims priority to U.S. Provisional Patent Application No. 62/152,468, filed Apr. 24, 2015, each of which is incorporated herein by reference as if set forth in its entirety.

STATEMENT REGARDING FEDERALLY SPONSORED RESEARCH/DEVELOPMENT

This invention was made with government support under DC010777 awarded by the National Institutes of Health. The government has certain rights in the invention.

BACKGROUND

The human vocal folds (VFs, sometimes referred to as vocal cords or vocal chords), which are essential to the production of speech (phonation), are made up of a pair of structures that are stretched horizontally across the top of the trachea, within the larynx. The VF inner region of is made up of the vocalis muscle, which has both passive and active mechanical properties. Passively, the vocalis muscle has a relatively stiff consistency (sometimes compared to the consistency of a stiff rubber band), while, as a muscle, its active contractile properties help control its precise location and level of stiffness.

The vocalis muscle is covered by two mechanically de-coupled regions, each containing multiple layers. The region making up the outer covering of the vocal fold is known as the vocal fold mucosa (VFM). The vocal fold mucosa includes the outermost squamous epithelium layer and a mucosal lamina propria layer directly underneath the squamous epithelium. The squamous epithelium, which is composed primarily of stratified vocal fold epithelial cells (VFEs), serves as an initial boundary of protection for the underlying tissue and helps regulate vocal fold hydration. The underlying mucosal lamina propria, which is composed primarily of loose fibrous and elastic components in a vascularized matrix that is populated by vocal fold fibroblasts (VFEs), provides a pliant cushion having the mechanical properties needed for the vocal folds to vibrate in a manner that facilitates phonation.

The vocal folds also include a third region interposed between the inner vocalis muscle and the outer mucosa: the vocal ligament. The vocal ligament, which includes two non-mucosal lamina propria layers (the intermediate lamina propria and the deep lamina propria), is composed primarily of elastic and collagenous fibers, which provide this intermediate region with its elastic mechanical integrity and durability. See, e.g., Hirano M. Structure and vibratory behavior of the vocal fold, in Sawashima M, Cooper F (eds) (1977), Dynamic aspects of speech production, University of Tokyo, Tokyo, Japan: 13-30.

When inhaling, the vocal folds are separated, to facilitate the free flow of air through the trachea. When holding one's breath, the vocal folds tighten and come together, completely shutting off the free flow of air through the trachea. During phonation, the vocal folds are in an intermediate position, and the controlled passage of air from the lungs through the trachea causes the mucosa of adjoining vocal folds in contact with each other to vibrate at a high frequency. This transduction of energy from air flow from the lungs into high frequency vocal fold vibration in turn results in airborne sound waves that can be heard as speech. See, e.g., Matsushita H. The vibratory mode of the vocal folds in the excised larynx, Folia Phoniatr (Basel) 27 (1975): 7-18. Accordingly, phonation requires that both vocal fold mucosae are biomechanically capable of aerodynamic-to-acoustic energy transfer and high-frequency vibration, and physiologically capable of maintaining a barrier against the airway lumen.

Voice impairment (dysphonia) affects an estimated 20 million people in the United States, resulting in reduced general and disease-specific quality of life[1], reduced occupational performance and attendance[2,3], and direct health care costs exceeding $11 billion per year[4,5]. Between 60 and 80% of voice complaints in the treatment-seeking population involve changes to the vocal fold (VF) mucosa[6]; severe mucosal impairment or loss due to trauma, disease, or disease resection often culminates in fibrosis and deterioration of VF vibratory capacity for voice[7].

Patients with significant VF mucosal damage have limited treatment options. Medialization of the impaired VF, achieved by delivering an implant or injectate to the paraglottic space[8-10], can improve VF closure and therefore voice, but does not address fibrotic changes within the extracellular matrix (ECM). Superficial injection of regenerative biomaterials offers an alternative means to improve VF viscoelasticity and vibratory function[11,12]; however, most biomaterials are not specifically engineered for the VF biomechanical environment, have limited residence time, and are not suited for large deficits involving extensive tissue loss. Creation of an organotypic bioengineered VF mucosa could theoretically bypass these challenges by providing on-demand tissue for transplantation that is both biomechanically appropriate for use as a dynamic sound source for voice production and capable of maintaining barrier function at the boundary of the upper and lower airways.

Tissue engineering of partial and complete VF mucosae has been attempted using decellularized ECM-based[13] and collagen[14,15] and fibrin[16,17] gel-based scaffolds, seeded with embryonic stem cell derivatives[15], adult stem cells[16,17], and terminally differentiated cells[13,14,18]. These organotypic culture approaches have generated engineered mucosae with desirable histologic features; however, to date, there is no benchmark culture system based solely on human-sourced VF cells against which stem cell-based approaches can be evaluated, no direct comparisons showing equivalency with native human VF mucosa, and most importantly, limited progress towards the restoration of physiologic function[17]. Significant advances have been hampered by the near-unavailability of disease-free primary human VF mucosal cells[19] and limited attention to the intricate protein- and anatomic substructure-level complexity that characterizes mucosal morphogenesis.

Accordingly, there is a need for improved non-immunogenic transplantable engineered mucosae that are biomechanically capable of aerodynamic-to-acoustic energy transfer and high-frequency vibration, and physiologically capable of maintaining a barrier against the airway lumen.

BRIEF SUMMARY

This application discloses engineered vocal fold mucosae made from isolated and purified human VF fibroblasts (VFF) and human VF epithelial cells (VFE) co-cultured under organotypic conditions. The engineered vocal fold mucosae show morphologic features of native tissue. Specifically, the engineered vocal fold mucosae include an engineered mucosal lamina propria layer comprising a collagen polymer matrix populated by human VFFs in contact with an engineered outer squamous epithelium layer made from cultured human VFEs. The engineered vocal fold mucosae show proteome-level evidence of mucosal morphogenesis and emerging extracellular matrix complexity, and rudimentary barrier function in vitro. When grafted into larynges ex vivo, the engineered vocal fold mucosae generate physiologically appropriate vibratory behavior and acoustic output that are indistinguishable from those of native VF tissue. When grafted into humanized mice in vivo, the mucosae survive and are well tolerated by the human adaptive immune system. These results show that the disclosed compositions and methods can be used to restore voice function in patients with otherwise untreatable VF mucosal disease or damage.

In a first aspect, the disclosure encompasses an engineered vocal fold mucosa that includes (a) an engineered non-vascularized lamina propria made up of a scaffold of polymerized collagen populated by a plurality of human vocal fold fibroblasts (VFFs); and (b) an engineered stratified squamous epithelium that includes a plurality of human vocal fold epithelial cells (VFEs) that is in contact with the engineered non-vascularized lamina propria. The engineered vocal fold mucosa is capable of exhibiting the vibratory function and acoustic output of a native vocal fold mucosa.

As used herein, the term "scaffold" refers to a polymerized collagen that forms a gel-like composition. The scaffold is not impervious to aqueous solutions and other liquids, which can readily flow into the scaffold. For example, if the cell-populated scaffold is immersed in a culture medium, the culture medium may be absorbed into the scaffold and come in contact with the cells populating the scaffold. In the engineered vocal fold mucosa, the boundaries of the scaffold within which the VFFs reside also define the boundaries of the engineered non-vascularized lamina propria. Accordingly, the outer boundary of the scaffold is referred to herein as the "surface" of the scaffold.

The engineered stratified squamous epithelium (and the VFEs comprising the engineered squamous epithelium) is outside of the scaffold, and thus has an inner boundary at the scaffold surface. The engineered stratified squamous epithelium extends outward from the scaffold surface to its outermost boundary, the epithelial surface or luminal epithelial surface. The squamous epithelium region that is closest to the inner boundary at the scaffold surface is known as the basal surface region, and the squamous epithelium region that is closest to the luminal epithelial surface is known as the epithelial surface region. As in native VF mucosae, in the engineered VF mucosae, the VFE in the basal region form processes that extend into the underlying lamina propria, consistent with epithelial anchoring and barrier-like structure formation.

By "human vocal fold fibroblasts" (VFFs), we mean fibroblasts that are isolated from the vocal fold mucosa of a human (i.e., primary human vocal fold fibroblasts), or cells that are descended from such isolated human vocal fold mucosa fibroblasts or their progeny. Accordingly, the term is not limited to primary human vocal fold fibroblasts, but also encompasses cells resulting from the continued culturing, proliferation and/or passaging of cells derived from primary human vocal fold fibroblasts or their progeny. By "isolated," we mean that the cells that have been removed from the native environment in which they originally resided. In the case of primary human vocal fold fibroblasts, the isolated cells are removed from the native extracellular matrix. The vocal fold mucosa from which the cells are isolated may have been obtained from a living human or from a human cadaver. In the case of a human cadaver, the vocal fold mucosa is preferably obtained less than six hours postmortem.

By "human vocal fold epithelial cells" (VFEs), we mean epithelial cells that are isolated from the vocal fold mucosa of a human (i.e., primary human vocal fold epithelial cells), or cells that are descended from such isolated human vocal fold mucosa epithelial cells or their progeny. Accordingly, the term is not limited to primary human vocal fold epithelial cells, but also encompasses cells resulting from the continued culture, proliferation and/or passaging of cells derived from primary human vocal fold epithelial cells or their progeny. By "isolated," we mean that the cells that have been removed from the native environment in which they originally resided. In the case of primary human vocal fold epithelial cells, the isolated cells are removed from the native squamous epithelium. The vocal fold mucosa from which the cells are isolated may have been obtained from a living human or from a human cadaver. In the case of a human cadaver, the vocal fold mucosa is preferably obtained less than six hours post-mortem.

The human vocal fold fibroblasts and human vocal fold epithelial cells do not include cells isolated from non-vocal fold mucosal tissue, such as cells isolated from generalized laryngeal mucosa or oral mucosa, or cells isolated from non-human subjects.

In some embodiments, the polymerized collagen is polymerized collagen, type I.

In some embodiments, the density of the VFFs populating the engineered non-vascularized lamina propria is from 100-300 cells/mm$^2$ or from 130-270 cells/mm$^2$.

In some embodiments, the engineered stratified squamous epithelium is between 30 and 70 um thick.

In some embodiments, one or more VFEs at both the basal and epithelial surface regions of the engineered stratified squamous epithelium express the basement membrane marker collagen, type IV.

In some embodiments, the engineered stratified squamous epithelium includes one or more Keratin 5$^+$ VFEs, and the basal region of the engineered stratified squamous epithelium does not have a higher percentage of Keratin 5$^+$ VFEs than the stratified squamous epithelium as a whole.

In some embodiments, one or more of the proteins listed in Table 1 below as being present in the engineered VF mucosa are included in the engineered VF mucosa. In some such embodiments, at least one of the included proteins is a protein that is not present in native VF mucosa.

In a second aspect, the disclosure encompasses an engineered vocal fold mucosa as described herein for use in treating voice impairment caused by vocal fold fibrosis or vocal fold mucosal tissue damage or loss.

In a third aspect, the disclosure encompasses an engineered vocal fold mucosa as described herein for use in manufacturing a composition for treating voice impairment caused by vocal fold fibrosis or vocal fold mucosal tissue damage or loss.

In a fourth aspect, the disclosure encompasses a method of treating voice impairment caused by vocal fold fibrosis or vocal fold mucosal tissue damage or loss. The method includes the step of implanting an engineered vocal fold mucosa as described herein into the larynx of a subject having a vocal impairment. As a result of performing this step, the degree of voice impairment is reduced.

In a fifth aspect, the disclosure encompasses a method of making an engineered vocal fold mucosa. The method includes the steps of (a) culturing a plurality of human vocal fold fibroblasts (VFFs) within a scaffold comprising polymerized collagen; and (b) culturing a plurality of human vocal fold epithelial cells (VFEs) on the scaffold surface. As a result of performing these steps, an engineered vocal fold mucosa is formed that includes an engineered stratified squamous epithelium in contact with an engineered non-vascularized lamina propria made of a polymerized collagen scaffold populated by a plurality of human VFFs within the scaffold.

In some embodiments, the polymerized collagen is polymerized collagen, type I.

In some embodiments, the step of culturing the plurality of human VFEs on the scaffold surface is first performed within an epithelial cell-oriented medium in which the human VFEs are immersed. In some such embodimements, the human VFEs are cultured for 1 to 3 days within the epithelial cell-oriented medium in which the human VFEs are immersed.

By "epithelial cell-oriented medium," we mean any medium known to or reasonably expected to support the maintenance, growth, and/or proliferation of human epithelial cells in culture, including, without limitation, the epithelial cell-oriented medium disclosed in the Example below.

In some embodiments, the step of culturing the plurality of human VFEs on the scaffold surface is later performed at an air-liquid interface on the scaffold surface, wherein the scaffold comprises a composition comprising both a fibroblast-oriented medium and a epithelial cell-oriented medium. As a result, the human VFEs stratify to form a squamous epithelium layer. In some such embodiments, the VFEs are cultured for 5 to 50 days at the air-liquid interface on the scaffold surface.

In some embodiments, the step of culturing the plurality of human VFFs within the scaffold is first performed when the scaffold includes a fibroblast-oriented medium, and later performed when the scaffold includes a composition comprising both a fibroblast-oriented medium and an epithelial cell-oriented medium.

By "fibroblast-oriented medium," we mean any medium known to or reasonably expected to support the maintenance, growth, and/or proliferation of human fibroblasts in culture, including, without limitation, the fibroblast-oriented medium disclosed in the Example below.

In some embodiments, prior to culturing the human VFFs within the scaffold, the human VFFs are seeded into the scaffold at a density of between $5\times10^4$ and $1\times10^6$ VFF/mL. In some such embodiments, the human VFFs are seeded into the scaffold by mixing the VFFs into a collagen composition wherein the collagen has not yet polymerized to form the scaffold. When the collagen subsequently polymerizes into a gel-like composition, the VFFs are cultured within the scaffold.

In some embodiments, the human VFFs are obtained by (a) seeding cells obtained from a human vocal fold mucosa onto an extracellular matrix (ECM)-coated surface, whereby some of the cells adhere to the ECM-coated surface and some of the cells remain free-floating and non-adherent; and (b) culturing the cells that adhere to the ECM-coated surface in fibroblast-oriented medium, resulting in a substantially pure subpopulation of human VFFs. In some such embodiments, the human VFEs are obtained by the further steps of (c) separately culturing the non-adherent cells in an epithelial cell-oriented medium, whereby the non-adherent cells become adherent, and (d) incubating the now-adherent cells in a composition comprising trypsin and removing one or more initially detached cells. In some such embodiments, the remaining adherent cells are detached and passaged into a separate epithelial cell-oriented medium, where the cells again become adherent. In some such embodiments, the passaged cells are again incubated in a composition comprising trypsin, and one or more initially detached cells are again removed, resulting in a substantially pure subpopulation of human VFEs.

In some embodiments, the step of culturing the VFEs, the step of culturing the VFFs, or both further include passaging the cultured cells at least twice. In some such embodiments, the human VFFs, the human VFEs, or both are obtained from the second passage, the third passage, the fourth passage, the fifth passage, the sixth passage, or any combination thereof. In some such embodiments, the human VFFs, the human VFEs, or both are obtained from the third passage.

In some embodiments, the cells are obtained from the human vocal fold mucosa by (a) mincing the human vocal fold mucosa; and (b) enzymatically digesting the minced mucosa to release the cells from the extracellular matrix (ECM).

In a sixth aspect, the disclosure encompasses an engineered vocal fold mucosa as made by the method described herein.

In a seventh aspect, the disclosure encompasses a method of separating cells obtained from human vocal fold mucosa into a substantially pure human VFF subpopulation. The method includes the steps of (a) seeding cells obtained from a human vocal fold mucosa onto an extracellular matrix (ECM)-coated surface, whereby some of the cells adhere to the ECM-coated surface and some of the cells remain free-floating and non-adherent; (b) culturing the cells that adhere to the ECM-coated surface in fibroblast-oriented medium, resulting in a substantially pure subpopulation of human VFFs. In some such embodiments, the cells are further separated into a VFE subpopulation by (c) separately culturing the non-adherent cells in an epithelial cell-oriented medium, whereby the non-adherent cells become adherent, and (d) incubating the now-adherent cells in a composition comprising trypsin and removing one or more initially detached cells. In some such embodiments, the remaining adherent cells are detached and passaged into a separate epithelial cell-oriented medium, where the cells again become adherent. In some such embodiments, the passaged cells are again incubated in a composition comprising trypsin, and one or more initially detached cells are again removed, resulting in a substantially pure subpopulation of human VFEs.

In some embodiments, the cells are obtained from the human vocal fold mucosa by (a) mincing the human vocal fold mucosa; and (b) enzymatically digesting the minced mucosa to release the cells from the extracellular matrix (ECM).

The disclosed compositions and methods are further detailed below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1B demonstrate explant culture of primary human VF mucosal cells. (A) Microscopy images of live cells growing in fibroblast-oriented medium, 14- and 21-days (d) post-seeding. Cells exhibited morphological variance at 14 d but appeared uniform at 21 d. White arrows indicate fibroblast-appearing cells with spindle/star-like somata and elongated processes; white arrowheads indicate epithelial-appearing cells with cuboidal somata and short processes. (B) Microscopy images of live cells growing in epithelial cell-oriented medium, 28 and 35 d post-seeding. Cells exhibited morphological variance with clear fibroblast contamination at 28 d. Non-epithelial cell growth continued at 35 d, leading to mixed-morphology cell sphere formation and difficulty with reattachment during culture passage. White arrows indicate fibroblast-appearing cells with spindle/star-like somata and elongated processes; white arrowheads indicate epithelial-appearing cells with cuboidal somata and short processes. Scale bar, 40 µm (A, B).

FIGS. 6A-6F present proteomic-based analysis of engineered VF mucosa compared to its isolated subcomponents. (A) Schematic illustrating experimental conditions. (B) Venn diagram summarizing proteome coverage and overlap in protein identifications across experimental conditions. FDR, false discovery rate. (C) Volcano plot summarizing normalized spectral abundance factor-based protein quantification in engineered mucosa versus VFF in scaffold (red data points) and VFE on scaffold (blue data points). The dashed rectangle denotes cutoff criteria for protein overrepresentation in engineered mucosa compared to the other conditions (fold change >4; Benjamini Hochberg-adjusted P<0.01). (D) Summary of enriched biological process ontology terms associated with the protein set exclusive to engineered mucosa or overrepresented in engineered mucosa compared to both VFF in scaffold and VFE on scaffold. The table lists the three most highly represented terms identified using the BiNGO enrichment and REViGO term redundancy algorithms, as well as the mechanistically relevant epidermis development term (a complete list of enriched biological process terms is presented in Table 5). The heatmap shows the relative abundance of overrepresented proteins that map to these biological process terms of interest. Pleiotropic proteins associated with multiple terms are assigned multiple rows in the heatmap. The enlarged region highlights 5 proteins associated with epidermis (in the context of mucosa, epithelium) development. (E) Immunohistochemical validation of overrepresented proteins LAMA5 (costained with COL4), KRT5, and JUP (costained with CDH1) in engineered and native VFmucosae. White arrows indicate KRT5+ VFE; white arrowheads indicate COL4+ signals in the deep epithelium and JUP+ VFE; and yellow arrows indicate LAMA5+COL4+ basal VFE in engineered mucosa, LAMA5+COL4+ basement membrane structures in native mucosa, and CDH1+JUP+ VFE. Scale bar, 50 mm; 25 mm (inset). (F) Transmucosal electrical resistance data showing significantly increased physiologic barrier function in engineered mucosa compared to scaffold only and VFF in scaffold, and no significant difference compared to VFE on scaffold. *, P<0.01; n.s., non-significant difference; error bars, s.e.m.

DETAILED DESCRIPTION

Figure 2A:
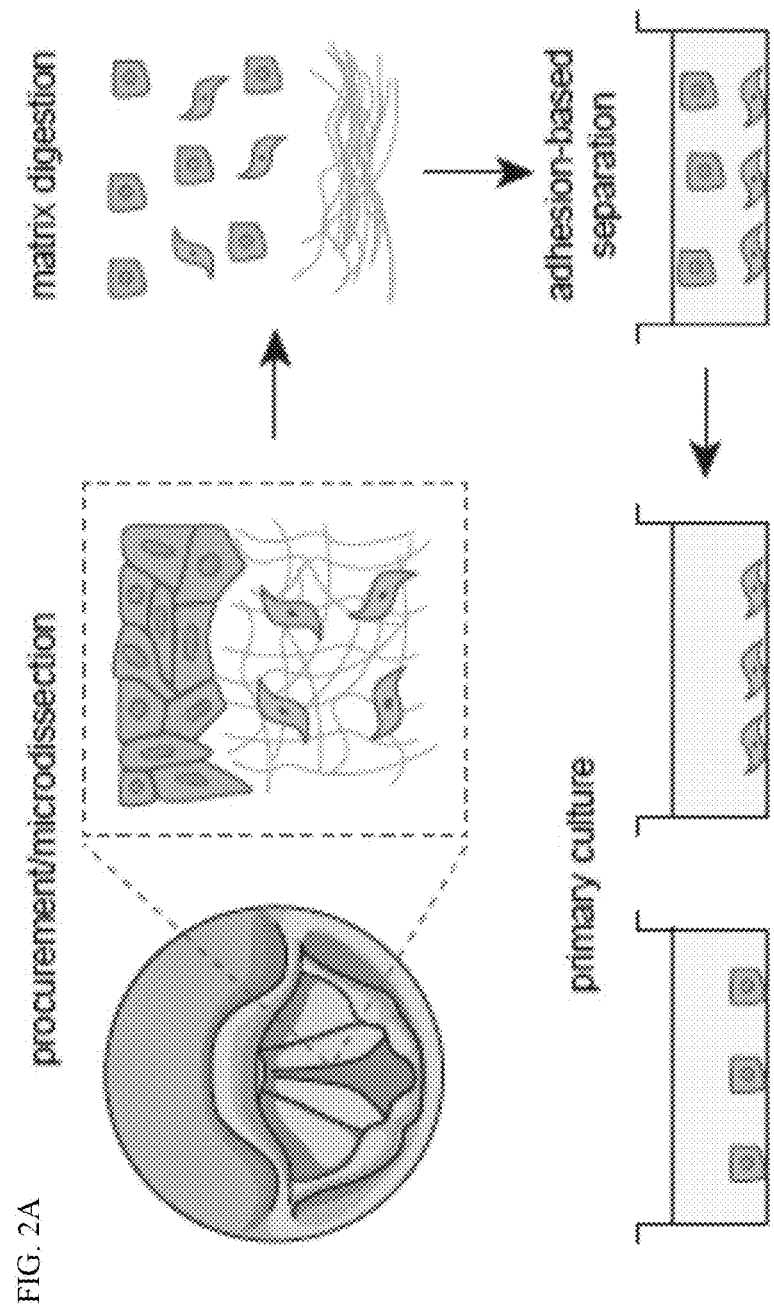
FIGS. 2A-2E demonstrate isolation, purification and expansion of primary VFF and VFE from human VF mucosa. (A) Schematic showing general procedure for cell isolation and purification. (B) Light microscopy images showing morphological characteristics of primary VFF and VFE in monolayer culture prior to first passage (left panels; unstained live cells) and at passage 3 (P3; center and right panels; fixed, H&E-stained cells). Black arrows indicate large VFF and VFE. Black arrowheads indicate VFE clusters. Scale bar, 30 µm. (C) Flow cytometry histograms and bar charts showing relative expression of the markers P4H-β, CD90, pan-keratin, keratin 14, keratin 19 and CD227 in VFF and VFE. Positive/negative gates (versus fluorescence-minus-one [FMO] control) are shown in gray; low/high gates are shown in black. (D) Flow cytometry dot plot showing complete separation of VFF and VFE populations via CD90 CD227 double staining. (E) Line graph summarizing VFF and VFE population doubling times from P1 to P6. *, $P<0.01$ (C, E); n.s., non-significant difference (C); error bars, s.e.m. (C, E).

This application discloses engineered vocal fold mucosae made from isolated and purified human vocal fold fibroblasts and isolated and purified human VF epithelial cells, co-cultured under organotypic conditions. When grafted into larynges ex vivo, the engineered vocal fold mucosae generate physiologically appropriate vibratory behavior and acoustic output that are indistinguishable from those of native VF tissue, thus demonstrating that they have the biomechanical properties that are essential for use as an implant in treating voice impairment due to vocal fold mucosal tissue damage, loss, or disease. In addition, when grafted into humanized mice in vivo (a transgenic mouse model supporting a functional human adaptive immune system; see Schulz, L. D., et al., *Nat. Rev Immunol* 12, 786-798 (2012)), the mucosae survive and are well tolerated by the human adaptive immune system, indicating that implanting the engineered mucosa into the larynx of a patient would likely not trigger rejection or immune system attack against the implant.

The inventors have found that using human vocal fold mucosal cells in the engineered vocal fold mucosa imparts the unique biomechanical and immunological properties that make the engineered mucosa useful as an implant for restoring vocal function in humans. Without being bound by any theory, human-sourced vocal fold mucosal cells are derived from cells that have been exposed to unique mechanical forces and vibration during voice production, and are thus specifically adapted to have the functional and underlying structural characteristics necessary to support phonation.

Regarding the human immunotolerance engendered by the grafted engineered vocal fold mucosa, the vocal fold mucosal cells may have immunoprivilege conferred by the unique position in the body of the cells from which they are derived. Specifically, humans are constantly inhaling a variety of potentially immunogenic foreign matter, much of which would come in contact with the vocal fold mucosae. If the vocal fold mucosal cells were immunologically active, the vocal fold mucosa would be continuously inflamed, resulting in chronic laryngitis and other airway problems. Thus, vocal fold mucosal cells may have evolved to favor and promote immunotolerance, as exhibited by the engineered vocal fold mucosa.

The engineered vocal fold mucosa is capable of exhibiting the vibratory function and acoustic output of a native vocal fold mucosa. Such capability can be measured using any of a number of specific tests known in the art, including, without limitation, the physiological, vibratory, and acoustic tests using ex vivo canine larynges that are described in detail in the Example below.

In the disclosed method of making the engineered vocal fold mucosa, the human VFFs may be cultured in a fibroblast-oriented medium or in a composition containing a fibroblast-oriented medium. The human VFEs may be cultured in a epithelial cell-oriented medium or in a composition containing an epithelial cell-oriented medium. By "fibroblast-oriented medium," we mean any medium known to or reasonably expected to support the maintenance, growth, and/or proliferation of human fibroblasts in culture, including, without limitation, the fibroblast-oriented medium disclosed in the Example below. By "epithelial cell-oriented medium," we mean any medium known to or reasonably expected to support the maintenance, growth, and/or proliferation of human airway epithelial cells in culture, including, without limitation, the epithelial cell-oriented medium disclosed in the Example below.

The human vocal fold mucosa can be useful for various in vitro and in vivo applications. Preparations for use in clinical applications must be obtained in accordance with regulations imposed by governmental agencies such as the U.S. Food and Drug Administration. Accordingly, in exemplary embodiments, the methods provided herein are conducted in accordance with Good Manufacturing Practices (GMPs), Good Tissue Practices (GTPs), and Good Laboratory Practices (GLPs). Reagents comprising animal derived components are not used, and all reagents are purchased from sources that are GMP-compliant. In the context of clinical manufacturing of a bioengineered implant for use in restoring vocal function in humans, GTPs govern cell donor consent, traceability, and infectious disease screening, whereas GMPs are relevant to the facility, processes, testing, and practices to produce consistently safe and effective products for human use. See Lu et al. *Stem Cells* 27: 2126-2135 (2009). Where appropriate, oversight of patient protocols by agencies and institutional panels is envisioned to ensure that informed consent is obtained; safety, bioactivity, appropriate dosage, and efficacy of products are studied in phases; results are statistically significant; and ethical guidelines are followed.

As used herein, the term "engineered tissue" (or similar term) refers to a tissue prepared in accordance with the methods of the invention. An acceptably engineered tissue displays physical characteristics typical of the type of the tissue in vivo and functional characteristics typical of the type of the tissue in vivo, i.e., has a functional activity. For example, physical characteristics of an engineered vocal fold mucosa can include the presence of a lamina propria layer and a squamous epithelium layer. Functional characteristics of an engineered vocal fold mucosa can include the capacity of the engineered tissue for exhibiting the vibratory function and acoustic output of a native vocal fold mucosa. As used herein, the term "bioengineered" generally refers to a tissue prepared in vitro using biological techniques including, for example, techniques of cell biology, biochemistry, tissue culture, and materials science.

The following abbreviations and acronyms are used in this application: VF, vocal fold; VFF, vocal fold fibroblasts; VFE, vocal fold epithelial cells; ECM, extracellular matrix.

Each of the publications cited in this application is incorporated by reference in its entirety and for all purposes. While specific embodiments and examples of the disclosed subject matter have been discussed herein, these examples are illustrative and not restrictive. Many variations will become apparent to those skilled in the art upon review of this specification and the claims below.

The following Example is offered for illustrative purposes only, and is not intended to limit the scope of the present invention in any way. Indeed, various modifications of the invention in addition to those shown and described herein will become apparent to those skilled in the art from the foregoing description and the following example and fall within the scope of the appended claims.

EXAMPLE

Bioengineered Vocal Fold Mucosa for Voice Restoration

In this Example, we generated bioengineered vocal fold mucosae from isolated and purified vocal fold fibroblasts (VFF) and epithelial cells (VFE). Specifically, we initially hypothesized that primary human-sourced VF mucosal cells, exposed to unique mechanical forces during human voice production[20,21], could be an appropriate cell source for the development of a bioengineered VF mucosa capable of recapitulating native VF physiologic function. We therefore isolated and purified primary vocal fold fibroblasts (VFF) and epithelial cells (VFE) from individual human donors and cultured these cells under 3D organotypic conditions, based on techniques commonly employed in skin and other mucosal systems[22,23]. The resulting engineered mucosae showed morphologic resemblance to native human VF mucosa, proteome-level evidence of active organogenesis/morphogenesis along with emerging ECM complexity, and rudimentary epithelial barrier function in vitro. Using a large animal ex vivo setup, we observed aerodynamic-to-acoustic energy transfer, periodic VF vibratory motion with physiologic mucosal wave travel, and acoustic output that were each indistinguishable from those generated by native tissue. Using a humanized mouse system, we implanted engineered VF mucosal auto- and allografts in vivo and documented robust graft survival with favorable tolerance by the human adaptive immune system. Taken together, these results indicate that the disclosed bioengineered mucosae have the potential to restore voice function in patients with otherwise untreatable VF mucosal disease.

Results

Isolation and Characterization of Primary Cells from Human VF Mucosa.

Primary VF mucosal cell culture is rarely feasible with disease-free tissue from human donors, as elective biopsy carries an unacceptable risk of lamina propria scar formation and dysphonia. For this reason, and because of associated technical challenges, there are no published reports of isolation, purification and primary culture of VFF and VFE from a single human donor. We obtained human tissue from cadavers at autopsy (<6 h post-mortem) and patients undergoing total laryngectomy for indications that did not include laryngeal disease (e.g., hypopharyngeal cancer, dysphagia with otherwise untreatable pulmonary aspiration) and then initially conducted primary explant culture in fibroblast- or epithelial cell-oriented medium. Fibroblast-oriented culture resulted in steady VFF proliferation and successful deletion of non-target cells, yielding a morphologically pure VFF population within 21 d (FIG. 1A); however, epithelial cell-oriented culture resulted in limited VFE proliferation alongside growth of non-epithelial cells, including those with fibroblastic morphology. We observed tangling of various cell subpopulations within the culture dish (FIG. 1B) and heterogeneous cell sphere formation leading to problems with reattachment during culture passage.

Figure 2B:
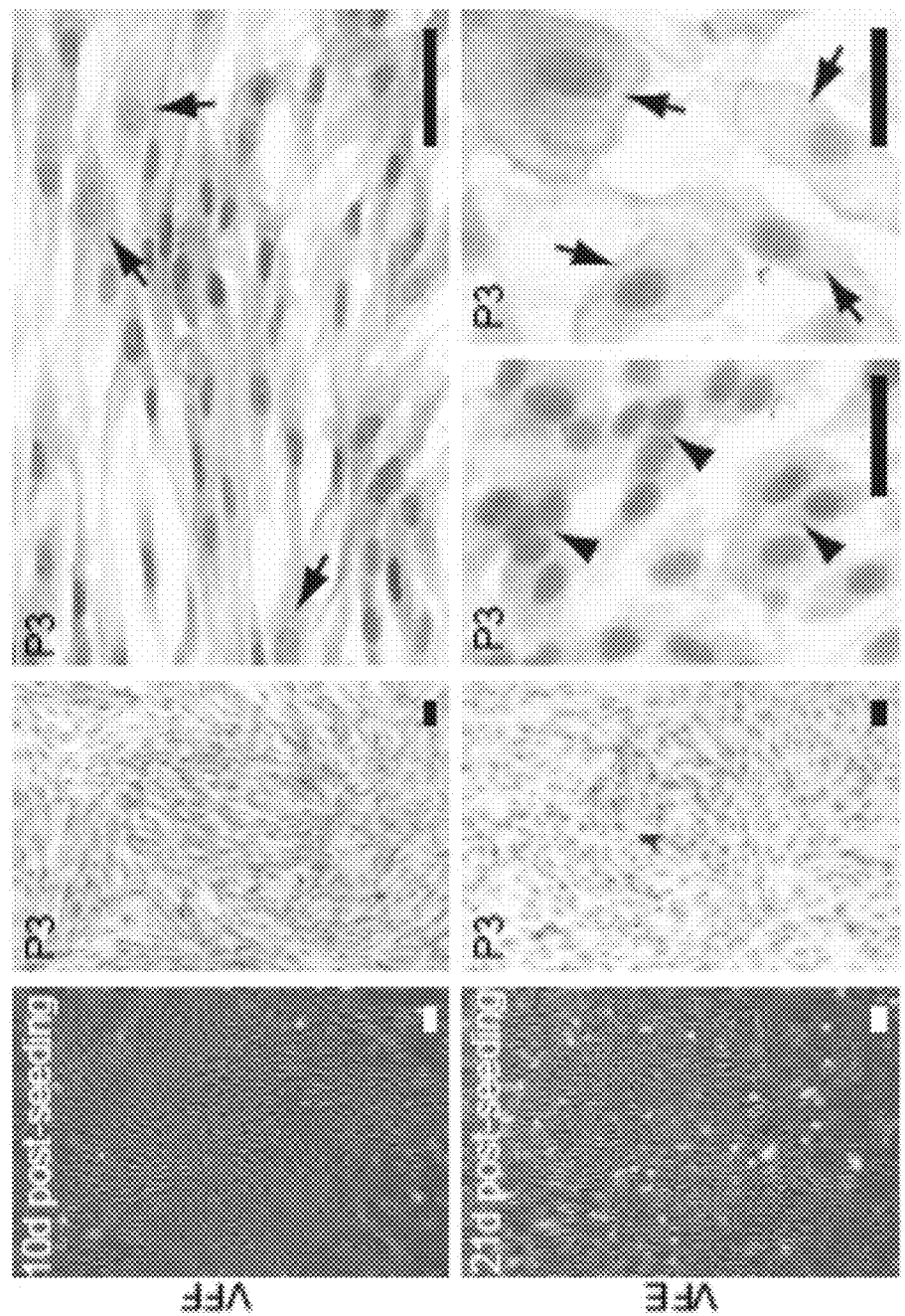

To address these issues, we developed an approach to better isolate and purify VFF and VFE from human VF mucosa (FIG. 2A). We microdissected and minced the mucosa; performed enzymatic digestion to release cells from the ECM; filtered, washed and pipetted cell clumps to release individual cells; separated the cells into VFF and VFE subpopulations based on their adhesion capacity on ECM-coated culture surfaces (see Materials and Methods below); and cultured under fibroblast- or epithelial cell-oriented conditions. These VFF and VFE proliferated well in primary culture and formed colonies containing generally homogenous cell morphology (FIG. 2B). VFF formed initial large colonies 10-15 d post-seeding: the majority of cells contained classic-appearing spindle/star-like somata and elongated processes. VFE formed initial colonies 20-25 d post-seeding: the majority of cells contained relatively large nuclei, cuboidal somata, and short processes. We observed a persistent subpopulation of morphologically similar but notably large cells in both VFF and VFE cultures.

Figure 2C:
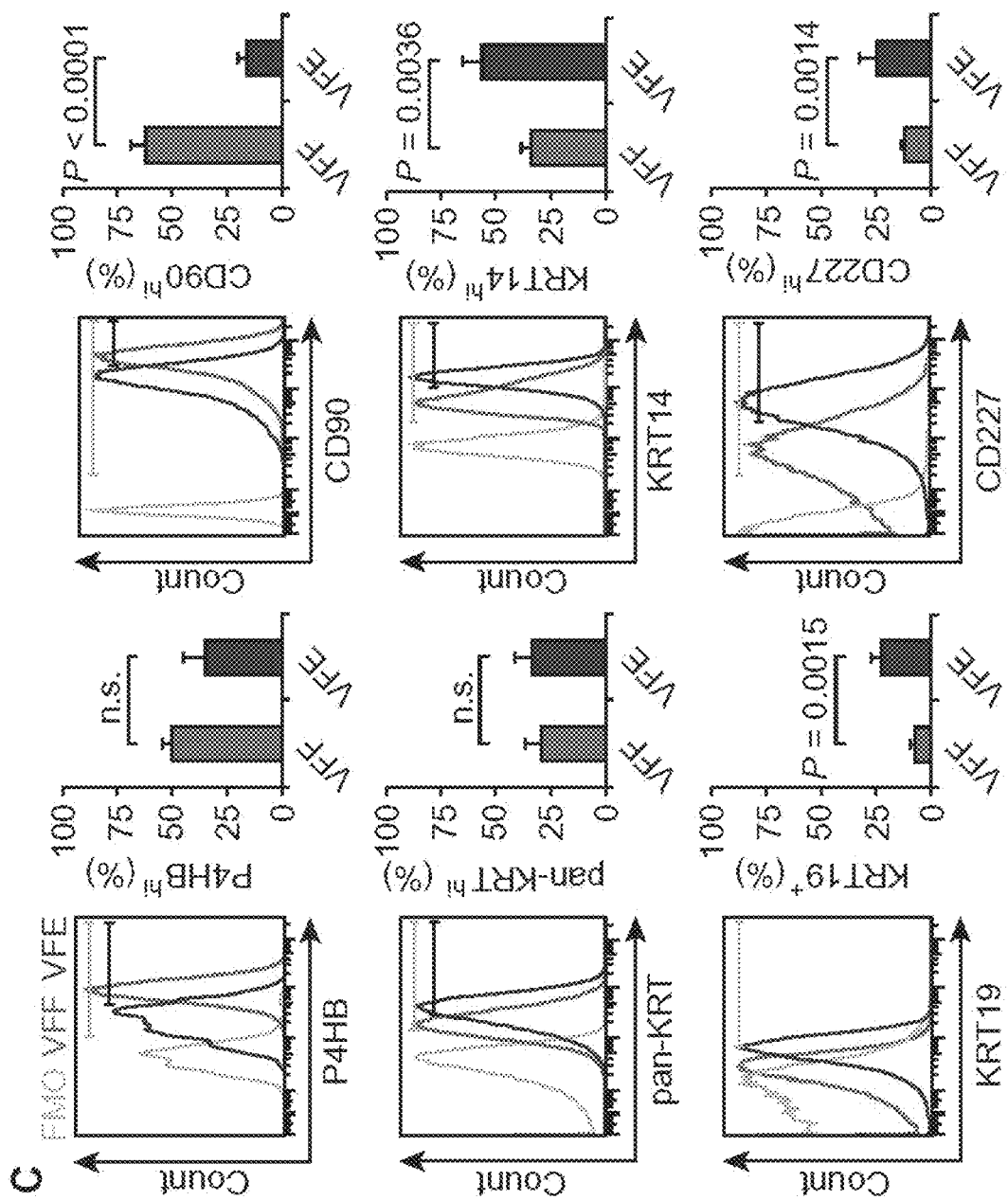

Fibroblasts and epithelial cells exhibit distinct immunomarkers in vivo but share expression of most markers (at different abundances) in vitro.[24,25] We therefore used a 6-marker flow cytometry panel to characterize the relative expression of classic fibroblast- and epithelial cell-associated proteins in our adhesion-separated VFF and VFE (FIG. 2C). Relative expression levels (based on low/high gating) were consistent with cell phenotype; however, as expected, single marker analysis was ineffective at completely separating the two subpopulations. VFF expressed more of the collagen synthesis enzyme prolyl-4-hydroxylase β (P4H-β) and fibroblast marker CD90 (also known as Thy-1) (P<0.01). VFF and VFE expressed equivalent pan-keratin (P=0.73), whereas VFE expressed more of the type I keratin isoforms 14 and 19, as well as the mucin-producing epithelial cell marker CD227 (also known as epithelial membrane antigen or mucin 1) (P<0.01). Subsequent double staining resulted in successful separation of these VF mucosal cells into $CD90^{hi}CD227^{lo}$ (VFF) and $CD90^{lo}CD227^{hi}$ (VFE) subpopulations (FIG. 2D), confirming the effectiveness of our isolation and purification workflow.

Figure 2E:
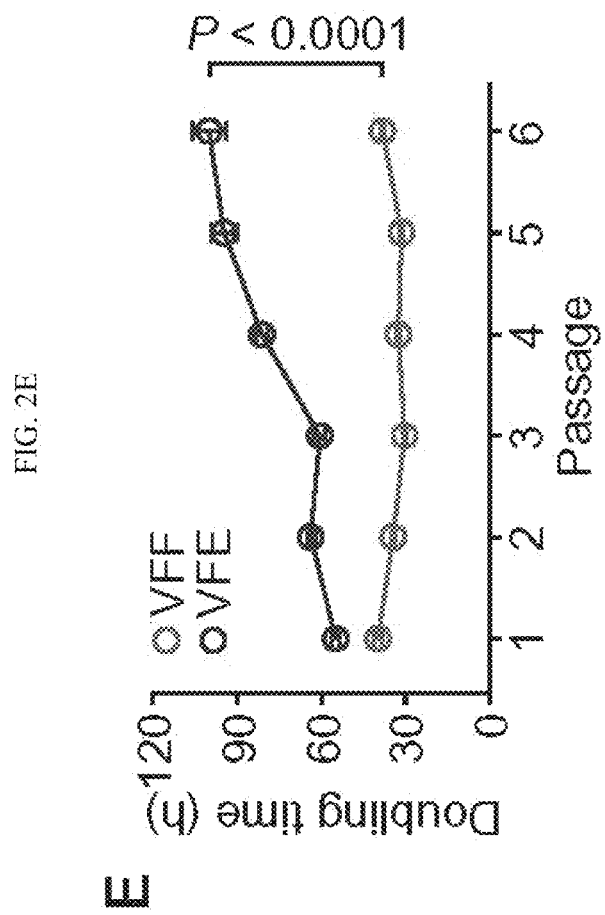
Figure 2D:
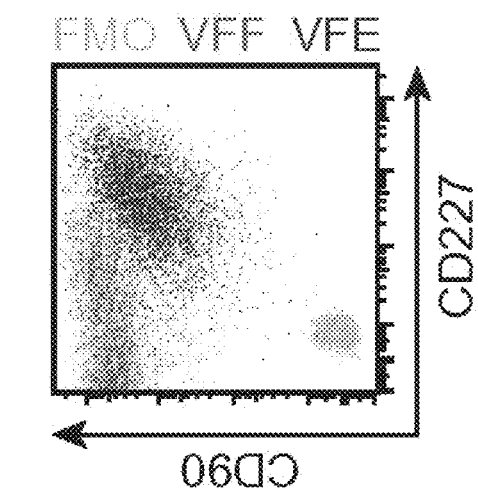

VFF maintained a consistent proliferation rate (30-40 h population doubling time) over 6 passages (FIG. 2E). VFE proliferated more slowly overall (P<0.01), initially maintaining a 55-65 h population doubling time that progressively increased across passages 4-6. We therefore used passage 3 cells for subsequent mucosal engineering experiments.

Assembly of 3D Engineered VF Mucosa.

Figure 3A:
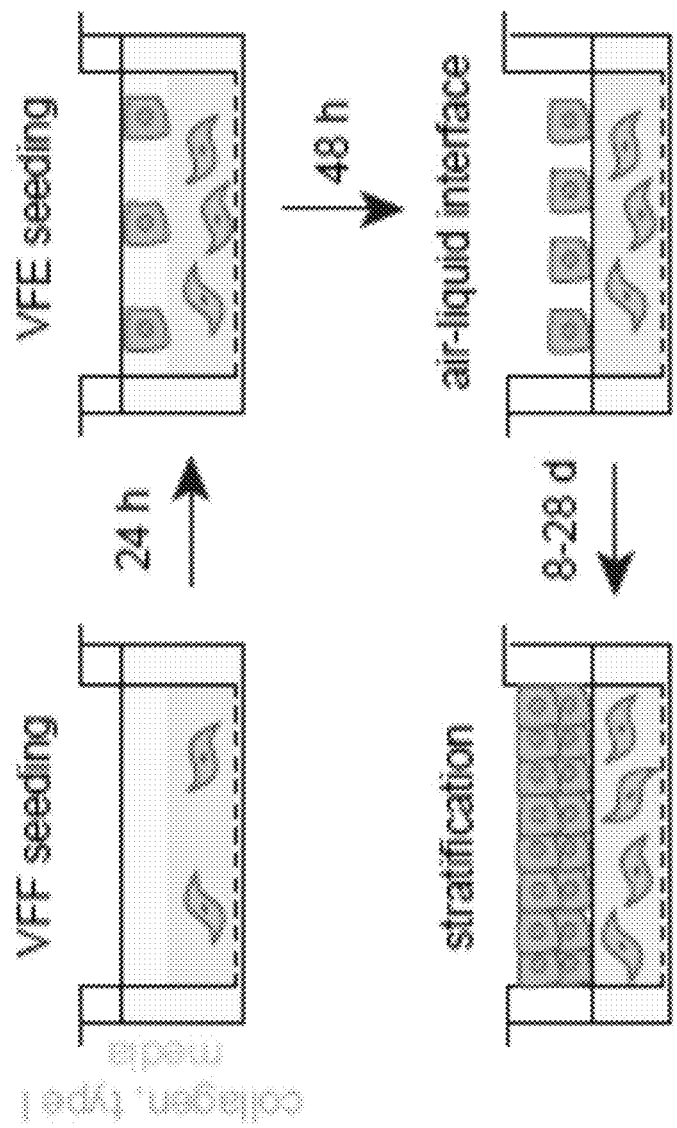
FIGS. 3A-3G demonstrate assembly of engineered human VF mucosa. (A) Schematic illustrating the experimental approach. (B) H&E- and Movat's pentachrome-stained sections showing comparable morphologic features in engineered and native mucosae. Black arrows indicate basal VFE cytoplasmic projections extending into the lamina propria. Scale bar, 100 µm (main images); 40 µm (insets). (C) Immunofluorescent images showing P4H-β, collagen, type IV, and e-cadherin staining patterns in engineered mucosa compared to native mucosa. White arrows indicate P4H-β− VFE, collagen, type IV+ basement membrane and luminal epithelial structures, and e-cadherin+ VFE. White arrowheads indicate P4H-β+ VFF and collagen, type IV+ VFF and vascular basement membrane structures in the lamina propria. Scale bar, 50 µm. (D) Venn diagram summarizing proteome coverage in engineered mucosa compared to native mucosa and scaffold only. FDR, false discovery rate. (E) Functional enrichment analysis of the engineered mucosa proteome. Enriched gene ontology terms are depicted as nodes connected by arrows that represent hierarchies and relationships between terms. Node size is proportional to the number of proteins assigned to a given term; node color represents the Benjamini Hochberg-corrected P-value corresponding to enrichment of the term. Functionally related ontology terms are labeled and grouped using colored ovals (biological process terms in green; molecular function terms in red; cellular component terms in blue). Organogenesis/morphogenesis and ECM functional groups are enlarged for better visualization of individual terms. (F) Heatmaps summarizing normalized spectral abundance factor-based quantification of proteins associated with the ontology terms highlighted in (E). A corresponding list of proteins and fold changes is presented in Table 3. (G) Rheologic data showing elastic (G) and viscous (G') moduli of engineered mucosa compared to native mucosa and scaffold only. *, $P<0.01$; n.s., non-significant difference; error bars, s.e.m.
Figure 4A:
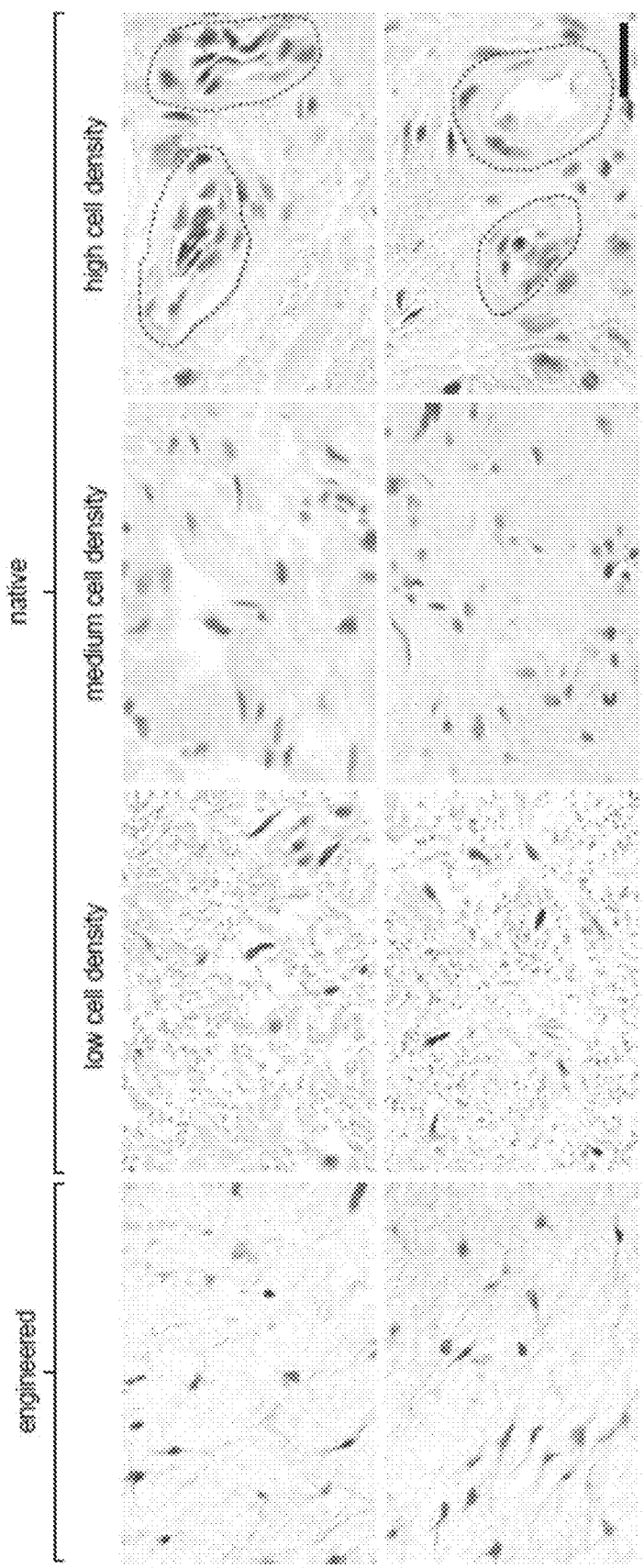
FIGS. 4A-4E demonstrate VFF distribution and contractile function in collagen, type I scaffold. (A) H&E-stained sections showing VFF density in engineered lamina propria (14 day culture of $2\times10^5$ VFF·mL$^{-1}$ collagen, type I) compared to native human VF lamina propria. Whereas cell density was relatively uniform throughout the engineered lamina propria, it varied considerably throughout the native lamina propria, in part due to the presence of high-cell-density vascular structures (black dashed lines). Cell density in the engineered lamina propria was most similar to the medium-cell-density, non-vascular region of the native lamina propria. Scale bar, 40 µm. (B) Bar graph showing overall cell density in engineered and native lamina propria. *, $P<0.01$; error bars, s.e.m. (C) Representative schematics and photographs illustrating progressive scaffold contraction following seeding of $2\times10^5$ VFF·mL$^{-1}$ collagen, type I. Scaffold contraction reached a plateau of ~70% of initial cross-sectional area at 96 hours (h) post-seeding; acellular scaffolds exhibited no contraction. (D) Bar graph showing matrix metalloproteinase (MMP) and tissue inhibitor of metalloproteinase (TIMP) production during 96 h culture of $2\times10^5$ VFF·mL$^{-1}$ collagen, type I. MMP/TIMP concentrations in culture supernatant reflect accumulation during the 24 h period from 24-48 h post-seeding, and again during the 24 h period from 72-96 h post-seeding. Mean values represent pooled samples from 6 independent biological replicates, assayed using a multiplexed protein array. Medium only was used as a negative control. (E) Immunofluorescent images showing VFF expression of the contractile protein α-actin 2 (ACTA2) in the engineered lamina propria at 48- and 96-hours post-seeding. White arrows indicate representative ACTA2+ VFF. Scaffold only is shown as a negative control. Scale bar, 100 µm (main image); 35 µm (inset).
Figure 4B:
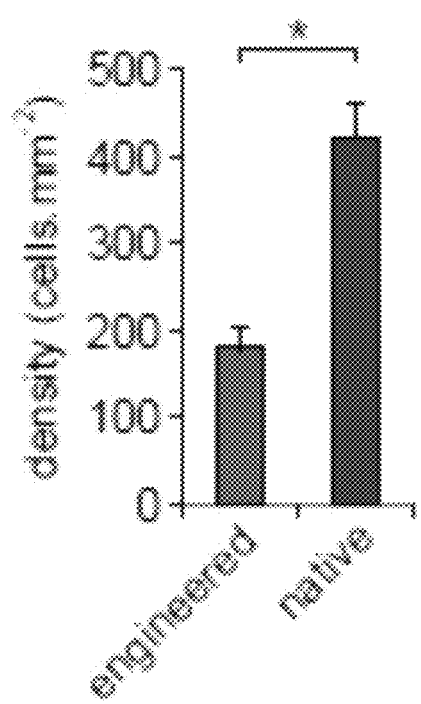
Figure 4C:
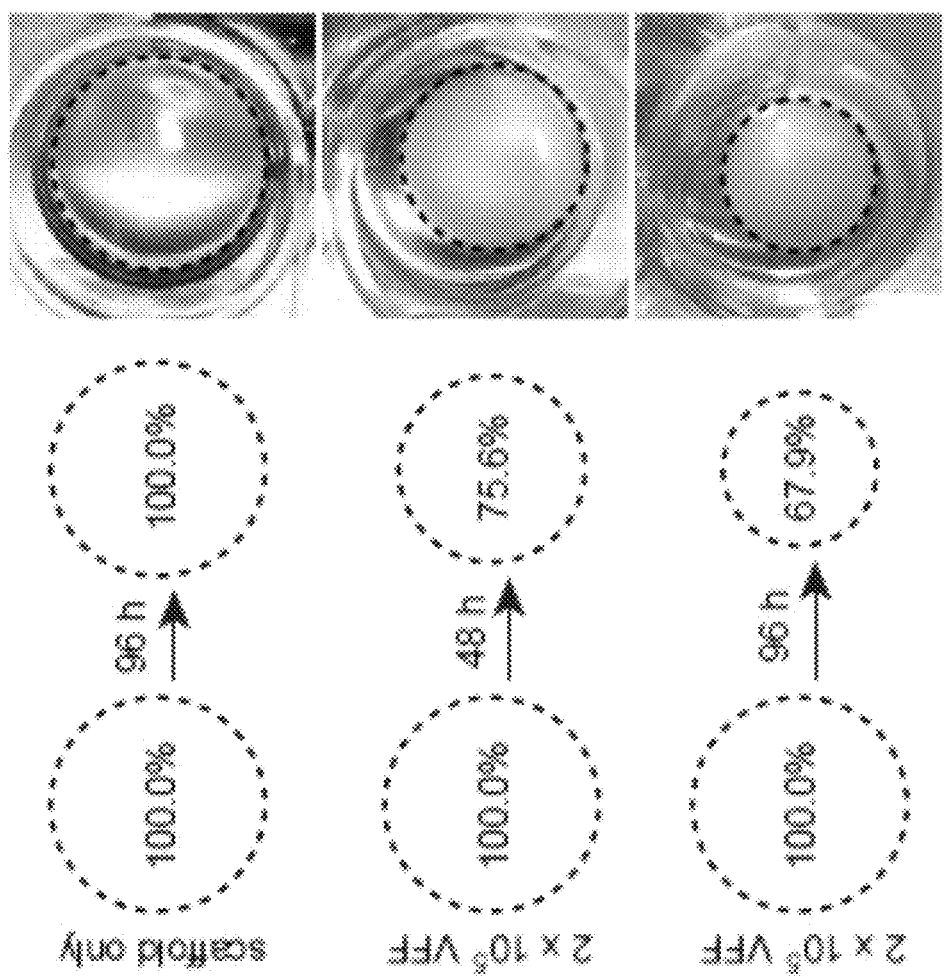
Figure 4D:
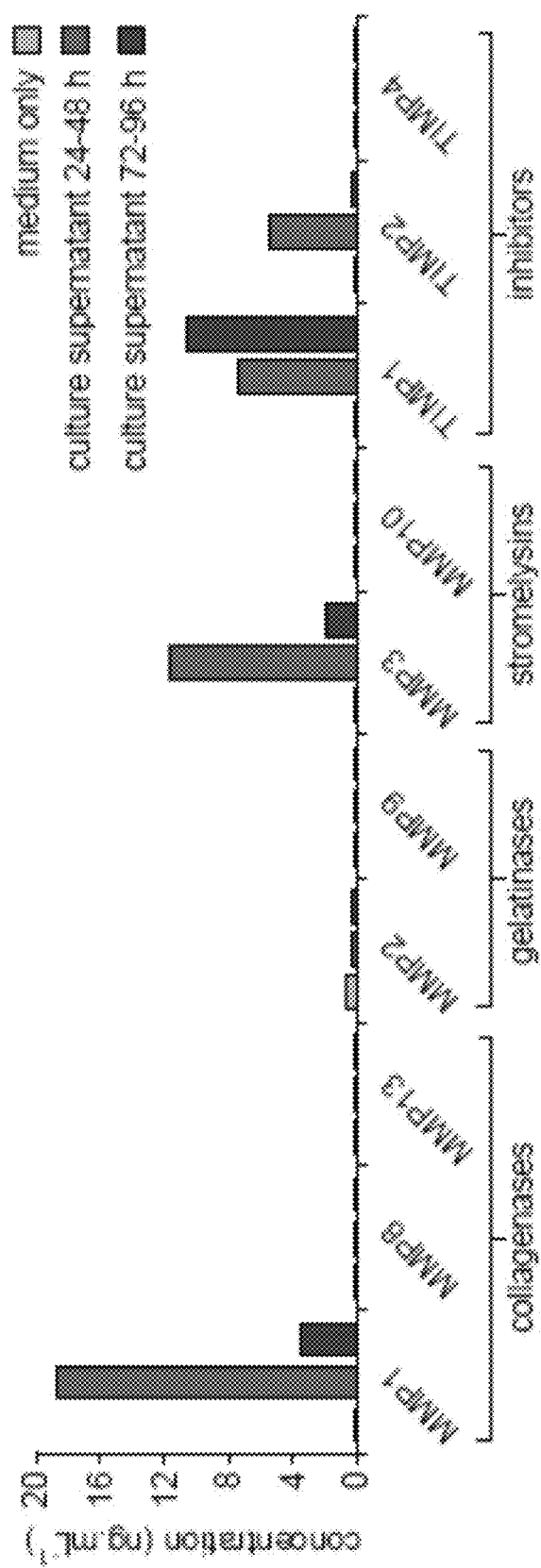
Figure 4E:
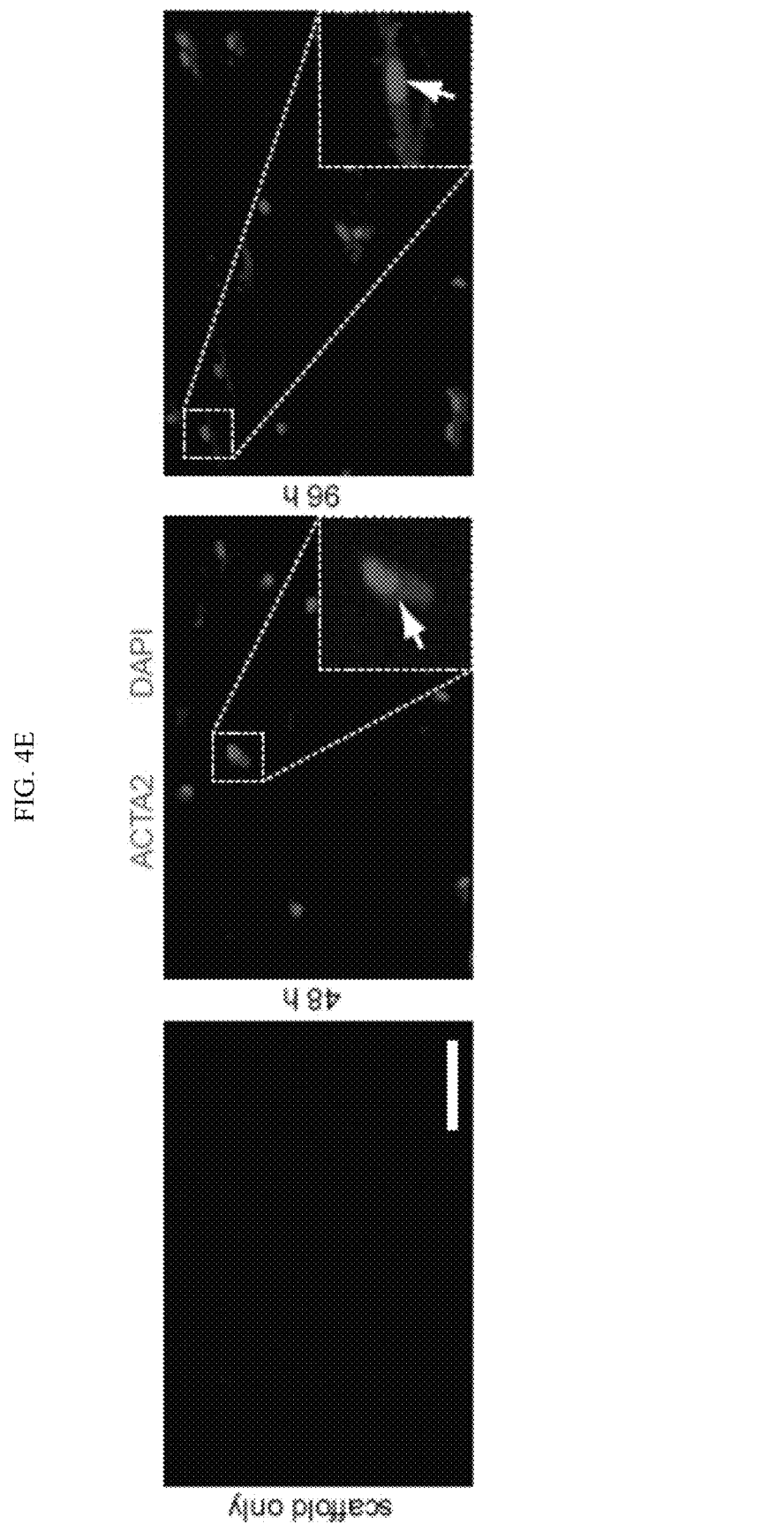

Having successfully identified a viable source of purified human primary cells, we pursued 3D organotypic culture (FIG. 3A) in polymerized collagen, type I, a primary ECM constituent of native human VF mucosa[26]. Initial trials using $2 \times 10^5$ VFF·$mL^{-1}$, without VFE, resulted in a final intrascaffold cell density comparable to the medium-cell-density, non-vascular region of the native lamina propria (FIG. 4a) and ~50% of mean cell density across the entire (vascularized) native lamina propria (P<0.01; FIG. 4B). We further observed moderate scaffold contraction over the first 96 h of culture (FIG. 4C), which corresponded to expression of a subset of matrix metalloproteinase (MMP) and tissue inhibitor of mellatoproteinase (TIMP) enzymes/inhibitors (FIG. 4D), as well as the contractile protein α-actin 2 (also known as α-smooth muscle actin) (FIG. 4E). We maintained this $2 \times 10^5$ VFF·$mL^{-1}$ seeding density in subsequent experiments, followed by VFE seeding at 24 h, media-immersed VFF-VFE coculture for 48 h, and coculture with VFE at the air-liquid interface for a further 8-28 d.

Figures 3B, 3C:
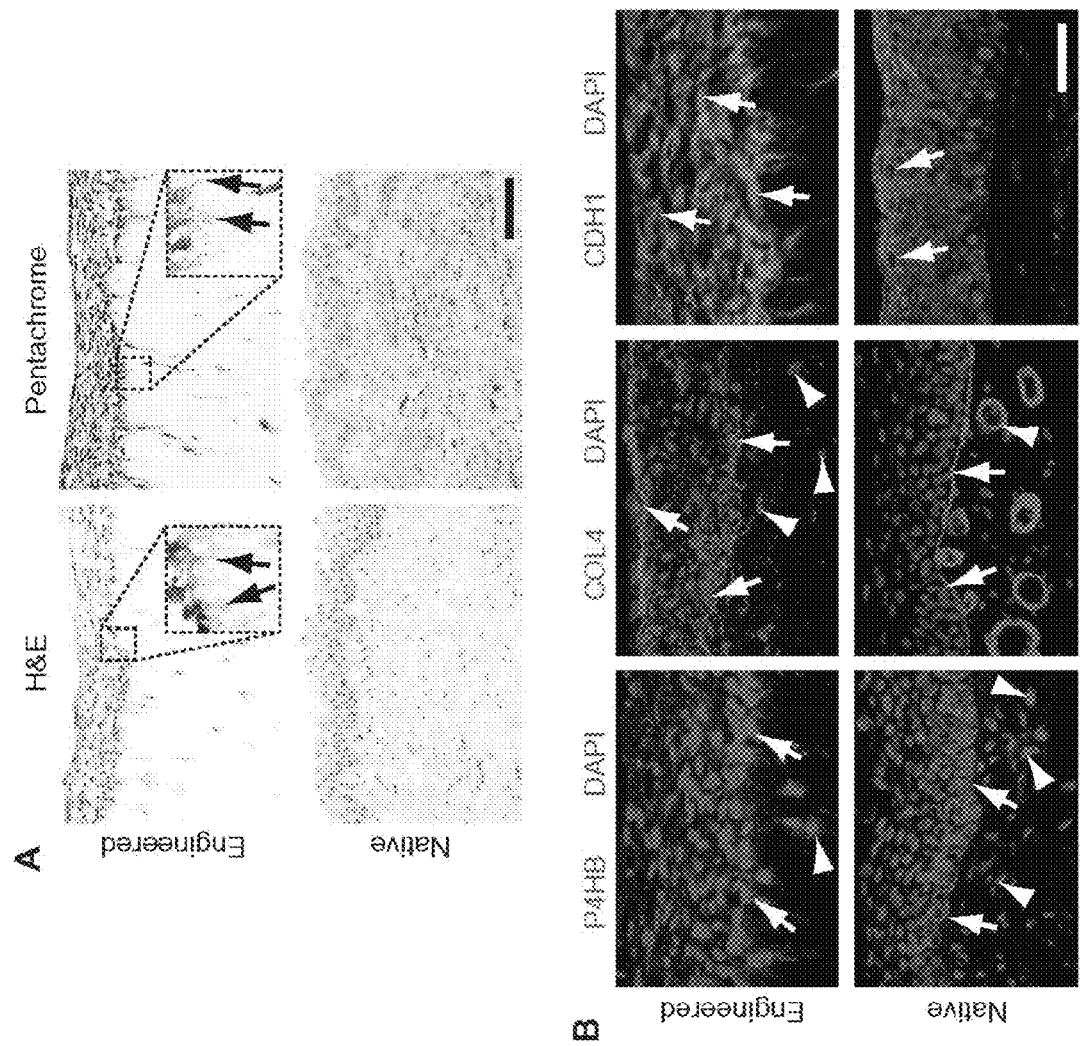
Figure 5B:
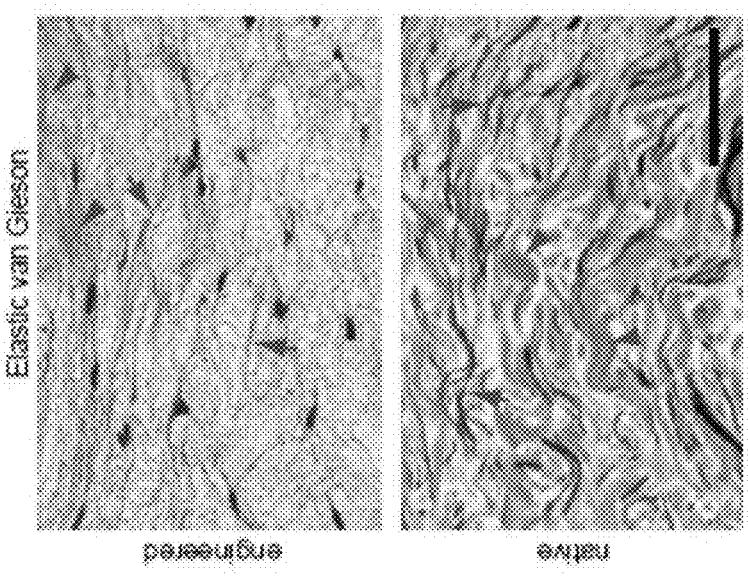
FIGS. 5A-5B present additional histologic characterization of engineered and native human VF lamina propria. (A) Alcian blue-stained sections showing glycosaminoglycan (GAG) distribution (blue) within the extracellular matrix (ECM). Hyaluronic acid (HA) abundance is indicated by the difference in signal intensity between adjacent (5 µm) sections treated with (right panels) and without (left panels) hyaluronidase. GAG and HA abundance were comparable in the engineered and native lamina propria. (B) Elastic van Gieson-stained sections showing elastin (black) and collagen (pink) fiber distribution within the ECM. The engineered ECM contained thin and sparsely distributed fibrous proteins and appeared immature compared to the native ECM. Blue arrows indicate elastin deposits/fibers; blue arrowheads indicate collagen deposits/fibers. Scale bar, 60 µm (A, B).
Figure 5A:
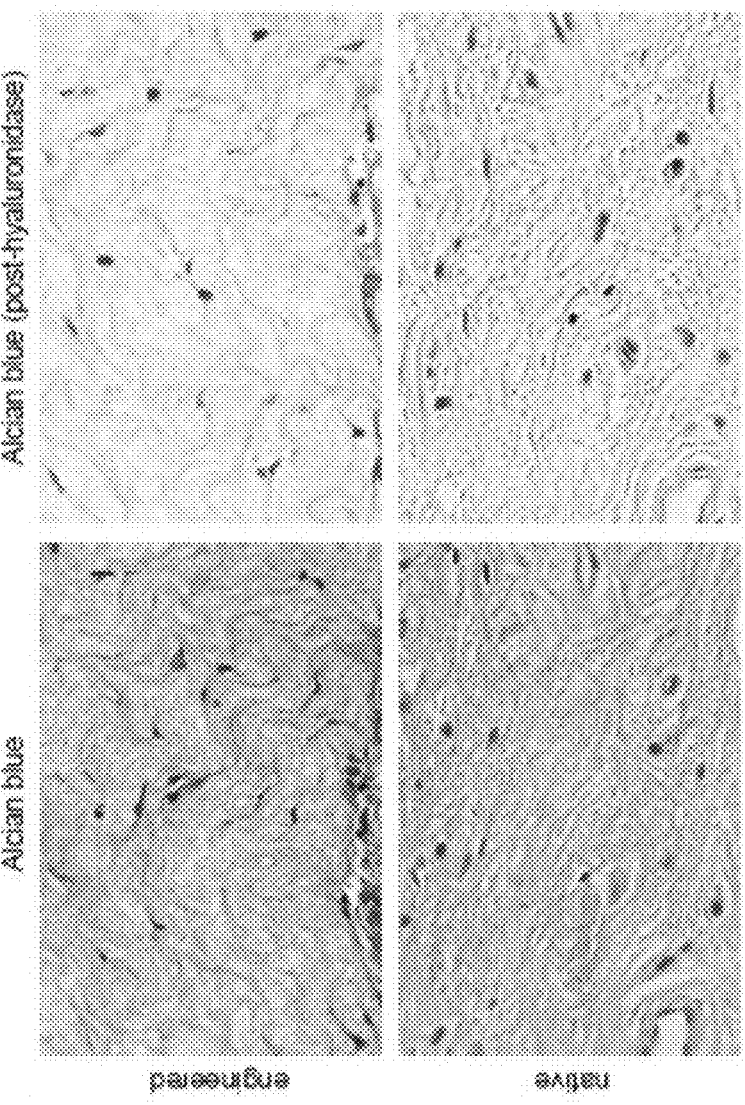

The engineered VF mucosa began to resemble native mucosa after 10-14 d in culture, exhibiting a ~50 μm-thick stratified squamous epithelium and sparsely cell populated lamina propria (FIG. 3B). Basal VFE processes extended into the underlying lamina propria, consistent with epithelial anchoring. The lamina propria contained glycosaminoglycans (GAGs), including the biomechanically important GAG hyaluronic acid[27] (FIG. 5A); however its ECM appeared immature overall, populated by sparsely distributed fibers that did not resemble the sophisticated ECM network of native mucosa (FIG. 5B). P4H-β$^+$ VFF were identified throughout the lamina propria, and P4H-β$^+$ VFE were preferentially localized to the basal epithelium near the basement membrane, as seen in native mucosa (FIG. 3C). Basal VFE also expressed the basement membrane marker collagen, type IV, which formed an emerging barrier-like structure in the subepithelium. Unlike native mucosa, however, a comparable collagen, type IV$^+$ structure was also observed at the luminal epithelial surface. The majority of VFE were E-cadherin$^+$, suggesting early establishment of intercellular junctional complexes that approximated those seen in native VF mucosa.

Figure 3D:
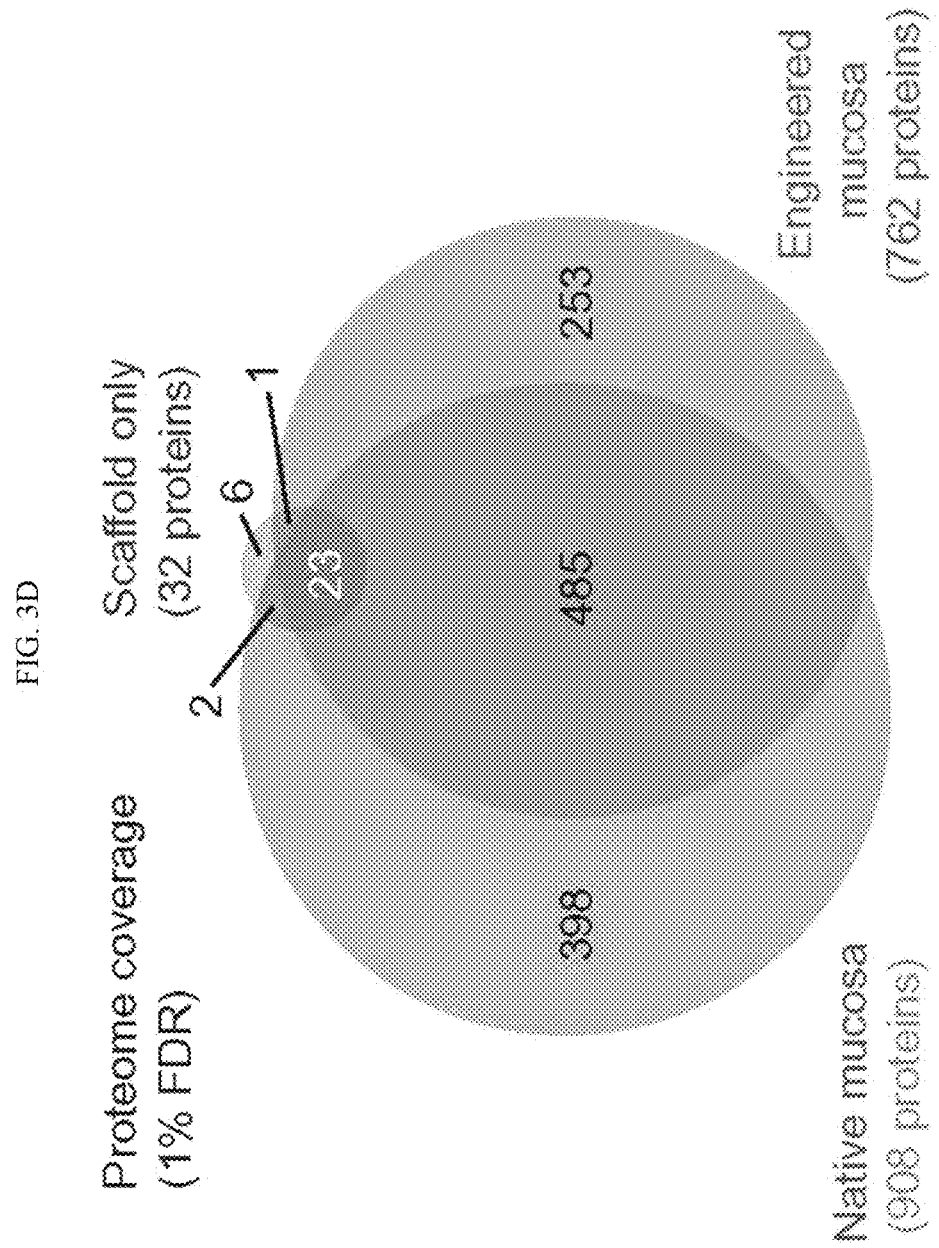
Figure 3E:
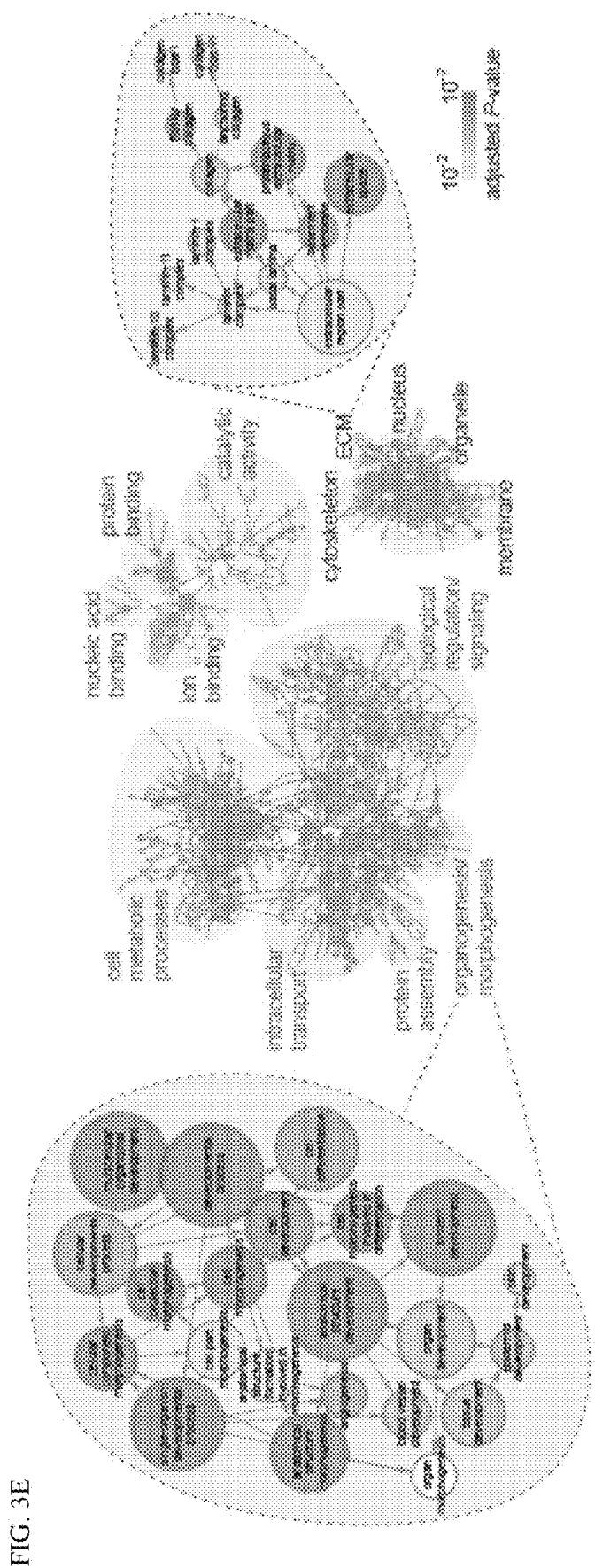
Figure 3F:
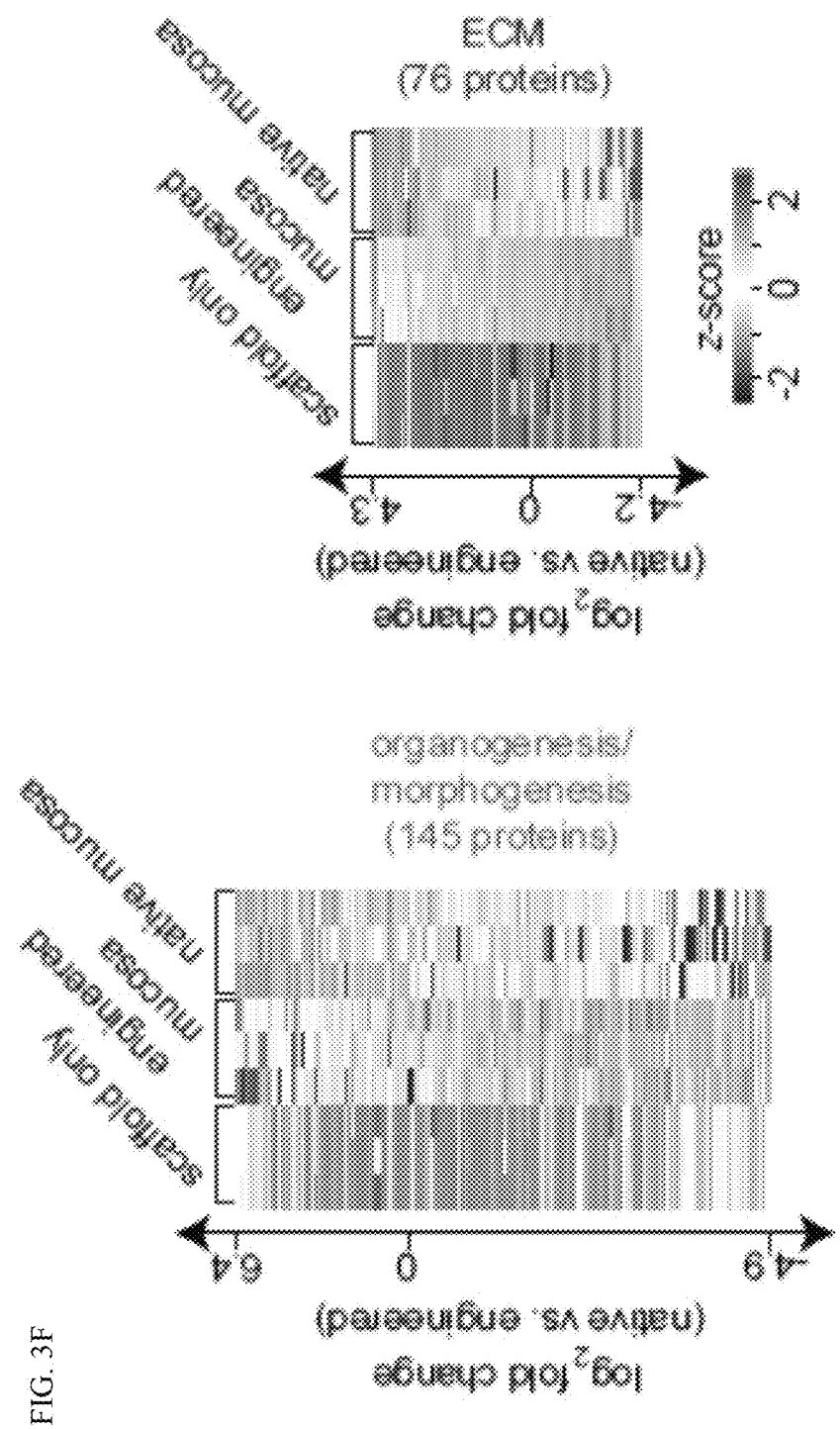
Figure 3G:
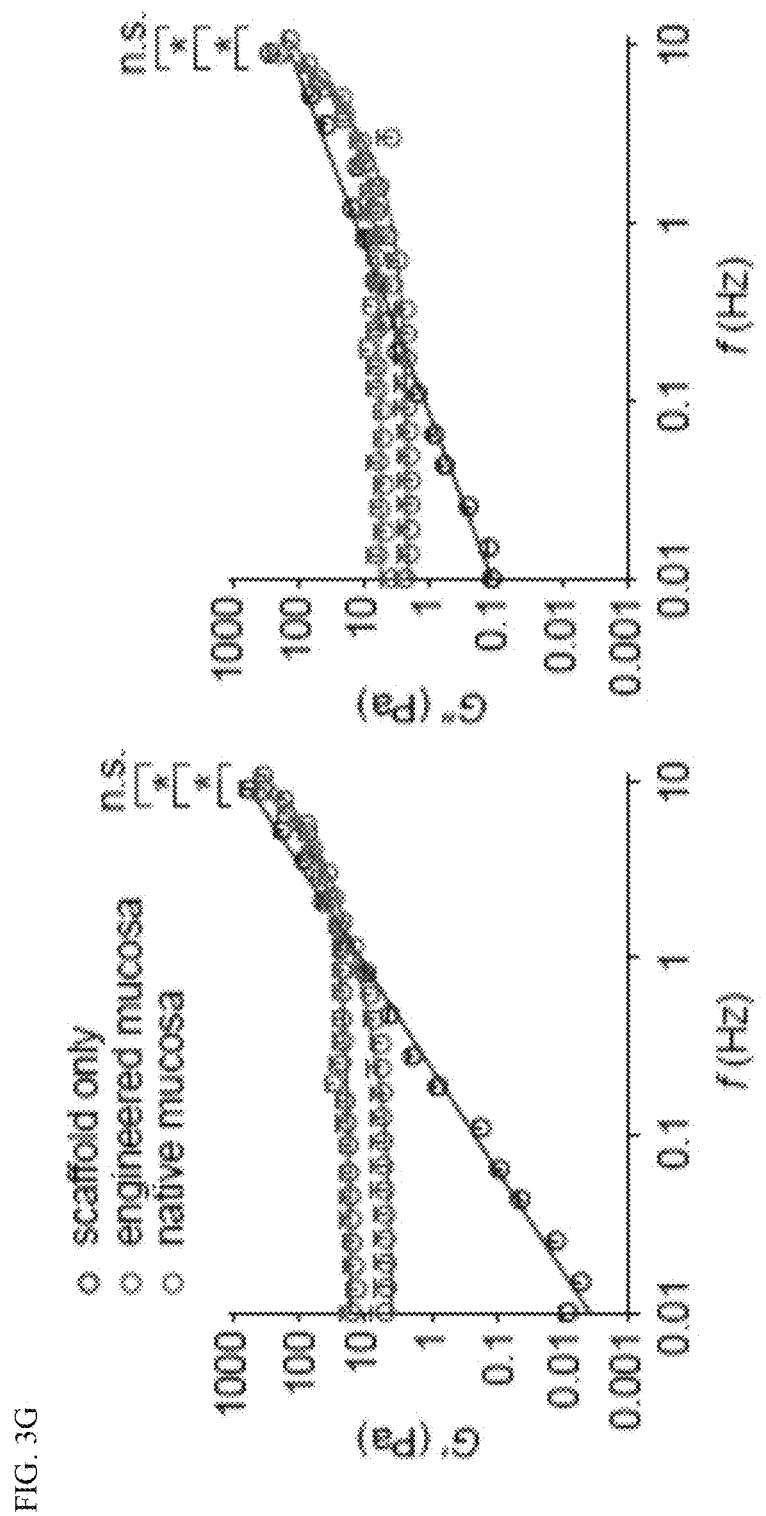

To further characterize the biological complexity of the engineered VF mucosa, we conducted discovery proteomic analysis using liquid chromatography-tandem mass spectrometry (LC-MS/MS). Using a 1% false discovery rate, we identified 762 unique proteins in the engineered mucosa, compared with 908 in the native mucosa and 32 in the collagen, type I-based scaffold (FIG. 3D; Table 1). Gene ontology-based enrichment analysis of the engineered VF mucosa proteome, as compared to the full human protein database (Uniprot), revealed a wide complement of functional protein sets (ontology terms) associated with various metabolic, catalytic, transport, binding and signaling processes; spanning an array of subcellular and extracellular locations (FIG. 3E; Table 2). We identified organogenesis/morphogenesis-specific ontology term enrichment, consistent with successful organotypic culture; as well as ECM terms indicative of protein complexes and anatomic substructures that are characteristic of native VF mucosa, such as the basal lamina, anchoring collagen and fibrillar collagen. Follow-up normalized spectral abundance factor (NSAF)-based quantitative analysis[28] showed strong correspondence between the engineered and native mucosae (FIG. 3F; Table 3), implying that most of the ECM subproteome in the engineered mucosa is attributable to new protein synthesis by VFF and VFE, rather than the original scaffold. We identified ECM proteins and glycoconjugates that are considered critical to the biomechanical capacity of native VF mucosa for self-sustained physiologic vibration[26, 29-32], including: multiple collagen isoforms; the elastin conduit fibrillin 1 and elastin microfibril interface-located protein (EMILIN) 1; the small leucine-rich repeat proteoglycans decorin, lumican and biglycan; and the glycoproteins fibronectin, fibulin 1 and tenascin X. These observations suggest that while the engineered lamina propria appeared immature on histologic analysis, its developing ECM is populated by a core set of protein constituents with the potential to support vibratory function. This conclusion was further supported by rheologic experiments showing that the viscoelastic profile of the engineered mucosa was more similar to that of the native mucosa (P=0.51 and 0.88 for elastic [G'] and viscous [G"] moduli, respectively; FIG. 3G) than that of the scaffold (P<0.01 for both G' and G").

Quantitative Proteomic Analysis of Engineered VF Mucosa Compared to its Isolated Subcomponents.

Figure 6D:
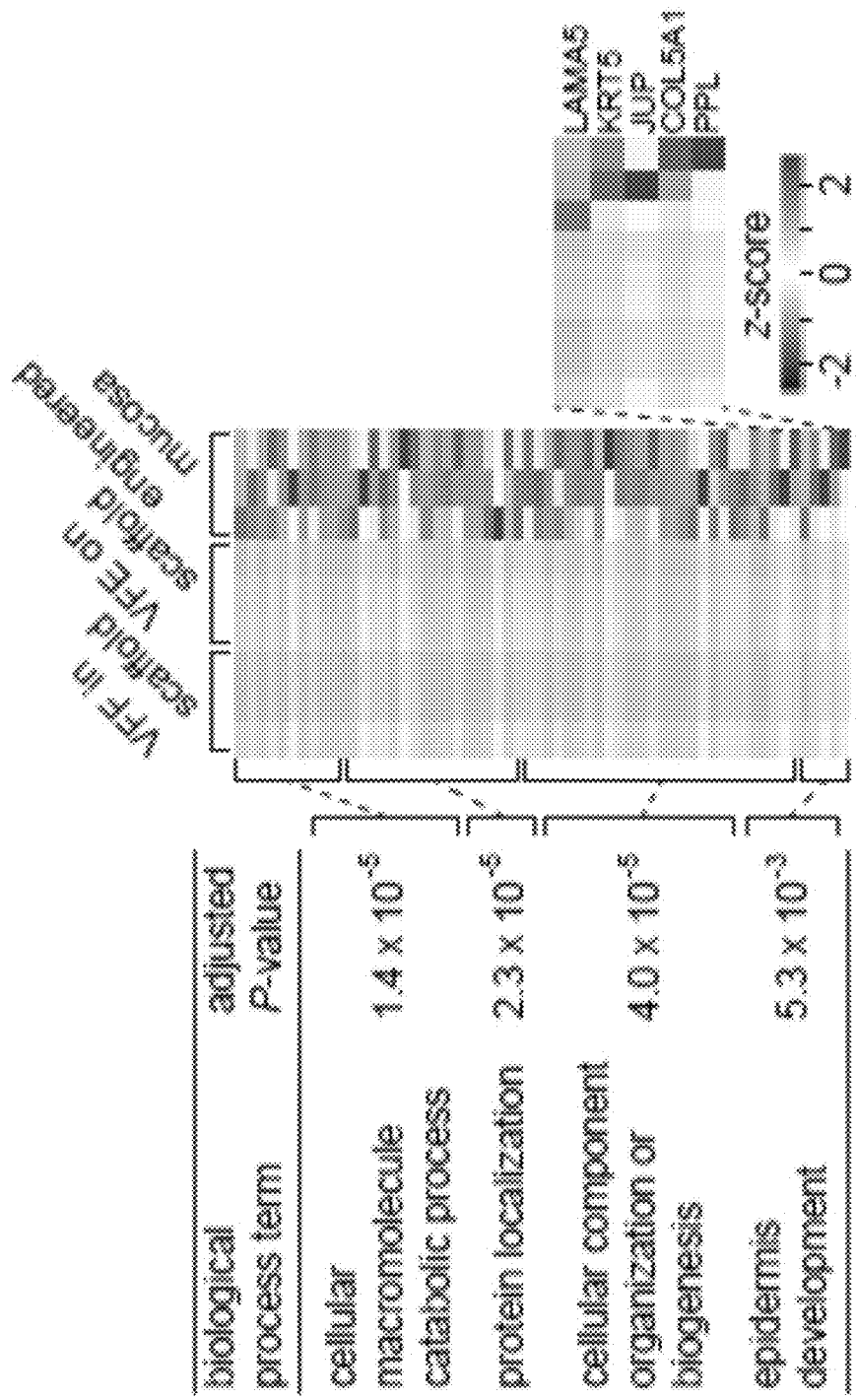
Figure 7A:
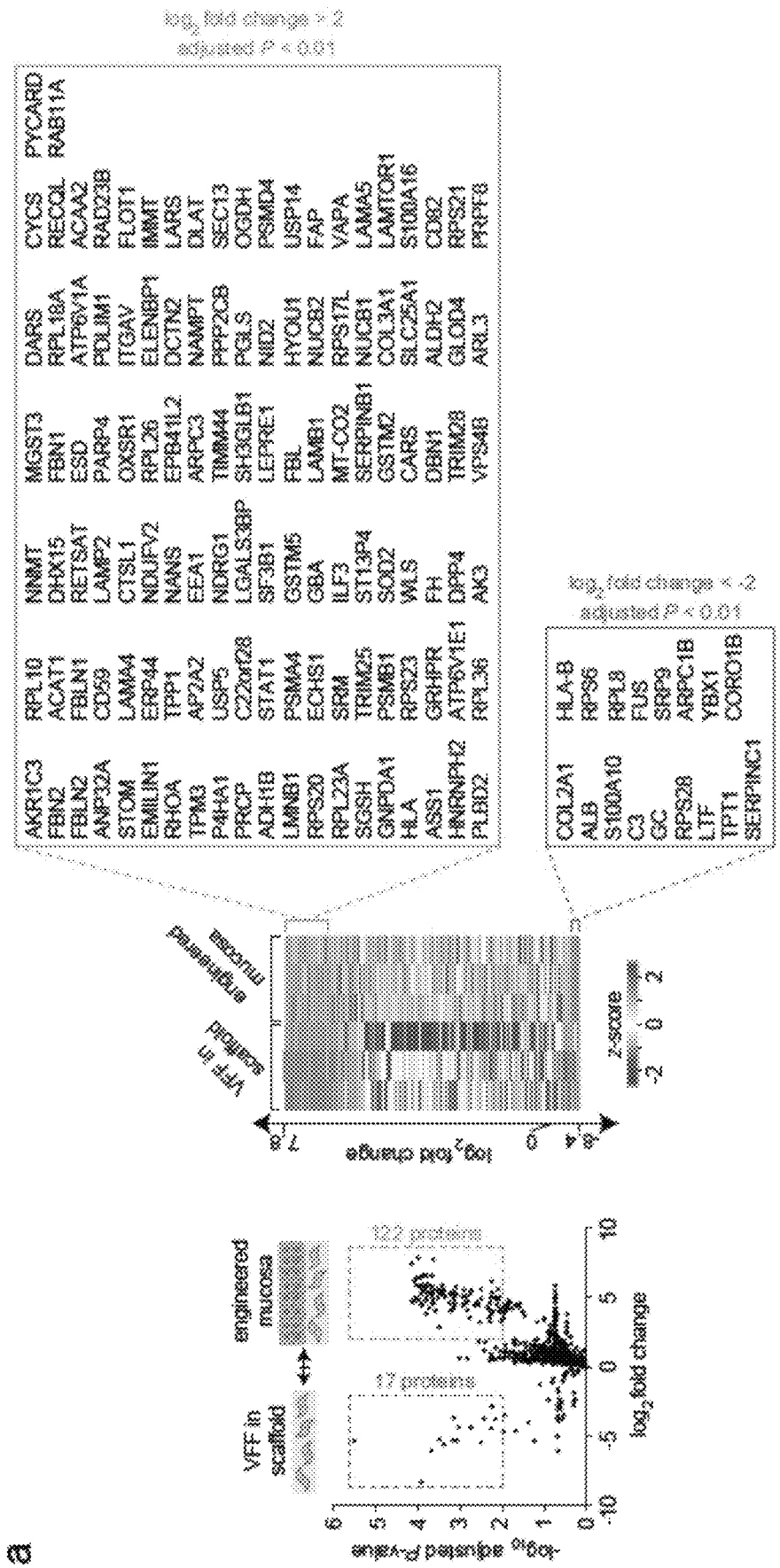
FIGS. 7A-7B present additional quantitative proteomic analysis of engineered VF mucosa compared to its isolated subcomponents. (A) Volcano plot and heatmap showing normalized spectral abundance factor-based protein quantification in engineered mucosa versus VFF in scaffold. The cyan dashed rectangle (Volcano plot) and square bracket (heatmap) denote cutoff criteria for protein overrepresentation in engineered mucosa compared to VFF in scaffold (fold change >4; Benjamini Hochberg-adjusted P<0.01); the magenta dashed rectangle (Volcano plot) and square bracket (heatmap) denote cutoff criteria for protein overrepresentation in VFF in scaffold compared to engineered mucosa (fold change <−4; Benjamini Hochberg-adjusted P<0.01). (B) Parallel analysis of engineered mucosa versus VFE on scaffold. The cyan dashed rectangle (Volcano plot) and square bracket (heatmap) denote cutoff criteria for protein overrepresentation in engineered mucosa compared to VFE on scaffold (fold change >4; Benjamini Hochberg-adjusted P<0.01); the magenta dashed rectangle (Volcano plot) and square bracket (heatmap) denote cutoff criteria for protein overrepresentation in VFE on scaffold compared to engineered mucosa (fold change <−4; Benjamini Hochberg-adjusted P<0.01). A complete list of overrepresented proteins with corresponding fold changes and P-values is presented in Table 4.
Figure 7B:
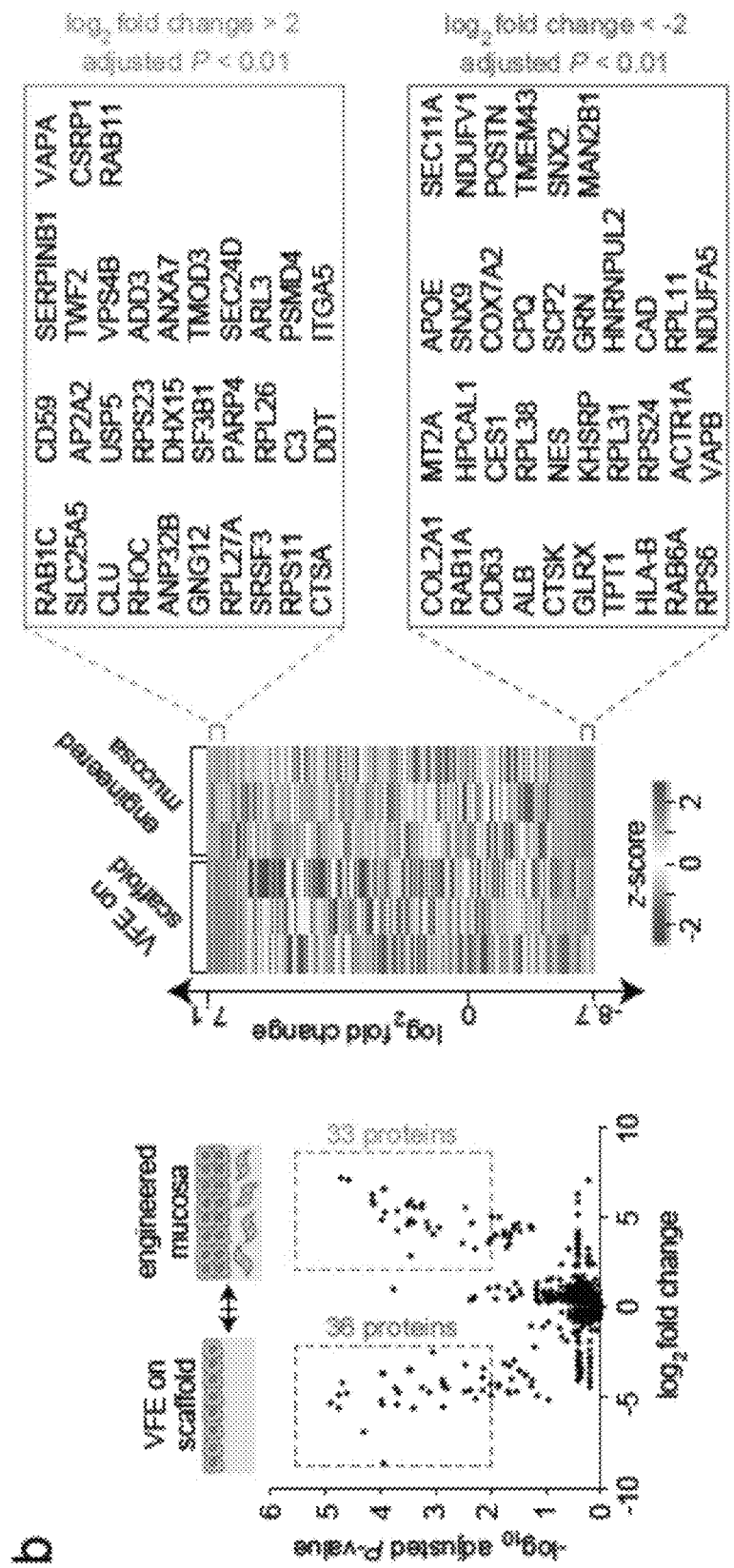

We pursued further quantitative proteomic analyses to identify protein complexes and functionality that were unique to the engineered VF mucosa, compared to its isolated subcomponents: VFF in collagen, type I scaffold and VFE on collagen, type I scaffold (FIG. 6A). Proteome coverage and overlap were generally comparable, with 528 proteins common to all three conditions and 59 proteins unique to the engineered mucosa (FIG. 6B; Table 1). NSAF-based analysis showed that the majority of differentially abundant proteins were overrepresented in engineered VF mucosa, as compared to the isolated subcomponents (fold change >4; adjusted P<0.01; FIG. 6C), suggesting upregulation of a specific protein set due to VFF-VFE synergy in organotypic culture. Subsequent pairwise comparisons indicated that the engineered mucosa proteome was most similar to VFE on scaffold and least similar to VFF in scaffold (69 versus 139 differentially abundant proteins, respectively; FIG. 7; Table 4), consistent with VFE being the predominant cell type in the engineered mucosa.

Next, we performed functional enrichment analysis of the protein set that was either exclusively identified or quantitatively overrepresented in engineered VF mucosa compared to both VFF in scaffold and VFE on scaffold. The most highly represented biological process ontology terms (adjusted $P<4\times10^{-5}$) indicated that the engineered mucosa was uniquely engaged in macromolecule catabolism, protein localization, and cellular component organization or biogenesis (FIG. 6D), suggesting dynamic structural assembly. Further evaluation of the deep ontology output revealed significant enrichment of additional terms relevant to mucosal assembly: cell-substrate junction assembly (adjusted $P=3\times10^{-3}$), epidermis development (adjusted $P=5.3\times10^{-3}$), adherens junction organization (adjusted $P=7.4\times10^{-3}$) and cell junction assembly (adjusted $P=8.7\times10^{-3}$) (Table 5). Enrichment of these ontology terms was driven by a common protein set that was significantly overrepresented in engineered VF mucosa compared to the other experimental conditions, consisting of the basal lamina constituent laminin 5, the basal epithelial cell marker keratin 5, the desmosome constituents junction plakoglobin (also known as γ-catenin) and periplakin, as well as collagen, type V.

Emergence of Immature Barrier Function in Engineered VF Mucosa.

Figure 6E:
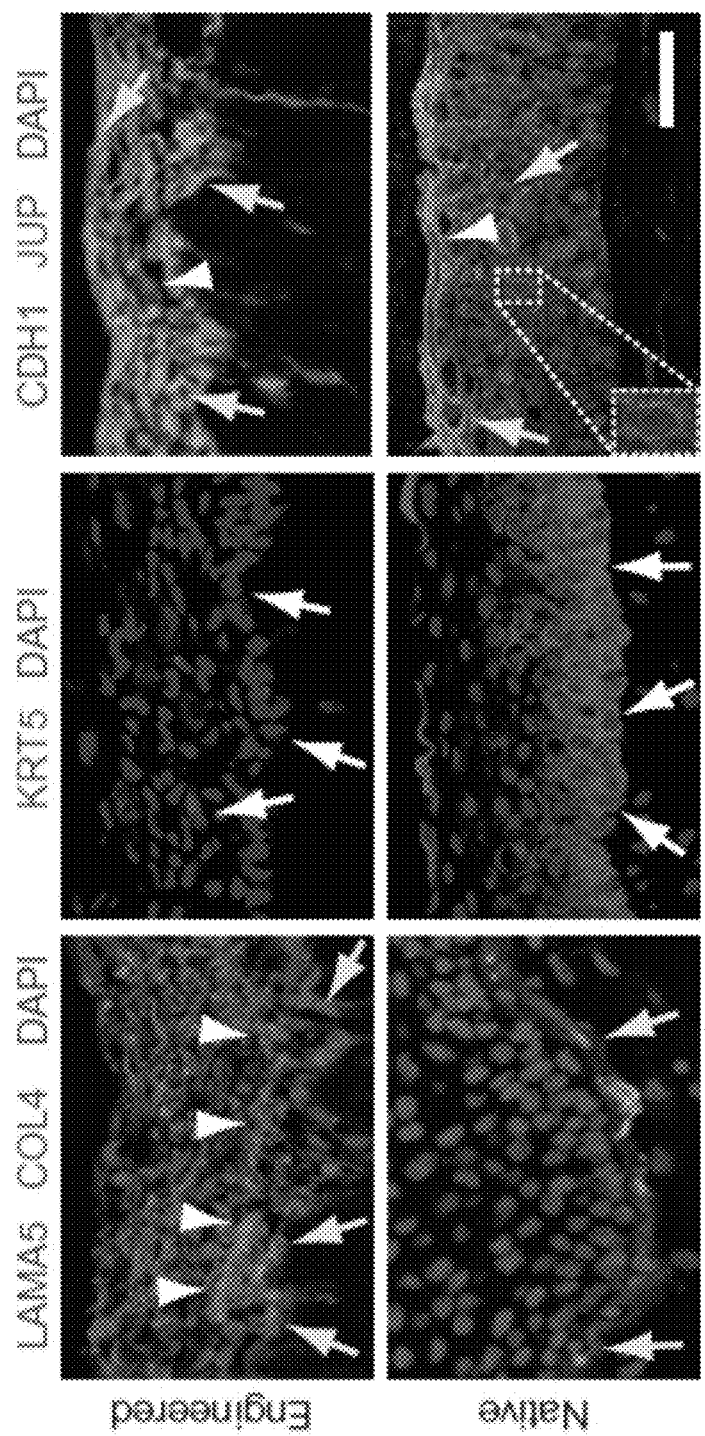

As our histologic and proteomic data suggested the emergence of basement membrane structures and epithelial junctional complexes under organotypic culture conditions, we performed follow-up immunovalidation of laminin 5, keratin 5 and junction plakoglobin expression in engineered VF mucosa, and compared the distribution of these proteins to native VF mucosa. Immunohistochemistry confirmed that each of these targets was expressed in the engineered VF epithelium but lacked the region-specific localization of native mucosa (FIG. 6E). Laminin 5 was expressed by basal and suprabasal VFE and showed intracellular colocalization with its functional partner collagen type IV, but these proteins did not form mature basal laminae as seen in native tissue. Keratin 5$^+$ VFE were scattered throughout the engineered epithelium but were not preferentially localized to the basal region. Junction plakoglobin was expressed by the majority of VFE and generally colocalized with its binding partner e-cadherin, but these proteins did not exhibit the intercellular distribution pattern of mature junctional complexes within native VF epithelium.

Figure 6F:
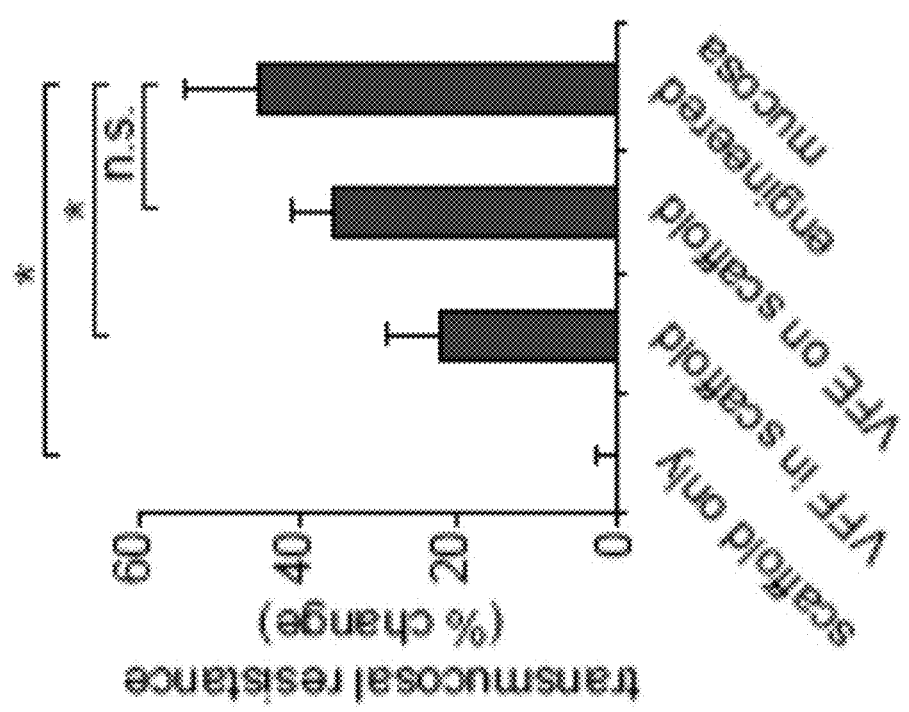

To further evaluate physiologic barrier function in the engineered mucosa, we conducted transmucosal electrical resistance experiments. These experiments required reducing fibroblast seeding density by ~3.5-fold (to $5.6\times10^4$ VFF·mL$^{-1}$) to reduce scaffold contraction and eliminate detachment from the insert wall. Under comparable culture conditions, the engineered mucosa had significantly greater resistance than scaffold only and VFF in scaffold (P<0.01), but showed no significant difference compared to VFE on scaffold (P=0.06; FIG. 6F), corroborating our immunohistochemical findings and confirming that while emerging basement membrane and epithelial junctional complexes were present, physiologic barrier function remained immature.

Ex Vivo Physiologic Function of Engineered VF Mucosa.

Figure 8A:
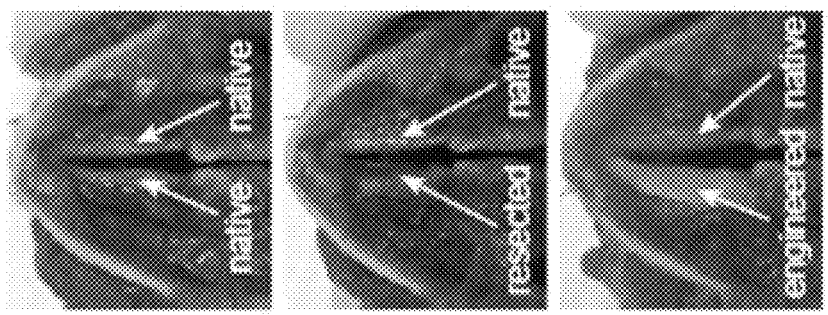
FIGS. 8A-8H demonstrate ex vivo physiologic performance of engineered VF mucosa in a large animal excised larynx setup. (A) Sequential photographs of a canine larynx under native conditions (upper panel), following unilateral VF mucosa resection (center panel), and following unilateral placement of engineered VF mucosa (lower panel). (B) Schematic illustrating the experimental conditions shown in (A) in coronal orientation in the excised larynx setup. HSDI, high-speed digital imaging; TA, thyroarytenoid. (C) Aerodynamic data showing phonation threshold pressure ($P_{th}$), subglottal pressure ($P_s$) and flow (U) relationships (i.e., glottal resistance [$R_g$] plots), aerodynamic input power ($P_{aero}$) and radiated acoustic output power ($P_{ac}$) relationships (i.e., glottal efficiency [$E_g$] plots). VF mucosa resection eliminated vibratory capacity below $P_s$=5 kPa (preventing $R_g$ and $E_g$ measurement under this condition), whereas the engineered mucosa restored function with comparable $R_g$ and $E_g$ to native mucosa. (D) HSDI-based glottal area analysis showing restoration of waveform morphology and area magnitude with placement of engineered VF mucosa. The upper panels represent sequential resection and engineered mucosa replacement within a single larynx. Grey arrows indicate the beginning, midpoint and endpoint of a single 5.8-ms-duration vibratory cycle. The yellow dashed ellipse indicates maximum glottal area. The yellow horizontal dashed line indicates the midmembranous plane used for subsequent kymographic analyses in (E, F). Scale bar, 3 mm. (E) Representative kymograms from the larynx presented in (D) showing restoration of typical vibratory physiology (lateral [left-right] phase similarity, vertical phase difference, mucosal wave excursion) following engineered VF mucosa replacement. Sinusoidal curve fitting ($R^2$>0.98) to the upper and lower VF margins (UM; LM) is shown for the native and engineered conditions. Red dashed lines indicate open and closed phases of a single vibratory cycle. Yellow dashed lines indicate UM and LM. $f_0$, fundamental frequency. (F) Analysis of lateral and vertical phase differences for all larynges and conditions, showing comparable vibratory physiology for native and engineered VF mucosae. #, contralateral VF mucosa condition used to calculate lateral phase difference; !, VF mucosa condition contralateral to that for which vertical phase difference is calculated. (G) Representative acoustic data showing time-domain signals (upper panels), narrowband spectrograms (center panels) and phase plots (lower panels). VF resection resulted in signal aperiodicity, loss of harmonic structure and deterministic chaos; the engineered mucosa restored signal periodicity and measurable $f_0$, harmonic structure and a closed phase trajectory. (H) Summary of qualitative acoustic signal typing for all larynges and conditions. Native and engineered VF mucosae generated near-periodic type 1 signals, whereas mucosal resection resulted in predominantly stochastic type 4 signals. Data from the same larynx are plotted in the same color (C, D, F, H); *, P<0.01 (C, D, H); n.s., non-significant difference (C, D, F, H). Data from a parallel experiment evaluating the ex vivo physiologic performance of human oral mucosa are presented in FIGS. 10A-10G.

Given the favorable morphologic and histologic appearance of engineered VF mucosa compared to native tissue, we scaled-up our engineering approach to create human-sized tissues, and evaluated their physiologic performance in a large animal excised larynx setup. This ex vivo approach holds key methodological advantages over in vivo techniques for studying VF physiology, due to greater control of anatomic, postural and aerodynamic input parameters, direct visual exposure of the VFs during vibration, and more precise multichannel measurement. We used canine larynges based on their anatomic similarity to human specimens and precedence in excised larynx studies[33-35] and collected sequential datasets from each larynx: (i) with bilateral native VFs intact, (ii) following unilateral VF mucosa resection to impair physiologic function, and (iii) following unilateral placement of engineered VF mucosa in an attempt to restore function (FIG. 8A).

Figure 8B:
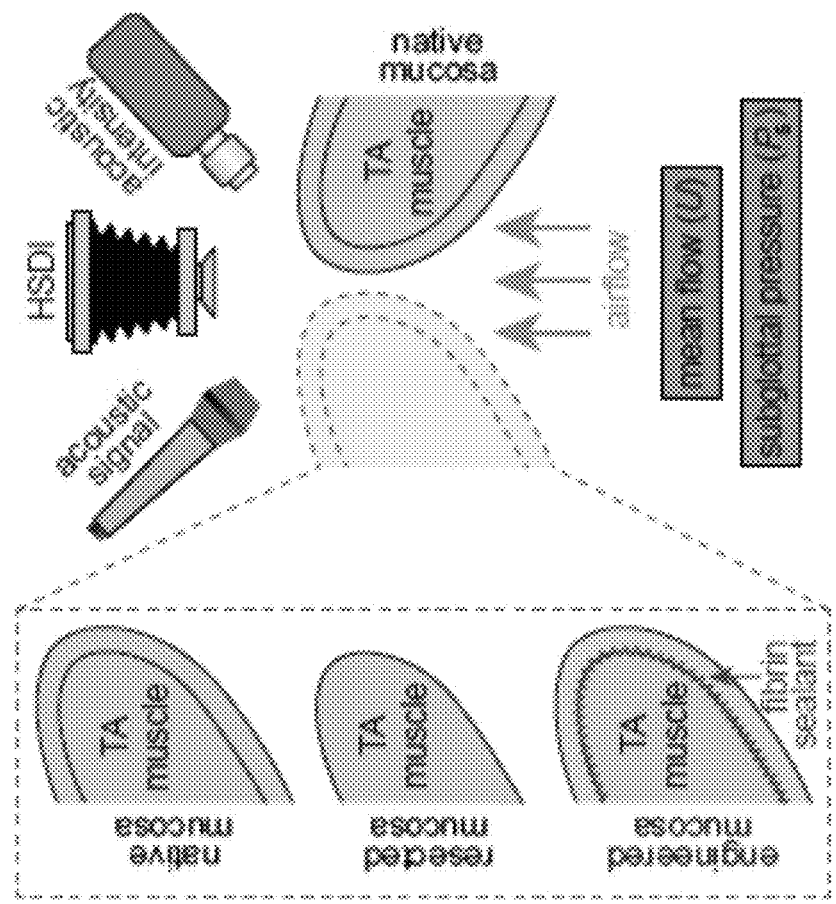
Figure 8C:
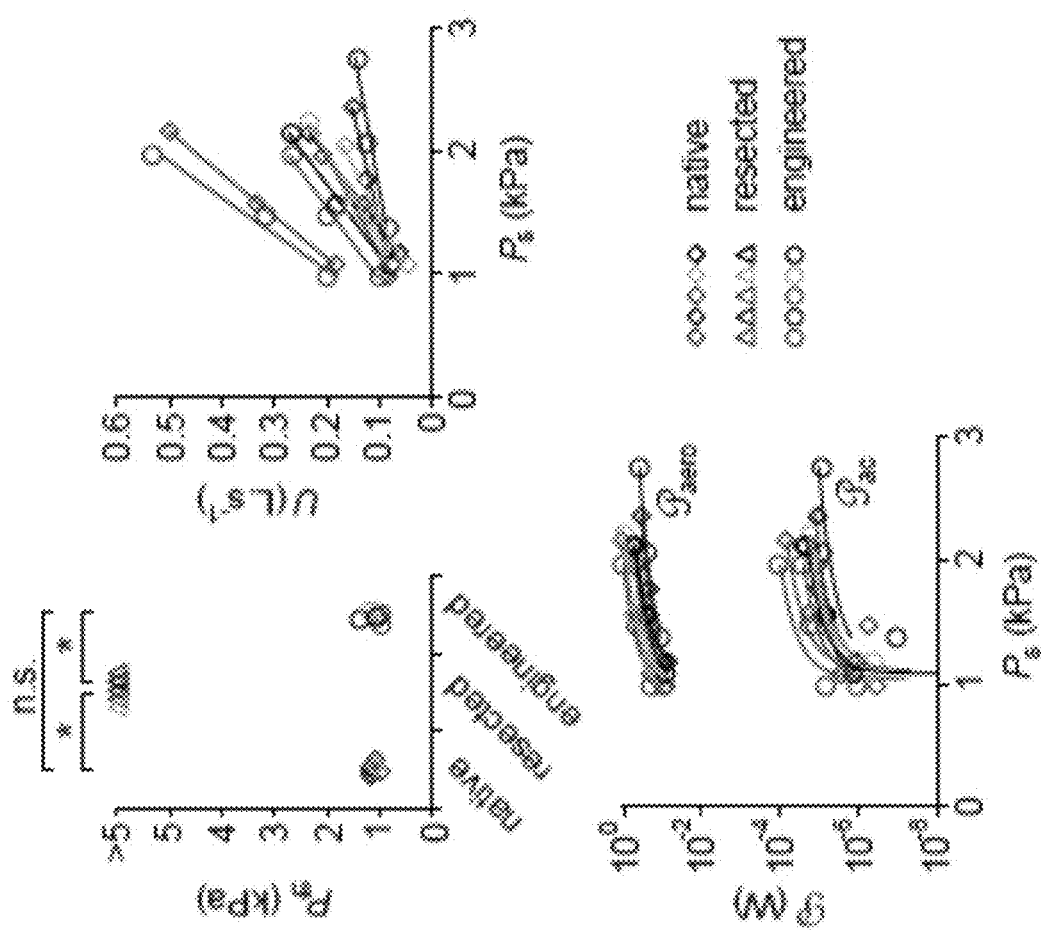

We collected a complete array of aerodynamic, high-speed digital imaging (HSDI) and acoustic data (FIG. 8B). Following arytenoid adduction, we delivered humidified air at gradually increasing subglottal pressures ($P_s$) to initiate flow (U)-induced VF vibration. Phonation threshold pressure ($P_{th}$), the minimum $P_s$ required to initiate vibration, was ~1 kPa in the native condition, but was eliminated at $P_s$ up to 5 kPa following VF mucosa resection (FIG. 8C). Placement of engineered mucosa restored vibration with comparable $P_{th}$ to the native condition (P=0.80). Native and engineered mucosae exhibited similar within-larynx glottal resistance ($R_g$), aerodynamic input power ($P_{aero}$), radiated acoustic power ($P_{ac}$), and glottal efficiency ($E_g$) (FIG. 8C). $P_{aero}$ to $P_{ac}$ loss resulted in $E_g$ values of ~$10^{-2}$-$10^{-4}$% across all runs, consistent with previously reported data from excised larynx experiments in the absence of a vocal tract[34].

Figure 8D:
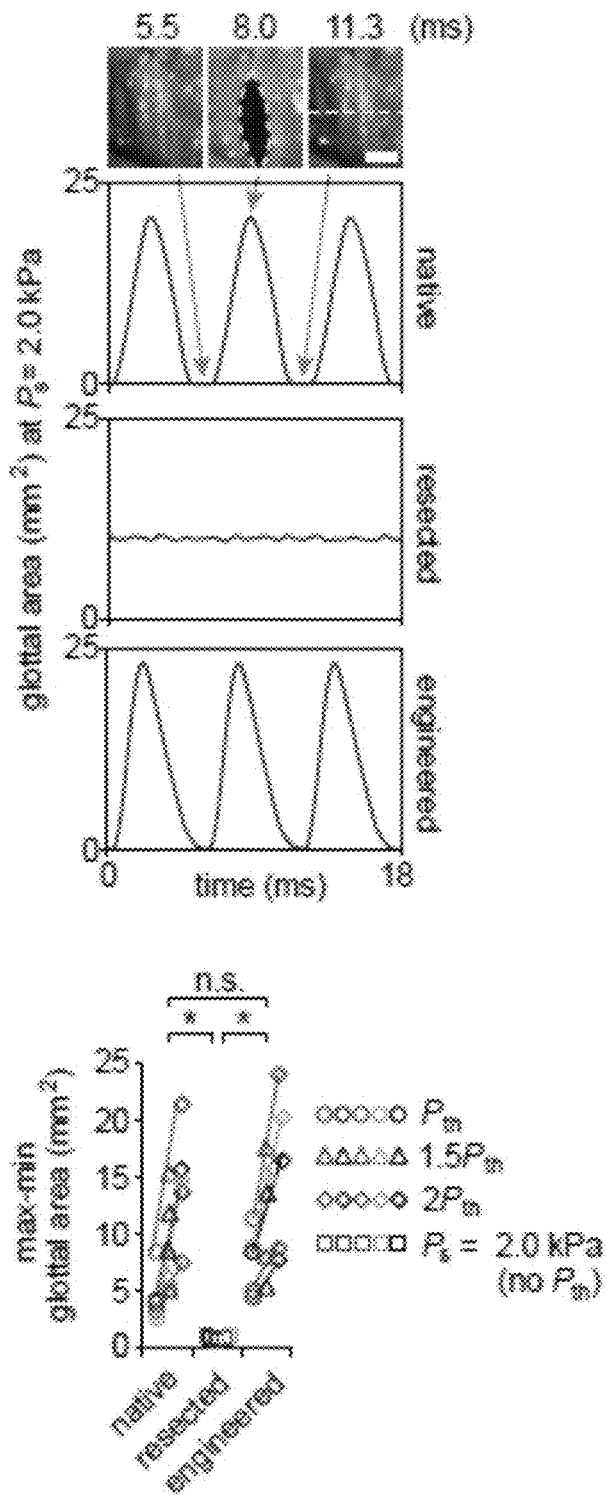
Figure 8E:
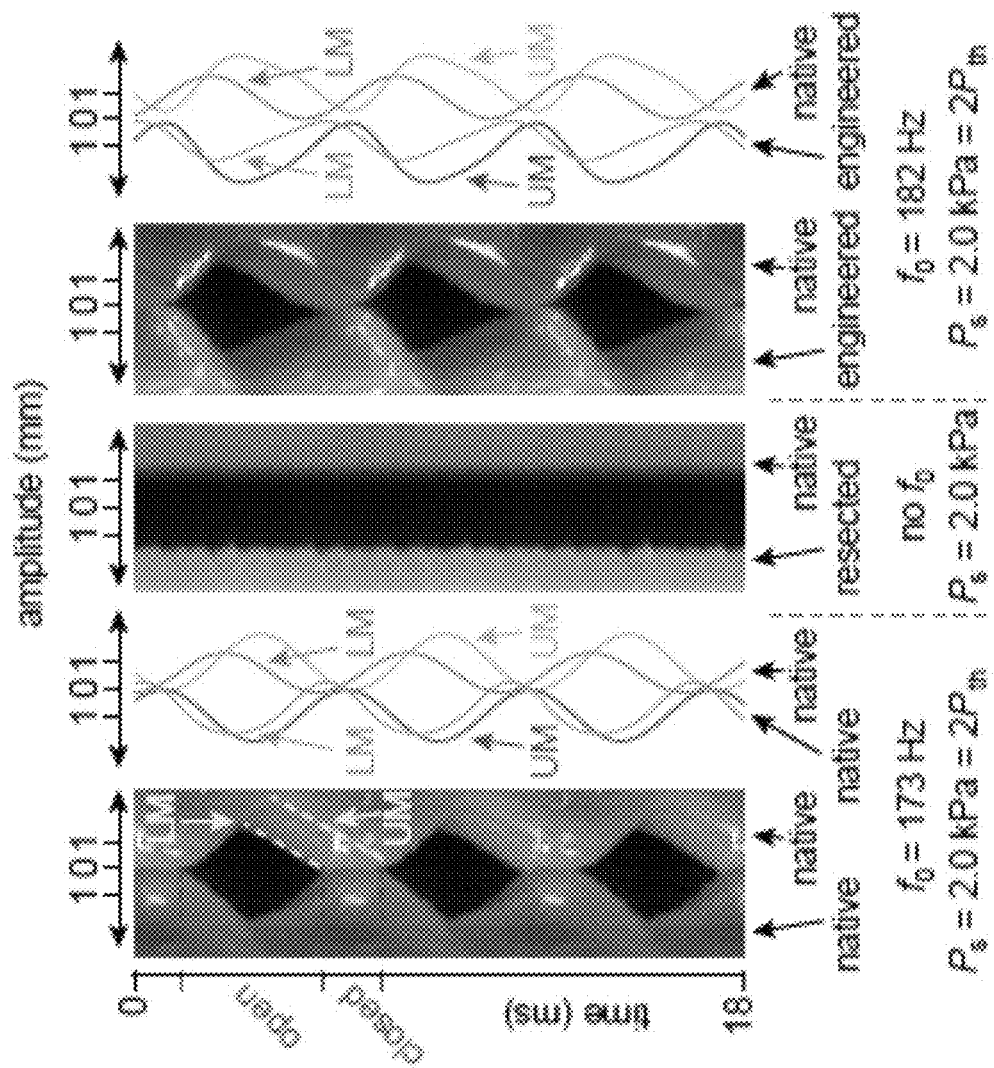
Figure 8F:
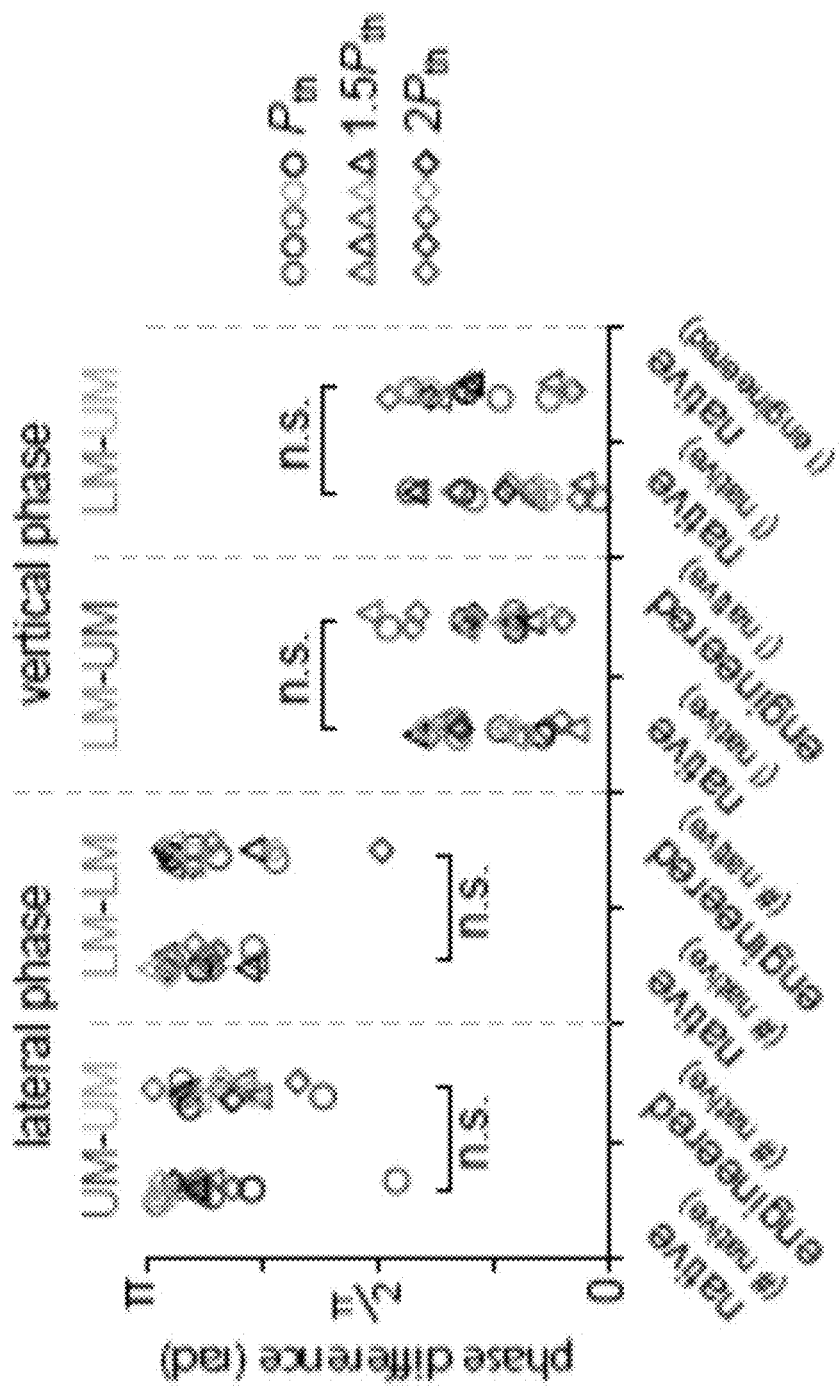
Figure 8G:
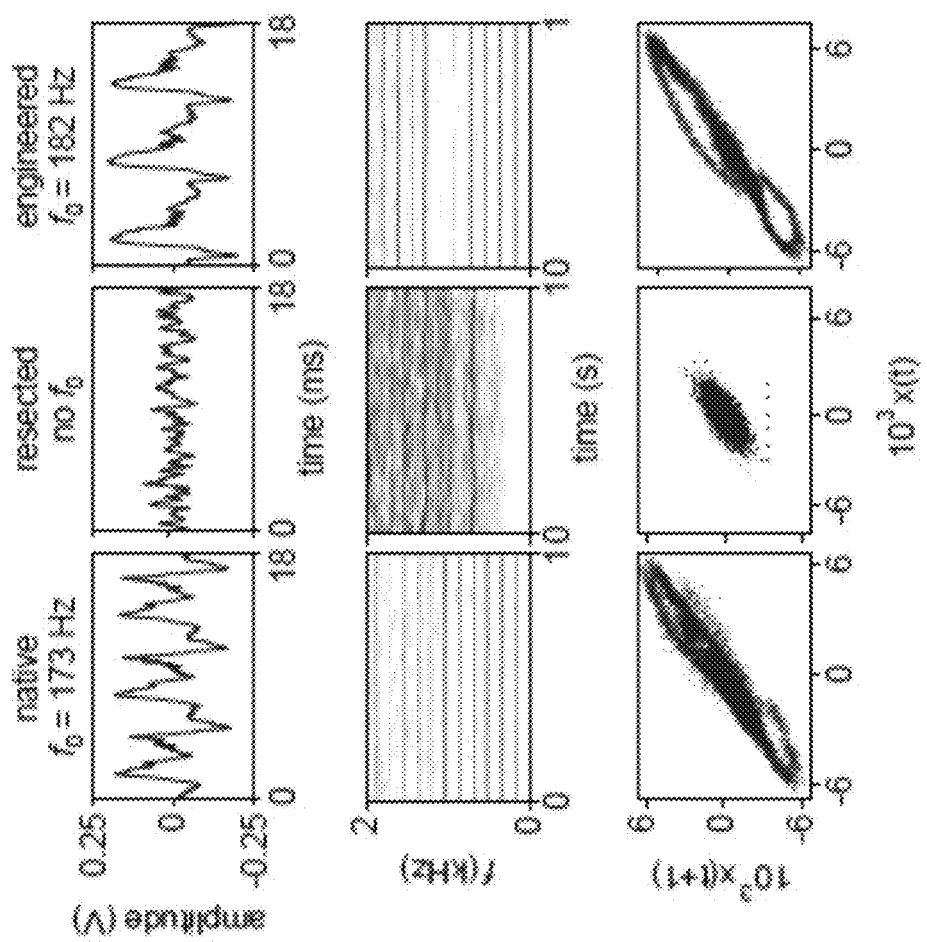
Figure 8H:
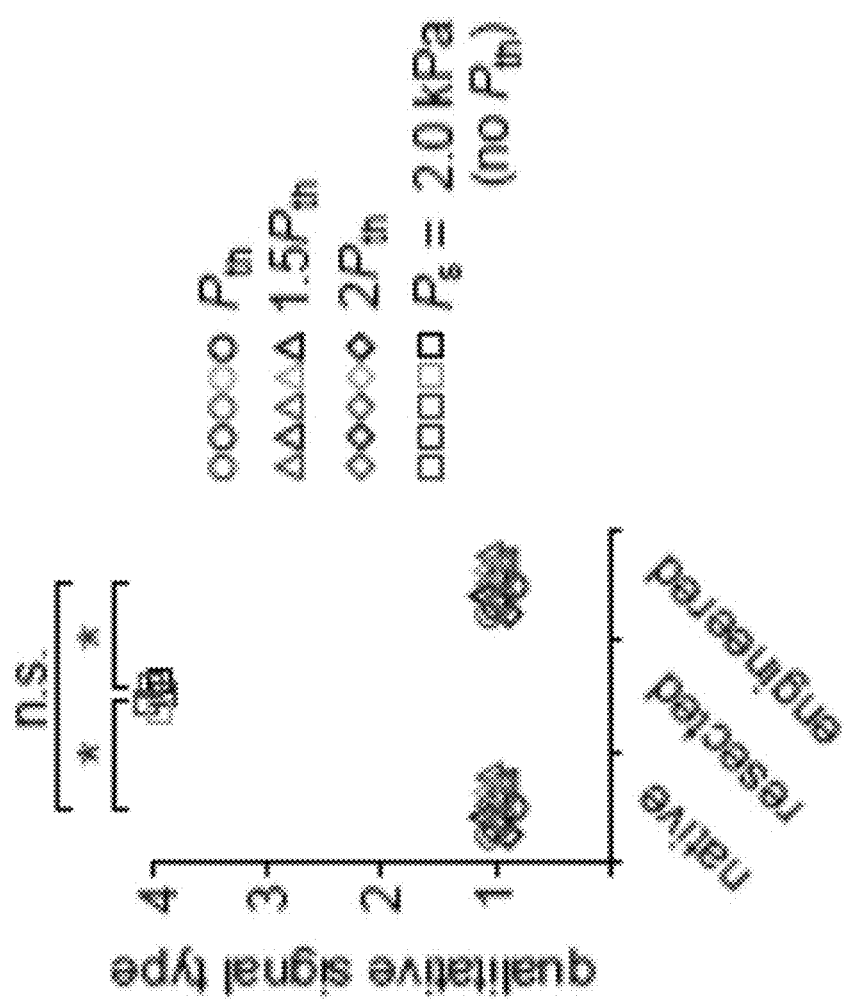

HSDI analysis showed restoration of typical vibratory physiology following engineered VF mucosa replacement. Glottal area waveforms and displacement values were similar to those generated by native mucosa, particularly for within-larynx comparisons (P=0.26; FIG. 8D). Engineered mucosa vibrated with a clear vertical phase difference between upper and lower margins (UM; LM), intact mucosal wave excursion, and lateral (left-right) phase symmetry with the contralateral VF (FIG. 8E). Using HSDI-extracted kymograms, we fitted sinusoidal curves to the UM and LM of each VF ($R^2>0.98$) and observed comparable phase differences for all pairwise comparisons within the experiment (P=0.09-0.76 for all comparisons; FIG. 8f). Acoustic analysis confirmed these vibratory physiology findings, showing restoration of signal periodicity, harmonic structure, and closed phase trajectories following placement of engineered mucosa (FIG. 8g). Using narrow-band spectrography-based qualitative signal typing[36,37], native and engineered mucosae-generated acoustic signals were uniformly categorized as type 1 (near-periodic), whereas signals associated with mucosal resection were uniformly categorized as type 4 (stochastic) (FIG. 8H). In total, the aerodynamic, vibratory and acoustic performance of the engineered mucosa was functionally equivalent to that of native tissue.

Figure 9A:
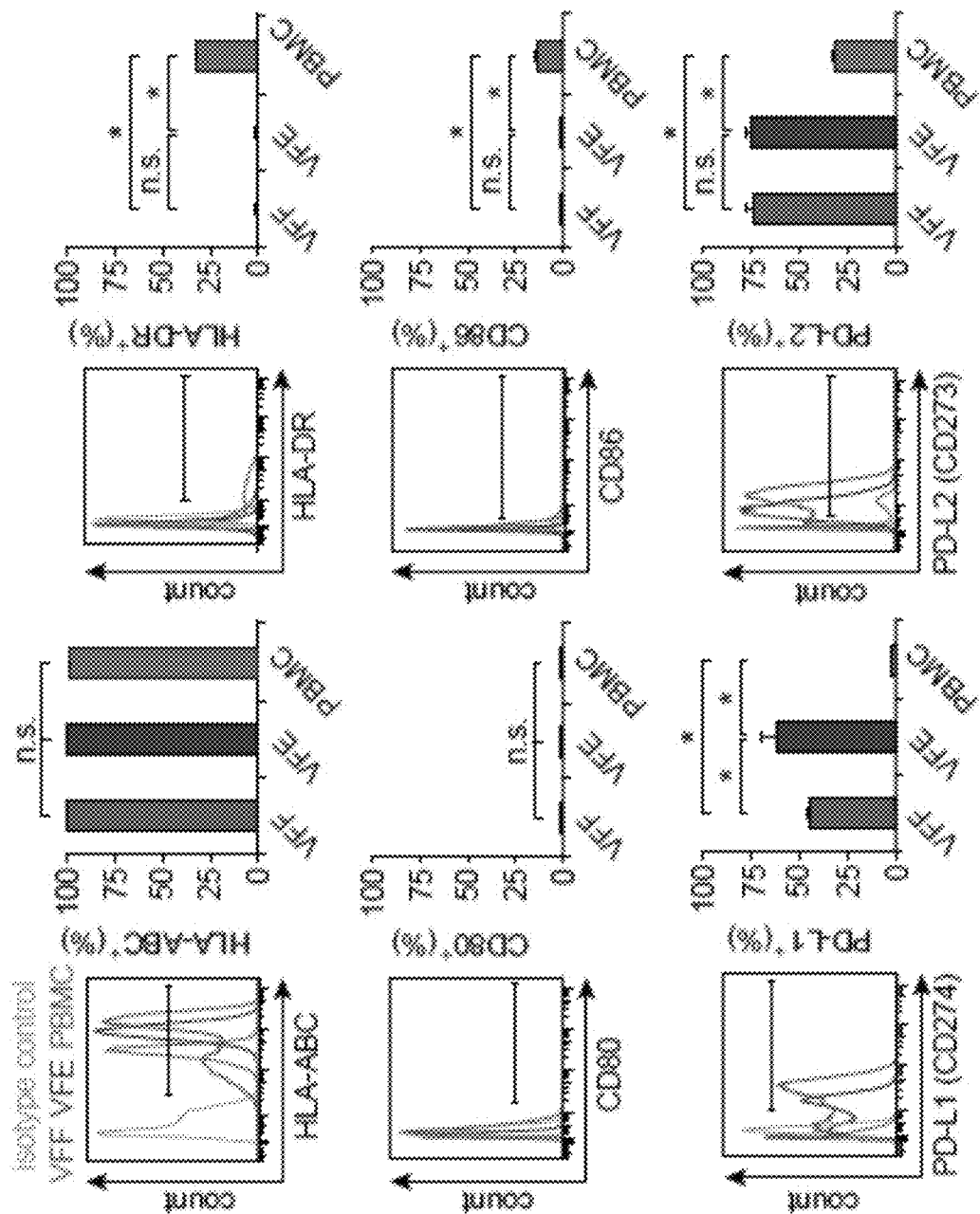
FIGS. 9A-9G demonstrate immunogenicity of engineered VF mucosa. (A) Flow cytometry histograms and bar charts showing expression of cell surface markers HLA-ABC, HLA-DR, CD80, CD86, PD-L1 (CD274) and PD-L2 (CD273) in VFF and VFE compared to peripheral blood mononuclear cell (PBMC) control. Gates are based on isotype controls. (B) Schematic illustrating the experimental approach used to evaluate in vivo immunogenicity via subrenal capsule auto/allograft transplantation in the humanized NOD-scid IL2r$^{\gamma null}$ (NSG) mouse model. GVHD, graft-versus-host disease; hPBL, human peripheral blood lymphocyte. (C) Line graph showing decrease in body mass of NSG mice following hPBL injection, compared to no hPBL control mice. Mice were euthanized in response to a >15% decrease in body mass and clinical signs of xenogeneic GVHD, which occurred 15-21 d post-hPBL injection. (D) Flow cytometry dot plots and bar graph confirming engraftment and proliferation of hCD45$^+$mCD45$^-$ human lymphocytes in the peripheral blood of NSG mice following hPBL injection. (E) Immunostained sections showing predominant hCD4$^-$ T helper cell infiltration and minimal hCD8$^+$ cytotoxic T cell infiltration of the engineered grafts, 15 d post-hPBL engraftment. Comparable staining patterns were observed in the auto- and allografts. Dashed black contour lines indicate the boundaries between the engineered human grafts (top) and the mouse kidneys (bottom). Scale bar, 500 µm. (F) Analysis of hFOXP3 expression by infiltrating hCD4⁺ T cells, 15 d post-hPBL engraftment. The immunofluorescent image shows representative hCD4 and hFOXP3 expression in the engineered allograft; the bar graph summarizes cell count data showing a higher percentage of hCD4⁺hFOXP3⁺ regulatory T cells in the engineered auto- and allografts compared to the mouse eyelid, a GVHD-affected positive control tissue. White arrows indicate hCD4⁺hFOXP3⁻ T helper cells; yellow arrows indicate hCD4⁺hFOXP3⁺ regulatory T cells; the white arrowhead indicates a hCD4⁻hFOXP3⁻ cell. Scale bar, 5 µm. (G) H&E-stained sections showing intact tissue morphology in the engineered auto- and allografts, compared to extensive cellular infiltration and destruction of naïve tissue morphology in the mouse eyelid at 15 d post-hPBL engraftment. Scale bar, 50 µm. *, $P<0.01$ (A, C, D, F); n.s., non-significant difference (A, F); error bars, s.e.m. (A, D, F).
Figure 9B:
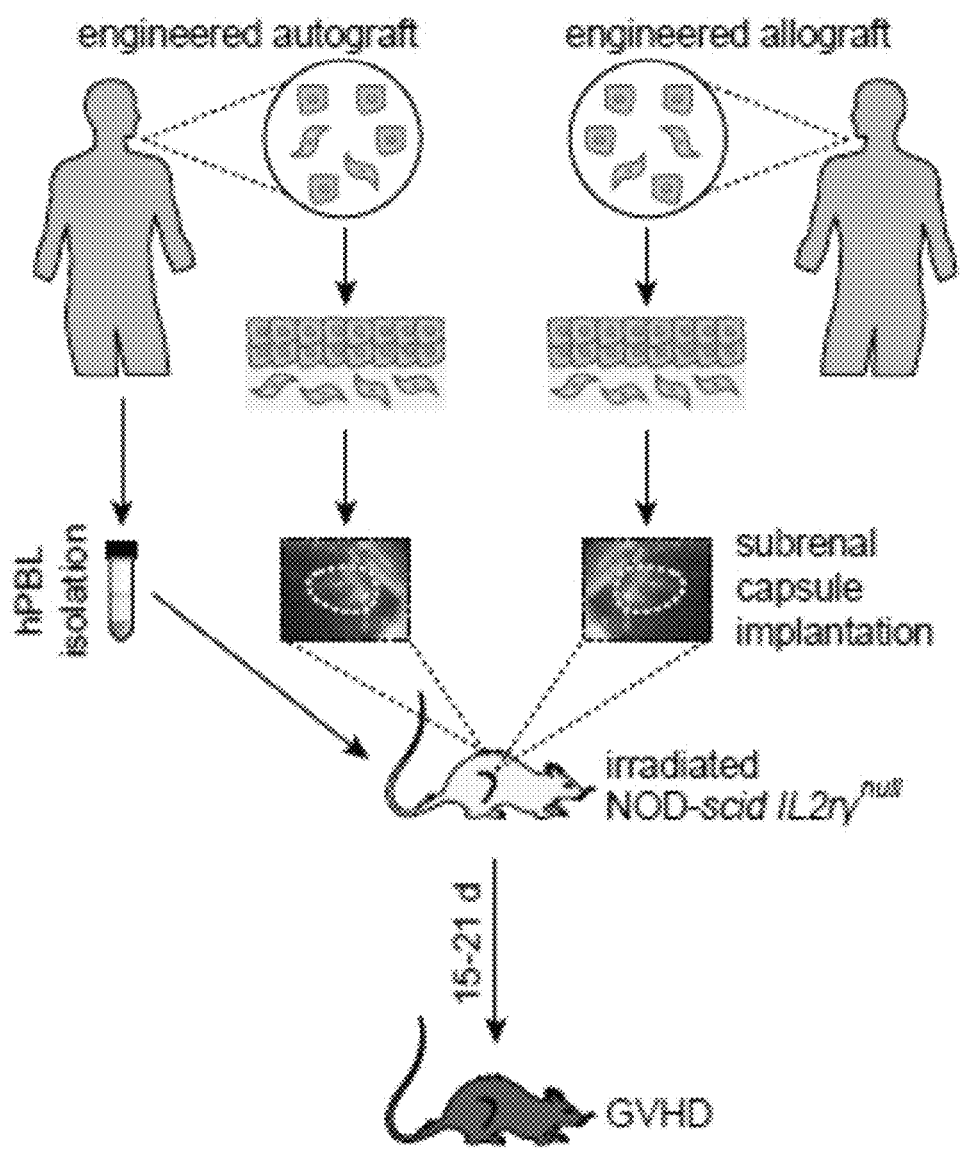
Figure 9C:
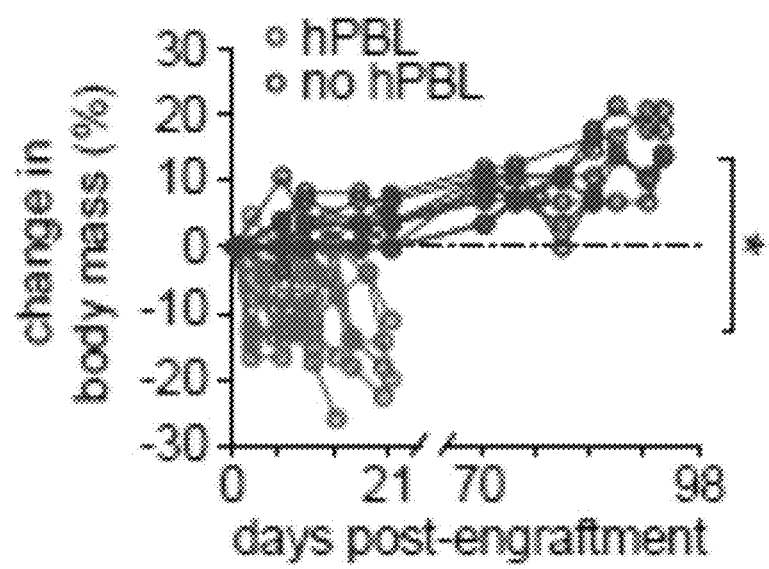
Figure 9D:
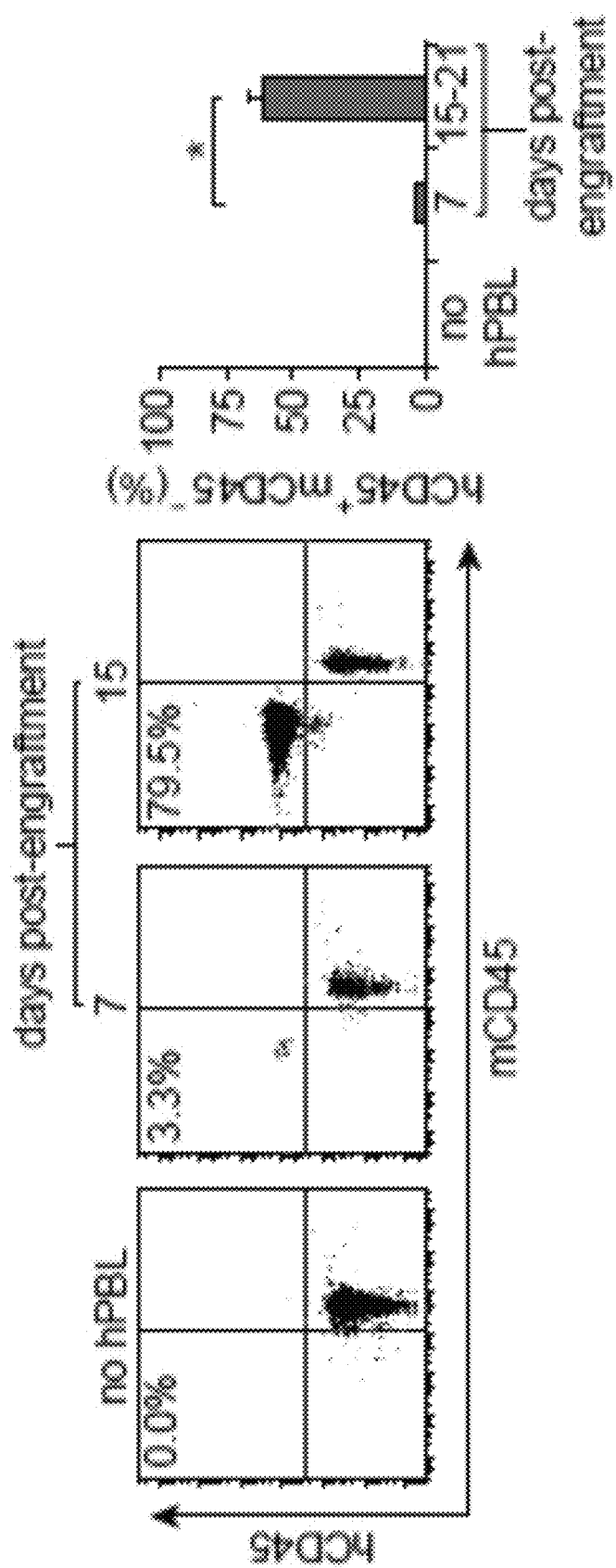
Figures 9E, 9F, 9G:
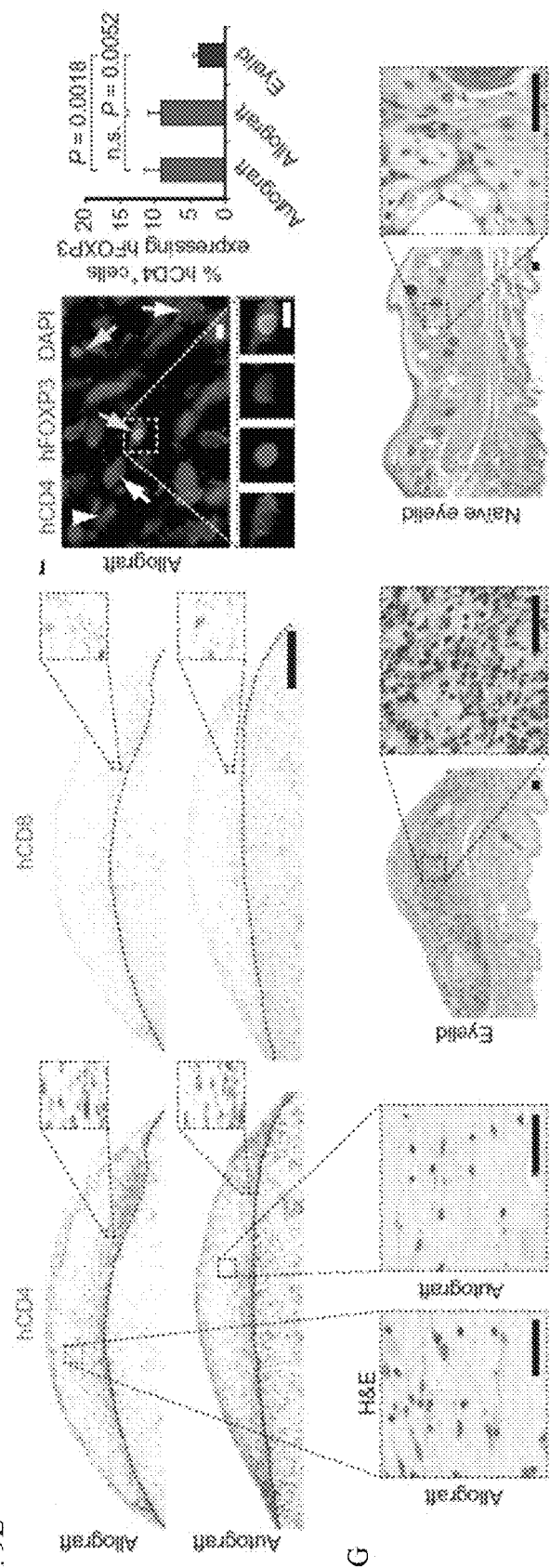

Using the same ex vivo experimental set-up, we next compared the physiologic function of engineered VF mucosa with that of human oral mucosa (FIG. 9A), an autologous free graft material traditionally used for reconstructing large VF mucosal deficits[38,39]. Oral mucosa vibrated with elevated $P_{th}$ (P<0.01; FIG. 9B), as well as reduced glottal area magnitude and mucosal wave excursion (P<0.01; FIGS. 9C, D), suggesting a poor viscosity match to native tissue[20,40]. Lateral and vertical phase differences were comparable across oral and engineered VF mucosa conditions (P=0.10-0.61 for all comparisons; FIG. 9E) and the oral mucosa generated type 1 acoustic signals with some harmonic structure in the majority of experimental runs (FIGS. 9F, G). These data indicate that, in addition to having comparable physiologic function to native VF mucosa, the engineered VF mucosa is superior to oral mucosa, a standard-of-care material used in current surgical practice.

Immunogenicity of Engineered VF Mucosa.

Figure 10A:
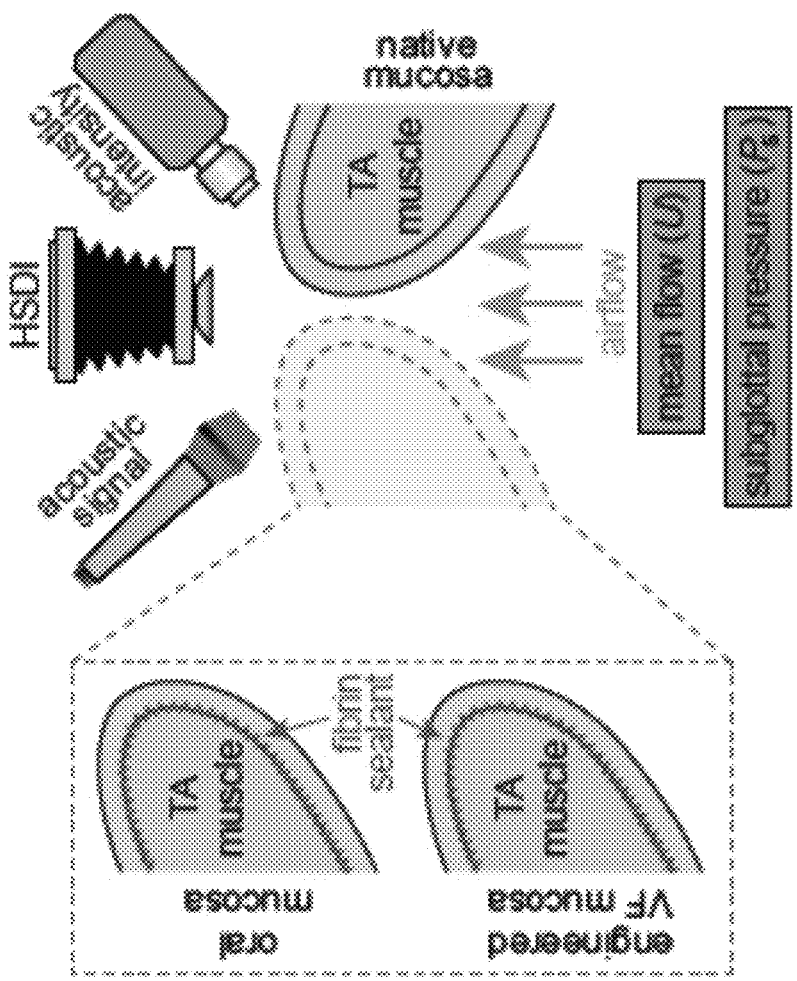
FIGS. 10A-10G demonstrate ex vivo physiologic performance of human oral mucosa, compared to that of engineered VF mucosa, in a large animal excised larynx setup. (A) Coronal orientation schematic illustrating unilateral placement of oral or engineered VF mucosa following resection of native VF mucosa. HSDI, high-speed digital imaging; TA, thyroarytenoid. (B) Phonation threshold pressure ($P_{th}$) data showing elevated threshold in the oral mucosa condition compared to the engineered VF mucosa condition. (C) HSDI-based glottal area analysis showing normal-appearing waveform morphology but reduced area magnitude in the oral mucosa condition compared to the engineered VF mucosa condition. $P_s$, subglottal pressure. (D) Representative kymogram from the larynx presented in (C) showing grossly intact lateral (left-right) phase symmetry but reduced vibratory amplitude and mucosal wave excursion following oral mucosa placement, compared to contralateral native VF mucosa. Sinusoidal curve fitting ($R^2>0.98$) to the upper and lower VF margins (UM; LM) is also shown. Red dashed lines indicate open and closed phases of a single vibratory cycle. Yellow dashed lines indicate UM and LM. $f_0$, fundamental frequency. (E) Analysis of lateral and vertical phase differences for all larynges in the oral and engineered VF mucosa conditions. No significant differences were observed. #, contralateral VF mucosa condition used to calculate lateral phase difference; !, VF mucosa condition contralateral to that for which vertical phase difference is calculated. (F) Acoustic data showing a representative time-domain signal (upper panel), narrowband spectrogram (center panel) and phase plot (lower panel) obtained from a larynx in the oral mucosa condition. Placement of oral mucosa resulted in a periodic signal with measurable $f_0$, some harmonic structure, and a closed phase trajectory. (G) Summary of qualitative acoustic signal typing for the oral and engineered VF mucosa conditions. Both mucosae generated near-periodic type 1 signals in the majority of experimental runs. The engineered VF mucosa data used for statistical comparisons (B, C, E, G) are presented in complete form in FIGS. 8A-H; *, $P<0.01$ (B, C); n.s., non-significant difference (E, G).

To further evaluate its potential for therapeutic implementation, we tested the immunogenicity of engineered VF mucosa and its constituent cells using flow cytometry and an in vivo transplantation assay. Previous work has shown that primary VFF express a cell-surface phenotype that is comparable to immunoprivileged mesenchymal stem cells[41], however no such data have been reported for VFE. VFF and VFE uniformly expressed the pan-major histocompatibility complex (MHC) class I marker human leukocyte antigen (HLA)-ABC (common to all nucleated cells), but were negative for the pan-MHC class II marker HLA-DR (associated with professional antigen-presenting cells), as well as the T cell costimulatory molecules CD80 and CD86 (FIG. 10A). Further, 45-75% of VFF and VFE expressed the T cell inhibiting and tolerance-promoting molecules programmed death-ligand (PD-L)1 and PD-L2 (also known as CD274 and CD273, respectively). These findings suggest that naïve VFF and VFE have limited antigen-presentation capacity and may actively promote immunotolerance in a transplantation context.

Given these encouraging in vitro data, we next evaluated in vivo survival and tolerance of engineered VF mucosa following subrenal capsule auto- and allograft transplantation in the humanized NOD-scid IL2rγ$^{null}$ (NSG) mouse. This transgenic model contains a targeted mutation causing complete silencing of the interleukin-2 receptor γ-chain (IL2rγ) locus, which results in severely restricted B, T, and natural killer (NK) cell development[42]. The NSG model supports engraftment of human peripheral blood lymphocytes (hPBL) and establishment of a functional human adaptive immune system, allowing evaluation of graft immunogenicity during the period prior to terminal xenogeneic graft-versus-host disease (GVHD).

Figure 10B:
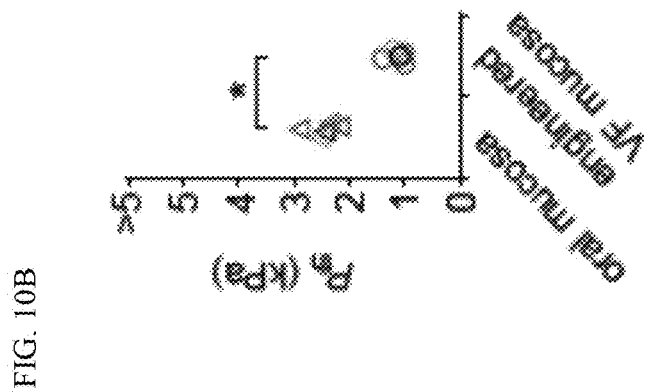
Figure 10E:
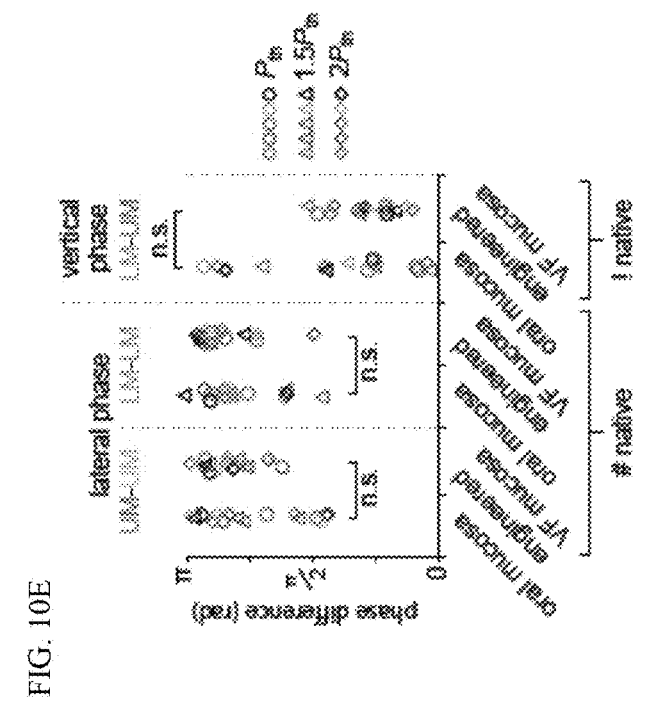
Figure 10D:
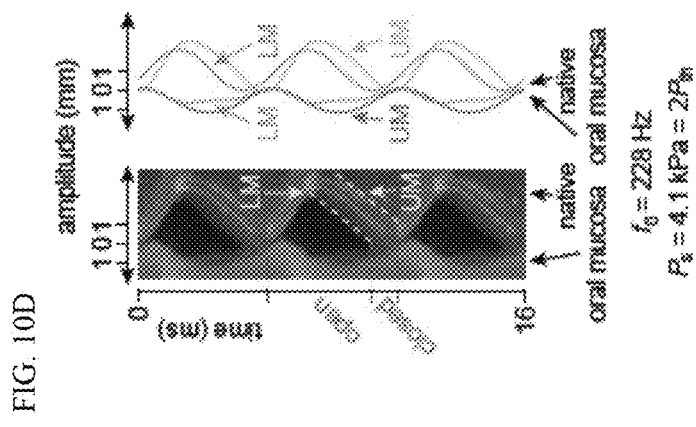
Figure 10C:
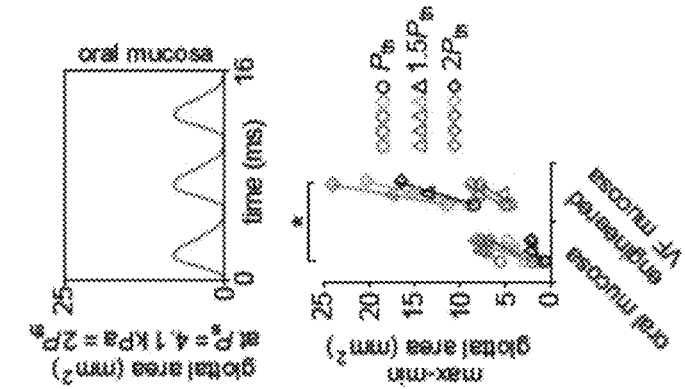
Figure 10G:
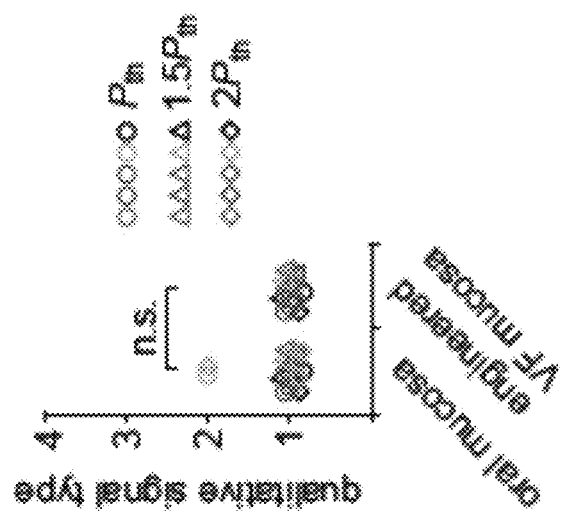
Figure 10F:
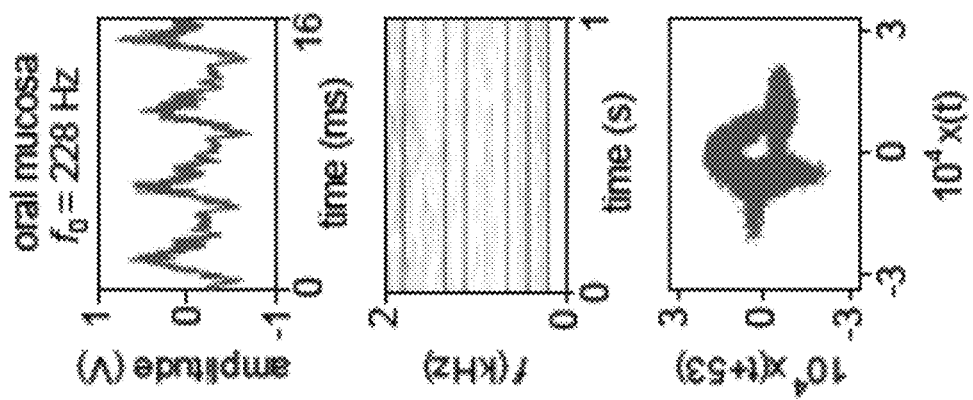

We implanted engineered VF mucosal grafts from unrelated human donors under the bilateral renal capsules of irradiated NSG mice, followed by intravenous delivery of 13×10$^6$ hPBL that were obtained from an original laryngeal tissue donor and autologous to one of the two grafts (FIG. 10B). Mice exhibited a significant decrease in body mass (P<0.01; FIG. 10C) and progressive onset of clinical GVHD signs following hPBL injection; flow cytometry analysis confirmed engraftment and subsequent proliferation of hCD45$^+$mCD45$^-$ human lymphocytes in mouse peripheral blood (FIG. 10D). Evaluation of graft outcomes 15-21 d post-hPBL engraftment showed predominant infiltration by hCD4$^+$ T helper cells and minimal infiltration by hCD8$^+$ cytotoxic T cells, with no observable difference between the auto- and allograft conditions (FIG. 10E). Follow-up analysis of forkhead box P3 (hFOXP3) coexpression by the infiltrating hCD4$^+$ cells revealed a significantly higher subpopulation of hCD4$^+$hFOXP3$^+$ regulatory T cells in the engineered auto- and allografts compared to the mouse eyelid, a GVHD-affected positive control tissue (P<0.01; FIG. 10F). This finding corresponded to preservation of tissue morphology in the engineered auto- and allografts, which contrasted with extensive cellular infiltration and destruction of naïve tissue morphology in the mouse eyelid (FIG. 10G).

Figure 11A:
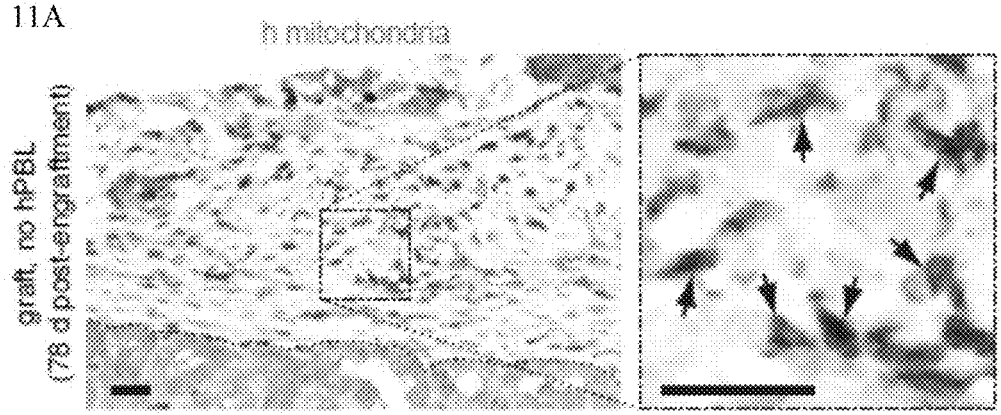
FIGS. 11A-11C present additional in vivo graft survival and immunogenicity data. (A) Immunostained sections showing long-term survival of engineered VF mucosa following subrenal capsule transplantation in the NOD-scid IL2rγ$^{null}$ (NSG) mouse. Black arrows indicate positive intracellular immunostaining of human mitochrondia, 78 days (d) following graft placement with no human peripheral blood lymphocyte (hPBL) injection. Scale bar, 30 µm. (B) Immunostained section showing long-term survival of the collagen, type I scaffold, 78 days following graft implantation with no hPBL injection. No hCD45 immunosignal was observed, consistent with the absence of human cells in both the implant and the NSG mouse recipient. Scale bar, 100 µm. (C) Immunostained section showing performance of the collagen, type I scaffold in the NSG mouse, 21 d following hPBL injection. Black arrows indicate hCD45⁺ lymphocytes at the boundary of the scaffold. No lymphocyte infiltration of the scaffold was observed. Separation of the scaffold and kidney represents artifact introduced by tissue processing and sectioning. Scale bar, 100 µm. The dashed black contour lines indicate the boundaries between the engineered human graft/collagen, type I scaffolds (top) and the mouse kidneys (bottom) (A, B, C).
Figure 11B:
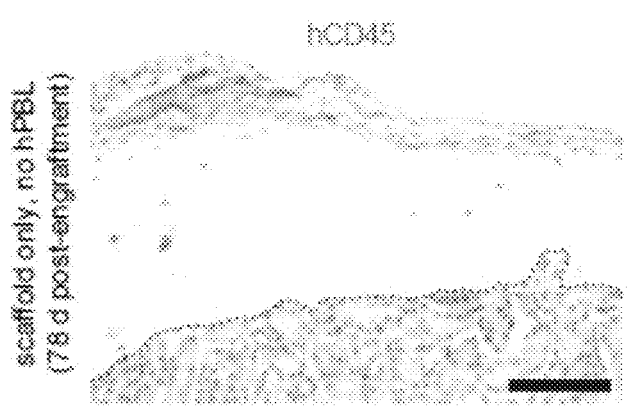
Figure 11C:
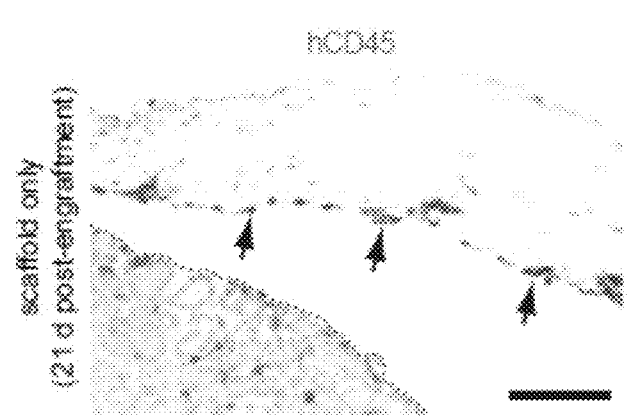

The identification of a robust subpopulation of regulatory T cells in the auto- and allografts, combined with the absence of tissue destruction in both conditions, suggests that engineered VF mucosa holds low immunogenicity and is well tolerated by the human adaptive immune system in vivo. Additional long-term experiments in NSG mice without hPBL challenge confirmed that the grafts survived and remained populated by human cells for the entire 70-98 days (d) experimental time course (FIG. 10C; FIG. 11A). The collagen, type I scaffold exhibited comparable long-term survival (FIG. 11B). When implanted in hPBL-induced humanized NSG mice, the acellular scaffold exhibited no hCD45$^+$ lymphocyte infiltration (FIG. 11C) despite active GVHD in the host, indicating absence of recognition by the human adaptive immune system. This observation is consistent with previous reports of minimal host response to xenogeneic collagen in human clinical applications[43].

Discussion

We have met a series of important milestones towards the development of a fully functioning bioengineered VF mucosa suitable for therapeutic transplantation. These milestones include: concurrent isolation and purification of primary VFF and VFE from individual human donors; 3D organotypic primary culture resulting in recapitulation of key morphologic features and emerging barrier function; confirmation of size scalability; restoration of normal-appearing physiologic vibratory function and acoustic output; and demonstration of tolerance by the human adaptive immune system. The robust biomechanical performance and low immunogenicity of this engineered VF mucosa indicates that our approach could be used to restore voice function in patients with otherwise untreatable VF mucosal impairment or loss.

Although difficult to obtain, and never previously isolated and purified in parallel, we used primary human VFF and VFE as a source of human VFFs and VFEs based on the rationale that these cells are ideally suited for VF mucosal organotypic culture due to their prolonged exposure to phonation-associated mechanical forces in vivo[20,21]. This approach was successful, and under permissive conditions the cells engaged in mucosal morphogenesis, contributing to assembly of a functional 3D tissue. Given that primary VF mucosal cells are not currently available for large-scale clinical therapeutics, utilization of alternative cell populations, such as embryonic stem cell derivatives[15], bone marrow-[44-46] or adipose-derived stem cells[16,17,47], or non-VF somatic cells[48], is an attractive future direction. Such cells might be differentiated towards a VF mucosal cell phenotype, and primed for successful VF organotypic culture and transplantation, by exposure to defined tensile and vibratory forces in a laryngeal bioreactor[49-51].

VF vibratory function and mucosal wave travel are highly dependent on tissue viscoelasticity[20], which in turn is a direct function of VFF-secreted ECM composition[29,30]. We seeded cells in a relatively simple collagen, type I-based scaffold material, selected for its cytocompatibility[43], high abundance in native human VF mucosa[26], and utility in previous organotypic culture systems[22,23] and tissue engineering applications[43]. This initial collagen matrix was augmented by endogenous ECM production by the seeded cells, and the engineered VF mucosa was further strengthened by VFF-driven contraction to the point that it was able to withstand physiologically relevant aerodynamic driving pressures (~1-3 kPa) and tissue vibration rates (~100-300 Hz) for accumulated time doses of 10-15 min during our ex vivo experiments.

Still, while physiologic function was comparable, the engineered VF mucosa did not show lamina propria fiber complexity equivalent to mature human VF mucosa. This observation is not surprising considering that, during human development, differentiation of the VF lamina propria ECM into a complex structure with depth-dependent fibrous protein distribution begins at postnatal age 2 months and is not complete until at least 13 years (y)[52]. Extended culture time, phonation-relevant dosing with mechanical forces (as noted above)[49-51], and/or the use of more architecturally relevant scaffold materials such as decellularized VF mucosa[53], may provide the additional microenvironmental cues needed to yield even greater maturation in vitro.

The engineered VF mucosa exhibited low immunogenicity when presented to the human adaptive immune system in vivo, suggesting that this primary cell-based approach itself has clinical potential in an allotransplantation scenario. Full development of this approach may require additional orthotopic transplantation experiments, with evaluation of long-term tolerance and physiologic outcomes. These experiments will allow the skilled artisan to determine the optimal nature and length of in vitro organotypic culture prior to transplantation, and the extent to which subsequent in vivo incorporation of host cells and their participation in ongoing ECM remodeling completes the regeneration process.

Free mucosal graft is a technically straightforward procedure in laryngeal reconstruction and, given its limited vascular demand, has high viability[39]. Key considerations in determining in vivo outcomes, therefore, may be the relative long-term immunoprivilege of the (primary or non-primary) cells used for organotypic culture, as well as the cumulative impact of the host response and local biomechanical environment on long-term graft remodeling.

In summary, this Example provides a framework for the efficient generation of physiologically relevant and clinically useful bioengineered VF mucosae. Beyond its direct potential for therapeutic use, this approach has application to the development of advanced in vitro model systems for VF mucosal disease modeling and preclinical testing of therapeutic agents.

Materials and Methods

Cell Isolation and Culture.

Human VF mucosae (n=10) were obtained from cadavers at autopsy (<6 h post-mortem) and patients undergoing total laryngectomy with no evidence of VF mucosal disease on routine clinical, endoscopic and radiographic work-up. Procurement was performed with approval of the University of Wisconsin-Madison Health Sciences Institutional Review Board (IRB). Each mucosa was microdissected from its underlying thyroaytenoid muscle, minced with scalpels, and incubated in PBS containing 7.5 mg·mL$^{-1}$ collagenase, type I (Wako) and 0.5 mg·mL$^{-1}$ DNase I (Sigma-Aldrich) at 37° C. using 50 Hz agitation for 1 h. Cells released from the ECM were strained through a 40 μm filter (BD Biosciences), rinsed and resuspended in fibroblast-oriented medium (DMEM containing 10% FBS and 100 U·mL$^{-1}$ antibiotic-antimycotic solution; Sigma-Aldrich), seeded on culture plates pre-coated with Earle's balanced salt solution (EBSS) containing 30 μg·mL$^{-1}$ collagen, type I, 10 μg·mL$^{-1}$ fibronectin and 10 μg·mL$^{-1}$ BSA[54], and incubated at 37° C. in 5% $CO_2$. After 30 min, free-floating non-adherent cells were collected, rinsed in epithelial cell-oriented medium (DMEM/Ham's F-12 supplemented with 15 μg·mL$^{-1}$ bovine pituitary extract, 10 ng·mL$^{-1}$ epidermal growth factor, 0.5 μg·mL$^{-1}$ epinephrine, 5 μg·mL$^{-1}$ insulin, 10 μg·mL$^{-1}$ transferrin, 10 ng·mL$^{-1}$ triiodo-L-thyronine, 0.5 μg·mL$^{-1}$ hydrocortisone, 0.1 ng·mL$^{-1}$ retinoic acid, 1.5 μg·mL$^{-1}$ albumin, 100 U·mL$^{-1}$ antibiotic-antimycotic solution, and 1% FBS; Sigma-Aldrich)[54], reseeded on pre-coated culture plates, and maintained in epithelial cell-oriented culture conditions. Adherent cells were maintained in fibroblast-oriented culture conditions.

Both cell populations were cultured at 37° C. in 5% $CO_2$ and passaged when 80% confluent. Given that epithelial cells, once attached, are more adherent than fibroblasts in 2D culture, we performed additional adherence-based VFE purification at passages 1 and 2, as follows. Cells were incubated with 0.05% trypsin-EDTA (Sigma-Aldrich) at 37° C. for 1 minute to detach contaminating VFF, rinsed with PBS, and then incubated with 0.25% trypsin-EDTA at 37° C. for 2 min to detach remaining VFE for subsequent passage. Cell passage was performed using 5×10$^3$ cells·cm$^{-2}$ seeding density. Cells intended for fixation and staining were seeded at 1-3×10$^3$ cells·cm$^{-2}$ density on slide chambers.

Cell Growth Kinetics.

Passage 1-6 VFF and VFE (n=4 biological replicates per condition) were plated at 3×10$^5$ cells·cm$^{-2}$ seeding density in 6-well plates and cultured at 37° C. in 5% $CO_2$. Cells were trypsinized and harvested after 96 hours, stained with trypan blue, and counted. All counts (at the time of cell seeding and harvest) were performed using a hematocytometer in technical quadruplicate. Cell plates were imaged to confirm cell trypsinization and complete detachment. Population doubling time was calculated as $2^N=C_f/C_i$, where N denotes doubling time, $C_f$ denotes the final cell count at time of harvest, and $C_i$ denotes the initial cell count at time of seeding[55].

3D Organotypic Culture.

We engineered 167 VF mucosae using 3D organotypic culture. Purified rat tail collagen, type I (BD Biosciences) was prepared to a final concentration of 2.4 mg·mL$^{-1}$ according to the manufacturer's instructions and seeded with 2×10$^5$ VFF·mL$^{-1}$. Mucosae used for transmucosal resistance experiments were prepared with a reduced fibroblast seeding density of 5.6×10$^4$ VFF·mL$^{-1}$ to reduce scaffold contraction and eliminate detachment from the insert wall. The cell-scaffold mixture was added to the apical chamber of a culture insert (0.14 mL per well of a 24-well insert with 0.4 μm pore size, 0.64 cm diameter, 0.3 cm$^2$ surface area; or 2.0 mL per well of a 6-well insert with 0.4 μm pore size, 2.31 cm diameter, 4.2 cm$^2$ surface area; BD Biosciences). The collagen-based scaffold was then polymerized at 37° C. for 40 min. Fibroblast-oriented medium was added to both apical and basolateral chambers and the cells were cultured for 24 hours. Next, VFE were seeded on the polymerized scaffold surface within the apical chamber (2×10$^5$ VFE per well of a 24-well insert; 2×10$^6$ VFE per well of a 6-well insert) and cultured in epithelial cell-oriented medium; a 1:1 ratio of fibroblast- and epithelial cell-oriented media was added to the basolateral chamber. After an additional 48 h, the epithelial cell-oriented medium was aspirated from the apical chamber, leaving VFE at the air-liquid interface. We continued organotypic culture for a total of 8-28 d with basolateral chamber media change every 48 h.

As initial histological assessment showed no difference in engineered VF mucosa morphology at 14 and 28 d, we performed all subsequent histological, immunohistochemical, proteomic, physiologic and immunologic assays on samples harvested at 14 d. Experimental comparisons involving the scaffold only, VFF in scaffold and VFE on scaffold involved identical culture conditions for the entire 14 d period.

Ex Vivo Physiologic Experiments.

Ex vivo physiologic data were collected using a previously reported experimental setup[56]. HSDI data were captured at 13,500 frames·$s^{-1}$ and calibrated for distance measurement in mm. Acoustic data were digitized at 48 kHz with 16-bit quantization. The microphone and sound level meter (dB A-weighted) were positioned 3 cm from the glottal midpoint.

Previously harvested and cryopreserved canine larynges (n=10) were thawed at 4° C. overnight and the epiglottis, aryepiglottic folds and false VFs were removed to maximize visual exposure of the true VFs. Arytenoid adduction procedures were performed using 5-0 sutures. Following instrument calibration, each larynx was mounted and then subjected to gradual increases in $P_s$ to obtain $P_{th}$. Aerodynamic, acoustic and HSDI data were then collected at $P_{th}$, 1.5$P_{th}$ and 2$P_{th}$. For 5 larynges, data were collected under native conditions, following unilateral VF mucosa resection, and following engineered VF mucosa placement. Additional data were collected in a parallel experiment using the remaining 5 larynges and previously cryopreserved human oral mucosa (n=5; harvested from cadavers at autopsy [<6 h post-mortem] under IRB exemption) in place of the engineered VF mucosa. The engineered VF or oral mucosa was attached to the underlying thyroarytenoid muscle using fibrin sealant (Tisseel; Baxter). All ex vivo tissues were draped with saline-soaked gauze between experimental runs to prevent dehydration.

$\vartheta_{ac}$ was derived from acoustic intensity in dB SPL, based on an assumption of uniform acoustic radiation from the glottis in all directions. $\vartheta_{aero}$ was calculated by multiplying $P_s$ in kPa by U in L·$s^{-1}$. $E_g$ was calculated by dividing $\vartheta_{ac}$ by $\vartheta_{aero}$ (both in W) and converting to a percentage. HSDI-based analyses of glottal area and vibratory phase differences were performed in Matlab (Mathworks) with implementation of previously described algorithms[57-60]. Acoustic time-domain plots and narrowband spectrograms (150 ms analysis window) were generated using Praat 5.3.41 (Paul Boersma and David Weenink, University of Amsterdam). Phase plots were generated as previously described[61]. Qualitative signal typing was performed using previously reported criteria[36,37].

Humanized Mouse Experiments.

hPBL were obtained with IRB approval and isolated from individuals with no known hematopoietic disorders via either leukapheresis using lymphocyte separation medium (Cellgro) or routine venipuncture with collection in a lavender-top Vacutainer® tube (BD Biosciences) followed by centrifugation and separation. All samples were subject to ACK lysis of red blood cells and frozen prior to experimental use.

NOD-scid IL2rγ$^{null}$ (NSG) mice aged 7-8 weeks (wk) were used for all in vivo experiments (n=23; Jackson Laboratory); protocols were approved by the University of Wisconsin School of Medicine and Public Health Animal Care and Use Committee. Mice were conditioned with sublethal (2.5 Gy) total body irradiation; 4 h following irradiation, engineered VF mucosae were implanted under the bilateral renal capsules. The following day, mice received an intravenous injection of 13×10$^6$ hPBL that were isolated from an original laryngeal tissue donor and autologous to one of the two engineered VF mucosal grafts. Additional mice were subject to the following conditions: engineered VF mucosal graft implantation followed by delivery of hPBL that were allogeneic to both grafts; engineered VF mucosal graft implantation followed by no hPBL delivery; acellular scaffold implantation followed by hPBL delivery; acellular scaffold implantation followed by no hPBL delivery (n=3-6 per condition).

Mice were monitored every 1-2 d for decrease in body mass and clinical signs consistent with GVHD, such as a hunched posture, ruffled fur, and mobility difficulty: mice who received hPBL were euthanized in response to a >15% decrease in body mass compared to baseline. Other mice were monitored for 70-98 d. Peripheral blood was collected at 7 d post-engraftment and at the experimental endpoint and processed for flow cytometry. Auto- and allografts, acellular scaffolds and eyelids (used as a positive control for xenogeneic GVHD) were harvested at the experimental endpoint and processed for histology and immunohistochemisty.

Flow Cytometry.

Cells were washed and suspended in staining buffer (Hanks' balanced salt solution (HBSS) containing 2% FBS and 10 mM HEPES). For cell surface staining, single cell suspensions were incubated with fluorochrome-conjugated antibodies. For intracellular staining, unstained or surface-stained cells were washed, then fixed and permeabilized using Cytofix/Cytoperm™ (BD Biosciences) according to the manufacturer's instructions. The permeabilized cells were then incubated with fluorochrome-conjugated antibodies against the intracellular targets, washed, and resuspended in staining buffer. All antibodies are listed in Table 6. Cells were also incubated with DAPI: a change in DAPI fluorescent intensity was used to gate live versus dead cells. Samples were run on a 4-laser, 14-color LSR II instrument (BD Biosciences) and data were analyzed using FlowJo 8.7.1 (Tree Star). We employed both isotype (Table 6) and fluorescence-minus-one (FMO) controls.

Histology, Immunocytochemistry and Immunohistochemistry.

Cells seeded on slide chambers were harvested after 2-3 days in culture and fixed using 2-4% paraformaldehyde. Native and engineered tissues were processed for paraffin (5 μm-thick) and frozen (8 μm-thick) sections. Routine H&E, Alcian blue (pH 2.5, with and without hyaluronidase digestion), Elastic van Gieson, and Movat's pentachrome histological staining was performed on both paraffin and frozen sections to evaluate morphology.

Frozen sections used for immunostaining were incubated with 0.5% Triton X-100 for 15 min, Image iT-FX (Life Technologies) for 30 min, and Block-Ace (AbD Serotech) and 5% donkey serum (Sigma-Aldrich) for 30 min. Fixed cells and sections were incubated with primary antibodies for 90 min followed by appropriate secondary antibodies for 90 min, with thorough wash steps between each incubation step. A complete list of antibodies is provided in Table 7. Following primary and secondary antibody incubations, cells and sections were counterstained with DAPI, covered with Vectashield antifade mounting medium (Vector Labs), and coverslipped.

Paraffin sections used for immunostaining were first processed for antigen retrieval in a decloaking chamber (Biocare Medical) using 10 mM citrate buffer (pH 6.0). Sections were permeabilized using 0.2% Triton X-100 for 10 minutes and incubated with 10% BSA in PBS for 60 minutes to block non-specific binding, prior to incubation with primary antibodies for 60 minutes (Table 7). Thorough washing was performed between each incubation step. For HRP-based detection, endogenous peroxidase was quenched using 3% hydrogen peroxide in PBS. ImmPRESS anti-mouse and anti-rabbit Ig HRP polymers were used for secondary detection (30 minutes incubation) and the ImmPACT DAB kit was used to develop the signal (all reagents from Vector Labs), according to the manufacturer's instructions. Sections were counterstained with hematoxylin, dehydrated, cleared and coverslipped.

All staining protocols were performed using 5-10 biological replicates, each with two technical replicates. Histological, immunocytochemical and immunohistochemical images were captured using a microscope (E-600; Nikon) equipped with a digital microscopy camera (DP-71; Olympus). Consistent exposure parameters were used for each immunostained protein of interest. Positive control tissues (Table 7) showed expected immunostaining patterns. Negative control sections, stained with an IgG isotype control or without the primary or secondary antibody, showed no immunoreactivity.

Histology- and immunohistochemistry-based cell counts were performed using 10 non-overlapping, high-magnification fields per biological replicate. For measurement of overall cell density in the engineered and native VF mucosae, 0.25 $mm^2$-sized fields were randomly sampled from the central lamina propria region. For measurement of $hCD4^-$ $hFOXP3^+$ cell density in the VF auto- and allografts, 0.1 $mm^2$-sized fields were randomly sampled from the deep lamina propria region of each graft (nearest the mouse kidney) as this region contained the greatest number of infiltrating cells. For measurement of $hCD4^+hFOXP3^+$ cell density in the mouse eyelid, 0.1 $mm^2$-sized fields were randomly sampled from the meibomian gland-containing region.

Proteomic Analyses.

Proteins were extracted from each sample (n=3 biological replicates per condition) by first adding 150 μL of 4% SDS, 0.1 M Tris-HCl (pH 7.6) and 0.1 M dithiothreitol. Next, samples were sonicated (alternating 20 s on/off cycles for 6 min) using a probe sonicator (XL2015 with PN/418 microtip; Misonix), heated to 95° C. for 7 min, and then centrifuged at 16,100 g at 20° C. for 5 min. A 30 μL aliquot of the supernatant was processed according to the filter-aided sample preparation (FASP) protocol for SDS removal and on-filter digestion[62,63]. Briefly, the supernatant was added to a 30,000 MWCO Vivacon 500 filter (Sartorius), washed, alkylated, and digested with trypsin (50:1 w/w protein-to-trypsin ratio) at 37° C. overnight. The digested sample was desalted using a Sep-Pak C18 1 cc Vac cartridge (Waters), evaporated to dryness in a vacuum centrifuge, and reconstituted in 5% acetonitrile and 2% formic acid in water.

The following mass spectrometry (MS) experiment was performed using two technical replicates per biological replicate. Approximately 1.2 μg of the protein digest, as estimated by a BCA assay (Pierce), was injected into a Waters nanoAcquity HPLC coupled to an ESI ion-trap/orbitrap mass spectrometer (LTQ Orbitrap Velos; Thermo Scientific). Peptides were separated on a 100 μm-inner-diameter column packed with 20 cm of 3 μm MAGIC aqC18 beads (Bruker-Michrom), which were packed against an in-house laser-pulled tip, and eluted at 0.3 μL·$min^{-1}$ in 0.1% formic acid with a gradient of increasing acetonitrile, over 2.5 h. A full-mass scan (300-1500 m/z) was performed in the orbitrap at a resolution of 60,000. The ten most intense peaks were then selected for fragmentation by high-energy collisional dissociation (HCD) at 42% collision energy, with a resolution of 7500 and isolation width of 2.5 m/z. Dynamic exclusion was enabled with a repeat count of 2 over 30 seconds (s) and an exclusion duration of 120 s.

We searched the mass spectra against appropriate organism protein databases (*Homo sapiens* and *Rattus norvegicus*; UniProt) using the SEQUEST algorithm within Proteome Discoverer (Thermo Scientific). We allowed two missed cleavages, required at least two unique peptides per protein identification, and filtered the results using a 1% peptide false discovery rate. Precursor mass tolerance was set to 25 ppm and 0.05 Da for fragment ion tolerance. Variable methionine and proline oxidation (+15.995 Da) and static carbamidomethylation of cysteines (+57.021 Da) were also used. Spectral counting-based protein quantification was performed using the normalized spectral abundance factor (NSAF) approach[28]. Further normalization, based on an assumption of comparable degradation of rat collagen across experimental conditions, was performed using a correction factor calculated from the NSAF values of the 10 most abundant proteins in the collagen, type I-based scaffold. The raw MS data files may be downloaded from the PeptideAtlas peptide data repository[64] using the dataset identifier PASS00271.

Protein Array.

Passage 3 VFF were seeded at a density of $2 \times 10^5$ cells·$mL^{-1}$ collagen, type I and cultured at 37° C. in 5% $CO_2$ for 96 h. Fibroblast-oriented medium was changed every 24 h. Culture supernatants were harvested 48 and 96 h post-seeding, pooled across 6 biological replicates per time point, and processed for measurement of MMP/TIMP concentrations using the Quantibody® Human MMP Array 1 platform (RayBiotech), according to the manufacturer's instructions. Medium only was used as a negative control. Each MMP/TIMP of interest was assayed in technical quadruplicate. The array was scanned and data processed using Q-Analyzer software (RayBiotech).

Rheologic Analyses.

Small-amplitude oscillatory shear measurements (n=4-12 biological replicates per condition) were performed in a Bohlin C-VOR rheometer (Malvern) using 15-mm parallel-plate geometry with a 0.3-0.6 mm gap size (adjusted according to the sample volume) at 37° C. Serrated plates were used to avoid sample slippage during testing. Frequency sweep tests were performed from 0.01-10 Hz under a constant applied stress of 3 Pa, which was determined as the linear viscoelastic limit via stress sweep tests.

Transmucosal Electrical Resistance Analyses.

Electrical resistance measurements (n=4 biological replicates per condition, each with two technical replicates) were performed in 24-well inserts using a Millicell-ERS volt-ohm meter (Millipore), according to the manufacturer's instructions. Samples were rinsed and fresh media were added to the basolateral and apical insert chambers 15-30 min prior to data collection. The resistance value of an insert containing fresh media but no scaffold or cells was subtracted from each sample measurement. Resistance values were then further normalized to the scaffold only condition.

Statistical Analyses.

Technical replicates were averaged and all statistical comparisons were performed using independent biological replicates. NSAF-based quantitative proteomic data were analyzed using a two-tailed Student's t test with implementation of Benjamin-Hochberg correction[65] to account for multiple testing. Gene ontology term enrichment analysis was performed using the BiNGO[66] (hypergeometric model with Benjamini-Hochberg correction) and REViGO[67] (Sim-Rel cutoff=0.4) algorithms. Ontology term enrichment schematics were generated using Cytoscape 2.8.2[68]. Other statistical testing was performed using SAS 9.2 (SAS Institute). Flow cytometry, rheology (comparison of slopes of each fitted curve), cell density, transmucosal resistance, $P_{th}$, and body mass data were analyzed using one-way ANOVA. Glottal area and vibratory phase data were analyzed using two-way ANOVA, with VF mucosa condition and $P_{th}$ as fixed effects, and their interaction term included. Cell proliferation data were also analyzed using two-way ANOVA, with cell type and culture passage as fixed effects, and their interaction term included. Data were first evaluated for normality and equality of variance using visual inspection of raw data plots and Levene's test; data were rank-transformed where needed to meet the equal variance assumptions of the Student's t test and ANOVA. In all ANOVA models, if the omnibus F test revealed a significant difference, pairwise comparisons were performed using Fisher's protected least significant difference method. Categorical acoustic signal typing data were analyzed using a chi-squared test. An initial (pre-correction) type I error rate of 0.01 was used for all statistical testing; quantitative proteomic data were subject to an additional fold change cutoff of 4. All P-values were two-sided.

REFERENCES CITED—BACKGROUND SECTION AND EXAMPLE

1. Cohen, S. M., Dupont, W. D. & Courey, M. S. Quality-of-life impact of non-neoplastic voice disorders: a meta-analysis. *Ann Otol Rhinol Laryngol* 115, 128-134 (2006).
2. Cohen, S. M., Kim, J., Roy, N., Asche, C. & Courey, M. S. The impact of laryngeal disorders on work-related dysfunction. *Laryngoscope* 122, 1589-1594 (2012).
3. Roy, N., Merrill, R. M., Thibeault, S. L., Gray, S. D. & Smith, E. M. Voice disorders in teachers and the general population: effects on work performance, attendance, and future career choices. *J Speech Lang Hear Res* 47, 542-551 (2004).
4. Verdolini, K. & Ramig, L. O. Review: occupational risks for voice problems. *Logoped Phoniatr Vocol* 26, 37-46 (2001).
5. Cohen, S. M., Kim, J., Roy, N., Asche, C. & Courey, M. S. Direct health care costs of laryngeal diseases and disorders. *Laryngoscope* 122, 1582-1588 (2012).
6. Coyle, S. M., Weinrich, B. D. & Stemple, J. C. Shifts in relative prevalence of laryngeal pathology in a treatment-seeking population. *J Voice* 15, 424-440 (2001).
7. Benninger, M. S. et al. Vocal fold scarring: current concepts and management. *Otolaryngol Head Neck Surg* 115, 474-482 (1996).
8. Koufman, J. A. & Isaacson, G. Laryngoplastic phonosurgery. *Otolaryngol Clin North Am* 24, 1151-1177 (1991).
9. Zeitels, S. M., Mauri, M. & Dailey, S. H. Medialization laryngoplasty with Gore-Tex for voice restoration secondary to glottal incompetence: indications and observations. *Ann Otol Rhinol Laryngol* 112, 180-184 (2003).
10. Ford, C. N., Bless, D. M. & Loftus, J. M. Role of injectable collagen in the treatment of glottic insufficiency: a study of 119 patients. *Ann Otol Rhinol Laryngol* 101, 237-247 (1992).
11. Caton, T., Thibeault, S. L., Klemuk, S. & Smith, M. E. Viscoelasticity of hyaluronan and nonhyaluronan based vocal fold injectables: implications for mucosal versus muscle use. *Laryngoscope* 117, 516-521 (2007).
12. Molteni, G. et al. Auto-crosslinked hyaluronan gel injections in phonosurgery. *Otolaryngol Head Neck Surg* 142, 547-553 (2010).
13. Xu, C. C., Chan, R. W. & Tirunagari, N. A biodegradable, acellular xenogeneic scaffold for regeneration of the vocal fold lamina propria. *Tissue Eng* 13, 551-566 (2007).
14. Yamaguchi, T., Shin, T. & Sugihara, H. Reconstruction of the laryngeal mucosa. A three-dimensional collagen gel matrix culture. *Arch Otolaryngol Head Neck Surg* 122, 649-654 (1996).
15. Leydon, C., Selekman, J. A., Palecek, S. & Thibeault, S. L. Human embryonic stem cell-derived epithelial cells in a novel in vitro model of vocal mucosa. *Tissue Eng Part A* 19, 2233-2241 (2013).
16. Long, J. L., Zuk, P., Berke, G. S. & Chhetri, D. K. Epithelial differentiation of adipose-derived stem cells for laryngeal tissue engineering. *Laryngoscope* 120, 125-131 (2010).
17. Long, J. L. et al. Functional testing of a tissue-engineered vocal fold cover replacement. *Otolaryngol Head Neck Surg* 142, 438-440 (2010).
18. Leydon, C., Wroblewski, M., Eichorn, N. & Sivasankar, M. A meta-analysis of outcomes of hydration intervention on phonation threshold pressure. *J Voice* 24, 637-643 (2010).
19. Chen, X. & Thibeault, S. L. Novel isolation and biochemical characterization of immortalized fibroblasts for tissue engineering vocal fold lamina propria. *Tissue Eng Part C Methods* 15, 201-212 (2009).
20. Titze, I. R. The physics of small-amplitude oscillation of the vocal folds. *J Acoust Soc Am* 83, 1536-1552 (1988).
21. Titze, I. R. On the relation between subglottal pressure and fundamental frequency in phonation. *J Acoust Soc Am* 85, 901-906 (1989).
22. Gangatirkar, P., Paquet-Fifield, S., Li, A., Rossi, R. & Kaur, P. Establishment of 3D organotypic cultures using human neonatal epidermal cells. *Nat Protoc* 2, 178-186 (2007).
23. Dongari-Bagtzoglou, A. & Kashleva, H. Development of a highly reproducible three-dimensional organotypic model of the oral mucosa. *Nat Protoc* 1, 2012-2018 (2006).
24. Koskull, von, H. & Virtanen, I. Induction of cytokeratin expression in human mesenchymal cells. *J Cell Physiol* 133, 321-329 (1987).
25. Langness, U. & Udenfriend, S. Collagen biosynthesis in nonfibroblastic cell lines. *Proc Natl Acad Sci USA* 71, 50-51 (1974).
26. Hahn, M. S., Kobler, J. B., Zeitels, S. M. & Langer, R. S. Quantitative and comparative studies of the vocal fold extracellular matrix II: collagen. *Ann Otol Rhinol Laryngol* 115, 225-232 (2006).
27. Chan, R. W., Gray, S. D. & Titze, I. R. The importance of hyaluronic acid in vocal fold biomechanics. *Otolaryngol Head Neck Surg* 124, 607-614 (2001).
28. Zybailov, B. et al. Statistical analysis of membrane proteome expression changes in Saccharomyces cerevisiae. *J Proteome Res* 5, 2339-2347 (2006).
29. Gray, S. D., Titze, I. R., Alipour, F. & Hammond, T. H. Biomechanical and histologic observations of vocal fold fibrous proteins. *Ann Otol Rhinol Laryngol* 109, 77-85 (2000).
30. Gray, S. D., Titze, I. R., Chan, R. W. & Hammond, T. H. Vocal fold proteoglycans and their influence on biomechanics. *Laryngoscope* 109, 845-854 (1999).
31. Hahn, M. S., Kobler, J. B., Starcher, B. C., Zeitels, S. M. & Langer, R. S. Quantitative and comparative studies of the vocal fold extracellular matrix. I: Elastic fibers and hyaluronic acid. *Ann Otol Rhinol Laryngol* 115, 156-164 (2006).
32. Hahn, M. S., Kobler, J. B., Zeitels, S. M. & Langer, R. S. Midmembranous vocal fold lamina propria proteoglycans across selected species. *Ann Otol Rhinol Laryngol* 114, 451-462 (2005).
33. Alipour, F., Scherer, R. C. & Finnegan, E. M. Pressure-flow relationships during phonation as a function of adduction. *J Voice* 11, 187-194 (1997).
34. Titze, I. R. in *Vocal physiology: voice production mechanisms and functions*. (Fujimura, O.) 227-238 (Raven Press, 1988).
35. Jiang, J. J. & Titze, I. R. A methodological study of hemilaryngeal phonation. *Laryngoscope* 103, 872-882 (1993).
36. Sprecher, A., Olszewski, A., Jiang, J. J. & Zhang, Y. Updating signal typing in voice: addition of type 4 signals. *J Acoust Soc Am* 127, 3710-3716 (2010).
37. Titze, I. R. *Workshop on acoustic voice analysis: summary statement*. (National Center for Voice and Speech, 1995).
38. Hirano, M. A technique for glottic reconstruction following vertical partial laryngectomy. *Auris Nasus Larynx* 5, 63-70 (1978).
39. Wang, Z., Pankratov, M. M., Rebeiz, E. E., Perrault, D. F. & Shapshay, S. M. Endoscopic diode laser welding of mucosal grafts on the larynx: a new technique. *Laryngoscope* 105, 49-52 (1995).
40. Finkelhor, B. J., Titze, I. R. & Durham, P. R. The effect of viscosity changes in the vocal folds on the range of oscillation. *J Voice* 1, 320-325 (1988).
41. Hanson, S. E. et al. Characterization of mesenchymal stem cells from human vocal fold fibroblasts. *Laryngoscope* 120, 546-551 (2010).
42. Shultz, L. D., Brehm, M. A., Garcia-Martinez, J. V. & Greiner, D. L. Humanized mice for immune system investigation: progress, promise and challenges. *Nat Rev Immunol* 12, 786-798 (2012).
43. Abou Neel, E. A. et al. Collagen—emerging collagen based therapies hit the patient. *Adv Drug Deliv Rev* 65, 429-456 (2013).
44. Svensson, B. et al. Injection of human mesenchymal stem cells improves healing of scarred vocal folds: analysis using a xenograft model. *Laryngoscope* 120, 1370-1375 (2010).
45. Svensson, B. et al. Injection of human mesenchymal stem cells improves healing of vocal folds after scar excision-A xenograft analysis. *Laryngoscope* 121, 2185-2190 (2011).
46. Quinchia Johnson, B. H., Fox, R., Chen, X. & Thibeault, S. L. Tissue regeneration of the vocal fold using bone marrow mesenchymal stem cells and synthetic extracellular matrix injections in rats. *Laryngoscope* 120, 537-545 (2010).
47. Park, H. et al. Three-dimensional hydrogel model using adipose-derived stem cells for vocal fold augmentation. *Tissue Eng Part A* 16, 535-543 (2010).
48. Chhetri, D. K. & Berke, G. S. Injection of cultured autologous fibroblasts for human vocal fold scars. *Laryngoscope* 121, 785-792 (2011).
49. Titze, I. R. et al. Design and validation of a bioreactor for engineering vocal fold tissues under combined tensile and vibrational stresses. *J Biomech* 37, 1521-1529 (2004).
50. Kutty, J. K. & Webb, K. Vibration stimulates vocal mucosa-like matrix expression by hydrogel-encapsulated fibroblasts. *J Tissue Eng Regen Med* 4, 62-72 (2010).
51. Gaston, J., Quinchia Rios, B., Bartlett, R. S., Berchtold, C. M. & Thibeault, S. L. The response of vocal fold fibroblasts and mesenchymal stromal cells to vibration. *PLoS One* 7, e30965 (2012).
52. Hartnick, C. J., Rehbar, R. & Prasad, V. Development and maturation of the pediatric human vocal fold lamina propria. *Laryngoscope* 115, 4-15 (2005).
53. Welham, N. V., Chang, Z., Smith, L. M. & Frey, B. L. Proteomic analysis of a decellularized human vocal fold mucosa scaffold using 2D electrophoresis and high-resolution mass spectrometry. *Biomaterials* 34, 669-676 (2013).
54. Yaghi, A., Zaman, A. & Dolovich, M. Primary human bronchial epithelial cells grown from explants. *J Vis Exp* e1789 (2010). doi:10.3791/1789
55. Lincoln, D. W., Whitney, R. G. & Smith, J. R. In vitro proliferation and lifespan of bovine aorta endothelial cells: response to conditioned media. *J Cell Sci* 56, 281-292 (1982).
56. Welham, N. V. et al. A rat excised larynx model of vocal fold scar. *J Speech Lang Hear Res* 52, 1008-1020 (2009).
57. Larsson, H., Hertegård, S., Lindestad, P.-Å. & Hammarberg, B. Vocal fold vibrations: high-speed imaging, kymography, and acoustic analysis: a preliminary report. *Laryngoscope* 110, 2117-2122 (2000).
58. Chen, X., Bless, D. M. & Yan, Y. A segmentation scheme based on rayleigh distribution model for extracting glottal waveform from high-speed laryngeal images. *Conf Proc IEEE Eng Med Biol Soc* 6, 6269-6272 (2005).
59. Jiang, J. J. et al. Quantitative study of mucosal wave via videokymography in canine larynges. *Laryngoscope* 110, 1567-1573 (2000).
60. Jiang, J. J., Zhang, Y., Kelly, M. P., Bieging, E. T. & Hoffman, M. R. An automatic method to quantify mucosal waves via videokymography. *Laryngoscope* 118, 1504-1510 (2008).
61. Zhang, Y., McGilligan, C., Zhou, L., Vig, M. & Jiang, J. J. Nonlinear dynamic analysis of voices before and after surgical excision of vocal polyps. *J Acoust Soc Am* 115, 2270-2277 (2004).
62. Wiśniewski, J. R., Zougman, A., Nagaraj, N. & Mann, M. Universal sample preparation method for proteome analysis. *Nat Methods* 6, 359-362 (2009).
63. Sheynkman, G. M., Shortreed, M. R., Frey, B. L. & Smith, L. M. Discovery and mass spectrometric analysis of novel splice-junction peptides using RNA-Seq. *Mol Cell Proteomics* 12, 2341-2353 (2013).
64. Desiere, F. et al. The PeptideAtlas project. *Nucleic Acids Res* 34, D655-8 (2006).
65. Benjamini, Y. & Hochberg, Y. Controlling the false discovery rate: a practical and powerful approach to multiple testing. *J R Stat Soc B* 57, 289-300 (1995).
66. Maere, S., Heymans, K. & Kuiper, M. BiNGO: a Cytoscape plugin to assess overrepresentation of gene ontology categories in biological networks. *Bioinformatics* 21, 3448-3449 (2005).
67. Supek, F., Bošnjak, M., Škunca, N. & Šmuc, T. REVIGO summarizes and visualizes long lists of gene ontology terms. *PLoS One* 6, e21800 (2011).
68. Cline, M. S. et al. Integration of biological networks and gene expression data using Cytoscape. *Nat Protoc* 2, 2366-2382 (2007).

TABLE 1

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| | | | Scaffold only | | | | |
| P02454 | Collagen alpha-1(I) chain | COL1A1 | *Rattus norvegicus* | 14562.52 | 74.88 | 79 | 16858 |
| P02466 | Collagen alpha-2(I) chain | COL1A2 | *Rattus norvegicus* | 10402.75 | 69.39 | 68 | 8327 |
| P13941 | Collagen alpha-1 (III) chain | COL3A1 | *Rattus norvegicus* | 475.78 | 11.41 | 8 | 456 |
| Q29RW1 | Myosin-4 | MYH4 | *Rattus norvegicus* | 414.90 | 15.58 | 15 | 101 |
| P02770 | Serum albumin | ALB | *Rattus norvegicus* | 285.30 | 25.99 | 14 | 74 |
| P50609 | Fibromodulin | FMOD | *Rattus norvegicus* | 255.20 | 19.68 | 5 | 58 |
| P04937 | Fibronectin | FN1 | *Rattus norvegicus* | 167.39 | 5.41 | 9 | 45 |
| P68035 | Actin, alpha cardiac muscle 1 | ACTC1 | *Rattus norvegicus* | 158.07 | 19.63 | 3 | 39 |
| P60711 | Actin, cytoplasmic 1 | ACTB | *Rattus norvegicus* | 113.85 | 20.53 | 3 | 28 |
| P01026 | Complement C3 | C3 | *Rattus norvegicus* | 89.00 | 2.53 | 3 | 25 |
| Q6IFW6 | Keratin, type I cytoskeletal 10 | KRT10 | *Rattus norvegicus* | 81.38 | 9.89 | 5 | 24 |
| P11517 | Hemoglobin subunit beta-2 | HBB2 | *Rattus norvegicus* | 66.34 | 40.14 | 5 | 23 |
| P00564 | Creatine kinase M-type | CKM | *Rattus norvegicus* | 92.71 | 20.21 | 6 | 22 |
| Q01129 | Decorin | DCN | *Rattus norvegicus* | 78.80 | 15.25 | 4 | 21 |
| P04797 | Glyceraldehyde-3-phosphate dehydrogenase | GAPDH | *Rattus norvegicus* | 42.24 | 14.71 | 3 | 19 |
| P63018 | Heat shock cognate 71 kDa protein | HSPA8 | *Rattus norvegicus* | 70.47 | 7.59 | 5 | 19 |
| Q6IMF3 | Keratin, type II cytoskeletal 1 | KRT1 | *Rattus norvegicus* | 64.27 | 5.60 | 3 | 19 |
| P01946 | Hemoglobin subunit alpha-1/2 | HBA1 | *Rattus norvegicus* | 74.27 | 35.21 | 3 | 17 |
| P47853 | Biglycan | BGN | *Rattus norvegicus* | 50.62 | 8.94 | 2 | 16 |
| P62260 | 14-3-3 protein epsilon | YWHAE | *Rattus norvegicus* | 44.11 | 8.63 | 2 | 15 |
| Q68FP1 | Gelsolin | GSN | *Rattus norvegicus* | 49.45 | 3.85 | 2 | 13 |
| Q6P6Q2 | Keratin, type II cytoskeletal 5 | KRT5 | *Rattus norvegicus* | 42.90 | 4.17 | 2 | 13 |
| P04462 | Myosin-8 (Fragment) | MYH8 | *Rattus norvegicus* | 32.58 | 19.07 | 2 | 11 |
| Q9Z1P2 | Alpha-actinin-1 | ACTN1 | *Rattus norvegicus* | 33.89 | 5.16 | 4 | 11 |
| Q62812 | Myosin-9 | MYH9 | *Rattus norvegicus* | 33.15 | 3.21 | 5 | 10 |
| P07335 | Creatine kinase B-type | CKB | *Rattus norvegicus* | 24.32 | 5.51 | 2 | 9 |
| P34058 | Heat shock protein HSP 90-beta | HSP90AB1 | *Rattus norvegicus* | 21.83 | 5.39 | 3 | 7 |
| P48037 | Annexin A6 | ANXA6 | *Rattus norvegicus* | 13.18 | 4.31 | 3 | 5 |
| Q63041 | Alpha-1-macroglobulin | A1M | *Rattus norvegicus* | 20.75 | 2.27 | 2 | 5 |
| P11980 | Pyruvate kinase isozymes M1/M2 | PKM | *Rattus norvegicus* | 17.00 | 7.53 | 2 | 4 |
| B0BNI5 | Olfactomedin-like protein 3 | OLFML3 | *Rattus norvegicus* | 15.93 | 9.85 | 2 | 3 |
| P04642 | L-lactate dehydrogenase A chain | LDHA | *Rattus norvegicus* | 11.00 | 7.53 | 2 | 3 |
| | | | VFF in scaffold | | | | |
| P02454 | Collagen alpha-1(I) chain | COL1A1 | *Rattus norvegicus* | 19037.82 | 70.06 | 82 | 23558 |
| P02452 | Collagen alpha-1(I) chain | COL1A1 | *Homo sapiens* | 9435.37 | 51.91 | 54 | 12141 |
| P02466 | Collagen alpha-2(I) chain | COL1A2 | *Rattus norvegicus* | 13087.50 | 67.49 | 67 | 11240 |
| P08123 | Collagen alpha-2(I) chain | COL1A2 | *Homo sapiens* | 3527.28 | 43.70 | 37 | 3038 |
| Q09666 | Neuroblast differentiation-associated protein AHNAK | AHNAK | *Homo sapiens* | 3901.70 | 45.53 | 121 | 1159 |
| P02751 | Fibronectin | FN1 | *Homo sapiens* | 2589.18 | 36.92 | 59 | 665 |
| P12111 | Collagen alpha-3(VI) chain | COL6A3 | *Homo sapiens* | 1935.31 | 24.99 | 59 | 587 |
| P21333 | Filamin-A | FLNA | *Homo sapiens* | 2125.93 | 37.97 | 65 | 524 |
| P08670 | Vimentin | VIM | *Homo sapiens* | 1767.03 | 59.23 | 34 | 518 |
| P60711 | Actin, cytoplasmic 1 | ACTB | *Rattus norvegicus* | 1522.82 | 63.20 | 16 | 411 |
| P35579 | Myosin-9 | MYH9 | *Homo sapiens* | 1580.80 | 37.96 | 56 | 396 |
| P12109 | Collagen alpha-1(VI) chain | COL6A1 | *Homo sapiens* | 901.30 | 23.35 | 15 | 378 |
| P14618 | Pyruvate kinase PKM | PKM | *Homo sapiens* | 1333.05 | 59.70 | 26 | 356 |
| P07355 | Annexin A2 | ANXA2 | *Homo sapiens* | 1335.76 | 58.11 | 20 | 350 |
| Q15149 | Plectin | PLEC | *Homo sapiens* | 1144.56 | 19.75 | 69 | 329 |
| P02545 | Prelamin-A/C [Cleaved into: Lamin-A/C] | LMNA | *Homo sapiens* | 1094.53 | 54.67 | 35 | 326 |
| P02458 | Collagen alpha-1(II) chain | COL2A1 | *Homo sapiens* | 430.06 | 7.87 | 5 | 305 |
| P07437 | Tubulin beta chain | TUBB | *Homo sapiens* | 1015.36 | 66.89 | 21 | 281 |
| Q00610 | Clathrin heavy chain 1 | CLTC | *Homo sapiens* | 1081.13 | 27.22 | 36 | 268 |
| O43707 | Alpha-actinin-4 | ACTN4 | *Homo sapiens* | 1000.62 | 51.37 | 36 | 265 |
| P68371 | Tubulin beta-4B chain | TUBB4B | *Homo sapiens* | 967.12 | 66.74 | 21 | 262 |
| P11021 | 78 kDA glucose-regulated protein | HSPA5 | *Homo sapiens* | 866.31 | 33.33 | 18 | 250 |
| P08238 | Heat Shock protein HSP 90-beta | HSP90AB1 | *Homo sapiens* | 880.50 | 33.01 | 18 | 238 |
| P11142 | Heat shock cognate 71 kDa protein | HSPA8 | *Homo sapiens* | 853.97 | 39.01 | 22 | 236 |
| P04408 | Glyceraldehyde-3-phosphate dehydrogenase | GAPDH | *Homo sapiens* | 790.07 | 46.87 | 12 | 235 |
| Q13885 | Tubulin beta-2A chain | TUBB2A | *Homo sapiens* | 780.66 | 56.63 | 18 | 221 |
| P15144 | Aminopeptidase N | ANPEP | *Homo sapiens* | 776.75 | 25.54 | 23 | 217 |
| P13941 | Collagen alpha-1(III) chain | COL3A1 | *Rattus norvegicus* | 235.58 | 12.03 | 11 | 217 |
| P12814 | Alpha-actinin-1 | ACTN1 | *Homo sapiens* | 771.27 | 36.77 | 27 | 215 |
| P68363 | Tubulin alpha-1B chain | TUBA1B | *Homo sapiens* | 753.76 | 50.55 | 18 | 215 |
| Q13509 | Tubulin beta-3 chain | TUBB3 | *Homo sapiens* | 668.44 | 36.89 | 14 | 201 |
| P00558 | Phosphoglycerate kinase 1 | PGK1 | *Homo sapiens* | 755.19 | 52.04 | 17 | 199 |
| P04083 | Annexin A1 | ANXA1 | *Homo sapiens* | 758.14 | 52.60 | 16 | 192 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P68104 | Elongation factor 1-alpha 1 | EEF1A1 | *Homo sapiens* | 761.73 | 33.98 | 11 | 188 |
| P68035 | Actin, alpha cardiac muscle 1 | ACTC1 | *Rattus norvegicus* | 611.13 | 32.89 | 10 | 188 |
| P07900 | Heat shock protein HSP 90-alpha | HSP90AA1 | *Homo sapiens* | 649.34 | 21.31 | 12 | 183 |
| P05539 | Collagen alpha-1(II) chain | COL2A1 | *Rattus norvegicus* | 293.86 | 5.50 | 4 | 177 |
| Q9Y490 | Talin-1 | TLN1 | *Homo sapiens* | 638.77 | 19.91 | 31 | 168 |
| P06576 | ATP synthase subunit beta, mitochondrial | ATP5B | *Homo sapiens* | 584.55 | 39.89 | 14 | 161 |
| P06733 | Alpha-enolase | ENO1 | *Homo sapiens* | 521.99 | 39.86 | 13 | 147 |
| P14625 | Endoplasmin | HSP90B1 | *Homo sapiens* | 515.39 | 25.28 | 15 | 144 |
| P08758 | Annexin A5 | ANXA5 | *Homo sapiens* | 478.42 | 55.31 | 15 | 141 |
| Q14764 | Major vault protein | MVP | *Homo sapiens* | 443.98 | 31.35 | 19 | 132 |
| P50454 | Serpin H1 | SERPINH1 | *Homo sapiens* | 533.29 | 41.15 | 13 | 131 |
| P04264 | Keratin, type II cytoskeletal 1 | KRT1 | *Homo sapiens* | 429.54 | 28.88 | 18 | 125 |
| P07585 | Decorin | DCN | *Homo sapiens* | 397.67 | 43.18 | 12 | 123 |
| Q9BUF5 | Tubulin beta-6 chain | TUBB6 | *Homo sapiens* | 397.03 | 33.86 | 13 | 122 |
| P46940 | Ras GTPase-activating-like protein IQGAP1 | IQGAP1 | *Homo sapiens* | 441.43 | 19.01 | 21 | 121 |
| P62805 | Histone H4 | HIST1H4A | *Homo sapiens* | 385.21 | 51.46 | 6 | 116 |
| P04075 | Fructose-bisphosphate aldolase A | ALDOA | *Homo sapiens* | 494.95 | 57.69 | 14 | 114 |
| O43852 | Calumenin | CALU | *Homo sapiens* | 447.18 | 44.76 | 14 | 114 |
| O60814 | Histone H2B type 1-K | HIST1H2BK | *Homo sapiens* | 314.19 | 34.92 | 4 | 112 |
| P08133 | Annexin A6 | ANXA6 | *Homo sapiens* | 404.62 | 33.73 | 18 | 111 |
| P11216 | Glycogen phosphorylase, brain form | PYGB | *Homo sapiens* | 415.67 | 28.23 | 19 | 110 |
| P62937 | Peptidyl-prolyl cis-trans isomerase A | PPIA | *Homo sapiens* | 393.57 | 55.76 | 9 | 110 |
| Q07065 | Cytoskeleton-associated protein 4 | CKAP4 | *Homo sapiens* | 378.99 | 38.70 | 18 | 105 |
| P63104 | 14-3-3 protein zeta/delta | YWHAZ | *Homo sapiens* | 352.91 | 37.14 | 8 | 103 |
| Q14315 | Filamin-C | FLNC | *Homo sapiens* | 456.37 | 11.12 | 18 | 101 |
| P07237 | protein disulfide-isomerase | P4HB | *Homo sapiens* | 383.52 | 35.63 | 15 | 101 |
| P00338 | L-lactate dehydrogenase A chain | LDHA | *Homo sapiens* | 340.74 | 37.95 | 11 | 101 |
| P13639 | Elongation factor 2 | EEF2 | *Homo sapiens* | 332.84 | 28.90 | 21 | 101 |
| P18669 | Phosphoglycerate mutase 1 | PGAM1 | *Homo sapiens* | 324.02 | 44.88 | 9 | 99 |
| P11413 | Glucose-6-phosphate 1-dehydrogenase | G6PD | *Homo sapiens* | 375.31 | 27.57 | 10 | 98 |
| P67936 | Tropomyosin alpha-4 chain | TPM4 | *Homo sapiens* | 340.33 | 47.58 | 13 | 98 |
| P60174 | Triosephosphate isomerase | TPI1 | *Homo sapiens* | 367.86 | 61.19 | 12 | 97 |
| P12110 | Collagen alpha-2(VI) chain | COL6A2 | *Homo sapiens* | 329.15 | 22.37 | 17 | 96 |
| P18206 | Vinculin | VCL | *Homo sapiens* | 294.56 | 26.81 | 21 | 94 |
| Q06830 | Peroxiredoxin-1 | PRDX1 | *Homo sapiens* | 397.52 | 52.26 | 9 | 93 |
| Q6NZI2 | Polymerase I and transcript release factor | PTRF | *Homo sapiens* | 339.44 | 28.21 | 9 | 92 |
| P10809 | 60 kDa heat shock protein, mitochondrial | HSPD1 | *Homo sapiens* | 336.47 | 28.27 | 13 | 91 |
| P25705 | ATP synthase subunit alpha, mitochondrial | ATP5A1 | *Homo sapiens* | 321.89 | 20.43 | 8 | 91 |
| P08107 | Heat shock 70 kDa protein 1A/1B | HSPA1A | *Homo sapiens* | 300.85 | 25.12 | 11 | 87 |
| P62260 | 14-3-3 protein epsilon | YWHAE | *Rattus norvegicus* | 264.94 | 40.00 | 8 | 87 |
| P06396 | Gelsolin | GSN | *Homo sapiens* | 359.55 | 21.10 | 12 | 86 |
| P27348 | 14-3-3 protein theta | YWHAQ | *Homo sapiens* | 294.97 | 38.37 | 7 | 86 |
| P30101 | Protein disulfide-isomerase A3 | PDIA3 | *Homo sapiens* | 293.81 | 28.12 | 11 | 86 |
| Q99536 | Synaptic vesicle membrane protein VAT-1 homolog | VAT1 | *Homo sapiens* | 294.87 | 29.77 | 7 | 85 |
| P23284 | Peptidyl-prolyl cis-trans isomerase B | PPIB | *Homo sapiens* | 268.90 | 40.28 | 9 | 85 |
| O00299 | Chloride intracellular channel protein 1 | CLIC1 | *Homo sapiens* | 342.42 | 63.90 | 11 | 84 |
| P09382 | Galectin-1 | LGALS1 | *Homo sapiens* | 300.65 | 46.67 | 5 | 84 |
| P02768 | Serum albumin | ALB | *Homo sapiens* | 319.64 | 6.73 | 4 | 83 |
| P55072 | Transitional endoplasmic reticulum ATPase | VCP | *Homo sapiens* | 344.40 | 26.30 | 14 | 82 |
| P29401 | Transketolase | TKT | *Homo sapiens* | 331.79 | 28.09 | 12 | 81 |
| P13489 | Ribonuclease inhibitor | RNH1 | *Homo sapiens* | 320.57 | 33.84 | 10 | 80 |
| P02461 | Collagen alpha-1(III) chain | COL3A1 | *Homo sapiens* | 119.06 | 9.75 | 9 | 77 |
| Q13813 | Spectrin alpha chain, non-erythrocytic 1 | SPTAN1 | *Homo sapiens* | 287.37 | 12.46 | 21 | 76 |
| Q16555 | Dihydropyrimidinase-related protein 2 | DPYSL2 | *Homo sapiens* | 285.66 | 35.14 | 12 | 74 |
| P38646 | Stress-70 protein, mitochondrial | HSPA9 | *Homo sapiens* | 275.92 | 17.23 | 9 | 74 |
| Q04828 | Aldo-keto reductase family 1 member C1 | AKR1C1 | *Homo sapiens* | 282.79 | 35.91 | 8 | 73 |
| Q9NZN4 | EH domain-containing protein 2 | EHD2 | *Homo sapiens* | 275.71 | 38.31 | 15 | 73 |
| P27797 | Calreticulin | CALR | *Homo sapiens* | 295.72 | 37.41 | 9 | 72 |
| P63244 | Guanine nucleotide-binding protein subunit | GNB2L1 | *Homo sapiens* | 254.12 | 55.84 | 11 | 72 |
| Q99715 | Collagen alpha-1(XII) chain | COL12A1 | *Homo sapiens* | 251.62 | 8.23 | 18 | 72 |
| P49368 | T-complex protein 1 subunit gamma | CCT3 | *Homo sapiens* | 251.20 | 29.17 | 11 | 72 |
| P53396 | ATP-citrate synthase | ACLY | *Homo sapiens* | 254.08 | 16.71 | 12 | 71 |
| P07195 | L-lactate dehydrogenase B chain | LDHB | *Homo sapiens* | 228.06 | 37.43 | 10 | 70 |
| P49327 | Fatty acid synthase | FASN | *Homo sapiens* | 276.72 | 11.87 | 18 | 69 |
| P23528 | Cofilin-1 | CFL1 | *Homo sapiens* | 283.28 | 56.02 | 8 | 68 |
| Q14204 | Cytoplasmic dynein 1 heavy chain 1 | DYNC1H1 | *Homo sapiens* | 240.66 | 6.03 | 21 | 67 |
| P51149 | Ras-related protein Rab-7a | RAB7A | *Homo sapiens* | 226.35 | 47.83 | 9 | 66 |
| P09211 | Glutathione S-transferase P | GSTP1 | *Homo sapiens* | 284.60 | 48.57 | 6 | 65 |
| P02765 | Alpha-2-HS-glycoprotein | AHSG | *Homo sapiens* | 248.58 | 5.45 | 3 | 64 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
| --- | --- | --- | --- | --- | --- | --- | --- |
| O60664 | Perilipin-3 | PLIN3 | *Homo sapiens* | 227.81 | 30.88 | 8 | 62 |
| P37802 | Transgelin-2 | TAGLN2 | *Homo sapiens* | 217.26 | 41.21 | 7 | 59 |
| P21980 | Protein-glutamine gamma-glutamyltransferase 2 | TGM2 | *Homo sapiens* | 200.88 | 13.54 | 6 | 58 |
| P08865 | 40S ribosomal protein SA | RPSA | *Homo sapiens* | 228.76 | 31.86 | 7 | 57 |
| Q03135 | Caveolin-1 | CAV1 | *Homo sapiens* | 206.84 | 63.48 | 9 | 57 |
| P40926 | Malate dehydrogenase, mitochondrial | MDH2 | *Homo sapiens* | 223.19 | 36.68 | 9 | 56 |
| P27824 | Calnexin | CANX | *Homo sapiens* | 209.31 | 15.37 | 6 | 56 |
| P60660 | Myosin light polypeptide 6 | MYL6 | *Homo sapiens* | 179.26 | 39.07 | 5 | 56 |
| P11766 | Alcohol dehydrogenase class-3 | ADH5 | *Homo sapiens* | 256.32 | 22.99 | 6 | 55 |
| P31946 | 14-3-3 protein beta/alpha | YWHAB | *Homo sapiens* | 197.15 | 28.46 | 5 | 55 |
| P04792 | Heat Shock protein beta-1 | HSPB1 | *Homo sapiens* | 193.74 | 49.76 | 7 | 55 |
| P07737 | Profilin-1 | PFN1 | *Homo sapiens* | 166.70 | 63.57 | 7 | 55 |
| P21796 | Voltage-dependent anion-selective channel protein 1 | VDAC1 | *Homo sapiens* | 235.02 | 27.21 | 6 | 54 |
| P05387 | 60S acidic ribosomal protein P2 | RPLP2 | *Homo sapiens* | 228.69 | 69.57 | 4 | 54 |
| P16152 | Carbonyl reductase [NADPH] 1 | CBR1 | *Homo sapiens* | 227.14 | 41.16 | 7 | 54 |
| P05388 | 60S acidic ribosomal protein P0 | RPLP0 | *Homo sapiens* | 222.31 | 35.02 | 7 | 54 |
| Q9H299 | SH3 domain-binding glutamic acid-rich-like protein 3 | SH3BGRL3 | *Homo sapiens* | 199.84 | 31.18 | 3 | 54 |
| Q15084 | Protein disulfide-isomerase A6 | PDIA6 | *Homo sapiens* | 196.61 | 32.50 | 9 | 54 |
| O75083 | WD repeat-containing protein 1 | WDR1 | *Homo sapiens* | 275.17 | 26.57 | 8 | 53 |
| P17301 | Integrin alpha-2 | ITGA2 | *Homo sapiens* | 197.72 | 11.52 | 9 | 53 |
| P46821 | Microtubule-associated protein 1B | MAP1B | *Homo sapiens* | 180.13 | 9.08 | 14 | 52 |
| P61158 | Actin-related protein 3 | ACTR3 | *Homo sapiens* | 222.55 | 37.80 | 10 | 51 |
| P26038 | Moesin | MSN | *Homo sapiens* | 180.77 | 19.83 | 12 | 51 |
| P35237 | Serpin B6 | SERPINB6 | *Homo sapiens* | 176.70 | 26.06 | 8 | 51 |
| P35908 | Keratin, type II cytoskeletal 2 epidermal | KRT2 | *Homo sapiens* | 168.33 | 22.54 | 11 | 51 |
| P00387 | NADH-cytochrome b5 reductase 3 | CYB5R3 | *Homo sapiens* | 188.27 | 31.56 | 7 | 50 |
| P61981 | 14-3-3 protein gamma | YWHAG | *Homo sapiens* | 172.74 | 24.70 | 5 | 50 |
| Q15365 | Poly(rC)-binding protein 1 | PCBP1 | *Homo sapiens* | 172.07 | 32.02 | 6 | 50 |
| P13645 | Keratin, type I cytoskeletal 10 | KRT10 | *Homo sapiens* | 165.38 | 29.28 | 12 | 50 |
| Q14697 | Neutral alpha-glucosidase AB | GANAB | *Homo sapiens* | 234.90 | 10.59 | 6 | 49 |
| Q01082 | Spectrin beta chain, non-erythrocytic 1 | SPTBN1 | *Homo sapiens* | 162.63 | 10.24 | 16 | 49 |
| Q9NZM1 | Myoferlin | MYOF | *Homo sapiens* | 184.03 | 9.70 | 13 | 48 |
| P22314 | Ubiquitin-like modifier-activating enzyme 1 | UBA1 | *Homo sapiens* | 182.43 | 15.03 | 11 | 48 |
| Q01518 | Adenylyl cyclase-associated protein 1 | CAP1 | *Homo sapiens* | 174.85 | 17.47 | 7 | 48 |
| Q15019 | Septin-2 | 41884 | *Homo sapiens* | 171.34 | 38.23 | 8 | 48 |
| P22626 | Heterogeneous nuclear ribonucleoproteins A2/B1 | HNRNPA2B1 | *Homo sapiens* | 156.70 | 20.11 | 6 | 48 |
| P23396 | 40S ribosomal protein S3 | RPS3 | *Homo sapiens* | 139.84 | 38.68 | 8 | 48 |
| P04843 | Dolichyl-diphosphooligosaccharide-protein glycosyltransferase subunit 1 | RPN1 | *Homo sapiens* | 185.20 | 23.56 | 9 | 47 |
| Q96AG4 | Leucine-rich repeat-containing protein 59 | LRRC59 | *Homo sapiens* | 172.33 | 23.45 | 5 | 47 |
| P21810 | Biglycan | BGN | *Homo sapiens* | 183.82 | 28.80 | 9 | 46 |
| P61978 | Heterogeneous nuclear ribonucleoprotein K | HNRNPK | *Homo sapiens* | 175.85 | 28.08 | 9 | 46 |
| P61204 | ADP-ribosylation factor 3 | ARF3 | *Homo sapiens* | 150.47 | 38.67 | 6 | 46 |
| P30050 | 60S ribosomal protein L12 | RPL12 | *Homo sapiens* | 168.79 | 54.55 | 6 | 45 |
| P30086 | Phosphatidylethanolamine-binding protein 1 | PEBP1 | *Homo sapiens* | 155.97 | 50.27 | 5 | 45 |
| P26641 | Elongation factor 1-gamma | EEF1G | *Homo sapiens* | 164.58 | 21.97 | 7 | 44 |
| P12882 | Myosin-1 | MYH1 | *Homo sapiens* | 160.33 | 8.92 | 12 | 44 |
| P62241 | 40S ribosomal protein S8 | RPS8 | *Homo sapiens* | 149.78 | 32.69 | 5 | 44 |
| P62424 | 60S ribosomal protein L7a | RPL7A | *Homo sapiens* | 144.33 | 18.42 | 5 | 44 |
| Q96D15 | Reticulocalbin-3 | RCN3 | *Homo sapiens* | 177.77 | 21.95 | 4 | 43 |
| P36578 | 60S ribosomal protein L4 | RPL4 | *Homo sapiens* | 136.85 | 13.35 | 5 | 43 |
| P30041 | Peroxiredoxin-6 | PRDX6 | *Homo sapiens* | 134.28 | 41.07 | 8 | 43 |
| Q92928 | Putative Ras-related protein Rab-1C | RAB1C | *Homo sapiens* | 129.95 | 22.89 | 4 | 43 |
| P04844 | Dolichyl-diphosphooligosaccharide--protein glycosyltransferase subunit 2 | RPN2 | *Homo sapiens* | 175.85 | 29.64 | 10 | 42 |
| P17655 | Calpain-2 catalytic subunit | CAPN2 | *Homo sapiens* | 161.98 | 17.43 | 8 | 42 |
| P00367 | Glutamate dehydrogenase 1, mitochondrial | GLUD1 | *Homo sapiens* | 157.44 | 25.63 | 10 | 42 |
| P49748 | Very long-chain specific acyl-CoA dehydrogenase, mitochondrial | ACADVL | *Homo sapiens* | 156.86 | 21.07 | 9 | 42 |
| P07339 | Cathepsin D | CTSD | *Homo sapiens* | 146.93 | 20.63 | 6 | 42 |
| P09525 | Annexin A4 | ANXA4 | *Homo sapiens* | 135.76 | 31.03 | 8 | 42 |
| Q96AY3 | Peptidyl-prolyl cis-trans isomerase FKBP10 | FKBP10 | *Homo sapiens* | 133.36 | 11.86 | 5 | 42 |
| Q9GZV4 | Eukaryotic translation initiation factor 5A-2 | EIF5A2 | *Homo sapiens* | 164.28 | 19.61 | 3 | 41 |
| P40939 | Trifunctional enzyme subunit alpha, mitochondrial | HADHA | *Homo sapiens* | 159.99 | 17.96 | 8 | 41 |
| O60701 | UDP-glucose 6-dehydrogenase | UGDH | *Homo sapiens* | 145.28 | 25.71 | 9 | 41 |
| P02538 | Keratin, type II cytoskeletal 6A | KRT6A | *Homo sapiens* | 139.17 | 26.77 | 13 | 41 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P18085 | ADP-ribosylation factor 4 | ARF4 | *Homo sapiens* | 122.95 | 48.89 | 8 | 41 |
| P24534 | Elongaton factor 1-beta | EEF1B2 | *Homo sapiens* | 172.02 | 20.44 | 3 | 40 |
| P68871 | Hemoglobin subunit beta | HBB | *Homo sapiens* | 134.50 | 38.78 | 5 | 40 |
| P50990 | T-complex protein 1 subunit theta | CCT8 | *Homo sapiens* | 134.31 | 16.97 | 7 | 40 |
| P12236 | ADP/ATP translocase 3 | SLC25A6 | *Homo sapiens* | 112.19 | 27.85 | 8 | 40 |
| P09972 | Fructose-bisphosphate aldolase C | ALDOC | *Homo sapiens* | 171.14 | 18.41 | 4 | 38 |
| P22392 | Nucleoside diphosphate kinase B | NME2 | *Homo sapiens* | 130.86 | 34.21 | 4 | 38 |
| P60842 | Eukaryotic initiation factor 4A-I | EIF4A1 | *Homo sapiens* | 119.34 | 13.30 | 4 | 38 |
| P05141 | ADP/ATP translocase 2 | SLC25A5 | *Homo sapiens* | 107.37 | 28.19 | 8 | 38 |
| P04080 | Cystatin-B | CSTB | *Homo sapiens* | 150.19 | 45.92 | 3 | 37 |
| P62158 | Calmodulin | CALM1 | *Homo sapiens* | 149.55 | 29.53 | 4 | 37 |
| P52209 | 6-phosphogluconate dehydrogenase, decarboxylating | PGD | *Homo sapiens* | 146.06 | 18.22 | 6 | 37 |
| P01033 | Metalloproteinase inhibitor 1 | TIMP1 | *Homo sapiens* | 145.27 | 28.02 | 4 | 37 |
| Q86VP6 | Cullin-associated NEDD8-dissociated protein 1 | CAND1 | *Homo sapiens* | 126.64 | 9.02 | 8 | 37 |
| Q07020 | 60S ribosomal protein L18 | RPL18 | *Homo sapiens* | 112.50 | 30.85 | 5 | 37 |
| P60033 | CD81 antigen | CD81 | *Homo sapiens* | 193.33 | 25.00 | 3 | 36 |
| P07858 | Cathepsin B | CTSB | *Homo sapiens* | 176.56 | 23.60 | 5 | 36 |
| Q9Y678 | Coatomer subunit gamma-1 | COPG1 | *Homo sapiens* | 151.53 | 10.41 | 6 | 36 |
| P52907 | F-actin-capping protein subunit alpha-1 | ALB | *Homo sapiens* | 138.39 | 34.62 | 6 | 36 |
| P19105 | Myosin regulatory light chain 12A | CAPZA1 | *Homo sapiens* | 134.09 | 39.18 | 5 | 36 |
| P21589 | 5'-nucleotidase | MYL12A | *Homo sapiens* | 125.92 | 18.82 | 8 | 36 |
| Q96KK5 | Histone H2A type 1-H | NT5E | *Homo sapiens* | 123.16 | 27.34 | 3 | 36 |
| P50995 | Annexin A11 | HIST1H2AH | *Homo sapiens* | 121.26 | 15.84 | 6 | 36 |
| Q969G5 | Protein kinase C delta-binding protein | ANXA11 | *Homo sapiens* | 119.53 | 25.29 | 6 | 36 |
| P52565 | Rho GDP-dissociation inhibitor 1 | PRKCDBP | *Homo sapiens* | 117.26 | 21.08 | 4 | 36 |
| P45880 | Voltage-dependent anion-selective channel protein 2 | ARHGDIA | *Homo sapiens* | 111.78 | 18.03 | 4 | 36 |
| Q96CX2 | BTB/POZ domain-containing protein KCTD12 | VDAC2 | *Homo sapiens* | 111.07 | 14.77 | 4 | 36 |
| P02770 | Serum albumin | KCTD12 | *Rattus norvegicus* | 139.43 | 5.92 | 3 | 36 |
| P62979 | Ubiquitin-40S ribosomal protein S27a | RPS27A | *Homo sapiens* | 119.99 | 33.97 | 4 | 35 |
| P40925 | Malate dehydrogenase, cytoplasmic | MDH1 | *Homo sapiens* | 115.14 | 25.15 | 6 | 35 |
| P05556 | Integrin beta-1 | ITGB1 | *Homo sapiens* | 114.15 | 9.77 | 6 | 35 |
| P50395 | Rab GDP dissociation inhibitor beta | FMOD | *Homo sapiens* | 126.73 | 21.35 | 6 | 34 |
| P61247 | 40S ribosomal protein S3a | GDI2 | *Homo sapiens* | 116.67 | 18.18 | 4 | 34 |
| P07384 | Calpain-1 catalytic subunit | RPS3A | *Homo sapiens* | 114.52 | 7.56 | 4 | 34 |
| P10599 | Thioredoxin | CAPN1 | *Homo sapiens* | 111.79 | 22.86 | 2 | 34 |
| P36955 | Pigment epithelium-derived factor | TXN | *Homo sapiens* | 111.21 | 11.96 | 4 | 34 |
| P07910 | Heterogeneous nuclear ribonucleoproteins C1/C2 | SERPINF1 | *Homo sapiens* | 96.99 | 13.07 | 4 | 34 |
| P50609 | Fibromodulin | HNRNPC | *Rattus norvegicus* | 129.65 | 11.17 | 3 | 34 |
| P62906 | 60S ribosomal protein L10a | RPL10A | *Homo sapiens* | 130.04 | 25.81 | 4 | 33 |
| P62888 | 60S ribosomal protein L30 | RPL30 | *Homo sapiens* | 113.47 | 34.78 | 3 | 33 |
| P51884 | Lumican | LUM | *Homo sapiens* | 107.66 | 24.56 | 6 | 33 |
| Q16658 | Fascin | FSCN1 | *Homo sapiens* | 128.33 | 17.04 | 7 | 32 |
| Q01813 | 6-phosphofructokinase type C | PFKP | *Homo sapiens* | 126.94 | 10.46 | 5 | 32 |
| P69905 | Hemoglobin subunit alpha | HBA1; | *Homo sapiens* | 124.85 | 28.17 | 3 | 32 |
| P04216 | Thy-1 membrane glycoprotein | THY1 | *Homo sapiens* | 121.63 | 24.22 | 3 | 32 |
| P14314 | Glucosidase 2 subunit beta | PRKCSH | *Homo sapiens* | 120.87 | 9.85 | 4 | 32 |
| P23219 | Prostaglandin G/H synthase 1 | PTGS1 | *Homo sapiens* | 120.15 | 12.85 | 5 | 32 |
| Q15293 | Reticulocalbin-1 | RCN1 | *Homo sapiens* | 118.65 | 22.36 | 4 | 32 |
| P04899 | Guanine nucleotide-binding protein G(i) subunit alpha-2 | GNAI2 | *Homo sapiens* | 117.69 | 20.28 | 5 | 32 |
| P78417 | Glutathione S-transferase omega-1 | GSTO1 | *Homo sapiens* | 97.78 | 19.92 | 4 | 32 |
| P55209 | Nucleosome assembly protein 1-like 1 | NAP1L1 | *Homo sapiens* | 125.54 | 14.58 | 4 | 31 |
| P62701 | 40S ribosomal protein S4, X isoform | RPS4X | *Homo sapiens* | 116.91 | 25.10 | 5 | 31 |
| P12956 | X-ray repair cross-complementing protein 6 | XRCC6 | *Homo sapiens* | 94.21 | 12.32 | 6 | 31 |
| Q16851 | UTP--glucose-1-phosphate uridylyltransferase | UGP2 | *Homo sapiens* | 154.66 | 12.60 | 4 | 30 |
| P06744 | Glucose-6-phosphate isomerase | GPI | *Homo sapiens* | 127.61 | 17.74 | 5 | 30 |
| Q9Y696 | Chloride intracellular channel protein 4 | CLIC4 | *Homo sapiens* | 122.96 | 40.32 | 7 | 30 |
| P30153 | Serine/threonine-protein phosphatase 2A 65 kDa regulatory subunit A alpha isoform | PPP2R1A | *Homo sapiens* | 116.53 | 19.52 | 7 | 30 |
| Q9NQC3 | Reticulon-4 | RTN4 | *Homo sapiens* | 105.15 | 9.65 | 6 | 30 |
| P34932 | Heat shock 70 kDa protein 4 | HSPA4 | *Homo sapiens* | 97.65 | 12.86 | 7 | 30 |
| Q15366 | Poly(rC)-binding protein 2 | PCBP2 | *Homo sapiens* | 96.66 | 14.79 | 4 | 30 |
| P83731 | 60S ribosomal protein L24 | DCN | *Homo sapiens* | 90.70 | 20.38 | 3 | 30 |
| P62249 | 40S ribosomal protein S16 | RPL24 | *Homo sapiens* | 85.51 | 22.60 | 3 | 30 |
| Q01129 | Decorin | RPS16 | *Rattus norvegicus* | 90.83 | 22.60 | 7 | 30 |
| P07108 | Acyl-CoA-binding protein | DBI | *Homo sapiens* | 129.14 | 50.57 | 3 | 29 |
| P29373 | Cellular retinoic acid-binding protein 2 | CRABP2 | *Homo sapiens* | 126.14 | 34.78 | 4 | 29 |

TABLE 1-continued

Lists of proteins identified in LC-MS/MS analysis of scaffold only, VFF in
scaffold, VFE on scaffold, engineered VF mucosa and native VF mucosa. Identifications
were based on a 1% false discovery rate. The scaffold was sourced from *Rattus norvegicus*;
VFF, VFE and native VF mucosa were sourced from *Homo sapiens*. Proteins are listed in order
of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P09651 | Heterogeneous nuclear ribonucleoprotein A1 | HNRNPA1 | *Homo sapiens* | 110.16 | 30.11 | 8 | 29 |
| P16070 | CD44 antigen | CD44 | *Homo sapiens* | 108.92 | 3.77 | 2 | 29 |
| O43390 | Heterogeneous nuclear ribonucleoprotein R | HNRNPR | *Homo sapiens* | 103.11 | 9.79 | 5 | 29 |
| P51991 | Heterogeneous nuclear ribonucleoprotein A3 | HNRNPA3 | *Homo sapiens* | 99.86 | 17.20 | 5 | 29 |
| P39019 | 40S ribosomal protein S19 | RPS19 | *Homo sapiens* | 84.77 | 35.86 | 7 | 29 |
| P07686 | Beta-hexosaminidase subunit beta | HEXB | *Homo sapiens* | 78.39 | 7.55 | 4 | 29 |
| Q04446 | 1,4-alpha-glucan-branching enzyme | GBE1 | *Homo sapiens* | 126.14 | 16.95 | 7 | 28 |
| P62829 | 60S ribosomal protein L23 | RPL23 | *Homo sapiens* | 103.56 | 25.00 | 7 | 28 |
| P10909 | Clusterin | CLU | *Homo sapiens* | 97.80 | 14.03 | 4 | 28 |
| P55786 | Puromycin-sensitive aminopeptidase | C3 | *Homo sapiens* | 86.55 | 5.98 | 5 | 28 |
| P00505 | Aspartate aminotransferase, mitochondrial | NPEPPS | *Homo sapiens* | 84.77 | 11.40 | 4 | 28 |
| P01026 | Complement C3 [Cleaved into: Complement C3 beta chain; Complement C3 alpha chain] | GOT2 | *Rattus norvegicus* | 90.69 | 1.74 | 2 | 28 |
| P35527 | Keratin, type I cytoskeletal 9 | KRT9 | *Homo sapiens* | 117.56 | 25.36 | 10 | 27 |
| P13667 | Protein disulfide-isomerase A4 | PDIA4 | *Homo sapiens* | 109.73 | 12.25 | 5 | 27 |
| P50991 | T-complex protein 1 subunit delta | CCT4 | *Homo sapiens* | 108.02 | 10.95 | 4 | 27 |
| Q00839 | Heterogeneous nuclear ribonucleoprotein U | HNRNPU | *Homo sapiens* | 96.33 | 12.97 | 6 | 27 |
| P30044 | Peroxiredoxin-5, mitochondrial | PRDX5 | *Homo sapiens* | 89.27 | 26.17 | 4 | 27 |
| P07602 | Proactivator polypeptide [Cleaved into: Saposin-A] | PSAP | *Homo sapiens* | 78.87 | 10.31 | 5 | 27 |
| P20810 | Calpastatin | CAST | *Homo sapiens* | 119.50 | 10.88 | 4 | 26 |
| P17931 | Galectin-3 | LGALS3 | *Homo sapiens* | 98.39 | 15.20 | 3 | 26 |
| P22105 | Tenascin-X | TNXB | *Homo sapiens* | 96.39 | 4.17 | 8 | 26 |
| P60903 | Protein S100-A10 | S100A10 | *Homo sapiens* | 95.99 | 17.53 | 2 | 26 |
| P62277 | 40S ribosomal protein S13 | RPS13 | *Homo sapiens* | 93.59 | 17.88 | 2 | 26 |
| P23634 | Plasma membrane calcium-transporting ATPase 4 | ATP2B4 | *Homo sapiens* | 93.32 | 6.29 | 5 | 26 |
| P32119 | Peroxiredoxin-2 | PRDX2 | *Homo sapiens* | 89.25 | 14.65 | 3 | 26 |
| P46782 | 40S ribosomal protein S5 [Cleaved into: 40S ribosomal protein S5, N-terminally processed] | RPS5 | *Homo sapiens* | 87.53 | 13.73 | 2 | 26 |
| P19823 | Inter-alpha-trypsin inhibitor heavy chain H2 | ITIH2 | *Homo sapiens* | 86.44 | 3.91 | 3 | 26 |
| Q14974 | Importin subunit beta-1 | KPNB1 | *Homo sapiens* | 82.63 | 13.70 | 8 | 26 |
| P53618 | Coatomer subunit beta | COPB1 | *Homo sapiens* | 81.46 | 12.38 | 8 | 26 |
| P31949 | Protein S100-A11 | S100A11 | *Homo sapiens* | 73.32 | 25.71 | 3 | 26 |
| P59998 | Actin-related protein 2/3 complex subunit 4 | ARPC4 | *Homo sapiens* | 71.67 | 17.86 | 3 | 26 |
| Q7KZF4 | Staphylococcal nuclease domain-containing protein 1 | SND1 | *Homo sapiens* | 100.24 | 8.35 | 5 | 25 |
| P18124 | 60S ribosomal protein L7 | RPL7 | *Homo sapiens* | 89.60 | 16.13 | 3 | 25 |
| Q12797 | Aspartyl/asparaginyl beta-hydroxylase | ASPH | *Homo sapiens* | 83.42 | 10.55 | 5 | 25 |
| Q8NBS9 | Thioredoxin domain-containing protein 5 | TXNDC5 | *Homo sapiens* | 111.81 | 9.26 | 3 | 24 |
| P47756 | F-actin-capping protein subunit beta | CAPZB | *Homo sapiens* | 97.32 | 17.33 | 3 | 24 |
| P47755 | F-actin-capping protein subunit alpha-2 | CAPZA2 | *Homo sapiens* | 93.19 | 28.67 | 5 | 24 |
| P06748 | Nucleophosmin | NPM1 | *Homo sapiens* | 88.64 | 12.24 | 3 | 24 |
| P15531 | Nucleoside diphosphate kinase A | NME1 | *Homo sapiens* | 82.11 | 33.55 | 4 | 24 |
| P01024 | Complement C3 | C3 | *Homo sapiens* | 79.98 | 2.47 | 3 | 24 |
| P53621 | Coatomer subunit alpha | COPA | *Homo sapiens* | 76.36 | 7.76 | 7 | 24 |
| O75915 | PRA1 family protein 3 | ARL6IP5 | *Homo sapiens* | 71.25 | 15.96 | 2 | 24 |
| Q15582 | Transforming growth factor-beta-induced protein ig-h3 | TGFBI | *Homo sapiens* | 71.03 | 7.91 | 4 | 24 |
| P60981 | Destrin | DSTN | *Homo sapiens* | 67.90 | 25.45 | 4 | 24 |
| P02774 | Vitamin D-binding protein | GC | *Homo sapiens* | 116.41 | 6.33 | 2 | 23 |
| P62263 | 40S ribosomal protein S14 | RPS14 | *Homo sapiens* | 90.99 | 27.81 | 3 | 23 |
| P63010 | AP-2 complex subunit beta | AP2B1 | *Homo sapiens* | 87.06 | 8.54 | 5 | 23 |
| O43399 | Tumor protein D54 | TPD52L2 | *Homo sapiens* | 85.22 | 24.27 | 3 | 23 |
| P62826 | GTP-binding nuclear protein Ran | RAN | *Homo sapiens* | 82.88 | 22.69 | 4 | 23 |
| P61106 | Ras-related protein Rab-14 | RAB14 | *Homo sapiens* | 82.68 | 25.58 | 3 | 23 |
| P08134 | Rho-related GTP-binding protein RhoC | RHOC | *Homo sapiens* | 78.51 | 26.94 | 4 | 23 |
| P17980 | 26S protease regulatory subunit 6A | PSMC3 | *Homo sapiens* | 76.14 | 17.08 | 5 | 23 |
| P62879 | Guanine nucleotide-binding protein G(I)/G(S)/G(T) subunit beta-2 | GNB2 | *Homo sapiens* | 69.24 | 15.59 | 5 | 23 |
| Q13838 | Spliceosome RNA helicase DDX39B | DDX39B | *Homo sapiens* | 68.43 | 10.51 | 4 | 23 |
| P02533 | Keratin, type I cytoskeletal 14 | KRT14 | *Homo sapiens* | 64.86 | 17.80 | 9 | 23 |
| O75390 | Citrate synthase, mitochondrial | CS | *Homo sapiens* | 63.78 | 10.09 | 4 | 23 |
| Q92743 | Serine protease HTRA1 | HTRA1 | *Homo sapiens* | 61.31 | 8.75 | 4 | 23 |
| P62269 | 40S ribosomal protein S18 | RPS18 | *Homo sapiens* | 60.45 | 16.45 | 3 | 23 |
| Q07021 | Complement component 1 Q subcomponent-binding protein mitochondrial | C1QBP | *Homo sapiens* | 94.64 | 12.06 | 3 | 22 |
| P62244 | 40S ribosomal protein S15a | RPS15A | *Homo sapiens* | 93.74 | 24.62 | 3 | 22 |
| P13693 | Translationally-controlled tumor protein | TPT1 | *Homo sapiens* | 82.09 | 12.21 | 2 | 22 |
| O60506 | Heterogeneous nuclear ribonucleoprotein Q | SYNCRIP | *Homo sapiens* | 80.19 | 13.16 | 6 | 22 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
| --- | --- | --- | --- | --- | --- | --- | --- |
| Q00325 | Phosphate carrier protein, mitochondrial | SLC25A3 | *Homo sapiens* | 75.91 | 14.64 | 4 | 22 |
| P78527 | DNA-dependent protein kinase catalytic subunit | PRKDC | *Homo sapiens* | 74.42 | 2.06 | 6 | 22 |
| P15880 | 40S ribosomal protein S2 | RPS2 | *Homo sapiens* | 71.50 | 16.04 | 4 | 22 |
| Q96TA1 | Niban-like protein 1 | FAM129B | *Homo sapiens* | 70.01 | 9.79 | 5 | 22 |
| P62857 | 40S ribosomal protein S28 | RPS28 | *Homo sapiens* | 69.54 | 33.33 | 2 | 22 |
| P02788 | Lactotransferrin | LTF | *Homo sapiens* | 61.38 | 4.23 | 3 | 22 |
| P62942 | Peptidyl-prolyl cis-trans isomerase FKBP1A | FKBP1A | *Homo sapiens* | 87.52 | 29.63 | 3 | 21 |
| P15559 | NAD(P)H dehydrogenase [quinone] 1 | NQO1 | *Homo sapiens* | 81.73 | 13.50 | 3 | 21 |
| O00159 | Unconventional myosin-Ic | MYO1C | *Homo sapiens* | 69.32 | 8.18 | 6 | 21 |
| Q9BSJ8 | Extended synaptotagmin-1 | ESYT1 | *Homo sapiens* | 66.23 | 8.70 | 7 | 21 |
| P02787 | Serotransferrin | TF | *Homo sapiens* | 66.03 | 16.76 | 8 | 21 |
| Q8WUM4 | Programmed cell death 6-interacting protein | PDCD6IP | *Homo sapiens* | 64.27 | 7.49 | 4 | 21 |
| P17967 | T-complex protein 1 subunit alpha | TCP1 | *Homo sapiens* | 61.00 | 10.79 | 5 | 21 |
| P16403 | Histone H1.2 | HIST1H1C | *Homo sapiens* | 57.53 | 15.49 | 3 | 21 |
| P05386 | 60S acidic ribosomal protein P1 | RPLP1 | *Homo sapiens* | 110.45 | 57.02 | 3 | 20 |
| P68036 | Ubiquitin-conjugating enzyme E2 L3 | UBE2L3 | *Homo sapiens* | 92.04 | 35.71 | 3 | 20 |
| P25398 | 40S ribosomal protein S12 | RPS12 | *Homo sapiens* | 84.49 | 31.82 | 3 | 20 |
| P31943 | Heterogeneous nuclear ribonucleoprotein H | HNRNPH1 | *Homo sapiens* | 76.64 | 10.02 | 3 | 20 |
| Q99623 | Prohibitin-2 | PHB2 | *Homo sapiens* | 76.40 | 16.72 | 4 | 20 |
| Q07954 | Prolow-density lipoprotein receptor-related protein 1 | LRP1 | *Homo sapiens* | 75.28 | 2.13 | 6 | 20 |
| P12955 | Xaa-Pro dipeptidase | PEPD | *Homo sapiens* | 74.39 | 8.32 | 3 | 20 |
| O95782 | AP-2 complex subunit alpha-1 | AP2A1 | *Homo sapiens* | 71.27 | 5.94 | 4 | 20 |
| P56134 | ATP synthase subunit f, mitochondrial | ATP5J2 | *Homo sapiens* | 61.83 | 25.53 | 2 | 20 |
| P26447 | Protein S100-A4 | S-100A4 | *Homo sapiens* | 61.18 | 28.71 | 3 | 20 |
| P08779 | Keratin, type I cytoskeletal 16 | KRT16 | *Homo sapiens* | 54.25 | 15.01 | 8 | 20 |
| P78371 | T-complex protein 1 subunit beta | CCT2 | *Homo sapiens* | 81.92 | 17.01 | 6 | 19 |
| P62140 | Serine/threonine-protein phosphatase PP1-beta catalytic subunit | PPP1CB | *Homo sapiens* | 67.52 | 21.41 | 6 | 19 |
| P29692 | Elongation factor 1-delta | EEF1D | *Homo sapiens* | 61.11 | 17.08 | 3 | 19 |
| P46783 | 40S ribosomal protein S10 | RPS10 | *Homo sapiens* | 58.94 | 14.55 | 2 | 19 |
| P19338 | Nucleolin | NCL | *Homo sapiens* | 58.45 | 9.30 | 5 | 19 |
| P13797 | Plastin-3 | PLS3 | *Homo sapiens* | 56.74 | 16.67 | 8 | 19 |
| Q6NXT2 | Histone H3.3C | H3F3C | *Homo sapiens* | 54.28 | 11.85 | 2 | 19 |
| P35606 | Coatomer subunit beta' | COPB2 | *Homo sapiens* | 52.01 | 10.82 | 7 | 19 |
| P46781 | 40S ribosomal protein S9 | RPS9 | *Homo sapiens* | 50.85 | 17.53 | 4 | 19 |
| P26599 | Polypyrimidine tract-binding protein 1 | PTBP1 | *Homo sapiens* | 75.12 | 15.63 | 4 | 18 |
| P31939 | Bifunctional purine biosynthesis protein PURH [Includes: Phosphoribosylaminoimidazolecarboxamide formyltransferase] | ATIC | *Homo sapiens* | 68.66 | 8.78 | 4 | 18 |
| P49755 | Transmembrane emp24 domain-containing protein 10 | TMED10 | *Homo sapiens* | 68.15 | 12.79 | 2 | 18 |
| P49411 | Elongation factor Tu, mitochondrial | TUFM | *Homo sapiens* | 66.68 | 18.58 | 5 | 18 |
| P14550 | Alcohol dehydrogenase [NADP(+)] | AKR1A1 | *Homo sapiens* | 63.84 | 13.54 | 4 | 18 |
| Q14195 | Dihydropyrimidinase-related protein 3 | DPYSL3 | *Homo sapiens* | 62.54 | 21.58 | 8 | 18 |
| Q15436 | Protein transport protein Sec23A | SEC23A | *Homo sapiens* | 60.90 | 5.75 | 3 | 18 |
| Q9Y2Q3 | Glutathione S-transferase kappa 1 | GSTK1 | *Homo sapiens* | 59.42 | 23.89 | 4 | 18 |
| Q14108 | Lysosome membrane protein 2 | SCARB2 | *Homo sapiens* | 58.13 | 9.00 | 3 | 18 |
| P48444 | Coatomer subunit delta | ARCN1 | *Homo sapiens* | 56.94 | 6.46 | 3 | 18 |
| P41250 | Glycine-tRNA ligase | GARS | *Homo sapiens* | 55.95 | 7.71 | 4 | 18 |
| Q04760 | Lactoylglutathione lyase | GLO1 | *Homo sapiens* | 54.07 | 19.57 | 3 | 18 |
| P50914 | 60S ribosomal protein L14 | RPL14 | *Homo sapiens* | 53.56 | 15.35 | 3 | 18 |
| P35232 | Prohibitin | PHB | *Homo sapiens* | 53.10 | 12.13 | 3 | 18 |
| P11940 | Polyadenylate-binding protein 1 | PABPC1 | *Homo sapiens* | 49.49 | 7.55 | 4 | 18 |
| Q9H4M9 | EH domain-containing protein 1 | EHD1 | *Homo sapiens* | 79.67 | 12.36 | 4 | 17 |
| Q15185 | Prostaglandin E synthase 3 | PTGES3 | *Homo sapiens* | 73.37 | 24.38 | 3 | 17 |
| Q13492 | Phosphatidylinositol-binding clathrin assembly protein | PICALM | *Homo sapiens* | 61.52 | 4.91 | 2 | 17 |
| P60953 | Cell division control protein 42 homolog | CDC42 | *Homo sapiens* | 61.37 | 20.42 | 3 | 17 |
| P54920 | Alpha-soluble NSF attachment protein | NAPA | *Homo sapiens* | 58.25 | 17.97 | 4 | 17 |
| O00571 | ATP-dependent RNA helicase DDX3X | DDX3X | *Homo sapiens* | 55.60 | 9.67 | 5 | 17 |
| Q13162 | Peroxiredoxin-4 | PRDX4 | *Homo sapiens* | 48.19 | 11.81 | 3 | 17 |
| P61160 | Actin-related protein 2 | ACTR2 | *Homo sapiens* | 44.56 | 17.77 | 6 | 17 |
| P30048 | Thioredoxin-dependent peroxide reductase, mitochondrial | PRDX3 | *Homo sapiens* | 79.84 | 18.75 | 2 | 16 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P62280 | 40S ribosomal protein S11 | RPS11 | *Homo sapiens* | 67.34 | 16.46 | 2 | 16 |
| Q8IUX7 | Adipocyte enhancer-binding protein 1 | AEBP1 | *Homo sapiens* | 65.82 | 5.96 | 4 | 16 |
| P55084 | Trifunctional enzyme subunit beta, mitochondrial | HADHB | *Homo sapiens* | 63.53 | 9.28 | 3 | 16 |
| Q07960 | Rho GTPase-activating protein 1 | ARHGAP1 | *Homo sapiens* | 62.30 | 14.81 | 4 | 16 |
| P98160 | Basement membrane-specific heparan sulfate proteoglycan core protein | HSPG2 | *Homo sapiens* | 61.92 | 1.80 | 5 | 16 |
| P54709 | Sodium/potassium-transporting ATPase subunit beta-3 | ATP1B3 | *Homo sapiens* | 58.07 | 17.20 | 3 | 16 |
| P37837 | Transaldolase | TALDO1 | *Homo sapiens* | 53.35 | 7.12 | 2 | 16 |
| P61224 | Ras-related protein Rap-1b | RAP1B | *Homo sapiens* | 49.98 | 20.65 | 3 | 16 |
| Q14103 | Heterogeneous nuclear ribonucleoprotein D0 | HNRNPD | *Homo sapiens* | 48.34 | 6.76 | 2 | 16 |
| P14866 | Heterogeneous nuclear ribonucleoprotein L | HNRNPL | *Homo sapiens* | 71.48 | 8.66 | 2 | 15 |
| P51636 | Caveolin-2 | CAV2 | *Homo sapiens* | 65.54 | 29.63 | 3 | 15 |
| O15511 | Actin-related protein 2/3 complex subunit 5 | ARPC5 | *Homo sapiens* | 61.90 | 20.53 | 2 | 15 |
| O43242 | 26S proteasome non-ATPase regulatory subunit 3 | PSMD3 | *Homo sapiens* | 61.84 | 5.62 | 2 | 15 |
| Q08211 | ATP-dependent RNA helicase A | DHX9 | *Homo sapiens* | 61.31 | 5.04 | 4 | 15 |
| Q15181 | Inorganic pyrophosphatase | PPA1 | *Homo sapiens* | 60.87 | 23.18 | 4 | 15 |
| P46777 | 60S ribosomal protein L5 | RPL5 | *Homo sapiens* | 60.47 | 19.87 | 4 | 15 |
| P61604 | 10 kDa heat shock protein, mitochondrial | HSPE1 | *Homo sapiens* | 58.06 | 33.33 | 3 | 15 |
| P10620 | Microsomal glutathione S-transferase 1 | MGST1 | *Homo sapiens* | 57.64 | 19.35 | 2 | 15 |
| Q13765 | Nascent polypeptide-associated complex subunit alpha | NACA | *Homo sapiens* | 56.71 | 18.60 | 3 | 15 |
| P17858 | 6-phosphofructokinase, liver type | PFKL | *Homo sapiens* | 55.45 | 6.54 | 3 | 15 |
| Q9P2E9 | Ribosome-binding protein 1 | RRBP1 | *Homo sapiens* | 52.97 | 6.60 | 6 | 15 |
| P16615 | Sarcoplasmic/endoplasmic reticulum calcium ATPase 2 | ATP2A2 | *Homo sapiens* | 52.48 | 5.37 | 4 | 15 |
| P15121 | Aldose reductase | AKR1B1 | *Homo sapiens* | 51.96 | 24.37 | 4 | 15 |
| Q8NC51 | Plasminogen activator inhibitor 1 RNA-binding protein | SERBP1 | *Homo sapiens* | 49.13 | 18.14 | 5 | 15 |
| P51659 | Peroxisomal multifunctional enzyme type 2 | HSD17B4 | *Homo sapiens* | 48.08 | 11.01 | 5 | 15 |
| P10155 | 60 kDa SS-A/Ro ribonucleoprotein | TROVE2 | *Homo sapiens* | 48.07 | 4.46 | 2 | 15 |
| O94979 | Protein transport protein Sec31A | SEC31A | *Homo sapiens* | 47.81 | 4.51 | 4 | 15 |
| P46778 | 60S ribosomal protein L21 | RPL21 | *Homo sapiens* | 46.39 | 27.50 | 3 | 15 |
| P78539 | Sushi repeat-containing protein SRPX | SRPX | *Homo sapiens* | 45.56 | 7.76 | 3 | 15 |
| P51148 | Ras-related protein Rab-5C | RAB5C | *Homo sapiens* | 44.79 | 23.15 | 4 | 15 |
| Q14847 | LIM and SH3 domain protein 1 | LASP1 | *Homo sapiens* | 44.78 | 14.18 | 3 | 15 |
| Q9ULV4 | Coronin-1C | CORO1C | *Homo sapiens* | 44.37 | 8.23 | 3 | 15 |
| O43776 | Asparagine--tRNA ligase, cytoplasmic | NARS | *Homo sapiens* | 43.41 | 8.94 | 4 | 15 |
| Q14152 | Eukaryotic translation initiation factor 3 subunit A | EIF3A | *Homo sapiens* | 42.47 | 3.47 | 4 | 15 |
| P35268 | 60S ribosomal protein L22 | RPL22 | *Homo sapiens* | 41.79 | 18.75 | 2 | 15 |
| P37235 | Hippocalcin-like protein 1 | HPCAL1 | *Homo sapiens* | 41.04 | 23.83 | 4 | 15 |
| P00441 | Superoxide dismutase [Cu—Zn] | SOD1 | *Homo sapiens* | 75.69 | 32.47 | 4 | 14 |
| Q99460 | 26S proteasome non-ATPase regulatory subunit 1 | PSMD1 | *Homo sapiens* | 69.67 | 5.46 | 3 | 14 |
| Q08431 | Lactadherin | MFGE8 | *Homo sapiens* | 67.71 | 8.53 | 2 | 14 |
| O95373 | Importin-7 | IPO7 | *Homo sapiens* | 61.22 | 4.53 | 3 | 14 |
| Q16181 | Septin-7 | 41889 | *Homo sapiens* | 55.03 | 13.50 | 4 | 14 |
| Q13200 | 26S proteasome non-ATPase regulatory subunit 2 | PSMD2 | *Homo sapiens* | 53.05 | 5.18 | 3 | 14 |
| Q9Y265 | RuvB-like 1 | RUVBL1 | *Homo sapiens* | 50.48 | 15.79 | 5 | 14 |
| Q9UBG0 | C-type mannose receptor 2 | MRC2 | *Homo sapiens* | 48.78 | 2.77 | 3 | 14 |
| P51571 | Translocon-associated protein subunit delta | SSR4 | *Homo sapiens* | 44.44 | 24.86 | 3 | 14 |
| Q9H8H3 | Methyltransferase-like protein 7A | METTL7A | *Homo sapiens* | 42.92 | 12.30 | 2 | 14 |
| Q16698 | 2,4-dienoyl-CoA reductase, mitochondrial | DECR1 | *Homo sapiens* | 40.03 | 13.73 | 3 | 14 |
| Q9UHD8 | Septin-9 | 41891 | *Homo sapiens* | 39.86 | 11.60 | 5 | 14 |
| Q9NVA2 | Septin-11 | 41893 | *Homo sapiens* | 38.96 | 11.19 | 4 | 14 |
| Q99829 | Copine-1 | CPNE1 | *Homo sapiens* | 38.95 | 6.33 | 3 | 14 |
| Q92499 | ATP-dependent RNA helicase DDX1 | DDX1 | *Homo sapiens* | 64.96 | 7.43 | 3 | 13 |
| P07099 | Epoxide hydrolase 1 | EPHX1 | *Homo sapiens* | 62.32 | 10.77 | 3 | 13 |
| Q99497 | Protein DJ-1 | PARK7 | *Homo sapiens* | 58.25 | 29.63 | 3 | 13 |
| P40227 | T-complex protein 1 subunit zeta | CCT6A | *Homo sapiens* | 57.05 | 6.97 | 2 | 13 |
| P28838 | Cytosol aminopeptidase | LAP3 | *Homo sapiens* | 51.95 | 12.33 | 4 | 13 |
| Q9UBI6 | Guanine nucleotide-binding protein G(I)/G(S)/G(O) subunit gamma-12 | GNG12 | *Homo sapiens* | 50.08 | 31.94 | 2 | 13 |
| O14818 | Proteasome subunit alpha type-7 | PSMA7 | *Homo sapiens* | 48.17 | 20.56 | 3 | 13 |
| P19367 | Hexokinase-1 | HK1 | *Homo sapiens* | 45.34 | 5.89 | 4 | 13 |
| P39023 | 60S ribosomal protein L3 | RPL3 | *Homo sapiens* | 44.04 | 12.66 | 3 | 13 |
| Q6YHK3 | CD109 antigen | CD109 | *Homo sapiens* | 42.37 | 7.47 | 7 | 13 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P46776 | 60S ribosomal protein L27a | RPL27A | *Homo sapiens* | 39.08 | 14.19 | 2 | 13 |
| Q99584 | Protein S100-A13 | S100A13 | *Homo sapiens* | 39.08 | 23.47 | 2 | 13 |
| Q15836 | Vesicle-associated membrane protein 3 | VAMP3 | *Homo sapiens* | 38.92 | 33.00 | 2 | 13 |
| Q92688 | Acidic leucine-rich nuclear phosphoprotein 32 family member B | ANP32B | *Homo sapiens* | 38.66 | 15.94 | 3 | 13 |
| Q9Y6N5 | Sulfide:quinone oxidoreductase, mitochondrial | SQRDL | *Homo sapiens* | 37.33 | 10.00 | 4 | 13 |
| P62318 | Small nuclear ribonucleoprotein Sm D3 | SNRPD3 | *Homo sapiens* | 34.78 | 15.08 | 2 | 13 |
| P01008 | Antithrombin-III | SERPINC1 | *Homo sapiens* | 45.87 | 4.31 | 2 | 12 |
| P28066 | Proteasome subunit alpha type-5 | PSMA5 | *Homo sapiens* | 43.47 | 22.41 | 3 | 12 |
| O75874 | Isocitrate dehydrogenase [NADP] cytoplasmic | IDH1 | *Homo sapiens* | 41.65 | 10.14 | 3 | 12 |
| P48047 | ATP synthase subunit O, mitochondrial | ATP5O | *Homo sapiens* | 40.13 | 29.11 | 4 | 12 |
| Q9BWM7 | Sideroflexin-3 | SFXN3 | *Homo sapiens* | 37.95 | 8.62 | 2 | 12 |
| P61088 | Ubiquitin-conjugating enzyme E2 N | UBE2N | *Homo sapiens* | 36.77 | 27.63 | 3 | 12 |
| Q05682 | Caldesmon | CALD1 | *Homo sapiens* | 36.05 | 5.30 | 4 | 12 |
| P38159 | RNA-binding motif protein, X chromosome | RBMX | *Homo sapiens* | 35.98 | 8.95 | 3 | 12 |
| O15260 | Surfeit locus protein 4 | SURF4 | *Homo sapiens* | 35.84 | 8.55 | 2 | 12 |
| P30493 | HLA class I histocompatibility antigen, B-55 alpha chain | HLA-B | *Homo sapiens* | 34.77 | 14.64 | 4 | 12 |
| P62851 | 40S ribosomal protein S25 | RPS25 | *Homo sapiens* | 34.69 | 16.00 | 3 | 12 |
| P27816 | Microtubule-associated protein 4 | MAP4 | *Homo sapiens* | 34.36 | 4.69 | 4 | 12 |
| P61353 | 60S ribosomal protein L27 | RPL27 | *Homo sapiens* | 33.55 | 27.94 | 3 | 12 |
| P52272 | Heterogeneous nuclear ribonucleoprotein M | HNRNPM | *Homo sapiens* | 33.53 | 7.67 | 4 | 12 |
| Q15417 | Calponin-3 | CNN3 | *Homo sapiens* | 33.42 | 10.64 | 3 | 12 |
| P49773 | Histidine triad nucleotide-binding protein 1 | HINT1 | *Homo sapiens* | 69.01 | 34.92 | 2 | 11 |
| Q15121 | Astrocytic phosphoprotein PEA-15 | PEA15 | *Homo sapiens* | 52.21 | 27.69 | 3 | 11 |
| Q12905 | Interleukin enhancer-binding factor 2 | ILF2 | *Homo sapiens* | 43.95 | 8.72 | 2 | 11 |
| P68402 | Platelet-activating factor acetylhydrolase IB subunit beta | PAFAH1B2 | *Homo sapiens* | 43.27 | 12.23 | 2 | 11 |
| P08253 | 72 kDa type IV collagenase | MMP2 | *Homo sapiens* | 42.46 | 10.91 | 4 | 11 |
| P62333 | 26S protease regulatory subunit 10B | PSMC6 | *Homo sapiens* | 41.19 | 14.91 | 4 | 11 |
| P36957 | Dihydrolipoyllysine-residue succinyltransferase component of 2-oxoglutarate dehydrogenase complex, mitochondrial | DLST | *Homo sapiens* | 40.04 | 10.15 | 3 | 11 |
| P61313 | 60S ribosomal protein L15 | RPL15 | *Homo sapiens* | 38.61 | 12.75 | 2 | 11 |
| P04632 | Calpain small subunit 1 | CAPNS1 | *Homo sapiens* | 36.46 | 16.42 | 3 | 11 |
| P11047 | Laminin subunit gamma-1 | LAMC1 | *Homo sapiens* | 36.41 | 1.74 | 2 | 11 |
| P08195 | 4F2 cell-surface antigen heavy chain | SLC3A2 | *Homo sapiens* | 34.57 | 4.13 | 2 | 11 |
| Q01105 | Protein SET | SET | *Homo sapiens* | 34.28 | 12.07 | 3 | 11 |
| Q9Y277 | Voltage-dependent anion-selective channel protein 3 | VDAC3 | *Homo sapiens* | 34.15 | 19.08 | 4 | 11 |
| P62753 | 40S ribosomal protein S6 | RPS6 | *Homo sapiens* | 31.26 | 10.84 | 2 | 11 |
| O14979 | Heterogeneous nuclear ribonucleoprotein D-like | HNRNPDL | *Homo sapiens* | 31.19 | 9.76 | 3 | 11 |
| P30040 | Endoplasmic reticulum resident protein 29 | ERP29 | *Homo sapiens* | 29.37 | 8.43 | 2 | 11 |
| O00410 | Importin-5 | IPO5 | *Homo sapiens* | 46.49 | 6.47 | 4 | 10 |
| Q8IWE2 | Protein NOXP20 | FAM114A1 | *Homo sapiens* | 45.84 | 5.68 | 2 | 10 |
| O14579 | Coatomer subunit epsilon | COPE | *Homo sapiens* | 44.19 | 6.82 | 2 | 10 |
| O00154 | Cytosolic acyl coenzyme A thioester hydrolase | ACOT7 | *Homo sapiens* | 41.44 | 12.37 | 3 | 10 |
| Q9Y3F4 | Serine-threonine kinase receptor-associated protein | STRAP | *Homo sapiens* | 41.18 | 8.86 | 2 | 10 |
| P09429 | High mobility group protein B1 | HMGB1 | *Homo sapiens* | 39.56 | 27.44 | 4 | 10 |
| O15144 | Actin-related protein 2/3 complex subunit 2 | ARPC2 | *Homo sapiens* | 36.55 | 18.00 | 3 | 10 |
| Q96CW1 | AP-2 complex subunit mu | AP2M1 | *Homo sapiens* | 32.81 | 12.87 | 4 | 10 |
| P84103 | Serine/arginine-rich splicing factor 3 | SRSF3 | *Homo sapiens* | 31.49 | 14.02 | 2 | 10 |
| O60763 | General vesicular transport factor p115 | USO1 | *Homo sapiens* | 31.07 | 5.41 | 4 | 10 |
| P40429 | 60S ribosomal protein L13a | RPL13A | *Homo sapiens* | 25.35 | 8.87 | 2 | 10 |
| Q6DD88 | Atlastin-3 | ATL3 | *Homo sapiens* | 40.84 | 12.38 | 4 | 9 |
| P09622 | Dihydrolipoyl dehydrogenase, mitochondrial | DLD | *Homo sapiens* | 40.56 | 6.48 | 2 | 9 |
| Q9BWD1 | Acetyl-CoA acetyltransferase, cytosolic | ACAT2 | *Homo sapiens* | 37.63 | 14.61 | 3 | 9 |
| Q00341 | Vigilin | HDLBP | *Homo sapiens* | 37.29 | 4.10 | 3 | 9 |
| Q99798 | Aconitate hydratase, mitochondrial | ACO2 | *Homo sapiens* | 36.61 | 4.49 | 2 | 9 |
| Q02878 | 60S ribosomal proteins L6 | RPL6 | *Homo sapiens* | 34.78 | 15.63 | 3 | 9 |
| Q15008 | 26S proteasome non-ATPase regulatory subunit 6 | PSMD6 | *Homo sapiens* | 34.04 | 7.20 | 2 | 9 |
| P21266 | Glutathione S-transferase Mu 3 | GSTM3 | *Homo sapiens* | 31.19 | 17.33 | 3 | 9 |
| P10301 | Ras-related protein R-Ras | RRAS | *Homo sapiens* | 29.36 | 12.84 | 2 | 9 |
| Q06323 | Proteasome activator complex subunit 1 | PSME1 | *Homo sapiens* | 26.97 | 23.29 | 4 | 9 |
| Q13557 | Calcium/calmodulin-dependent protein kinase type II subunit delta | CAMK2D | *Homo sapiens* | 23.13 | 8.62 | 3 | 9 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P21964 | Catechol O-methyltransferase | COMT | *Homo sapiens* | 34.16 | 8.49 | 2 | 8 |
| P63167 | Dynein light chain 1, cytoplasmic | DYNLL1 | *Homo sapiens* | 33.21 | 37.08 | 2 | 8 |
| Q02952 | A-kinase anchor protein 12 | AKAP12 | *Homo sapiens* | 32.58 | 3.42 | 3 | 8 |
| P16278 | Beta-galactosidase | GLB1 | *Homo sapiens* | 29.46 | 3.69 | 2 | 8 |
| P62081 | 40S ribosomal protein S7 | RPS7 | *Homo sapiens* | 27.65 | 17.53 | 2 | 8 |
| P31937 | 3-hydroxyisobutyrate dehydrogenase, mitochondrial | HIBADH | *Homo sapiens* | 27.07 | 7.14 | 2 | 8 |
| Q96QK1 | Vacuolar protein sorting-associated protein 35 | VPS35 | *Homo sapiens* | 26.95 | 2.89 | 2 | 8 |
| P33176 | Kinesin-1 heavy chain | KIF5B | *Homo sapiens* | 26.86 | 2.80 | 2 | 8 |
| P61019 | Ras-related protein Rab-2A | RAB2A | *Homo sapiens* | 26.44 | 18.87 | 3 | 8 |
| O00231 | 26S proteasome non-ATPase regulatory subunit 11 | PSMD11 | *Homo sapiens* | 25.87 | 8.77 | 3 | 8 |
| P26373 | 60S ribosomal protein L13 | RPL13 | *Homo sapiens* | 25.81 | 10.90 | 2 | 8 |
| Q13724 | Mannosyl-oligosaccharide glucosidase | MOGS | *Homo sapiens* | 25.51 | 3.58 | 2 | 8 |
| O95816 | BAG family molecular chaperone regulator 2 | BAG2 | *Homo sapiens* | 24.67 | 13.27 | 2 | 8 |
| P06703 | Protein S100-A6 | S100A6 | *Homo sapiens* | 24.35 | 37.78 | 2 | 8 |
| P34897 | Serine hydroxymethyltransferase, mitochondrial | SHMT2 | *Homo sapiens* | 24.35 | 10.32 | 4 | 8 |
| P17844 | Probable ATP-dependent RNA helicase DDX5 | DDX5 | *Homo sapiens* | 24.22 | 5.86 | 3 | 8 |
| O94905 | Erlin-2 | ERLIN2 | *Homo sapiens* | 23.59 | 6.49 | 2 | 8 |
| P08648 | Integrin alpha-5 | ITGA5 | *Homo sapiens* | 23.55 | 5.62 | 4 | 8 |
| P62917 | 60S ribosomal protein L8 | RPL8 | *Homo sapiens* | 22.51 | 10.51 | 2 | 8 |
| P01023 | Alpha-2-macroglobulin | A2M | *Homo sapiens* | 20.91 | 2.04 | 3 | 8 |
| P26022 | Pentraxin-related protein PTX3 | PTX3 | *Homo sapiens* | 20.28 | 13.12 | 4 | 8 |
| P07814 | Bifunctional glutamate/proline--tRNA ligase | EPRS | *Homo sapiens* | 34.10 | 2.18 | 2 | 7 |
| Q6IBS0 | Twinfilin-2 | TWF2 | *Homo sapiens* | 29.62 | 9.74 | 2 | 7 |
| P49257 | Protein ERGIC-53 | LMAN1 | *Homo sapiens* | 28.55 | 10.39 | 2 | 7 |
| O75368 | SH3 domain-binding glutamic acid-rich-like protein | SH3BGRL | *Homo sapiens* | 26.17 | 26.32 | 2 | 7 |
| Q07666 | KH domain-contaning, RNA-binding, signal transduction-associated protein 1 | KHDRBS1 | *Homo sapiens* | 24.96 | 7.67 | 2 | 7 |
| P46977 | Dolichyl-diphosphooligosaccharide--protein glycosyltransferase subunit STT3A | STT3A | *Homo sapiens* | 24.54 | 3.69 | 2 | 7 |
| Q7L2H7 | Eukaryotic translation initiation factor 3 subunit M | EIF3M | *Homo sapiens* | 24.21 | 6.95 | 2 | 7 |
| Q15847 | Adipogenesis regulatory factor | ADIRF | *Homo sapiens* | 23.65 | 59.21 | 2 | 7 |
| P48643 | T-complex protein 1 subunit epsilon | CCT5 | *Homo sapiens* | 23.35 | 11.83 | 4 | 7 |
| P12268 | Inosine-5'-monophosphate dehydrogenase 2 | IMPDH2 | *Homo sapiens* | 23.35 | 9.73 | 3 | 7 |
| Q63ZY3 | KN motif and ankyrin repeat domain-containing protein 2 | KANK2 | *Homo sapiens* | 23.26 | 4.70 | 3 | 7 |
| P22102 | Trifunctional purine biosynthetic protein adenosine-3 [Includes: Phosphoribosylamine--glycine ligase] | GART | *Homo sapiens* | 22.93 | 2.67 | 2 | 7 |
| P49458 | Signal recognition particle 9 kDa protein | SRP9 | *Homo sapiens* | 22.86 | 23.26 | 2 | 7 |
| P05023 | Sodium/potassium-transporting ATPase subunit alpha-1 | ATP1A1 | *Homo sapiens* | 22.17 | 3.91 | 3 | 7 |
| P02792 | Ferritin light chain | FTL | *Homo sapiens* | 22.12 | 26.86 | 3 | 7 |
| P35613 | Basigin | BSG | *Homo sapiens* | 21.87 | 8.31 | 2 | 7 |
| P18621 | 60S ribosomal protein L17 | RPL17 | *Homo sapiens* | 21.02 | 17.93 | 3 | 7 |
| P11177 | Pyruvate dehydrogenase E1 component subunit beta, mitochondrial | PDHB | *Homo sapiens* | 19.98 | 8.91 | 2 | 7 |
| P62330 | ADP-ribosylation factor 6 | ARF6 | *Homo sapiens* | 19.84 | 12.57 | 2 | 7 |
| Q99832 | T-complex protein 1 subunit eta | CCT7 | *Homo sapiens* | 19.63 | 7.92 | 3 | 7 |
| P35637 | RNA-binding protein FUS | FUS | *Homo sapiens* | 19.53 | 6.27 | 2 | 7 |
| P42677 | 40S ribosomal protein S27 | RPS27 | *Homo sapiens* | 19.53 | 25.00 | 2 | 7 |
| P31948 | Stress-induced-phosphoprotein 1 | STIP1 | *Homo sapiens* | 19.50 | 7.73 | 3 | 7 |
| P26640 | Valine--tRNA ligase | VARS | *Homo sapiens* | 18.39 | 1.98 | 2 | 7 |
| P15586 | N-acetylglucosamine-6-sulfatase | GNS | *Homo sapiens* | 18.07 | 4.71 | 2 | 7 |
| P62191 | 26S protease regulatory subunit 4 | PSMC1 | *Homo sapiens* | 30.43 | 8.18 | 2 | 6 |
| Q13423 | NAD(P) transhydrogenase, mitochondrial | NNT | *Homo sapiens* | 28.78 | 3.41 | 2 | 6 |
| P09960 | Leukotriene A-4 hydrolase | LTA4H | *Homo sapiens* | 26.18 | 5.07 | 2 | 6 |
| P22695 | Cytochrome b-c1 complex subunit 2, mitochondrial | UQCRC22 | *Homo sapiens* | 24.46 | 10.82 | 3 | 6 |
| P10619 | Lysosomal protective protein | CTSA | *Homo sapiens* | 22.01 | 5.00 | 2 | 6 |
| P23381 | Tryptophan--tRNA ligase, cytoplasmic | WARS | *Homo sapiens* | 21.16 | 5.73 | 2 | 6 |
| P02794 | Ferritin heavy chain | FTH1 | *Homo sapiens* | 20.44 | 33.33 | 3 | 6 |
| P55010 | Eukaryotic translation initiation factor 5 | EIF5 | *Homo sapiens* | 18.71 | 9.98 | 3 | 6 |
| P35555 | Fibrillin-1 | FBN1 | *Homo sapiens* | 18.54 | 2.16 | 4 | 6 |
| P39656 | Dolichyl-diphosphooligosaccharide-protein glycosyltransferase 48 kDa subunit | DDOST | *Homo sapiens* | 18.03 | 7.89 | 3 | 6 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| Q13425 | Beta-2-syntrophin | SNTB2 | *Homo sapiens* | 17.22 | 3.89 | 2 | 6 |
| Q99961 | Endophilin-A2 | SH3GL1 | *Homo sapiens* | 17.15 | 8.97 | 2 | 6 |
| P54136 | Arginine--tRNA ligase, cytoplasmic | RARS | *Homo sapiens* | 17.09 | 3.64 | 2 | 6 |
| P20073 | Annexin A7 | ANXA7 | *Homo sapiens* | 15.98 | 8.20 | 3 | 6 |
| Q15113 | Procollagen C-endopeptidase enhancer 1 | PCOLCE | *Homo sapiens* | 15.72 | 6.01 | 2 | 6 |
| P30085 | UMP-CMP kinase | CMPK1 | *Homo sapiens* | 24.26 | 16.84 | 2 | 5 |
| Q16881 | Thioredoxin reductase 1, cytoplasmic | TXNRD1 | *Homo sapiens* | 22.69 | 5.86 | 2 | 5 |
| P00568 | Adenylate kinase isoenzyme 1 | AK1 | *Homo sapiens* | 19.57 | 19.07 | 2 | 5 |
| P43243 | Matrin-3 | MATR3 | *Homo sapiens* | 18.67 | 6.02 | 3 | 5 |
| O95292 | Vesicle-associated membrane protein-associated protein B/C | VAPB | *Homo sapiens* | 16.59 | 10.70 | 2 | 5 |
| O43237 | Cytoplasmic dynein 1 light intermediate chain 2 | DYNC1LI2 | *Homo sapiens* | 16.24 | 5.08 | 2 | 5 |
| P23526 | Adenosylhomocysteinase | AHCY | *Homo sapiens* | 15.78 | 10.65 | 3 | 5 |
| P13804 | Electron transfer flavoprotein subunit alpha, mitochondrial | ETFA | *Homo sapiens* | 15.40 | 8.71 | 2 | 5 |
| P13010 | X-ray repair cross-complementing protein 5 | XRCC5 | *Homo sapiens* | 15.04 | 6.42 | 3 | 5 |
| Q01995 | Transgelin | TAGLN | *Homo sapiens* | 15.00 | 12.44 | 2 | 5 |
| P60900 | Proteasome subunit alpha type-6 | PSMA6 | *Homo sapiens* | 14.55 | 10.16 | 2 | 5 |
| P07996 | Thrombospondin-1 | THBS1 | *Homo sapiens* | 14.55 | 1.97 | 2 | 5 |
| Q9UEY8 | Gamma-adducin | ADD3 | *Homo sapiens* | 14.49 | 3.54 | 2 | 5 |
| O60488 | Long-chain-fatty-acid--CoA ligase 4 | ACSL4 | *Homo sapiens* | 13.17 | 4.36 | 2 | 5 |
| Q15942 | Zyxin | ZYX | *Homo sapiens* | 22.91 | 6.64 | 2 | 4 |
| O14980 | Exportin-1 | XPO1 | *Homo sapiens* | 22.59 | 4.20 | 2 | 4 |
| O75131 | Copine-3 | CPNE3 | *Homo sapiens* | 18.51 | 6.33 | 2 | 4 |
| Q99714 | 3-hydroxyacyl-CoA dehydrogenase type-2 | HSD17B10 | *Homo sapiens* | 17.39 | 16.48 | 2 | 4 |
| O94855 | Protein transport protein Sec24D | SEC24D | *Homo sapiens* | 16.72 | 2.91 | 2 | 4 |
| P21291 | Cysteine and glycine-rich protein 1 | CSRP1 | *Homo sapiens* | 16.40 | 19.17 | 2 | 4 |
| Q9BVK6 | Transmembrane emp24 domain-containing protein 9 | TMED9 | *Homo sapiens* | 15.78 | 14.47 | 2 | 4 |
| Q13283 | Res GTPase-activating protein-binding protein 1 | G3BP1 | *Homo sapiens* | 15.21 | 6.01 | 2 | 4 |
| Q9NYL9 | Tropomodulin-3 | TMOD3 | *Homo sapiens* | 14.89 | 9.38 | 2 | 4 |
| P62195 | 26S protease regulatory subunit 8 | PSMC5 | *Homo sapiens* | 14.87 | 12.07 | 3 | 4 |
| P55884 | Eukaryotic translation initiation factor 3 subunit B | EIF3B | *Homo sapiens* | 14.81 | 4.67 | 2 | 4 |
| P33527 | Multidrug resistance-associated protein 1 | ABCC1 | *Homo sapiens* | 13.99 | 2.02 | 2 | 4 |
| O15143 | Actin-related protein 2/3 complex subunit 1B | ARPC1B | *Homo sapiens* | 13.50 | 11.83 | 3 | 4 |
| Q9Y262 | Eukaryotic translation initiation factor 3 subunit L | EIF3L | *Homo sapiens* | 13.47 | 3.55 | 2 | 4 |
| Q02809 | Procollagen-lysine, 2-oxoglutarate 5-dioxygenase 1 | PLOD1 | *Homo sapiens* | 13.29 | 3.71 | 2 | 4 |
| P23246 | Splicing factor, proline- and glutamine-rich | SFPQ | *Homo sapiens* | 13.13 | 6.22 | 3 | 4 |
| P30046 | D-dopachrome decarboxylase | DDT | *Homo sapiens* | 12.61 | 19.49 | 2 | 4 |
| Q9NQW7 | Xaa-Pro aminopeptidase 1 | XPNPEP1 | *Homo sapiens* | 12.18 | 4.82 | 2 | 4 |
| Q9NR31 | GTP-binding protein SAR1a | SAR1A | *Homo sapiens* | 12.08 | 15.66 | 2 | 4 |
| Q03252 | Lamin-B2 | LMNB2 | *Homo sapiens* | 11.81 | 5.67 | 3 | 4 |
| P78344 | Eukaryotic translation initiation factor 4 gamma 2 | EIF4G2 | *Homo sapiens* | 11.24 | 2.32 | 2 | 4 |
| P41252 | Isoleucine-tRNA ligase, cytoplasmic | IARS | *Homo sapiens* | 11.24 | 2.69 | 3 | 4 |
| Q7L576 | Cytoplasmic FMR1-interacting protein 1 | CYFIP1 | *Homo sapiens* | 11.23 | 1.84 | 2 | 4 |
| P67809 | Nuclease-sensitive element-binding protein 1 | YBX1 | *Homo sapiens* | 10.94 | 11.11 | 2 | 4 |
| P35611 | Alpha-adducin | ADD1 | *Homo sapiens* | 10.23 | 4.21 | 2 | 4 |
| Q9BR76 | Coronin-1B | CORO1B | *Homo sapiens* | 10.19 | 3.48 | 2 | 4 |
| P27695 | DNA-(apurinic or apyrimidinic site) lyase | APEX1 | *Homo sapiens* | 16.69 | 11.01 | 2 | 3 |
| O15460 | Prolyl 4-hydroxylase subunit alpha-2 | P4HA2 | *Homo sapiens* | 14.16 | 6.17 | 2 | 3 |
| Q96HE7 | ERO1-like protein alpha | ERO1L | *Homo sapiens* | 13.09 | 7.26 | 2 | 3 |
| P61769 | Beta-2-microglobulin [Cleaved into: Beta-2-microglobulin form pI 5.3] | BaM | *Homo sapiens* | 11.85 | 26.89 | 2 | 3 |
| PI4854 | Cytochrome c oxidase subunit 6B1 | COX6B1 | *Homo sapiens* | 11.35 | 33.72 | 2 | 3 |
| P00390 | Glutathione reductase, mitochondrial | GSR | *Homo sapiens* | 11.32 | 6.32 | 2 | 3 |
| P13798 | Acylamino-acid-releasing enzyme | APEH | *Homo sapiens* | 10.86 | 4.78 | 2 | 3 |
| Q08257 | Quinone oxidoreductase | CRYZ | *Homo sapiens* | 9.95 | 10.64 | 2 | 3 |
| Q9NTK5 | Obg-like ATPase 1 | OLA1 | *Homo sapiens* | 9.88 | 7.32 | 2 | 3 |
| Q13418 | Integrin-linked protein kinase | ILK | *Homo sapiens* | 9.86 | 8.63 | 3 | 3 |
| P61009 | Signal peptidase complex subunit 3 | SPCS3 | *Homo sapiens* | 9.85 | 12.78 | 2 | 3 |
| Q969H8 | UPF0556 protein C19orf10 | C19ORF10 | *Homo sapiens* | 9.71 | 15.03 | 2 | 3 |
| P05455 | Lupus La protein | SSB | *Homo sapiens* | 9.57 | 6.37 | 2 | 3 |
| P51858 | Hepatoma-derived growth factor | HDGF | *Homo sapiens* | 9.38 | 13.75 | 2 | 3 |
| O00425 | Insulin-like growth factor 2 mRNA-binding protein 3 | IGF2BP3 | *Homo sapiens* | 8.88 | 5.18 | 2 | 3 |
| P20042 | Eukaryotic translation initiation factor 2 subunit 2 | EIF2S2 | *Homo sapiens* | 8.84 | 8.11 | 2 | 3 |
| P62495 | Eukaryotic peptide chain release factor subunit 1 | ETF1 | *Homo sapiens* | 8.74 | 6.41 | 2 | 3 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P11279 | Lysosome-associated membrane glycoprotein 1 | LAMP1 | *Homo sapiens* | 8.45 | 6.00 | 2 | 3 |
| Q9NUQ9 | Protein FAM49B | FAM49B | *Homo sapiens* | 8.18 | 8.64 | 2 | 3 |
| Q14247 | Src substrate cortactin | CTTN | *Homo sapiens* | 8.15 | 3.64 | 2 | 3 |
| P27708 | CAD protein [Includes: Glutamine-dependent carbamoyl-phosphate synthase] | CAD | *Homo sapiens* | 7.94 | 0.94 | 2 | 3 |
| Q9NSE4 | isoleucine-tRNA ligase, mitochondrial | IARS2 | *Homo sapiens* | 7.76 | 2.08 | 2 | 3 |
| Q9H4A4 | Aminopeptidase B | RNPEP | *Homo sapiens* | 7.62 | 3.54 | 2 | 3 |
| P62913 | 60S ribosomal protein L11 | RPL11 | *Homo sapiens* | 7.39 | 12.92 | 2 | 3 |
| P39060 | Collagen alpha-1(XVIII) chain [Cleaved into: Endostatin] | COL18A1 | *Homo sapiens* | 11.40 | 2.85 | 2 | 2 |
| P26368 | Splicing factor U2AF 65 kDa subunit | U2AF2 | *Homo sapiens* | 8.61 | 6.11 | 2 | 2 |
| Q687X5 | Metalloreductase STEAP4 | STEAP4 | *Homo sapiens* | 7.68 | 7.19 | 2 | 2 |
| P31153 | S-adenosylmethionine synthase isoform type-2 | MAT2A | *Homo sapiens* | 7.36 | 9.11 | 2 | 2 |
| Q9Y240 | C-type lectin domain family 11 member A | CLEC11A | *Homo sapiens* | 6.98 | 8.98 | 2 | 2 |
| P50213 | Isocitrate dehydrogenase [NAD] subunit alpha, mitochondrial | IDH3A | *Homo sapiens* | 6.43 | 10.38 | 2 | 2 |
| Q09028 | Histone-binding protein RBBP4 | RBBP4 | *Homo sapiens* | 6.37 | 4.94 | 2 | 2 |
| P32969 | 60S ribosomal protein L9 | RPL9 | *Homo sapiens* | 6.36 | 11.46 | 2 | 2 |
| P21399 | Cytoplasmic aconitate hydratase | ACO1 | *Homo sapiens* | 6.23 | 3.15 | 2 | 2 |
| P00492 | Hypoxanthine-guanine phosphoribosyltransferase | HPRT1 | *Homo sapiens* | 6.12 | 10.55 | 2 | 2 |
| P49591 | Serine--tRNA ligase, cytoplasmic | SARS | *Homo sapiens* | 5.72 | 5.45 | 2 | 2 |
| P30520 | Adenylosuccinate synthetase isozyme 2 | ADSS | *Homo sapiens* | 5.55 | 4.61 | 2 | 2 |
| P22234 | Multifunctional protein ADE2 [Includes: Phosphoribosylaminoimidazole-succinocarboxamide synthase] | PAICS | *Homo sapiens* | 5.35 | 6.12 | 2 | 2 |
| P11586 | C-1-tetrahydrofolate synthase, cytoplasmic | MTHFD1 | *Homo sapiens* | 5.21 | 2.78 | 2 | 2 |
| Q92616 | Translational activator GCN1 | GCN1L1 | *Homo sapiens* | 5.02 | 1.05 | 2 | 2 |
| VFE on scaffold | | | | | | | |
| P02454 | Collagen alpha-1(I) chain | COL1A1 | *Rattus norvegicus* | 19462.74 | 69.79 | 79 | 24841 |
| P02452 | Collegen alpha-1(I) chain | COL1A1 | *Homo sapiens* | 9931.72 | 59.97 | 58 | 13046 |
| P02466 | Collagen alpha-2(I) chain | COL1A2 | *Rattus norvegicus* | 12949.24 | 67.49 | 67 | 11720 |
| P08123 | Collagen alpha-2(I) chain | COL1A2 | *Homo sapiens* | 3724.87 | 54.32 | 41 | 3438 |
| Q09666 | Neuroblast differentiation-associated protein AHNAK | AHNAK | *Homo sapiens* | 3402.71 | 42.18 | 112 | 1007 |
| P12111 | Collagen alpha-3(VI) chain | COL6A3 | *Homo sapiens* | 3044.09 | 31.82 | 76 | 895 |
| P02461 | Collagen alpha-1(III) chain | COL3A1 | *Homo sapiens* | 661.63 | 21.01 | 17 | 826 |
| P02751 | Fibronectin | FN1 | *Homo sapiens* | 2864.69 | 38.56 | 65 | 739 |
| P12109 | Collegen alpha-1(VI) chain | COL6A1 | *Homo sapiens* | 1371.07 | 28.02 | 21 | 680 |
| P08670 | Vimeritin | VIM | *Homo sapiens* | 2057.68 | 54.72 | 32 | 597 |
| P21333 | Filamin-A | FLNA | *Homo sapiens* | 1970.03 | 38.23 | 62 | 483 |
| Q15149 | Plectin | PLEC | *Homo sapiens* | 1624.20 | 24.68 | 81 | 445 |
| P35579 | Myosin-9 | MYH9 | *Homo sapiens* | 1870.54 | 35.56 | 53 | 433 |
| P60711 | Actin cytoplasmic 1 | ACTB | *Rattus norvegicus* | 1567.81 | 61.87 | 16 | 410 |
| P02545 | Prelamin-A/C [Cleaved into: Lamin-A/C] | LMNA | *Homo sapiens* | 1315.37 | 53.16 | 33 | 387 |
| P14618 | Pyruvate kinase PKM | PKM | *Homo sapiens* | 1486.10 | 61.21 | 28 | 383 |
| P02458 | Collagen alpha-1(II) chain | COL2A1 | *Homo sapiens* | 529.20 | 5.85 | 4 | 344 |
| P07355 | Annexin A2 | ANXA2 | *Homo sapiens* | 1284.07 | 56.11 | 20 | 331 |
| P11021 | 78 kDa glucose-regulated protein | HSPA5 | *Homo sapiens* | 1128.68 | 38.53 | 21 | 310 |
| Q00610 | Clathrin heavy chain 1 | CLTC | *Homo sapiens* | 1224.44 | 29.91 | 38 | 306 |
| P04406 | Glyceraldehyde-3-phosphate dehydrogenase | GAPDH | *Homo sapiens* | 1064.45 | 53.13 | 13 | 306 |
| P07437 | Tubulin beta chain | TUBB | *Homo sapiens* | 1124.26 | 66.89 | 21 | 304 |
| P12814 | Alpha-actinin-1 | ACTN1 | *Homo sapiens* | 1094.44 | 47.76 | 33 | 293 |
| P68371 | Tubulin beta-4B chain | TUBB4B | *Homo sapiens* | 1083.09 | 70.56 | 22 | 288 |
| P15144 | Aminopeptidase N | ANPEP | *Homo sapiens* | 990.71 | 27.82 | 25 | 278 |
| P13941 | Collagen alpha-1(III) chain | COL3A1 | *Rattus norvegicus* | 294.49 | 10.59 | 9 | 278 |
| P11142 | Heat shock cognate 71 kDa protein | HSPAB | *Homo sapiens* | 996.23 | 41.33 | 22 | 263 |
| Q13885 | Tubulin beta-2A chain | TUBB2A | *Homo sapiens* | 876.91 | 61.12 | 19 | 245 |
| P12110 | Collagen alpha-2(VI) chain | COL6A2 | *Homo sapiens* | 667.72 | 31.80 | 23 | 244 |
| P00558 | Phosphoglycerate kinase 1 | PGK1 | *Homo sapiens* | 936.31 | 52.04 | 17 | 234 |
| P08238 | Heat shock protein HSP 90-beta | HSP90AB1 | *Homo sapiens* | 839.05 | 33.84 | 20 | 229 |
| O43707 | Alpha-actinin-4 | ACTN4 | *Homo sapiens* | 855.61 | 49.62 | 32 | 228 |
| P68363 | Tubulin alpha-1B chain | TUBA1B | *Homo sapiens* | 785.85 | 48.78 | 15 | 222 |
| Q13509 | Tubulin beta-3 chain | TUBB3 | *Homo sapiens* | 741.48 | 42.44 | 15 | 220 |
| P06758 | Annexin A5 | ANXA5 | *Homo sapiens* | 758.36 | 67.50 | 18 | 219 |
| P68035 | Actin alpha cardiac muscle 1 | ACTC1 | *Rattus norvegicus* | 720.51 | 43.77 | 12 | 217 |
| P05539 | Collagen alpha-1(II) chain | COL2A1 | *Rattus norvegicus* | 361.49 | 5.00 | 3 | 212 |
| P66576 | ATP synthase subunit beta; mitochondrial | ATP5B | *Homo sapiens* | 754.28 | 42.72 | 16 | 209 |
| P68104 | Elongation factor 1-alpha 1 | EEF1A1 | *Homo sapiens* | 842.24 | 34.20 | 11 | 203 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P07900 | Heat shock protein HSP 90-alpha | HSP90AA1 | *Homo sapiens* | 727.70 | 29.51 | 19 | 201 |
| P04083 | Annexin A1 | ANXA1 | *Homo sapiens* | 807.88 | 52.60 | 16 | 199 |
| Q9Y490 | Talin-1 | TLN1 | *Homo sapiens* | 832.01 | 20.90 | 30 | 198 |
| P14625 | Endoplasmin | HSP90B1 | *Homo sapiens* | 722.04 | 32.88 | 21 | 197 |
| P08133 | Annexin A6 | ANXA6 | *Homo sapiens* | 685.55 | 45.17 | 22 | 186 |
| P50454 | Serpin H1 | SERPINH1 | *Homo sapiens* | 779.11 | 50.00 | 15 | 185 |
| P04075 | Fructose-bisphosphate aldolase A | ALDOA | *Homo sapiens* | 742.79 | 65.66 | 17 | 175 |
| P06733 | Alpha-enolase | ENO1 | *Homo sapiens* | 607.87 | 54.15 | 16 | 168 |
| Q04828 | Aldo-keta reductase family 1 member C1 | AKR1C1 | *Homo sapiens* | 671.12 | 49.85 | 12 | 165 |
| P29401 | Transketolase | TKT | *Homo sapiens* | 690.60 | 39.33 | 17 | 157 |
| P07237 | Protein disulfide-isomerase | P4HB | *Homo sapiens* | 602.33 | 48.62 | 21 | 157 |
| P60174 | Triosephosphate isomerase | TPI1 | *Homo sapiens* | 601.01 | 66.08 | 14 | 155 |
| P18206 | Vinculin | VCL | *Homo sapiens* | 521.43 | 35.36 | 28 | 154 |
| P06396 | Gelsolin | GSN | *Homo sapiens* | 657.52 | 23.66 | 14 | 152 |
| Q16555 | Dihydropyrimidinase-related protein 2 | DPYSL2 | *Homo sapiens* | 619.56 | 48.95 | 17 | 152 |
| P07585 | Decorin | DCN | *Homo sapiens* | 513.00 | 45.96 | 14 | 151 |
| Q14764 | Major vault protein | MVP | *Homo sapiens* | 515.55 | 34.04 | 20 | 147 |
| P46940 | Ras GTPase-activating-like protein IQGAP1 | IQGAP1 | *Homo sapiens* | 567.55 | 20.16 | 21 | 142 |
| P13639 | Elongation factor 2 | EEF2 | *Homo sapiens* | 460.85 | 31.12 | 23 | 142 |
| P30101 | Protein disulfide-isomerase A3 | PDIA3 | *Homo sapiens* | 482.71 | 42.97 | 16 | 137 |
| Q9BUF5 | Tubulin beta-6 chain | TUBB6 | *Homo sapiens* | 454.39 | 58.07 | 18 | 137 |
| P07602 | Proactivator polypeptide [Cleaved into: Saposin-A] | PSAP | *Homo sapiens* | 264.99 | 26.91 | 13 | 137 |
| P62937 | Peptidyl-prolyl cis-trans isomerase A | PPIA | *Homo sapiens* | 494.59 | 55.76 | 9 | 136 |
| P62805 | Histone H4 | HIST1H4A | *Homo sapiens* | 449.47 | 51.46 | 6 | 131 |
| P55072 | Transitional endoplasmic reticulum ATPase | VCP | *Homo sapiens* | 519.55 | 43.18 | 23 | 129 |
| P11413 | Glucose-6-phosphate 1-dehydrogenese | G6PD | *Homo sapiens* | 488.37 | 40.78 | 15 | 129 |
| P18669 | Phosphoglycerate mutase 1 | PGAM1 | *Homo sapiens* | 467.11 | 44.88 | 9 | 129 |
| O43852 | Calumenin | CALU | *Homo sapiens* | 526.31 | 52.38 | 14 | 127 |
| P16152 | Carbonyl reductase [NADPH] 1 | CBR1 | *Homo sapiens* | 493.61 | 58.12 | 11 | 123 |
| Q9NZN4 | EH domain-containing protein 2 | EHD2 | *Homo sapiens* | 471.67 | 49.91 | 18 | 122 |
| P13489 | Ribonuclease inhibitor | RNH1 | *Homo sapiens* | 471.22 | 44.47 | 13 | 121 |
| P35555 | Fibrillin-1 | FBN1 | *Homo sapiens* | 395.19 | 13.79 | 25 | 114 |
| P49327 | Fatty acid synthese | FASN | *Homo sapiens* | 444.87 | 15.13 | 23 | 112 |
| P62260 | 14-3-3 protein epsilon | YWHAE | *Rattus norvegicus* | 333.75 | 40.00 | 8 | 112 |
| P00338 | L-lactate dehydrogenase A chain | LDHA | *Homo sapiens* | 389.25 | 39.16 | 11 | 111 |
| Q99536 | Synaptic vesicle membrane protein VAT-1 homolog | VAT1 | *Homo sapiens* | 418.13 | 35.37 | 8 | 110 |
| Q06830 | Peroxiredoxin-1 | PRDX1 | *Homo sapiens* | 432.15 | 56.78 | 10 | 109 |
| P98095 | Fibulin-2 | FBLN2 | *Homo sapiens* | 415.65 | 19.85 | 15 | 109 |
| O60814 | Histone H2B type 1-K | HIST1H2BK | *Homo sapiens* | 305.88 | 34.92 | 4 | 109 |
| O14315 | Filamin-C | FLNC | *Homo sapiens* | 459.99 | 11.08 | 17 | 107 |
| Q07065 | Cytoskeleton-associated protein 4 | CKAP4 | *Homo sapiens* | 394.33 | 38.37 | 18 | 105 |
| P27348 | 14-3-3 protein theta | YWHAQ | *Homo sapiens* | 347.51 | 38.37 | 7 | 104 |
| P63104 | 14-3-3 protein zeta/delta | YWHAZ | *Homo sapiens* | 339.16 | 42.86 | 8 | 103 |
| Q9NZM1 | Myoferlin | MYOF | *Homo sapiens* | 387.07 | 13.93 | 19 | 101 |
| P10899 | 60 kDa heat shock protein, mitochondrial | HSPD1 | *Homo sapiens* | 386.96 | 31.59 | 14 | 101 |
| P38646 | Stress-70 protein, mitochondrial | HSPA9 | *Homo sapiens* | 378.75 | 21.50 | 11 | 100 |
| Q14204 | Cytoplasmic dynein 1 heavy Chain 1 | DYNC1H1 | *Homo sapiens* | 360.00 | 9.00 | 29 | 100 |
| P35556 | Fibrillin-2 | FBN2 | *Homo sapiens* | 371.59 | 8.04 | 15 | 97 |
| P67936 | Tropomyosin alpha-4 chain | TPM4 | *Homo sapiens* | 342.85 | 47.98 | 13 | 96 |
| P23284 | Peptidyl-prolyl cis-trans isomerase B | PPIB | *Homo sapiens* | 305.17 | 40.28 | 9 | 96 |
| P26038 | Moesin | MSN | *Homo sapiens* | 353.35 | 26.34 | 15 | 95 |
| P25705 | ATP synthase subunit alpha, mitochondrial | ATP5A1 | *Homo sapiens* | 358.61 | 25.86 | 10 | 94 |
| O00299 | Chloride intracellular channel protein 1 | CLIC1 | *Homo sapiens* | 355.52 | 68.88 | 12 | 94 |
| P27797 | Calreticulin | CALR | *Homo sapiens* | 386.83 | 39.57 | 10 | 92 |
| P42330 | Aldo-keto reductase family 1 member C3 | AKR1C3 | *Homo sapiens* | 386.79 | 42.72 | 9 | 92 |
| P09382 | Galectin-1 | LGALS1 | *Homo sapiens* | 336.73 | 46.67 | 5 | 92 |
| P07195 | L-lactate dehydrogenase B chain | LDHB | *Homo sapiens* | 301.77 | 37.72 | 12 | 92 |
| Q6NZ12 | Polymerase I and transcript release factor | PTRF | *Homo sapiens* | 366.06 | 25.38 | 8 | 91 |
| Q13813 | Spectrin alpha chain, non-erythrocytic 1 | SPTAN1 | *Homo sapiens* | 349.51 | 13.43 | 21 | 91 |
| P23528 | Cofilin-1 | CFL1 | *Homo sapiens* | 381.58 | 57.83 | 10 | 90 |
| P36955 | Pigment epithelium-derived factor | SERPINF1 | *Homo sapiens* | 334.75 | 22.01 | 7 | 90 |
| P51149 | Ras-related protein Rab-7a | RAB7A | *Homo sapiens* | 325.35 | 60.87 | 10 | 90 |
| P07858 | Cathepsin B | CTSB | *Homo sapiens* | 373.17 | 31.27 | 9 | 89 |
| P27824 | Calnexin | CANX | *Homo sapiens* | 339.30 | 23.65 | 11 | 89 |
| P40926 | Malate dehydrogenase, mitochondrial | MDH2 | *Homo sapiens* | 319.47 | 44.38 | 11 | 89 |
| P51884 | Lumican | LUM | *Homo sapiens* | 289.27 | 32.25 | 9 | 89 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P53396 | ATP-citrate synthase | ACLY | *Homo sapiens* | 328.72 | 19.71 | 14 | 86 |
| P40939 | Trifunctional enzyme subunit alpha, mitochondrial | HADHA | *Homo sapiens* | 340.14 | 17.96 | 8 | 83 |
| Q96AY3 | Peptidyl-prolyl cis-trans isomerase FKBP10 | FKBP10 | *Homo sapiens* | 271.61 | 19.42 | 9 | 81 |
| P02792 | Ferritin light chain | FTL | *Homo sapiens* | 388.87 | 36.00 | 5 | 80 |
| P30041 | Peroxiredoxin-6 | PRDX6 | *Homo sapiens* | 281.65 | 48.66 | 9 | 80 |
| P60842 | Eukaryotic initiation factor 4A-1 | EIF4A1 | *Homo sapiens* | 263.67 | 33.50 | 11 | 80 |
| Q15084 | Protein disulfide-isomerase A6 | PDIA6 | *Homo sapiens* | 288.09 | 29.32 | 8 | 79 |
| P04264 | keratin, type II cytoskeletal 1 | KRT1 | *Homo sapiens* | 271.98 | 18.48 | 10 | 79 |
| P07686 | Beta-hexosaminidase subunit beta | HEXB | *Homo sapiens* | 232.74 | 13.31 | 6 | 79 |
| P49368 | T-Complex protein 1 subunit gamma | CCT3 | *Homo sapiens* | 283.18 | 29.17 | 11 | 78 |
| P09211 | Glutathione S-transferase P | GSTP1 | *Homo sapiens* | 330.61 | 53.33 | 8 | 77 |
| P37802 | Transgelin-2 | TAGLN2 | *Homo sapiens* | 299.87 | 57.29 | 9 | 77 |
| P16278 | Beta-galactosidase | GLB1 | *Homo sapiens* | 281.54 | 24.37 | 11 | 77 |
| P21796 | Voltage-dependent anion-selective channel protein 1 | VDAC1 | *Homo sapiens* | 304.95 | 27.21 | 6 | 76 |
| P63244 | Guanine nucleotide-binding protein subunit beta-2-like 1 | GNB2L1 | *Homo sapiens* | 273.34 | 55.84 | 11 | 76 |
| P11766 | Alcohol dehydrogenase class-3 | ADH5 | *Homo sapiens* | 338.18 | 22.99 | 6 | 74 |
| P05388 | 60S acidic ribosomal protein P0 | RPLP0 | *Homo sapiens* | 303.07 | 37.85 | 8 | 74 |
| Q96AG4 | Leucine-rich repeat-containing protein 59 | LRRC59 | *Homo sapiens* | 280.57 | 31.60 | 6 | 74 |
| Q07954 | Prolow-density lipoprotein receptor-related protein 1 | LRP1 | *Homo sapiens* | 276.43 | 4.91 | 15 | 71 |
| P08865 | 40S ribosomal protein SA | RPSA | *Homo sapiens* | 274.72 | 36.61 | 8 | 71 |
| P61981 | 14-3-3 protein gamma | YWHAG | *Homo sapiens* | 224.58 | 28.74 | 6 | 71 |
| P26641 | Elongation factor 1-gamma | EEF1G | *Homo sapiens* | 271.89 | 28.60 | 11 | 70 |
| O60664 | Perilipin-3 | PLIN3 | *Homo sapiens* | 268.33 | 35.02 | 9 | 70 |
| O01082 | Spectrin beta chain, non-erythrocytic 1 | SPTBN1 | *Homo sapiens* | 239.23 | 11.59 | 18 | 70 |
| P09525 | Annexin A4 | ANXA4 | *Homo sapiens* | 228.82 | 34.80 | 9 | 70 |
| O75083 | WD repeat-containing protein 1 | WDR1 | *Homo sapiens* | 358.76 | 26.73 | 9 | 69 |
| O96D15 | Reticulocalbin-3 | RCN3 | *Homo sapiens* | 299.70 | 30.79 | 6 | 69 |
| Q9Y6N5 | Sulfide quinone oxidoreductase, mitochondrial | SQRDL | *Homo sapiens* | 253.49 | 28.00 | 10 | 69 |
| P07996 | Thrombospondin-1 | THBS1 | *Homo sapiens* | 241.05 | 14.36 | 10 | 69 |
| P40925 | Malate dehydrogenase, cytoplasmic | MDH1 | *Homo sapiens* | 231.53 | 25.15 | 6 | 68 |
| Q15019 | Septin-2 | 41884 | *Homo sapiens* | 267.59 | 42.66 | 9 | 67 |
| Q15385 | Poly(rC)-binding protein 1 | PCBP1 | *Homo sapiens* | 231.29 | 26.93 | 5 | 67 |
| P07737 | Profilin-1 | PFN1 | *Homo sapiens* | 216.78 | 63.57 | 7 | 67 |
| P62820 | Ras-related protein Rab-1A | RAB1A | *Homo sapiens* | 206.51 | 51.22 | 8 | 67 |
| P06744 | Glucose-6-phosphate isomerase | GPI | *Homo sapiens* | 266.65 | 29.57 | 10 | 66 |
| P22314 | Ubiquitin-like modifier-activating enzyme 1 | UBA1 | *Homo sapiens* | 250.03 | 20.42 | 14 | 66 |
| P12882 | Myosin-1 | MYH1 | *Homo sapiens* | 235.28 | 11.55 | 17 | 65 |
| P07339 | Cathepsin D | CTSD | *Homo sapiens* | 209.54 | 31.07 | 9 | 65 |
| P18085 | ADP-ribosylation factor 4 | ARF4 | *Homo sapiens* | 201.61 | 60.56 | 9 | 65 |
| P04844 | Dolichyl-diphosphooligosaccharide-protein glycosyltransferase subunit 2 | RPN2 | *Homo sapiens* | 298.04 | 23.61 | 10 | 64 |
| Q03135 | Caveolin-1 | CAV1 | *Homo sapiens* | 225.24 | 52.25 | 7 | 64 |
| P04792 | Heat shock protein beta-1 | HSPB1 | *Homo sapiens* | 217.66 | 39.51 | 7 | 64 |
| P45880 | Voltage-dependent anion-selective channel protein 2 | VDAC2 | *Homo sapiens* | 212.61 | 32.99 | 7 | 64 |
| P60660 | Myosin light polypeptide 6 | MYL6 | *Homo sapiens* | 206.89 | 48.34 | 7 | 64 |
| P08107 | Heat shock 70 kDa protein 1A/1B | HSPA1A | *Homo sapiens* | 205.34 | 19.81 | 9 | 64 |
| P02794 | Ferritin heavy chain | FTH1 | *Homo sapiens* | 276.77 | 51.91 | 7 | 63 |
| Q01518 | Adenylyl cyclase-associated protein 1 | CAP1 | *Homo sapiens* | 232.42 | 30.95 | 11 | 63 |
| P21980 | Protein-glutamine gamma-glutamyltransferase 2 | TGM2 | *Homo sapiens* | 232.14 | 15.43 | 7 | 63 |
| P05387 | 60S acidic ribosomal protein P2 | RPLP2 | *Homo sapiens* | 256.84 | 69.57 | 4 | 62 |
| Q15293 | Reticulocalbin-1 | RCN1 | *Homo sapiens* | 254.49 | 37.16 | 7 | 62 |
| P04843 | Dolichyl-diphosphooligosaccharide-protein glycosyltransferase subunit 1 | RPN1 | *Homo sapiens* | 235.08 | 30.81 | 12 | 62 |
| P55786 | Puromycin-sensitive aminopeptidase | NPEPPS | *Homo sapiens* | 200.99 | 13.93 | 10 | 62 |
| Q9Y6C2 | EMILIN-1 | EMILIN1 | *Homo sapiens* | 210.60 | 14.76 | 11 | 60 |
| P31946 | 14-3-3 protein beta/alpha | YWHAB | *Homo sapiens* | 189.82 | 28.46 | 5 | 60 |
| P07108 | Acyl-CoA-binding protein | DBI | *Homo sapiens* | 235.46 | 50.57 | 3 | 59 |
| P50395 | Rab GDP dissociation inhibitor beta | GDI2 | *Homo sapiens* | 221.44 | 41.80 | 12 | 59 |
| P15121 | Aldose reductase | AKR1B1 | *Homo sapiens* | 216.09 | 36.39 | 7 | 59 |
| P61978 | Heterogeneous nuclear ribonucleoprotein K | HNRNPK | *Homo sapiens* | 211.91 | 29.59 | 10 | 59 |
| P53618 | Coatomer subunit beta | COPB1 | *Homo sapiens* | 199.75 | 18.68 | 11 | 59 |
| P62241 | 40S ribosomal protein S8 | RPS8 | *Homo sapiens* | 201.29 | 41.35 | 7 | 58 |
| Q86VP6 | Cullin-associated NEDD8-dissociated protein 1 | CAND1 | *Homo sapiens* | 199.18 | 10.24 | 9 | 58 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P30044 | Peroxiredoxin-5, mitochondrial | PRDX5 | *Homo sapiens* | 186.74 | 50.00 | 7 | 58 |
| P36578 | 60S ribosomal protein L4 | RPL4 | *Homo sapiens* | 178.67 | 14.75 | 5 | 58 |
| P61158 | Actin-related protein 3 | ACTR3 | *Homo sapiens* | 237.38 | 34.93 | 9 | 57 |
| Q9NQC3 | Reticulon-4 | RTN4 | *Homo sapiens* | 227.04 | 9.65 | 6 | 57 |
| P11216 | Glycogen phosphorylase, brain form | PYGB | *Homo sapiens* | 208.18 | 18.86 | 11 | 57 |
| Q14108 | Lysosome membrane protein 2 | SCARB2 | *Homo sapiens* | 200.13 | 19.46 | 6 | 57 |
| P23396 | 40S ribosomal protein S3 | RPS3 | *Homo sapiens* | 172.16 | 52.26 | 10 | 57 |
| P68871 | Hemoglobin subunit beta | HBB | *Homo sapiens* | 165.75 | 59.86 | 7 | 57 |
| P12236 | ADP/ATP translocase 3 | SLC25A6 | *Homo sapiens* | 161.18 | 21.81 | 6 | 57 |
| O60701 | UDP-glucose 6-dehydrogenase | UGDH | *Homo sapiens* | 218.40 | 38.06 | 13 | 56 |
| P00387 | NADH-cytochrome b5 reductase 3 | CYB5R3 | *Homo sapiens* | 205.94 | 53.16 | 9 | 56 |
| P30050 | 60S ribosomal protein L12 | RPL12 | *Homo sapiens* | 202.07 | 54.55 | 6 | 56 |
| P35237 | Serpin B6 | SERPINB6 | *Homo sapiens* | 201.97 | 32.18 | 9 | 56 |
| Q96KK5 | Histone H2A type 1-H | HIST1H2AH | *Homo sapiens* | 198.46 | 27.34 | 3 | 56 |
| P61204 | ADP-ribosylation factor 3 | ARF3 | *Homo sapiens* | 186.09 | 50.28 | 7 | 56 |
| P63241 | Eukaryotic translation initiation factor 5A-1 | EIF5A | *Homo sapiens* | 251.09 | 27.27 | 4 | 55 |
| P49748 | Very long-chain specific acyl-CoA dehydrogenase, mitochondrial | ACADVL | *Homo sapiens* | 226.83 | 16.64 | 7 | 55 |
| P50995 | Annexin A11 | ANXA11 | *Homo sapiens* | 186.26 | 12.87 | 5 | 55 |
| P53621 | Coatomer subunit alpha | COPA | *Homo sapiens* | 169.57 | 12.01 | 10 | 55 |
| P52209 | 6-Phosphogluconate dehydrogenase, decarboxylating | PGD | *Homo sapiens* | 219.84 | 20.50 | 7 | 54 |
| P30086 | Phosphatidylethanolamine-binding protein 1 | PEBP1 | *Homo sapiens* | 214.04 | 64.71 | 7 | 54 |
| Q9H299 | SH3 domain-binding glutamic acid-rich-like protein 3 | SH3BGRL3 | *Homo sapiens* | 210.88 | 31.18 | 3 | 54 |
| P17655 | Calpain-2 catalytic subunit | CAPN2 | *Homo sapiens* | 196.98 | 18.86 | 9 | 54 |
| P22392 | Nucleoside diphosphate kinase B | NME2 | *Homo sapiens* | 185.09 | 52.63 | 6 | 54 |
| Q15582 | Transforming growth factor-beta-induced protein ig-h3 | TGFBI | *Homo sapiens* | 171.73 | 7.91 | 4 | 54 |
| Q14697 | Neutral alpha-glucosidase AB | GANAB | *Homo sapiens* | 244.51 | 13.35 | 9 | 53 |
| P09972 | Fructose-bisphosphate aldolase C | ALDOC | *Homo sapiens* | 233.02 | 18.41 | 4 | 53 |
| Q9Y696 | Chloride intracellular channel protein 4 | CLIC4 | *Homo sapiens* | 225.06 | 67.98 | 12 | 53 |
| P13667 | Protein disulfide-isomerase A4 | PDIA4 | *Homo sapiens* | 216.49 | 17.05 | 8 | 53 |
| P78527 | DNA-dependent protein kinase catalytic subunit | PRKDC | *Homo sapiens* | 203.70 | 5.28 | 14 | 53 |
| P31939 | Bifunctional purine biosynthesis protein PURH [Includes: Phosphoribosylaminoimidazolecarboxamide formyltransferase] | ATIC | *Homo sapiens* | 188.54 | 15.71 | 7 | 52 |
| P02768 | Serum albumin | ALB | *Homo sapiens* | 201.86 | 3.94 | 3 | 51 |
| P52565 | Rho GDP-dissociation inhibitor 1 | ARHGDIA | *Homo sapiens* | 186.59 | 21.08 | 4 | 51 |
| P52907 | F-actin-capping protein subunit alpha-1 | CAPZA1 | *Homo sapiens* | 181.06 | 41.26 | 7 | 51 |
| O75874 | Isocitrate dehydrogenase [NADP] cytoplasmic | IDH1 | *Homo sapiens* | 167.93 | 27.78 | 9 | 51 |
| P14550 | Alcohol dehydrogenase [NADP(+)] | AKR1A1 | *Homo sapiens* | 176.30 | 23.38 | 7 | 50 |
| P22626 | Heterogeneous nuclear ribonucleoproteins A2/B1 | HNRNPA2B1 | *Homo sapiens* | 166.97 | 28.05 | 8 | 50 |
| P41250 | Glycine-tRNA ligase | GARS | *Homo sapiens* | 161.46 | 14.21 | 7 | 50 |
| P12956 | X-ray repair cross-complementing protein 6 | XRCC6 | *Homo sapiens* | 156.89 | 23.15 | 10 | 50 |
| Q04446 | 1,4-alpha-glucan-branching enzyme | GBE1 | *Homo sapiens* | 206.81 | 20.66 | 9 | 49 |
| Q6IUX7 | Adipocyte enhancer-binding protein 1 | AEBP1 | *Homo sapiens* | 205.43 | 10.71 | 8 | 49 |
| P00367 | Glutamate dehydrogenase 1, mitochondrial | GLUD1 | *Homo sapiens* | 193.31 | 16.31 | 6 | 49 |
| P24534 | Elongation factor 1-beta | EEF1B2 | *Homo sapiens* | 183.36 | 28.44 | 5 | 49 |
| P42224 | Signal transducer and activator of transcription 1-alpha/beta | STAT1 | *Homo sapiens* | 176.41 | 20.80 | 12 | 49 |
| P55209 | Nucleosome assembly protein 1-like 1 | NAP1L1 | *Homo sapiens* | 200.78 | 14.58 | 4 | 48 |
| Q9Y678 | Coatomer subunit gamma-1 | COPG1 | *Homo sapiens* | 196.07 | 12.36 | 7 | 48 |
| P14314 | Glucosidase 2 subunit beta | PRKCSH | *Homo sapiens* | 180.64 | 14.58 | 6 | 48 |
| Q96CX2 | BTB/POZ domain-containing protein KCTD12 | KCTD12 | *Homo sapiens* | 136.59 | 14.77 | 4 | 47 |
| P50609 | Fibromodulin | FMOD | *Rattus norvegicus* | 170.37 | 19.68 | 5 | 47 |
| P50990 | T-complex protein 1 subunit theta | CCT8 | *Homo sapiens* | 149.29 | 17.34 | 7 | 46 |
| P10599 | Thioredoxin | TXN | *Homo sapiens* | 149.25 | 31.43 | 4 | 46 |
| P30153 | Serine/threonine-protein phosphatase 2A 65 kDa regulatory subunit A alpha isoform | PPP2R1A | *Homo sapiens* | 182.68 | 18.51 | 7 | 45 |
| P55084 | Trifunctional enzyme subunit beta, mitochondrial | HADHB | *Homo sapiens* | 171.75 | 23.21 | 7 | 45 |
| P62158 | Calmodulin | CALM1 | *Homo sapiens* | 183.48 | 44.30 | 5 | 44 |
| P32119 | Peroxiredoxin-2 | PRDX2 | *Homo sapiens* | 160.79 | 14.65 | 3 | 44 |
| P49411 | Elongation factor Tu, mitochondrial | TUFM | *Homo sapiens* | 161.57 | 15.27 | 4 | 43 |
| P62979 | Ubiquitin-40S ribosomal protein S27a | RPS27A | *Homo sapiens* | 152.11 | 33.97 | 4 | 43 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| O00159 | Unconventional myosin-Ic | MYO1C | *Homo sapiens* | 151.42 | 14.58 | 11 | 43 |
| P34932 | Heat shock 70 kDa protein 4 | HSPA4 | *Homo sapiens* | 149.37 | 15.95 | 9 | 43 |
| Q9P2E9 | Ribosome-binding protein 1 | RRBP1 | *Homo sapiens* | 147.57 | 11.70 | 10 | 43 |
| Q99497 | Protein DJ-1 | PARK7 | *Homo sapiens* | 164.37 | 42.33 | 6 | 42 |
| P62701 | 40S ribosomal protein S4, X isoform | RPS4X | *Homo sapiens* | 150.60 | 29.66 | 7 | 42 |
| P29692 | Elongation factor 1-delta | EEF1D | *Homo sapiens* | 136.02 | 32.38 | 7 | 42 |
| Q8NBS9 | Thioredoxin domain-containing protein 5 | TXNDC5 | *Homo sapiens* | 165.03 | 18.98 | 6 | 41 |
| P19105 | Myosin regulatory light chain 12A | MYL12A | *Homo sapiens* | 161.76 | 39.18 | 5 | 41 |
| Q14974 | Importin subunit beta-1 | KPNB1 | *Homo sapiens* | 157.88 | 19.18 | 11 | 41 |
| P39687 | Acidic leucine-rich nuclear phosphoprotein 32 family member A | ANP32A | *Homo sapiens* | 137.22 | 12.85 | 3 | 41 |
| P30048 | Thioredoxin-dependent peroxide reductase, mitochondrial | PRDX3 | *Homo sapiens* | 222.53 | 28.91 | 4 | 40 |
| P47755 | F-actin-capping protein subunit alpha-2 | CAPZA2 | *Homo sapiens* | 156.24 | 23.43 | 4 | 40 |
| P17931 | Galectin-3 | LGALS3 | *Homo sapiens* | 154.89 | 25.60 | 5 | 40 |
| P09651 | Heterogeneous nuclear ribonucleoprotein A1 | HNRNPA1 | *Homo sapiens* | 142.70 | 22.31 | 6 | 40 |
| P51991 | Heterogeneous nuclear ribonucleoprotein A3 | HNRNPA3 | *Homo sapiens* | 139.93 | 21.96 | 6 | 40 |
| P07384 | Calpain-1 catalytic subunit | CAPN1 | *Homo sapiens* | 135.52 | 9.24 | 5 | 40 |
| O95782 | AP-2 complex subunit alpha-1 | AP2A1 | *Homo sapiens* | 134.84 | 13.20 | 9 | 40 |
| P48444 | Coatomer subunit delta | ARCN1 | *Homo sapiens* | 132.91 | 15.46 | 5 | 40 |
| P04080 | Cystatin-B | CSTB | *Homo sapiens* | 158.66 | 45.92 | 3 | 39 |
| O43390 | Heterogeneous nuclear ribonucleoprotein R | HNPNPR | *Homo sapiens* | 142.15 | 8.53 | 4 | 39 |
| P61247 | 40S ribosomal protein S3a | RPS3A | *Homo sapiens* | 133.56 | 18.18 | 4 | 39 |
| P04899 | Guanine nucleotide-binding protein G(i) subunit alpha-2 | GNAI2 | *Homo sapiens* | 131.68 | 17.18 | 4 | 39 |
| Q16658 | Fascin | FSCN1 | *Homo sapiens* | 167.69 | 26.37 | 9 | 38 |
| Q07021 | Complement component 1 Q subcomponent-binding protein, mitochondrial | C1QBP | *Homo sapiens* | 166.75 | 12.06 | 3 | 38 |
| P62829 | 60S ribosomal protein L23 | RPL23 | *Homo sapiens* | 162.51 | 25.00 | 2 | 38 |
| P07099 | Epoxide hydrolase 1 | EPHX1 | *Homo sapiens* | 158.47 | 27.47 | 9 | 38 |
| P50991 | T-complex protein 1 subunit delta | CCT4 | *Homo sapiens* | 151.63 | 10.76 | 4 | 38 |
| P27105 | Erythrocyte band 7 integral membrane protein | STOM | *Homo sapiens* | 142.49 | 41.32 | 7 | 38 |
| P15559 | NAD(P)H dehydrogenase [quinone] 1 | NQO1 | *Homo sapiens* | 141.57 | 17.15 | 4 | 38 |
| Q00839 | Heterogeneous nuclear ribonucleoprotein U | HNRNPU | *Homo sapiens* | 135.88 | 15.03 | 7 | 38 |
| P27816 | Microtubule-associated protein 4 | MAP4 | *Homo sapiens* | 125.87 | 9.64 | 7 | 38 |
| P00966 | Argininosuccinate synthase | ASS1 | *Homo sapiens* | 125.52 | 14.81 | 4 | 38 |
| P19338 | Nucleolin | NCL | *Homo sapiens* | 125.15 | 13.66 | 8 | 38 |
| P37837 | Transaldolase | TALDO1 | *Homo sapiens* | 121.68 | 14.24 | 4 | 38 |
| P06753 | Tropomyosin alpha-3 chain | TPM3 | *Homo sapiens* | 119.22 | 13.38 | 5 | 38 |
| Q15366 | Poly(rC)-binding protein 2 | PCBP2 | *Homo sapiens* | 118.11 | 11.78 | 3 | 38 |
| Q01129 | Decorin | DCN | *Rattus norvegicus* | 107.47 | 18.64 | 6 | 38 |
| P06748 | Nucleophosmin | NPM1 | *Homo sapiens* | 144.28 | 24.49 | 8 | 37 |
| P62906 | 60S ribosomal protein L10a | RPL10A | *Homo sapiens* | 141.74 | 25.81 | 4 | 37 |
| Q12797 | Aspartyl/asparaginyl beta-hydroxylase | ASPH | *Homo sapiens* | 139.39 | 15.44 | 8 | 37 |
| P16615 | Sarcoplasmic/endoplasmic reticulum calcium ATPase 2 | ATP2A2 | *Homo sapiens* | 124.62 | 9.12 | 7 | 37 |
| P46782 | 40S ribosomal protein S5 [Cleaved into: 40S ribosomal protein S5, N-terminally processed] | RPS5 | *Homo sapiens* | 122.17 | 17.65 | 3 | 37 |
| Q07020 | 60S ribosomal protein L18 | RPL18 | *Homo sapiens* | 117.66 | 30.85 | 5 | 37 |
| P50914 | 60S ribosomal protein L14 | RPL14 | *Homo sapiens* | 109.86 | 15.35 | 3 | 37 |
| P62244 | 40S ribosomal protein S15a | RPS15A | *Homo sapiens* | 138.62 | 30.00 | 4 | 36 |
| P13645 | Keratin, type I cytoskeletal 10 | KRT10 | *Homo sapiens* | 117.06 | 21.40 | 9 | 36 |
| P56134 | ATP synthase subunit 1, mitochondrial | ATP5J2 | *Homo sapiens* | 110.17 | 25.53 | 2 | 36 |
| P07910 | Heterogeneous nuclear ribonucleoproteins C1/C2 | HNRNPC | *Homo sapiens* | 102.07 | 15.03 | 4 | 36 |
| P78371 | T-complex protein 1 subunit beta | CCT2 | *Homo sapiens* | 159.70 | 25.61 | 9 | 35 |
| P05534 | HLA class I histocompatibility antigen, A-24 alpha chain | HLA-A | *Homo sapiens* | 127.63 | 30.14 | 7 | 35 |
| P62888 | 60S ribosomal protein L30 | RPL30 | *Homo sapiens* | 127.35 | 34.78 | 3 | 35 |
| Q16698 | 2,4-dienoyl-CoA reductase, mitochondrial | DECR1 | *Homo sapiens* | 112.19 | 17.91 | 4 | 35 |
| Q9Y265 | RuvB-like 1 | RUVBL1 | *Homo sapiens* | 110.51 | 23.03 | 7 | 35 |
| P42785 | Lysosomal Pro-X carboxypeptidase | PRCP | *Homo sapiens* | 118.66 | 9.48 | 3 | 34 |
| Q969G5 | Protein kinase C delta-binding protein | PRKCDBP | *Homo sapiens* | 114.93 | 17.24 | 4 | 34 |
| P62424 | 60S ribosamal protein L7a | RPL7A | *Homo sapiens* | 105.69 | 15.04 | 4 | 34 |
| P60981 | Destrin | DSTN | *Homo sapiens* | 102.99 | 20.00 | 3 | 34 |
| P62879 | Guanine nucleotide-binding protein G(I)/G(S)/G(T) subunit beta-2 | GNB2 | *Homo sapiens* | 98.15 | 15.29 | 4 | 34 |
| Q92743 | Serine protease HTRA1 | HTRA1 | *Homo sapiens* | 97.18 | 11.25 | 5 | 34 |
| P00441 | Superoxide dismutase [Cu—Zn] | SOD1 | *Homo sapiens* | 191.85 | 32.47 | 4 | 33 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| Q15181 | Inorganic pyrophosphatase | PPA1 | *Homo sapiens* | 145.98 | 35.99 | 7 | 33 |
| P63010 | AP-2 complex subunit beta | AP2B1 | *Homo sapiens* | 127.86 | 13.13 | 7 | 33 |
| P15531 | Nucleoside diphosphate kinase A | NME1 | *Homo sapiens* | 123.53 | 51.97 | 6 | 33 |
| P08473 | Neprilysin | MME | *Homo sapiens* | 120.47 | 13.07 | 7 | 33 |
| P62826 | GTP-binding nuclear protein Ran | RAN | *Homo sapiens* | 117.10 | 34.26 | 6 | 33 |
| P17980 | 26S protease regulatory subunit 6A | PSMC3 | *Homo sapiens* | 110.28 | 21.41 | 6 | 33 |
| Q43776 | Asparagine--tRNA ligase, cytoplasmic | NARS | *Homo sapiens* | 107.40 | 19.71 | 8 | 33 |
| P15880 | 40S ribosomal protein S2 | RPS2 | *Homo sapiens* | 101.99 | 19.45 | 5 | 33 |
| P31949 | Protein S100-A11 | S100A11 | *Homo sapiens* | 93.44 | 40.95 | 4 | 33 |
| P68036 | Ubiquitin-conjugating enzyme E2L3 | UBE2L3 | *Homo sapiens* | 143.93 | 35.71 | 3 | 32 |
| P17301 | Integrin alpha-2 | ITGA2 | *Homo sapiens* | 128.38 | 6.77 | 5 | 32 |
| P16070 | CD44 antigen | CD44 | *Homo sapiens* | 126.71 | 3.77 | 2 | 32 |
| P69905 | Hemoglobin subunit alpha | HBA1; | *Homo sapiens* | 115.45 | 28.17 | 3 | 32 |
| P61106 | Ras-related protein Rab-14 | RAB14 | *Homo sapiens* | 104.55 | 16.74 | 3 | 32 |
| P62249 | 40S ribosomal protein S16 | RPS16 | *Homo sapiens* | 89.33 | 20.55 | 3 | 32 |
| Q16851 | UTP-glucose-1-phosphate uridylyltransferase | UGP2 | *Homo sapiens* | 150.43 | 12.60 | 4 | 31 |
| P60033 | CD81 antigen | CD81 | *Homo sapiens* | 144.01 | 25.00 | 3 | 31 |
| P23142 | Fibulin-1 | FBLN1 | *Homo sapiens* | 139.79 | 20.91 | 7 | 31 |
| P28066 | Proteasome subunit alpha type-5 | PSMA5 | *Homo sapiens* | 127.88 | 35.27 | 5 | 31 |
| P49755 | Transmembrane emp24 domain-containing protein 10 | TMED10 | *Homo sapiens* | 125.42 | 16.89 | 3 | 31 |
| Q06323 | Proteasome activator-complex subunit 1 | PSME1 | *Homo sapiens* | 110.60 | 27.71 | 8 | 31 |
| Q13838 | Spliceosome RNA helicase DDX39B | DDX39B | *Homo sapiens* | 104.76 | 22.43 | 6 | 31 |
| P61586 | Transforming protein RhoA | RHOA | *Homo sapiens* | 103.88 | 32.64 | 5 | 31 |
| P78539 | Sushi repeat-containing protein SRPX | SRPX | *Homo sapiens* | 94.78 | 7.76 | 3 | 31 |
| P15586 | N-acetyglucosamine-6-sulfatase | GNS | *Homo sapiens* | 93.73 | 11.23 | 4 | 31 |
| P59998 | Actin-related protein 2/3 complex subunit 4 | ARPC4 | *Homo sapiens* | 92.41 | 35.71 | 5 | 31 |
| Q9BSJ8 | Extended synaptotagmin-1 | ESYT1 | *Homo sapiens* | 92.29 | 7.34 | 6 | 31 |
| P25396 | 40S ribosomal protein S12 | RPS12 | *Homo sapiens* | 129.03 | 31.82 | 3 | 30 |
| Q5T9L3 | Protein wntless homolog | WLS | *Homo sapiens* | 127.49 | 9.80 | 4 | 30 |
| P20810 | Calpastatin | CAST | *Homo sapiens* | 124.88 | 10.88 | 4 | 30 |
| P00325 | Alcohol dehydrogenase 1B | ADH1B | *Homo sapiens* | 118.70 | 26.67 | 7 | 30 |
| P23219 | Prostaglandin G/H synthase 1 | PTGS1 | *Homo sapiens* | 113.71 | 12.85 | 5 | 30 |
| Q00325 | Phosphate carrier protein, mitochondrial | SLC25A3 | *Homo sapiens* | 102.13 | 19.06 | 5 | 30 |
| P45926 | Glucosemine-6-phosphate isomerase 1 | GNPDA1 | *Homo sapiens* | 93.67 | 21.11 | 4 | 30 |
| P28838 | Cytosol aminopeptidase | LAP3 | *Homo sapiens* | 120.58 | 14.64 | 5 | 29 |
| P17858 | 5-phosphofructokinase, liver type | PFKL | *Homo sapiens* | 112.91 | 14.49 | 8 | 29 |
| Q96TA1 | Niban-like protein 1 | FAM129B | *Homo sapiens* | 108.73 | 14.88 | 7 | 29 |
| P62277 | 40S ribosomal protein S13 | RPS13 | *Homo sapiens* | 106.57 | 18.54 | 3 | 29 |
| Q96QK1 | Vacuolar protein sorting-associated protein 35 | VPS35 | *Homo sapiens* | 100.71 | 12.06 | 7 | 29 |
| P39019 | 40S ribosomal protein S19 | RPS19 | *Homo sapiens* | 94.38 | 30.34 | 6 | 29 |
| Q13162 | Peroxiredoxin-4 | PRDX4 | *Homo sapiens* | 93.42 | 37.64 | 7 | 29 |
| Q14103 | Heterogeneous nuclear ritonucleoprotein D0 | HNRNPD | *Homo sapiens* | 85.53 | 14.65 | 4 | 29 |
| Q6NXT2 | Histone H3.3C | H3F3C | *Homo sapiens* | 77.14 | 11.85 | 2 | 29 |
| P26599 | Polypyrimidine tract-binding protein 1 | PTBP1 | *Homo sapiens* | 129.28 | 12.62 | 4 | 28 |
| P62942 | Peptidyl-prolyl cis-trans isomerase FKBP1A | FKBP1A | *Homo sapiens* | 129.28 | 29.63 | 3 | 28 |
| P18124 | 60S ribosomal protein L7 | RPL7 | *Homo sapiens* | 105.73 | 23.39 | 4 | 26 |
| P98160 | Basement membrane-specific heparan sulfate proteoglycan core protein | HSPG2 | *Homo sapiens* | 104.99 | 2.37 | 7 | 28 |
| P62140 | Serine/threonine-protein phosphatase PP1-beta catalytic subunit | PPP1CB | *Homo sapiens* | 102.12 | 18.96 | 5 | 28 |
| P51686 | N-sulphoglucosamine sulphohydrolase | SGSH | *Homo sapiens* | 101.57 | 8.37 | 3 | 28 |
| P21399 | Cytoplasmic aconitate hydratase | ACO1 | *Homo sapiens* | 98.99 | 11.81 | 7 | 28 |
| P08253 | 72 kDa type IV collagenase | MMP2 | *Homo sapiens* | 95.34 | 10.91 | 4 | 28 |
| O00571 | ATP-dependent RNA helicase DDX3X | DDX3X | *Homo sapiens* | 91.46 | 9.67 | 5 | 28 |
| O9Y2Q3 | Glutathione S-transferase kappa 1 | GSTK1 | *Homo sapiens* | 90.89 | 33.63 | 6 | 28 |
| P35232 | Prohibitin | PHB | *Homo sapiens* | 88.99 | 28.31 | 6 | 28 |
| Q9Y277 | Voltage-dependent anion-selective channel protein 3 | VDAC3 | *Homo sapiens* | 81.75 | 14.49 | 3 | 28 |
| P51659 | Peroxisomal multifunctional enzyme type 2 | HSD17B4 | *Homo sapiens* | 106.47 | 10.87 | 5 | 27 |
| Q05682 | Caldesmon | CALD1 | *Homo sapiens* | 85.52 | 5.17 | 4 | 27 |
| P46783 | 40S ribosomal protein S10 | RPS10 | *Homo sapiens* | 86.11 | 14.55 | 2 | 27 |
| P83731 | 60S ribosomal protein L24 | RPL24 | *Homo sapiens* | 80.95 | 20.38 | 3 | 27 |
| P30040 | Endoplasmic reticulum resident protein 29 | ERP29 | *Homo sapiens* | 73.20 | 14.18 | 3 | 27 |
| P62269 | 40S ribosomal protein S18 | RPS18 | *Homo sapiens* | 71.59 | 16.45 | 3 | 27 |
| Q96HE7 | ERO1-like protein alpha | ERO1L | *Homo sapiens* | 114.32 | 22.44 | 6 | 26 |
| Q16181 | Septin-7 | 41889 | *Homo sapiens* | 100.36 | 21.97 | 6 | 26 |
| P43235 | Cathepsin K | CTSK | *Homo sapiens* | 99.90 | 19.45 | 3 | 26 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P40261 | Nicotinamide N-methyltransferase | NNMT | *Homo sapiens* | 99.01 | 21.97 | 4 | 26 |
| O43399 | Tumor protein D54 | TPD52L2 | *Homo sapiens* | 96.02 | 36.41 | 5 | 26 |
| P21266 | Glutathione S-transferase Mu 3 | ALB | *Homo sapiens* | 84.67 | 22.67 | 4 | 26 |
| P08962 | CD63 antigen | GSTM3 | *Homo sapiens* | 72.76 | 7.56 | 2 | 26 |
| P02770 | Serum albumin | CD63 | *Rattus norvegicus* | 93.78 | 4.28 | 2 | 26 |
| P22695 | Cytochrome b-c1 complex subunit 2, mitochondrial | UQCRC2 | *Homo sapiens* | 104.25 | 16.78 | 5 | 25 |
| P39023 | 60S ribosomal protein L3 | RPL3 | *Homo sapiens* | 103.60 | 20.84 | 6 | 25 |
| Q00341 | Vigilin | HDLBP | *Homo sapiens* | 103.20 | 4.10 | 3 | 25 |
| Q01813 | 6-phosphofructokinase type C | PFKP | *Homo sapiens* | 97.67 | 13.14 | 6 | 25 |
| P12955 | Xaa-Pro dipeptidase | PEPD | *Homo sapiens* | 92.15 | 8.32 | 3 | 25 |
| P27487 | Dipeptidyl peptidase 4 | DPP4 | *Homo sapiens* | 90.72 | 10.44 | 6 | 25 |
| P05413 | Fatty acid-binding protein, heart | FABP3 | *Homo sapiens* | 88.34 | 45.86 | 6 | 25 |
| P35908 | Keratin, type II cytoskeletal 2 epidermal | KRT2 | *Homo sapiens* | 85.90 | 11.58 | 6 | 25 |
| P21589 | 5′-nucleotidase | NT5E | *Homo sapiens* | 85.75 | 15.85 | 6 | 25 |
| O75915 | PRA1 family protein 3 | ARL6IP5 | *Homo sapiens* | 81.97 | 15.96 | 2 | 25 |
| P05556 | Integrin beta-1 | ITGB1 | *Homo sapiens* | 80.76 | 6.02 | 4 | 25 |
| Q8WUW4 | Programmed cell death 6-interacting protein | PDCD6IP | *Homo sapiens* | 74.74 | 7.37 | 5 | 25 |
| P78417 | Glutathione S-transferase omega-1 | GSTO1 | *Homo sapiens* | 74.27 | 7.88 | 2 | 25 |
| P46781 | 40S ribosomal protein S9 | RPS9 | *Homo sapiens* | 68.19 | 13.40 | 3 | 25 |
| P14866 | Heterogeneous nuclear ribonucleoprotein L | HNRNPL | *Homo sapiens* | 123.31 | 8.66 | 2 | 24 |
| P40227 | T-complex protein 1 subunit zeta | CCT6A | *Homo sapiens* | 112.14 | 25.05 | 7 | 24 |
| Q12905 | Interleukin enhancer-binding factor 2 | ILF2 | *Homo sapiens* | 105.67 | 12.82 | 3 | 24 |
| Q7KZF4 | Staphylococcal nuclease domain-containing protein 1 | SND1 | *Homo sapiens* | 99.88 | 13.19 | 7 | 24 |
| P02765 | Alpha-2-HS-glycoprotein | AHSG | *Homo sapiens* | 90.57 | 5.45 | 2 | 24 |
| O60506 | Heterogeneous nuclear ribonucleoprotein Q | SYNCRIP | *Homo sapiens* | 90.57 | 11.88 | 5 | 24 |
| P23634 | Plasma membrane calcium-transporting ATPase 4 | ATP284 | *Homo sapiens* | 85.12 | 2.50 | 2 | 24 |
| P10155 | 60 kDa SS-A/Ro ribonucleoprotein | TROVE2 | *Homo sapiens* | 79.15 | 4.46 | 2 | 24 |
| O00231 | 26S proteasome non-ATPase regulatory subunit 11 | PSMD11 | *Homo sapiens* | 75.89 | 8.77 | 3 | 24 |
| P61088 | Ubiquitin-conjugating enzyme E2 N | UBE2N | *Homo sapiens* | 71.94 | 41.45 | 5 | 24 |
| P05386 | 60S acidic ribosomal protein P1 | RPLP1 | *Homo sapiens* | 110.40 | 51.75 | 2 | 23 |
| O15460 | Prolyl 4-hydroxylase subunit alpha-2 | P4HA2 | *Homo sapiens* | 101.78 | 12.90 | 5 | 23 |
| P13693 | Translationally-controlled tumor protein | TPT1 | *Homo sapiens* | 94.17 | 12.21 | 2 | 23 |
| P10620 | Microsomal glutathione S-transferase 1 | MGST1 | *Homo sapiens* | 89.77 | 27.10 | 3 | 23 |
| Q99623 | Prohibitin-2 | PHB2 | *Homo sapiens* | 82.71 | 25.42 | 6 | 23 |
| P61604 | 10 kDa heat shock protein, mitochondrial | HSPE1 | *Homo sapiens* | 82.34 | 25.49 | 2 | 23 |
| Q8NHP8 | Putative phospholipase B-like 2 | PLBD2 | *Homo sapiens* | 81.14 | 8.49 | 4 | 23 |
| P35754 | Glutaredoxin-1 | GLRX | *Homo sapiens* | 75.29 | 30.19 | 2 | 23 |
| P17987 | T-complex protein 1 subunit alpha | TCP1 | *Homo sapiens* | 66.48 | 8.45 | 4 | 23 |
| P16403 | Histone H1.2 | HIST1H1C | *Homo sapiens* | 63.40 | 19.72 | 4 | 23 |
| P01033 | Metalloproteinase inhibitor 1 | TIMP1 | *Homo sapiens* | 90.30 | 28.02 | 4 | 22 |
| P60866 | 40S ribosomal protein S20 | RPS20 | *Homo sapiens* | 87.96 | 19.33 | 2 | 22 |
| P04179 | Superoxide dismutase [Mn], mitochondrial | SOD2 | *Homo sapiens* | 84.22 | 22.97 | 4 | 22 |
| P01889 | HLA class I histocompatibility antigen, B-7 alpha chain | HLA-B | *Homo sapiens* | 80.41 | 20.72 | 5 | 22 |
| Q9UBG0 | C-type mannose receptor 2 | MRC2 | *Homo sapiens* | 79.01 | 4.12 | 4 | 22 |
| O94979 | Protein transport protein Sec31A | SEC31A | *Homo sapiens* | 75.45 | 4.67 | 4 | 22 |
| P07711 | Cathepsin L1 | CTSL | *Homo sapiens* | 72.15 | 8.41 | 2 | 22 |
| P25789 | Proteasome subunit alpha type-4 | PSMA4 | *Homo sapiens* | 67.06 | 21.46 | 3 | 22 |
| P61160 | Actin-related protein 2 | ACTR2 | *Homo sapiens* | 63.07 | 12.94 | 4 | 22 |
| Q9UHD8 | Septin-9 | 41891 | *Homo sapiens* | 62.81 | 13.14 | 5 | 22 |
| P35268 | 60S ribosomal protein L22 | RPL22 | *Homo sapiens* | 62.65 | 18.75 | 2 | 22 |
| P30084 | Enoyl-CoA hydratase, mitochondrial | ECHS1 | *Homo sapiens* | 96.93 | 19.31 | 3 | 21 |
| O14773 | Tripeptidyl-peptidase 1 | TPP1 | *Homo sapiens* | 81.36 | 8.17 | 3 | 21 |
| P62333 | 26S protease regulatory subunit 10B | PSMC6 | *Homo sapiens* | 79.86 | 11.83 | 3 | 21 |
| P54709 | Sodium/potassium-transporting ATPase subunit beta-3 | ATP1B3 | *Homo sapiens* | 76.45 | 17.20 | 3 | 21 |
| P13010 | X-ray repair cross-complementing protein 5 | XRCC5 | *Homo sapiens* | 76.09 | 11.34 | 5 | 21 |
| P39656 | Dolichyl-diphosphooligosaccharide-protein glycosyltransferase 48 kDa subunit | DDOST | *Homo sapiens* | 75.49 | 16.23 | 5 | 21 |
| Q16881 | Thioredoxin reductase 1, cytoplasmic | TXNRD1 | *Homo sapiens* | 73.59 | 10.02 | 4 | 21 |
| Q9NR45 | Sialic acid synthase | NANS | *Homo sapiens* | 73.04 | 15.88 | 3 | 21 |
| P13674 | Prolyl 4-hydroxylase subunit alpha-1 | P4HA1 | *Homo sapiens* | 72.31 | 14.98 | 6 | 21 |
| P47756 | F-actin-capping protein subunit beta | CAPZB | *Homo sapiens* | 71.92 | 20.94 | 4 | 21 |
| P61313 | 60S ribosomal protein L15 | RPL15 | *Homo sapiens* | 70.62 | 17.16 | 3 | 21 |
| P11047 | Laminin subunit gamma-1 | LAMC1 | *Homo sapiens* | 66.17 | 5.90 | 7 | 21 |
| P51148 | Ras-related protein Rab-5C | RAB5C | *Homo sapiens* | 63.90 | 23.15 | 4 | 21 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| O75390 | Citrate synthase, mitochondrial | CS | *Homo sapiens* | 60.12 | 7.73 | 3 | 21 |
| P62263 | 40S ribosomal protein S14 | RPS14 | *Homo sapiens* | 87.52 | 21.19 | 2 | 20 |
| Q13724 | Mannosyl-oligosaccharide glucosidase | MOGS | *Homo sapiens* | 84.85 | 3.58 | 2 | 20 |
| P36543 | V-type proton ATPase subunit E 1 | ATP6V1E1 | *Homo sapiens* | 79.06 | 6.19 | 2 | 20 |
| P13797 | Plastin-3 | PLS3 | *Homo sapiens* | 70.30 | 10.79 | 5 | 20 |
| P54920 | Alpha-soluble NSF attachment protein | NAPA | *Homo sapiens* | 68.68 | 28.47 | 6 | 20 |
| P27635 | 60S ribosomal protein L10 | RPL10 | *Homo sapiens* | 64.27 | 23.83 | 3 | 20 |
| Q04760 | Lactoylglutathione lyase | GLO1 | *Homo sapiens* | 63.58 | 14.67 | 2 | 20 |
| P26640 | Valine-tRNA ligase | VARS | *Homo sapiens* | 62.47 | 3.88 | 4 | 20 |
| O94905 | Erlin-2 | ERLIN2 | *Homo sapiens* | 61.85 | 16.81 | 4 | 20 |
| O14979 | Heterogeneous nuclear ribonucleoprotein D-like | HNRNPDL | *Homo sapiens* | 61.35 | 9.76 | 3 | 20 |
| P13473 | Lysosome-associated membrane glycoprotein 2 | LAMP2 | *Homo sapiens* | 57.75 | 7.07 | 3 | 20 |
| P11940 | Polyadenylate-binding protein 1 | PABPC1 | *Homo sapiens* | 56.47 | 9.91 | 5 | 20 |
| P20340 | Ras-related protein Rab-6A | RAB6A | *Homo sapiens* | 54.52 | 22.12 | 4 | 20 |
| P62318 | Small nuclear ribonucleoprotein Sm D3 | SNRPD3 | *Homo sapiens* | 53.58 | 15.08 | 2 | 20 |
| Q99460 | 26S proteasome non-ATPase regulatory subunit 1 | PSMD1 | *Homo sapiens* | 109.07 | 5.46 | 3 | 19 |
| Q9BS26 | Endoplasmic reticulum resident protein 44 | ERP44 | *Homo sapiens* | 90.29 | 15.27 | 4 | 19 |
| Q15185 | Prostaglandin E synthase 3 | PTGES3 | *Homo sapiens* | 87.82 | 18.13 | 2 | 19 |
| P29373 | Cellular retinoic acid-binding protein 2 | CRABP2 | *Homo sapiens* | 84.96 | 34.78 | 4 | 19 |
| P20618 | Proteasome subunit beta type-1 | PSMB1 | *Homo sapiens* | 79.58 | 21.16 | 3 | 19 |
| Q9Y3I0 | tRNA-splicing ligase RtcB homolog | RTCB | *Homo sapiens* | 75.39 | 13.47 | 4 | 19 |
| O14818 | Proteasome subunit alpha type-7 | PSMA7 | *Homo sapiens* | 74.40 | 28.63 | 4 | 19 |
| P51636 | Caveolin-2 | CAV2 | *Homo sapiens* | 71.42 | 20.99 | 2 | 19 |
| P35606 | Coatomer subunit beta' | COPB2 | *Homo sapiens* | 67.84 | 10.49 | 6 | 19 |
| Q15836 | Vesicle-associated membrane protein 3 | VAMP3 | *Homo sapiens* | 67.54 | 33.00 | 2 | 19 |
| P21810 | Biglycan | BGN | *Homo sapiens* | 65.73 | 10.87 | 3 | 19 |
| Q99715 | Collagen alpha-1(XII) chain | COL12A1 | *Homo sapiens* | 63.88 | 3.40 | 7 | 19 |
| Q13557 | Calcium/calmodulin-dependent protein kinase type II subunit delta | CAMK2D | *Homo sapiens* | 63.08 | 16.03 | 5 | 19 |
| P00505 | Aspartate aminotransferase, mitochondrial | GOT2 | *Homo sapiens* | 60.55 | 14.42 | 5 | 19 |
| P02786 | Transferrin receptor protein 1 | TFRC | *Homo sapiens* | 56.99 | 5.00 | 3 | 19 |
| P04062 | Glucosylceramidase | GBA | *Homo sapiens* | 54.01 | 4.48 | 2 | 19 |
| Q9NVA2 | Septin-11 | 41869 | *Homo sapiens* | 51.50 | 8.86 | 3 | 19 |
| Q8IWE2 | Protein NOXP20 | FAM114A1 | *Homo sapiens* | 76.12 | 14.03 | 5 | 18 |
| Q9NVJ2 | ADP-ribosylation factor-like protein 8B | ARL8B | *Homo sapiens* | 72.50 | 34.95 | 5 | 18 |
| P07814 | Bifunctional glutamate/proline--tRNA ligase | EPRS | *Homo sapiens* | 71.04 | 4.70 | 4 | 18 |
| Q9UNM6 | 26S proteasome non-ATPase regulatory subunit 13 | PSMD13 | *Homo sapiens* | 69.95 | 18.62 | 5 | 18 |
| Q13200 | 26S proteasome non-ATPase regulatory subunit 2 | PSMD2 | *Homo sapiens* | 68.87 | 9.47 | 6 | 18 |
| Q07960 | Rho GTPase-activating protein 1 | ARHGAP1 | *Homo sapiens* | 68.44 | 14.35 | 4 | 18 |
| P36957 | Dihydrolipoyllysine-residue succinyltransferase component of 2-oxoglutarate dehydrogenase complex, mitochondrial | DLST | *Homo sapiens* | 66.31 | 12.80 | 4 | 18 |
| Q13492 | Phosphatidylinositol-binding clathrin assembly protein | PICALM | *Homo sapiens* | 61.69 | 4.91 | 2 | 18 |
| P13804 | Electron transfer flavoprotein subunit alpha, mitochondrial | ETFA | *Homo sapiens* | 59.21 | 25.53 | 6 | 18 |
| P62753 | 40S ribosomal protein S6 | RPS6 | *Homo sapiens* | 57.11 | 18.88 | 4 | 18 |
| P11279 | Lysosome-associated membrane glycoprotein 1 | LAMP1 | *Homo sapiens* | 54.87 | 10.55 | 4 | 18 |
| Q15075 | Early endosome antigen 1 | EEA1 | *Homo sapiens* | 54.84 | 4.61 | 5 | 18 |
| Q9UHA4 | Ragulator complex protein LAMTOR3 | LAMTOR3 | *Homo sapiens* | 53.15 | 30.65 | 2 | 18 |
| P49773 | Histidine triad nucleotide-binding protein 1 | HINT1 | *Homo sapiens* | 114.80 | 53.97 | 3 | 17 |
| P04632 | Calpain small subunit 1 | CAPNS1 | *Homo sapiens* | 72.67 | 44.40 | 5 | 17 |
| Q9H4M9 | EH domain-containing protein 1 | EHD1 | *Homo sapiens* | 72.21 | 14.42 | 5 | 17 |
| O75367 | Core histone macro-H2A.1 | H2AFY | *Homo sapiens* | 72.16 | 13.44 | 3 | 17 |
| O15144 | Actin-related protein 2/3 complex subunit 2 | ARPC2 | *Homo sapiens* | 66.66 | 21.67 | 4 | 17 |
| Q9NYU2 | UDP-glucose:glycoprotein glucosyltransferase 1 | UGGT1 | *Homo sapiens* | 63.95 | 6.17 | 6 | 17 |
| Q9UIJ7 | GTP:AMP phosphotransferase AK3, mitochondrial | AK3 | *Homo sapiens* | 62.60 | 18.50 | 3 | 17 |
| Q7L2H7 | Eukaryotic translation initiation factor 3 subunit M | EIF3M | *Homo sapiens* | 60.36 | 15.78 | 4 | 17 |
| P62857 | 40S ribosomal protein S28 | RPS28 | *Homo sapiens* | 58.87 | 33.33 | 2 | 17 |
| Q02878 | 60S ribosomal protein L6 | RPL6 | *Homo sapiens* | 58.47 | 15.63 | 3 | 17 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| Q15436 | Protein transport protein Sec23A | SEC23A | *Homo sapiens* | 57.10 | 3.53 | 2 | 17 |
| P61224 | Ras-related protein Rap-1b | RAP1B | *Homo sapiens* | 57.06 | 27.72 | 4 | 17 |
| P51571 | Translocon-associated protein subunit delta | SSR4 | *Homo sapiens* | 55.54 | 23.12 | 3 | 17 |
| P26447 | Protein S100-A4 | S100A4 | *Homo sapiens* | 53.79 | 28.71 | 3 | 17 |
| Q14847 | LIM and SH3 domain protein 1 | LASP1 | *Homo sapiens* | 53.29 | 21.84 | 5 | 17 |
| Q12884 | Seprase | FAP | *Homo sapiens* | 52.54 | 7.63 | 5 | 17 |
| P02795 | Metallothionein-2 | MT2A | *Homo sapiens* | 51.33 | 21.31 | 2 | 17 |
| P38159 | RNA-binding motif protein, X chromosome | RBMX | *Homo sapiens* | 48.65 | 8.95 | 3 | 17 |
| P62081 | 40S ribosomal protein S7 | RPS7 | *Homo sapiens* | 77.61 | 38.66 | 4 | 16 |
| P21964 | Catechol O-methyltransferase | COMT | *Homo sapiens* | 69.40 | 19.93 | 4 | 16 |
| P48047 | ATP synthase subunit O, mitochondrial | ATP5O | *Homo sapiens* | 66.42 | 39.44 | 5 | 16 |
| P62195 | 26S protease regulatory subunit 8 | PSMC5 | *Homo sapiens* | 55.47 | 18.23 | 5 | 16 |
| P20674 | Cytochrome c oxidase subunit 5A, mitochondrial | COX5A | *Homo sapiens* | 51.48 | 26.67 | 3 | 16 |
| Q9UHG3 | Prenylcysteine oxidase 1 | PCYOX1 | *Homo sapiens* | 48.05 | 11.88 | 4 | 16 |
| P10301 | Ras-related protein R-Ras | RRAS | *Homo sapiens* | 47.42 | 12.84 | 2 | 16 |
| P20700 | Lamin-B1 | LMNB1 | *Homo sapiens* | 43.93 | 5.46 | 4 | 16 |
| P37235 | Hippocalcin-like protein 1 | HPCAL1 | *Homo sapiens* | 40.95 | 17.10 | 3 | 16 |
| P39060 | Collagen alpha-1(XVIII) chain [Cleaved into: Endostetin] | COL18A1 | *Homo sapiens* | 85.90 | 4.45 | 4 | 15 |
| P63173 | 60S ribosomal protein L38 | RPL38 | *Homo sapiens* | 73.59 | 35.71 | 2 | 15 |
| O43242 | 26S proteasome non-APase regulatory subunit 3 | PSMD3 | *Homo sapiens* | 65.74 | 7.68 | 3 | 15 |
| P46777 | 60S ribosomal protein L5 | RPL5 | *Homo sapiens* | 65.57 | 23.91 | 5 | 15 |
| P63167 | Dynein light chain 1, cytoplasmic | DNYLL1 | *Homo sapiens* | 64.99 | 37.08 | 2 | 15 |
| Q9BWD1 | Acetyl-CoA acetyltransferase, cytosolic | ACAT2 | *Homo sapiens* | 63.92 | 22.92 | 4 | 15 |
| P19623 | Spermidine synthase | SRM | *Homo sapiens* | 63.90 | 37.09 | 6 | 15 |
| P12268 | Inosine-5'-monophosphate dehydrogenase 2 | IMPDH2 | *Homo sapiens* | 63.68 | 5.84 | 2 | 15 |
| P61769 | Beta-2-microglobulin [Cleaved into: Beta-2-microglobulin from pI 5.3] | B2M | *Homo sapiens* | 62.44 | 35.29 | 3 | 15 |
| P09622 | Dihydrolipoyl dehydrogenase, mitochondrial | DLD | *Homo sapiens* | 62.33 | 6.48 | 2 | 15 |
| O95373 | Importin-7 | IPO7 | *Homo sapiens* | 61.73 | 4.43 | 3 | 15 |
| P49257 | Protein ERGIC-53 | LMAN1 | *Homo sapiens* | 60.05 | 10.39 | 2 | 15 |
| P00390 | Glutathione reductase, mitochondrial | GSR | *Homo sapiens* | 52.89 | 11.88 | 3 | 15 |
| P61019 | Ras-related protein Rab-2A | RAB2A | *Homo sapiens* | 50.25 | 23.58 | 4 | 15 |
| P23141 | Liver carboxylesterase 1 | CES1 | *Homo sapiens* | 50.07 | 7.58 | 3 | 15 |
| O60763 | General vesicular transport factor p115 | USO1 | *Homo sapiens* | 49.72 | 6.24 | 4 | 15 |
| Q9H8H3 | Methyltransferase-like protein 7A | METTL7A | *Homo sapiens* | 48.17 | 12.30 | 2 | 15 |
| P09960 | Leukotriene A-4 hydrolase | LTA4H | *Homo sapiens* | 47.92 | 6.71 | 3 | 15 |
| Q9UHL4 | Dipeptidyl peptidase 2 | DPP7 | *Homo sapiens* | 44.72 | 4.47 | 2 | 15 |
| Q01995 | Transgelin | TAGLN | *Homo sapiens* | 44.12 | 21.39 | 3 | 15 |
| P41252 | Isoleucine--tRNA ligase, cytoplamic | IARS | *Homo sapiens* | 39.65 | 3.49 | 4 | 15 |
| P61970 | Nuclear transport factor 2 | NUTF2 | *Homo sapiens* | 66.79 | 33.86 | 2 | 14 |
| Q92499 | ATP-dependent RNA helicase DDX1 | DDX1 | *Homo sapiens* | 66.78 | 7.43 | 3 | 14 |
| O14980 | Exportin-1 | XPO1 | *Homo sapiens* | 65.25 | 5.23 | 3 | 14 |
| P68402 | Platelet-activating factor acetylhydrolase IB subunit beta | PAFAH1B2 | *Homo sapiens* | 53.86 | 20.96 | 3 | 14 |
| P31943 | Heterogeneous nuclear ribonucleoprotein H | HNRNPH1 | *Homo sapiens* | 52.62 | 14.25 | 4 | 14 |
| P46778 | 60S ribosomal protein L21 | RPL21 | *Homo sapiens* | 47.80 | 27.50 | 3 | 14 |
| Q32P28 | Prolyl 3-hydroxylase 1 | LEPRE1 | *Homo sapiens* | 47.36 | 5.71 | 3 | 14 |
| Q95816 | BAG family molecular chaperone regulator 2 | BAG2 | *Homo sapiens* | 46.92 | 13.27 | 2 | 14 |
| Q92945 | Far upstream element-binding protein 2 | KHSRP | *Homo sapiens* | 45.76 | 5.63 | 3 | 14 |
| P62847 | 40S ribosomal protein S24 | RPS24 | *Homo sapiens* | 45.06 | 20.30 | 2 | 14 |
| Q9ULV4 | Coronin-1C | CORO1C | *Homo sapiens* | 43.61 | 9.07 | 3 | 14 |
| Q99584 | Protein S100-A13 | S100A13 | *Homo sapiens* | 43.40 | 23.47 | 2 | 14 |
| Q9Y3A6 | Transmembrane emp24 domain-containing protein 5 | TMED5 | *Homo sapiens* | 42.79 | 10.04 | 2 | 14 |
| P62750 | 60S ribosomal protein L23a | RPL23A | *Homo sapiens* | 42.75 | 21.15 | 3 | 14 |
| O15260 | Surfeit locus protein 4 | SURF4 | *Homo sapiens* | 42.65 | 11.90 | 3 | 14 |
| P19404 | NADH dehydrogenase [ubiquinone] flavoprotein 2, mitochondrial | NDUFV2 | *Homo sapiens* | 42.13 | 9.24 | 2 | 14 |
| P48681 | Nestin | NES | *Homo sapiens* | 39.33 | 1.48 | 2 | 14 |
| Q9NQW7 | Xaa-Pro aminopeptidase 1 | XPNPEP1 | *Homo sapiens* | 38.25 | 4.82 | 2 | 14 |
| Q99829 | Copine-1 | CPNE1 | *Homo sapiens* | 37.60 | 4.66 | 2 | 14 |
| P06703 | Protein S100-A6 | S100A6 | *Homo sapiens* | 36.86 | 36.67 | 2 | 14 |
| P61163 | Alpha-centractin | ACTR1A | *Homo sapiens* | 55.95 | 14.89 | 3 | 13 |
| Q08211 | ATP-dependent RNA helicase A | DHX9 | *Homo sapiens* | 54.67 | 6.14 | 5 | 13 |
| P38606 | V-type proton ATPase catalytic subunit A | ATP6V1A | *Homo sapiens* | 54.37 | 17.34 | 6 | 13 |
| Q99714 | 3-hydroxyacyl-CoA dehydrogenase type-2 | HSD17B10 | *Homo sapiens* | 54.15 | 31.03 | 4 | 13 |
| P27701 | CD82 antigen | CD82 | *Homo sapiens* | 49.98 | 10.49 | 2 | 13 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| Q13765 | Nascent polypeptide-associated complex subunit alpha | NACA | *Homo sapiens* | 49.28 | 18.60 | 3 | 13 |
| P14854 | Cytochrome c oxidase subunit 6B1 | COX6B1 | *Homo sapiens* | 48.91 | 47.67 | 3 | 13 |
| P06756 | Integrin alpha-V | ITGAV | *Homo sapiens* | 45.52 | 11.45 | 7 | 13 |
| P26373 | 60S ribosomal protein L13 | RPL13 | *Homo sapiens* | 44.56 | 15.64 | 3 | 13 |
| Q02809 | Procollagen-lysine, 2-oxoglutarate 5-dioxygenase 1 | PLOD1 | *Homo sapiens* | 44.26 | 7.43 | 4 | 13 |
| P62899 | 60S ribosomal protein L31 | RPL31 | *Homo sapiens* | 42.96 | 18.40 | 2 | 13 |
| P60953 | Cell division control protein 42 homolog | CDC42 | *Homo sapiens* | 42.70 | 20.42 | 3 | 13 |
| Q6NUM9 | All-trans-retinol 13,14-reductase | RETSAT | *Homo sapiens* | 41.53 | 4.92 | 2 | 13 |
| Q01105 | Protein SET | SET | *Homo sapiens* | 40.71 | 18.28 | 4 | 13 |
| P05455 | Lupus La protein | SSB | *Homo sapiens* | 39.96 | 12.50 | 4 | 13 |
| P31948 | Stress-induced-phosphoprotein 1 | STIP1 | *Homo sapiens* | 39.18 | 7.73 | 3 | 13 |
| P54136 | Arginine-tRNA ligase, cyloplasmic | RARS | *Homo sapiens* | 38.86 | 10.61 | 6 | 13 |
| Q92841 | Probable ATP-dependent RNA helicase DDX17 | DDX17 | *Homo sapiens* | 38.01 | 7.27 | 5 | 13 |
| P62330 | ADP-ribosylation factor 6 | ARF6 | *Homo sapiens* | 37.62 | 12.57 | 2 | 13 |
| Q13228 | Selenium-binding protein 1 | SELENBP1 | *Homo sapiens* | 37.11 | 13.98 | 5 | 13 |
| Q14152 | Eukaryotic translation initiation factor 3 subunit A | EIF3A | *Homo sapiens* | 37.07 | 4.27 | 5 | 13 |
| P05023 | Sodium/potassium-transporting ATPase subunit alpha-1 | ATP1A1 | *Homo sapiens* | 36.70 | 5.28 | 4 | 13 |
| Q70UQ0 | Inhibitor of nuclear factor kappa-B kinase-interacting protein | IKBIP | *Homo sapiens* | 36.29 | 6.57 | 2 | 13 |
| O14579 | Coatomer subunit epsilon | COPE | *Homo sapiens* | 57.73 | 6.82 | 2 | 12 |
| P46063 | ATP-dependent DNA helicase Q1 | RECQL | *Homo sapiens* | 51.17 | 6.63 | 3 | 12 |
| Q9UBQ7 | Glyoxylate reductase/hydroxypyruvate reductase | GRHPR | *Homo sapiens* | 49.69 | 17.38 | 3 | 12 |
| Q07666 | KH domain-containing, RNA-binding, signal transduction-associated protein 1 | KHDRBS1 | *Homo sapiens* | 47.70 | 7.67 | 2 | 12 |
| Q16363 | Laminin subunit alpha-4 | LAMA4 | *Homo sapiens* | 46.26 | 4.55 | 6 | 12 |
| P46821 | Microtubule-associated protein 1B | MAP1B | *Homo sapiens* | 46.16 | 4.62 | 7 | 12 |
| P24752 | Acetyl-CoA acetyltransferase, mitochondrial | ACAT1 | *Homo sapiens* | 42.51 | 9.84 | 3 | 12 |
| O75368 | SH3 domain-binding glutamic acid-rich-like protein | SH3BGRL | *Homo sapiens* | 42.33 | 35.09 | 3 | 12 |
| O95292 | Vesicle-associated membrane protein-associated protein B/C | VAPB | *Homo sapiens* | 40.84 | 10.70 | 2 | 12 |
| Q13418 | Integrin-linked protein kinase | ILK | *Homo sapiens* | 40.30 | 14.38 | 4 | 12 |
| P80303 | Nucleobinding-2 | NUCB2 | *Homo sapiens* | 40.20 | 7.14 | 2 | 12 |
| P49589 | Cysteine-tRNA ligase, cytoplasmic | CARS | *Homo sapiens* | 40.10 | 4.68 | 2 | 12 |
| Q9P2J5 | Leucine-tRNA ligase, cytoplasmic | LARS | *Homo sapiens* | 39.68 | 2.98 | 3 | 12 |
| P23526 | Adenosylhomocysteinase | AHCY | *Homo sapiens* | 39.58 | 13.43 | 4 | 12 |
| Q14112 | Nidogen-2 | NID2 | *Homo sapiens* | 39.09 | 7.71 | 6 | 12 |
| P55884 | Eukaryotic translation initiation factor 3 subunit B | EIF3B | *Homo sapiens* | 38.13 | 5.90 | 4 | 12 |
| O15145 | Actin-related protein 2/3 complex subunit 3 | ARPC3 | *Homo sapiens* | 37.32 | 13.48 | 2 | 12 |
| P02649 | Apolipoprotein E | APOE | *Homo sapiens* | 37.22 | 8.52 | 2 | 12 |
| P55795 | Heterogeneous nuclear ribonucleoprotein H2 | HNRNPH2 | *Homo sapiens* | 36.67 | 10.47 | 3 | 12 |
| Q99439 | Calponin-2 | CNN2 | *Homo sapiens* | 36.58 | 13.27 | 3 | 12 |
| P62917 | 60S ribosomal protein L8 | RPL8 | *Homo sapiens* | 34.54 | 25.29 | 5 | 12 |
| P60900 | Proteasome subunit alpha type-6 | PSMA6 | *Homo sapiens* | 34.38 | 10.16 | 2 | 12 |
| Q71UM5 | 40S ribosomal protein S27-like | RPS27L | *Homo sapiens* | 33.77 | 38.10 | 3 | 12 |
| Q03252 | Lamin-B2 | LMNB2 | *Homo sapiens* | 33.19 | 9.50 | 6 | 12 |
| Q15323 | Keratin, type I cuticular Ha1 | KRT31 | *Homo sapiens* | 56.86 | 10.34 | 3 | 11 |
| Q15121 | Astrocytic phosphoprotein PEA-15 | PEA15 | *Homo sapiens* | 54.65 | 27.69 | 3 | 11 |
| Q6DD88 | Atlastin-3 | ATL3 | *Homo sapiens* | 53.61 | 11.46 | 3 | 11 |
| O15511 | Actin-related protein 2/3 complex subunit 5 | ARPC5 | *Homo sapiens* | 53.45 | 20.53 | 2 | 11 |
| Q9Y3F4 | Serine-threonine kinase receptor-associated protein | STRAP | *Homo sapiens* | 49.03 | 8.86 | 2 | 11 |
| P49591 | Serine-tRNA ligase, cytoplasmic | SARS | *Homo sapiens* | 48.84 | 16.54 | 5 | 11 |
| P07954 | Fumarate hydratase, mitochondrial | FH | *Homo sapiens* | 48.14 | 8.63 | 2 | 11 |
| Q15008 | 26S proteasom non-ATPase regulatory subunit 6 | PSMD6 | *Homo sapiens* | 46.03 | 7.20 | 2 | 11 |
| Q6IAA8 | Ragulator complex protein LAMTOR1 | LAMTOR1 | *Homo sapiens* | 45.57 | 15.53 | 2 | 11 |
| P23246 | Splicing factor, proline- and glutamine-rich | SFPQ | *Homo sapiens* | 44.03 | 6.93 | 4 | 11 |
| Q02618 | Nucleobindin-1 | NUCB1 | *Homo sapiens* | 41.49 | 6.29 | 2 | 11 |
| Q9Y5X1 | Sorting nexin-9 | SNX9 | *Homo sapiens* | 41.27 | 7.39 | 3 | 11 |
| P31937 | 3-hydroxyisobutyrate dehydrogenase, mitochondrial | HIBADH | *Homo sapiens* | 40.12 | 7.14 | 2 | 11 |
| Q99632 | T-complex protein 1 subunit eta | CCT7 | *Homo sapiens* | 39.69 | 11.97 | 4 | 11 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P22087 | rRNA 2'-O-methyltransferase fibrillarin | FBL | *Homo sapiens* | 38.41 | 12.15 | 3 | 11 |
| Q9NR31 | GTP-binding protein SAR1a | SAR1A | *Homo sapiens* | 37.09 | 21.72 | 3 | 11 |
| P43487 | Ran-specific GTPase-activating protein | RANBP1 | *Homo sapiens* | 36.66 | 16.92 | 2 | 11 |
| Q8IZP2 | Putative protein FAM10A4 | ST13P4 | *Homo sapiens* | 36.63 | 17.08 | 3 | 11 |
| P51858 | Hepatoma-derived growth factor | HDGF | *Homo sapiens* | 36.37 | 13.75 | 2 | 11 |
| Q13263 | Transcription intermediary factor 1-beta | TRIM28 | *Homo sapiens* | 35.01 | 5.87 | 3 | 11 |
| O60282 | Kinesin heavy chain isoform 5C | KIF5C | *Homo sapiens* | 34.89 | 2.51 | 2 | 11 |
| Q9NZ08 | Endoplasmic reticulum aminopeptidase 1 | ERAP1 | *Homo sapiens* | 33.59 | 5.84 | 4 | 11 |
| Q13561 | Dynactin subunit 2 | DCTN2 | *Homo sapiens* | 33.10 | 8.23 | 2 | 11 |
| Q14258 | E3 ubiquitin/ISG15 ligase TRIM25 | TRIM25 | *Homo sapiens* | 32.68 | 6.03 | 3 | 11 |
| P00403 | Cytochrome c oxidase subunit 2 | MT-CO2 | *Homo sapiens* | 31.76 | 20.26 | 3 | 11 |
| Q15417 | Calponin-3 | CNN3 | *Homo sapiens* | 29.35 | 7.60 | 2 | 11 |
| P14406 | Cytochrome C oxidase subunit 7A2, mitochondrial | COX7A2 | *Homo sapiens* | 28.49 | 27.71 | 2 | 11 |
| P28799 | Granulins | GRN | *Homo sapiens* | 48.40 | 8.43 | 2 | 10 |
| P28331 | NADH-ubiquinone oxidoreductase 75 kDa subunit, mitochondrial | NDUFS1 | *Homo sapiens* | 48.36 | 7.84 | 3 | 10 |
| Q92597 | Protein NDRG1 | NDRG1 | *Homo sapiens* | 44.52 | 8.88 | 2 | 10 |
| P48643 | T-complex protein 1 subunit epsilon | CCT5 | *Homo sapiens* | 44.52 | 12.20 | 4 | 10 |
| P00568 | Adenylate kinase isoenzyme 1 | AK1 | *Homo sapiens* | 44.50 | 25.77 | 4 | 10 |
| O00410 | Importin-5 | IPO5 | *Homo sapiens* | 44.31 | 5.10 | 3 | 10 |
| P04216 | Thy-1 membrane glycoprotein | THY1 | *Homo sapiens* | 42.19 | 15.53 | 2 | 10 |
| P62191 | 26S protease regulatory subunit 4 | PSMC1 | *Homo sapiens* | 41.71 | 8.18 | 2 | 10 |
| P61916 | Epididymal secretory protein E1 | NPC2 | *Homo sapiens* | 41.08 | 25.83 | 2 | 10 |
| Q53GQ0 | Estradiol 17-beta-dehydrogenase 12 | HSD17B12 | *Homo sapiens* | 40.53 | 14.10 | 3 | 10 |
| P09429 | High mobility group protein B1 | HMGB1 | *Homo sapiens* | 38.34 | 21.86 | 3 | 10 |
| Q9NTK5 | Obg-like ATPase 1 | OLA1 | *Homo sapiens* | 38.07 | 11.11 | 3 | 10 |
| Q96CW1 | AP-2 complex subunit mu | AP2M1 | *Homo sapiens* | 36.90 | 15.17 | 4 | 10 |
| P99999 | Cytochrome c | CYCS | *Homo sapiens* | 36.48 | 24.76 | 2 | 10 |
| P22102 | Trifunctional purine biosynthetic protein adenosine-3 [Includes: Phosphoribosylamine--glycine ligase] | GART | *Homo sapiens* | 35.51 | 2.67 | 2 | 10 |
| P38117 | Electron transfer flavoprotein subunit beta | ETFB | *Homo sapiens* | 35.36 | 10.20 | 2 | 10 |
| P10253 | Lysosomal alpha-glucosidase | GAA | *Homo sapiens* | 34.48 | 4.94 | 3 | 10 |
| P14868 | Aspartate--tRNA ligase, cytoplasmic | DARS | *Homo sapiens* | 34.20 | 7.78 | 3 | 10 |
| P18621 | 60S ribosomal protein L17 | RPL17 | *Homo sapiens* | 32.59 | 17.93 | 3 | 10 |
| P46977 | Dolichyl-diphosphooligosaccharide-protein glycosyltransferase subunit STT3A | STT3A | *Homo sapiens* | 32.58 | 3.69 | 2 | 10 |
| P55735 | Protein SEC13 homolog | SEC13 | *Homo sapiens* | 30.57 | 15.22 | 3 | 10 |
| Q9Y646 | Carboxypeptidase Q | CPQ | *Homo sapiens* | 29.57 | 4.24 | 2 | 10 |
| O95747 | Serine/threonine-protein kinase OSR1 | OXSR1 | *Homo sapiens* | 28.78 | 4.93 | 2 | 10 |
| Q16795 | NADH dehydrogenase [ubiquinone] 1 alpha subcomplex subunit 9, mitochondrial | NDUFA9 | *Homo sapiens* | 28.28 | 9.28 | 3 | 10 |
| Q13425 | Beta-2-syntrophin | SNTB2 | *Homo sapiens* | 27.91 | 3.89 | 2 | 10 |
| Q9HC38 | Glyoxalase domain-containing protein 4 | GLOD4 | *Homo sapiens* | 26.47 | 7.35 | 2 | 10 |
| P22307 | Non-specifc lipid-transfer protein | SCP2 | *Homo sapiens* | 25.98 | 3.47 | 2 | 10 |
| P25787 | Proteasome subunit alpha type-2 | PSMA2 | *Homo sapiens* | 41.91 | 27.78 | 4 | 9 |
| Q02952 | A-kinase, anchor protein 12 | AKAP12 | *Homo sapiens* | 41.76 | 7.58 | 6 | 9 |
| P09619 | Platelet-derived growth factor receptor beta | PDGFRB | *Homo sapiens* | 41.28 | 5.24 | 3 | 9 |
| O00154 | Cytosolic acyl coenzyme A thioester hydrolase | ACOT7 | *Homo sapiens* | 36.65 | 12.37 | 3 | 9 |
| O14880 | Microsomal glutathione S-transferase 3 | MGST3 | *Homo sapiens* | 36.64 | 23.03 | 2 | 9 |
| O15143 | Actin-related protein 2/3 complex subunit 1B | ARPC1B | *Homo sapiens* | 36.57 | 18.55 | 4 | 9 |
| O75131 | Copine-3 | CPNE3 | *Homo sapiens* | 34.80 | 6.33 | 2 | 9 |
| P80723 | Brain acid soluble protein 1 | BASP1 | *Homo sapiens* | 33.15 | 18.94 | 3 | 9 |
| Q1KMD3 | Heterogeneous nuclear ribonucleoprotein U-like protein 2 | HNRNPUL2 | *Homo sapiens* | 32.68 | 4.82 | 2 | 9 |
| Q9Y4L1 | Hypoxia up-regulated protein 1 | HYOU1 | *Homo sapiens* | 31.81 | 6.81 | 4 | 9 |
| Q9Y371 | Endophilin-B1 | SH3GLB1 | *Homo sapiens* | 28.93 | 7.40 | 2 | 9 |
| O43615 | Mitochondrial import inner membrane translocase subunit TIM44 | TIMM44 | *Homo sapiens* | 28.91 | 5.09 | 2 | 9 |
| Q9Y3U8 | 60S ribosomal protein L36 | RPL36 | *Homo sapiens* | 26.89 | 21.90 | 3 | 9 |
| P35613 | Basigin | BSG | *Homo sapiens* | 26.77 | 8.31 | 2 | 9 |
| O94832 | Unconventional myosin-Id | MYO1D | *Homo sapiens* | 26.14 | 2.49 | 2 | 9 |
| Q9BWM7 | Sideroflexin-3 | SFXN3 | *Homo sapiens* | 26.01 | 8.62 | 2 | 9 |
| P84098 | 60S ribosomal protein L19 | RPL19 | *Homo sapiens* | 25.73 | 13.27 | 2 | 9 |
| Q9UM54 | Unconventional myosin-VI | MYO6 | *Homo sapiens* | 25.66 | 2.16 | 2 | 9 |
| P62851 | 40S ribosomal protein S25 | RPS25 | *Homo sapiens* | 24.91 | 16.00 | 2 | 9 |
| P27695 | DNA-(apurinic or apyrimidinic site) lyase | APEX1 | *Homo sapiens* | 41.98 | 29.87 | 5 | 8 |
| P30085 | UMP-CMP kinase | CMPK1 | *Homo sapiens* | 37.21 | 16.84 | 2 | 8 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P10768 | S-formylglutathione hydrolase | ESD | *Homo sapiens* | 34.83 | 25.18 | 4 | 8 |
| Q9Y224 | UPF0568 protein C14orf166 | C14ORF166 | *Homo sapiens* | 30.19 | 22.54 | 4 | 8 |
| P43490 | Nicotinamide phosphoribosyltransferase | NAMPT | *Homo sapiens* | 29.74 | 8.35 | 2 | 8 |
| P43243 | Matrin-3 | MATR3 | *Homo sapiens* | 28.76 | 7.20 | 4 | 8 |
| P54578 | Ubiquitin carboxyl-terminal hydrolase 14 | USP14 | *Homo sapiens* | 27.29 | 5.87 | 2 | 8 |
| Q9UJ70 | N-acetyl-D-glucosamine kinase | NAGK | *Homo sapiens* | 24.55 | 17.73 | 4 | 8 |
| P52272 | Heterogeneous nuclear ribonucleoprotein M | HNRNPM | *Homo sapiens* | 24.43 | 4.79 | 3 | 8 |
| O95336 | 6-phosphogluconolactonase | PGLS | *Homo sapiens* | 24.35 | 17.05 | 3 | 8 |
| P0CW22 | 40S ribosomal protein S17-like | RPS17L | *Homo sapiens* | 24.28 | 39.26 | 4 | 8 |
| P27708 | CAD protein [Includes: Glutamine-dependent carbamoyl-phosphate synthase] | CAD | *Homo sapiens* | 22.05 | 0.90 | 2 | 8 |
| Q02543 | 60S ribosomal protein L18a | RPL18A | *Homo sapiens* | 19.31 | 8.52 | 2 | 8 |
| P48147 | Prolyl endopeptidase | PREP | *Homo sapiens* | 32.74 | 7.61 | 3 | 7 |
| Q9ULZ3 | Apoptosis-associated speck-like protein containing a CARD | PYCARD | *Homo sapiens* | 31.58 | 20.00 | 3 | 7 |
| P09936 | Ubiquitin carboxyl-terminal hydrolase isozyme L1 | UCHL1 | *Homo sapiens* | 30.85 | 30.04 | 4 | 7 |
| P28161 | Glutathione S-transferase Mu 2 | GSTM2 | *Homo sapiens* | 28.86 | 28.90 | 4 | 7 |
| O75955 | Flotillin-1 | FLOT1 | *Homo sapiens* | 27.63 | 11.24 | 3 | 7 |
| P53007 | Tricarboxylate transport protein, mitochondrial | SLC25A1 | *Homo sapiens* | 27.37 | 11.25 | 3 | 7 |
| Q02218 | 2-oxoglutarate dehydrogenase, mitochondrial | OGDH | *Homo sapiens* | 26.92 | 7.72 | 4 | 7 |
| P23381 | Tryptophan--tRNA ligase, cytoplasmic | WARS | *Homo sapiens* | 25.94 | 6.16 | 2 | 7 |
| P19367 | Hexokinase-1 | HK1 | *Homo sapiens* | 25.59 | 4.14 | 3 | 7 |
| Q969H6 | UPF0556 protein C19orf10 | C19ORF10 | *Homo sapiens* | 24.70 | 15.03 | 2 | 7 |
| P07942 | Laminin subunit beta-1 | LAMB1 | *Homo sapiens* | 23.93 | 2.69 | 3 | 7 |
| P06865 | Beta-hexosaminidase subunit alpha | HEXA | *Homo sapiens* | 23.56 | 7.75 | 3 | 7 |
| Q63ZY3 | KN motif and ankyrin repeat domain-containing protein 2 | KANK2 | *Homo sapiens* | 22.46 | 4.70 | 3 | 7 |
| Q9UQ80 | Proliferation-associated protein 2G4 | PA2G4 | *Homo sapiens* | 22.38 | 13.20 | 3 | 7 |
| Q96FQ6 | Protein S100-A16 | S100A16 | *Homo sapiens* | 22.13 | 22.33 | 2 | 7 |
| P67775 | Serine/threonine-protein phosphatase 2A catalytic subunit alpha isoform | PPP2CA | *Homo sapiens* | 21.41 | 15.86 | 3 | 7 |
| P05091 | Aldehyde dehydrogenase, mitochondrial | ALDH2 | *Homo sapiens* | 21.31 | 5.80 | 2 | 7 |
| Q16718 | NADH dehydrogenase [ubiquinone] 1 alpha subcomplex subunit 5 | NDUF45 | *Homo sapiens* | 20.43 | 22.41 | 2 | 7 |
| P10644 | cAMP-dependent protein kinase type I-alpha regulatory subunit | PRKAR1A | *Homo sapiens* | 20.35 | 9.19 | 2 | 7 |
| P55010 | Eukaryotic translation initiation factor 5 | EIF5 | *Homo sapiens* | 20.27 | 5.57 | 2 | 7 |
| P20042 | Eukaryotic translation initiation factor 2 subunit 2 | EIF2S2 | *Homo sapiens* | 20.09 | 8.11 | 2 | 7 |
| P61353 | 60S ribosomal protein L27 | RPL27 | *Homo sapiens* | 19.64 | 21.32 | 2 | 7 |
| Q13451 | Peptidyl-prolyl cis-trans isomerase FKBP5 | FKBP5 | *Homo sapiens* | 19.41 | 6.58 | 2 | 7 |
| O60488 | Long-chain-fatty-acid--CoA ligase 4 | ACSL4 | *Homo sapiens* | 18.27 | 4.36 | 2 | 7 |
| P62913 | 60S ribosomal protein L11 | RPL11 | *Homo sapiens* | 17.77 | 12.92 | 2 | 7 |
| P40429 | 60S ribosomal protein L13a | RPL13A | *Homo sapiens* | 17.62 | 8.87 | 2 | 7 |
| P43304 | Glycerol-3-phosphate dehydrogenase, mitochondrial | GPD2 | *Homo sapiens* | 31.91 | 6.05 | 2 | 6 |
| P51685 | 20S proteasome non-ATPase regulatory subunit 7 | PSMD7 | *Homo sapiens* | 31.27 | 12.65 | 2 | 6 |
| Q16643 | Drebrin | DBN1 | *Homo sapiens* | 29.77 | 6.32 | 2 | 6 |
| P31930 | Cytochrome b-c1 complex subunit 1, mitochondrial | UQCRC1 | *Homo sapiens* | 29.16 | 8.54 | 2 | 6 |
| O43491 | Band 4.1-like protein 2 | EPB41L2 | *Homo sapiens* | 28.75 | 3.58 | 2 | 6 |
| P21281 | V-type proton ATPase subunit B, brain isoform | ATP6V1B2 | *Homo sapiens* | 28.46 | 6.65 | 2 | 6 |
| O00151 | PDZ and LIM domain Protein 1 | PDLIM1 | *Homo sapiens* | 27.03 | 17.33 | 3 | 6 |
| Q08380 | Galectin-3-binding protein | LGALS3BP | *Homo sapiens* | 22.65 | 7.52 | 3 | 6 |
| Q15063 | Periostin | POSTIN | *Homo sapiens* | 22.25 | 4.31 | 2 | 6 |
| P30043 | Flavin reductase | BLVRB | *Homo sapiens* | 21.34 | 12.14 | 2 | 6 |
| P39059 | Collagen alpha-1(XV) chain [Cleaved into: Restin] | COL15A1 | *Homo sapiens* | 19.86 | 2.88 | 2 | 6 |
| Q13126 | S-methyl-5'-thioadenosine phosphorylase | MTAP | *Homo sapiens* | 19.56 | 20.49 | 3 | 6 |
| P35871 | Phosphoglucomutase-1 | PGM1 | *Homo sapiens* | 19.51 | 7.83 | 3 | 6 |
| P49821 | NADH dehydrogenase [ubiquinone] flavoprotein 1, mitochondrial | NDUFV1 | *Homo sapiens* | 19.40 | 7.97 | 2 | 6 |
| P13798 | Acylamino-acid-releasing enzyme | APEH | *Homo sapiens* | 19.12 | 4.78 | 2 | 6 |
| P35998 | 26S protease regulatory subunit 7 | PSMC2 | *Homo sapiens* | 19.00 | 5.08 | 2 | 6 |
| P48735 | Isocitrate dehydrogenase [NADP], mitochondrial | IDH2 | *Homo sapiens* | 18.47 | 5.97 | 2 | 6 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P42765 | 3-ketoacyl-CoA thiolase, mitochondrial | ACAA2 | *Homo sapiens* | 18.27 | 7.81 | 2 | 6 |
| O9Y262 | Eukaryotic translation initiation factor 3 subunit L | EIF3L | *Homo sapiens* | 18.24 | 3.55 | 2 | 6 |
| P10515 | Dihydrolipoyllysine-residue acetyltransferase component or pyruvate dehydrogenase complex, mitochondrial | DLAT | *Homo sapiens* | 17.45 | 5.87 | 3 | 6 |
| P52630 | Signal transducer and activator of transcription 2 | STAT2 | *Homo sapiens* | 17.26 | 2.82 | 2 | 6 |
| Q9Y376 | Calcium-binding protein 39 | CAB39 | *Homo sapiens* | 16.98 | 6.16 | 2 | 6 |
| Q9Y230 | RuvB-like 2 | RUVBL2 | *Homo sapiens* | 16.90 | 6.21 | 3 | 6 |
| Q15758 | Neutral amino acid transporter B(0) | SLC1A5 | *Homo sapiens* | 16.35 | 4.44 | 2 | 6 |
| Q13488 | V-type proton ATPase 116 kDa subunit a isoform 3 | TCIRG1 | *Homo sapiens* | 16.17 | 2.65 | 2 | 6 |
| P67812 | Signal peptidase complex catalytic subunit SEC11A | SEC11A | *Homo sapiens* | 15.79 | 9.50 | 2 | 6 |
| Q9BTV4 | Transmembrane protein 43 | TMEM43 | *Homo sapiens* | 15.70 | 9.00 | 2 | 6 |
| P54819 | Adenylate kinase 2, mitochondrial | AK2 | *Homo sapiens* | 26.93 | 13.81 | 2 | 5 |
| Q08431 | Lactadherin | MFGE8 | *Homo sapiens* | 23.70 | 8.53 | 2 | 5 |
| Q15363 | Transmembrane emp24 domain-containing protein 2 | TMED2 | *Homo sapiens* | 22.92 | 13.93 | 2 | 5 |
| Q99798 | Aconitate hydratase, mitochondrial | ACO2 | *Homo sapiens* | 21.59 | 7.18 | 3 | 5 |
| P47897 | Glutamine--tRNA ligase | QARS | *Homo sapiens* | 20.09 | 3.74 | 2 | 5 |
| Q9BVK6 | Transmembrane emp24 domain-containing protein 9 | TMED9 | *Homo sapiens* | 19.41 | 14.47 | 2 | 5 |
| P49720 | Proteasome subunit beta type-3 | PSMB3 | *Homo sapiens* | 18.74 | 23.90 | 3 | 5 |
| O75947 | ATP Synthase subunit d, mitochondrial | ATP5H | *Homo sapiens* | 18.55 | 23.60 | 2 | 5 |
| Q8NC51 | Plasminogen activator inhibitor 1 RNA-binding protein | SERBP1 | *Homo sapiens* | 17.47 | 12.01 | 3 | 5 |
| Q14247 | Src substrate cortactin | CTTN | *Homo sapiens* | 17.46 | 4.73 | 2 | 5 |
| P56537 | Eukaryotic translation initiation factor 6 | EIF6 | *Homo sapiens* | 16.72 | 13.88 | 2 | 5 |
| P32969 | 60S ribosomal protein L9 | PPL9 | *Homo sapiens* | 16.46 | 15.63 | 3 | 5 |
| P53004 | Biliverdin reductase A | BLVRA | *Homo sapiens* | 16.33 | 10.47 | 2 | 5 |
| Q8IVL6 | Prolyl 3-hydroxylase 3 | LEPREL2 | *Homo sapiens* | 16.32 | 4.21 | 2 | 5 |
| Q99961 | Endophilin-A2 | SH3GL1 | *Homo sapiens* | 16.27 | 12.23 | 3 | 5 |
| P34897 | Serine hydroxymethyltransferase, mitochondrial | SHMT2 | *Homo sapiens* | 16.25 | 4.96 | 2 | 5 |
| O75489 | NADH dehydrogenase [ubiquinone] iron-sulfur protein 3, mitochondrial | NDUFS3 | *Homo sapiens* | 15.69 | 9.09 | 2 | 5 |
| P54802 | Alpha-N-acetylglucosaminidase | NAGLU | *Homo sapiens* | 15.09 | 3.77 | 2 | 5 |
| P22105 | Tenascin-X | TNXB | *Homo sapiens* | 14.73 | 0.44 | 2 | 5 |
| P78344 | Eukaryotic translation initiation factor 4 gamma 2 | EIF4G2 | *Homo sapiens* | 14.65 | 2.32 | 2 | 5 |
| Q15392 | Delta(24)-sterol reductase | DHCR24 | *Homo sapiens* | 14.52 | 5.23 | 2 | 5 |
| P11586 | C-1-tetrahydrofolate synthase, cytoplasmic | MTHFD1 | *Homo sapiens* | 14.51 | 7.49 | 4 | 5 |
| P00491 | Purine nucleoside phosphorylase | PNP | *Homo sapiens* | 14.37 | 9.69 | 2 | 5 |
| Q16891 | Mitochondrial inner membrane protein | IMMT | *Homo sapiens* | 13.52 | 4.35 | 2 | 5 |
| Q7L576 | Cytoplasmic FMR1-interacting protein 1 | CYFIP1 | *Homo sapiens* | 13.35 | 1.84 | 2 | 5 |
| O60749 | Sorting nexin-2 | SNX2 | *Homo sapiens* | 13.17 | 5.97 | 3 | 5 |
| Q13510 | Acid ceramidase | ASAH1 | *Homo sapiens* | 23.59 | 10.13 | 2 | 4 |
| Q15942 | Zyxin | ZYX | *Homo sapiens* | 22.85 | 6.64 | 2 | 4 |
| P05198 | Eukaryotic translation initation factor 2 subunit 1 | EIF2S1 | *Homo sapiens* | 19.39 | 13.65 | 2 | 4 |
| P26639 | Threonine--tRNA ligase, cytoplasmic | TARS | *Homo sapiens* | 18.59 | 7.61 | 3 | 4 |
| Q9UL46 | Proteasome activator complex subunit 2 | PSME2 | *Homo sapiens* | 17.60 | 12.13 | 2 | 4 |
| Q9Y2B0 | Protein canopy homolog 2 | CNPY2 | *Homo sapiens* | 16.38 | 17.03 | 2 | 4 |
| Q04837 | Single-stranded DNA-binding protein, mitochondrial | SSBP1 | *Homo sapiens* | 16.36 | 22.30 | 2 | 4 |
| P04040 | Catalase | CAT | *Homo sapiens* | 16.25 | 6.07 | 2 | 4 |
| Q9BQG0 | Myb-binding protein 1A | MYBBP1A | *Homo sapiens* | 14.03 | 3.92 | 4 | 4 |
| P24539 | ATP synthase subunit b, mitochondrial | ATP5F1 | *Homo sapiens* | 13.65 | 14.84 | 3 | 4 |
| Q92896 | Golgi apparatus protein 1 | GLG1 | *Homo sapiens* | 13.63 | 4.92 | 3 | 4 |
| O00764 | Pyridoxal kinase | PDXK | *Homo sapiens* | 12.53 | 9.29 | 2 | 4 |
| P08195 | 4F2 cell-surface antigen heavy chain | SLC3A2 | *Homo sapiens* | 12.44 | 4.13 | 2 | 4 |
| P11177 | Pyruvate dehydrogenase E1 component subunit beta, mitochondrial | PDHB | *Homo sapiens* | 12.43 | 8.91 | 2 | 4 |
| P42704 | Leucine-rich PPR motif-containing protein, mitochondrial | LRPPRC | *Homo sapiens* | 12.09 | 2.44 | 3 | 4 |
| Q9NSE4 | Isoleucine-tRNA ligase, mitochondrial | IARS2 | *Homo sapiens* | 12.01 | 3.16 | 3 | 4 |
| Q09028 | Histone-binding protein RBBP4 | RBBP4 | *Homo sapiens* | 11.31 | 4.94 | 2 | 4 |
| Q13641 | Trophoblast glycoprotein | TPBG | *Homo sapiens* | 11.29 | 6.90 | 2 | 4 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| Q8TED1 | Probable glutathione peroxidase 8 | GPX8 | *Homo sapiens* | 11.12 | 14.35 | 2 | 4 |
| P02533 | Keratin, type I cytoskeletal 14 | KRT14 | *Homo sapiens* | 10.56 | 5.72 | 3 | 4 |
| P63220 | 40S ribosomal protein S21 | RPS21 | *Homo sapiens* | 9.98 | 22.89 | 2 | 4 |
| P29966 | Myristoylated alanine-rich C-kinase substrate | MARCKS | *Homo sapiens* | 15.74 | 19.28 | 2 | 3 |
| P13861 | cAMP-dependent protein kinase type II-alpha regulatory subunit | PRKAR2A | *Homo sapiens* | 14.72 | 7.92 | 2 | 3 |
| Q16401 | 26S proteasome non-ATPase regulatory subunit 5 | PSMD5 | *Homo sapiens* | 13.99 | 6.35 | 2 | 3 |
| P15848 | Arylsulfatase B | ARSB | *Homo sapiens* | 11.33 | 4.69 | 2 | 3 |
| P60983 | Glia maturation factor beta | GMFB | *Homo sapiens* | 10.95 | 23.94 | 2 | 3 |
| P51648 | Fatty aldehyde dehydrogenase | ALDH3A2 | *Homo sapiens* | 10.57 | 6.39 | 2 | 3 |
| Q92905 | COP9 signalosome complex subunit 5 | COPS5 | *Homo sapiens* | 9.88 | 6.89 | 2 | 3 |
| O00754 | Lysosomal alpha-mannosidase | MAN2B1 | *Homo sapiens* | 9.77 | 4.06 | 3 | 3 |
| P00492 | Hypoxanthine-guanine phosphoribosyltransferase | HPRT1 | *Homo sapiens* | 9.69 | 10.55 | 2 | 3 |
| Q8NBJ5 | Procollagen galactosyltransferase 1 | COLGALT1 | *Homo sapiens* | 9.09 | 3.70 | 2 | 3 |
| P22234 | Multifunctional protein ADE2 [Includes: Phosphoribosylaminoimidazole-succinocarboxamide synthase] | PAICS | *Homo sapiens* | 8.98 | 6.59 | 2 | 3 |
| Q92973 | Transportin-1 | TNPO1 | *Homo sapiens* | 8.69 | 4.01 | 2 | 3 |
| O00263 | AP-3 complex subunit beta-1 | AP3B1 | *Homo sapiens* | 8.64 | 2.19 | 2 | 3 |
| Q13619 | Cullin-4A | CUL4A | *Homo sapiens* | 8.46 | 3.16 | 2 | 3 |
| O14737 | Programmed cell death protein 5 | PDCD5 | *Homo sapiens* | 8.38 | 17.60 | 2 | 3 |
| P61009 | Signal peptidase complex subunit 3 | SPCS3 | *Homo sapiens* | 7.69 | 12.78 | 2 | 3 |
| P24821 | Tenascin | TNC | *Homo sapiens* | 10.38 | 2.18 | 2 | 2 |
| O43504 | Ragulator complex protein LAMTOR5 | LAMTOR5 | *Homo sapiens* | 9.61 | 43.96 | 2 | 2 |
| P58546 | Myotrophin | MTPN | *Homo sapiens* | 8.58 | 23.73 | 2 | 2 |
| O43809 | Cleavage and polyadenylation specificity factor subunit 5 | NUDT21 | *Homo sapiens* | 7.44 | 14.54 | 2 | 2 |
| Q9Y240 | C-type lectin domain family 11 member A | CLEC11A | *Homo sapiens* | 7.24 | 8.98 | 2 | 2 |
| P15289 | Arylsulfatase A | ARSA | *Homo sapiens* | 6.60 | 6.11 | 2 | 2 |
| Q6P2Q9 | Pre-mRNA-processing-splicing factor 8 | PRPF8 | *Homo sapiens* | 5.80 | 1.24 | 2 | 2 |
| | | Engineered VF mucosa | | | | | |
| P02454 | Collagen alpha-1(I) chain | COL1A1 | *Rattus norvegicus* | 17939.13 | 67.17 | 76 | 23308 |
| P02452 | Collagen alpha-1(I) chain | COL1A1 | *Homo sapiens* | 9692.90 | 59.90 | 58 | 12942 |
| P02466 | Collagen alpha-2(I) chain | COL1A2 | *Rattus norvegicus* | 12133.22 | 66.84 | 65 | 11242 |
| P08123 | Collagen alpha-2(I) chain | COL1A2 | *Homo sapiens* | 3559.41 | 53.00 | 41 | 3375 |
| Q09666 | Neuroblast differentiation-associated protein AHNAK | AHNAK | *Homo sapiens* | 4681.98 | 48.56 | 130 | 1337 |
| P02461 | Collagen alpha-1(III) chain | COL3A1 | *Homo sapiens* | 1086.61 | 25.24 | 23 | 1275 |
| P12111 | Collagen alpha-3(VI) chain | COL6A3 | *Homo sapiens* | 3130.59 | 32.61 | 82 | 922 |
| P12109 | Collagen alpha-1(VI) chain | COL6A1 | *Homo sapiens* | 1617.48 | 36.74 | 22 | 761 |
| P02751 | Fibronectin | FN1 | *Homo sapiens* | 2824.49 | 38.14 | 62 | 711 |
| P08670 | Vimentin | VIM | *Homo sapiens* | 2203.33 | 54.72 | 32 | 629 |
| P21333 | Filamin-A | FLNA | *Homo sapiens* | 2379.16 | 38.12 | 65 | 583 |
| Q15149 | Plectin | PLEC | *Homo sapiens* | 1740.04 | 24.12 | 79 | 495 |
| P35579 | Myosin-9 | MYH9 | *Homo sapiens* | 2004.50 | 38.72 | 58 | 485 |
| P02545 | Prelamin-A/C [Cleaved into: Lamin-A/C] | LMNA | *Homo sapiens* | 1569.62 | 56.78 | 36 | 449 |
| P60711 | Actin, cytoplasmic 1 | ACTB | *Rattus norvegicus* | 1773.20 | 63.20 | 16 | 446 |
| P14618 | Pyruvate kinase PKM | PKM | *Homo sapiens* | 1609.00 | 59.70 | 26 | 406 |
| P07437 | Tubulin beta chain | TUBB | *Homo sapiens* | 1561.07 | 68.92 | 22 | 406 |
| P07355 | Annexin A2 | ANXA2 | *Homo sapiens* | 1571.61 | 61.95 | 21 | 399 |
| P68371 | Tubulin beta-4B chain | TUBB4B | *Homo sapiens* | 1482.06 | 72.58 | 23 | 382 |
| P04406 | Glyceraldehyde-3-phosphate dehydrogenase | GAPDH | *Homo sapiens* | 1281.24 | 48.36 | 14 | 338 |
| P15144 | Aminopeptidase N | ANPEP | *Homo sapiens* | 1205.90 | 25.44 | 24 | 325 |
| Q13885 | Tubulin beta-2A chain | TUBB2A | *Homo sapiens* | 1196.37 | 65.17 | 21 | 319 |
| Q00610 | Clathrin heavy chain 1 | CLTC | *Homo sapiens* | 1321.28 | 26.81 | 34 | 315 |
| P11021 | 78 kDa glucose-regulated protein | HSPA5 | *Homo sapiens* | 1056.41 | 37.31 | 20 | 293 |
| P02458 | Collagen alpha-1(II) chain | COL2A1 | *Homo sapiens* | 434.49 | 5.65 | 4 | 291 |
| Q13509 | Tubulin beta-3 chain | TUBB3 | *Homo sapiens* | 964.94 | 40.67 | 15 | 286 |
| P68104 | Elongation factor 1-alpha 1 | EEF1A1 | *Homo sapiens* | 1185.32 | 34.20 | 11 | 285 |
| O43707 | Alpha-actinin-4 | ACTN4 | *Homo sapiens* | 1087.17 | 46.65 | 32 | 284 |
| P12814 | Alpha-actinin-1 | ACTN1 | *Homo sapiens* | 1005.57 | 37.33 | 26 | 274 |
| P13941 | Collagen alpha-1(III) chain | COL3A1 | *Rattus norvegicus* | 328.06 | 11.69 | 10 | 273 |
| P68363 | Tubulin alpha-1B chain | TUBA1B | *Homo sapiens* | 936.85 | 47.01 | 16 | 269 |
| P12110 | Collagen alpha-2(VI) chain | COL6A2 | *Homo sapiens* | 749.27 | 28.46 | 21 | 268 |
| P00558 | Phosphoglycerate kinase 1 | PGK1 | *Homo sapiens* | 1079.13 | 52.04 | 17 | 265 |
| P11142 | Heat shock cognate 71 kDa protein | HSPA8 | *Homo sapiens* | 954.88 | 39.94 | 21 | 246 |
| P08238 | Heat shock protein HSP 90-beta | HSP90AB1 | *Homo sapiens* | 895.47 | 33.01 | 18 | 234 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P06576 | ATP synthase subunit beta, mitochondrial | ATP5B | *Homo sapiens* | 847.43 | 42.72 | 15 | 232 |
| Q9Y490 | Talin-1 | TLN1 | *Homo sapiens* | 941.93 | 18.30 | 27 | 229 |
| P68035 | Actin, alpha cardiac muscle 1 | ACTC1 | *Rattus norvegicus* | 734.75 | 40.85 | 11 | 226 |
| P08758 | Annexin A5 | ANXA5 | *Homo sapiens* | 788.33 | 67.19 | 18 | 213 |
| P50454 | Serpin H1 | SERPINH1 | *Homo sapiens* | 914.27 | 43.78 | 14 | 210 |
| P06733 | Alpha-enolase | ENO1 | *Homo sapiens* | 747.38 | 48.85 | 16 | 209 |
| P04083 | Annexin A1 | ANXA1 | *Homo sapiens* | 841.45 | 50.00 | 15 | 206 |
| P07900 | Heat shock protein HSP 90-alpha | HSP90AA1 | *Homo sapiens* | 758.22 | 22.81 | 15 | 204 |
| P14625 | Endoplasmin | HSP90B1 | *Homo sapiens* | 738.44 | 30.88 | 20 | 202 |
| P08133 | Annexin A6 | ANXA6 | *Homo sapiens* | 735.45 | 43.54 | 22 | 195 |
| P60174 | Triosephosphate isomerase | TPI1 | *Homo sapiens* | 760.58 | 66.08 | 14 | 190 |
| Q14764 | Major vault protein | MVP | *Homo sapiens* | 622.39 | 32.03 | 20 | 180 |
| Q04828 | Aldo-keto reductase family 1 member C1 | AKR1C1 | *Homo sapiens* | 706.40 | 43.96 | 12 | 178 |
| Q9BUF5 | Tubulin beta-6 chain | TUBB6 | *Homo sapiens* | 606.14 | 38.79 | 14 | 178 |
| P04075 | Fructose-bisphosphate aldolase A | ALDOA | *Homo sapiens* | 754.74 | 60.99 | 15 | 176 |
| P46940 | Ras GTPase-activating-like protein IQGAP1 | IQGAP1 | *Homo sapiens* | 687.20 | 19.79 | 23 | 175 |
| P04264 | Keratin, type II cytoskeletal 1 | KRT1 | *Homo sapiens* | 612.98 | 36.34 | 24 | 173 |
| P13639 | Elongation factor 2 | EEF2 | *Homo sapiens* | 541.61 | 29.95 | 23 | 169 |
| P06396 | Gelsolin | GSN | *Homo sapiens* | 729.67 | 24.68 | 14 | 165 |
| P35555 | Fibrillin-1 | FBN1 | *Homo sapiens* | 596.23 | 17.24 | 30 | 164 |
| Q16555 | Dihydropyrimidinase-related protein 2 | DPYSL2 | *Homo sapiens* | 640.36 | 41.96 | 15 | 159 |
| Q9NZN4 | EH domain-containing protein 2 | EHD2 | *Homo sapiens* | 632.37 | 38.31 | 16 | 159 |
| Q14315 | Filamin-C | FLNC | *Homo sapiens* | 690.18 | 10.94 | 17 | 158 |
| O60814 | histone H2B type 1-K | HIST1H2BK | *Homo sapiens* | 439.34 | 28.57 | 3 | 157 |
| P62937 | Peptidyl-prolyl cis-trans isomerase A | PPIA | *Homo sapiens* | 553.28 | 55.76 | 9 | 156 |
| P29401 | Transketolase | TKT | *Homo sapiens* | 648.74 | 33.71 | 15 | 155 |
| P18669 | Phosphoglycerate mutase 1 | PGAM1 | *Homo sapiens* | 546.57 | 45.28 | 10 | 149 |
| P00338 | L-lactate dehydrogenase A chain | LDHA | *Homo sapiens* | 503.58 | 37.95 | 11 | 147 |
| O43852 | Calumenin | CALU | *Homo sapiens* | 598.11 | 42.54 | 13 | 146 |
| P07237 | Protein disulfide-isomerase | P4HB | *Homo sapiens* | 552.43 | 38.58 | 17 | 144 |
| Q13813 | Spectrin alpha chain, non-erythrocytic 1 | SPTAN1 | *Homo sapiens* | 514.56 | 13.55 | 22 | 134 |
| P11413 | Glucose-6-phosphate 1-dehydrogenase | G6PD | *Homo sapiens* | 503.50 | 36.89 | 13 | 134 |
| P18206 | Vinculin | VCL | *Homo sapiens* | 461.06 | 28.22 | 22 | 134 |
| P30101 | Protein disulfide-isomerase A3 | PDIA3 | *Homo sapiens* | 465.94 | 37.23 | 15 | 132 |
| P07585 | Decorin | DCN | *Homo sapiens* | 444.03 | 43.18 | 12 | 130 |
| P55072 | Transitional endoplasmic reticulum ATPase | VCP | *Homo sapiens* | 506.92 | 32.13 | 18 | 129 |
| P11216 | Glycogen phosphorylase, brain form | PYGB | *Homo sapiens* | 485.45 | 28.47 | 19 | 127 |
| Q07065 | Cytoskeleton-associated protein 4 | CKAP4 | *Homo sapiens* | 472.22 | 41.86 | 20 | 127 |
| P27348 | 14-3-3 protein theta | YWHAQ | *Homo sapiens* | 444.22 | 42.45 | 9 | 127 |
| P62260 | 14-3-3 protein epsilon | YWHAE | *Rattus norvegicus* | 375.64 | 40.00 | 8 | 124 |
| P63104 | 14-3-3 protein zeta/delta | YWHAZ | *Homo sapiens* | 432.53 | 41.22 | 8 | 120 |
| Q06830 | Peroxiredoxin-1 | PRDX1 | *Homo sapiens* | 480.66 | 60.30 | 10 | 119 |
| P09382 | Galectin-1 | LGALS1 | *Homo sapiens* | 434.09 | 46.67 | 5 | 119 |
| P16152 | Carbonyl reductase [NADPH] 1 | CBR1 | *Homo sapiens* | 478.30 | 52.35 | 10 | 118 |
| P67936 | Tropomyosin alpha-4 chain | TPM4 | *Homo sapiens* | 419.41 | 48.79 | 14 | 118 |
| O00299 | Chloride intracellular channel protein 1 | CLIC1 | *Homo sapiens* | 454.50 | 60.17 | 10 | 116 |
| P62805 | Histone H4 | HIST1H4A | *Homo sapiens* | 407.94 | 52.43 | 7 | 116 |
| Q14204 | Cytoplasmic dynein 1 heavy chain 1 | DYNC1H1 | *Homo sapiens* | 395.38 | 7.68 | 26 | 113 |
| P07195 | L-lactate dehydrogenase B chain | LDHB | *Homo sapiens* | 366.01 | 37.72 | 12 | 113 |
| P27797 | Calreticulin | CALR | *Homo sapiens* | 468.52 | 37.41 | 9 | 111 |
| P13489 | Ribonuclease inhibitor | RNH1 | *Homo sapiens* | 451.04 | 40.35 | 12 | 111 |
| Q99536 | Synaptic vesicle membrane protein VAT-1 homolog | VAT1 | *Homo sapiens* | 425.08 | 32.06 | 8 | 106 |
| P63244 | Guanine nucleotide-binding protein subunit beta-2-like 1 | GNB2L1 | *Homo sapiens* | 387.23 | 58.68 | 12 | 104 |
| Q01082 | Spectrin beta chain, non-erythrocytic 1 | SPTBN1 | *Homo sapiens* | 384.44 | 12.10 | 20 | 104 |
| P22314 | Ubiquitin-like modifier-activating enzyme 1 | UBA1 | *Homo sapiens* | 382.34 | 23.72 | 16 | 104 |
| P10809 | 60 kDa heat shock protein, mitochondrial | HSPD1 | *Homo sapiens* | 394.59 | 27.05 | 12 | 103 |
| P23264 | Peptidyl-prolyl cis-trans isomerase B | PPIB | *Homo sapiens* | 334.48 | 36.57 | 8 | 103 |
| Q03135 | Caveolin-1 | CAV1 | *Homo sapiens* | 373.84 | 63.48 | 9 | 102 |
| P09211 | Glutathione S-transferase P | GSTP1 | *Homo sapiens* | 429.56 | 53.33 | 8 | 101 |
| O60664 | Perilipin-3 | PLIN3 | *Homo sapiens* | 386.15 | 37.79 | 10 | 101 |
| P53396 | ATP-citrate synthase | ACLY | *Homo sapiens* | 383.16 | 17.80 | 13 | 101 |
| P08107 | Heat shock 70 kDa protein 1A/1B | HSPA1A | *Homo sapiens* | 357.20 | 28.71 | 14 | 101 |
| P42330 | Aldo-keto reductase family 1 member C3 | AKR1C3 | *Homo sapiens* | 412.36 | 35.60 | 9 | 99 |
| P25705 | ATP synthase subunit alpha, mitochondrial | ATP5A1 | *Homo sapiens* | 390.18 | 22.24 | 9 | 98 |
| P23528 | Cofilin-1 | CFL1 | *Homo sapiens* | 402.40 | 57.23 | 9 | 97 |
| Q6NZI2 | Polymerase I and transcript release factor | PTRF | *Homo sapiens* | 370.34 | 25.84 | 9 | 96 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| Q9NZM1 | Myoferlin | MYOF | *Homo sapiens* | 359.24 | 14.65 | 20 | 96 |
| P07602 | Proactivator polypeptide [Cleaved into: Saposin-A] | PSAP | *Homo sapiens* | 229.01 | 20.23 | 10 | 96 |
| P40926 | Malate dehydrogenase, mitochondrial | MDH2 | *Homo sapiens* | 368.82 | 42.31 | 10 | 95 |
| P36955 | Pigment epithelium-derived factor | SERPINF1 | *Homo sapiens* | 342.17 | 25.84 | 10 | 95 |
| P35556 | Fibrilin-2 | FBN2 | *Homo sapiens* | 354.09 | 7.14 | 14 | 92 |
| P38646 | Stress-70 protein, mitochondrial | HSPA9 | *Homo sapiens* | 350.09 | 21.06 | 10 | 91 |
| P40939 | Trifunctional enzyme subunit alpha, mitochondrial | HADHA | *Homo sapiens* | 366.81 | 17.17 | 8 | 90 |
| P51884 | Lumican | LUM | *Homo sapiens* | 301.46 | 29.29 | 8 | 90 |
| P21980 | Protein-glutamine gamma-glutamyltransferase | TGM2 | *Homo sapiens* | 335.23 | 20.96 | 10 | 89 |
| P49368 | T-complex protein 1 subunit gamma | CCT3 | *Homo sapiens* | 331.43 | 29.17 | 11 | 89 |
| P05388 | 60S acidic ribosomal protein P0 | RPLP0 | *Homo sapiens* | 366.21 | 37.85 | 8 | 88 |
| P37802 | Transgelin-2 | TAGLN2 | *Homo sapiens* | 348.12 | 46.73 | 8 | 88 |
| P51149 | Ras-related protein Rab-7a | RAB7A | *Homo sapiens* | 315.29 | 42.51 | 7 | 88 |
| Q15019 | Septin-2 | 41884 | *Homo sapiens* | 343.22 | 42.66 | 9 | 86 |
| Q96AY3 | Peptidyl-prolyl cis-trans isomerase FKBP-10 | FKBP10 | *Homo sapiens* | 287.19 | 20.79 | 9 | 85 |
| P26038 | Moesin | MSN | *Homo sapiens* | 334.03 | 23.22 | 13 | 84 |
| P27824 | Calnexin | CANX | *Homo sapiens* | 327.37 | 19.26 | 9 | 84 |
| P06744 | Glucose-6-phosphate isomerase | GPI | *Homo sapiens* | 340.63 | 27.78 | 9 | 83 |
| P61978 | Heterogeneous nuclear ribonucleoprotein K | HNRNPK | *Homo sapiens* | 314.43 | 29.59 | 10 | 83 |
| P11766 | Alcohol dehydrogenase class-3 | ADH5 | *Homo sapiens* | 385.13 | 22.99 | 6 | 82 |
| P49327 | Fatty acid synthase | FASN | *Homo sapiens* | 344.44 | 10.51 | 16 | 82 |
| P21796 | Voltage-dependent anion-selective channel protein 1 | VDAC1 | *Homo sapiens* | 326.64 | 27.21 | 6 | 82 |
| P30041 | Peroxiredoxin-6 | PRDX6 | *Homo sapiens* | 299.10 | 44.64 | 8 | 82 |
| Q86VP6 | Cullin-associated NEDD8-dissociated protein 1 | CAND1 | *Homo sapiens* | 279.60 | 11.30 | 10 | 82 |
| P60660 | Myosin light polypeptide 5 | MYL6 | *Homo sapiens* | 263.81 | 48.34 | 7 | 82 |
| P09525 | Annexin A4 | ANXA4 | *Homo sapiens* | 276.12 | 35.11 | 9 | 81 |
| P53618 | Coatomer subunit beta | COPB1 | *Homo sapiens* | 240.03 | 17.00 | 11 | 77 |
| P98095 | Fibulin-2 | FBLN2 | *Homo sapiens* | 297.15 | 17.15 | 13 | 76 |
| P07858 | Cathepsin B | CTSB | *Homo sapiens* | 325.77 | 28.02 | 7 | 75 |
| P05387 | 60S acidic ribosomal protein P2 | RPLP2 | *Homo sapiens* | 312.25 | 76.52 | 5 | 75 |
| P31946 | 14-3-3 protein beta/alpha | YWHAB | *Homo sapiens* | 256.23 | 32.52 | 6 | 74 |
| P61981 | 14-3-3 protein gamma | YWHAG | *Homo sapiens* | 253.62 | 20.65 | 4 | 74 |
| P07686 | Beta-hexosaminidase subunit beta | HEXB | *Homo sapiens* | 223.90 | 11.69 | 5 | 74 |
| O75083 | WD repeat-containing protein 1 | WDR1 | *Homo sapiens* | 403.80 | 26.24 | 8 | 73 |
| Q04446 | 1,4-alpha-glucan-branching enzyme | GBE1 | *Homo sapiens* | 322.94 | 20.66 | 9 | 73 |
| P45880 | Voltage-dependent anion-selective channel protein 2 | VDAC2 | *Homo sapiens* | 262.24 | 25.85 | 5 | 73 |
| P04844 | Dolichyl-diphosphooligosaccharide--protein glycosyltransferase subunit 2 | RPN2 | *Homo sapiens* | 295.08 | 28.68 | 11 | 72 |
| P08865 | 40S ribosomal protein SA | RPSA | *Homo sapiens* | 285.15 | 36.95 | 8 | 72 |
| P00387 | NADH-cytochrome b5 reductase 3 | CYB5R3 | *Homo sapiens* | 280.81 | 31.56 | 7 | 71 |
| P78527 | DNA-dependent protein kinase catalytic subunit | PRKDC | *Homo sapiens* | 267.13 | 5.77 | 15 | 71 |
| P02792 | Ferritn light chain | FTL | *Homo sapiens* | 323.33 | 36.00 | 5 | 70 |
| P52209 | 6-phosphogluconate dehydrogenase, decarboxylating | PGD | *Homo sapiens* | 281.42 | 18.22 | 6 | 70 |
| P02768 | Serum albumin | ALB | *Homo sapiens* | 281.23 | 3.94 | 3 | 70 |
| P09972 | Fructose-bisphosphate aldolase C | ALDOC | *Homo sapiens* | 303.97 | 22.53 | 5 | 69 |
| Q07954 | Prolow-density lipoproten receptor-related protein 1 | LRP1 | *Homo sapiens* | 255.24 | 5.02 | 16 | 69 |
| P07339 | Cathepsin D | CTSD | *Homo sapiens* | 246.82 | 20.63 | 6 | 69 |
| Q15582 | Transforming growth factor-beta-induced protein ig-h3 | TGFBI | *Homo sapiens* | 219.77 | 10.54 | 6 | 69 |
| P07737 | Profilin-1 | PFN1 | *Homo sapiens* | 216.88 | 64.29 | 8 | 69 |
| Q9Y678 | Coatomer subunit gamma-1 | COPG1 | *Homo sapiens* | 274.16 | 10.41 | 6 | 68 |
| P26641 | Elongation factor 1-gamma | EEF1G | *Homo sapiens* | 269.96 | 24.49 | 8 | 68 |
| Q96AG4 | Leucine-rich repeat-containing protein 59 | LRRC59 | *Homo sapiens* | 259.13 | 31.60 | 6 | 68 |
| P61158 | Actin-related protein 3 | ACTR3 | *Homo sapiens* | 296.73 | 27.75 | 8 | 67 |
| Q15084 | Protein disulfide-isomerase A6 | PDIA6 | *Homo sapiens* | 252.32 | 32.50 | 9 | 67 |
| P50995 | Annexin A11 | ANXA11 | *Homo sapiens* | 233.06 | 12.87 | 5 | 67 |
| P62241 | 40S ribosomal protein S8 | RPS8 | *Homo sapiens* | 227.53 | 31.73 | 5 | 67 |
| Q9H299 | SH3 domain-binding glutamic acid-rich-like protein 3 | SH3BGRL3 | *Homo sapiens* | 248.90 | 31.18 | 3 | 66 |
| P19105 | Myosin regulatory light chain 12A | MYL12A | *Homo sapiens* | 243.16 | 39.18 | 5 | 66 |
| O60701 | UDP-glucose 6-dehydrogenase | UGDH | *Homo sapiens* | 237.32 | 37.45 | 14 | 66 |
| P52907 | F-actin-capping protein subunit alpha-1 | CAPZA1 | *Homo sapiens* | 256.92 | 41.26 | 7 | 65 |
| Q9NQC3 | Reticulon-4 | RTN4 | *Homo sapiens* | 252.94 | 9.65 | 6 | 65 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P40925 | Malate dehydrogenase, cytoplasmic | MDH1 | *Homo sapiens* | 225.55 | 24.55 | 6 | 65 |
| Q15365 | Poly(rC)-binding protein 1 | PCBP1 | *Homo sapiens* | 225.32 | 32.02 | 6 | 65 |
| P22626 | Heterogeneous nuclear ribonucleoproteins A2/B1 | HNRNPA2B1 | *Homo sapiens* | 223.70 | 30.88 | 9 | 65 |
| P12236 | ADP/ATP translocase 3 | SLC25A6 | *Homo sapiens* | 178.86 | 28.52 | 8 | 65 |
| Q14697 | Neutral alpha-glucosidase AB | GANAB | *Homo sapiens* | 308.38 | 13.67 | 9 | 64 |
| P60842 | Eukaryotic initiation factor 4A-I | EIF4A1 | *Homo sapiens* | 212.29 | 21.67 | 7 | 63 |
| Q96D15 | Reticulocalbin-3 | RCN3 | *Homo sapiens* | 267.03 | 27.13 | 5 | 62 |
| P30086 | Phosphatidylethanolamine-binding protein 1 | PEBP1 | *Homo sapiens* | 260.87 | 56.15 | 6 | 62 |
| Q01518 | Adenylyl cyclase-associated protein 1 | CAP1 | *Homo sapiens* | 227.58 | 23.79 | 9 | 62 |
| Q14974 | Importin subunit beta-1 | KPNB1 | *Homo sapiens* | 227.02 | 17.01 | 10 | 62 |
| P55786 | Puromycin-sensitive aminopeptidase | NPEPPS | *Homo sapiens* | 202.84 | 13.93 | 10 | 62 |
| P17655 | Calpain-2 catalytic subunit | CAPN2 | *Homo sapiens* | 230.99 | 17.43 | 7 | 61 |
| P04792 | Heat shock protein beta-1 | HSPB1 | *Homo sapiens* | 221.22 | 40.00 | 7 | 61 |
| Q92928 | Putative Ras-related protein Rab-1C | RAB1C | *Homo sapiens* | 189.19 | 31.34 | 5 | 61 |
| P23396 | 40S ribosomal protein S3 | RPS3 | *Homo sapiens* | 182.60 | 52.26 | 10 | 61 |
| P04843 | Dolichyl-diphosphooligosaccharide--protein glycosyltransferase subunit 1 | RPN1 | *Homo sapiens* | 231.88 | 17.96 | 7 | 60 |
| P15121 | Aldose reductase | AKR1B1 | *Homo sapiens* | 225.73 | 33.86 | 6 | 60 |
| Q00839 | Heterogeneous nuclear ribonucleoprotein U | HNRNPU | *Homo sapiens* | 224.96 | 15.03 | 7 | 60 |
| P35237 | Serpin B6 | SERPINB6 | *Homo sapiens* | 208.98 | 23.67 | 7 | 60 |
| Q969G5 | Protein kinase C delta-binding protein | PRKCDBP | *Homo sapiens* | 200.31 | 31.03 | 7 | 60 |
| P36578 | 60S ribosomal protein L4 | RPL4 | *Homo sapiens* | 196.11 | 19.20 | 7 | 60 |
| P17301 | Integrin alpha-2 | ITGA2 | *Homo sapiens* | 231.23 | 14.31 | 11 | 59 |
| P00367 | Glutamate dehydrogenase 1, mitochondrial | GLUD1 | *Homo sapiens* | 221.30 | 20.43 | 8 | 59 |
| O00159 | Unconventional myosin-Ic | MYO1C | *Homo sapiens* | 204.23 | 15.71 | 12 | 59 |
| P12956 | X-ray repair cross-complementing protein 6 | XRCC6 | *Homo sapiens* | 190.12 | 20.53 | 10 | 58 |
| Q16658 | Fascin | FSCN1 | *Homo sapiens* | 227.09 | 20.08 | 8 | 57 |
| P22392 | Nucleoside diphosphate kinase B | NME2 | *Homo sapiens* | 196.95 | 40.13 | 5 | 57 |
| Q96CX2 | BTB/POZ domain-containing protein KCTD12 | KCTD12 | *Homo sapiens* | 173.33 | 14.77 | 4 | 57 |
| P05141 | ADP/ATP translocase 2 | SLC25A5 | *Homo sapiens* | 157.41 | 25.17 | 7 | 57 |
| P35527 | Keratin, type I cytoskeletal 9 | KRT9 | *Homo sapiens* | 274.80 | 30.82 | 12 | 56 |
| Q8IUX7 | Adipocyte enhancer-binding protein 1 | AEBP1 | *Homo sapiens* | 245.03 | 10.71 | 8 | 56 |
| P50990 | T-complex protein 1 subunit theta | CCT8 | *Homo sapiens* | 199.96 | 19.16 | 8 | 56 |
| P18085 | ADP-ribosylation factor 4 | ARF4 | *Homo sapiens* | 173.35 | 48.89 | 8 | 56 |
| P02794 | Ferritin heavy chain | FTH1 | *Homo sapiens* | 271.23 | 46.45 | 8 | 55 |
| Q9Y696 | Chloride intracellular channel protein 4 | CLIC4 | *Homo sapiens* | 221.19 | 54.15 | 8 | 55 |
| P49748 | Very long-chain specific acyl-CoA dehydrogenase, mitochondrial | ACADVL | *Homo sapiens* | 219.10 | 20.00 | 9 | 55 |
| P98160 | Basement membrane-specific heparan sulfate proteoglycan core protein | HSPG2 | *Homo sapiens* | 208.59 | 5.01 | 14 | 55 |
| Q14108 | Lysosome membrane protein 2 | SCARB2 | *Homo sapiens* | 194.36 | 19.46 | 6 | 55 |
| P62424 | 60S ribosomal protein L7a | RPL7A | *Homo sapiens* | 182.21 | 29.70 | 7 | 55 |
| P63241 | Eukaryotic translation initiation factor 5A-1 | EIF5A | *Homo sapiens* | 232.00 | 30.52 | 5 | 54 |
| P07108 | Acyl-CoA-binding protein | DBI | *Homo sapiens* | 224.72 | 50.57 | 3 | 54 |
| P30153 | Serine/threonine-protein phosphatase 2A 65 kDa regulatory subunit A alpha isoform | PPP2R1A | *Homo sapiens* | 217.26 | 19.02 | 7 | 54 |
| P30050 | 60S ribosomal protein L12 | RPL12 | *Homo sapiens* | 198.47 | 54.55 | 6 | 54 |
| P16278 | Beta-galactosidase | GLB1 | *Homo sapiens* | 198.03 | 11.23 | 6 | 54 |
| P53621 | Coatomer subunit alpha | COPA | *Homo sapiens* | 169.83 | 10.78 | 10 | 54 |
| P60033 | CD81 antigen | CD81 | *Homo sapiens* | 252.20 | 25.00 | 3 | 53 |
| P21810 | Biglycan | BGN | *Homo sapiens* | 223.44 | 24.73 | 8 | 53 |
| P13667 | Protein disulfide-isomerase A4 | PDIA4 | *Homo sapiens* | 220.61 | 16.90 | 7 | 53 |
| Q96KK5 | Histone H2A type 1-H | HIST1H2AH | *Homo sapiens* | 188.17 | 27.34 | 3 | 53 |
| P37837 | Transaldolase | TALDO1 | *Homo sapiens* | 169.53 | 14.24 | 4 | 53 |
| P52565 | Rho GDP-dissociation inhibitor 1 | ARHGDIA | *Homo sapiens* | 191.81 | 21.08 | 4 | 52 |
| Q9P2E9 | Ribosome-binding protein 1 | RRBP1 | *Homo sapiens* | 182.04 | 11.63 | 10 | 52 |
| P61204 | ADP-ribosylation factor 3 | ARF3 | *Homo sapiens* | 175.59 | 38.67 | 6 | 52 |
| P68871 | Hemoglobin subunit beta | HBB | *Homo sapiens* | 167.11 | 53.74 | 6 | 52 |
| Q99497 | Protein DJ-1 | PARK7 | *Homo sapiens* | 200.89 | 29.63 | 4 | 51 |
| P21589 | 5'-nucleotidase | NT5E | *Homo sapiens* | 178.39 | 26.31 | 11 | 51 |
| P46821 | Microtubule-associated protein 1B | MAP1B | *Homo sapiens* | 172.54 | 8.35 | 13 | 51 |
| Q15293 | Reticulocalbin-1 | RCN1 | *Homo sapiens* | 204.33 | 29.91 | 6 | 50 |
| P07910 | Heterogeneous nuclear ribonucleoproteins C1/C2 | HNRNPC | *Homo sapiens* | 147.42 | 18.30 | 5 | 50 |
| P09651 | Heterogeneous nuclear ribonucleoprotein A1 | HNRNPA1 | *Homo sapiens* | 178.69 | 22.58 | 6 | 49 |
| Q99715 | Collagen alpha-1(XII) chain | COL12A1 | *Homo sapiens* | 178.41 | 5.91 | 12 | 49 |
| P61247 | 40S ribosomal protein S3a | RPS3A | *Homo sapiens* | 175.98 | 18.18 | 4 | 49 |
| P10599 | Thioredoxin | TXN | *Homo sapiens* | 159.77 | 42.86 | 5 | 49 |
| Q9Y6N5 | Sulfide: quinone oxidoreductase, mitochondrial | SQRDL | *Homo sapiens* | 168.71 | 28.00 | 10 | 48 |

TABLE 1-continued

Lists of proteins identified in LC-MS/MS analysis of scaffold only, VFF in
scaffold, VFE on scaffold, engineered VF mucosa and native VF mucosa. Identifications
were based on a 1% false discovery rate. The scaffold was sourced from *Rattus norvegicus*;
VFF, VFE and native VF mucosa were sourced from *Homo sapiens*. Proteins are listed in order
of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P50395 | Rab GDP dissociation inhibitor beta | GDI2 | *Homo sapiens* | 180.18 | 27.64 | 9 | 47 |
| O43390 | Heterogeneous nuclear ribonucleoprotein R | HNRNPR | *Homo sapiens* | 178.95 | 8.53 | 4 | 47 |
| Q01813 | 6-phosphofructokinase type C | PFKP | *Homo sapiens* | 178.62 | 9.31 | 5 | 47 |
| P07384 | Calpain-1 catalytic subunit | CAPN1 | *Homo sapiens* | 157.93 | 12.61 | 6 | 47 |
| P55209 | Nucleosome assembly protein 1-like 1 | NAP1L1 | *Homo sapiens* | 188.64 | 17.14 | 5 | 46 |
| P47755 | F-actin-capping protein subunit alpha-2 | CAPZA2 | *Homo sapiens* | 173.61 | 28.67 | 6 | 46 |
| P14550 | Alcohol dehydrogenase [NADP(+)] | AKR1A1 | *Homo sapiens* | 169.26 | 13.54 | 4 | 46 |
| P50609 | Fibromodulin | FMOD | *Rattus norvegicus* | 162.36 | 14.10 | 4 | 46 |
| P24534 | Elongation factor 1-beta | EEF1B2 | *Homo sapiens* | 195.28 | 20.44 | 3 | 45 |
| P04080 | Cystatin-B | CSTB | *Homo sapiens* | 183.06 | 45.92 | 3 | 45 |
| P14314 | Glucosidase 2 subunit beta | PRKCSH | *Homo sapiens* | 171.16 | 9.85 | 4 | 45 |
| P46782 | 40S ribosomal protein S5 [Cleaved into: 40S ribosomal protein S5, N-terminally processed] | RPS5 | *Homo sapiens* | 157.22 | 18.14 | 3 | 45 |
| P22105 | Tenascin-X | TNXB | *Homo sapiens* | 152.49 | 5.99 | 10 | 45 |
| Q07020 | 60S ribosomal protein L18 | RPL18 | *Homo sapiens* | 146.31 | 30.85 | 5 | 45 |
| P50991 | T-complex protein 1 subunit delta | CCT4 | *Homo sapiens* | 186.69 | 8.53 | 3 | 44 |
| P62158 | Calmodulin | CALM1 | *Homo sapiens* | 185.02 | 29.53 | 3 | 44 |
| O95782 | AP-2 complex subunit alpha-1 | AP2A1 | *Homo sapiens* | 159.92 | 9.52 | 7 | 44 |
| P17980 | 26S protease regulatory subunit 6A | PSMC3 | *Homo sapiens* | 155.58 | 29.61 | 8 | 44 |
| P30044 | Peroxiredoxin-5, mitochondrial | PRDX5 | *Homo sapiens* | 142.09 | 34.11 | 5 | 44 |
| P48444 | Coatomer subunit delta | ARCN1 | *Homo sapiens* | 128.85 | 9.00 | 4 | 44 |
| P16403 | Histone H1.2 | HIST1H1C | *Homo sapiens* | 127.74 | 15.49 | 4 | 44 |
| P23219 | Prostaglandin G/H synthase 1 | PTGS1 | *Homo sapiens* | 174.36 | 12.85 | 5 | 43 |
| P62826 | GTP-binding nuclear protein Ran | RAN | *Homo sapiens* | 156.07 | 39.35 | 7 | 43 |
| P34932 | Heat shock 70 kDa protein 4 | HSPA4 | *Homo sapiens* | 142.63 | 12.88 | 7 | 43 |
| P13645 | Keratin, type I cytoskeletal 10 | KRT10 | *Homo sapiens* | 134.26 | 20.03 | 9 | 43 |
| P55084 | Trifunctional enzyme subunit beta, mitochondrial | HADHB | *Homo sapiens* | 160.26 | 19.20 | 7 | 42 |
| P04899 | Guanine nucleotide-binding protein G(i) subunit alpha-2 | GNAI2 | *Homo sapiens* | 149.06 | 17.18 | 4 | 42 |
| P11047 | Laminin subunit gamma-1 | LAMC1 | *Homo sapiens* | 141.74 | 6.53 | 7 | 42 |
| P12882 | Myosin-1 | MYH1 | *Homo sapiens.* | 159.40 | 5.98 | 8 | 41 |
| P62701 | 40S ribosomal protein S4, X isoform | RPS4X | *Homo sapiens* | 146.21 | 29.66 | 7 | 41 |
| P51991 | Heterogeneous nuclear ribonucleoprotein A3 | HNRNP43 | *Homo sapiens* | 140.08 | 17.20 | 5 | 41 |
| Q15366 | Poly(rC)-binding protein 2 | PCBP2 | *Homo sapiens* | 126.95 | 14.79 | 4 | 41 |
| P50914 | 60S ribosomal protein L14 | RPL14 | *Homo sapiens* | 118.43 | 20.93 | 4 | 41 |
| P05386 | 60S acidic ribosomal protein P1 | RPLP1 | *Homo sapiens* | 214.61 | 51.75 | 2 | 40 |
| P62906 | 60S ribosomal protein L10a | RPL10A | *Homo sapiens* | 160.47 | 25.81 | 4 | 40 |
| P10909 | Clusterin | CLU | *Homo sapiens* | 142.36 | 13.81 | 4 | 40 |
| P15531 | Nucleoside diphosphate kinase A | NME1 | *Homo sapiens* | 140.96 | 39.47 | 5 | 40 |
| P27105 | Erythrocyte band 7 integral membrane protein | STOM | *Homo sapiens* | 138.94 | 24.65 | 5 | 40 |
| Q12797 | Aspartyl/asparaginyl beta-hydroxylase | ASPH | *Homo sapiens* | 138.22 | 10.55 | 5 | 40 |
| P32119 | Peroxiredoxin-2 | PRDX2 | *Homo sapiens* | 137.82 | 19.70 | 4 | 40 |
| P39687 | Acidic leucine-rich nuclear phosphoprotein 32 family member A | ANP32A | *Homo sapiens* | 133.72 | 12.85 | 3 | 40 |
| P05556 | Integrin beta-1 | ITGB1 | *Homo sapiens* | 128.26 | 12.28 | 8 | 40 |
| P27816 | Microtubule-associated protein 4 | MAP4 | *Homo sapiens* | 122.94 | 9.90 | 8 | 40 |
| Q9Y6C2 | EMILIN-1 | EMILIN1 | *Homo sapiens* | 140.17 | 9.45 | 6 | 39 |
| P08134 | Rho-related GTP-binding protein RhoC | RHOC | *Homo sapiens* | 138.88 | 32.64 | 5 | 39 |
| P62979 | Ubiquitin-40S ribosomal protein S27a | RPS27A | *Homo sapiens* | 138.38 | 33.97 | 4 | 39 |
| P19338 | Nucleolin | NCL | *Homo sapiens* | 136.47 | 13.66 | 8 | 39 |
| P78371 | T-complex protein 1 subunit beta | CCT2 | *Homo sapiens* | 160.95 | 27.29 | 10 | 38 |
| P69905 | Hemoglobin subunit alpha | HBA1 | *Homo sapiens* | 143.65 | 48.59 | 4 | 38 |
| P62277 | 40S ribosomal protein S13 | RPS13 | *Homo sapiens* | 139.22 | 18.54 | 3 | 38 |
| P17931 | Galectin-3 | LGALS3 | *Homo sapiens* | 137.26 | 28.40 | 6 | 38 |
| P61586 | Transforming protein RhoA | RHOA | *Homo sapiens* | 134.81 | 38.86 | 6 | 38 |
| Q13838 | Spliceosome RNA helicase DDX39B | DDX39B | *Homo sapiens* | 132.68 | 22.43 | 6 | 38 |
| P41250 | Glycine-tRNA ligase | GARS | *Homo sapiens* | 120.83 | 10.42 | 5 | 38 |
| P31949 | Protein S100-A11 | S100A11 | *Homo sapiens* | 110.54 | 25.71 | 3 | 38 |
| Q16851 | UTP-glucose-1-phosphate uridylyltransferase | UGP2 | *Homo sapiens* | 192.68 | 10.24 | 3 | 37 |
| Q7KZF4 | Staphylococcal nuclease domain-containing protein 1 | SND1 | *Homo sapiens* | 139.09 | 13.52 | 8 | 37 |
| P31939 | Bifunctional purine biosynthesis protein PURH [Includes: Phosphoribosylaminoimidazolecarboxamide formyltransferase] | ATIC | *Homo sapiens* | 136.29 | 9.97 | 5 | 37 |
| P48047 | ATP synthase subunit O, mitochondrial | ATP5O | *Homo sapiens* | 127.11 | 44.60 | 6 | 37 |
| P61106 | Ras-related protein Rab-14 | RAB14 | *Homo sapiens* | 127.06 | 30.70 | 4 | 37 |
| O75874 | Isocitrate dehydrogenase [NADP] cytoplasmic | IDH1 | *Homo sapiens* | 121.13 | 21.01 | 6 | 37 |
| O43776 | Asparagine-tRNA ligase, cytoplasmic | NARS | *Homo sapiens* | 119.15 | 18.43 | 8 | 37 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P56134 | ATP synthase subunit f, mitochondrial | ATP5J2 | *Homo sapiens* | 117.20 | 25.53 | 2 | 37 |
| P62249 | 40S ribosomal protein S16 | RPS16 | *Homo sapiens* | 108.15 | 22.60 | 3 | 37 |
| Q8NBS9 | Thioredoxin domain-containing protein 5 | TXNDC5 | *Homo sapiens* | 165.47 | 9.26 | 3 | 36 |
| Q12905 | Interleukin enhancer-binding factor 2 | ILF2 | *Homo sapiens* | 139.27 | 11.28 | 3 | 36 |
| Q9UBG0 | C-type mannose receptor 2 | MRC2 | *Homo sapiens* | 134.77 | 4.87 | 5 | 36 |
| P06753 | Tropomyosin alpha-3 chain | TPM3 | *Homo sapiens* | 111.21 | 13.38 | 5 | 36 |
| P62942 | Peptidyl-prolyl cis-trans isomerase FKBP1A | FKBP1A | *Homo sapiens* | 158.27 | 29.63 | 3 | 35 |
| Q07021 | Complement component 1 Q subcomponent-binding protein, mitochondrial | C1QBP | *Homo sapiens* | 157.66 | 12.06 | 3 | 35 |
| P26599 | Polypyrimidine tract-binding protein 1 | PTBP1 | *Homo sapiens* | 155.40 | 14.12 | 5 | 35 |
| P49411 | Elongation factor Tu, mitochondrial | TUFM | *Homo sapiens* | 138.71 | 15.27 | 4 | 35 |
| P63010 | AP-2 complex subunit beta | AP2B1 | *Homo sapiens* | 131.57 | 10.46 | 7 | 35 |
| P08253 | 72 kDa type IV collagenase | MMP2 | *Homo sapiens* | 125.40 | 13.64 | 5 | 35 |
| P13674 | Prolyl 4-hydroxylase subunit alpha-1 | P4HA1 | *Homo sapiens* | 121.33 | 14.98 | 6 | 35 |
| P35908 | Keratin, type II cytoskeletal 2 epidermal | KRT2 | *Homo sapiens* | 110.24 | 14.71 | 8 | 35 |
| Q13162 | Peroxiredoxin-4 | PRDX4 | *Homo sapiens* | 109.40 | 16.97 | 4 | 35 |
| P00441 | Superoxide dismutase [Cu—Zn] | SOD1 | *Homo sapiens* | 201.61 | 32.47 | 4 | 34 |
| P68036 | Ubiquitin-conjugating enzyme E2 L3 | UBE2L3 | *Homo sapiens* | 166.53 | 35.71 | 3 | 34 |
| P07099 | Epoxide hydrolase 1 | EPHX1 | *Homo sapiens* | 151.01 | 21.76 | 7 | 34 |
| O43399 | Tumor protein D54 | TPD52L2 | *Homo sapiens* | 134.95 | 31.07 | 4 | 34 |
| P23634 | Plasma membrane calcium-transporting ATPase 4 | ATP2B4 | *Homo sapiens* | 133.50 | 3.46 | 3 | 34 |
| P15559 | NAD(P)H dehydrogenase [quinone] 1 | NQO1 | *Homo sapiens* | 125.60 | 13.50 | 3 | 34 |
| P51659 | Peroxisomal multifunctional enzyme type 2 | HSD17B4 | *Homo sapiens* | 122.52 | 14.67 | 7 | 34 |
| P04259 | Keratin, type II cytoskeletal 6B | KRT6B | *Homo sapiens* | 118.21 | 20.21 | 10 | 34 |
| P16615 | Sarcoplasmic/endoplasmic reticulum calcium ATPase 2 | ATP2A2 | *Homo sapiens* | 117.26 | 9.98 | 8 | 34 |
| Q00325 | Phosphate carrier protein, mitochondrial | SLC25A3 | *Homo sapiens* | 115.25 | 19.06 | 5 | 34 |
| P62140 | Serine/threonine-protein phosphatase PP1-beta catalytic subunit | PPP1CB | *Homo sapiens* | 115.19 | 18.96 | 5 | 34 |
| Q96TA1 | Niban-like protein 1 | FAM129B | *Homo sapiens* | 113.43 | 9.65 | 5 | 34 |
| P39019 | 40S ribosomal protein S19 | RPS19 | *Homo sapiens* | 109.71 | 30.34 | 5 | 34 |
| P62879 | Guanine nucleotide-binding protein G(I)/G(S)/G(T) subunit beta-2 | GNB2 | *Homo sapiens* | 109.17 | 15.59 | 5 | 34 |
| P29692 | Elongation factor 1-delta | EEF1D | *Homo sapiens* | 108.71 | 13.17 | 3 | 34 |
| P48783 | 40S ribosomal protein S10 | RPS10 | *Homo sapiens* | 107.63 | 14.55 | 2 | 34 |
| Q6NXT2 | Histone H3.3C | H3F3C | *Homo sapiens* | 89.79 | 11.85 | 2 | 34 |
| P20810 | Calpastatin | CAST | *Homo sapiens* | 141.21 | 10.88 | 4 | 33 |
| P17858 | 6-phosphofructokinase, liver type | PFKL | *Homo sapiens* | 136.89 | 6.28 | 3 | 33 |
| P62888 | 60S ribosomal protein L30 | RPL30 | *Homo sapiens* | 131.49 | 51.30 | 4 | 33 |
| Q16698 | 2,4-dienoyl-CoA reductase, mitochondrial | DECR1 | *Homo sapiens* | 121.31 | 13.73 | 3 | 33 |
| P15880 | 40S ribosomal protein S2 | RPS2 | *Homo sapiens* | 117.17 | 16.04 | 4 | 33 |
| P18124 | 60S ribosomal protein L7 | RPL7 | *Homo sapiens* | 116.55 | 16.13 | 3 | 33 |
| P62269 | 40S ribosomal protein S18 | RPS18 | *Homo sapiens* | 88.00 | 16.45 | 3 | 33 |
| P16070 | CD44 antigen | CD44 | *Homo sapiens* | 131.22 | 3.77 | 2 | 32 |
| P49755 | Transmembrane emp24 domain-containing protein 10 | TMED10 | *Homo sapiens* | 124.36 | 22.37 | 5 | 32 |
| Q9Y265 | RuvB-like 1 | RUVBL1 | *Homo sapiens* | 113.28 | 23.03 | 7 | 32 |
| P61224 | Ras-related protein Rap-1b | RAP1B | *Homo sapiens* | 104.67 | 26.09 | 4 | 32 |
| Q92688 | Acidic leucine-rich nuclear phosphoprotein 32 family member B | ANP32B | *Homo sapiens* | 103.10 | 21.12 | 4 | 32 |
| Q9BSJ8 | Extended synaptotagmin-1 | ESYT1 | *Homo sapiens* | 102.79 | 7.61 | 6 | 32 |
| P78417 | Glutathione S-transferase omega-1 | GSTO1 | *Homo sapiens* | 95.20 | 19.92 | 4 | 32 |
| P00325 | Alcohol dehydrogenase 1B | ADH1B | *Homo sapiens* | 125.69 | 20.00 | 7 | 31 |
| P62244 | 40S ribosomal protein S15a | RPS15A | *Homo sapiens* | 122.31 | 24.62 | 3 | 31 |
| P47756 | F-actin-capping protein subunit beta | CAPZB | *Homo sapiens* | 117.28 | 20.22 | 4 | 31 |
| P42785 | Lysosomal Pro-X carboxypeptidase | PRCP | *Homo sapiens* | 110.84 | 9.48 | 3 | 31 |
| Q14103 | Heterogeneous nuclear ribonucleoprotein D0 | HNRNPD | *Homo sapiens* | 94.78 | 13.52 | 4 | 31 |
| Q01129 | Decorin | DCN | *Rattus norvegicus* | 90.56 | 11.86 | 4 | 31 |
| P14866 | Heterogeneous nuclear ribonucleoprotein L | HNRNPL | *Homo sapiens* | 162.20 | 13.07 | 3 | 30 |
| P06748 | Nucleophosmin | NPM1 | *Homo sapiens* | 125.44 | 21.77 | 5 | 30 |
| O60506 | Heterogeneous nuclear ribonucleoprotein Q | SYNCRIP | *Homo sapiens* | 112.80 | 14.77 | 6 | 30 |
| Q96QK1 | Vacuolar protein sorting-associated protein 35 | VPS35 | *Homo sapiens* | 100.86 | 9.55 | 6 | 30 |
| O00231 | 26S proteasome non-ATPase regulatory subunit 11 | PSMD11 | *Homo sapiens* | 95.64 | 8.77 | 3 | 30 |
| O14979 | Heterogeneous nuclear ribonucleoprotein D-like | HNRNPDL | *Homo sapiens* | 94.56 | 9.76 | 3 | 30 |
| Q8WUM4 | Programmed cell death 6-interacting protein | PDCD6IP | *Homo sapiens* | 92.50 | 5.88 | 4 | 30 |
| P59998 | Actin-related protein 2/3 complex subunit 4 | ARPC4 | *Homo sapiens* | 84.05 | 27.98 | 5 | 30 |
| Q9H4M9 | EH domain-containing protein 1 | EHD1 | *Homo sapiens* | 129.70 | 14.42 | 5 | 29 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P01033 | Metalloproteinase inhibitor 1 | TIMP1 | *Homo sapiens* | 127.55 | 22.22 | 3 | 29 |
| P28066 | Proteasome subunit alpha type-5 | PSMA5 | *Homo sapiens* | 117.57 | 35.27 | 5 | 29 |
| Q07960 | Rho GTPase-activating protein 1 | ARHGAP1 | *Homo sapiens* | 111.12 | 14.35 | 4 | 29 |
| P02765 | Alpha-2-HS-glycoprotein | AHSG | *Homo sapiens* | 111.09 | 7.08 | 4 | 29 |
| P10155 | 60 kDa SS-A/Ro ribonucleoprotein | TROVE2 | *Homo sapiens* | 101.48 | 4.46 | 2 | 29 |
| P21399 | Cytoplasmic aconitate hydratase | ACO1 | *Homo sapiens* | 92.08 | 9.67 | 6 | 29 |
| P83731 | 60S ribosomal protein L24 | RPL24 | *Homo sapiens* | 90.95 | 20.38 | 3 | 29 |
| O00571 | ATP-dependent RNA helicase DDX3X | DDX3X | *Homo sapiens* | 90.65 | 10.12 | 5 | 29 |
| P35232 | Prohibitin | PHB | *Homo sapiens* | 85.95 | 20.96 | 5 | 29 |
| P46781 | 40S ribosomal protein S9 | RPS9 | *Homo sapiens* | 79.12 | 25.77 | 6 | 29 |
| P62829 | 60S ribosomal protein L23 | RPL23 | *Homo sapiens* | 125.59 | 25.00 | 2 | 28 |
| P25398 | 40S ribosomal protein S12 | RPS12 | *Homo sapiens* | 123.76 | 31.82 | 3 | 28 |
| Q08211 | ATP-dependent RNA helicase A | DHX9 | *Homo sapiens* | 119.13 | 4.65 | 4 | 28 |
| Q16181 | Septin-7 | 41889 | *Homo sapiens* | 111.98 | 18.76 | 6 | 28 |
| P62333 | 26S protease regulatory subunit 10B | PSMC6 | *Homo sapiens* | 103.91 | 14.91 | 4 | 28 |
| P13010 | X-ray repair cross-complementing protein 5 | XRCC5 | *Homo sapiens* | 101.49 | 10.66 | 5 | 28 |
| Q13492 | Phosphatidylinositol-binding clathrin assembly protein | PICALM | *Homo sapiens* | 100.88 | 4.91 | 2 | 28 |
| P35606 | Coatomer subunit beta | COPB2 | *Homo sapiens* | 93.08 | 9.05 | 6 | 28 |
| P07996 | Thrombospondin-1 | THBS1 | *Homo sapiens* | 82.64 | 3.25 | 3 | 28 |
| P29373 | Cellular retinoic acid-binding protein 2 | CRABP2 | *Homo sapiens* | 124.05 | 24.64 | 3 | 27 |
| Q00341 | Vigilin | HDLBP | *Homo sapiens* | 109.99 | 4.89 | 4 | 27 |
| P54709 | Sodium/potassium-transporting ATPase subunit beta-3 | ATP1B3 | *Homo sapiens* | 101.67 | 17.20 | 3 | 27 |
| P49257 | Protein ERGIC-53 | LMAN1 | *Homo sapiens* | 98.91 | 14.51 | 3 | 27 |
| Q06323 | Proteasome activator complex subunit 1 | PSME1 | *Homo sapiens* | 95.33 | 30.52 | 8 | 27 |
| P61313 | 60S ribosomal protein L15 | RPL15 | *Homo sapiens* | 89.98 | 12.75 | 2 | 27 |
| P35268 | 60S ribosomal protein L22 | RPL22 | *Homo sapiens* | 82.39 | 18.75 | 2 | 27 |
| Q96HE7 | ERO1-like protein alpha | ERO1L | *Homo sapiens* | 113.81 | 13.25 | 4 | 26 |
| P28838 | Cytosol aminopeptidase | LAP3 | *Homo sapiens* | 110.86 | 12.33 | 4 | 26 |
| Q9NVA2 | Septin-11 | 41893 | *Homo sapiens* | 78.83 | 8.86 | 3 | 26 |
| P20700 | Lamin-B1 | LMNB1 | *Homo sapiens* | 74.71 | 10.24 | 6 | 26 |
| P51636 | Caveolin-2 | CAV2 | *Homo sapiens* | 111.42 | 29.63 | 3 | 25 |
| P60866 | 40S ribosomal protein S20 | RPS20 | *Homo sapiens* | 101.62 | 19.33 | 2 | 25 |
| O14818 | Proteasome subunit alpha type-7 | PSMA7 | *Homo sapiens* | 98.96 | 20.56 | 3 | 25 |
| Q9UBI6 | Guanine nucleotide-binding protein G(I)/G(S)/G(O) subunit gamma-12 | GNG12 | *Homo sapiens* | 97.88 | 31.94 | 2 | 25 |
| P13647 | Keratin, type II cytoskeletal 5 | KRT5 | *Homo sapiens* | 86.02 | 13.90 | 8 | 25 |
| O75915 | PRA1 family protein 3 | ARL6IP5 | *Homo sapiens* | 84.77 | 15.96 | 2 | 25 |
| Q9Y2Q3 | Glutathione S-transferase kappa 1 | GSTK1 | *Homo sapiens* | 82.98 | 28.76 | 5 | 25 |
| P62750 | 60S ribosomal protein L23a | RPL23A | *Homo sapiens* | 78.51 | 15.38 | 2 | 25 |
| P46776 | 60S ribosomal protein L27a | RPL27A | *Homo sapiens* | 74.00 | 14.19 | 2 | 25 |
| Q92743 | Serine protease HTRA1 | HTRA1 | *Homo sapiens* | 73.77 | 8.75 | 4 | 25 |
| P17987 | T-complex protein 1 subunit alpha | TCP1 | *Homo sapiens* | 73.10 | 6.29 | 3 | 25 |
| P30048 | Thioredoxin-dependent peroxide reductase, mitochondrial | PRDX3 | *Homo sapiens* | 121.36 | 23.44 | 3 | 24 |
| P62263 | 40S ribosomal protein S14 | RPS14 | *Homo sapiens* | 102.96 | 27.81 | 3 | 24 |
| P07814 | Bifunctional glutamate/proline--tRNA ligase | EPRS | *Homo sapiens* | 96.07 | 4.30 | 4 | 24 |
| P60953 | Cell division control protein 42 homolog | CDC42 | *Homo sapiens* | 91.80 | 20.42 | 3 | 24 |
| P51688 | N-sulphoglucosamine sulphohydrolase | SGSH | *Homo sapiens* | 90.99 | 8.37 | 3 | 24 |
| Q13765 | Nascent polypeptide-associated complex subunit alpha | NACA | *Homo sapiens* | 90.13 | 12.56 | 2 | 24 |
| P01893 | Putative HLA class I histocompatibility antigen, alpha chain H | HLA-H | *Homo sapiens* | 89.43 | 18.23 | 4 | 24 |
| P52272 | Heterogeneous nuclear ribonucleoprotein M | HNRNPM | *Homo sapiens* | 83.38 | 9.73 | 5 | 24 |
| P54920 | Alpha-soluble NSF attachment protein | NAPA | *Homo sapiens* | 81.50 | 22.37 | 5 | 24 |
| P26373 | 60S ribosomal protein L13 | RPL13 | *Homo sapiens* | 80.65 | 10.90 | 2 | 24 |
| P26447 | Protein S100-A4 | S100A4 | *Homo sapiens* | 72.92 | 28.71 | 4 | 24 |
| P39060 | Collagen alpha-1(XVIII) chain [Cleaved into: Endostatin] | COL18A1 | *Homo sapiens* | 72.74 | 3.93 | 3 | 24 |
| P78539 | Sushi repeat-containing protein SRPX | SRPX | *Homo sapiens* | 72.54 | 7.76 | 3 | 24 |
| Q9UHD8 | Septin-9 | 41891 | *Homo sapiens* | 70.31 | 10.07 | 4 | 24 |
| P46926 | Glucosamine-6-phosphate isomerase 1 | GNPDA1 | *Homo sapiens* | 70.28 | 14.19 | 3 | 24 |
| P61160 | Actin-related protein 2 | ACTR2 | *Homo sapiens* | 70.14 | 17.26 | 5 | 24 |
| Q15185 | Prostaglandin E synthase 3 | PTGES3 | *Homo sapiens* | 117.88 | 26.25 | 3 | 23 |
| O95373 | Importin-7 | IPO7 | *Homo sapiens* | 104.71 | 4.53 | 3 | 23 |
| Q16881 | Thioredoxin reductase 1, cytoplasmic | TXNRD1 | *Homo sapiens* | 90.34 | 8.17 | 3 | 23 |
| P10620 | Microsomal glutathione S-tansferase 1 | MGST1 | *Homo sapiens* | 87.69 | 27.10 | 3 | 23 |
| Q13200 | 26S proteasome non-ATPase regulatory subunit 2 | PSMD2 | *Homo sapiens* | 78.79 | 10.24 | 6 | 23 |

TABLE 1-continued

Lists of proteins identified in LC-MS/MS analysis of scaffold only, VFF in
scaffold, VFE on scaffold, engineered VF mucosa and native VF mucosa. Identifications
were based on a 1% false discovery rate. The scaffold was sourced from *Rattus norvegicus*;
VFF, VFE and native VF mucosa were sourced from *Homo sapiens*. Proteins are listed in order
of descending peptide spectra matches.

| UniProt accession number | Protein name | Gene symbol | Organism | Score | Sequence coverage (%) | Unique peptides | Peptide spectra matches |
|---|---|---|---|---|---|---|---|
| Q9H8H3 | Methyltransferase-like protein 7A | METTL7A | *Homo sapiens* | 77.76 | 12.30 | 2 | 23 |
| P55795 | Heterogeneous nuclear ribonucleoprotein H2 | HNRNPH2 | *Homo sapiens* | 76.64 | 10.47 | 3 | 23 |
| Q05682 | Caldesmon | CALD1 | *Homo sapiens* | 76.04 | 3.66 | 3 | 23 |
| P00966 | Argininosuccinate synthase | ASS1 | *Homo sapiens* | 71.74 | 10.19 | 3 | 23 |
| P51148 | Ras-related protein Rab-5C | RAB5C | *Homo sapiens* | 68.22 | 23.15 | 4 | 23 |
| O75390 | Citrate synthase, mitochondrial | CS | *Homo sapiens* | 67.17 | 10.09 | 4 | 23 |
| Q99829 | Copine-1 | CPNE1 | *Homo sapiens* | 66.73 | 4.66 | 2 | 23 |
| Q92499 | ATP-dependent RNA helicase DDX1 | DDX1 | *Homo sapiens* | 112.53 | 7.43 | 3 | 22 |
| Q08431 | Lactadherin | MFGE8 | *Homo sapiens* | 106.96 | 8.53 | 2 | 22 |
| Q15121 | Astrocytic phosphoprotein PEA-15 | PEA15 | *Homo sapiens* | 105.97 | 36.92 | 4 | 22 |
| Q15181 | Inorganic pyrophosphatase | PPA1 | *Homo sapiens* | 96.51 | 17.65 | 4 | 22 |
| Q99623 | Prohibitin-2 | PHB2 | *Homo sapiens* | 91.02 | 21.07 | 5 | 22 |
| P62280 | 40S ribosomal protein S11 | RPS11 | *Homo sapiens* | 89.31 | 24.68 | 3 | 22 |
| P04216 | Thy-1 membrane glycoprotein | THY1 | *Homo sapiens* | 84.64 | 15.53 | 2 | 22 |
| P06703 | Protein S100-A6 | S100A6 | *Homo sapiens* | 84.38 | 37.78 | 3 | 22 |
| P12955 | Xaa-Pro dipeptidase | PEPD | *Homo sapiens* | 80.36 | 8.32 | 3 | 22 |
| Q04760 | Lactoylglutathione lyase | GLO1 | *Homo sapiens* | 70.31 | 14.67 | 2 | 22 |
| Q6NHP8 | Putative phospholipase B-like 2 | PLBD2 | *Homo sapiens* | 69.68 | 8.49 | 4 | 22 |
| P84103 | Serine/arginine-rich splicing factor 3 | SRSF3 | *Homo sapiens* | 69.34 | 14.02 | 2 | 22 |
| P27635 | 60S ribosomal protein L10 | RPL10 | *Homo sapiens* | 69.17 | 11.21 | 2 | 22 |
| Q14152 | Eukaryotic translation initiation factor 3 subunit A | EIF3A | *Homo sapiens* | 66.86 | 5.57 | 6 | 22 |
| P61088 | Ubiquitin-conjugating enzyme E2 N | UBE2N | *Homo sapiens* | 63.81 | 34.87 | 4 | 22 |
| P62318 | Small nuclear ribonucleoprotein Sm D3 | SNRPD3 | *Homo sapiens* | 62.37 | 15.08 | 2 | 22 |
| Q99460 | 26S proteasome non-ATPase regulatory subunit 1 | PSMD1 | *Homo sapiens* | 120.05 | 6.72 | 4 | 21 |
| P23142 | Fibulin-1 | FBLN1 | *Homo sapiens* | 84.86 | 13.23 | 4 | 21 |
| P68402 | Platelet-activating factor acetylhydrolase IB subunit beta | PAFAH1B2 | *Homo sapiens* | 83.14 | 12.23 | 2 | 21 |
| P10619 | Lysosomal protective protein | CTSA | *Homo sapiens* | 82.10 | 5.00 | 2 | 21 |
| P31943 | Heterogeneous nuclear ribouncleoprotein H | HNRNPH1 | *Homo sapiens* | 80.87 | 7.57 | 2 | 21 |
| P24752 | Acetyl-CoA acetyltransferase, mitochondrial | ACAT1 | *Homo sapiens* | 78.01 | 9.84 | 3 | 21 |
| P51571 | Translocon-associated protein subunits delta | SSR4 | *Homo sapiens* | 74.54 | 24.86 | 3 | 21 |
| Q15836 | Vesicle-associated membrane protein 3 | VAMP3 | *Homo sapiens* | 72.83 | 33.00 | 2 | 21 |
| Q14847 | LIM and SH3 domain protein 1 | LASP1 | *Homo sapiens* | 67.61 | 17.62 | 4 | 21 |
| Q99584 | Protein S100-A13 | S100A13 | *Homo sapiens* | 65.57 | 23.47 | 2 | 21 |
| Q9Y277 | Voltage-dependent anion-selective channel protein 3 | VDAC3 | *Homo sapiens* | 62.19 | 12.01 | 3 | 21 |
| P13797 | Plastin-3 | PLS3 | *Homo sapiens* | 62.18 | 14.76 | 7 | 21 |
| P02533 | Keratin, type I cytoskeletal 14 | KRT14 | *Homo sapiens* | 61.78 | 16.74 | 7 | 21 |
| P60981 | Destrin | DSTN | *Homo sapiens* | 60.55 | 20.00 | 3 | 21 |
| Q15417 | Calponin-3 | CNN3 | *Homo sapiens* | 55.43 | 13.98 | 4 | 21 |
| Q9BS26 | Endoplasmic reticulum resident protein 44 | ERP44 | *Homo sapiens* | 112.39 | 11.58 | 3 | 20 |
| O94973 | AP-2 complex subunit alpha-2 | AP2A2 | *Homo sapiens* | 87.35 | 7.24 | 4 | 20 |
| O14579 | Coatomer subunit epsilon | COPE | *Homo sapiens* | 84.58 | 19.48 | 5 | 20 |
| O14773 | Tripeptidyl-peptidase 1 | TPP1 | *Homo sapiens* | 80.43 | 8.17 | 3 | 20 |
| P13987 | CD59 glycoprotein | CD59 | *Homo sapiens* | 70.28 | 18.75 | 2 | 20 |
| P31937 | 3-hydroxyisobutyrate dehydrogenase, mitochondrial | HIBADH | *Homo sapiens* | 69.39 | 7.14 | 2 | 20 |
| P46778 | 60S ribosomal protein L21 | RPL21 | *Homo sapiens* | 68.85 | 27.50 | 3 | 20 |
| Q16363 | Laminin subunit alpha-4 | LAMA4 | *Homo sapiens* | 66.46 | 2.14 | 3 | 20 |
| P15586 | N-acetylglucosamine-6-sulfatase | GNS | *Homo sapiens* | 60.55 | 6.88 | 3 | 20 |
| P11940 | Polyadenylate-binding protein 1 | PABPC1 | *Homo sapiens* | 54.28 | 7.55 | 4 | 20 |
| P30040 | Endoplasmic reticulum resident protein 29 | ERP29 | *Homo sapiens* | 54.08 | 14.18 | 3 | 20 |
| Q9Y3F4 | Serine-threonine kinase receptor-associated protein | STRAP | *Homo sapiens* | 86.18 | 8.86 | 2 | 19 |
| Q7L2H7 | Eukaryotic translation initiation factor 3 subunit M | EIF3M | *Homo sapiens* | 74.90 | 15.78 | 4 | 19 |
| Q9Y3I0 | tRNA-splicing ligase RtcB homolog | RTCB | *Homo sapiens* | 73.48 | 13.47 | 4 | 19 |
| Q9NVJ2 | ADP-ribosylation factor-like protein 8B | ARL8B | *Homo sapiens* | 72.73 | 19.89 | 2 | 19 |
| P04632 | Calpain small subunit 1 | CAPNS1 | *Homo sapiens* | 72.63 | 16.42 | 3 | 19 |
| P00568 | Adenylate kinase isoenzyme 1 | AK1 | *Homo sapiens* | 68.07 | 31.96 | 4 | 19 |
| P42224 | Signal transducer and activator of transcription 1-alpha/beta | STAT1 | *Homo sapiens* | 67.24 | 9.73 | 5 | 19 |
| Q02878 | 60S ribosomal protein L6 | RPL6 | *Homo sapiens* | 66.73 | 15.63 | 3 | 19 |
| O94979 | Protein transport protein Sec31A | SEC31A | *Homo sapiens* | 58.06 | 3.11 | 3 | 19 |
| P45974 | Ubiquitin carboxyl-terminal hydrolase 5 | USP5 | *Homo sapiens* | 56.52 | 2.68 | 2 | 19 |
| P38159 | RNA-binding motif protein, X chromosome | RBMX | *Homo sapiens* | 54.92 | 8.70 | 3 | 19 |
| Q13557 | Calcium/calmodulin-dependent protein kinase type II subunit delta | CAMK2D | *Homo sapiens* | 51.92 | 11.02 | 4 | 19 |
| P84074 | Neuron-specific calcium-binding protein hippocalcin | HPCA | *Homo sapiens* | 48.64 | 19.69 | 3 | 19 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P40227 | T-complex protein 1 subunit zeta | CCT6A | *Homo sapiens* | 87.47 | 9.23 | 3 | 18 |
| O43242 | 26S proteasome non-ATPase regulatory subunit 3 | PSMD3 | *Homo sapiens* | 79.83 | 7.68 | 3 | 18 |
| P30084 | Enoyl-CoA hydratase, mitochondrial | ECHS1 | *Homo sapiens* | 78.24 | 13.10 | 2 | 18 |
| O00410 | Importin-5 | IPO5 | *Homo sapiens* | 78.12 | 7.66 | 5 | 18 |
| P46777 | 60S ribosomal protein L5 | RPL5 | *Homo sapiens* | 71.13 | 23.91 | 5 | 18 |
| Q15008 | 26S proteasome non-ATPase regulatory subunit 6 | PSMD6 | *Homo sapiens* | 69.46 | 7.20 | 2 | 18 |
| O15511 | Actin-related protein 2/3 complex subunit 5 | ARPC5 | *Homo sapiens* | 66.82 | 29.14 | 3 | 18 |
| Q15436 | Protein transport protein Sec23A | SEC23A | *Homo sapiens* | 61.38 | 3.53 | 2 | 18 |
| P19623 | Spermidine synthase | SRM | *Homo sapiens* | 59.81 | 21.19 | 4 | 18 |
| Q02809 | Procollagen-lysine, 2-oxoglutarate 5-dioxygenase 1 | PLOD1 | *Homo sapiens* | 58.99 | 5.91 | 3 | 18 |
| P62081 | 40S ribosomal proten S7 | RPS7 | *Homo sapiens* | 58.91 | 17.53 | 2 | 18 |
| P25789 | Proteasome subunit alpha type-4 | PSMA4 | *Homo sapiens* | 47.57 | 13.03 | 2 | 18 |
| Q9UBQ7 | Glyoxylate reductase/hydroxypyruvate reductase | GRHPR | *Homo sapiens* | 84.31 | 17.38 | 3 | 17 |
| P20618 | Proteasome subunit beta type-1 | PSMB1 | *Homo sapiens* | 77.13 | 15.35 | 2 | 17 |
| P21964 | Catechol O-methyltransferase | COMT | *Homo sapiens* | 76.86 | 8.49 | 2 | 17 |
| O15460 | Prolyl 4-hydroxylase subunit alpha-2 | P4HA2 | *Homo sapiens* | 75.70 | 11.03 | 4 | 17 |
| P62191 | 26S protease regulatory subunit 4 | PSMC1 | *Homo sapiens* | 75.48 | 10.91 | 3 | 17 |
| P63167 | Dynein light chain 1, cytoplasmic | DYNLL1 | *Homo sapiens* | 72.59 | 37.08 | 2 | 17 |
| P09429 | High mobility group protein B1 | HMGB1 | *Homo sapiens* | 72.42 | 20.93 | 3 | 17 |
| Q13724 | Mannosyl-oligosaccharide glucosidase | MOGS | *Homo sapiens* | 70.23 | 7.53 | 4 | 17 |
| P19367 | Hexokinase-1 | HK1 | *Homo sapiens* | 64.34 | 8.62 | 6 | 17 |
| P23526 | Adenosylhomocysteinase | AHCY | *Homo sapiens* | 62.16 | 10.65 | 3 | 17 |
| P39023 | 60S ribosomal protein L3 | RPL3 | *Homo sapiens* | 58.60 | 17.87 | 5 | 17 |
| P10301 | Ras-related protein R-Ras | RRAS | *Homo sapiens* | 55.83 | 12.84 | 2 | 17 |
| Q96CW1 | AP-2 complex sabunit mu | AP2M1 | *Homo sapiens* | 55.49 | 12.87 | 4 | 17 |
| P61353 | 60S ribosomal protein L27 | RPL27 | *Homo sapiens* | 54.78 | 27.94 | 3 | 17 |
| P11279 | Lysosome-associated membrane glycoprotein 1 | LAMP1 | *Homo sapiens* | 54.76 | 6.63 | 3 | 17 |
| Q14258 | E3 ubiquitin/ISG15 ligase TRIM25 | TRIM25 | *Homo sapiens* | 53.67 | 3.81 | 2 | 17 |
| P62266 | 40S ribosomal protein S23 | RPS23 | *Homo sapiens* | 53.61 | 13.99 | 2 | 17 |
| P22695 | Cytochrome b-c1 complex subunit 2, mitochondrial | UQCRC2 | *Homo sapiens* | 67.34 | 13.91 | 4 | 16 |
| P36543 | V-type proton ATPase subunit E1 | ATP6V1E1 | *Homo sapiens* | 65.25 | 6.19 | 2 | 16 |
| P61604 | 10 kDa heat shock protein, mitochondrial | HSPE1 | *Homo sapiens* | 58.13 | 33.33 | 3 | 16 |
| P40261 | Nicotinamide N-methyltransferase | NNMT | *Homo sapiens* | 57.15 | 18.18 | 3 | 16 |
| Q63ZY3 | KN motif and ankyrin repeat domain-containing protein 2 | KANK2 | *Homo sapiens* | 56.52 | 4.70 | 3 | 16 |
| P21266 | Glutathione S-transferase Mu 3 | GSTM3 | *Homo sapiens* | 53.50 | 20.44 | 4 | 16 |
| O15260 | Surfeit locus protein 4 | SURF4 | *Homo sapiens* | 53.47 | 8.55 | 2 | 16 |
| P05455 | Lupus La protein | SSB | *Homo sapiens* | 50.85 | 12.99 | 4 | 16 |
| O15144 | Actin-related protein 2/3 complex subunit 2 | ARPC2 | *Homo sapiens* | 50.68 | 12.67 | 4 | 16 |
| Q6NUM9 | All-trans-retinol 13,14-reductase | RETSAT | *Homo sapiens* | 49.04 | 4.92 | 2 | 16 |
| O43143 | Putative pre-mRNA-splicing factor ATP-dependent RNA helicase DHX15 | DHX15 | *Homo sapiens* | 47.67 | 2.89 | 2 | 16 |
| Q9Y3U8 | 60S ribosomal protein L36 | RPL36 | *Homo sapiens* | 47.12 | 30.48 | 4 | 16 |
| P42677 | 40S ribosomal protein S27 | RPS27 | *Homo sapiens* | 46.35 | 25.00 | 2 | 16 |
| P26640 | Valine-tRNA ligase | VARS | *Homo sapiens* | 44.08 | 3.64 | 4 | 16 |
| P26908 | Collagen alpha-1(V) chain | COL5A1 | *Homo sapiens* | 17.63 | 3.10 | 3 | 16 |
| P35613 | Basigin | BSG | *Homo sapiens* | 47.61 | 8.31 | 2 | 15 |
| P07711 | Cathepsin L1 | CTSL | *Homo sapiens* | 46.98 | 8.41 | 2 | 15 |
| O94905 | Erlin-2 | ERLIN2 | *Homo sapiens* | 45.32 | 10.91 | 3 | 15 |
| P31948 | Stress-induced-phosphoprotein 1 | STIP1 | *Homo sapiens* | 41.60 | 9.39 | 4 | 15 |
| P13473 | Lysosome-associated membrane glycoprotein 2 | LAMP2 | *Homo sapiens* | 41.41 | 7.07 | 3 | 15 |
| P61970 | Nuclear transport factor 2 | NUTF2 | *Homo sapiens* | 67.00 | 33.86 | 2 | 14 |
| P46439 | Glutathione S-transferase Mu 5 | GSTM5 | *Homo sapiens* | 65.44 | 11.93 | 2 | 14 |
| Q8IWE2 | Protein NOXP20 | FAM114A1 | *Homo sapiens* | 63.09 | 5.68 | 2 | 14 |
| Q92597 | Protein NDRG1 | NDRG1 | *Homo sapiens* | 61.64 | 8.88 | 2 | 14 |
| O75533 | Splicing factor 3B subunit 1 | SF3B1 | *Homo sapiens* | 60.00 | 2.45 | 2 | 14 |
| O75368 | SH3 domain-binding glutamic acid-rich-like protein | SH3BGRL | *Homo sapiens* | 53.79 | 37.72 | 3 | 14 |
| P23246 | Splicing factor, proline- and glutamine-rich | SFPQ | *Homo sapiens* | 52.82 | 9.05 | 5 | 14 |
| Q08380 | Galectin-3-binding protein | LGALS3BP | *Homo sapiens* | 51.25 | 7.52 | 3 | 14 |
| O60763 | General vesicular transport factor p115 | USO1 | *Homo sapiens* | 48.56 | 3.85 | 3 | 14 |
| P46977 | Dolichyl-diphosphooligosaccharide--protein glycosyltransferase subunit STT3A | STT3A | *Homo sapiens* | 47.82 | 5.25 | 3 | 14 |
| Q15075 | Early endosome antigen 1 | EEA1 | *Homo sapiens* | 47.08 | 3.97 | 4 | 14 |
| O95816 | BAG family molecular chaperone regulator 2 | BAG2 | *Homo sapiens* | 47.06 | 13.27 | 2 | 14 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| Q9NR45 | Sialic acid synthase | NANS | *Homo sapiens* | 46.21 | 15.88 | 3 | 14 |
| P51858 | Hepatoma-derived growth factor | HDGF | *Homo sapiens* | 45.76 | 14.17 | 3 | 14 |
| P00505 | Aspartate aminotransferase, mitochondrial | GOT2 | *Homo sapiens* | 45.71 | 14.42 | 5 | 14 |
| Q01105 | Protein SET | SET | *Homo sapiens* | 45.04 | 12.07 | 3 | 14 |
| P61019 | Ras-related protein Rab-2A | RAB2A | *Homo sapiens* | 42.23 | 10.85 | 2 | 14 |
| P19404 | NADH dehydrogenase [ubiquinone] flavoprotein 2, mitochondrial | NDUFV2 | *Homo sapiens* | 41.82 | 9.24 | 2 | 14 |
| P55884 | Eukaryotic translation initiation factor 3 subunit B | EIF3B | *Homo sapiens* | 40.54 | 5.90 | 4 | 14 |
| Q13425 | Beta-2-syntrophin | SNTB2 | *Homo sapiens* | 39.75 | 3.89 | 2 | 14 |
| P54136 | Arginine--tRNA ligase, cytoplasmic | RARS | *Homo sapiens* | 38.18 | 6.97 | 4 | 14 |
| P49773 | Histidine triad nucleotide-binding protein 1 | HINT1 | *Homo sapiens* | 83.21 | 34.92 | 2 | 13 |
| P27695 | DNA-(apurinic or apyrimidinic site) lyase | APEX1 | *Homo sapiens* | 63.88 | 22.96 | 4 | 13 |
| Q53GQ0 | Estradiol 17-beta-dehydrogenase 12 | HSD17B12 | *Homo sapiens* | 54.92 | 9.62 | 2 | 13 |
| Q5T9L3 | Protein wntless homolog | WLS | *Homo sapiens* | 54.68 | 8.13 | 3 | 13 |
| O14880 | Microsomal glutathione S-transferase 3 | MGST3 | *Homo sapiens* | 54.48 | 23.03 | 2 | 13 |
| P07954 | Fumarate hydratase, mitochondrial | FH | *Homo sapiens* | 53.05 | 7.45 | 2 | 13 |
| Q8IZP2 | Putative protein FAM10A4 | ST13P4 | *Homo sapiens* | 51.61 | 17.08 | 3 | 13 |
| O75131 | Copine-3 | CPNE3 | *Homo sapiens* | 50.89 | 10.80 | 3 | 13 |
| P14854 | Cytochrome c oxidase subunit 6B1 | COX6B1 | *Homo sapiens* | 50.34 | 33.72 | 2 | 13 |
| Q9UIJ7 | GTP:AMP phosphotransferase AK3, mitochondrial | AK3 | *Homo sapiens* | 50.04 | 12.78 | 2 | 13 |
| P23381 | Tryptophan-tRNA ligase, cytoplasmic | WARS | *Homo sapiens* | 50.02 | 5.73 | 2 | 13 |
| Q12906 | Interleukin enhancer-binding factor 3 | ILF3 | *Homo sapiens* | 49.53 | 12.53 | 7 | 13 |
| P27487 | Dipeptidyl peptidase 4 | DPP4 | *Homo sapiens* | 48.49 | 6.66 | 4 | 13 |
| Q9BWD1 | Acetyl-CoA acetyltransferase, cylosolic | ACAT2 | *Homo sapiens* | 47.57 | 14.61 | 3 | 13 |
| P43243 | Matrin-3 | MATR3 | *Homo sapiens* | 46.57 | 6.02 | 3 | 13 |
| P55010 | Eukaryotic translation initiation factor 5 | EIF5 | *Homo sapiens* | 45.49 | 9.98 | 3 | 13 |
| P04179 | Superoxide dismutase [Mn], mitochondrial | SOD2 | *Homo sapiens* | 43.52 | 22.97 | 4 | 13 |
| P62330 | ADP-ribosylation factor 6 | ARF6 | *Homo sapiens* | 40.96 | 24.57 | 3 | 13 |
| P41252 | Isoleucine--tRNA ligase, cytoplasmic | IARS | *Homo sapiens* | 38.88 | 4.75 | 5 | 13 |
| P04062 | Glucosylceramidase | GBA | *Homo sapiens* | 36.15 | 7.09 | 3 | 13 |
| P60900 | Proteasome subunit alpha type-6 | PSMA6 | *Homo sapiens* | 36.13 | 10.16 | 2 | 13 |
| O43491 | Band 4.1-like protein 2 | EPB41L2 | *Homo sapiens* | 51.57 | 6.57 | 4 | 12 |
| P10768 | S-formylglutathione hydrolase | ESD | *Homo sapiens* | 48.41 | 10.64 | 2 | 12 |
| P36957 | Dihydrolipoyllysine-residue succinyltransferase component of 2-oxoglutarate dehydrogenase complex, mitochondrial | DLST | *Homo sapiens* | 46.29 | 7.73 | 2 | 12 |
| P61254 | 60S ribosomal protein L26 | RPL26 | *Homo sapiens* | 39.66 | 12.41 | 2 | 12 |
| O15145 | Actin-related protein 2/3 complex subunit 3 | ARPC3 | *Homo sapiens* | 39.11 | 13.48 | 2 | 12 |
| P08195 | 4F2 cell-surface antigen heavy chain | SLC3A42 | *Homo sapiens* | 38.01 | 4.13 | 2 | 12 |
| Q9UKK3 | Poly [ADP-ribose] polymerase 4 | PARP4 | *Homo sapiens* | 37.80 | 1.68 | 2 | 12 |
| Q03252 | Lamin-B2 | LMNB2 | *Homo sapiens* | 35.36 | 7.83 | 5 | 12 |
| O95747 | Serine/threonine-protein kinase OSR1 | OXSR1 | *Homo sapiens* | 35.02 | 4.93 | 2 | 12 |
| P39656 | Dolichyl-diphosphooligosaccharide--protein glycosyltransferase 48 kDa subunit | DDOST | *Homo sapiens* | 33.93 | 12.28 | 5 | 12 |
| P78344 | Eukaryotic translation initiation factor 4 gamma 2 | EIF4G2 | *Homo sapiens* | 31.94 | 2.32 | 2 | 12 |
| Q6IBS0 | Twinfilin-2 | TWF2 | *Homo sapiens* | 46.21 | 15.19 | 3 | 11 |
| P22087 | rRNA 2'-O-methyltransferase fibrillarin | FBL | *Homo sapiens* | 45.97 | 9.35 | 2 | 11 |
| Q96KP4 | Cytosolic non-specific dipeptidase | CNDP2 | *Homo sapiens* | 44.17 | 6.74 | 2 | 11 |
| P09622 | Dihydrolipoyl dehydrogenase, mitochondrial | DLD | *Homo sapiens* | 42.94 | 6.48 | 2 | 11 |
| Q99798 | Aconitate hydratase, mitochondrial | ACO2 | *Homo sapiens* | 42.91 | 7.18 | 3 | 11 |
| P04040 | Catalase | CAT | *Homo sapiens* | 42.83 | 11.20 | 4 | 11 |
| Q07666 | KH domain-containing, RNA-binding, signal transduction-associated protein 1 | KHDRBS1 | *Homo sapiens* | 42.69 | 7.67 | 2 | 11 |
| P07942 | Laminin subunit beta-1 | LAMB1 | *Homo sapiens* | 41.56 | 2.07 | 2 | 11 |
| P00390 | Glutathione reductase, mitochondrial | GSR | *Homo sapiens* | 39.02 | 6.32 | 2 | 11 |
| Q9Y371 | Endophilin-B1 | SH3GLB1 | *Homo sapiens* | 38.47 | 6.85 | 2 | 11 |
| P62195 | 26S protease regulatory subunit 8 | PSMC5 | *Homo sapiens* | 37.79 | 12.07 | 3 | 11 |
| Q9BWM7 | Sideroflexin-3 | SFXN3 | *Homo sapiens* | 35.68 | 11.69 | 3 | 11 |
| P00403 | Cytochrome c oxidase subunit 2 | MT-CO2 | *Homo sapiens* | 35.42 | 11.45 | 2 | 11 |
| O43615 | Mitochondrial import inner membrane translocase subunit TIM44 | C3 | *Homo sapiens* | 33.97 | 5.09 | 2 | 11 |
| P30046 | D-dopachrome decarboxylase | TIMM44 | *Homo sapiens* | 33.74 | 19.49 | 2 | 11 |
| Q32P28 | Prolyl 3-hydroxylase 1 | DDT | *Homo sapiens* | 32.20 | 3.40 | 2 | 11 |
| P30740 | Leukocyte elastase inhibitor | LEPRE1 | *Homo sapiens* | 31.82 | 6.60 | 2 | 11 |
| Q9ULV4 | Coronin-1C | SERPINB1 | *Homo sapiens* | 30.15 | 4.85 | 2 | 11 |
| Q60488 | Long-chain-fatty-acid--CoA ligase 4 | CORO1C | *Homo sapiens* | 29.03 | 4.36 | 2 | 11 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P01026 | Complement C3 [Cleaved into: Complement C3 beta chain; Complement C3 alpha chain] | ACSL4 | *Rattus norvegicus* | 34.28 | 1.74 | 2 | 11 |
| Q16643 | Drebrin | DBN1 | *Homo sapiens* | 48.88 | 8.63 | 3 | 10 |
| Q02952 | A-kinase anchor protein 12 | AKAP12 | *Homo sapiens* | 48.74 | 6.51 | 5 | 10 |
| P28161 | Glutathione S-transferase Mu 2 | GSTM2 | *Homo sapiens* | 47.15 | 33.03 | 5 | 10 |
| O75367 | Core histone macro-H2A.1 | H24FY | *Homo sapiens* | 42.46 | 15.59 | 3 | 10 |
| O14980 | Exportin-1 | XPO1 | *Homo sapiens* | 42.26 | 6.35 | 4 | 10 |
| P38606 | V-type proton ATPase catalytic subunit A | ATP6V1A | *Homo sapiens* | 40.66 | 8.91 | 3 | 10 |
| O00151 | PDZ and LIM domain protein 1 | PDLIM1 | *Homo sapiens* | 39.15 | 15.20 | 3 | 10 |
| P14868 | Aspartate--tRNA ligase, cytoplasmic | DARS | *Homo sapiens* | 37.60 | 7.98 | 3 | 10 |
| Q13418 | Integrin-linked protein kinase | ILK | *Homo sapiens* | 37.04 | 9.73 | 3 | 10 |
| Q14195 | Dihydropyrimidinase-related protein 3 | DPYSL3 | *Homo sapiens* | 36.24 | 19.12 | 6 | 10 |
| P49589 | Cysteine-tRNA ligase, cytoplasmic | CARS | *Homo sapiens* | 34.54 | 4.68 | 2 | 10 |
| P18621 | 60S ribosomal protein L17 | RPL17 | *Homo sapiens* | 34.48 | 13.59 | 3 | 10 |
| P06756 | Integrin alpha-V | ITGAV | *Homo sapiens* | 34.31 | 7.35 | 4 | 10 |
| O75351 | Vacuolar protein sorting-associated protein 4B | VPS4B | *Homo sapiens* | 32.55 | 6.98 | 2 | 10 |
| P02786 | Transferrin receptor protein 1 | TFRC | *Homo sapiens* | 31.04 | 2.89 | 2 | 10 |
| Q9NQW7 | Xaa-Pro aminopeptidase 1 | XPNPEP1 | *Homo sapiens* | 30.08 | 4.82 | 2 | 10 |
| Q99961 | Endophilin-A2 | SH3GL1 | *Homo sapiens* | 30.00 | 12.23 | 3 | 10 |
| P34897 | Serine hydroxymethyltransferase, mitochondrial | SHMT2 | *Homo sapiens* | 29.51 | 7.54 | 3 | 10 |
| P06865 | Beta-hexosaminidase subunit alpha | HEXA | *Homo sapiens* | 29.46 | 6.24 | 3 | 10 |
| Q13263 | Transcription intermediary factor 1-beta | TRIM28 | *Homo sapiens* | 26.56 | 5.87 | 3 | 10 |
| Q02543 | 60S ribosomal protein L18a | RPL18A | *Homo sapiens* | 25.80 | 9.66 | 2 | 10 |
| P16401 | Histone H1.5 | HIST1H1B | *Homo sapiens* | 25.79 | 10.18 | 2 | 10 |
| P48643 | T-complex protein 1 subunit epsilon | CCT5 | *Homo sapiens* | 40.56 | 15.71 | 5 | 9 |
| P48147 | Prolyl endopeptidase | PREP | *Homo sapiens* | 36.97 | 5.49 | 2 | 9 |
| P61769 | Beta-2-microglobulin [Cleaved into: Beta-2-microglobulin form pI 5.3] | B2M | *Homo sapiens* | 35.59 | 35.29 | 3 | 9 |
| Q13228 | Selenium-binding protein 1 | SELENBP1 | *Homo sapiens* | 34.80 | 11.65 | 4 | 9 |
| P09960 | Leukotriene A-4 hydrolase | LTA4H | *Homo sapiens* | 34.51 | 6.71 | 3 | 9 |
| Q92882 | Osteoclast-stimulating factor 1 | OSTF1 | *Homo sapiens* | 33.24 | 17.29 | 2 | 9 |
| P43490 | Nicotinamide phosphoribosyltransferase | NAMPT | *Homo sapiens* | 32.14 | 8.35 | 2 | 9 |
| P12268 | Inosine-5'-monophosphate dehydrogenase 2 | IMPDH2 | *Homo sapiens* | 31.91 | 5.84 | 2 | 9 |
| P22102 | Trifunctional purine biosynthetic protein adenosine-3 [Includes: Phosphoribosylamine-glycine ligase] | GART | *Homo sapiens* | 31.74 | 2.67 | 2 | 9 |
| P13804 | Electron transfer flavoprotein subunit alpha, mitochondrial | ETFA | *Homo sapiens* | 29.91 | 13.81 | 3 | 9 |
| P62714 | Serine/threonine-protein phosphatase 2A catalytic subunit beta isoform | PPP2CB | *Homo sapiens* | 29.25 | 16.50 | 3 | 9 |
| P13798 | Acylamino-acid-releasing enzyme | APEH | *Homo sapiens* | 29.20 | 4.78 | 2 | 9 |
| O95336 | 6-phosphogluconolactonase | PGLS | *Homo sapiens* | 29.02 | 17.05 | 3 | 9 |
| Q14112 | Nidogen-2 | NID2 | *Homo sapiens* | 28.75 | 2.76 | 3 | 3 |
| P20073 | Annexin A7 | ANXA7 | *Homo sapiens* | 28.58 | 8.40 | 3 | 9 |
| Q9NZ08 | Endoplasmic reticulum aminopeptidase 1 | ERAP1 | *Homo sapiens* | 27.64 | 4.36 | 3 | 9 |
| Q13561 | Dynactin subunit 2 | DCTN2 | *Homo sapiens* | 27.33 | 8.23 | 2 | 9 |
| Q9UEY8 | Gamma-adducin | ADD3 | *Homo sapiens* | 26.05 | 7.51 | 4 | 9 |
| Q9UHL4 | Dipeptidyl peptidase 2 | DPP7 | *Homo sapiens* | 25.73 | 4.47 | 2 | 9 |
| Q92841 | Probable ATP-dependent RNA helicase DDX17 | DDX17 | *Homo sapiens* | 25.28 | 6.17 | 4 | 9 |
| P62910 | 60S ribosomal protein L32 | RPL32 | *Homo sapiens* | 24.56 | 27.41 | 3 | 9 |
| Q16401 | 26S proteasome non-ATPase regulatory subunit 5 | PSMD5 | *Homo sapiens* | 30.76 | 9.33 | 3 | 8 |
| Q02818 | Nucleobindin-1 | NUCB1 | *Homo sapiens* | 30.34 | 6.29 | 2 | 8 |
| Q9NTK5 | Obg-like ATPase 1 | OLA1 | *Homo sapiens* | 30.03 | 8.33 | 2 | 8 |
| Q9UHG3 | Prenylcysteine oxidase 1 | PCYOX1 | *Homo sapiens* | 29.06 | 7.33 | 2 | 8 |
| P08473 | Neprilysin | MME | *Homo sapiens* | 26.86 | 10.40 | 5 | 8 |
| P84098 | 60S ribosomal protein L19 | RPL19 | *Homo sapiens* | 26.10 | 13.27 | 2 | 8 |
| P19823 | Inter-alpha-trypsin inhibitor heavy chain H2 | ITIH2 | *Homo sapiens* | 25.74 | 2.75 | 2 | 8 |
| P30626 | Sorcin | SRI | *Homo sapiens* | 24.78 | 11.11 | 2 | 8 |
| Q9NYL9 | Tropomodulin-3 | TMOD3 | *Homo sapiens* | 24.64 | 7.10 | 2 | 8 |
| P53999 | Activated RNA polymerase II transcriptional coactivator p15 | SUB1 | *Homo sapiens* | 23.69 | 18.90 | 2 | 8 |
| Q9UJ70 | N-acetyl-D-glucosamine kinase | NAGK | *Homo sapiens* | 23.68 | 11.92 | 3 | 8 |
| P62851 | 40S ribosomal protein S25 | RPS25 | *Homo sapiens* | 23.28 | 16.00 | 2 | 8 |
| P0CW22 | 40S ribosomal protein S17-like | RPS17L | *Homo sapiens* | 23.16 | 15.56 | 2 | 8 |
| P80303 | Nucleobindin-2 | NUCB2 | *Homo sapiens* | 22.85 | 5.95 | 2 | 8 |
| P28845 | Corticosteroid 11-beta-dehydrogenase isozyme 1 | HSD11B1 | *Homo sapiens* | 22.65 | 10.96 | 2 | 8 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| O43237 | Cytoplasmic dynein 1 light intermediate chain 2 | DYNC1LI2 | *Homo sapiens* | 22.33 | 5.08 | 2 | 8 |
| Q9NYU2 | UDP-glucose:glycoprotein glycosyltransferase 1 | UGGT1 | *Homo sapiens* | 22.30 | 3.79 | 4 | 8 |
| Q9Y4L1 | Hypoxia up-regulated protein 1 | HYOU1 | *Homo sapiens* | 20.71 | 2.80 | 2 | 8 |
| P05023 | Sodium/potassium-transporting ATPase subunit alpha-1 | ATP1A1 | *Homo sapiens* | 20.70 | 3.52 | 3 | 8 |
| P54727 | UV excision repair protein RAD23 homolog B | RAD23B | *Homo sapiens* | 30.83 | 7.09 | 2 | 7 |
| O75955 | Flotilin-1 | FLOT1 | *Homo sapiens* | 29.59 | 6.79 | 2 | 7 |
| P49591 | Serine-tRNA ligase, cytoplasmic | SARS | *Homo sapiens* | 29.21 | 11.67 | 3 | 7 |
| P46063 | ATP-dependent DNA helicase Q1 | RECQL | *Homo sapiens* | 28.61 | 5.08 | 2 | 7 |
| P53007 | Tricarboxylate transport protein, mitochondrial | SLC25A1 | *Homo sapiens* | 25.56 | 11.25 | 3 | 7 |
| Q9UQ80 | Proliferation-associated protein 2G4 | PA2G4 | *Homo sapiens* | 25.34 | 8.38 | 2 | 7 |
| O94855 | Protein transport protein Sec24D | SEC24D | *Homo sapiens* | 23.19 | 2.71 | 2 | 7 |
| P05091 | Aldehyde dehydrogenase, mitochondrial | ALDH2 | *Homo sapiens* | 23.16 | 13.73 | 4 | 7 |
| Q15847 | Adipogenesis regulatory factor | ADIRF | *Homo sapiens* | 22.08 | 59.21 | 2 | 7 |
| Q9UM54 | Unconventional myosin-VI | MYO6 | *Homo sapiens* | 21.91 | 2.16 | 2 | 7 |
| P42765 | 3-ketoacyl-CoA thiolase, mitochondrial | ACAA2 | *Homo sapiens* | 21.44 | 7.81 | 2 | 7 |
| Q9NR31 | GTP-binding protein SAR1a | SAR1A | *Homo sapiens* | 21.19 | 21.72 | 3 | 7 |
| P99999 | Cytochrome c | CYCS | *Homo sapiens* | 20.83 | 24.76 | 2 | 7 |
| Q9HC38 | Glyoxalase domain-containing protein 4 | GLOD4 | *Homo sapiens* | 20.63 | 7.35 | 2 | 7 |
| Q99832 | T-complex protein 1 subunit eta | CCT7 | *Homo sapiens* | 20.23 | 4.79 | 2 | 7 |
| Q5SSJ5 | Heterochromatin protein 1-binding protein 3 | HP1BP3 | *Homo sapiens* | 19.85 | 4.70 | 2 | 7 |
| P36405 | ADP-ribosylation factor-like protein 3 | ARL3 | *Homo sapiens* | 19.10 | 12.64 | 2 | 7 |
| P50281 | Matrix metalloproteinase-14 | MMP14 | *Homo sapiens* | 19.03 | 4.12 | 2 | 7 |
| P40429 | 60S ribosomal protein L13a | RPL13A | *Homo sapiens* | 18.87 | 8.87 | 2 | 7 |
| Q13510 | Acid ceramidase | ASAH1 | *Homo sapiens* | 30.44 | 10.13 | 2 | 6 |
| Q99714 | 3-hydroxyacyl-CoA dehydrogenase type-2 | HSD17B10 | *Homo sapiens* | 25.28 | 16.48 | 2 | 6 |
| Q13423 | NAD(P) transhydrogenase, mitochondrial | NNT | *Homo sapiens* | 24.97 | 4.51 | 3 | 6 |
| P29966 | Myristoylated alanine-rich C-kinase substrate | MARCKS | *Homo sapiens* | 24.68 | 25.00 | 3 | 6 |
| O43681 | ATPase ASNA1 | ASNA1 | *Homo sapiens* | 22.72 | 8.91 | 2 | 6 |
| P05198 | Eukaryotic translation initiation factor 2 subunit 1 | EIF2S1 | *Homo sapiens* | 21.96 | 14.92 | 3 | 6 |
| P55036 | 26S proteasome non-ATPase regulatory subunit 4 | PSMD4 | *Homo sapiens* | 21.86 | 11.94 | 3 | 6 |
| P26368 | Splicing factor U2AF 65 kDa subunit | U2AF2 | *Homo sapiens* | 21.60 | 6.11 | 2 | 6 |
| P49189 | 4-trimethylaminobutyraldehyde dehydrogenase | ALDH9A1 | *Homo sapiens* | 20.13 | 5.26 | 2 | 6 |
| P09936 | Ubiquitin carboxyl-terminal hydrolase isozyme L1 | UCHL1 | *Homo sapiens* | 19.71 | 14.35 | 2 | 6 |
| Q02218 | 2-oxoglutarate dehydrogenase, mitochondrial | OGDH | *Homo sapiens* | 19.31 | 5.38 | 4 | 6 |
| Q9UNM6 | 26S proteasome non-ATPase, regulatory subunit 13 | PSMD13 | *Homo sapiens* | 18.66 | 9.57 | 3 | 6 |
| P09110 | 3-ketoacyl-CoA thiolase, peroxisomal | ACAA1 | *Homo sapiens* | 18.52 | 7.78 | 2 | 6 |
| Q9P2J5 | Leucine--tRNA ligase, cytoplasmic | LARS | *Homo sapiens* | 17.83 | 1.79 | 2 | 6 |
| P10515 | Dihydrolipoyllysine-residue acetyltransferase component of pyruvate dehydrogenase complex, mitochondrial | DLAT | *Homo sapiens* | 17.46 | 4.48 | 2 | 6 |
| Q9Y262 | Eukaryotic translation initiation factor 3 subunit L | EIF3L | *Homo sapiens* | 17.30 | 3.55 | 2 | 6 |
| P55735 | Protein SEC13 homolog | SEC13 | *Homo sapiens* | 17.22 | 13.35 | 3 | 6 |
| P25788 | Proteasome subunit alpha type-3 | PSMA3 | *Homo sapiens* | 17.13 | 14.12 | 3 | 6 |
| P32969 | 60S ribosomal protein L9 | RPL9 | *Homo sapiens* | 16.93 | 11.46 | 3 | 6 |
| Q16891 | Mitochondrial inner membrane protein | IMMT | *Homo sapiens* | 16.26 | 4.35 | 2 | 6 |
| Q16531 | DNA damage-binding protein 1 | DDB1 | *Homo sapiens* | 24.08 | 3.07 | 2 | 5 |
| P49419 | Alpha-aminoadipic semialdehyde dehydrogenase | ALDH7A1 | *Homo sapiens* | 19.67 | 5.94 | 2 | 5 |
| P05413 | Fatty acid-binding protein, heart | FABP3 | *Homo sapiens* | 19.47 | 31.58 | 3 | 5 |
| P80723 | Brain acid soluble protein 1 | BASP1 | *Homo sapiens* | 19.41 | 18.50 | 2 | 5 |
| Q92905 | COP9 signalosome complex subunit 5 | COPS5 | *Homo sapiens* | 17.81 | 6.89 | 2 | 5 |
| P54578 | Ubiquitin carboxyl-terminal hydrolase 14 | USP14 | *Homo sapiens* | 16.08 | 5.87 | 2 | 5 |
| Q12884 | Seprase | FAP | *Homo sapiens* | 15.64 | 2.76 | 2 | 5 |
| Q9P0L0 | Vesicle-associated membrane protein-associated protein A | VAPA | *Homo sapiens* | 15.58 | 11.24 | 2 | 5 |
| P10253 | Lysosomal alpha-glucosidase | GAA | *Homo sapiens* | 15.19 | 3.05 | 2 | 5 |
| Q99439 | Calponin-2 | CNN2 | *Homo sapiens* | 15.15 | 12.30 | 3 | 5 |
| Q969H8 | UPF0556 protein C19orf10 | C19ORF10 | *Homo sapiens* | 14.99 | 15.03 | 2 | 5 |
| P00491 | Purine nucleoside phosphorylase | PNP | *Homo sapiens* | 14.91 | 9.69 | 2 | 5 |
| Q9NSE4 | Isoleucine--tRNA ligase, mitochondrial | IARS2 | *Homo sapiens* | 14.69 | 3.16 | 3 | 5 |
| Q09028 | Histone-binding protein RBBP4 | RBBP4 | *Homo sapiens* | 14.18 | 4.94 | 2 | 5 |
| P52630 | Signal transducer and activator of transcription 2 | STAT2 | *Homo sapiens* | 13.75 | 2.82 | 2 | 5 |
| P08648 | Integrin alpha-5 | ITGA5 | *Homo sapiens* | 12.87 | 2.00 | 2 | 5 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
| --- | --- | --- | --- | --- | --- | --- | --- |
| P06454 | Prothymosin alpha [Cleaved into: Prothymosin alpha, N-terminally processed; Thymosin alpha-1] | PTMA | *Homo sapiens* | 12.15 | 20.72 | 2 | 5 |
| P43304 | Glycerol-3-phosphate dehydrogenase, mitochondrial | GPD2 | *Homo sapiens* | 18.91 | 4.81 | 2 | 4 |
| Q9ULZ3 | Apoptosis-associated speck-like protein containing a CARD | PYCARD | *Homo sapiens* | 17.85 | 12.82 | 2 | 4 |
| O00154 | Cytosolic acyl coenzyme A thioester hydrolase | ACOT7 | *Homo sapiens* | 17.76 | 9.47 | 2 | 4 |
| P21291 | Cysteine and glycine-rich protein 1 | CSRP1 | *Homo sapiens* | 16.70 | 20.21 | 2 | 4 |
| P27701 | CD82 antigen | CD82 | *Homo sapiens* | 15.88 | 10.49 | 2 | 4 |
| P11586 | C-1-tetrahydrofolate synthase, cytoplasmic | MTHFD1 | *Homo sapiens* | 15.19 | 5.24 | 3 | 4 |
| Q6IAA8 | Ragulator complex protein LAMTOR1 | LAMTOR1 | *Homo sapiens* | 15.17 | 15.53 | 2 | 4 |
| O15230 | Laminin subunit alpha-5 | LAMA5 | *Homo sapiens* | 14.56 | 0.97 | 2 | 4 |
| Q6P2Q9 | Pre-mRNA-processing-splicing factor 8 | PRPF8 | *Homo sapiens* | 14.44 | 1.24 | 2 | 4 |
| O60437 | Periplakin | PPL | *Homo sapiens* | 14.03 | 3.13 | 3 | 4 |
| Q96FQ6 | Protein S100-A16 | S100A16 | *Homo sapiens* | 13.82 | 22.33 | 2 | 4 |
| O00303 | Eukaryotic translation initiation factor 3 subunit F | EIF3F | *Homo sapiens* | 13.71 | 7.28 | 2 | 4 |
| P43487 | Ran-specific GTPase-activating protein | RANBP1 | *Homo sapiens* | 13.26 | 16.92 | 2 | 4 |
| O00425 | Insulin-like growth factor 2 mRNA-binding protein 3 | IGF2BP3 | *Homo sapiens* | 12.21 | 5.18 | 2 | 4 |
| Q9Y230 | RuvB-like 2 | RUVBL2 | *Homo sapiens* | 12.00 | 9.50 | 3 | 4 |
| P55060 | Exportin-2 | CSE1L | *Homo sapiens* | 11.83 | 3.40 | 2 | 4 |
| P20674 | Cytochrome c oxidase subunit 5A, mitochondrial | COX5A | *Homo sapiens* | 11.58 | 16.00 | 2 | 4 |
| P35611 | Alpha-adducin | ADD1 | *Homo sapiens* | 11.18 | 4.21 | 2 | 4 |
| P10644 | cAMP-dependent protein kinase type I-alpha regulatory subunit | PRKAR1A | *Homo sapiens* | 11.12 | 9.19 | 2 | 4 |
| Q9NUQ9 | Protein FAM49B | FAM49B | *Homo sapiens* | 10.88 | 8.64 | 2 | 4 |
| O95302 | Peptidyl-prolyl cis-trans isomerase FKBP9 | FKBP9 | *Homo sapiens* | 10.34 | 4.56 | 2 | 4 |
| P63220 | 40S ribosomal protein S21 | RPS21 | *Homo sapiens* | 10.11 | 22.89 | 2 | 4 |
| P49720 | Proteasome subunit beta type-3 | PSMB3 | *Homo sapiens* | 12.83 | 15.12 | 2 | 3 |
| P62491 | Ras-related protein Rab-11A | RAB11A | *Homo sapiens* | 12.02 | 11.11 | 2 | 3 |
| Q2TAA2 | Isoamyl acelate-hydrolyzing esterase 1 homolog | IAH1 | *Homo sapiens* | 12.02 | 10.89 | 2 | 3 |
| Q08257 | Quinone oxidoreductase | CRYZ | *Homo sapiens* | 11.77 | 10.64 | 2 | 3 |
| O75694 | Nuclear pore complex protein Nup155 | NUP155 | *Homo sapiens* | 11.59 | 2.23 | 2 | 3 |
| Q14247 | Src substrate cortactin | CTTN | *Homo sapiens* | 10.48 | 4.73 | 2 | 3 |
| Q8IVL6 | Prolyl 3-hydroxylase 3 | LEPREL2 | *Homo sapiens* | 10.19 | 4.21 | 2 | 3 |
| P00492 | Hypoxanthine-guanine phosphoribosyltransferase | HPRT1 | *Homo sapiens* | 9.71 | 10.55 | 2 | 3 |
| Q9P0J0 | NADH dehydrogenase [ubiquinone] 1 alpha subcomplex subunit 13 | NDUFA13 | *Homo sapiens* | 9.66 | 9.72 | 2 | 3 |
| Q86UP2 | Kinectin | KTN1 | *Homo sapiens* | 9.51 | 2.21 | 2 | 3 |
| O75489 | NADH dehydrogenase [ubiquinone] iron-sulfur protein 3, mitochondrial | NDUFS3 | *Homo sapiens* | 9.34 | 15.53 | 3 | 3 |
| Q9UL46 | Proteasome activator complex subunit 2 | PSME2 | *Homo sapiens* | 8.76 | 12.13 | 2 | 3 |
| Q13057 | Bifunctional coenzyme A synthase | COASY | *Homo sapiens* | 8.68 | 4.96 | 2 | 3 |
| P48163 | NADP-dependent malic enzyme | ME1 | *Homo sapiens* | 8.67 | 5.24 | 2 | 3 |
| Q13488 | V-type proton ATPase 116 kDa subunit a isoform 3 | TCIRG1 | *Homo sapiens* | 8.61 | 2.65 | 2 | 3 |
| Q9H845 | Acyl-CoA dehydrogenase family member 9, mitochondrial | ACAD9 | *Homo sapiens* | 8.54 | 4.35 | 2 | 3 |
| P60228 | Eukaryotic translation initiation factor 3 subunit E | EIF3E | *Homo sapiens* | 8.48 | 4.94 | 2 | 3 |
| Q15758 | Neutral amino acid transporter B(0) | SLC1A5 | *Homo sapiens* | 7.94 | 4.44 | 2 | 3 |
| Q96AC1 | Fermitin family homolog 2 | FERMT2 | *Homo sapiens* | 7.61 | 3.82 | 2 | 3 |
| P22234 | Multifunctional protein ADE2 [Includes: Phosphoribosylaminoimidazole-succinocarboxamide synthase] | PAICS | *Homo sapiens* | 7.51 | 6.59 | 2 | 3 |
| P14923 | Junction plakoglobin | JUP | *Homo sapiens* | 9.12 | 3.76 | 2 | 2 |
| Q687X5 | Metalloreductase STEAP4 | STEAP4 | *Homo sapiens* | 8.11 | 7.19 | 2 | 2 |
| P18859 | ATP synthase-coupling factor 6, mitochondrial | ATP5J | *Homo sapiens* | 7.62 | 26.85 | 2 | 2 |
| Q14766 | Latent-transforming growth factor beta-binding protein 1 | LTBP1 | *Homo sapiens* | 7.23 | 1.69 | 2 | 2 |
| Q6YHK3 | CD109 antigen | CD109 | *Homo sapiens* | 7.08 | 1.87 | 2 | 2 |
| O14737 | Programmed cell death protein 5 | PDCD5 | *Homo sapiens* | 6.87 | 19.20 | 2 | 2 |
| Q9Y3B3 | Transmembrane emp24 domain-containing protein 7 | TMED7 | *Homo sapiens* | 6.13 | 11.16 | 2 | 2 |
| Q9Y240 | C-type lectin domain family 11 member A | CLEC11A | *Homo sapiens* | 6.11 | 8.98 | 2 | 2 |
| P48735 | Isocitrate dehydrogenase [NADP] mitochondrial | IDH2 | *Homo sapiens* | 6.06 | 5.97 | 2 | 2 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P42704 | Leucine-rich PPR motif-containing protein, mitochondrial | LRPPRC | *Homo sapiens* | 5.73 | 2.22 | 2 | 2 |
| Q15819 | Ubiquitin-conjugating enzyme E2 variant 2 | UBE2V2 | *Homo sapiens* | 5.19 | 13.79 | 2 | 2 |
| Q9C0C2 | 182 kDa tankyrase-1-binding protein | TNKS1BP1 | *Homo sapiens* | 4.83 | 1.56 | 2 | 2 |
| Native VF mucosa | | | | | | | |
| P02768 | Serum albumin | ALB | *Homo sapiens* | 9377.55 | 78.49 | 52 | 2323 |
| P02452 | Collagen alpha-1(I) chain | COL1A1 | *Homo sapiens* | 1727.89 | 43.65 | 37 | 2130 |
| P12109 | Collagen alpha-1(VI) chain | COL6A1 | *Homo sapiens* | 3245.57 | 49.22 | 34 | 1464 |
| P12111 | Collagen alpha-3(VI) chain | COL6A3 | *Homo sapiens* | 5535.48 | 37.46 | 92 | 1447 |
| P08123 | Collagen alpha-2(I) chain | COL1A2 | *Homo sapiens* | 1753.82 | 37.70 | 31 | 1416 |
| P02461 | Collagen alpha-1(III) chain | COL3A1 | *Homo sapiens* | 1145.04 | 33.77 | 30 | 1365 |
| P13647 | Keratin, type II cytoskeletal 5 | KRT5 | *Homo sapiens* | 4377.87 | 61.36 | 49 | 1272 |
| Q9UKX2 | Myosin-2 | MYH2 | *Homo sapiens* | 5300.08 | 60.79 | 135 | 1228 |
| P35555 | Fibrilin-1 | FBN1 | *Homo sapiens* | 4497.74 | 38.56 | 75 | 1166 |
| P02675 | Fibrinogen beta chain | FGB | *Homo sapiens* | 3486.23 | 70.67 | 30 | 1070 |
| P12882 | Myosin-1 | MYH1 | *Homo sapiens* | 4537.67 | 58.17 | 125 | 1060 |
| P13646 | Keratin, type I cytoskeletal 13 | KRT13 | *Homo sapiens* | 3623.18 | 63.97 | 34 | 1001 |
| P02538 | Keratin, type II cytosketetal 6A | KRT6A | *Homo sapiens* | 3925.12 | 63.48 | 46 | 999 |
| Q09666 | Neuroblast differentiation-associated protein AHNAK | AHNAK | *Homo sapiens* | 3348.49 | 37.64 | 95 | 933 |
| P35579 | Myosin-9 | MYH9 | *Homo sapiens* | 3935.56 | 49.29 | 81 | 909 |
| P22105 | Tenascin-X | TNXB | *Homo sapiens* | 3631.59 | 35.42 | 90 | 902 |
| P04259 | Keratin, type II cytoskeletal 6B | KRT6B | *Homo sapiens* | 3609.25 | 56.91 | 42 | 900 |
| P01024 | Complement C3 | C3 | *Homo sapiens* | 3126.18 | 51.11 | 63 | 763 |
| P02533 | Keratin, type I cytoskeletal 14 | KRT14 | *Homo sapiens* | 2848.68 | 71.19 | 35 | 756 |
| P08727 | Keratin, type I cytoskeletal 19 | KRT19 | *Homo sapiens* | 2653.17 | 84.50 | 36 | 731 |
| P15924 | Desmoplakin | DSP | *Homo sapiens* | 2903.43 | 35.36 | 84 | 725 |
| P60709 | Actin, cytoplasmic 1 | ACTB | *Homo sapiens* | 2698.92 | 64.00 | 18 | 696 |
| Q15149 | Plectin | PLEU | *Homo sapiens* | 2779.52 | 29.76 | 97 | 696 |
| P19013 | Keratin, type II cytoskeletal 4 | KRT4 | *Homo sapiens* | 2651.92 | 62.73 | 35 | 685 |
| P02679 | Fibrinogen gamma chain | FGG | *Homo sapiens* | 2758.21 | 77.04 | 29 | 677 |
| P68133 | Actin, alpha skeletal muscle | ACTA1 | *Homo sapiens* | 2630.03 | 66.84 | 20 | 663 |
| P01023 | Alpha-2-macroglobulin | A2M | *Homo sapiens* | 2609.50 | 51.76 | 51 | 560 |
| P12110 | Collagen alpha-2(VI) chain | COL6A2 | *Homo sapiens* | 1699.58 | 37.49 | 33 | 649 |
| P68032 | Actin, alpha cardiac muscle 1 | ACTC1 | *Homo sapiens* | 2619.50 | 66.84 | 20 | 645 |
| P12883 | Myosin-7 | MYH7 | *Homo sapiens* | 2691.89 | 52.20 | 97 | 637 |
| P02671 | Fibrinogen alpha chain | FGA | *Homo sapiens* | 1988.48 | 41.22 | 32 | 621 |
| P08670 | Vimentin | VIM | *Homo sapiens* | 2279.55 | 71.46 | 37 | 596 |
| Q8WZ42 | Titin | TTN | *Homo sapiens* | 2540.73 | 10.62 | 200 | 584 |
| P02787 | Serotransferrin | TF | *Homo sapiens* | 2398.90 | 63.04 | 39 | 574 |
| P01009 | Alpha-1-antitrypsin | SERPINA1 | *Homo sapiens* | 2181.30 | 58.61 | 27 | 539 |
| Q00610 | Clathrin heavy chain 1 | CLTC | *Homo sapiens* | 2208.17 | 47.34 | 53 | 495 |
| O43707 | Alpha-actinin-4 | ACTN4 | *Homo sapiens* | 2157.22 | 64.54 | 43 | 494 |
| Q01546 | Keratin, type II cytoskeletal 2 oral | KRT76 | *Homo sapiens* | 1104.99 | 14.73 | 12 | 492 |
| P02545 | Prelamin-A/C | LMNA | *Homo sapiens* | 1738.37 | 54.07 | 37 | 473 |
| P19012 | Keratin, type I cytoskeletal 15 | KRT15 | *Homo sapiens* | 1698.59 | 67.32 | 28 | 464 |
| P07355 | Annexin A2 | ANXA2 | *Homo sapiens* | 1886.30 | 67.55 | 24 | 462 |
| P68371 | Tubulin beta-4B chain | TUBB4B | *Homo sapiens* | 2035.19 | 72.58 | 23 | 462 |
| P02751 | Fibronectin | FN1 | *Homo sapiens* | 2046.04 | 41.74 | 58 | 458 |
| P07437 | Tubulin beta chain | TUBB | *Homo sapiens* | 2039.92 | 72.75 | 23 | 455 |
| P00738 | Haploglobin | HP | *Homo sapiens* | 1785.78 | 61.58 | 24 | 453 |
| P01011 | Alpha-1-antichymotrypsin | SERPINA3 | *Homo sapiens* | 1446.96 | 50.35 | 18 | 425 |
| P06576 | ATP synthase subunit beta, mitochondrial | ATP5B | *Homo sapiens* | 1859.52 | 66.16 | 23 | 410 |
| P01857 | Ig gamma-1 chain C region | IGHG1 | *Homo sapiens* | 1887.72 | 50.61 | 12 | 406 |
| P00450 | Ceruloplasmin | CP | *Homo sapiens* | 1918.16 | 46.29 | 29 | 398 |
| P01859 | Ig gamma-2 chain C region | IGHG2 | *Homo sapiens* | 1801.70 | 51.53 | 11 | 392 |
| P51888 | Prolargin | PRELP | *Homo sapiens* | 1226.46 | 47.12 | 15 | 387 |
| P04083 | Annexin A1 | ANXA1 | *Homo sapiens* | 1651.02 | 64.45 | 21 | 382 |
| P04406 | Glyceraldehyde-3-phosphate dehydrogenase | GAPDH | *Homo sapiens* | 1670.21 | 73.73 | 17 | 376 |
| P68363 | Tubulin alpha-1B chain | TUBA1B | *Homo sapiens* | 1568.91 | 66.96 | 18 | 350 |
| Q71U36 | Tubulin alpha-1A chain | TUBA1A | *Homo sapiens* | 1565.01 | 68.96 | 18 | 349 |
| P08779 | Keratin, type I cytoskeletal 16 | KRT16 | *Homo sapiens* | 1255.62 | 52.64 | 25 | 346 |
| Q04695 | Keratin, type I cytoskeletal 17 | KRT17 | *Homo sapiens* | 1278.10 | 79.63 | 32 | 345 |
| P05787 | Keratin, type II cytoskeletal 8 | KRT8 | *Homo sapiens* | 1167.17 | 48.03 | 24 | 342 |
| P21333 | Filamin-A | FLNA | *Homo sapiens* | 1423.87 | 35.17 | 54 | 341 |
| Q13885 | Tubulin beta-2A chain | TUBB2A | *Homo sapiens* | 1387.87 | 56.40 | 16 | 341 |
| Q9BQE3 | Tubulin alpha-1C chain | TUBA1C | *Homo sapiens* | 1498.39 | 69.27 | 18 | 332 |
| P14618 | Pyruvate kinase isozymes M1/M2 | PKM | *Homo sapiens* | 1344.45 | 68.17 | 28 | 328 |
| Q15063 | Periostin | POSTN | *Homo sapiens* | 1387.00 | 43.54 | 25 | 327 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P58107 | Epiplakin | EPPK1 | *Homo sapiens* | 1409.85 | 46.90 | 45 | 321 |
| P07585 | Decorin | DCN | *Homo sapiens* | 1226.95 | 49.30 | 15 | 317 |
| P14923 | Junction plakoglobin | JUP | *Homo sapiens* | 1478.56 | 55.17 | 28 | 314 |
| P35609 | Alpha-actinin-2 | ACTN2 | *Homo sapiens* | 1213.25 | 55.48 | 38 | 305 |
| P20774 | Mimecan | OGN | *Homo sapiens* | 1230.96 | 44.30 | 13 | 301 |
| P21810 | Biglycan | BGN | *Homo sapiens* | 1169.94 | 51.09 | 14 | 293 |
| P12814 | Alpha-actinin-1 | ACTN1 | *Homo sapiens* | 1088.32 | 34.87 | 27 | 291 |
| P00488 | Coagulation factor XIII A chain | F13A1 | *Homo sapiens* | 1224.31 | 40.57 | 21 | 291 |
| P08107 | Heat shock 70 kDa protein 1A/1B | HSPA1A | *Homo sapiens* | 1201.31 | 55.38 | 25 | 291 |
| P01876 | Ig alpha-1 chain C region | IGHA1 | *Homo sapiens* | 1328.87 | 50.42 | 11 | 291 |
| P02788 | Lactotransferrin | LTF | *Homo sapiens* | 1000.06 | 67.61 | 39 | 283 |
| P13639 | Elongation factor 2 | EEF2 | *Homo sapiens* | 998.65 | 37.18 | 24 | 79 |
| Q13813 | Spectrin alpha chain, non-erythrocytic 1 | SPTAN1 | *Homo sapiens* | 1389.63 | 27.71 | 42 | 276 |
| P02647 | Apolipoprotein A-I | APOA1 | *Homo sapiens* | 1111.22 | 70.79 | 22 | 274 |
| P01860 | Ig gamma-3 chain C region | IGHG3 | *Homo sapiens* | 1182.07 | 45.09 | 11 | 273 |
| P11142 | Heat shock cognate 71 kDa protein | HSPA8 | *Homo sapiens* | 1142.75 | 39.16 | 21 | 272 |
| P06899 | Histone H2B type 1-J | HIST1H2BJ | *Homo sapiens* | 740.33 | 40.48 | 5 | 271 |
| P68871 | Hemoglobin subunit beta | HBB | *Homo sapiens* | 1083.28 | 88.44 | 12 | 271 |
| P08758 | Annexin A5 | ANXA5 | *Homo sapiens* | 1003.25 | 56.56 | 17 | 268 |
| P11021 | 78 kDa glucose-regulated protein | HSPA5 | *Homo sapiens* | 958.13 | 39.60 | 22 | 265 |
| Q15582 | Transforming growth factor-beta-induced protein ig-h3 | TGFBI | *Homo sapiens* | 996.01 | 49.19 | 24 | 264 |
| P69905 | Hemoglobin subunit alpha | HBA1; | *Homo sapiens* | 1419.48 | 83.80 | 8 | 262 |
| P08603 | Complement factor H | CFH | *Homo sapiens* | 966.16 | 38.67 | 32 | 257 |
| P46940 | Ras GTPase-activating-like protein IQGAP1 | IQGAP1 | *Homo sapiens* | 1173.73 | 26.55 | 28 | 253 |
| P06732 | Creatine kinase M-type | CKM | *Homo sapiens* | 997.59 | 63.78 | 17 | 252 |
| P02790 | Hemopexin | HPX | *Homo sapiens* | 1318.29 | 50.65 | 14 | 251 |
| P20908 | Collagen alpha-1(V) chain | COL5A1 | *Homo sapiens* | 159.61 | 3.97 | 4 | 248 |
| P01834 | Ig kappa chain C region | IGKC | *Homo sapiens* | 998.31 | 80.19 | 6 | 243 |
| P06396 | Gelsolin | GSN | *Homo sapiens* | 1156.49 | 32.99 | 15 | 241 |
| P06733 | Alpha-enolase | ENO1 | *Homo sapiens* | 813.18 | 60.37 | 18 | 239 |
| Q02388 | Collagen alpha-1(VII) chain | COL7A1 | *Homo sapiens* | 896.99 | 17.87 | 33 | 238 |
| P55083 | Microfibril-associated glycoprotein 4 | MFAP4 | *Homo sapiens* | 1345.67 | 44.71 | 5 | 236 |
| P51884 | Lumican | LUM | *Homo sapiens* | 756.06 | 37.87 | 11 | 235 |
| P02763 | Alpha-1-acid glycoprotein 1 | ORM1 | *Homo sapiens* | 917.03 | 44.78 | 9 | 233 |
| P01861 | Ig gamma-4 chain C region | IGHG4 | *Homo sapiens* | 988.15 | 50.76 | 9 | 231 |
| P10909 | Clusterin | CLU | *Homo sapiens* | 867.40 | 29.18 | 12 | 226 |
| P04075 | Fructose-bisphosphate aldolase A | ALDOA | *Homo sapiens* | 1022.74 | 75.55 | 18 | 225 |
| P00558 | Phosphoglycerate kinase 1 | PGK1 | *Homo sapiens* | 1016.26 | 58.03 | 18 | 222 |
| P55072 | Transitional endoplasmic reticulum ATPase | VCP | *Homo sapiens* | 935.67 | 46.77 | 24 | 221 |
| Q9BXN1 | Asporin | ASPN | *Homo sapiens* | 876.49 | 46.05 | 13 | 220 |
| P25705 | ATP synthase subunit alpha, mitochondrial | ATP5A1 | *Homo sapiens* | 825.16 | 46.84 | 19 | 219 |
| P04004 | Vitronectin | VTN | *Homo sapiens* | 976.05 | 37.24 | 11 | 219 |
| Q01082 | Spectrin beta chain, non-erythrocytic 1 | SPTBN1 | *Homo sapiens* | 1081.58 | 25.34 | 36 | 213 |
| P09493 | Tropomyosin alpha-1 chain | TPM1 | *Homo sapiens* | 776.98 | 55.99 | 23 | 211 |
| P14625 | Endoplasmin | HSP90B1 | *Homo sapiens* | 887.48 | 33.00 | 21 | 209 |
| P13929 | Beta-enolase | ENO3 | *Homo sapiens* | 760.72 | 55.99 | 16 | 206 |
| P98160 | Basement membrane-specific heparan sulfate proteoglycan core protein | HSPG2 | *Homo sapiens* | 872.27 | 17.29 | 41 | 202 |
| P60174 | Triosephosphate isomerase | TPI1 | *Homo sapiens* | 777.86 | 65.73 | 13 | 197 |
| P01877 | Ig alpha-2 chain C region | IGHA2 | *Homo sapiens* | 1024.76 | 48.24 | 9 | 195 |
| P04792 | Heat shock protein beta-1 | HSPB1 | *Homo sapiens* | 872.68 | 76.59 | 12 | 194 |
| P02144 | Myoglobin | MB | *Homo sapiens* | 881.11 | 65.58 | 11 | 192 |
| P16615 | Sarcoplasmic/endoplasmic reticulum calcium ATPase 2 | ATP2A2 | *Homo sapiens* | 728.60 | 32.63 | 23 | 190 |
| P07900 | Heat shock protein HSP 90-alpha | HSP90AA1 | *Homo sapiens* | 744.33 | 30.05 | 18 | 190 |
| P40939 | Trifunctional enzyme subunit alpha, mitochondrial | HADHA | *Homo sapiens* | 857.52 | 40.10 | 17 | 187 |
| P68104 | Elongation factor 1-alpha 1 | EEF1A1 | *Homo sapiens* | 851.60 | 40.04 | 13 | 186 |
| P07951 | Tropomyosin beta chain | TPM2 | *Homo sapiens* | 648.46 | 59.86 | 22 | 186 |
| P12035 | Keratin, type II cytoskeletal 3 | KRT3 | *Homo sapiens* | 641.16 | 16.40 | 14 | 184 |
| P30101 | Protein disulfide-isomerase A3 | PDIA3 | *Homo sapiens* | 913.05 | 47.92 | 19 | 183 |
| P10809 | 60 kDa heat shock protein, mitochondrial | HSPD1 | *Homo sapiens* | 881.81 | 51.66 | 21 | 179 |
| Q9BUF5 | Tubulin beta-6 chain | TUBB6 | *Homo sapiens* | 642.15 | 48.21 | 15 | 178 |
| P23142 | Fibulin-1 | FBLN1 | *Homo sapiens* | 891.96 | 34.85 | 17 | 174 |
| P00338 | L-lactate dehydrogenase A chain | LDHA | *Homo sapiens* | 670.19 | 57.23 | 17 | 171 |
| P04264 | Keratin, type II cytoskeletal 1 | KRT1 | *Homo sapiens* | 591.46 | 24.38 | 16 | 171 |
| Q86VB7 | Scavenger receptor cysteine-rich type 1 protein M130 | CD163 | *Homo sapiens* | 870.30 | 29.84 | 20 | 168 |
| P06753 | Tropomyosin alpha-3 chain | TPM3 | *Homo sapiens* | 616.79 | 60.56 | 25 | 165 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P35749 | Myosin-11 | MYH11 | *Homo sapiens* | 691.99 | 12.12 | 16 | 162 |
| P07237 | Protein disulfide-isomerase | P4HB | *Homo sapiens* | 666.06 | 47.24 | 19 | 162 |
| Q99798 | Aconitate hydratase mitochondrial | ACO2 | *Homo sapiens* | 794.47 | 48.97 | 22 | 161 |
| P08238 | Heat shock protein HSP 90-beta | HSP90AB1 | *Homo sapiens* | 587.99 | 28.31 | 18 | 161 |
| P00387 | NADH-cytochrome b5 reductase 3 | CYB5R3 | *Homo sapiens* | 1074.76 | 57.14 | 9 | 161 |
| P40926 | Malate dehydrogenase, mitochondrial | MDH2 | *Homo sapiens* | 588.03 | 53.55 | 14 | 161 |
| P05976 | Myosin light chain 1/3, skeletal muscle isoform | MYL1 | *Homo sapiens* | 690.54 | 79.90 | 15 | 157 |
| P08133 | Annexin A6 | ANXA6 | *Homo sapiens* | 603.14 | 36.40 | 18 | 156 |
| P62805 | Histone H4 | HIST1H4A | *Homo sapiens* | 530.41 | 53.40 | 8 | 155 |
| Q06830 | Peroxiredoxin-1 | PRDX1 | *Homo sapiens* | 888.30 | 60.80 | 10 | 155 |
| P19652 | Alpha-1-acid glycoprotein 2 | ORM2 | *Homo sapiens* | 616.30 | 39.30 | 6 | 154 |
| P67936 | Tropomyosin alpha-4 chain | TPM4 | *Homo sapiens* | 549.57 | 54.44 | 17 | 151 |
| O60437 | Periplakin | PPL | *Homo sapiens* | 650.26 | 22.38 | 24 | 151 |
| Q9NZN4 | EH domain-containing protein 2 | EHD2 | *Homo sapiens* | 772.61 | 40.15 | 12 | 150 |
| Q14764 | Major vault protein | MVP | *Homo sapiens* | 671.11 | 36.17 | 20 | 150 |
| Q92954 | Proteoglycan 4 | PRG4 | *Homo sapiens* | 569.98 | 7.91 | 9 | 150 |
| P04003 | C4b-binding protein alpha chain | C4BPA | *Homo sapiens* | 657.08 | 43.55 | 16 | 149 |
| P00747 | Plasminogen | PLG | *Homo sapiens* | 713.50 | 41.11 | 18 | 149 |
| P04220 | Ig mu heavy chain disease protein | MUCB | *Homo sapiens* | 773.97 | 38.11 | 9 | 148 |
| O14983 | Sarcoplasmic/endoplasmic reticulum calcium ATPase 1 | ATP2A1 | *Homo sapiens* | 617.91 | 34.07 | 25 | 145 |
| P38646 | Stress-70 protein, mitochondrial | HSPA9 | *Homo sapiens* | 602.67 | 31.81 | 15 | 145 |
| P01871 | Ig mu chain C region | IGHM | *Homo sapiens* | 537.31 | 39.60 | 13 | 142 |
| P00352 | Retinal dehydrogenase 1 | ALDH1A1 | *Homo sapiens* | 638.57 | 46.91 | 14 | 141 |
| P27824 | Calnexin | CANX | *Homo sapiens* | 653.49 | 29.73 | 11 | 141 |
| P00739 | Haptoglobin-related protein | HPR | *Homo sapiens* | 534.40 | 30.17 | 13 | 137 |
| Q16555 | Dihydropyrimidinase-related protein 2 | DPYSL2 | *Homo sapiens* | 566.07 | 42.48 | 15 | 133 |
| P08865 | 40S ribosomal protein SA | RPSA | *Homo sapiens* | 700.13 | 45.42 | 7 | 133 |
| Q7Z7G0 | Target of Nesh-SH3 | ABI3BP | *Homo sapiens* | 519.78 | 22.33 | 15 | 132 |
| P32926 | Desmoglein-3 | DSG3 | *Homo sapiens* | 524.96 | 22.72 | 15 | 131 |
| P54652 | Heat shock-related 70 kDa protein 2 | HSP42 | *Homo sapiens* | 483.73 | 15.34 | 9 | 130 |
| P09525 | Annexin A4 | ANXA4 | *Homo sapiens* | 478.40 | 40.13 | 11 | 128 |
| P02749 | Beta-2-glycoprotein 1 | APOH | *Homo sapiens* | 514.23 | 47.25 | 10 | 128 |
| P11217 | Glycogen phosphorylase, muscle form | PYGM | *Homo sapiens* | 524.04 | 36.94 | 22 | 125 |
| P19823 | Inter-alpha-typsin inhibitor heavy chain H2 | ITIH2 | *Homo sapiens* | 624.95 | 22.09 | 13 | 125 |
| P13645 | Keratin, type I cystoskeletal 10 | KRT10 | *Homo sapiens* | 411.32 | 38.36 | 17 | 124 |
| P68431 | Histone H3.1 | HIST1H3A | *Homo sapiens* | 549.86 | 35.29 | 3 | 123 |
| P62937 | Peptidyl-prolyl cis-trans isomerase A | PPIA | *Homo sapiens* | 496.09 | 54.55 | 7 | 123 |
| P12236 | ADP/ATP translocase 3 | SLC25A6 | *Homo sapiens* | 396.51 | 36.58 | 8 | 121 |
| P27797 | Calreticulin | CALR | *Homo sapiens* | 526.24 | 53.96 | 12 | 121 |
| Q13642 | Four and a half LIM domains protein 1 | FHL1 | *Homo sapiens* | 453.77 | 36.22 | 9 | 121 |
| P12235 | ADP/ATP translocase 1 | SLC25A4 | *Homo sapiens* | 404.10 | 43.62 | 11 | 126 |
| P19105 | Myosin regulatory light chain 12A | MYL12A | *Homo sapiens* | 444.26 | 50.88 | 7 | 120 |
| P04114 | Apolipoprotein B-100 | APOB | *Homo sapiens* | 581.35 | 8.81 | 25 | 120 |
| P0C0L4 | Complement C4-A | C4A | *Homo sapiens* | 525.25 | 21.04 | 20 | 119 |
| P13611 | Versican core protein | VCAN | *Homo sapiens* | 621.17 | 6.63 | 14 | 119 |
| P07339 | Cathepsin D | CTSD | *Homo sapiens* | 425.52 | 30.83 | 10 | 117 |
| P09211 | Glutathione S-transferase P | GSTP1 | *Homo sapiens* | 559.18 | 60.48 | 9 | 116 |
| Q08043 | Alpha-actinin-3 | ACTN3 | *Homo sapiens* | 412.61 | 16.98 | 13 | 116 |
| Q14624 | Inter-alpha-trypsin inhibitor heavy chain H4 | ITIH4 | *Homo sapiens* | 432.28 | 26.45 | 15 | 116 |
| P08729 | Keratin, type II cytoskeletal 7 | KRT7 | *Homo sapiens* | 350.55 | 36.46 | 17 | 116 |
| P63104 | 14-3-3 protein zeta/delta | YWHAZ | *Homo sapiens* | 363.16 | 43.27 | 8 | 115 |
| P06744 | Glucose-6-phosphate isomerase | GPI | *Homo sapiens* | 514.97 | 39.61 | 13 | 115 |
| P02042 | Hemoglobin subunit delta | HBD | *Homo sapiens* | 504.88 | 57.82 | 9 | 114 |
| P07195 | L-lactate dehydrogenase B Chain | LDHB | *Homo sapiens* | 397.81 | 30.54 | 11 | 113 |
| P37802 | Transgelin-2 | TAGLN2 | *Homo sapiens* | 412.88 | 44.22 | 7 | 112 |
| P0CG05 | Ig lambda-2 chain C regions | IGLC2 | *Homo sapiens* | 306.17 | 74.53 | 5 | 112 |
| Q07507 | Dermatopontin | DPT | *Homo sapiens* | 516.65 | 60.70 | 7 | 111 |
| Q14195 | Dihydropyrimidinase-retated protein 3 | DPYSL3 | *Homo sapiens* | 510.80 | 42.63 | 14 | 110 |
| P04844 | Dolichyl-diphosphooligosaccharide-protein glycosyltransferase subunit 2 | RPN2 | *Homo sapiens* | 515.84 | 35.18 | 12 | 108 |
| Q13835 | Plakophilin-1 | PKP1 | *Homo sapiens* | 419.65 | 26.64 | 14 | 107 |
| P04843 | Dolichyl-diphosphooligosaccharide-protein glycosyltransferase subunit 1 | RPN1 | *Homo sapiens* | 511.79 | 35.26 | 14 | 107 |
| P06702 | Protein S100-A9 | S100A9 | *Homo sapiens* | 462.23 | 74.56 | 7 | 107 |
| P08572 | Collagen alpha-2(IV) chain | COL4A2 | *Homo sapiens* | 148.22 | 7.48 | 7 | 105 |
| P61978 | Heterogeneous nuclear ribonucleoprotein K | HNRNPK | *Homo sapiens* | 395.65 | 25.27 | 8 | 101 |
| P05091 | Aldehyde dehydrogenase, mitochondrial | ALDH2 | *Homo sapiens* | 303.86 | 31.14 | 12 | 100 |
| P00367 | Glutamate dehydrogenase 1, mitochondrial | GLUD1 | *Homo sapiens* | 394.06 | 35.48 | 14 | 100 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P30086 | Phosphatidylethanolamine-binding protein 1 | PEBP1 | *Homo sapiens* | 565.01 | 70.59 | 8 | 100 |
| P01008 | Antithrombin-III | SERPINC1 | *Homo sapiens* | 418.47 | 32.54 | 12 | 99 |
| P36578 | 60S ribosomal protein L4 | RPL4 | *Homo sapiens* | 379.47 | 32.55 | 11 | 99 |
| P24844 | Myosin regulatory light polypeptide 9 | MYL9 | *Homo sapiens* | 404.88 | 56.40 | 7 | 98 |
| P02774 | Vitamin D-binding protein | GC | *Homo sapiens* | 425.10 | 29.32 | 10 | 98 |
| P17661 | Desmin | DES | *Homo sapiens* | 352.16 | 41.91 | 19 | 97 |
| P30048 | Thioredoxin-dependent peroxide reductase, mitochondrial | PRDX3 | *Homo sapiens* | 533.07 | 48.05 | 7 | 97 |
| P31949 | Protein S100-A11 | S100A11 | *Homo sapiens* | 439.33 | 71.43 | 6 | 97 |
| P23528 | Cofilin-1 | CFL1 | *Homo sapiens* | 418.44 | 63.25 | 9 | 96 |
| P04217 | Alpha-1B-glycoprotein | A1BG | *Homo sapiens* | 398.41 | 38.79 | 11 | 96 |
| P35221 | Catenin alpha-1 | CTNNA1 | *Homo sapiens* | 449.17 | 42.49 | 20 | 95 |
| Q12805 | EGF-containing fibulin-like extracellular matrix protein 1 | EFEMP1 | *Homo sapiens* | 462.35 | 39.35 | 12 | 95 |
| P05141 | ADP/ATP translocase 2 | SLC25A5 | *Homo sapiens* | 308.16 | 27.52 | 7 | 95 |
| P17174 | Aspartate aminotransferase, cytoplasmic | GOT1 | *Homo sapiens* | 386.92 | 52.78 | 16 | 94 |
| P63244 | Guanine nucleotide-binding protein subunit beta-2-like 1 | GNB2L1 | *Homo sapiens* | 428.30 | 52.37 | 10 | 94 |
| P05783 | Keratin, type I cytoskeletal 18 | KRT18 | *Homo sapiens* | 313.43 | 44.42 | 13 | 92 |
| P17540 | Creatine kinase S-type, mitochondrial | CKMT2 | *Homo sapiens* | 380.25 | 49.16 | 14 | 92 |
| P60660 | Myosin light polypeptide 6 | MYL6 | *Homo sapiens* | 335.10 | 52.98 | 8 | 92 |
| P22352 | Glutathione peroxidase 3 | GPX3 | *Homo sapiens* | 296.23 | 29.20 | 5 | 92 |
| P62258 | 14-3-3 protein epsilon | YWHAE | *Homo sapiens* | 273.86 | 33.33 | 8 | 90 |
| P00751 | Complement factor B | CFB | *Homo sapiens* | 335.25 | 28.01 | 14 | 90 |
| P12532 | Creatine kinase U-type, mitochondrial | CKMT1A | *Homo sapiens* | 451.15 | 37.17 | 9 | 90 |
| Q14315 | Filamin-C | FLNC | *Homo sapiens* | 343.94 | 13.72 | 23 | 90 |
| P39656 | Dolichyl-diphosphooligosaccharide-protein glycosyltransferase 48 kDa subunit | DDOST | *Homo sapiens* | 642.76 | 25.22 | 6 | 90 |
| P40925 | Malate dehydrogenase, cytoplasmic | MDH1 | *Homo sapiens* | 339.35 | 36.23 | 9 | 89 |
| Q00872 | Myosin-binding protein C, slow-type | MYBPC1 | *Homo sapiens* | 320.23 | 26.29 | 22 | 89 |
| P22695 | Cytochrome b-c1 complex subunit 2, mitochondrial | UQCRC2 | *Homo sapiens* | 372.95 | 36.20 | 12 | 89 |
| Q7Z406 | Myosin-14 | MYH14 | *Homo sapiens* | 346.95 | 5.26 | 7 | 89 |
| Q96A32 | Myosin regulatory light chain 2, skeletal muscle isoform | MYLPF | *Homo sapiens* | 301.63 | 69.82 | 11 | 88 |
| P05388 | 60S acidic ribosomal protein P0 | RPLP0 | *Homo sapiens* | 281.69 | 39.43 | 8 | 88 |
| Q05639 | Elongation factor 1-alpha 2 | EEF1A2 | *Homo sapiens* | 402.16 | 30.67 | 9 | 87 |
| P98095 | Fibulin-2 | FBLN2 | *Homo sapiens* | 355.37 | 22.97 | 16 | 87 |
| P00568 | Adenylate kinase isoenzyme 1 | AK1 | *Homo sapiens* | 457.63 | 46.91 | 7 | 86 |
| P61626 | Lysozyme C | LYZ | *Homo sapiens* | 396.57 | 46.62 | 5 | 86 |
| P18669 | Phosphoglycerate mutase 1 | PGAM1 | *Homo sapiens* | 367.15 | 59.84 | 11 | 86 |
| P62917 | 60S ribosomal protein L8 | RPL8 | *Homo sapiens* | 397.44 | 36.96 | 6 | 86 |
| Q14204 | Cytoplasmic dynein 1 heavy chain 1 | DYNC1H1 | *Homo sapiens* | 405.37 | 7.25 | 19 | 85 |
| P29401 | Transketolase | TKT | *Homo sapiens* | 482.56 | 31.94 | 9 | 85 |
| P02750 | Leucine-rich alpha-2-glycoprotein | LRG1 | *Homo sapiens* | 377.99 | 41.50 | 9 | 84 |
| P21980 | Protein-glutamine gamma-glutamyltransferase 2 | TGM2 | *Homo sapiens* | 357.31 | 30.57 | 13 | 84 |
| P18206 | Vinculin | VCL | *Homo sapiens* | 289.28 | 23.46 | 17 | 84 |
| P61981 | 14-3-3 protein gamma | YWHAG | *Homo sapiens* | 329.88 | 42.51 | 7 | 83 |
| P21964 | Catechol O-methyltransferase | COMT | *Homo sapiens* | 392.61 | 52.40 | 9 | 83 |
| P62424 | 60S ribosomal protein L7a | RPL7A | *Homo sapiens* | 299.36 | 35.34 | 10 | 83 |
| P0DJI8 | Serum amyloid A-1 protein | SAA1 | *Homo sapiens* | 370.93 | 66.39 | 7 | 83 |
| P05023 | Sodium/potassium-transporting ATPase subunit alpha-1 | ATP1A1 | *Homo sapiens* | 290.15 | 17.69 | 13 | 81 |
| P62158 | Calmodulin | CALM1 | *Homo sapiens* | 307.86 | 46.98 | 7 | 81 |
| P55084 | Trifunctional enzyme subunit beta, mitochondrial | HADHB | *Homo sapiens* | 360.39 | 39.03 | 11 | 81 |
| Q14697 | Neutral alpha-glucosidase AB | GANAB | *Homo sapiens* | 415.60 | 25.00 | 12 | 81 |
| P62879 | Guanine nucleotide-binding protein G(I)/G(S)/G(T) subunit beta-2 | GNB2 | *Homo sapiens* | 308.38 | 52.35 | 11 | 81 |
| P07858 | Cathepsin B | CTSB | *Homo sapiens* | 379.84 | 27.73 | 7 | 80 |
| P06748 | Nucleophosmin | NPM1 | *Homo sapiens* | 408.27 | 24.15 | 5 | 80 |
| P05155 | Plasma protease C1 inhibitor | SERPING1 | *Homo sapiens* | 295.14 | 22.40 | 10 | 79 |
| Q15084 | Protein disulfide-isomerase A6 | PDIA6 | *Homo sapiens* | 302.05 | 33.41 | 9 | 79 |
| P24821 | Tenascin | TNC | *Homo sapiens* | 328.11 | 16.13 | 19 | 79 |
| P31947 | 14-3-3 protein sigma | SFN | *Homo sapiens* | 358.29 | 55.65 | 10 | 78 |
| Q03135 | Caveolin-1 | CAV1 | *Homo sapiens* | 368.92 | 46.63 | 6 | 78 |
| P35222 | Catenin beta-1 | CTNNB1 | *Homo sapiens* | 428.51 | 16.77 | 8 | 78 |
| P26038 | Moesin | MSN | *Homo sapiens* | 287.39 | 24.09 | 11 | 78 |
| P22897 | Macrophage mannose receptor 1 | MRC1 | *Homo sapiens* | 357.42 | 15.87 | 14 | 78 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| Q15365 | Poly(rC)-binding protein 1 | PCBP1 | *Homo sapiens* | 349.30 | 32.02 | 7 | 78 |
| P11216 | Glycogen phosphorylase, brain form | PYGB | *Homo sapiens* | 311.63 | 22.18 | 13 | 78 |
| P21796 | Voltage-dependent anion-selective channel protein 1 | VDAC1 | *Homo sapiens* | 295.47 | 51.24 | 9 | 77 |
| P27348 | 14-3-3 protein theta | YWHAQ | *Homo sapiens* | 238.77 | 38.78 | 8 | 76 |
| P45378 | Troponin T, fast skeletal muscle | TNNT3 | *Homo sapiens* | 371.79 | 36.80 | 11 | 76 |
| Q92928 | Putative Ras-related protein Rab-1C | RAB1C | *Homo sapiens* | 204.29 | 31.34 | 5 | 76 |
| P52895 | Aldo-keto reductase family 1 member C2 | AKR1C2 | *Homo sapiens* | 370.32 | 36.53 | 7 | 75 |
| P02792 | Ferritin light chain | FTL | *Homo sapiens* | 374.53 | 44.57 | 6 | 74 |
| P27105 | Erythrocyte band 7 integral membrane protein | STOM | *Homo sapiens* | 355.48 | 39.24 | 6 | 74 |
| P61204 | ADP-ribosylation factor 3 | ARF3 | *Homo sapiens* | 264.46 | 54.70 | 8 | 73 |
| P63241 | Eukaryotic translation initiation factor 5A-1 | EIF5A | *Homo sapiens* | 402.91 | 61.69 | 7 | 73 |
| Q8TDL5 | BPI fold-containing family B member 1 | BPIFB1 | *Homo sapiens* | 280.43 | 39.88 | 13 | 73 |
| P35232 | Prohibitin | PHB | *Homo sapiens* | 392.68 | 47.06 | 7 | 73 |
| P00505 | Aspartate aminotransferase, mitochondrial | GOT2 | *Homo sapiens* | 322.70 | 40.00 | 11 | 73 |
| P17931 | Galectin-3 | LGALS3 | *Homo sapiens* | 276.89 | 28.40 | 6 | 73 |
| O95994 | Anterior gradient protein 2 homolog | AGR2 | *Homo sapiens* | 266.91 | 54.86 | 6 | 72 |
| P26641 | Elongation factor 1-gamma | EEF1G | *Homo sapiens* | 241.88 | 26.32 | 8 | 71 |
| P23396 | 40S ribosomal protein S3 | RPS3 | *Homo sapiens* | 262.77 | 50.62 | 10 | 71 |
| P45880 | Voltage-dependent anion-selective channel protein 2 | VDAC2 | *Homo sapiens* | 309.07 | 38.78 | 8 | 71 |
| Q08211 | ATP-dependent RNA helicase A | DHX9 | *Homo sapiens* | 350.79 | 11.97 | 9 | 70 |
| P05387 | 60S acidic ribosomal protein P2 | RPLP2 | *Homo sapiens* | 308.01 | 85.22 | 6 | 70 |
| P31946 | 14-3-3 protein beta/alpha | YWHAB | *Homo sapiens* | 223.98 | 34.55 | 7 | 69 |
| P09972 | Fructose-bisphosphate aldolase C | ALDOC | *Homo sapiens* | 307.69 | 20.33 | 5 | 69 |
| P30740 | Leukocyte elastase inhibitor | SERPINB1 | *Homo sapiens* | 297.65 | 34.83 | 8 | 69 |
| P39023 | 60S ribosomal protein L3 | RPL3 | *Homo sapiens* | 308.88 | 26.30 | 8 | 69 |
| P62081 | 40S ribosomal protein S7 | RPS7 | *Homo sapiens* | 329.43 | 37.11 | 4 | 69 |
| Q01469 | Fatty acid-binding protein, epidermal | FABP5 | *Homo sapiens* | 304.75 | 41.48 | 5 | 68 |
| P15259 | Phosphoglycerate mutase 2 | PGAM2 | *Homo sapiens* | 295.35 | 56.92 | 12 | 68 |
| P30041 | Peroxiredoxin-6 | PRDX6 | *Homo sapiens* | 299.12 | 37.05 | 6 | 68 |
| P52209 | 6-phosphogluconate dehydrogenase, decarboxylating | PGD | *Homo sapiens* | 348.83 | 19.25 | 6 | 67 |
| P31040 | Succinate dehydrogenase [ubiquinone] flavoprotein subunit, mitochondrial | SDHA | *Homo sapiens* | 321.54 | 20.93 | 9 | 67 |
| P07099 | Epoxide hydrolase 1 | EPHX1 | *Homo sapiens* | 330.10 | 32.75 | 7 | 67 |
| P22626 | Heterogeneous nuclear ribonucleoproteins A2/B1 | HNRNPA2B1 | *Homo sapiens* | 239.94 | 25.78 | 9 | 67 |
| P62701 | 40S ribosomal protein S4, X isoform | RPS4X | *Homo sapiens* | 227.75 | 41.44 | 10 | 67 |
| P07384 | Calpain-1 catalytic subunit | CAPN1 | *Homo sapiens* | 258.35 | 26.47 | 11 | 66 |
| P99999 | Cytochrome c | CYCS | *Homo sapiens* | 241.24 | 48.57 | 5 | 66 |
| Q16777 | Histone H2A type 2-C | HIST2H2AC | *Homo sapiens* | 184.31 | 63.57 | 6 | 66 |
| P52272 | Heterogeneous nuclear ribonucleoprotein M | HNRNPM | *Homo sapiens* | 236.69 | 21.51 | 12 | 66 |
| P60842 | Eukaryotic initiation factor 4A-I | EIF4A1 | *Homo sapiens* | 210.21 | 41.38 | 12 | 66 |
| P10916 | Myosin regulatory light chain 2, ventricular/cardiac muscle isoform | MYL2 | *Homo sapiens* | 242.44 | 77.71 | 10 | 66 |
| Q6NZI2 | Polymerase I and transcript release factor | PTRF | *Homo sapiens* | 253.00 | 22.56 | 7 | 66 |
| P29508 | Serpin B3 | SERPINB3 | *Homo sapiens* | 230.90 | 37.44 | 11 | 66 |
| Q9Y490 | Talin-1 | TLN1 | *Homo sapiens* | 245.23 | 11.26 | 15 | 66 |
| P39060 | Collagen alpha-1(XVIII) chain | COL18A1 | *Homo sapiens* | 311.69 | 7.58 | 6 | 66 |
| Q13361 | Microfibrillar-associated protein 5 | MFAP5 | *Homo sapiens* | 229.94 | 18.50 | 3 | 65 |
| P32119 | Peroxiredoxin-2 | PRDX2 | *Homo sapiens* | 302.38 | 32.32 | 6 | 65 |
| P01042 | Kininogen-1 | KNG1 | *Homo sapiens* | 254.20 | 21.89 | 9 | 64 |
| P13489 | Ribonuclease inhibitor | RNH1 | *Homo sapiens* | 294.50 | 31.67 | 8 | 64 |
| Q9HCY8 | Protein S100-A414 | S100A14 | *Homo sapiens* | 240.31 | 65.38 | 5 | 64 |
| P04179 | Superoxide dismutase [Mn], mitochondrial | SOD2 | *Homo sapiens* | 285.33 | 61.71 | 7 | 64 |
| O75390 | Citrate synthase, mitochondrial | CS | *Homo sapiens* | 348.67 | 30.26 | 8 | 63 |
| P08294 | Extracellular superoxide dismutase [Cu—Zn] | SOD3 | *Homo sapiens* | 255.58 | 26.67 | 5 | 63 |
| Q15661 | Tryptase alpha/beta-1 | TPSAB1 | *Homo sapiens* | 232.08 | 22.18 | 6 | 63 |
| Q9Y277 | Voltage-dependent anion-selective channel protein 3 | VDAC3 | *Homo sapiens* | 225.78 | 27.21 | 5 | 63 |
| P00403 | Cytochrome c oxidase subunit 2 | MT-CO2 | *Homo sapiens* | 210.74 | 20.26 | 3 | 62 |
| P49411 | Elongation factor Tu, mitochondrial | TUFM | *Homo sapiens* | 266.69 | 25.00 | 8 | 62 |
| P26599 | Polypyrimidine tract-binding protein 1 | PTBP1 | *Homo sapiens* | 332.59 | 32.20 | 9 | 62 |
| P09382 | Galectin-1 | LGALS1 | *Homo sapiens* | 210.45 | 65.93 | 6 | 61 |
| P00734 | Prothrombin | F2 | *Homo sapiens* | 251.04 | 30.23 | 12 | 61 |
| P31415 | Calsequestrin-1 | CASQ1 | *Homo sapiens* | 318.32 | 29.29 | 7 | 61 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P25311 | Zinc-alpha-2-glycoprotein | AZGP1 | *Homo sapiens* | 254.10 | 29.53 | 6 | 61 |
| P48735 | Isocitrate dehydrogenase [NADP], mitochondrial | IDH2 | *Homo sapiens* | 207.55 | 27.65 | 11 | 60 |
| P09622 | Dihydrolipoyl dehydrogenase, mitochondrial | DLD | *Homo sapiens* | 333.83 | 20.24 | 6 | 60 |
| Q6DD88 | Atlastin-3 | ATL3 | *Homo sapiens* | 348.75 | 32.72 | 8 | 59 |
| P13010 | X-ray repair cross-complementing protein 5 | XRCC5 | *Homo sapiens* | 310.59 | 25.55 | 10 | 59 |
| P22392 | Nucleoside diphosphate kinase B | NME2 | *Homo sapiens* | 226.78 | 35.53 | 4 | 59 |
| P27635 | 60S ribosomal protein L10 | RPL10 | *Homo sapiens* | 253.21 | 36.92 | 8 | 59 |
| P30153 | Serine/threonine-protein phosphatase 2A 65 kDa regulatory subunit A alpha isoform | PPP2R1A | *Homo sapiens* | 245.66 | 14.09 | 5 | 58 |
| P18085 | ADP-ribosylation factor 4 | ARF4 | *Homo sapiens* | 200.39 | 48.33 | 7 | 58 |
| O43852 | Calumenin | CALU | *Homo sapiens* | 344.28 | 36.19 | 6 | 58 |
| Q99714 | 3-hydroxyacyl-CoA dehydrogenase type-2 | HSD17B10 | *Homo sapiens* | 256.09 | 44.83 | 7 | 58 |
| P47929 | Galectin-7 | LGALS7 | *Homo sapiens* | 267.04 | 55.15 | 5 | 58 |
| P50914 | 60S ribosomal protein L14 | RPL14 | *Homo sapiens* | 164.83 | 24.19 | 5 | 58 |
| P04080 | Cystatin-B | CSTB | *Homo sapiens* | 255.39 | 45.92 | 3 | 57 |
| P12277 | Creatine kinase B-type | CKB | *Homo sapiens* | 243.55 | 38.85 | 9 | 57 |
| P08590 | Myosin light chain 3 | MYL3 | *Homo sapiens* | 180.14 | 47.69 | 8 | 57 |
| P15880 | 40S ribosomal protein S2 | RPS2 | *Homo sapiens* | 247.88 | 25.94 | 5 | 57 |
| P50454 | Serpin H1 | SERPINH1 | *Homo sapiens* | 255.28 | 42.11 | 12 | 57 |
| Q96TA1 | Niban-like protein 1 | FAM129B | *Homo sapiens* | 273.85 | 13.40 | 6 | 57 |
| P48047 | ATP synthase subunit O, mitochondrial | ATP5O | *Homo sapiens* | 198.34 | 44.60 | 6 | 56 |
| P07954 | Fumarate hydratase, mitochondrial | FH | *Homo sapiens* | 315.14 | 24.12 | 5 | 56 |
| Q99623 | Prohibitin-2 | PHB2 | *Homo sapiens* | 201.31 | 37.12 | 8 | 56 |
| P02743 | Serum amyloid P-component | APCS | *Homo sapiens* | 175.11 | 25.11 | 6 | 56 |
| P20929 | Nebulin | NEB | *Homo sapiens* | 181.95 | 5.88 | 21 | 56 |
| P62979 | Ubiquitin-40S ribosomal protein S27a | RPS27A | *Homo sapiens* | 194.01 | 28.21 | 3 | 56 |
| P07910 | Heterogeneous nuclear ribonucleoproteins C1/C2 | HNRNPC | *Homo sapiens* | 178.69 | 20.92 | 7 | 55 |
| P50995 | Annexin A11 | ANXA11 | *Homo sapiens* | 193.16 | 21.98 | 9 | 54 |
| P02649 | Apolipoprotein E | APOE | *Homo sapiens* | 205.73 | 31.55 | 7 | 54 |
| P04632 | Calpain small subunit 1 | CAPNS1 | *Homo sapiens* | 267.00 | 30.97 | 4 | 54 |
| O75367 | Core histone macro-H2A.1 | H2AFY | *Homo sapiens* | 224.12 | 29.03 | 7 | 54 |
| Q32P51 | Heterogeneous nuclear ribonucleoprotein A1-like 2 | HNRNPA1L2 | *Homo sapiens* | 198.73 | 23.13 | 7 | 54 |
| P16403 | Histone H1.2 | HIST1H1C | *Homo sapiens* | 158.83 | 20.19 | 7 | 53 |
| Q9NZM1 | Myoferlin | MYOF | *Homo sapiens* | 225.43 | 8.98 | 11 | 53 |
| P05109 | Protein S100-A8 | S100A8 | *Homo sapiens* | 162.26 | 40.86 | 4 | 53 |
| Q14134 | Tripartite motif-containing protein 29 | TRIM29 | *Homo sapiens* | 210.80 | 21.43 | 9 | 53 |
| P35443 | Thrombospondin-4 | THBS4 | *Homo sapiens* | 243.36 | 25.39 | 13 | 53 |
| Q05707 | Collagen alpha-1(XIV) chain | COL14A1 | *Homo sapiens* | 231.55 | 8.35 | 11 | 52 |
| Q99497 | Protein DJ-1 | PARK7 | *Homo sapiens* | 236.62 | 56.61 | 6 | 52 |
| Q13838 | Spliceosome RNA helicase DDX39B | DDX39B | *Homo sapiens* | 210.91 | 18.93 | 5 | 52 |
| P35527 | Keratin, type I cytoskeletal 9 | KRT9 | *Homo sapiens* | 258.81 | 18.94 | 7 | 51 |
| O94973 | AP-2 complex subunit alpha-2 | AP2A2 | *Homo sapiens* | 229.57 | 14.91 | 7 | 51 |
| Q14574 | Desmocollin-3 | DSC3 | *Homo sapiens* | 284.04 | 16.52 | 8 | 51 |
| P04899 | Guanine nucleotide-binding protein G(i) subunit alpha-2 | GNAI2 | *Homo sapiens* | 181.43 | 32.39 | 8 | 51 |
| P0C0S5 | Histone H2A.Z | H2AFZ | *Homo sapiens* | 157.41 | 42.97 | 4 | 51 |
| P46777 | 60S ribosomal protein L5 | RPL5 | *Homo sapiens* | 211.39 | 23.57 | 5 | 51 |
| P05386 | 60S acidic ribosomal protein P1 | RPLP1 | *Homo sapiens* | 201.61 | 66.67 | 3 | 51 |
| O75083 | WD repeat-containing protein 1 | WDR1 | *Homo sapiens* | 312.47 | 33.00 | 9 | 51 |
| Q02218 | 2-oxoglutarate dehydrogenase, mitochondrial | OGDH | *Homo sapiens* | 284.56 | 18.18 | 9 | 51 |
| P60033 | CD81 antigen | CD81 | *Homo sapiens* | 232.36 | 25.00 | 3 | 50 |
| P09429 | High mobility group protein B1 | HMGB1 | *Homo sapiens* | 221.28 | 27.91 | 5 | 50 |
| P30838 | Aldehyde dehydrogenase, dimeric NADP-preferring | ALDH3A1 | *Homo sapiens* | 188.52 | 29.36 | 7 | 50 |
| P16152 | Carbonyl reductase [NADPH] 1 | CBR1 | *Homo sapiens* | 205.13 | 53.07 | 11 | 49 |
| P46782 | 40S ribosomal protein S5 | RPS5 | *Homo sapiens* | 160.59 | 33.33 | 6 | 49 |
| P01880 | Ig delta chain C region | IGHD | *Homo sapiens* | 265.21 | 32.29 | 7 | 49 |
| P23284 | Peptidyl-prolyl cis-trans isomerase B | PPIB | *Homo sapiens* | 154.32 | 43.52 | 9 | 49 |
| P61158 | Actin-related protein 3 | ACTR3 | *Homo sapiens* | 229.45 | 20.10 | 4 | 48 |
| P01620 | Ig kappa chain V-III region SIE | KV302 | *Homo sapiens* | 210.50 | 39.45 | 3 | 48 |
| Q9H8H3 | Methyltransferase-like protein 7A | METTL7A | *Homo sapiens* | 172.04 | 31.56 | 5 | 48 |
| Q9NQC3 | Reticulon-4 | RTN4 | *Homo sapiens* | 230.34 | 7.30 | 5 | 48 |
| Q9Y3Z3 | SAM domain and HD domain-containing protein 1 | SAMHD1 | *Homo sapiens* | 215.44 | 23.32 | 9 | 48 |
| P54296 | Myomesin-2 | MYOM2 | *Homo sapiens* | 209.59 | 18.09 | 13 | 48 |
| P21926 | CD9 antigen | CD9 | *Homo sapiens* | 267.46 | 15.35 | 2 | 47 |
| P43490 | Nicotinamide phosphoribosyltransferase | NAMPT | *Homo sapiens* | 265.35 | 33.20 | 9 | 47 |

TABLE 1-continued

Lists of proteins identified in LC-MS/MS analysis of scaffold only, VFF in
scaffold, VFE on scaffold, engineered VF mucosa and native VF mucosa. Identifications
were based on a 1% false discovery rate. The scaffold was sourced from *Rattus norvegicus*;
VFF, VFE and native VF mucosa were sourced from *Homo sapiens*. Proteins are listed in order
of descending peptide spectra matches.

| UniProt accession number | Protein name | Gene symbol | Organism | Score | Sequence coverage (%) | Unique peptides | Peptide spectra matches |
| --- | --- | --- | --- | --- | --- | --- | --- |
| P48788 | Troponin I, fast skeletal muscle | TNNI2 | *Homo sapiens* | 247.76 | 42.86 | 8 | 47 |
| P17655 | Calpain-2 catalytic subunit | CAPN2 | *Homo sapiens* | 228.83 | 20.57 | 7 | 47 |
| Q00839 | Heterogeneous nuclear ribonucleoprotein U | HNRNPU | *Homo sapiens* | 201.33 | 12.36 | 5 | 47 |
| Q02878 | 60S ribosomal protein L6 | RPL6 | *Homo sapiens* | 164.14 | 26.39 | 7 | 46 |
| P25398 | 40S ribosomal protein S12 | RPS12 | *Homo sapiens* | 204.42 | 47.73 | 5 | 46 |
| A6NMZ7 | Collagen alpha-6(VI) chain | COL6A6 | *Homo sapiens* | 223.43 | 9.72 | 13 | 46 |
| Q92817 | Envoplakin | EVPL | *Homo sapiens* | 238.79 | 11.95 | 13 | 46 |
| P62263 | 40S ribosomal protein S14 | RPS14 | *Homo sapiens* | 191.81 | 63.58 | 5 | 45 |
| P62241 | 40S ribosomal protein S8 | RPS8 | *Homo sapiens* | 158.52 | 34.62 | 6 | 45 |
| P43304 | Glycerol-3-phosphate dehydrogenase, mitochondrial | GPD2 | *Homo sapiens* | 237.37 | 13.76 | 5 | 45 |
| P15121 | Aldose reductase | AKR1B1 | *Homo sapiens* | 205.46 | 27.22 | 5 | 44 |
| P02747 | Complement C1q subcomponent subunit C | C1QC | *Homo sapiens* | 149.99 | 25.31 | 5 | 44 |
| P02748 | Complement component C9 | C9 | *Homo sapiens* | 175.08 | 13.60 | 6 | 44 |
| P24534 | Elongation factor 1-beta | EEF1B2 | *Homo sapiens* | 185.03 | 34.67 | 4 | 44 |
| Q07020 | 60S ribosomal protein L18 | RPL18 | *Homo sapiens* | 144.36 | 25.00 | 4 | 44 |
| P61247 | 40S ribosomal protein S3a | RPS3A | *Homo sapiens* | 176.21 | 21.59 | 4 | 44 |
| P00441 | Superoxide dismutase [Cu—Zn] | SOD1 | *Homo sapiens* | 360.54 | 53.90 | 3 | 44 |
| Q01995 | Transgelin | TAGLN | *Homo sapiens* | 133.46 | 31.34 | 5 | 44 |
| O75369 | Filamin-B | FLNB | *Homo sapiens* | 153.21 | 4.96 | 8 | 44 |
| P26022 | Pentraxin-related protein PTX3 | PTX3 | *Homo sapiens* | 169.22 | 22.57 | 7 | 44 |
| P09758 | Tumor-associated calcium signal transducer 2 | TACSTD2 | *Homo sapiens* | 189.68 | 32.82 | 7 | 44 |
| Q6Y2Q3 | Glutathione S-transferase kappa 1 | GSTK1 | *Homo sapiens* | 190.62 | 32.74 | 5 | 43 |
| Q00325 | Phosphate carrier protein, mitochondrial | SLC25A3 | *Homo sapiens* | 152.13 | 19.06 | 5 | 43 |
| Q06323 | Proteasome activator complex subunit 1 | PSME1 | *Homo sapiens* | 162.04 | 23.29 | 5 | 43 |
| Q16647 | Prostacyclin synthase | PTGIS | *Homo sapiens* | 161.75 | 33.60 | 11 | 43 |
| P29034 | Protein S100-A2 | S100A2 | *Homo sapiens* | 137.60 | 27.55 | 4 | 43 |
| Q9Y6N5 | Sulfide:quinone oxidoreductase, mitochondrial | SQRDL | *Homo sapiens* | 157.67 | 23.78 | 8 | 43 |
| P78371 | T-complex protein 1 subunit beta | CCT2 | *Homo sapiens* | 204.85 | 25.05 | 8 | 43 |
| P22314 | Ubiquitin-like modifier-activating enzyme 1 | UBA1 | *Homo sapiens* | 159.50 | 12.00 | 8 | 43 |
| Q04917 | 14-3-3 protein eta | YWHAH | *Homo sapiens* | 123.80 | 18.29 | 4 | 42 |
| P05997 | Collagen alpha-2(V) chain | COL5A2 | *Homo sapiens* | 51.56 | 4.47 | 4 | 42 |
| P00390 | Glutathione reductase, mitochondrial | GSR | *Homo sapiens* | 187.41 | 23.18 | 6 | 42 |
| P52597 | Heterogeneous nuclear ribonucleoprotein F | HNRNPF | *Homo sapiens* | 194.08 | 21.69 | 5 | 42 |
| P18428 | Lipopolysaccharide-binding protein | LBP | *Homo sapiens* | 191.95 | 14.76 | 5 | 42 |
| P12273 | Prolactin-inducible protein | PIP | *Homo sapiens* | 165.44 | 39.04 | 4 | 42 |
| P07737 | Profilin-1 | PFN1 | *Homo sapiens* | 121.34 | 53.57 | 6 | 42 |
| Q15286 | Ras-related protein Rab-35 | RAB35 | *Homo sapiens* | 116.52 | 19.90 | 3 | 42 |
| Q07960 | Rho GTPase-activating protein 1 | ARHGAP1 | *Homo sapiens* | 185.83 | 24.60 | 5 | 42 |
| P62888 | 60S ribosomal protein L30 | RPL30 | *Homo sapiens* | 156.93 | 51.30 | 4 | 42 |
| P31930 | Cytochrome b-c1 complex subunit 1, mitochondrial | UQCRC1 | *Homo sapiens* | 194.33 | 30.00 | 8 | 42 |
| P02746 | Complement C1q subcomponent subunit B | C1QB | *Homo sapiens* | 151.74 | 20.55 | 4 | 42 |
| P49748 | Very long-chain specific acyl-CoA dehydrogenase, mitochondrial | ACADVL | *Homo sapiens* | 188.16 | 17.10 | 7 | 41 |
| P56134 | ATP synthase subunit f, mitochondrial | ATP5J2 | *Homo sapiens* | 128.69 | 25.53 | 2 | 41 |
| O14880 | Microsomal glutathione S-transferase 3 | MGST3 | *Homo sapiens* | 209.57 | 33.55 | 3 | 41 |
| P61106 | Ras-related protein Rab-14 | RAB14 | *Homo sapiens* | 139.72 | 33.02 | 4 | 41 |
| P32969 | 60S ribosomal protein L9 | RPL9 | *Homo sapiens* | 206.78 | 50.52 | 7 | 41 |
| Q01518 | Adenylyl cyclase-associated protein 1 | CAP1 | *Homo sapiens* | 116.36 | 18.11 | 6 | 41 |
| P0DJI9 | Serum amyloid A-2 protein | SAA2 | *Homo sapiens* | 152.96 | 47.54 | 5 | 41 |
| P02760 | Protein AMBP | AMBP | *Homo sapiens* | 130.27 | 20.17 | 5 | 40 |
| O00571 | ATP-dependent RNA helicase DDX3X | DDX3X | *Homo sapiens* | 136.76 | 14.80 | 7 | 40 |
| P04196 | Histidine-rich glycoprotein | HRG | *Homo sapiens* | 146.71 | 23.24 | 8 | 40 |
| P19338 | Nucleolin | NCL | *Homo sapiens* | 118.67 | 17.89 | 8 | 40 |
| P62826 | GTP-binding nuclear protein Ran | RAN | *Homo sapiens* | 140.71 | 29.63 | 5 | 40 |
| P30050 | 60S ribosomal protein L12 | RPL12 | *Homo sapiens* | 142.78 | 54.55 | 6 | 40 |
| Q16851 | UTP--glucose-1-phosphate uridylyltransferase | UGP2 | *Homo sapiens* | 180.79 | 24.02 | 8 | 40 |
| P30044 | Peroxiredoxin-5, mitochondrial | PRDX5 | *Homo sapiens* | 134.47 | 39.25 | 6 | 40 |
| P15144 | Aminopeptidase N | ANPEP | *Homo sapiens* | 199.99 | 10.44 | 5 | 39 |
| Q9Y281 | Cofilin-2 | CFL2 | *Homo sapiens* | 145.82 | 43.98 | 5 | 39 |
| P14854 | Cytochrome c oxidase subunit 6B1 | COX6B1 | *Homo sapiens* | 138.41 | 56.98 | 4 | 39 |
| Q14974 | Importin subunit beta-1 | KPNB1 | *Homo sapiens* | 167.13 | 10.96 | 6 | 39 |
| P18621 | 60S ribosomal protein L17 | RPL17 | *Homo sapiens* | 170.36 | 37.50 | 6 | 39 |
| P62829 | 60S ribosomal protein L23 | RPL23 | *Homo sapiens* | 159.78 | 25.00 | 2 | 39 |
| P46783 | 40S ribosomal protein S10 | RPS10 | *Homo sapiens* | 125.03 | 23.64 | 3 | 39 |
| Q15019 | Septin-2 | 41884 | *Homo sapiens* | 201.93 | 22.44 | 5 | 39 |
| Q9BTV4 | Transmembrane protein 43 | TMEM43 | *Homo sapiens* | 256.33 | 26.25 | 5 | 39 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P02585 | Troponin C, skeletal muscle | TNNC2 | *Homo sapiens* | 160.86 | 56.25 | 6 | 39 |
| P08574 | Cytochrome c1, heme protein, mitochondrial | CYC1 | *Homo sapiens* | 176.16 | 20.00 | 4 | 39 |
| P36957 | Dihydrolipoyllysine-residue succinyltransferase component of 2-oxoglutarate dehydrogenase complex, mitochondrial | DLST | *Homo sapiens* | 118.88 | 16.56 | 6 | 39 |
| P08697 | Alpha-2-antiplasmin | SERPINF2 | *Homo sapiens* | 212.46 | 16.50 | 4 | 38 |
| P31943 | Heterogeneous nuclear ribonucleoprotein H | HNRNPH1 | *Homo sapiens* | 143.80 | 16.26 | 5 | 38 |
| P19827 | Inter-alpha-trypsin inhibitor heavy chain H1 | ITIH1 | *Homo sapiens* | 172.16 | 9.22 | 5 | 38 |
| P12956 | X-ray repair cross-complementing protein 6 | XRCC6 | *Homo sapiens* | 128.28 | 18.06 | 8 | 38 |
| P01617 | Ig kappa chain V-II region TEW | KV204 | *Homo sapiens* | 147.26 | 32.74 | 2 | 38 |
| P20700 | Lamin-B1 | LMNB1 | *Homo sapiens* | 115.63 | 22.01 | 10 | 38 |
| P53621 | Coatomer subunit alpha | COPA | *Homo sapiens* | 177.86 | 10.05 | 6 | 38 |
| P20674 | Cytochrome c oxidase subunit 5A, mitochondrial | COX5A | *Homo sapiens* | 152.37 | 48.00 | 6 | 38 |
| Q16891 | Mitochondrial inner membrane, protein | IMMT | *Homo sapiens* | 196.93 | 13.98 | 6 | 37 |
| P62906 | 60S ribosomal protein L10a | RPL10A | *Homo sapiens* | 151.26 | 31.80 | 6 | 37 |
| P35268 | 60S ribosomal protein L22 | RPL22 | *Homo sapiens* | 208.22 | 39.06 | 3 | 37 |
| P46781 | 40S ribosomol protein S9 | RPS9 | *Homo sapiens* | 93.51 | 29.38 | 6 | 37 |
| P49368 | T-complex protein 1 subunit gamma | CCT3 | *Homo sapiens* | 139.77 | 24.95 | 9 | 37 |
| P13805 | Troponin T, slow skeletal muscle | TNNT1 | *Homo sapiens* | 178.15 | 26.62 | 6 | 37 |
| O14773 | Tripeptidyl-peptidase 1 | TPP1 | *Homo sapiens* | 175.66 | 19.72 | 5 | 37 |
| P15088 | Mast cell carboxypeptidase A | CPA3 | *Homo sapiens* | 100.59 | 16.31 | 6 | 37 |
| P21397 | Amine oxidase [flavin-containing] A | MAOA | *Homo sapiens* | 210.61 | 23.34 | 7 | 36 |
| O00264 | Membrane-associated progesterone receptor component 1 | PGRMC1 | *Homo sapiens* | 230.02 | 26.15 | 2 | 36 |
| P62841 | 40S ribosomal protein S15 | RPS15 | *Homo sapiens* | 217.34 | 60.69 | 5 | 36 |
| P62847 | 40S ribosomal protein S24 | RPS24 | *Homo sapiens* | 114.91 | 28.57 | 3 | 36 |
| Q99832 | T-complex protein 1 subunit eta | CCT7 | *Homo sapiens* | 174.83 | 16.21 | 5 | 36 |
| P02756 | Transthyretin | TTR | *Homo sapiens* | 198.08 | 58.50 | 5 | 36 |
| P50395 | Rab GDP dissociation inhibitor beta | GDI2 | *Homo sapiens* | 184.88 | 29.21 | 7 | 35 |
| Q15366 | Poly(rC)-binding protein 2 | PCBP2 | *Homo sapiens* | 124.46 | 28.77 | 6 | 35 |
| P36871 | Phosphoglucomutase-1 | PGM1 | *Homo sapiens* | 117.76 | 26.51 | 9 | 35 |
| P60953 | Cell division control protein 42 homolog | CDC42 | *Homo sapiens* | 132.02 | 40.31 | 5 | 35 |
| Q03252 | Lamin-B2 | LMNB2 | *Homo sapiens* | 99.19 | 16.67 | 8 | 34 |
| O00151 | PDZ and LIM domain protein 1 | PDLIM1 | *Homo sapiens* | 219.59 | 20.97 | 3 | 34 |
| P61313 | 60S ribosomal protein L15 | RPL15 | *Homo sapiens* | 116.87 | 24.02 | 4 | 34 |
| P63010 | AP-2 complex subunit beta | AP2B1 | *Homo sapiens* | 144.72 | 8.96 | 4 | 33 |
| P52907 | F-actin-capping protein subunit alpha-1 | CAPZA1 | *Homo sapiens* | 118.74 | 22.38 | 4 | 33 |
| O00299 | Chloride intracellular channel protein 1 | CLIC1 | *Homo sapiens* | 100.54 | 24.90 | 5 | 33 |
| P59665 | Neutrophil defensin 1 | DEFA1 | *Homo sapiens* | 99.41 | 20.21 | 3 | 33 |
| P30084 | Enoyl-CoA hydratase, mitochondrial | ECHS1 | *Homo sapiens* | 110.92 | 16.21 | 3 | 33 |
| P02794 | Ferritin heavy chain | FTH1 | *Homo sapiens* | 190.73 | 38.80 | 4 | 33 |
| P31150 | Rab GDP dissociation inhibitor alpha | GDI1 | *Homo sapiens* | 177.37 | 19.91 | 4 | 33 |
| O43390 | Heterogeneous nuclear ribonucleoprotein R | HNRNPR | *Homo sapiens* | 123.66 | 11.22 | 6 | 33 |
| P28331 | NADH-ubiquinone oxidoreductase 75 kDa subunit, mitochondrial | NDUFS1 | *Homo sapiens* | 146.80 | 14.86 | 6 | 33 |
| P62140 | Serine/threonine-protein phosphatase PP1-beta catalytic subunit | PPP1CB | *Homo sapiens* | 144.77 | 25.69 | 5 | 33 |
| P08134 | Rho-related GTP-binding protein RhoC | RHOC | *Homo sapiens* | 113.02 | 36.27 | 4 | 33 |
| Q96FQ6 | Protein S100-A16 | S100A16 | *Homo sapiens* | 111.92 | 63.11 | 5 | 33 |
| Q10567 | AP-1 complex subunit beta-1 | AP1B1 | *Homo sapiens* | 155.87 | 4.95 | 3 | 33 |
| P51648 | Fatty aldehyde dehydrogenase | ALDH3A2 | *Homo sapiens* | 101.08 | 11.34 | 4 | 32 |
| P61769 | Beta-2-microglobulin | B2M | *Homo sapiens* | 129.55 | 35.29 | 3 | 32 |
| P30042 | ES1 protein homolog, mitochondrial | C21orf33 | *Homo sapiens* | 184.38 | 26.87 | 3 | 32 |
| Q14103 | Heterogeneous nuclear ribonucleoprotein D0 | HNRNPD | *Homo sapiens* | 96.00 | 19.72 | 5 | 32 |
| P46778 | 60S ribosomal protein L21 | RPL21 | *Homo sapiens* | 112.78 | 31.87 | 4 | 32 |
| P62910 | 60S ribosomal protein L32 | RPL32 | *Homo sapiens* | 102.48 | 27.41 | 3 | 32 |
| P18124 | 60S ribosomal protein L7 | RPL7 | *Homo sapiens* | 123.75 | 34.27 | 7 | 32 |
| P51991 | Heterogeneous nuclear ribonucleoprotein A3 | HNRNPA3 | *Homo sapiens* | 118.23 | 18.52 | 6 | 32 |
| P62249 | 40S ribosomal protein S16 | RPS16 | *Homo sapiens* | 92.94 | 30.14 | 4 | 32 |
| P62269 | 40S ribosomal protein S18 | RPS18 | *Homo sapiens* | 82.25 | 36.84 | 6 | 32 |
| Q8NBS9 | Thioredoxin domain-containing protein 5 | TXNDC5 | *Homo sapiens* | 190.89 | 16.90 | 5 | 32 |
| P55268 | Laminin subunit beta-2 | LAMB2 | *Homo sapiens* | 137.11 | 7.79 | 7 | 32 |
| P07108 | Acyl-CoA-binding protein | DBI | *Homo sapiens* | 158.66 | 41.38 | 2 | 31 |
| Q96KP4 | Cytosolic non-specific dipeptidase | CNDP2 | *Homo sapiens* | 124.80 | 17.05 | 5 | 31 |
| P02511 | Alpha-crystallin B chain | CRYAB | *Homo sapiens* | 115.45 | 34.29 | 5 | 31 |
| P49773 | Histidine triad nucleotide-binding protein 1 | HINT1 | *Homo sapiens* | 238.93 | 54.76 | 3 | 31 |
| Q15181 | Inorganic pyrophosphatase | PPA1 | *Homo sapiens* | 106.49 | 28.72 | 5 | 31 |
| P83731 | 60S ribosomal protein L24 | RPL24 | *Homo sapiens* | 103.39 | 19.11 | 3 | 31 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| Q53EL6 | Programmed cell death protein 4 | PDCD4 | *Homo sapiens* | 151.18 | 11.73 | 3 | 31 |
| P29692 | Elongation factor 1-delta | EEF1D | *Homo sapiens* | 121.20 | 21.71 | 4 | 30 |
| P01625 | Ig kappa chain V-IV region Len | KV402 | *Homo sapiens* | 123.28 | 23.68 | 2 | 30 |
| P55558 | Phospholipid transfer protein | PLTP | *Homo sapiens* | 118.29 | 16.63 | 5 | 30 |
| P51148 | Ras-related protein Rab-5C | RAB5C | *Homo sapiens* | 88.46 | 18.06 | 3 | 30 |
| Q02543 | 60S ribosomal protein L18a | RPL18A | *Homo sapiens* | 82.92 | 25.00 | 4 | 30 |
| P0CW22 | 40S ribosomal protein S17-like | RPS17L | *Homo sapiens* | 84.85 | 49.63 | 4 | 30 |
| P39019 | 40S ribosomal protein S19 | RPS19 | *Homo sapiens* | 93.93 | 43.45 | 7 | 30 |
| P24752 | Acetyl-CoA acetyltransferase, mitochondrial | ACAT1 | *Homo sapiens* | 102.46 | 16.63 | 5 | 30 |
| P36955 | Pigment epithelium-derived factor | SERPINF1 | *Homo sapiens* | 123.08 | 27.03 | 6 | 30 |
| P28838 | Cytosol aminopeptidase | LAP3 | *Homo sapiens* | 128.37 | 16.18 | 5 | 29 |
| P00395 | Cytochrome c oxidase subunit 1 | MT-CO1 | *Homo sapiens* | 114.84 | 7.60 | 2 | 29 |
| P10915 | Hyaluronan and proteoglycan link protein 1 | HAPLN1 | *Homo sapiens* | 128.51 | 36.16 | 7 | 29 |
| O75112 | LIM domain-binding protein 3 | LDB3 | *Homo sapiens* | 159.55 | 12.38 | 6 | 29 |
| O14210 | Lymphocyte antigen 6D | LY6D | *Homo sapiens* | 85.31 | 16.41 | 2 | 29 |
| Q13162 | Peroxiredoxin-4 | PRDX4 | *Homo sapiens* | 110.59 | 26.57 | 5 | 29 |
| P51149 | Ras-related protein Rab-7a | RAB7A | *Homo sapiens* | 91.57 | 46.38 | 7 | 29 |
| Q13228 | Selenium-binding protein 1 | SELENBP1 | *Homo sapiens* | 140.38 | 25.21 | 7 | 29 |
| P23246 | Splicing factor, proline- and glutamine-rich | SFPQ | *Homo sapiens* | 146.88 | 6.79 | 3 | 29 |
| P03973 | Antileukoproteinase | SLPI | *Homo sapiens* | 105.65 | 20.45 | 2 | 29 |
| P49755 | Transmembrane emp24 domain-containing protein 10 | TMED10 | *Homo sapiens* | 95.34 | 18.26 | 4 | 29 |
| P07919 | Cytochrome b-c1 complex subunit 6, mitochondrial | UQCRH | *Homo sapiens* | 151.77 | 29.67 | 2 | 29 |
| P00325 | Alcohol dehydrogenase 1B | ADH1B | *Homo sapiens* | 143.26 | 15.73 | 5 | 28 |
| P07451 | Carbonic anhydrase 3 | CA3 | *Homo sapiens* | 103.24 | 45.77 | 7 | 28 |
| P08311 | Cathepsin G | CTSG | *Homo sapiens* | 86.82 | 18.43 | 4 | 28 |
| P23946 | Chymase | CMA1 | *Homo sapiens* | 104.09 | 38.87 | 7 | 28 |
| P15311 | Ezrin | EZR | *Homo sapiens* | 94.52 | 10.41 | 5 | 28 |
| P08237 | 6-phosphofructokinase, muscle type | PFKM | *Homo sapiens* | 103.32 | 22.82 | 10 | 28 |
| Q96AG4 | Leucine-rich repeat-containing protein 59 | LRRC59 | *Homo sapiens* | 102.16 | 16.61 | 4 | 28 |
| P11177 | Pyruvate dehydrogenase E1 component subunit beta, mitochondrial | PDHB | *Homo sapiens* | 107.90 | 25.35 | 6 | 28 |
| Q687X5 | Metalloreductase STEAP4 | STEAP4 | *Homo sapiens* | 127.59 | 20.26 | 6 | 28 |
| P10599 | Thioredoxin | TXN | *Homo sapiens* | 101.16 | 48.57 | 4 | 28 |
| P13928 | Annexin A8 | ANXA8 | *Homo sapiens* | 98.25 | 28.44 | 6 | 28 |
| O00159 | Unconventional myosin-Ic | MYO1C | *Homo sapiens* | 129.53 | 5.36 | 3 | 28 |
| Q9UL46 | Proteasome activator complex subunit 2 | PSME2 | *Homo sapiens* | 132.41 | 19.67 | 3 | 28 |
| O15143 | Actin-related protein 2/3 complex subunit 1B | ARPC1B | *Homo sapiens* | 148.32 | 13.71 | 3 | 27 |
| Q9BRX8 | Redox-regulatory protein FAM213A | FAM213A | *Homo sapiens* | 72.57 | 16.59 | 3 | 27 |
| O60716 | Catenin delta-1 | CTNND1 | *Homo sapiens* | 99.36 | 10.95 | 8 | 27 |
| Q9UBI6 | Guanine, nucleotide-binding protein G(I)/G(S)/G(O) subunit gamma-12 | GNG12 | *Homo sapiens* | 104.99 | 56.94 | 3 | 27 |
| P62899 | 60S ribosomal protein L31 | RPL31 | *Homo sapiens* | 72.73 | 18.40 | 2 | 27 |
| P62277 | 40S ribosomal protein S13 | RPS13 | *Homo sapiens* | 103.45 | 25.17 | 4 | 27 |
| Q7KZF4 | Staphylococcal nuclease domain-containing protein 1 | SND1 | *Homo sapiens* | 148.87 | 15.60 | 6 | 27 |
| P50990 | T-complex protein 1 subunit theta | CCT8 | *Homo sapiens* | 82.21 | 14.42 | 6 | 27 |
| Q53GQ0 | Estradiol 17-beta-dehydrogenase 12 | HSD17B12 | *Homo sapiens* | 109.00 | 26.60 | 6 | 27 |
| P10316 | HLA class I histocompatibility antigen, A-69 alpha chain | HLA-A | *Homo sapiens* | 102.31 | 29.32 | 7 | 26 |
| P30481 | HLA class I histocompatibility antigen, B-44 alpha chain | HLA-B | *Homo sapiens* | 106.48 | 19.89 | 5 | 20 |
| P05090 | Apolipoprotein D | APOD | *Homo sapiens* | 79.01 | 24.34 | 5 | 26 |
| P00918 | Carbonic anhydrase 2 | CA2 | *Homo sapiens* | 94.23 | 23.85 | 4 | 26 |
| P17858 | 6-phosphofructokinase, liver type | PFKL | *Homo sapiens* | 110.94 | 13.33 | 5 | 26 |
| P01598 | Ig kappa chain V-I region EU | KV106 | *Homo sapiens* | 111.02 | 26.85 | 2 | 26 |
| P08559 | Pyruvate dehydrogenase E1 component subunit alpha, somatic form, mitochondrial | PDHA1 | *Homo sapiens* | 133.81 | 18.46 | 4 | 26 |
| P78527 | DNA-dependent protein kinase catalytic subunit | PRKDC | *Homo sapiens* | 124.68 | 3.83 | 8 | 26 |
| Q86TD4 | Sarcalumenin | SRL | *Homo sapiens* | 88.38 | 7.30 | 6 | 26 |
| Q15185 | Prostaglandin E synthase 3 | PTGES3 | *Homo sapiens* | 94.89 | 18.13 | 2 | 26 |
| P16070 | CD44 antigen | CD44 | *Homo sapiens* | 99.10 | 6.87 | 4 | 26 |
| P54709 | Sodium/potassium-transporting ATPase subunit beta-3 | ATP1B3 | *Homo sapiens* | 104.69 | 17.20 | 3 | 25 |
| O94905 | Erlin-2 | ERLIN2 | *Homo sapiens* | 77.46 | 17.99 | 4 | 25 |
| Q9BSJ8 | Extended synaptotagmin-1 | ESYT1 | *Homo sapiens* | 90.36 | 5.89 | 4 | 25 |
| Q92597 | Protein NDRG1 | NDRG1 | *Homo sapiens* | 119.80 | 22.34 | 5 | 25 |
| Q9UQ80 | Proliferation-associated protein 2G4 | PA2G4 | *Homo sapiens* | 91.68 | 17.51 | 4 | 25 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P42766 | 60S ribosomal protein L35 | RPL35 | *Homo sapiens* | 91.31 | 23.58 | 3 | 25 |
| P54920 | Alpha-soluble NSF attachment protein | NAPA | *Homo sapiens* | 78.90 | 15.93 | 4 | 25 |
| P59998 | Actin-related protein 2/3 complex subunit 4 | ARPC4 | *Homo sapiens* | 67.76 | 11.31 | 2 | 24 |
| O75947 | ATP synthase subunit d, mitochondrial | ATP5H | *Homo sapiens* | 69.10 | 22.36 | 3 | 24 |
| O14958 | Calsequestrin-2 | CASQ2 | *Homo sapiens* | 126.06 | 28.82 | 6 | 24 |
| P13073 | Cytochrome c oxidase subunit 4 isoform 1, mitochondrial | COX4I1 | *Homo sapiens* | 80.35 | 19.53 | 3 | 24 |
| Q16698 | 2,4-dienoyl-CoA reductase, mitochondrial | DECR1 | *Homo sapiens* | 107.00 | 20.60 | 4 | 24 |
| P63167 | Dynein light chain 1, cytoplasmic | DYNLL1 | *Homo sapiens* | 73.08 | 49.44 | 3 | 24 |
| P16401 | Histone H1.5 | HIST1H1B | *Homo sapiens* | 72.23 | 14.60 | 4 | 24 |
| P54819 | Adenylate kinase 2, mitochondrial | AK2 | *Homo sapiens* | 112.91 | 21.34 | 3 | 24 |
| O75489 | NADH dehydrogenase [ubiquinone] iron-sulfur protein 3, mitochondrial | NDUFS3 | *Homo sapiens* | 90.78 | 21.97 | 4 | 24 |
| Q8NC51 | Plasminogen activator inhibitor 1 RNA-binding protein | SERBP1 | *Homo sapiens* | 77.71 | 13.73 | 3 | 24 |
| P62244 | 40S ribosomal protein S15a | RPS15A | *Homo sapiens* | 118.12 | 40.00 | 4 | 24 |
| P17987 | T-complex protein 1 subunit alpha | TCP1 | *Homo sapiens* | 72.80 | 21.40 | 8 | 24 |
| P50991 | T-complex proten 1 subunit delta | CCT4 | *Homo sapiens* | 89.75 | 5.38 | 2 | 24 |
| Q99536 | Synaptic vesicle membrane protein VAT-1 homolog | VAT1 | *Homo sapiens* | 78.40 | 15.78 | 4 | 24 |
| P08195 | 4F2 cell-surface antigen heavy chain | SLC3A2 | *Homo sapiens* | 85.62 | 8.41 | 4 | 24 |
| P52179 | Myomesin-1 | MYOM1 | *Homo sapiens* | 92.87 | 6.94 | 7 | 24 |
| P14550 | Alcohol dehydrogenase [NADP(+)] | AKR1A1 | *Homo sapiens* | 96.16 | 22.46 | 4 | 23 |
| P10768 | S-formylglutathione hydrolase | ESD | *Homo sapiens* | 103.70 | 33.33 | 5 | 23 |
| Q12907 | Vesicular integral-membrane protein VIP36 | LMAN2 | *Homo sapiens* | 114.58 | 27.53 | 5 | 23 |
| P26373 | 60S ribosomal protein L13 | RPL13 | *Homo sapiens* | 80.63 | 16.11 | 3 | 23 |
| P61353 | 60S ribosomal protein L27 | RPL27 | *Homo sapiens* | 68.13 | 41.91 | 5 | 23 |
| P62851 | 40S ribosomal protein S25 | RPS25 | *Homo sapiens* | 75.11 | 24.00 | 4 | 23 |
| P26447 | Protein S100-A4 | S100A4 | *Homo sapiens* | 66.34 | 19.80 | 2 | 23 |
| Q9GZM7 | Tubulointerstitial nephritis antigen-like | TINAGL1 | *Homo sapiens* | 89.95 | 16.92 | 4 | 23 |
| Q13510 | Acid ceramidase | ASAH1 | *Homo sapiens* | 107.39 | 10.13 | 2 | 23 |
| P05556 | Integrin beta-1 | ITGB1 | *Homo sapiens* | 83.72 | 12.03 | 5 | 23 |
| P11766 | Alcohol dehydrogenase class-3 | ADH5 | *Homo sapiens* | 111.95 | 31.82 | 5 | 22 |
| Q9HDC9 | Adipocyte plasma membrane-associated protein | APMAP | *Homo sapiens* | 140.36 | 16.35 | 3 | 22 |
| P00915 | Carbonic anhydrase 1 | CA1 | *Homo sapiens* | 83.52 | 17.62 | 3 | 22 |
| Q97065 | Cytoskeleton-associated protein 4 | CKAP4 | *Homo sapiens* | 73.48 | 22.92 | 10 | 22 |
| P53618 | Coatomer subunit beta | COPB1 | *Homo sapiens* | 101.52 | 5.35 | 3 | 22 |
| Q9Y3I0 | tRNA-splicing ligase RtcB homolog | RTCB | *Homo sapiens* | 94.04 | 16.44 | 3 | 22 |
| O43169 | Cytochrome b5 type B | CYB5B | *Homo sapiens* | 145.18 | 36.30 | 2 | 22 |
| Q8IZP2 | Putative protein FAM10A4 | ST13P4 | *Homo sapiens* | 100.91 | 18.33 | 3 | 22 |
| P52565 | Rho GDP-dissociation inhibitor 1 | ARHGDIA | *Homo sapiens* | 90.83 | 25.00 | 4 | 22 |
| Q02978 | Mitochondrial 2-oxoglutarate/malate carrier protein | SLC25A11 | *Homo sapiens* | 72.43 | 22.61 | 6 | 22 |
| P62857 | 40S ribosomal protein S28 | RPS28 | *Homo sapiens* | 74.20 | 33.33 | 2 | 22 |
| Q16181 | Septin-7 | 41889 | *Homo sapiens* | 127.43 | 9.38 | 2 | 22 |
| P01591 | Immunoglobulin J chain | IGJ | *Homo sapiens* | 67.29 | 23.27 | 3 | 22 |
| P23229 | Integrin alpha-6 | ITGA6 | *Homo sapiens* | 115.73 | 8.05 | 5 | 22 |
| Q9BVK6 | Transmembrane emp24 domain-containing protein 9 | TMED9 | *Homo sapiens* | 93.53 | 25.53 | 4 | 22 |
| P01019 | Angiotensinogen | AGT | *Homo sapiens* | 99.05 | 11.13 | 3 | 21 |
| Q9ULZ3 | Apoptosis-associated speck-like protein containing a CARD | PYCARD | *Homo sapiens* | 100.42 | 15.90 | 2 | 21 |
| O75531 | Barrier-to-autointegration factor | BANF1 | *Homo sapiens* | 78.08 | 40.45 | 2 | 21 |
| P61604 | 10 kDa heat shock protein, mitochondrial | HSPE1 | *Homo sapiens* | 79.74 | 25.49 | 2 | 21 |
| P02741 | C-reactive protein | CRP | *Homo sapiens* | 58.24 | 17.41 | 5 | 21 |
| P02765 | Alpha-2-HS-glycoprotein | AHSG | *Homo sapiens* | 97.90 | 16.89 | 3 | 21 |
| Q14152 | Eukaryotic translation initiation factor 3 subunit A | EIF3A | *Homo sapiens* | 61.17 | 5.14 | 5 | 21 |
| Q9UN36 | Protein NDRG2 | NDRG2 | *Homo sapiens* | 110.96 | 30.46 | 5 | 21 |
| P07225 | Vitamin K-dependent protein S | PROS1 | *Homo sapiens* | 120.92 | 6.07 | 2 | 21 |
| P62750 | 60S ribosomal protein L23a | RPL23A | *Homo sapiens* | 62.82 | 21.15 | 3 | 21 |
| P23297 | Protein S100-A1 | S100A1 | *Homo sapiens* | 93.09 | 23.40 | 2 | 21 |
| Q07666 | KH domain-containing. RNA-binding, signal transduction-associated protein 1 | KHDRBS1 | *Homo sapiens* | 107.45 | 7.67 | 2 | 21 |
| Q9BS26 | Endoplasmic reticulum resident protein 44 | ERP44 | *Homo sapiens* | 146.67 | 17.49 | 4 | 21 |
| Q96QK1 | Vacuolar protein sorting-associatad protein 35 | VPS35 | *Homo sapiens* | 65.50 | 7.29 | 4 | 21 |
| Q03591 | Complement factor H-related protein 1 | CFHR1 | *Homo sapiens* | 74.21 | 18.48 | 4 | 21 |
| P16144 | Integrin beta-4 | ITGB4 | *Homo sapiens* | 99.62 | 4.72 | 4 | 21 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P11279 | Lysosome-associated membrane glycoprotein 1 | LAMP1 | *Homo sapiens* | 83.40 | 8.63 | 3 | 21 |
| P27695 | DNA-(apurinic or apyrimidinic site) lyase | APEX1 | *Homo sapiens* | 94.50 | 16.98 | 3 | 20 |
| Q12797 | Aspartyl/asparaginyl beta-hydroxylase | ASPH | *Homo sapiens* | 94.75 | 7.26 | 3 | 20 |
| Q9UGM3 | Deleted in malignant brain tumors 1 protein | DMBT1 | *Homo sapiens* | 72.30 | 15.04 | 3 | 25 |
| O75874 | Isocitrate dehydrogenase [NADP] cytoplasmic | IDH1 | *Homo sapiens* | 87.46 | 18.60 | 5 | 20 |
| P60866 | 40S ribosomal protein S20 | RPS20 | *Homo sapiens* | 80.66 | 19.33 | 2 | 20 |
| P04271 | Protein S100-B | S100B | *Homo sapiens* | 130.02 | 40.22 | 2 | 20 |
| P07602 | Proactivator polypeptide | PSAP | *Homo sapiens* | 50.52 | 6.49 | 3 | 20 |
| P68036 | Ubiquitin-conjugating enzyme E2 L3 | UBE2L3 | *Homo sapiens* | 111.70 | 24.03 | 2 | 20 |
| P06727 | Apolipoprotein A-IV | APOA4 | *Homo sapiens* | 57.03 | 16.67 | 5 | 19 |
| Q9NVJ2 | ADP-ribosylation factor-like protein 8B | ARL8B | *Homo sapiens* | 89.71 | 22.58 | 3 | 19 |
| P36542 | ATP synthase subunit gamma, mitochondrial | ATP5C1 | *Homo sapiens* | 51.19 | 21.48 | 4 | 19 |
| P51659 | Peroxisomal multifunctional enzyme type 2 | HSD17B4 | *Homo sapiens* | 102.09 | 13.45 | 5 | 19 |
| O60506 | Heterogeneous nuclear ribonucleoprotein Q | SYNCR1P | *Homo sapiens* | 55.74 | 7.87 | 4 | 19 |
| P01765 | Ig heavy chain V-III region TIL | HV304 | *Homo sapiens* | 90.67 | 26.09 | 2 | 19 |
| P42704 | Leucine-rich PPR motif-containing protein, mitochondrial | LRPPRC | *Homo sapiens* | 65.49 | 6.53 | 6 | 19 |
| Q53GG5 | PDZ and LIM domain protein 3 | PDLIM3 | *Homo sapiens* | 106.45 | 15.66 | 3 | 19 |
| P46776 | 60S ribosomal protein L27a | RPL27A | *Homo sapiens* | 52.70 | 14.86 | 2 | 19 |
| P63316 | Troponin C, slow skeletal and cardiac muscles | TNNC1 | *Homo sapiens* | 70.44 | 16.15 | 3 | 19 |
| Q9BXX0 | EMILIN-2 | EMILIN2 | *Homo sapiens* | 66.38 | 4.94 | 3 | 19 |
| Q16836 | Hydroxyacyl-coenzyme A dehydrogenase, mitochondrial | HADH | *Homo sapiens* | 91.31 | 36.62 | 5 | 19 |
| Q9HC84 | Mucin-5B | MUC5B | *Homo sapiens* | 70.98 | 3.04 | 4 | 19 |
| P22061 | Protein-L-isoaspartate(D-aspartate) O-methyltransferase | PCMT1 | *Homo sapiens* | 122.95 | 26.43 | 2 | 19 |
| Q92841 | Probable ATP-dependent RNA helicase DDX17 | DDX17 | *Homo sapiens* | 63.73 | 13.03 | 6 | 19 |
| P02656 | Apolipoprotein C-III | APOC3 | *Homo sapiens* | 81.52 | 27.27 | 2 | 18 |
| P35606 | Coatomer subunit beta' | COPB2 | *Homo sapiens* | 70.13 | 12.58 | 6 | 18 |
| P13804 | Electron transfer flavoprotein subunit alpha, mitochondrial | ETFA | *Homo sapiens* | 55.74 | 13.81 | 3 | 18 |
| P01766 | Ig heavy chain V-III region BRO | HV305 | *Homo sapiens* | 83.54 | 25.00 | 2 | 18 |
| P50213 | Isocitrate dehydrogenase [NAD] subunit alpha, mitochondrial | IDH3A | *Homo sapiens* | 89.89 | 17.76 | 4 | 18 |
| Q99538 | Legumain | LGMN | *Homo sapiens* | 76.81 | 10.16 | 2 | 18 |
| Q04760 | Lactoylglutathione lyase | GLO1 | *Homo sapiens* | 51.46 | 29.89 | 4 | 18 |
| P55209 | Nucleosome assembly protein 1-like 1 | NAP1L1 | *Homo sapiens* | 71.86 | 19.95 | 4 | 18 |
| P62280 | 40S ribosomal protein S11 | RPS11 | *Homo sapiens* | 59.38 | 31.65 | 4 | 18 |
| P62753 | 40S ribosomal protein S6 | RPS6 | *Homo sapiens* | 63.34 | 14.86 | 3 | 18 |
| Q14108 | Lysosome membrane protein 2 | SCARB2 | *Homo sapiens* | 80.31 | 11.09 | 3 | 18 |
| P40227 | T-complex protein 1 subunit zeta | CCT6A | *Homo sapiens* | 120.87 | 12.62 | 3 | 18 |
| P45974 | Ubiquitin carboxyl-terminal hydrolase 5 | USP5 | *Homo sapiens* | 86.69 | 8.86 | 3 | 18 |
| Q14CN2 | Calcium-activated chloride channel regulator 4 | CLCA4 | *Homo sapiens* | 68.23 | 13.06 | 6 | 18 |
| Q9UMN6 | 26S proteosome non-ATPase regulatory subunit 13 | PSMD13 | *Homo sapiens* | 80.72 | 13.03 | 3 | 18 |
| P02730 | Band 3 anion transport protein | SLC4A1 | *Homo sapiens* | 89.76 | 10.98 | 5 | 17 |
| P34810 | Macrosialin | CD68 | *Homo sapiens* | 96.51 | 15.25 | 2 | 17 |
| P78417 | Glutathione S-transferase omega-1 | GSTO1 | *Homo sapiens* | 48.66 | 7.88 | 2 | 17 |
| P11940 | Polyadenylate-binding protein 1 | PABPC1 | *Homo sapiens* | 55.95 | 10.38 | 5 | 17 |
| P62913 | 60S ribosomal protein L11 | RPL11 | *Homo sapiens* | 56.30 | 12.92 | 2 | 17 |
| P42677 | 40S ribosomal protein S27 | RPS27 | *Homo sapiens* | 48.36 | 28.57 | 2 | 17 |
| Q9UHD8 | Septin-9 | 41891 | *Homo sapiens* | 69.77 | 8.70 | 3 | 17 |
| P51571 | Translocon-associated protein subunit delta | SSR4 | *Homo sapiens* | 56.50 | 24.86 | 3 | 17 |
| P40394 | Alcohol dehydrogenase class 4 mu/sigma chain | ADH7 | *Homo sapiens* | 124.34 | 14.51 | 3 | 17 |
| P20073 | Annexin A7 | ANXA7 | *Homo sapiens* | 67.13 | 9.63 | 3 | 17 |
| Q5SSJ5 | Heterochromatin protein 1-binding protein 3 | HP1BP3 | *Homo sapiens* | 64.95 | 6.87 | 2 | 17 |
| P20591 | Interferon-induced GTP-binding protein Mx1 | MX1 | *Homo sapiens* | 88.82 | 16.47 | 6 | 17 |
| P35611 | Alpha-adducin | ADD1 | *Homo sapiens* | 92.65 | 8.41 | 3 | 16 |
| P24539 | ATP synthase subunit b, mitochondrial | ATP5F1 | *Homo sapiens* | 57.61 | 19.53 | 4 | 16 |
| P02462 | Collagen alpha-1(IV) chain | COL4A1 | *Homo sapiens* | 61.11 | 4.79 | 5 | 16 |
| P08246 | Neutrophil elastase | ELANE | *Homo sapiens* | 108.82 | 20.60 | 2 | 16 |
| P52566 | Rho GDP-dissociation inhibitor 2 | ARHGDIB | *Homo sapiens* | 77.52 | 33.83 | 3 | 16 |
| Q1KMD3 | Heterogeneous nuclear ribonucleoprotein U-like protein 2 | HNRNPUL2 | *Homo sapiens* | 62.82 | 10.98 | 4 | 16 |
| Q9Y4L1 | Hypoxia up-regulated protein 1 | HYOU1 | *Homo sapiens* | 66.01 | 9.21 | 5 | 16 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P05198 | Eukaryotic translation initiation factor 2 subunit 1 | EIF2S1 | *Homo sapiens* | 64.58 | 23.81 | 4 | 16 |
| Q16795 | NADH denydrogenase [Ubiquinone] 1 alpha subcomplex subunit 9, mitochondrial | NDUFA9 | *Homo sapiens* | 51.83 | 17.77 | 5 | 16 |
| Q14980 | Nuclear mitotic apparatus protein 1 | NUMA1 | *Homo sapiens* | 89.24 | 2.84 | 3 | 16 |
| Q9UMS4 | Pre-mRNA-processing factor 19 | PRPF19 | *Homo sapiens* | 79.00 | 6.35 | 2 | 16 |
| Q15046 | Lysine-tRNA ligase | KARS | *Homo sapiens* | 51.73 | 9.21 | 3 | 16 |
| P22735 | Protein-glutamine gamma-glutamyltransferase K | TGM1 | *Homo sapiens* | 62.57 | 12.12 | 5 | 16 |
| Q9Y3B3 | Transmembrane emp24 domain-containing protein 7 | TMED7 | *Homo sapiens* | 65.77 | 19.64 | 3 | 16 |
| P47985 | Cytochrome b-c1 complex subunit Rieske, miochondrial | UQCRFS1 | *Homo sapiens* | 76.88 | 17.52 | 3 | 16 |
| O75339 | Cartilage intermediate layer protein 1 | CILP | *Homo sapiens* | 49.16 | 4.65 | 4 | 16 |
| P11047 | Laminin subunit gamma-1 | LAMC1 | *Homo sapiens* | 58.80 | 5.03 | 5 | 16 |
| P13796 | Plastin-2 | LCP1 | *Homo sapiens* | 56.95 | 11.32 | 5 | 16 |
| P61160 | Actin-related protein 2 | ACTR2 | *Homo sapiens* | 43.44 | 8.88 | 3 | 15 |
| O15144 | Actin-related protein 2/3 complex subunit 2 | ARPC2 | *Homo sapiens* | 53.55 | 28.67 | 6 | 15 |
| P07358 | Complement component C8 beta chain | C8B | *Homo sapiens* | 69.74 | 8.12 | 2 | 15 |
| O75131 | Copine-3 | CPNE3 | *Homo sapiens* | 67.21 | 11.17 | 4 | 15 |
| P22087 | rRNA 2'-O-methyltransferase fibrillanin | FBL | *Homo sapiens* | 50.51 | 15.89 | 4 | 15 |
| Q93052 | Lipoma-preferred partner | LPP | *Homo sapiens* | 96.40 | 3.92 | 2 | 15 |
| Q9UHQ9 | NADH-cytochrome b5 reductase 1 | CYB5R1 | *Homo sapiens* | 107.11 | 15.41 | 2 | 15 |
| P13667 | Protein disulfide-isomerase A4 | PDIA4 | *Homo sapiens* | 45.77 | 10.85 | 5 | 15 |
| Q15437 | Protein transport protein Sec23B | SEC23B | *Homo sapiens* | 64.93 | 6.52 | 2 | 15 |
| P48643 | T-complex protein 1 subunit epsilon | CCT5 | *Homo sapiens* | 71.26 | 14.97 | 4 | 15 |
| P49419 | Alpha-aminoadipic semialdehyde dehydrogenase | ALDH7A1 | *Homo sapiens* | 47.15 | 16.33 | 5 | 15 |
| P01031 | Complement C5 | C5 | *Homo sapiens* | 60.01 | 5.19 | 5 | 15 |
| O14561 | Acyl carrier protein, mitochondrial | NDUFAB1 | *Homo sapiens* | 63.69 | 15.38 | 2 | 14 |
| O00499 | Myc box-dependent-interacting protein 1 | BIN1 | *Homo sapiens* | 61.79 | 14.67 | 5 | 14 |
| P30043 | Flavin reductase (NADPH) | BLVRB | *Homo sapiens* | 45.07 | 23.79 | 3 | 14 |
| P55290 | Cadherin-13 | CDH13 | *Homo sapiens* | 63.95 | 4.91 | 2 | 14 |
| Q13938 | Calcyphosin | CAPS | *Homo sapiens* | 49.97 | 26.98 | 4 | 14 |
| P42126 | Enoyl-CoA delta isomerase 1, mitochondrial | ECI1 | *Homo sapiens* | 44.26 | 20.53 | 4 | 14 |
| Q9H4M9 | EH domain-containing protein 1 | EHD1 | *Homo sapiens* | 58.11 | 7.49 | 2 | 14 |
| P19367 | Hexokinase-1 | HK1 | *Homo sapiens* | 52.93 | 9.16 | 6 | 14 |
| O60662 | Kelch repeat and BTB domain-containing protein 10 | KLHL41 | *Homo sapiens* | 58.11 | 8.42 | 5 | 14 |
| P10620 | Microsomal glutathione S-transferase 1 | MGST1 | *Homo sapiens* | 39.47 | 18.71 | 2 | 14 |
| Q13765 | Nascent polypeptide-associated complex subunit alpha | NACA | *Homo sapiens* | 45.56 | 12.56 | 2 | 14 |
| O95299 | NADH dehydrogenase [ubiquinone] 1 alpha subcomplex subunit 10, mitochondrial | NDUFA10 | *Homo sapiens* | 71.85 | 13.24 | 2 | 14 |
| Q9UHG3 | Prenylcysteine oxidase 1 | PCYOX1 | *Homo sapiens* | 50.92 | 12.28 | 4 | 14 |
| Q15293 | Reticulocalbin-1 | RCN1 | *Homo sapiens* | 54.12 | 18.13 | 4 | 14 |
| Q07955 | Serine/arginine-rich splicing factor 1 | SRSF1 | *Homo sapiens* | 46.76 | 17.34 | 3 | 14 |
| P30626 | Sorcin | SRI | *Homo sapiens* | 52.69 | 16.16 | 2 | 14 |
| Q04837 | Single-stranded DNA-binding protein mitochondrial | SSBP1 | *Homo sapiens* | 45.28 | 32.43 | 3 | 14 |
| Q9UJZ1 | Stomatin-like protein 2 | STOML2 | *Homo sapiens* | 49.54 | 17.13 | 3 | 14 |
| O75746 | Calcium-binding mitochondrial carrier protein Aralar1 | SLC25A12 | *Homo sapiens* | 73.38 | 8.11 | 2 | 14 |
| Q9Y6C2 | EMILIN-1 | EMILIN1 | *Homo sapiens* | 49.93 | 8.56 | 6 | 14 |
| Q07954 | Prolow-density lipoprotein receptor-related protein 1 | LRP1 | *Homo sapiens* | 62.18 | 2.07 | 5 | 14 |
| P36952 | Serpin B5 | SERPINB5 | *Homo sapiens* | 55.15 | 14.13 | 3 | 14 |
| P20290 | Transcription factor BTF3 | BTF3 | *Homo sapiens* | 74.92 | 22.82 | 2 | 13 |
| P02745 | Complement C1q subcomponent subunit A | C1QA | *Homo sapiens* | 75.24 | 13.47 | 2 | 13 |
| P47756 | F-actin-capping protein subunit beta | CAPZB | *Homo sapiens* | 51.06 | 26.35 | 4 | 13 |
| Q9Y678 | Coatomer subunit gamma-1 | COPG1 | *Homo sapiens* | 48.48 | 11.21 | 4 | 13 |
| P05413 | Fatty acid-binding protein, heart | FABP3 | *Homo sapiens* | 41.42 | 38.35 | 4 | 13 |
| P14314 | Glucosidase 2 subunit beta | PRKCSH | *Homo sapiens* | 51.99 | 11.36 | 5 | 13 |
| O00303 | Eukaryotic translation initiation factor 3 subunit F | EIF3F | *Homo sapiens* | 53.04 | 19.05 | 4 | 13 |
| P04434 | Ig kappa chain V-III region VH (Fragment) | KV310 | *Homo sapiens* | 33.54 | 23.28 | 2 | 13 |
| O00232 | 26S proteasome non-ATPase regulatory subunit 12 | PSMD12 | *Homo sapiens* | 45.14 | 7.46 | 2 | 13 |
| P98179 | Putative RNA-binding protein 3 | RBM3 | *Homo sapiens* | 66.79 | 31.85 | 2 | 13 |
| P21589 | 5'-nucleotidase | NT5E | *Homo sapiens* | 54.86 | 9.23 | 2 | 12 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| P00966 | Argininosuccinate synthase | ASS1 | *Homo sapiens* | 69.29 | 10.19 | 2 | 12 |
| P08571 | Monocyte differentiaton antigen CD14 | CD14 | *Homo sapiens* | 50.36 | 14.40 | 3 | 12 |
| Q9ULV4 | Coronin-1C | CORO1C | *Homo sapiens* | 75.32 | 13.29 | 2 | 12 |
| P21912 | Succinate dehydrogenase [ubiquinone] iron-sulfur subunit, mitochondrial | SDHB | *Homo sapiens* | 44.99 | 10.71 | 2 | 12 |
| P35573 | Glycogen debrenching enzyme | AGL | *Homo sapiens* | 60.07 | 3.26 | 3 | 12 |
| Q96AB3 | Isochorismatase domain-containing protein 2, mitochondrial | ISOC2 | *Homo sapiens* | 55.91 | 25.85 | 2 | 12 |
| P30085 | UMP-CMP kinase | CMPK1 | *Homo sapiens* | 56.96 | 22.96 | 3 | 12 |
| P80188 | Neutrophil gelatinase-associated lipocalin | LCN2 | *Homo sapiens* | 35.66 | 26.77 | 3 | 12 |
| P61970 | Nuclear transport factor 2 | NUTF2 | *Homo sapiens* | 70.89 | 33.86 | 2 | 12 |
| O75915 | PRA1 family protein 3 | ARL6IP5 | *Homo sapiens* | 42.87 | 15.96 | 2 | 12 |
| P62491 | Ras-related protein Rab-11A | RAB11A | *Homo sapiens* | 36.42 | 16.20 | 3 | 12 |
| P84098 | 60S ribosomal protein L19 | RPL19 | *Homo sapiens* | 35.15 | 30.10 | 6 | 12 |
| Q01105 | Protein SET | SET | *Homo sapiens* | 69.40 | 17.24 | 2 | 12 |
| P39687 | Acidic leucine-rich nuclear phosphoprotein 32 family member A | ANP32A | *Homo sapiens* | 38.78 | 14.06 | 3 | 11 |
| Q96CW1 | AP-2 complex subunit mu | AP2M1 | *Homo sapiens* | 50.41 | 11.72 | 3 | 11 |
| P02652 | Apolipoprotein A-II | APOA2 | *Homo sapiens* | 30.45 | 39.00 | 3 | 11 |
| P18859 | ATP synthase-coupling factor 6, mitochondrial | ATP5J | *Homo sapiens* | 45.89 | 30.56 | 2 | 11 |
| Q99715 | Collagen alpha-1(XII) chain | COL12A1 | *Homo sapiens* | 42.85 | 1.99 | 4 | 11 |
| Q9Y394 | Dehydrogenase/reductase SDR family member 7 | DHRS7 | *Homo sapiens* | 51.65 | 16.52 | 3 | 11 |
| O43143 | Putative pre-mRNA-splicing factor ATP-dependant RNA helicase DHX15 | DHX15 | *Homo sapiens* | 35.61 | 4.28 | 2 | 11 |
| P11166 | Solute carrier family 2, facilitated glucose transporter member 1 | SLC2A1 | *Homo sapiens* | 29.34 | 6.30 | 3 | 11 |
| P38159 | RNA-binding motif protein, X chromosome | RBMX | *Homo sapiens* | 31.82 | 5.37 | 2 | 11 |
| P01714 | Ig lambda chain V-III region SH | LV301 | *Homo sapiens* | 37.60 | 25.00 | 2 | 11 |
| P23368 | NAD-dependent malic enzyme, mitochondrial | ME2 | *Homo sapiens* | 64.29 | 15.07 | 3 | 11 |
| Q9Y6C9 | Mitochondrial carrier homolog 2 | MTCH2 | *Homo sapiens* | 42.05 | 16.83 | 3 | 11 |
| P49821 | NADH dehydrogenase [ubiquinone] flavoprotein 1, mitochondrial | NDUFV1 | *Homo sapiens* | 40.34 | 17.24 | 4 | 11 |
| Q9Y2J8 | Protein-arginine deiminase type-2 | PADI2 | *Homo sapiens* | 55.16 | 5.56 | 2 | 11 |
| P01833 | Polymeric immunoglobulin receptor | PIGR | *Homo sapiens* | 59.96 | 4.84 | 2 | 11 |
| P61019 | Ras-related protein Rab-2A | RAB2A | *Homo sapiens* | 38.60 | 12.74 | 2 | 11 |
| P40763 | Signal transducer and activator of transcription 3 | STAT3 | *Homo sapiens* | 75.61 | 8.70 | 3 | 11 |
| Q15363 | Transmembrane emp24 domain-containing protein 2 | TMED2 | *Homo sapiens* | 37.40 | 18.41 | 3 | 11 |
| P07996 | Thrombospondin-1 | THBS1 | *Homo sapiens* | 51.87 | 2.74 | 2 | 11 |
| O75643 | U5 small nuclear ribonucleoprotein 200 kDa helicase | SNRNP200 | *Homo sapiens* | 58.36 | 4.21 | 4 | 11 |
| Q15029 | 116 kDa U5 small nuclear ribonucleoprotein component | EFTUD2 | *Homo sapiens* | 69.20 | 3.81 | 2 | 11 |
| Q9UH99 | SUN domain-containing protein 2 | SUN2 | *Homo sapiens* | 49.31 | 10.46 | 4 | 11 |
| O75533 | Splicing factor 3B subunit 1 | SF3B1 | *Homo sapiens* | 48.28 | 2.45 | 2 | 11 |
| P46977 | Dolichyl-diphosphooligosaccharide-protein glycosyltransferase subunit STT3A | STT3A | *Homo sapiens* | 64.42 | 5.82 | 2 | 11 |
| Q16658 | Fascin | FSCN1 | *Homo sapiens* | 51.61 | 8.11 | 2 | 10 |
| Q9NZ01 | Very-long-chain enoyl-CoA reductase | TECR | *Homo sapiens* | 36.79 | 9.42 | 2 | 10 |
| P08263 | Glutathione S-transferase A1 | GSTA1 | *Homo sapiens* | 28.39 | 17.57 | 3 | 10 |
| Q13751 | Laminin subunit beta-3 | LAMB3 | *Homo sapiens* | 41.29 | 6.06 | 4 | 10 |
| P37837 | Transaldolase | TALDO1 | *Homo sapiens* | 32.08 | 14.54 | 4 | 10 |
| Q6ZMU5 | Tripartite motif-containing protein 72 | TRIM72 | *Homo sapiens* | 52.07 | 14.47 | 4 | 10 |
| P53634 | Dipeptidyl peptidase 1 | CTSC | *Homo sapiens* | 42.71 | 12.31 | 3 | 10 |
| P14543 | Nidogen-1 | NID1 | *Homo sapiens* | 41.25 | 5.53 | 4 | 10 |
| Q9NYU2 | UDP-glucose:glycoprotein glycosyltransferase 1 | UGGT1 | *Homo sapiens* | 34.11 | 6.88 | 5 | 10 |
| B0FP48 | Uroplakin-3b-like protein | UPK3BL | *Homo sapiens* | 29.21 | 13.31 | 3 | 10 |
| P61163 | Alpha-centractin | ACTR1A | *Homo sapiens* | 38.24 | 10.11 | 2 | 9 |
| P04745 | Alpha-amylase 1 | AMY1A | *Homo sapiens* | 49.22 | 15.07 | 4 | 9 |
| P51572 | B-cell receptor-associated protein 31 | BCAP31 | *Homo sapiens* | 25.93 | 21.54 | 4 | 9 |
| P24592 | Insulin-like growth factor-binding protein 6 | IGFBP6 | *Homo sapiens* | 48.09 | 18.33 | 2 | 9 |
| Q13421 | Mesothelin | MSLN | *Homo sapiens* | 42.32 | 6.35 | 2 | 9 |
| P22307 | Non-specific lipid-transfer protein | SCP2 | *Homo sapiens* | 26.93 | 6.95 | 3 | 9 |
| P55786 | Puromycin-sensitive aminopeptidase | NPEPPS | *Homo sapiens* | 30.12 | 6.42 | 3 | 9 |
| P61254 | 60S ribosomal protein L26 | RPL26 | *Homo sapiens* | 23.65 | 17.93 | 3 | 9 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
| --- | --- | --- | --- | --- | --- | --- | --- |
| P67812 | Signal peptidase complex catalytic subunit SEC11A | SEC11A | *Homo sapiens* | 22.32 | 15.64 | 3 | 9 |
| Q5VXT5 | Synaptophysin-like protein 2 | SYPL2 | *Homo sapiens* | 33.05 | 10.66 | 2 | 9 |
| P13693 | Translationally-controlled tumor protein | TPT1 | *Homo sapiens* | 31.41 | 12.21 | 2 | 9 |
| Q9UDW1 | Cytochrome b-c1 complex subunit 9 | UQCR10 | *Homo sapiens* | 29.74 | 38.10 | 2 | 9 |
| Q6YHK3 | CD109 antigen | CD109 | *Homo sapiens* | 30.44 | 3.88 | 3 | 8 |
| Q9Y224 | UPF0568 protein C14orf166 | C14orf166 | *Homo sapiens* | 41.55 | 17.62 | 3 | 8 |
| Q16610 | Extracellular matrix protein 1 | ECM1 | *Homo sapiens* | 35.88 | 6.67 | 2 | 8 |
| Q13347 | Eukaryotic translation initiation factor 3 subunit I | EIF3I | *Homo sapiens* | 36.42 | 16.31 | 3 | 8 |
| P40261 | Nicotinamide N-methyltransferase | NNMT | *Homo sapiens* | 39.05 | 12.12 | 2 | 8 |
| O75340 | Programmed cell death protein 6 | PDCD6 | *Homo sapiens* | 25.68 | 12.57 | 2 | 8 |
| P62714 | Serine/threonine-protein phosphatase 2A catalytic subunit beta isoform | PPP2CB | *Homo sapiens* | 42.30 | 12.94 | 2 | 8 |
| P28066 | Proteasome subunit alpha type-5 | PSMA5 | *Homo sapiens* | 35.94 | 29.88 | 4 | 8 |
| P61224 | Ras-related protein Rap-1b | RAP1B | *Homo sapiens* | 25.05 | 26.09 | 4 | 8 |
| Q9Y265 | RuvB-like 1 | RUVBL1 | *Homo sapiens* | 28.51 | 8.99 | 3 | 8 |
| P61619 | Protein transport protein Sec61 subunit alpha isoform 1 | SEC61A1 | *Homo sapiens* | 28.34 | 6.51 | 2 | 8 |
| Q8TCJ2 | Dolichyl-diphosphooligosaccharide--protein glycosyltransferase subunit STT3B | STT3B | *Homo sapiens* | 38.82 | 3.51 | 2 | 8 |
| Q92896 | Golgi apparatus protein 1 | GLG1 | *Homo sapiens* | 48.26 | 4.92 | 3 | 8 |
| P10515 | Dihydrolipoyllysine-residue acetyltransferase component of pyruvate dehydrogenase complex, mitochondrial | DLAT | *Homo sapiens* | 31.01 | 10.51 | 4 | 8 |
| Q6NUK1 | Calcium-binding mitochondrial carrier protein SCaMC-1 | SLC25A24 | *Homo sapiens* | 21.03 | 6.92 | 3 | 8 |
| O43488 | Aflatoxin B1 aldehyde reductase member 2 | AKR7A2 | *Homo sapiens* | 44.29 | 13.37 | 2 | 7 |
| O15511 | Actin-related protein 2/3 complex subunit 5 | ARPC5 | *Homo sapiens* | 27.05 | 21.19 | 2 | 7 |
| P34897 | Serine hydroxymethyltransferase, mitochondrial | SHMT2 | *Homo sapiens* | 18.65 | 5.36 | 2 | 7 |
| P07305 | Histone H1.0 | H1F0 | *Homo sapiens* | 17.16 | 11.34 | 2 | 7 |
| Q12906 | Interleukin enhancer-binding factor 3 | ILF3 | *Homo sapiens* | 21.77 | 4.47 | 3 | 7 |
| Q08380 | Galectin-3-binding protein | LGALS3BP | *Homo sapiens* | 29.58 | 4.96 | 2 | 7 |
| P16050 | Arachidonate 15-lipoxygenase | ALOX15 | *Homo sapiens* | 33.24 | 6.19 | 2 | 7 |
| P01700 | Ig lambda chain V-I region HA | LV102 | *Homo sapiens* | 19.51 | 18.75 | 2 | 7 |
| Q99972 | Myocilin | MYOC | *Homo sapiens* | 20.28 | 10.91 | 4 | 7 |
| Q96AC1 | Fermitin family homolog 2 | FERMT2 | *Homo sapiens* | 22.01 | 5.00 | 2 | 7 |
| Q9Y446 | Plakophilin-3 | PKP3 | *Homo sapiens* | 25.64 | 6.15 | 3 | 7 |
| P25786 | Proteasome subunit alpha type-1 | PSMA1 | *Homo sapiens* | 32.33 | 19.77 | 3 | 7 |
| Q99460 | 26S proteasome non-ATPase regulatory subunit 1 | PSMD1 | *Homo sapiens* | 30.78 | 5.98 | 3 | 7 |
| P06703 | Protein S100-A6 | S100A6 | *Homo sapiens* | 24.60 | 40.00 | 3 | 7 |
| P23526 | Adenosylhomocysteinase | AHCY | *Homo sapiens* | 25.52 | 10.65 | 3 | 7 |
| Q96PL1 | Secretoglobin family 3A member 2 | SCGB3A2 | *Homo sapiens* | 27.23 | 33.33 | 2 | 7 |
| P54577 | Tyrosine--tRNA ligase, cytoplasmic | YARS | *Homo sapiens* | 34.21 | 10.61 | 3 | 7 |
| O60701 | UDP-glucose 6-dehydrogenase | UGDH | *Homo sapiens* | 22.69 | 8.30 | 2 | 7 |
| P40121 | Macrophage-capping protein | CAPG | *Homo sapiens* | 27.36 | 13.51 | 3 | 7 |
| Q7L2H7 | Eukaryotic translation initiation factor 3 subunit M | EIF3M | *Homo sapiens* | 34.24 | 12.57 | 3 | 7 |
| Q6YN16 | Hydroxysteroid dehydrogenase-like protein 2 | HSDL2 | *Homo sapiens* | 27.28 | 8.85 | 2 | 7 |
| Q969G5 | Protein kinase C delta-binding protein | PRKCDBP | *Homo sapiens* | 24.98 | 13.79 | 3 | 7 |
| P35613 | Basigin | BSG | *Homo sapiens* | 25.29 | 8.31 | 2 | 6 |
| P09871 | Complement C1s subcomponent | C1S | *Homo sapiens* | 23.20 | 4.36 | 2 | 6 |
| Q92499 | ATP-dependent RNA helicase DDX1 | DDX1 | *Homo sapiens* | 28.65 | 6.89 | 3 | 6 |
| Q9UBX5 | Fibulin-5 | FBLN5 | *Homo sapiens* | 19.62 | 6.70 | 2 | 6 |
| O75955 | Flotillin-1 | FLOT1 | *Homo sapiens* | 20.47 | 7.73 | 2 | 6 |
| P21695 | Glycerol-3-phosphate dehydrogenase [NAD(+)], cytoplasmic | GPD1 | *Homo sapiens* | 27.44 | 22.64 | 4 | 6 |
| O14558 | Heat shock protein beta-6 | HSPB6 | *Homo sapiens* | 23.37 | 21.88 | 2 | 6 |
| P20810 | Calpastatin | CAST | *Homo sapiens* | 25.02 | 6.21 | 2 | 6 |
| Q12995 | Interleukin enhancer-binding factor 2 | ILF2 | *Homo sapiens* | 23.04 | 18.97 | 4 | 6 |
| P48729 | Casein kinase I isoform alpha | CSNK1A1 | *Homo sapiens* | 15.74 | 8.53 | 2 | 6 |
| P80748 | Ig lambda chain V-III region LOI | LV302 | *Homo sapiens* | 19.76 | 21.62 | 2 | 6 |
| P51970 | NADH dehydrogenase [ubiquinone] 1 alpha subcomplex subunit 8 | NDUFA8 | *Homo sapiens* | 21.24 | 29.07 | 3 | 6 |
| Q6P2Q9 | Pre-mRNA-processing-splicing factor 8 | PRPF8 | *Homo sapiens* | 27.11 | 1.88 | 2 | 6 |
| P62333 | 26S protease regulatory subunit 10B | PSMC6 | *Homo sapiens* | 22.70 | 7.97 | 2 | 6 |
| P63000 | Ras-related C3 botulinum toxin substrate 1 | RAC1 | *Homo sapiens* | 16.60 | 22.40 | 4 | 6 |
| Q15393 | Splicing factor 3B subunit 3 | SF3B3 | *Homo sapiens* | 28.58 | 3.20 | 2 | 6 |

TABLE 1-continued

Lists of proteins identified in LC-MS/MS analysis of scaffold only, VFF in scaffold, VFE on scaffold, engineered VF mucosa and native VF mucosa. Identifications were based on a 1% false discovery rate. The scaffold was sourced from *Rattus norvegicus*; VFF, VFE and native VF mucosa were sourced from *Homo sapiens*. Proteins are listed in order of descending peptide spectra matches.

| UniProt accession number | Protein name | Gene symbol | Organism | Score | Sequence coverage (%) | Unique peptides | Peptide spectra matches |
|---|---|---|---|---|---|---|---|
| O75368 | SH3 domain-binding glutamic acid-rich-like protein | SH3BGRL | Homo sapiens | 16.99 | 27.19 | 2 | 6 |
| P26640 | Valine-tRNA ligase | VARS | Homo sapiens | 25.03 | 2.37 | 2 | 6 |
| P61421 | V-type proton ATPase subunit d 1 | ATP6V0D1 | Homo sapiens | 20.75 | 10.26 | 2 | 6 |
| Q14254 | Flotillin-2 | FLOT2 | Homo sapiens | 22.29 | 7.24 | 2 | 6 |
| P27169 | Serum paraoxonase/arylesterase 1 | PON1 | Homo sapiens | 19.01 | 21.97 | 3 | 6 |
| P04275 | von Willebrand factor | VWF | Homo sapiens | 18.91 | 1.03 | 2 | 6 |
| P51858 | Hepatoma-derived growth factor | HDGF | Homo sapiens | 21.84 | 14.17 | 2 | 5 |
| Q96CX2 | BTB/POZ domain-containing protein KCTD12 | KCTD12 | Homo sapiens | 13.69 | 7.08 | 2 | 5 |
| Q13753 | Laminin subunit gamma-2 | LAMC2 | Homo sapiens | 29.52 | 4.11 | 2 | 5 |
| P43243 | Matrin-3 | MATR3 | Homo sapiens | 15.97 | 3.78 | 2 | 5 |
| Q9NP98 | Myozenin-1 | MYOZ1 | Homo sapiens | 25.04 | 11.04 | 2 | 5 |
| Q9P2E9 | Ribosome-binding protein 1 | RRBP1 | Homo sapiens | 13.24 | 2.34 | 3 | 5 |
| P49458 | Signal recognition particle 9 kDa protein | SRP9 | Homo sapiens | 14.05 | 23.26 | 2 | 5 |
| P42224 | Signal transducer and activator of transcription 1-alpha/beta | STAT1 | Homo sapiens | 18.45 | 4.00 | 2 | 5 |
| O14907 | Tax1-binding protein 3 | TAX1BP3 | Homo sapiens | 18.96 | 28.23 | 2 | 5 |
| Q04446 | 1,4-alpha-glucan-branching enzyme | GBE1 | Homo sapiens | 20.75 | 5.13 | 2 | 5 |
| O15230 | Laminin subunit alpha-5 | LAMA5 | Homo sapiens | 29.62 | 1.35 | 2 | 5 |
| Q00341 | Vigilin | HDLBP | Homo sapiens | 24.79 | 3.08 | 2 | 5 |
| P30049 | ATP synthase subunit delta, mitochondrial | ATP5D | Homo sapiens | 12.28 | 13.69 | 2 | 4 |
| P23141 | Liver carboxylesterase 1 | CES1 | Homo sapiens | 14.18 | 5.47 | 2 | 4 |
| Q9UBQ7 | Glyoxylate reductase/hydroxypyruvate reductase | GRHPR | Homo sapiens | 17.86 | 12.20 | 2 | 4 |
| P07686 | Beta-hexosaminidase subunit beta | HEXB | Homo sapiens | 18.55 | 8.63 | 2 | 4 |
| P05455 | Lupus La protein | SSB | Homo sapiens | 17.39 | 10.78 | 3 | 4 |
| P19404 | NADH dehydrogenase [ubiquinone] flavoprotein 2, mitochondrial | NDUFV2 | Homo sapiens | 10.94 | 9.64 | 2 | 4 |
| Q13423 | NAD(P) transhydrogenase, mitochondrial | NNT | Homo sapiens | 21.45 | 3.41 | 2 | 4 |
| P04181 | Ornithine aminotransferase, mitochondrial | OAT | Homo sapiens | 11.54 | 7.29 | 2 | 4 |
| P11498 | Pyruvate carboxylase, mitochondrial | PC | Homo sapiens | 24.43 | 3.40 | 2 | 4 |
| Q00765 | Receptor expression-enhancing protein 5 | REEP5 | Homo sapiens | 11.75 | 10.05 | 2 | 4 |
| Q9NVA2 | Septin-11 | 41893 | Homo sapiens | 9.98 | 4.90 | 2 | 4 |
| Q01130 | Serine/arginine-rich splicing factor 2 | SRSF2 | Homo sapiens | 13.67 | 12.67 | 2 | 4 |
| P38606 | V-type proton ATPase catalytic subunit A | ATP6V1A | Homo sapiens | 15.43 | 7.46 | 3 | 4 |
| O14980 | Exportin-1 | XPO1 | Homo sapiens | 21.82 | 3.27 | 2 | 4 |
| Q8IVF2 | Protein AHNAK2 | AHNAK2 | Homo sapiens | 11.71 | 5.18 | 2 | 4 |
| Q9UBG3 | Cornulin | CRNN | Homo sapiens | 15.63 | 16.77 | 4 | 4 |
| Q06033 | Inter-alpha-trypsin inhibitor heavy chain H3 | ITIH3 | Homo sapiens | 20.77 | 5.51 | 2 | 4 |
| Q16787 | Laminin subunit alpha-3 | LAMA3 | Homo sapiens | 25.74 | 1.32 | 2 | 4 |
| P62330 | ADP-ribosylation factor 6 | ARF6 | Homo sapiens | 11.13 | 20.00 | 2 | 3 |
| P50402 | Emerin | EMD | Homo sapiens | 11.98 | 16.54 | 2 | 3 |
| P15104 | Glutamine synthetase | GLUL | Homo sapiens | 11.91 | 9.92 | 2 | 3 |
| P10644 | cAMP-dependent protein kinase type I-alpha regulatory subunit | PRKAR1A | Homo sapiens | 13.14 | 7.87 | 2 | 3 |
| P13473 | Lysosome-associated membrane glycoprotein 2 | LAMP2 | Homo sapiens | 9.53 | 4.88 | 2 | 3 |
| Q9BQ69 | O-acetyl-ADP-ribose deacetylase MACROD1 | MACROD1 | Homo sapiens | 15.78 | 11.38 | 2 | 3 |
| P53007 | Tricarboxylate transport protein, mitochondrial | SLC25A1 | Homo sapiens | 13.07 | 15.11 | 2 | 3 |
| P49327 | Fatty acid synthase | FASN | Homo sapiens | 13.24 | 2.35 | 3 | 3 |
| P07476 | Involucrin | IVL | Homo sapiens | 14.25 | 6.84 | 2 | 3 |
| Q5VTT5 | Myomesin-3 | MYOM3 | Homo sapiens | 12.97 | 4.73 | 3 | 3 |
| P07814 | Bifunctional glutamate/proline-tRNA ligase | EPRS | Homo sapiens | 17.22 | 3.24 | 2 | 3 |
| P12830 | Cadherin-1 | CDH1 | Homo sapiens | 6.40 | 4.08 | 2 | 2 |
| P04040 | Catalase | CAT | Homo sapiens | 8.25 | 6.45 | 2 | 2 |
| Q13217 | DnaJ homolog subfamiy C member 3 | DNAJC3 | Homo sapiens | 9.96 | 9.72 | 2 | 2 |
| Q9UBY9 | Heat shock protein beta-7 | HSPB7 | Homo sapiens | 6.55 | 18.82 | 2 | 2 |
| Q9Y262 | Eukaryotic translation initiation factor 3 subunit L | EIF3L | Homo sapiens | 9.03 | 4.26 | 2 | 2 |
| Q92804 | TATA-binding protein-associated factor 2N | TAF15 | Homo sapiens | 5.57 | 4.39 | 2 | 2 |
| P02753 | Retinol-binding protein 4 | RBP4 | Homo sapiens | 6.32 | 9.95 | 2 | 2 |
| Q8NB12 | SET and MYND domain containing protein 1 | SMYD1 | Homo sapiens | 5.69 | 6.53 | 2 | 2 |
| Q9NSE4 | Isoleucine-tRNA ligase, mitochondrial | IARS2 | Homo sapiens | 6.92 | 2.77 | 2 | 2 |
| Q9HD45 | Transmembrane 9 superfamily member 3 | TM9SF3 | Homo sapiens | 6.34 | 5.26 | 2 | 2 |
| Q9P0L0 | Vesicle-associated membrane protein-associated protein A | VAPA | Homo sapiens | 8.47 | 14.06 | 2 | 2 |

TABLE 2

Gene ontology (biological process, cellular component and molecular function) terms enriched in the engineered VF mucosa proteome. Enriched ontology terms were identified using the BINGO algorithm. The term list shown here corresponds to the functional enrichment map presented in FIG. 3E. Terms are listed in order of ascending Benjamini Hochberg-adjusted P-value.

| Gene ontology term | Description | Adjusted P-value |
| --- | --- | --- |
| GO:44444 | cytoplasmic part | 0.00E+00 |
| GO:5737 | cytoplasm | 0.00E+00 |
| GO:5829 | cytosol | 0.00E+00 |
| GO:44424 | intracellular part | 0.00E+00 |
| GO:44422 | organelle part | 0.00E+00 |
| GO:44446 | intracellular organelle part | 0.00E+00 |
| GO:5515 | protein binding | 0.00E+00 |
| GO:5622 | intracellular | 0.00E+00 |
| GO:43226 | organelle | 0.00E+00 |
| GO:43229 | intracellular organelle | 0.00E+00 |
| GO:44464 | cell part | 0.00E+00 |
| GO:5623 | cell | 0.00E+00 |
| GO:16043 | cellular component organization | 0.00E+00 |
| GO:71840 | cellular component organization or biogenesis | 0.00E+00 |
| GO:43227 | membrane-bounded organelle | 1.54E−98 |
| GO:9056 | catabolic process | 1.32E−97 |
| GO:32991 | macromolecular complex | 7.91E−96 |
| GO:43231 | intracellular membrane-bounded organelle | 2.82E−92 |
| GO:1901575 | organic substance catabolic process | 1.10E−90 |
| GO:31974 | membrane-enclosed lumen | 6.02E−90 |
| GO:43233 | organelle lumen | 3.94E−89 |
| GO:44248 | cellular catabolic process | 5.02E−86 |
| GO:5575 | cellular component | 6.23E−84 |
| GO:44281 | small molecule metabolic process | 1.14E−83 |
| GO:16071 | mRNA metabolic process | 1.40E−83 |
| GO:70013 | intracellular organelle lumen | 8.21E−83 |
| GO:16032 | viral reproduction | 4.94E−82 |
| GO:44764 | multi-organism cellular process | 6.49E−82 |
| GO:22411 | cellular component disassembly | 1.09E−77 |
| GO:19083 | viral transcription | 2.90E−77 |
| GO:44710 | single-organism metabolic process | 3.71E−77 |
| GO:9987 | cellular process | 5.80E−77 |
| GO:43933 | macromolecular complex subunit organization | 6.37E−75 |
| GO:44237 | cellular metabolic process | 1.39E−74 |
| GO:22415 | viral reproductive process | 8.03E−74 |
| GO:19080 | viral genome expression | 1.63E−73 |
| GO:6614 | SRP-dependent cotranslational protein targeting to membrane | 3.08E−73 |
| GO:22626 | cytosolic ribosome | 3.50E−72 |
| GO:19058 | viral infectious cycle | 3.83E−72 |
| GO:45047 | protein targeting to ER | 8.85E−72 |
| GO:6414 | translational elongation | 1.01E−71 |
| GO:72599 | establishment of protein localization to endoplasmic reticulum | 1.59E−71 |
| GO:6613 | cotranslational protein targeting to membrane | 1.59E−71 |
| GO:6415 | translational termination | 2.24E−71 |
| GO:71822 | protein complex subunit organization | 3.93E−71 |
| GO:184 | nuclear-transcribed mRNA catabolic process, nonsense-mediated decay | 6.64E−71 |
| GO:70972 | protein localization to endoplasmic reticulum | 1.49E−70 |
| GO:5488 | binding | 6.41E−69 |
| GO:43624 | cellular protein complex disassembly | 3.58E−68 |
| GO:71704 | organic substance metabolic process | 4.71E−68 |
| GO:43241 | protein complex disassembly | 3.35E−66 |
| GO:44699 | single-organism process | 3.35E−66 |
| GO:51649 | establishment of localization in cell | 4.99E−66 |
| GO:51641 | cellular localization | 7.77E−66 |
| GO:6612 | protein targeting to membrane | 5.56E−64 |
| GO:32984 | macromolecular complex disassembly | 2.81E−63 |
| GO:31988 | membrane-bounded vesicle | 4.70E−63 |
| GO:43228 | non-membrane-bounded organelle | 8.25E−63 |
| GO:43232 | intracellular non-membrane-bounded organelle | 8.25E−63 |
| GO:31982 | vesicle | 1.13E−62 |
| GO:44238 | primary metabolic process | 1.22E−62 |
| GO:44703 | multi-organism reproductive process | 4.22E−62 |
| GO:46700 | heterocycle catabolic process | 1.06E−61 |
| GO:34655 | nucleobase-containing compound catabolic process | 1.21E−61 |
| GO:6402 | mRNA catabolic process | 2.73E−61 |
| GO:46907 | intracellular transport | 3.34E−61 |
| GO:30529 | ribonucleoprotein complex | 3.34E−61 |
| GO:6413 | translational initiation | 3.74E−61 |
| GO:1901361 | organic cyclic compound catabolic process | 4.66E−61 |
| GO:44270 | cellular nitrogen compound catabolic process | 5.09E−61 |
| GO:956 | nuclear-transcribed mRNA catabolic process | 5.26E−61 |
| GO:44763 | single-organism cellular process | 5.79E−61 |
| GO:19439 | aromatic compound catabolic process | 6.81E−61 |
| GO:51704 | multi-organism process | 1.33E−60 |

TABLE 2-continued

Gene ontology (biological process, cellular component and molecular function) terms enriched in the engineered VF mucosa proteome. Enriched ontology terms were identified using the BINGO algorithm. The term list shown here corresponds to the functional enrichment map presented in FIG. 3E. Terms are listed in order of ascending Benjamini Hochberg-adjusted P-value.

| Gene ontology term | Description | Adjusted P-value |
| --- | --- | --- |
| GO:16482 | cytoplasmic transport | 1.49E−59 |
| GO:44445 | cytosolic part | 1.05E−58 |
| GO:33036 | macromolecule localization | 2.01E−58 |
| GO:6401 | RNA catabolic process | 2.63E−58 |
| GO:45184 | establishment of protein localization | 9.90E−58 |
| GO:8104 | protein localization | 1.15E−57 |
| GO:6807 | nitrogen compound metabolic process | 1.41E−57 |
| GO:72594 | establishment of protein localization to organelle | 5.33E−57 |
| GO:15031 | protein transport | 6.04E−57 |
| GO:5198 | structural molecule activity | 6.40E−57 |
| GO:6605 | protein targeting | 1.79E−56 |
| GO:9057 | macromolecule catabolic process | 3.33E−56 |
| GO:8152 | metabolic process | 1.14E−55 |
| GO:42470 | melanosome | 1.61E−55 |
| GO:48770 | pigment granule | 1.61E−55 |
| GO:44391 | ribosomal subunit | 3.17E−54 |
| GO:34641 | cellular nitrogen compound metabolic process | 2.68E−53 |
| GO:6886 | intracellular protein transport | 7.01E−53 |
| GO:34613 | cellular protein localization | 5.66E−52 |
| GO:70727 | cellular macromolecule localization | 7.49E−52 |
| GO:33365 | protein localization to organelle | 3.51E−51 |
| GO:71702 | organic substance transport | 3.13E−50 |
| GO:44265 | cellular macromolecule catabolic process | 4.07E−50 |
| GO:70062 | extracellular vesicular exosome | 1.53E−49 |
| GO:43230 | extracellular organelle | 6.40E−49 |
| GO:65010 | extracellular membrane-bounded organelle | 6.40E−49 |
| GO:1901360 | organic cyclic compound metabolic process | 1.66E−48 |
| GO:43234 | protein complex | 9.14E−47 |
| GO:51179 | localization | 3.29E−46 |
| GO:6412 | translation | 3.94E−45 |
| GO:6139 | nucleobase-containing compound metabolic process | 6.37E−45 |
| GO:44765 | single-organism transport | 7.39E−45 |
| GO:6725 | cellular aromatic compound metabolic process | 1.36E−44 |
| GO:46483 | heterocycle metabolic process | 2.02E−44 |
| GO:6810 | transport | 1.09E−43 |
| GO:16023 | cytoplasmic membrane-bounded vesicle | 1.22E−43 |
| GO:51234 | establishment of localization | 1.39E−43 |
| GO:6950 | response to stress | 4.03E−43 |
| GO:31410 | cytoplasmic vesicle | 7.10E−43 |
| GO:3674 | molecular_function | 1.05E−41 |
| GO:22414 | reproductive process | 2.79E−41 |
| GO:3 | reproduction | 4.55E−41 |
| GO:22625 | cytosolic large ribosomal subunit | 6.24E−41 |
| GO:1901564 | organonitrogen compound metabolic process | 6.68E−40 |
| GO:65008 | regulation of biological quality | 2.85E−39 |
| GO:8150 | biological_process | 4.53E−39 |
| GO:3723 | RNA binding | 1.55E−38 |
| GO:31090 | organelle membrane | 5.16E−38 |
| GO:44085 | cellular component biogenesis | 1.31E−37 |
| GO:5739 | mitochondrion | 4.26E−36 |
| GO:48519 | negative regulation of biological process | 6.90E−36 |
| GO:50896 | response to stimulus | 9.53E−36 |
| GO:43170 | macromolecule metabolic process | 8.41E−35 |
| GO:19538 | protein metabolic process | 1.33E−34 |
| GO:9058 | biosynthetic process | 1.60E−34 |
| GO:48518 | positive regulation of biological process | 1.91E−34 |
| GO:42221 | response to chemical stimulus | 2.82E−34 |
| GO:6091 | generation of precursor metabolites and energy | 2.92E−34 |
| GO:6996 | organelle organization | 7.00E−34 |
| GO:1901576 | organic substance biosynthetic process | 1.24E−33 |
| GO:44267 | cellular protein metabolic process | 1.59E−33 |
| GO:22607 | cellular component assembly | 2.25E−33 |
| GO:22627 | cytosolic small ribosomal subunit | 2.29E−33 |
| GO:10467 | gene expression | 3.90E−33 |
| GO:48522 | positive regulation of cellular process | 9.45E−33 |
| GO:48523 | negative regulation of cellular process | 2.65E−32 |
| GO:44428 | nuclear part | 4.50E−32 |
| GO:5786 | endoplasmic reticulum lumen | 5.08E−32 |
| GO:10941 | regulation of cell death | 1.06E−31 |
| GO:1901135 | carbohydrate derivative metabolic process | 1.90E−31 |
| GO:43067 | regulation of programmed cell death | 2.42E−31 |
| GO:42961 | regulation of apoptotic process | 4.67E−31 |
| GO:65003 | macromolecular complex assembly | 7.55E−31 |
| GO:8219 | cell death | 1.01E−30 |

TABLE 2-continued

Gene ontology (biological process, cellular component and molecular function) terms enriched in the engineered VF mucosa proteome. Enriched ontology terms were identified using the BINGO algorithm. The term list shown here corresponds to the functional enrichment map presented in FIG. 3E. Terms are listed in order of ascending Benjamini Hochberg-adjusted P-value.

| Gene ontology term | Description | Adjusted P-value |
|---|---|---|
| GO:2478 | antigen processing and presentation of exogenous peptide antigen | 1.13E−30 |
| GO:16265 | death | 1.55E−30 |
| GO:5783 | endoplasmic reticulum | 2.16E−30 |
| GO:19884 | antigen processing and presentation of exogenous antigen | 2.36E−30 |
| GO:5840 | ribosome | 4.50E−30 |
| GO:48002 | antigen processing and presentation of peptide antigen | 4.87E−30 |
| GO:6082 | organic acid metabolic process | 6.10E−30 |
| GO:15934 | large ribosomal subunit | 6.56E−30 |
| GO:55114 | oxidation-reduction process | 6.89E−30 |
| GO:43436 | oxoacid metabolic process | 1.21E−29 |
| GO:44249 | cellular biosynthetic process | 1.46E−29 |
| GO:44260 | cellular macromolecule metabolic process | 1.92E−29 |
| GO:1901565 | organonitrogen compound catabolic process | 2.57E−29 |
| GO:3735 | structural constituent of ribosome | 3.22E−29 |
| GO:31981 | nuclear lumen | 9.80E−29 |
| GO:70887 | cellular response to chemical stimulus | 1.14E−28 |
| GO:19752 | carboxylic acid metabolic process | 1.39E−28 |
| GO:16070 | RNA metabolic process | 2.30E−28 |
| GO:2376 | immune system process | 3.98E−28 |
| GO:44421 | extracellular region part | 5.42E−28 |
| GO:51701 | interaction with host | 1.05E−27 |
| GO:44432 | endoplasmic reticulum part | 1.06E−27 |
| GO:5856 | cytoskeleton | 2.82E−27 |
| GO:51246 | regulation of protein metabolic process | 3.88E−27 |
| GO:55086 | nucleobase-containing small molecule metabolic process | 5.77E−27 |
| GO:10033 | response to organic substance | 8.11E−27 |
| GO:44419 | interspecies interaction between organisms | 1.16E−26 |
| GO:44403 | symbiosis, encompassing mutualism through parasitism | 1.16E−26 |
| GO:48610 | cellular process involved in reproduction | 1.49E−26 |
| GO:44707 | single-multicellular organism process | 1.76E−26 |
| GO:15980 | energy derivation by oxidation of organic compounds | 1.98E−26 |
| GO:32268 | regulation of cellular protein metabolic process | 2.06E−26 |
| GO:19048 | virus-host interaction | 4.98E−26 |
| GO:9117 | nucleotide metabolic process | 5.91E−26 |
| GO:44429 | mitochondrial part | 7.15E−26 |
| GO:90304 | nucleic acid metabolic process | 7.67E−26 |
| GO:6753 | nucleoside phosphate metabolic process | 1.43E−25 |
| GO:7599 | hemostasis | 2.09E−25 |
| GO:32501 | multicellular organismal process | 5.52E−25 |
| GO:65007 | biological regulation | 6.18E−25 |
| GO:31967 | organelle envelope | 1.01E−24 |
| GO:16044 | cellular membrane organization | 1.04E−24 |
| GO:16192 | vesicle-mediated transport | 1.63E−24 |
| GO:61024 | membrane organization | 1.97E−24 |
| GO:6521 | regulation of cellular amino acid metabolic process | 2.66E−24 |
| GO:2474 | antigen processing and presentation of peptide antigen via MHC class I | 4.07E−24 |
| GO:1901136 | carbohydrate derivative catabolic process | 4.47E−24 |
| GO:15935 | small ribosomal subunit | 4.47E−24 |
| GO:31975 | envelope | 5.21E−24 |
| GO:50817 | coagulation | 5.86E−24 |
| GO:7596 | blood coagulation | 5.86E−24 |
| GO:51128 | regulation of cellular component organization | 6.44E−24 |
| GO:5634 | nucleus | 1.10E−23 |
| GO:6457 | protein folding | 1.64E−23 |
| GO:5759 | mitochondrial matrix | 2.58E−23 |
| GO:30198 | extracellular matrix organization | 3.21E−23 |
| GO:43062 | extracellular structure organization | 3.57E−23 |
| GO:19882 | antigen processing and presentation | 4.64E−23 |
| GO:42060 | wound healing | 1.15E−22 |
| GO:50878 | regulation of body fluid levels | 2.65E−22 |
| GO:12505 | endomembrane system | 3.32E−22 |
| GO:42802 | identical protein binding | 3.74E−22 |
| GO:19637 | organophosphate metabolic process | 4.07E−22 |
| GO:6461 | protein complex assembly | 4.58E−22 |
| GO:70271 | protein complex biogenesis | 5.33E−22 |
| GO:33238 | regulation of cellular amine metabolic process | 1.01E−21 |
| GO:50789 | regulation of biological process | 1.02E−21 |
| GO:12501 | programmed cell death | 1.48E−21 |
| GO:51436 | negative regulation of ubiquitin-protein ligase activity involved in mitotic cell cycle | 1.52E−21 |
| GO:6163 | purine nucleotide metabolic process | 3.11E−21 |
| GO:10608 | posttranscriptional regulation of gene expression | 3.26E−21 |
| GO:72413 | signal transduction involved in mitotic cell cycle checkpoint | 4.50E−21 |
| GO:72431 | signal transduction involved in mitotic G1 DNA damage checkpoint | 4.50E−21 |
| GO:6977 | DNA damage response, signal transduction by p53 class mediator resulting in cell cycle arrest | 4.50E−21 |

TABLE 2-continued

Gene ontology (biological process, cellular component and molecular function) terms enriched in the engineered VF mucosa proteome. Enriched ontology terms were identified using the BINGO algorithm. The term list shown here corresponds to the functional enrichment map presented in FIG. 3E. Terms are listed in order of ascending Benjamini Hochberg-adjusted P-value.

| Gene ontology term | Description | Adjusted P-value |
| --- | --- | --- |
| GO:72401 | signal transduction involved in DNA integrity checkpoint | 6.36E−21 |
| GO:72422 | signal transduction involved in DNA damage checkpoint | 6.36E−21 |
| GO:72521 | purine-containing compound metabolic process | 6.79E−21 |
| GO:1901657 | glycosyl compound metabolic process | 7.55E−21 |
| GO:6915 | apoptotic process | 8.15E−21 |
| GO:51437 | positive regulation of ubiquitin-protein ligase activity involved in mitotic cell cycle | 8.83E−21 |
| GO:72395 | signal transduction involved in cell cycle checkpoint | 8.83E−21 |
| GO:30330 | DNA damage response, signal transduction by p53 class mediator | 1.01E−20 |
| GO:51443 | positive regulation of ubiquitin-protein ligase activity | 1.22E−20 |
| GO:9059 | macromolecule biosynthetic process | 1.40E−20 |
| GO:46128 | purine ribonucleoside metabolic process | 1.88E−20 |
| GO:42278 | purine nucleoside metabolic process | 2.12E−20 |
| GO:9150 | purine ribonucleotide metabolic process | 2.60E−20 |
| GO:19693 | ribose phosphate metabolic process | 2.60E−20 |
| GO:6417 | regulation of translation | 3.49E−20 |
| GO:51351 | positive regulation of ligase activity | 3.91E−20 |
| GO:51352 | negative regulation of ligase activity | 4.43E−20 |
| GO:51444 | negative regulation of ubiquitin-protein ligase activity | 4.43E−20 |
| GO:2479 | antigen processing and presentation of exogenous peptide antigen via MHC class I, TAP-dependent | 4.55E−20 |
| GO:44433 | cytoplasmic vesicle part | 4.95E−20 |
| GO:72331 | signal transduction by p53 class mediator | 5.62E−20 |
| GO:51439 | regulation of ubiquitin-protein ligase activity involved in mitotic cell cycle | 5.98E−20 |
| GO:72523 | purine-containing compound catabolic process | 7.54E−20 |
| GO:44092 | negative regulation of molecular function | 7.54E−20 |
| GO:9259 | ribonucleotide metabolic process | 7.56E−20 |
| GO:19899 | enzyme binding | 8.81E−20 |
| GO:42590 | antigen processing and presentation of exogenous peptide antigen via MHC class I | 1.05E−19 |
| GO:44783 | G1 DNA damage checkpoint | 1.08E−19 |
| GO:31571 | mitotic G1 DNA damage checkpoint | 1.08E−19 |
| GO:9119 | ribonucleoside metabolic process | 1.19E−19 |
| GO:9611 | response to wounding | 1.38E−19 |
| GO:6195 | purine nucleotide catabolic process | 1.86E−19 |
| GO:2000134 | negative regulation of G1/S transition of mitotic cell cycle | 1.94E−19 |
| GO:9116 | nucleoside metabolic process | 1.95E−19 |
| GO:6152 | purine nucleoside catabolic process | 2.05E−19 |
| GO:46130 | purine ribonucleoside catabolic process | 2.05E−19 |
| GO:36094 | small molecule binding | 2.44E−19 |
| GO:42770 | signal transduction in response to DNA damage | 2.61E−19 |
| GO:44430 | cytoskeletal part | 3.07E−19 |
| GO:42454 | ribonucleoside catabolic process | 3.11E−19 |
| GO:71944 | cell periphery | 3.38E−19 |
| GO:43086 | negative regulation of catalytic activity | 3.86E−19 |
| GO:2576 | platelet degranulation | 4.41E−19 |
| GO:9164 | nucleoside catabolic process | 5.11E−19 |
| GO:48856 | anatomical structure development | 5.49E−19 |
| GO:71158 | positive regulation of cell cycle arrest | 5.77E−19 |
| GO:1901658 | glycosyl compound catabolic process | 6.25E−19 |
| GO:50794 | regulation of cellular process | 6.81E−19 |
| GO:51248 | negative regulation of protein metabolic process | 1.03E−18 |
| GO:32502 | developmental process | 1.05E−18 |
| GO:51716 | cellular response to stimulus | 1.12E−18 |
| GO:9166 | nucleotide catabolic process | 1.18E−18 |
| GO:9205 | purine ribonucleoside triphosphate metabolic process | 1.23E−18 |
| GO:32269 | negative regulation of cellular protein metabolic process | 1.31E−18 |
| GO:48731 | system development | 1.36E−18 |
| GO:9154 | purine ribonucleotide catabolic process | 1.40E−18 |
| GO:32270 | positive regulation of cellular protein metabolic process | 1.43E−18 |
| GO:9261 | ribonucleotide catabolic process | 1.45E−18 |
| GO:43168 | anion binding | 1.48E−18 |
| GO:9144 | purine nucleoside triphosphate metabolic process | 1.53E−18 |
| GO:9199 | ribonucleoside triphosphate metabolic process | 1.59E−18 |
| GO:34645 | cellular macromolecule biosynthetic process | 1.63E−18 |
| GO:1901292 | nucleoside phosphate catabolic process | 1.64E−18 |
| GO:51438 | regulation of ubiquitin-protein ligase activity | 1.67E−18 |
| GO:44773 | mitotic DNA damage checkpoint | 2.06E−18 |
| GO:31145 | anaphase-promoting complex-dependent proteasomal ubiquitin-dependent protein catabolic process | 2.06E−18 |
| GO:33554 | cellular response to stress | 2.39E−18 |
| GO:2000045 | regulation of G1/S transition of mitotic cell cycle | 3.48E−18 |
| GO:46434 | organophosphate catabolic process | 3.74E−18 |
| GO:5654 | nucleoplasm | 3.91E−18 |
| GO:51340 | regulation of ligase activity | 4.15E−18 |
| GO:43202 | lysosomal lumen | 4.56E−18 |

TABLE 2-continued

Gene ontology (biological process, cellular component and molecular function) terms enriched in the engineered VF mucosa proteome.
Enriched ontology terms were identified using the BINGO algorithm. The term list shown here corresponds to the functional
enrichment map presented in FIG. 3E. Terms are listed in order of ascending Benjamini Hochberg-adjusted P-value.

| Gene ontology term | Description | Adjusted P-value |
|---|---|---|
| GO:5975 | carbohydrate metabolic process | 4.84E−18 |
| GO:9141 | nucleoside triphosphate metabolic process | 4.84E−18 |
| GO:6986 | response to unfolded protein | 5.15E−18 |
| GO:44774 | mitotic DNA integrity checkpoint | 5.47E−18 |
| GO:35966 | response to topologically incorrect protein | 6.03E−18 |
| GO:10565 | regulation of cellular ketone metabolic process | 6.03E−18 |
| GO:31397 | negative regulation of protein ubiquitination | 6.34E−18 |
| GO:48471 | perinuclear region of cytoplasm | 7.05E−18 |
| GO:1901265 | nucleoside phosphate binding | 8.41E−18 |
| GO:5775 | vacuolar lumen | 1.45E−17 |
| GO:90 | mitotic anaphase | 1.55E−17 |
| GO:15629 | actin cytoskeleton | 1.74E−17 |
| GO:166 | nucleotide binding | 1.83E−17 |
| GO:31398 | positive regulation of protein ubiquitination | 1.96E−17 |
| GO:51322 | anaphase | 2.09E−17 |
| GO:16491 | oxidoreductase activity | 2.23E−17 |
| GO:9203 | ribonucleoside triphosphate catabolic process | 2.23E−17 |
| GO:9207 | purine ribonucleoside triphosphate catabolic process | 2.23E−17 |
| GO:9146 | purine nucleoside triphosphate catabolic process | 2.51E−17 |
| GO:9143 | nucleoside triphosphate catabolic process | 3.05E−17 |
| GO:45333 | cellular respiration | 3.05E−17 |
| GO:5886 | plasma membrane | 3.46E−17 |
| GO:87 | M phase of mitotic cell cycle | 4.52E−17 |
| GO:44770 | cell cycle phase transition | 5.24E−17 |
| GO:44772 | mitotic cell cycle phase transition | 5.24E−17 |
| GO:51247 | positive regulation of protein metabolic process | 7.30E−17 |
| GO:6458 | 'de novo' protein folding | 9.71E−17 |
| GO:7275 | multicellular organismal development | 1.04E−16 |
| GO:502 | proteasome complex | 1.42E−16 |
| GO:2000602 | regulation of interphase of mitotic cell cycle | 1.42E−16 |
| GO:19866 | organelle inner membrane | 2.10E−16 |
| GO:43161 | proteasomal ubiquitin-dependent protein catabolic process | 2.17E−16 |
| GO:31966 | mitochondrial membrane | 2.20E−16 |
| GO:51259 | protein oligomerization | 2.85E−16 |
| GO:71156 | regulation of cell cycle arrest | 3.27E−16 |
| GO:5740 | mitochondrial envelope | 3.37E−16 |
| GO:10498 | proteasomal protein catabolic process | 3.39E−16 |
| GO:44271 | cellular nitrogen compound biosynthetic process | 3.57E−16 |
| GO:30168 | platelet activation | 3.67E−16 |
| GO:90068 | positive regulation of cell cycle process | 4.24E−16 |
| GO:279 | M phase | 5.00E−16 |
| GO:1901362 | organic cyclic compound biosynthetic process | 6.09E−16 |
| GO:5730 | nucleolus | 6.44E−16 |
| GO:278 | mitotic cell cycle | 6.78E−16 |
| GO:6006 | glucose metabolic process | 8.30E−16 |
| GO:9892 | negative regulation of metabolic process | 8.50E−16 |
| GO:34654 | nucleobase-containing compound biosynthetic process | 1.38E−15 |
| GO:51082 | unfolded protein binding | 1.60E−15 |
| GO:32879 | regulation of localization | 1.88E−15 |
| GO:5576 | extracellular region | 1.92E−15 |
| GO:22402 | cell cycle process | 2.13E−15 |
| GO:904 | cell morphogenesis involved in differentiation | 2.28E−15 |
| GO:44767 | single-organism developmental process | 2.78E−15 |
| GO:280 | nuclear division | 3.26E−15 |
| GO:7067 | mitosis | 3.26E−15 |
| GO:42803 | protein homodimerization activity | 3.30E−15 |
| GO:44724 | single-organism carbohydrate catabolic process | 3.96E−15 |
| GO:44093 | positive regulation of molecular function | 4.06E−15 |
| GO:209 | protein polyubiquitination | 4.93E−15 |
| GO:16052 | carbohydrate catabolic process | 6.89E−15 |
| GO:44723 | single-organism carbohydrate metabolic process | 7.22E−15 |
| GO:5743 | mitochondrial inner membrane | 8.83E−15 |
| GO:7049 | cell cycle | 9.62E−15 |
| GO:51084 | 'de novo' posttranslational protein folding | 1.02E−14 |
| GO:71310 | cellular response to organic substance | 1.02E−14 |
| GO:34622 | cellular macromolecular complex assembly | 1.23E−14 |
| GO:84 | S phase of mitotic cell cycle | 1.27E−14 |
| GO:44437 | vacuolar part | 1.27E−14 |
| GO:5793 | endoplasmic reticulum-Golgi intermediate compartment | 1.32E−14 |
| GO:19438 | aromatic compound biosynthetic process | 1.39E−14 |
| GO:31396 | regulation of protein ubiquitination | 1.50E−14 |
| GO:51320 | S phase | 1.73E−14 |
| GO:31400 | negative regulation of protein modification process | 2.26E−14 |
| GO:31324 | negative regulation of cellular metabolic process | 2.34E−14 |

TABLE 2-continued

Gene ontology (biological process, cellular component and molecular function) terms enriched in the engineered VF mucosa proteome. Enriched ontology terms were identified using the BINGO algorithm. The term list shown here corresponds to the functional enrichment map presented in FIG. 3E. Terms are listed in order of ascending Benjamini Hochberg-adjusted P-value.

| Gene ontology term | Description | Adjusted P-value |
| --- | --- | --- |
| GO:5773 | vacuole | 2.41E−14 |
| GO:30659 | cytoplasmic vesicle membrane | 2.82E−14 |
| GO:48285 | organelle fission | 3.14E−14 |
| GO:31325 | positive regulation of cellular metabolic process | 3.16E−14 |
| GO:5615 | extracellular space | 3.23E−14 |
| GO:6520 | cellular amino acid metabolic process | 3.96E−14 |
| GO:43167 | ion binding | 4.35E−14 |
| GO:18130 | heterocycle biosynthetic process | 5.13E−14 |
| GO:902 | cell morphogenesis | 6.14E−14 |
| GO:51129 | negative regulation of cellular component organization | 6.16E−14 |
| GO:31401 | positive regulation of protein modification process | 6.41E−14 |
| GO:6396 | RNA processing | 7.17E−14 |
| GO:82 | G1/S transition of mitotic cell cycle | 7.24E−14 |
| GO:9893 | positive regulation of metabolic process | 9.47E−14 |
| GO:5764 | lysosome | 1.27E−13 |
| GO:6928 | cellular component movement | 1.45E−13 |
| GO:8092 | cytoskeletal protein binding | 1.49E−13 |
| GO:44259 | multicellular organismal macromolecule metabolic process | 1.52E−13 |
| GO:8380 | RNA splicing | 1.52E−13 |
| GO:12506 | vesicle membrane | 1.60E−13 |
| GO:10605 | negative regulation of macromolecule metabolic process | 1.66E−13 |
| GO:323 | lytic vacuole | 1.84E−13 |
| GO:3729 | mRNA binding | 1.90E−13 |
| GO:5996 | monosaccharide metabolic process | 2.03E−13 |
| GO:46364 | monosaccharide biosynthetic process | 2.19E−13 |
| GO:3779 | actin binding | 2.20E−13 |
| GO:22617 | extracellular matric disassembly | 2.28E−13 |
| GO:10035 | response to inorganic substance | 2.35E−13 |
| GO:31012 | extracellular matrix | 3.04E−13 |
| GO:377 | RNA splicing, via transesterification reactions with bulged adenosine as nucleophile | 3.19E−13 |
| GO:398 | mRNA splicing, via spliceosome | 3.19E−13 |
| GO:1901991 | negative regulation of mitotic cell cycle phase transition | 3.52E−13 |
| GO:32963 | collagen metabolic process | 3.85E−13 |
| GO:7093 | mitotic cell cycle checkpoint | 3.86E−13 |
| GO:42645 | mitochondrial nucleoid | 4.70E−13 |
| GO:375 | RNA splicing, via transesterification reactions | 5.09E−13 |
| GO:16616 | oxidoreductase activity, acting on the CH—OH group of donors, NAD or NADP as acceptor | 5.09E−13 |
| GO:16614 | oxidoreductase activity, acting on CH—OH group of donors | 6.41E−13 |
| GO:9295 | nucleoid | 6.79E−13 |
| GO:65009 | regulation of molecular function | 6.89E−13 |
| GO:44236 | multicellular organismal metabolic process | 6.89E−13 |
| GO:51130 | positive regulation of cellular component organization | 7.06E−13 |
| GO:19318 | hexose metabolic process | 7.22E−13 |
| GO:5200 | structural constituent of cytosketeton | 8.23E−13 |
| GO:16020 | membrane | 9.24E−13 |
| GO:9653 | anatomical structure morphogenesis | 9.56E−13 |
| GO:30574 | collagen catabolic process | 9.67E−13 |
| GO:30029 | actin filament-based process | 1.05E−12 |
| GO:42175 | nuclear outer membrane-endoplasmic reticulum membrane network | 1.38E−12 |
| GO:43069 | negative regulation of programmed cell death | 1.49E−12 |
| GO:1775 | cell activation | 1.75E−12 |
| GO:43254 | regulation of protein complex assembly | 1.78E−12 |
| GO:77 | DNA damage checkpoint | 1.92E−12 |
| GO:50790 | regulation of catalytic activity | 2.00E−12 |
| GO:46983 | protein dimerization activity | 2.02E−12 |
| GO:32989 | cellular component morphogenesis | 2.17E−12 |
| GO:17111 | nucleoside-triphosphatase activity | 2.21E−12 |
| GO:42995 | cell projection | 2.48E−12 |
| GO:46365 | monosaccharide catabolic process | 2.72E−12 |
| GO:43085 | positive regulation of catalytic activity | 4.06E−12 |
| GO:5681 | spliceosomal complex | 4.31E−12 |
| GO:9986 | cell surface | 4.34E−12 |
| GO:44087 | regulation of cellular component biogenesis | 4.70E−12 |
| GO:31570 | DNA integrity checkpoint | 4.80E−12 |
| GO:31399 | regulation of protein modification process | 5.08E−12 |
| GO:44243 | multicellular organismal catabolic process | 5.08E−12 |
| GO:16462 | pyrophosphatase activity | 5.29E−12 |
| GO:51049 | regulation of transport | 5.76E−12 |
| GO:3824 | catalytic activity | 6.58E−12 |
| GO:22624 | proteasome accessory complex | 6.62E−12 |
| GO:18279 | protein N-linked glycosylation via asparagine | 7.02E−12 |
| GO:44420 | extracellular matrix part | 7.27E−12 |
| GO:5578 | proteinaceous extracellular matrix | 7.34E−12 |
| GO:32403 | protein complex binding | 7.34E−12 |

TABLE 2-continued

Gene ontology (biological process, cellular component and molecular function) terms enriched in the engineered VF mucosa proteome.
Enriched ontology terms were identified using the BINGO algorithm. The term list shown here corresponds to the functional
enrichment map presented in FIG. 3E. Terms are listed in order of ascending Benjamini Hochberg-adjusted P-value.

| Gene ontology term | Description | Adjusted P-value |
| --- | --- | --- |
| GO:1901990 | regulation of mitotic cell cycle phase transition | 7.37E−12 |
| GO:7411 | axon guidance | 7.68E−12 |
| GO:5201 | extracellular matrix structural constituent | 7.72E−12 |
| GO:18196 | peptidyl-asparagine modification | 8.21E−12 |
| GO:16818 | hydrolase activity, acting on acid anhydrides, in phosphorus-containing anhydrides | 8.29E−12 |
| GO:22613 | ribonucleoprotein complex biogenesis | 8.33E−12 |
| GO:60548 | negative regulation of cell death | 9.66E−12 |
| GO:32069 | regulation of nuclease activity | 9.69E−12 |
| GO:19320 | hexose catabolic process | 1.12E−11 |
| GO:43066 | negative regulation of apoptotic process | 1.26E−11 |
| GO:6007 | glucose catabolic process | 1.43E−11 |
| GO:16817 | hydrolase activity, acting on acid anhydrides | 1.44E−11 |
| GO:5938 | cell cortex | 1.62E−11 |
| GO:97159 | organic cyclic compound binding | 1.62E−11 |
| GO:1901066 | guanosine-containing compound metabolic process | 1.71E−11 |
| GO:9060 | aerobic respiration | 1.80E−11 |
| GO:6575 | cellular modified amino acid metabolic process | 1.85E−11 |
| GO:19886 | antigen processing and presentation of exogenous peptide antigen via MHC class II | 2.16E−11 |
| GO:32787 | monocarboxylic acid metabolic process | 2.19E−11 |
| GO:6397 | mRNA processing | 2.61E−11 |
| GO:6099 | tricarboxylic acid cycle | 2.63E−11 |
| GO:48199 | vesicle targeting, to, from or within Golgi | 2.68E−11 |
| GO:6987 | activation of signaling protein activity involved in unfolded protein response | 2.69E−11 |
| GO:48193 | Golgi vesicle transport | 2.72E−11 |
| GO:6081 | cellular aldehyde metabolic process | 3.22E−11 |
| GO:42743 | hydrogen peroxide metabolic process | 3.22E−11 |
| GO:48858 | cell projection morphogenesis | 3.36E−11 |
| GO:2495 | antigen processing and presentation of peptide antigen via MHC class II | 3.39E−11 |
| GO:30030 | cell projection organization | 3.51E−11 |
| GO:32774 | RNA biosynthetic process | 3.51E−11 |
| GO:33043 | regulation of organelle organization | 3.65E−11 |
| GO:32075 | positive regulation of nuclease activity | 4.14E−11 |
| GO:30968 | endoplasmic reticulum unfolded protein response | 4.25E−11 |
| GO:43603 | cellular amide metabolic process | 4.27E−11 |
| GO:30154 | cell differentiation | 4.42E−11 |
| GO:6984 | ER-nucleus signaling pathway | 4.53E−11 |
| GO:71013 | catalytic step 2 spliceosome | 4.63E−11 |
| GO:48667 | cell morphogenesis involved in neuron differentiation | 4.66E−11 |
| GO:1901363 | heterocyclic compound binding | 4.87E−11 |
| GO:16209 | antioxidant activity | 5.02E−11 |
| GO:22403 | cell cycle phase | 5.24E−11 |
| GO:32990 | cell part morphogenesis | 6.26E−11 |
| GO:5789 | endoplasmic reticulum membrane | 6.26E−11 |
| GO:5102 | receptor binding | 6.83E−11 |
| GO:48666 | neuron development | 7.55E−11 |
| GO:30036 | actin cytoskeleton organization | 9.08E−11 |
| GO:15630 | microtubule cytoskeleton | 9.52E−11 |
| GO:6487 | protein N-linked glycosylation | 1.07E−10 |
| GO:1901700 | response to oxygen-containing compound | 1.20E−10 |
| GO:72593 | reactive oxygen species metabolic process | 1.23E−10 |
| GO:7010 | cytoskeleton organization | 1.23E−10 |
| GO:34620 | cellular response to unfolded protein | 1.28E−10 |
| GO:51920 | peroxiredoxin activity | 1.35E−10 |
| GO:48468 | cell development | 1.42E−10 |
| GO:46039 | GTP metabolic process | 1.45E−10 |
| GO:6805 | xenobiotic metabolic process | 1.61E−10 |
| GO:6518 | peptide metabolic process | 1.67E−10 |
| GO:7409 | axonogenesis | 1.67E−10 |
| GO:10604 | positive regulation of macromolecule metabolic process | 1.75E−10 |
| GO:48583 | regulation of response to stimulus | 1.78E−10 |
| GO:71466 | cellular response to xenobiotic stimulus | 1.78E−10 |
| GO:48869 | cellular developmental process | 1.86E−10 |
| GO:32386 | regulation of intracellular transport | 1.87E−10 |
| GO:51329 | interphase of mitotic cell cycle | 1.87E−10 |
| GO:44712 | single-organism catabolic process | 1.96E−10 |
| GO:44282 | small molecule catabolic process | 1.96E−10 |
| GO:6901 | vesicle coating | 2.16E−10 |
| GO:22008 | neurogenesis | 2.20E−10 |
| GO:31175 | neuron projection development | 2.29E−10 |
| GO:51325 | interphase | 2.35E−10 |
| GO:6793 | phosphorus metabolic process | 2.44E−10 |
| GO:6732 | coenzyme metabolic process | 2.51E−10 |
| GO:16787 | hydrolase activity | 2.72E−10 |
| GO:9410 | response to xenobiotic stimulus | 3.05E−10 |

TABLE 2-continued

Gene ontology (biological process, cellular component and molecular function) terms enriched in the engineered VF mucosa proteome. Enriched ontology terms were identified using the BINGO algorithm. The term list shown here corresponds to the functional enrichment map presented in FIG. 3E. Terms are listed in order of ascending Benjamini Hochberg-adjusted P-value.

| Gene ontology term | Description | Adjusted P-value |
| --- | --- | --- |
| GO:1901069 | guanosine-containing compound catabolic process | 3.20E−10 |
| GO:42592 | homeostatic process | 4.46E−10 |
| GO:34614 | cellular response to reactive oxygen species | 4.84E−10 |
| GO:6790 | sulfur compound metabolic process | 5.66E−10 |
| GO:16051 | carbohydrate biosynthetic process | 5.99E−10 |
| GO:6900 | membrane budding | 6.08E−10 |
| GO:30016 | myofibril | 6.27E−10 |
| GO:8064 | regulation of actin polymerization or depolymerization | 6.35E−10 |
| GO:30832 | regulation of actin filament length | 7.03E−10 |
| GO:32970 | regulation of actin filament-based process | 7.06E−10 |
| GO:48699 | generation of neurons | 7.12E−10 |
| GO:16050 | vesicle organization | 8.37E−10 |
| GO:48812 | neuron projection morphogenesis | 8.77E−10 |
| GO:6094 | gluconeogenesis | 8.91E−10 |
| GO:35967 | cellular response to topologically incorrect protein | 8.99E−10 |
| GO:19362 | pyridine nucleotide metabolic process | 8.99E−10 |
| GO:46496 | nicotinamide nucleotide metabolic process | 8.99E−10 |
| GO:1882 | nucleoside binding | 9.47E−10 |
| GO:3924 | GTPase activity | 9.63E−10 |
| GO:45087 | innate immune response | 1.07E−09 |
| GO:6184 | GTP catabolic process | 1.25E−09 |
| GO:17076 | purine nucleotide binding | 1.37E−09 |
| GO:30863 | cortical cytoskeleton | 1.58E−09 |
| GO:90066 | regulation of anatomical structure size | 1.60E−09 |
| GO:6446 | regulation of translational initiation | 1.84E−09 |
| GO:6629 | lipid metabolic process | 1.85E−09 |
| GO:32555 | purine ribonucleotide binding | 2.00E−09 |
| GO:43292 | contractile fiber | 2.05E−09 |
| GO:32940 | secretion by cell | 2.16E−09 |
| GO:5811 | lipid particle | 2.16E−09 |
| GO:32550 | purine ribonucleoside binding | 2.21E−09 |
| GO:19941 | modification-dependent protein catabolic process | 2.28E−09 |
| GO:6913 | nucleocytoplasmic transport | 2.29E−09 |
| GO:1883 | purine nucleoside binding | 2.29E−09 |
| GO:6903 | vesicle targeting | 2.44E−09 |
| GO:43632 | modification-dependent macromolecule catabolic process | 2.57E−09 |
| GO:32549 | ribonucleoside binding | 2.76E−09 |
| GO:32535 | regulation of cellular component size | 2.84E−09 |
| GO:22900 | electron transport chain | 2.91E−09 |
| GO:51169 | nuclear transport | 2.93E−09 |
| GO:6749 | glutathione metabolic process | 3.01E−09 |
| GO:7346 | regulation of mitotic cell cycle | 3.06E−09 |
| GO:72524 | pyridine-containing compound metabolic process | 3.06E−09 |
| GO:10564 | regulation of cell cycle process | 3.17E−09 |
| GO:35639 | purine ribonucleoside triphosphate binding | 3.42E−09 |
| GO:40011 | locomotion | 3.54E−09 |
| GO:42274 | ribosomal small subunit biogenesis | 3.54E−09 |
| GO:32553 | ribonucleotide binding | 3.56E−09 |
| GO:6887 | exocytosis | 3.65E−09 |
| GO:51168 | cofactor metabolic process | 3.74E−09 |
| GO:9719 | response to endogenous stimulus | 3.89E−09 |
| GO:23051 | regulation of signaling | 4.35E−09 |
| GO:52547 | regulation of peptidase activity | 4.56E−09 |
| GO:6112 | energy reserve metabolic process | 4.56E−09 |
| GO:42744 | hydrogen peroxide catabolic process | 4.60E−09 |
| GO:2504 | antigen processing and presentation of peptide or polysaccharide antigen via MHC class II | 4.67E−09 |
| GO:1901988 | negative regulation of cell cycle phase transition | 4.68E−09 |
| GO:46903 | secretion | 4.73E−09 |
| GO:6508 | proteolysis | 4.83E−09 |
| GO:6511 | ubiquitin-dependent protein catabolic process | 5.14E−09 |
| GO:30833 | regulation of actin filament polymerization | 5.14E−09 |
| GO:35964 | COPI-coated vesicle budding | 5.17E−09 |
| GO:48205 | COPI coating of Golgi vesicle | 5.17E−09 |
| GO:48200 | Golgi transport vesicle coating | 5.17E−09 |
| GO:5178 | integrin binding | 5.33E−09 |
| GO:34599 | cellular response to oxidative stress | 6.28E−09 |
| GO:6979 | response to oxidative stress | 6.28E−09 |
| GO:70301 | cellular response to hydrogen peroxide | 6.65E−09 |
| GO:46034 | ATP metabolic process | 6.86E−09 |
| GO:6796 | phosphate-containing compound metabolic process | 7.41E−09 |
| GO:30834 | regulation of actin filament depolymerization | 7.55E−09 |
| GO:44257 | cellular protein catabolic process | 7.83E−09 |
| GO:75 | cell cycle checkpoint | 7.96E−09 |
| GO:42254 | ribosome biogenesis | 8.31E−09 |

TABLE 2-continued

Gene ontology (biological process, cellular component and molecular function) terms enriched in the engineered VF mucosa proteome. Enriched ontology terms were identified using the BINGO algorithm. The term list shown here corresponds to the functional enrichment map presented in FIG. 3E. Terms are listed in order of ascending Benjamini Hochberg-adjusted P-value.

| Gene ontology term | Description | Adjusted P-value |
|---|---|---|
| GO:10646 | regulation of cell communication | 8.45E−09 |
| GO:30139 | endocytic vesicle | 8.46E−09 |
| GO:50662 | coenzyme binding | 8.94E−09 |
| GO:22904 | respiratory electron transport chain | 9.17E−09 |
| GO:30182 | neuron differentiation | 9.24E−09 |
| GO:30017 | sarcomere | 9.24E−09 |
| GO:44700 | single organism signaling | 9.45E−09 |
| GO:23052 | signaling | 9.45E−09 |
| GO:7154 | cell communication | 9.75E−09 |
| GO:48194 | Golgi vesicle budding | 9.85E−09 |
| GO:34976 | response to endoplasmic reticulum stress | 1.01E−08 |
| GO:32271 | regulation of protein polymerization | 1.01E−08 |
| GO:44449 | contractile fiber part | 1.03E−08 |
| GO:1901701 | cellular response to oxygen-containing compound | 1.12E−08 |
| GO:5635 | nuclear envelope | 1.16E−08 |
| GO:19319 | hexose biosynthetic process | 1.22E−08 |
| GO:48513 | organ development | 1.25E−08 |
| GO:1901987 | regulation of cell cycle phase transition | 1.32E−08 |
| GO:51603 | proteolysis involved in cellular protein catabolic process | 1.33E−08 |
| GO:7399 | nervous system development | 1.42E−08 |
| GO:16054 | organic acid catabolic process | 1.42E−08 |
| GO:46395 | carboxylic acid catabolic process | 1.42E−08 |
| GO:6200 | ATP catabolic process | 1.43E−08 |
| GO:31252 | cell leading edge | 1.43E−08 |
| GO:6733 | oxidoreduction coenzyme metabolic process | 1.52E−08 |
| GO:19222 | regulation of metabolic process | 1.75E−08 |
| GO:9605 | response to external stimulus | 1.91E−08 |
| GO:10638 | positive regulation of organelle organization | 1.95E−08 |
| GO:51650 | establishment of vesicle localization | 2.15E−08 |
| GO:30199 | collagen fibril organization | 2.15E−08 |
| GO:42542 | response to hydrogen peroxide | 2.28E−08 |
| GO:48037 | cofactor binding | 2.29E−08 |
| GO:7044 | cell-substrate junction assembly | 2.40E−08 |
| GO:44273 | sulfur compound catabolic process | 2.48E−08 |
| GO:5604 | basement membrane | 2.51E−08 |
| GO:16684 | oxidoreductase activity, acting on peroxide as acceptor | 2.51E−08 |
| GO:4601 | peroxidase activity | 2.51E−08 |
| GO:1901137 | carbohydrate derivative biosynthetic process | 2.83E−08 |
| GO:30496 | midbody | 2.99E−08 |
| GO:30155 | regulation of cell adhesion | 2.99E−08 |
| GO:32956 | regulation of actin cytoskeleton organization | 3.05E−08 |
| GO:42127 | regulation of cell proliferation | 3.24E−08 |
| GO:51270 | regulation of cellular component movement | 3.31E−08 |
| GO:6952 | defense response | 3.56E−08 |
| GO:6897 | endocytosis | 3.59E−08 |
| GO:3988 | acetyl-CoA C-acyltransferase activity | 3.65E−08 |
| GO:7165 | signal transduction | 3.69E−08 |
| GO:30163 | protein catabolic process | 3.70E−08 |
| GO:51336 | regulation of hydrolase activity | 3.96E−08 |
| GO:16528 | sarcoplasm | 3.97E−08 |
| GO:16667 | oxidoreductase activity, acting on a sulfur group of donors | 4.02E−08 |
| GO:51693 | actin filament capping | 4.08E−08 |
| GO:302 | response to reactive oxygen species | 4.13E−08 |
| GO:22618 | ribonucleoprotein complex assembly | 4.64E−08 |
| GO:51493 | regulation of cytoskeleton organization | 4.80E−08 |
| GO:42330 | taxis | 4.80E−08 |
| GO:6935 | chemotaxis | 4.80E−08 |
| GO:42641 | actomyosin | 4.84E−08 |
| GO:6096 | glycolysis | 5.05E−08 |
| GO:60255 | regulation of macromolecule metabolic process | 5.40E−08 |
| GO:6739 | NADP metabolic process | 5.75E−08 |
| GO:1725 | stress fiber | 5.77E−08 |
| GO:19725 | cellular homeostasis | 5.78E−08 |
| GO:51726 | regulation of cell cycle | 6.18E−08 |
| GO:34329 | cell junction assembly | 6.71E−08 |
| GO:1525 | angiogenesis | 6.72E−08 |
| GO:6974 | response to DNA damage stimulus | 7.29E−08 |
| GO:22603 | regulation of anatomical structure morphogenesis | 7.40E−08 |
| GO:10948 | negative regulation of cell cycle process | 7.42E−08 |
| GO:5832 | chaperonin-containing T-complex | 7.84E−08 |
| GO:19901 | protein kinase binding | 8.03E−08 |
| GO:31406 | carboxylic acid binding | 8.03E−08 |
| GO:6921 | cellular component disassembly involved in execution phase of apoptosis | 8.10E−08 |
| GO:71826 | ribonucleoprotein complex subunit organization | 8.21E−08 |

TABLE 2-continued

Gene ontology (biological process, cellular component and molecular function) terms enriched in the engineered VF mucosa proteome.
Enriched ontology terms were identified using the BINGO algorithm. The term list shown here corresponds to the functional
enrichment map presented in FIG. 3E. Terms are listed in order of ascending Benjamini Hochberg-adjusted P-value.

| Gene ontology term | Description | Adjusted P-value |
| --- | --- | --- |
| GO:19900 | kinase binding | 8.36E−08 |
| GO:48029 | monosaccharide binding | 8.78E−08 |
| GO:5794 | Golgi apparatus | 9.87E−08 |
| GO:51239 | regulation of multicellular organismal process | 9.88E−08 |
| GO:50661 | NADP binding | 9.88E−08 |
| GO:30120 | vesicle coat | 9.88E−08 |
| GO:60341 | regulators of cellular localization | 9.95E−08 |
| GO:31333 | negative regulation of protein complex assembly | 1.06E−07 |
| GO:30662 | coated vesicle membrane | 1.22E−07 |
| GO:5080 | protein kinase C binding | 1.25E−07 |
| GO:9888 | tissue development | 1.27E−07 |
| GO:2001233 | regulation of apoptotic signaling pathway | 1.38E−07 |
| GO:97194 | execution phase of apoptosis | 1.39E−07 |
| GO:5583 | fibrillar collagen | 1.47E−07 |
| GO:51235 | maintenance of location | 1.54E−07 |
| GO:48584 | positive regulation of response to stimulus | 1.63E−07 |
| GO:51656 | establishment of organelle localization | 1.66E−07 |
| GO:42383 | sarcolemma | 1.78E−07 |
| GO:30141 | secretory granule | 1.78E−07 |
| GO:34330 | cell junction organization | 1.89E−07 |
| GO:30835 | negative regulation of actin filament depolymerization | 1.92E−07 |
| GO:52548 | regulation of endopeptidase activity | 2.21E−07 |
| GO:1726 | ruffle | 2.27E−07 |
| GO:50793 | regulation of developmental process | 2.33E−07 |
| GO:15036 | disulfide oxidoreductase activity | 2.33E−07 |
| GO:80134 | regulation of response to stress | 2.37E−07 |
| GO:51287 | NAD binding | 2.50E−07 |
| GO:32432 | actin filament bundle | 2.54E−07 |
| GO:42026 | protein refolding | 2.63E−07 |
| GO:48585 | negative regulation of response to stimulus | 2.63E−07 |
| GO:44448 | cell cortex part | 2.93E−07 |
| GO:5516 | calmodulin binding | 2.93E−07 |
| GO:9055 | electron carrier activity | 2.93E−07 |
| GO:34660 | ncRNA metabolic process | 3.19E−07 |
| GO:51640 | organelle localization | 3.40E−07 |
| GO:31589 | cell-substrate adhesion | 3.47E−07 |
| GO:7015 | actin filament organization | 3.58E−07 |
| GO:16864 | intramolecular oxidoreductase activity, transposing S—S bonds | 3.73E−07 |
| GO:3756 | protein disulfide isomerase activity | 3.73E−07 |
| GO:9966 | regulation of signal transduction | 3.76E−07 |
| GO:23057 | negative regulation of signaling | 4.15E−07 |
| GO:48407 | platelet-derived growth factor binding | 4.45E−07 |
| GO:44262 | cellular carbohydrate metabolic process | 4.45E−07 |
| GO:43687 | post-translational protein modification | 4.60E−07 |
| GO:35556 | intracellular signal transduction | 4.65E−07 |
| GO:10038 | response to metal ion | 5.16E−07 |
| GO:60314 | regulation of ryanodine-sensitive calcium-release channel activity | 5.22E−07 |
| GO:16862 | intramolecular oxidoreductase activity, interconverting keto- and enol-groups | 5.22E−07 |
| GO:30490 | maturation of SSU-rRNA | 5.41E−07 |
| GO:9628 | response to abiotic stimulus | 5.59E−07 |
| GO:51087 | chaperone binding | 5.68E−07 |
| GO:10952 | positive regulation of peptidase activity | 5.74E−07 |
| GO:30137 | COPI-coated vesicle | 6.86E−07 |
| GO:6740 | NADPH regeneration | 6.86E−07 |
| GO:16887 | ATPase activity | 6.95E−07 |
| GO:51260 | protein homooligomerization | 7.13E−07 |
| GO:18193 | peptidyl-amino acid modification | 7.13E−07 |
| GO:30126 | COPI vesicle coat | 7.16E−07 |
| GO:34446 | substrate adhesion-dependent cell spreading | 8.63E−07 |
| GO:5525 | GTP binding | 8.65E−07 |
| GO:80090 | regulation of primary metabolic process | 8.86E−07 |
| GO:6027 | glycosaminoglycan catabolic process | 8.91E−07 |
| GO:97458 | neuron part | 9.20E−07 |
| GO:16860 | intramolecular oxidoreductase activity | 9.23E−07 |
| GO:9968 | negative regulation of signal transduction | 9.28E−07 |
| GO:1568 | blood vessel development | 9.58E−07 |
| GO:30663 | COPI-coated vesicle membrane | 9.68E−07 |
| GO:5509 | calcium ion binding | 1.16E−06 |
| GO:5874 | microtubule | 1.17E−06 |
| GO:10648 | negative regulation of cell communication | 1.19E−06 |
| GO:10942 | positive regulation of cell death | 1.21E−06 |
| GO:46930 | pore complex | 1.35E−06 |
| GO:51291 | protein heterooligomerization | 1.35E−06 |
| GO:32561 | guanyl ribonucleotide binding | 1.38E−06 |

TABLE 2-continued

Gene ontology (biological process, cellular component and molecular function) terms enriched in the engineered VF mucosa proteome. Enriched ontology terms were identified using the BINGO algorithm. The term list shown here corresponds to the functional enrichment map presented in FIG. 3E. Terms are listed in order of ascending Benjamini Hochberg-adjusted P-value.

| Gene ontology term | Description | Adjusted P-value |
| --- | --- | --- |
| GO:1901698 | response to nitrogen compound | 1.39E−06 |
| GO:30334 | regulation of cell migration | 1.48E−06 |
| GO:44255 | cellular lipid metabolic process | 1.57E−06 |
| GO:43122 | regulation of I-kappaB kinase/NF-kappaB cascade | 1.57E−06 |
| GO:31347 | regulation of defense response | 1.59E−06 |
| GO:19001 | guanyl nucleotide binding | 1.64E−06 |
| GO:16408 | C-acyltransferase activity | 1.66E−06 |
| GO:33119 | negative regulation of RNA splicing | 1.66E−06 |
| GO:5581 | collagen | 1.73E−06 |
| GO:60205 | cytoplasmic membrane-bounded vesicle lumen | 1.78E−06 |
| GO:6909 | phagocytosis | 1.81E−06 |
| GO:7160 | cell-matrix adhesion | 1.86E−06 |
| GO:8022 | protein C-terminus binding | 1.86E−06 |
| GO:51262 | protein tetramerization | 1.89E−06 |
| GO:31983 | vesicle lumen | 2.03E−06 |
| GO:31323 | regulation of cellular metabolic process | 2.08E−06 |
| GO:42255 | ribosome assembly | 2.21E−06 |
| GO:32154 | cleavage furrow | 2.42E−06 |
| GO:15949 | nucleobase-containing small molecule interconversion | 2.42E−06 |
| GO:30135 | coated vesicle | 2.54E−06 |
| GO:10243 | response to organic nitrogen | 2.61E−06 |
| GO:44711 | single-organism biosynthetic process | 2.79E−06 |
| GO:3697 | single-stranded DNA binding | 2.79E−06 |
| GO:72359 | circulatory system development | 2.80E−06 |
| GO:72358 | cardiovascular system development | 2.80E−06 |
| GO:32272 | negative regulation of protein polymerization | 2.93E−06 |
| GO:30554 | adenyl nucleotide binding | 3.00E−06 |
| GO:8544 | epidermis development | 3.03E−06 |
| GO:6955 | immune response | 3.14E−06 |
| GO:51168 | nuclear export | 3.14E−06 |
| GO:1944 | vasculature development | 3.18E−06 |
| GO:51236 | establishment of RNA localization | 3.39E−06 |
| GO:50657 | nucleic acid transport | 3.39E−06 |
| GO:50658 | RNA transport | 3.39E−06 |
| GO:17148 | negative regulation of translation | 3.43E−06 |
| GO:2000145 | regulation of cell motility | 3.48E−06 |
| GO:30837 | negative regulation of actin filament polymerization | 3.49E−06 |
| GO:1901028 | regulation of mitochondrial outer membrane permeabilization | 3.60E−06 |
| GO:6364 | rRNA processing | 3.68E−06 |
| GO:22610 | biological adhesion | 3.69E−06 |
| GO:43005 | neuron projection | 3.85E−06 |
| GO:30660 | Golgi-associated vesicle membrane | 3.89E−06 |
| GO:22604 | regulation of cell morphogenesis | 3.94E−06 |
| GO:44283 | small molecule biosynthetic process | 4.02E−06 |
| GO:44459 | plasma membrane part | 4.04E−06 |
| GO:51050 | positive regulation of transport | 4.15E−06 |
| GO:72522 | purine-containing compound biosynthetic process | 4.17E−06 |
| GO:5798 | Golgi-associated vesicle | 4.18E−06 |
| GO:51289 | protein homotetramerization | 4.22E−06 |
| GO:16567 | protein ubiquitination | 4.25E−06 |
| GO:45859 | regulation of protein kinase activity | 4.28E−06 |
| GO:30666 | endocytic vesicle membrane | 4.62E−06 |
| GO:32559 | adenyl ribonucleotide binding | 4.67E−06 |
| GO:51648 | vesicle localization | 4.71E−06 |
| GO:19843 | rRNA binding | 4.92E−06 |
| GO:4857 | enzyme inhibitor activity | 5.22E−06 |
| GO:10821 | regulation of mitochondrion organization | 5.33E−06 |
| GO:43244 | regulation of protein complex disassembly | 5.65E−06 |
| GO:40012 | regulation of locomotion | 5.65E−06 |
| GO:6403 | RNA localization | 5.96E−06 |
| GO:16651 | oxidoreductase activity, acting on NAD(P)H | 5.96E−06 |
| GO:30512 | negative regulation of transforming growth factor beta receptor signaling pathway | 5.96E−06 |
| GO:6026 | aminoglycan catabolic process | 5.96E−06 |
| GO:9100 | glycoprotein metabolic process | 6.14E−06 |
| GO:5518 | collagen binding | 6.20E−06 |
| GO:42340 | keratan sulfate catabolic process | 6.42E−06 |
| GO:8143 | poly(A) RNA binding | 6.42E−06 |
| GO:2682 | regulation of immune system process | 6.54E−06 |
| GO:32153 | cell division site | 6.85E−06 |
| GO:32155 | cell division site part | 6.85E−06 |
| GO:8238 | exopeptidase activity | 6.90E−06 |
| GO:48514 | blood vessel morphogenesis | 7.01E−06 |
| GO:70647 | protein modification by small protein conjugation or removal | 7.09E−06 |
| GO:43549 | regulation of kinase activity | 7.11E−06 |

TABLE 2-continued

Gene ontology (biological process, cellular component and molecular function) terms enriched in the engineered VF mucosa proteome. Enriched ontology terms were identified using the BINGO algorithm. The term list shown here corresponds to the functional enrichment map presented in FIG. 3E. Terms are listed in order of ascending Benjamini Hochberg-adjusted P-value.

| Gene ontology term | Description | Adjusted P-value |
| --- | --- | --- |
| GO:16072 | rRNA metabolic process | 7.30E−06 |
| GO:61134 | peptidase regulator activity | 7.39E−06 |
| GO:5905 | coated pit | 7.39E−06 |
| GO:16053 | organic acid biosynthetic process | 7.93E−06 |
| GO:46394 | carboxylic acid biosynthetic process | 7.93E−06 |
| GO:7155 | cell adhesion | 7.99E−06 |
| GO:31093 | platelet alpha granule lumen | 7.99E−06 |
| GO:1901879 | regulation of protein depolymerization | 8.23E−06 |
| GO:6098 | pentose-phosphate shunt | 8.47E−06 |
| GO:6890 | retrograde vesicle-mediated transport, Golgi to ER | 8.47E−06 |
| GO:10822 | positive regulation of mitochondrion organization | 9.36E−06 |
| GO:4364 | glutathione transferase activity | 9.36E−06 |
| GO:10627 | regulation of intracellular protein kinase cascade | 9.58E−06 |
| GO:15035 | protein disulfide oxidoreductase activity | 9.78E−06 |
| GO:43206 | extracellular fibril organization | 9.99E−06 |
| GO:97435 | fibril organization | 9.99E−06 |
| GO:48025 | negative regulation of mRNA splicing, via spliceosome | 9.99E−06 |
| GO:43065 | positive regulation of apoptotic process | 1.01E−05 |
| GO:6892 | post-Golgi vesicle-mediated transport | 1.01E−05 |
| GO:5782 | peroxisomal matrix | 1.03E−05 |
| GO:31907 | microbody lumen | 1.03E−05 |
| GO:6937 | regulation of muscle contraction | 1.04E−05 |
| GO:44242 | cellular lipid catabolic process | 1.07E−05 |
| GO:19003 | GDP binding | 1.08E−05 |
| GO:6144 | purine nucleobase metabolic process | 1.08E−05 |
| GO:16529 | sarcoplasmic reticulum | 1.10E−05 |
| GO:9112 | nucleobase metabolic process | 1.12E−05 |
| GO:70848 | response to growth factor stimulus | 1.19E−05 |
| GO:43068 | positive regulation of programmed cell death | 1.32E−05 |
| GO:51338 | regulation of transferase activity | 1.34E−05 |
| GO:16835 | carbon-oxygen lyase activity | 1.36E−05 |
| GO:19838 | growth factor binding | 1.38E−05 |
| GO:5524 | ATP binding | 1.41E−05 |
| GO:10880 | regulation of release of sequestered calcium ion into cytosol by sarcoplasmic reticulum | 1.44E−05 |
| GO:1900739 | regulation of protein insertion into mitochondrial membrane involved in apoptotic signaling pathway | 1.44E−05 |
| GO:1900740 | positive regulation of protein insertion into mitochondrial membrane involved in apoptotic signaling pathway | 1.44E−05 |
| GO:9165 | nucleotide biosynthetic process | 1.44E−05 |
| GO:30864 | cortical actin cytoskeleton | 1.45E−05 |
| GO:42451 | purine nucleoside biosynthetic process | 1.47E−05 |
| GO:46129 | purine ribonucleoside biosynthetic process | 1.47E−05 |
| GO:2000116 | regulation of cysteine-type endopeptidase activity | 1.50E−05 |
| GO:32446 | protein modification by small protein conjugation | 1.50E−05 |
| GO:15931 | nucleobase-containing compound transport | 1.52E−05 |
| GO:14070 | response to organic cyclic compound | 1.54E−05 |
| GO:55117 | regulation of cardiac muscle contraction | 1.56E−05 |
| GO:70925 | organelle assembly | 1.57E−05 |
| GO:90101 | negative regulation of transmembrane receptor protein serine/threonine kinase signaling pathway | 1.64E−05 |
| GO:28 | ribosomal small subunit assembly | 1.71E−05 |
| GO:462 | maturation of SSU-rRNA from tricistronic rRNA transcript (SSU-rRNA, 5.8S rRNA, LSU-rRNA) | 1.71E−05 |
| GO:4032 | alditol: NADP + 1-oxidoreductase activity | 1.71E−05 |
| GO:19322 | pentose biosynthetic process | 1.71E−05 |
| GO:51345 | positive regulation of hydrolase activity | 1.72E−05 |
| GO:8284 | positive regulation of cell proliferation | 1.80E−05 |
| GO:5885 | Arp2/3 protein complex | 1.83E−05 |
| GO:45785 | positive regulation of cell adhesion | 1.90E−05 |
| GO:60627 | regulation of vesicle-mediated transport | 1.97E−05 |
| GO:6164 | purine nucleotide biosynthetic process | 2.03E−05 |
| GO:32880 | regulation of protein localization | 2.14E−05 |
| GO:9068 | aspartate family amino acid catabolic process | 2.15E−05 |
| GO:70717 | poly-purine tract binding | 2.15E−05 |
| GO:50686 | negative regulation of mRNA processing | 2.15E−05 |
| GO:70482 | response to oxygen levels | 2.19E−05 |
| GO:71103 | DNA conformation change | 2.28E−05 |
| GO:1901293 | nucleoside phosphate biosynthetic process | 2.30E−05 |
| GO:70993 | translation preinitiation complex | 2.31E−05 |
| GO:33290 | eukaryotic 48S preinitiation complex | 2.31E−05 |
| GO:16282 | eukaryotic 43S preinitiation complex | 2.31E−05 |
| GO:31968 | organelle outer membrane | 2.49E−05 |
| GO:8135 | translation factor activity, nucleic acid binding | 2.49E−05 |
| GO:1901019 | regulation of calcium ion transmembrane transporter activity | 2.51E−05 |
| GO:5766 | endosome | 2.58E−05 |
| GO:6416 | tRNA aminoacylation for protein translation | 2.64E−05 |

TABLE 2-continued

Gene ontology (biological process, cellular component and molecular function) terms enriched in the engineered VF mucosa proteome.
Enriched ontology terms were identified using the BINGO algorithm. The term list shown here corresponds to the functional
enrichment map presented in FIG. 3E. Terms are listed in order of ascending Benjamini Hochberg-adjusted P-value.

| Gene ontology term | Description | Adjusted P-value |
| --- | --- | --- |
| GO:43648 | dicarboxylic acid metabolic process | 2.68E−05 |
| GO:90288 | negative regulation of cellular response to growth factor stimulus | 2.68E−05 |
| GO:9152 | purine ribonucleotide biosynthetic process | 2.77E−05 |
| GO:43623 | cellular protein complex assembly | 2.83E−05 |
| GO:46390 | ribose phosphate biosynthetic process | 2.87E−05 |
| GO:35337 | fatty-acyl-CoA metabolic process | 2.90E−05 |
| GO:1731 | formation of translation preinitiation complex | 2.90E−05 |
| GO:8379 | thioredoxin peroxidase activity | 3.01E−05 |
| GO:35583 | sequestering of TGFbeta in extracellular matrix | 3.01E−05 |
| GO:19682 | glyceraldehyde-3-phosphate metabolic process | 3.01E−05 |
| GO:42776 | mitochondrial ATP synthesis coupled proton transport | 3.01E−05 |
| GO:3012 | muscle system process | 3.07E−05 |
| GO:60249 | anatomical structure homeostasis | 3.15E−05 |
| GO:43281 | regulation of cysteine-type endopeptidase activity involved in apoptotic process | 3.22E−05 |
| GO:44548 | S100 protein binding | 3.25E−05 |
| GO:45727 | positive regulation of translation | 3.33E−05 |
| GO:51592 | response to calcium ion | 3.37E−05 |
| GO:19904 | protein domain specific binding | 3.37E−05 |
| GO:32388 | positive regulation of intracellular transport | 3.37E−05 |
| GO:55072 | iron ion homeostasis | 3.66E−05 |
| GO:30100 | regulation of endocytosis | 3.70E−05 |
| GO:34504 | protein localization to nucleus | 3.91E−05 |
| GO:31091 | platelet alpha granule | 4.11E−05 |
| GO:35338 | long-chain fatty-acyl-CoA biosynthetic process | 4.15E−05 |
| GO:72350 | tricarboxylic acid metabolic process | 4.15E−05 |
| GO:1901566 | organonitrogen compound biosynthetic process | 4.15E−05 |
| GO:51170 | nuclear import | 4.18E−05 |
| GO:5815 | microtubule organizing center | 4.29E−05 |
| GO:43039 | tRNA aminoacylation | 4.29E−05 |
| GO:43038 | amino acid activation | 4.29E−05 |
| GO:16197 | endosomal transport | 4.29E−05 |
| GO:2001242 | regulation of intrinsic apoptotic signaling pathway | 4.39E−05 |
| GO:71363 | cellular response to growth factor stimulus | 4.39E−05 |
| GO:4177 | aminopeptidase activity | 4.49E−05 |
| GO:3727 | single-stranded RNA binding | 4.61E−05 |
| GO:51301 | cell division | 4.94E−05 |
| GO:16853 | isomerase activity | 4.96E−05 |
| GO:6942 | regulation of striated muscle contraction | 4.96E−05 |
| GO:3008 | system process | 4.96E−05 |
| GO:34774 | secretory granule lumen | 5.19E−05 |
| GO:55082 | cellular chemical homeostasis | 5.23E−05 |
| GO:72329 | monocarboxylic acid catabolic process | 5.27E−05 |
| GO:10562 | positive regulation of phosphorus metabolic process | 5.46E−05 |
| GO:45937 | positive regulation of phosphate metabolic process | 5.46E−05 |
| GO:1666 | response to hypoxia | 5.46E−05 |
| GO:19798 | procollagen-proline dioxygenase activity | 5.54E−05 |
| GO:60316 | positive regulation of ryanodine-sensitive calcium-release channel activity | 5.56E−05 |
| GO:6554 | lysine catabolic process | 5.56E−05 |
| GO:6553 | lysine metabolic process | 5.56E−05 |
| GO:44438 | microbody part | 5.69E−05 |
| GO:44439 | peroxisomal part | 5.69E−05 |
| GO:90257 | regulation of muscle system process | 5.72E−05 |
| GO:5643 | nuclear pore | 5.72E−05 |
| GO:5813 | centrosome | 5.72E−05 |
| GO:35383 | thioester metabolic process | 5.96E−05 |
| GO:6637 | acyl-CoA metabolic process | 5.96E−05 |
| GO:17015 | regulation of transforming growth factor beta receptor signaling pathway | 6.01E−05 |
| GO:19867 | outer membrane | 6.10E−05 |
| GO:1901185 | negative regulation of ERBB signaling pathway | 6.19E−05 |
| GO:42059 | negative regulation of epidermal growth factor receptor signaling pathway | 6.19E−05 |
| GO:42579 | microbody | 6.23E−05 |
| GO:5777 | peroxisome | 6.23E−05 |
| GO:36293 | response to decreased oxygen levels | 6.28E−05 |
| GO:44431 | Golgi apparatus part | 6.34E−05 |
| GO:35384 | thioester biosynthetic process | 6.39E−05 |
| GO:71616 | acyl-CoA biosynthetic process | 6.39E−05 |
| GO:43021 | ribonucleoprotein complex binding | 6.50E−05 |
| GO:6611 | protein export from nucleus | 7.10E−05 |
| GO:2001257 | regulation of cation channel activity | 7.10E−05 |
| GO:43123 | positive regulation of I-kappaB kinase/NF-kappaB cascade | 7.13E−05 |
| GO:30133 | transport vesicle | 7.36E−05 |
| GO:6334 | nucleosome assembly | 7.54E−05 |
| GO:34399 | nuclear periphery | 7.92E−05 |
| GO:51271 | negative regulation of cellular component movement | 7.98E−05 |

TABLE 2-continued

Gene ontology (biological process, cellular component and molecular function) terms enriched in the engineered VF mucosa proteome. Enriched ontology terms were identified using the BINGO algorithm. The term list shown here corresponds to the functional enrichment map presented in FIG. 3E. Terms are listed in order of ascending Benjamini Hochberg-adjusted P-value.

| Gene ontology term | Description | Adjusted P-value |
|---|---|---|
| GO:50840 | extracellular matrix binding | 8.01E−05 |
| GO:51028 | mRNA transport | 8.47E−05 |
| GO:90287 | regulation of cellular response to growth factor stimulus | 8.47E−05 |
| GO:70402 | NADPH binding | 8.84E−05 |
| GO:60315 | negative regulation of ryanodine-sensitive calcium-release channel activity | 8.84E−05 |
| GO:4029 | aldehyde dehydrogenase (NAD) activity | 8.84E−05 |
| GO:16042 | lipid catabolic process | 8.84E−05 |
| GO:7052 | mitotic spindle organization | 9.18E−05 |
| GO:31941 | filamentous actin | 9.18E−05 |
| GO:9260 | ribonucleotide biosynthetic process | 9.27E−05 |
| GO:10881 | regulation of cardiac muscle contraction by regulation of the release of sequestered calcium ion | 9.32E−05 |
| GO:90114 | COPII-coated vesicle budding | 9.32E−05 |
| GO:48208 | COPII vesicle coating | 9.32E−05 |
| GO:48207 | vesicle targeting, rough ER to cis-Golgi | 9.32E−05 |
| GO:46949 | fatty-acyl-CoA biosynthetic process | 9.32E−05 |
| GO:42325 | regulation of phosphorylation | 9.46E−05 |
| GO:10811 | positive regulation of cell-substrate adhesion | 9.72E−05 |
| GO:70201 | regulation of establishment of protein localization | 9.72E−05 |
| GO:51051 | negative regulation of transport | 9.81E−05 |
| GO:1901880 | negative regulation of protein depolymerization | 9.83E−05 |
| GO:33674 | positive regulation of kinase activity | 9.87E−05 |
| GO:50900 | leukocyte migration | 1.01E−04 |
| GO:2001056 | positive regulation of cysteine-type endopeptidase activity | 1.02E−04 |
| GO:16477 | cell migration | 1.03E−04 |
| GO:17038 | protein import | 1.03E−04 |
| GO:9051 | pentose-phosphate shunt, oxidative branch | 1.08E−04 |
| GO:43259 | laminin-10 complex | 1.08E−04 |
| GO:3985 | acetly-CoA C-acetyltransferase activity | 1.08E−04 |
| GO:30388 | fructose 1,6-biphosphate metabolic process | 1.08E−04 |
| GO:42455 | ribonucleoside biosynthetic process | 1.09E−04 |
| GO:31334 | positive regulation of protein complex assembly | 1.09E−04 |
| GO:45454 | cell redox homeostasis | 1.10E−04 |
| GO:6450 | regulation of translational fidelity | 1.18E−04 |
| GO:31543 | peptidyl-proline dioxygenase activity | 1.18E−04 |
| GO:55080 | cation homeostasis | 1.19E−04 |
| GO:48306 | calcium-dependent protein binding | 1.20E−04 |
| GO:45860 | positive regulation of protein kinase activity | 1.22E−04 |
| GO:30246 | carbohydrate binding | 1.25E−04 |
| GO:33764 | steroid dehydrogenase activity, acting on the CH—OH group of donors, NAD or NADP as acceptor | 1.27E−04 |
| GO:51347 | positive regulation of transferase activity | 1.31E−04 |
| GO:70208 | protein heterotrimerization | 1.32E−04 |
| GO:51238 | sequestering of metal ion | 1.32E−04 |
| GO:1934 | positive regulation of protein phosphorylation | 1.32E−04 |
| GO:43242 | negative regulation of protein complex disassembly | 1.32E−04 |
| GO:10522 | regulation of calcium ion transport into cytosol | 1.32E−04 |
| GO:9066 | aspartate family amino acid metabolic process | 1.33E−04 |
| GO:33143 | regulation of intracellular steroid hormone receptor signaling pathway | 1.33E−04 |
| GO:44440 | endosomal part | 1.35E−04 |
| GO:4812 | aminoacyl-tRNA ligase activity | 1.37E−04 |
| GO:2000026 | regulation of multicellular organismal development | 1.39E−04 |
| GO:1932 | regulation of protein phosphorylation | 1.43E−04 |
| GO:35336 | long-chain fatty-acyl-CoA metabolic process | 1.48E−04 |
| GO:51279 | regulation of release of sequestered calcium ion into cytosol | 1.51E−04 |
| GO:3746 | translation elongation factor activity | 1.51E−04 |
| GO:16875 | ligase activity, forming carbon-oxygen bonds | 1.54E−04 |
| GO:16876 | ligase activity, forming aminoacyl-tRNA and related compounds | 1.54E−04 |
| GO:31497 | chromatin assembly | 1.55E−04 |
| GO:10950 | positive regulation of endopeptidase activity | 1.58E−04 |
| GO:32993 | protein-DNA complex | 1.58E−04 |
| GO:10951 | negative regulation of endopeptidase activity | 1.65E−04 |
| GO:71495 | cellular response to endogenous stimulus | 1.68E−04 |
| GO:44744 | protein targeting to nucleus | 1.68E−04 |
| GO:6606 | protein import into nucleus | 1.68E−04 |
| GO:44427 | chromosomal part | 1.70E−04 |
| GO:9163 | nucleoside biosynthetic process | 1.71E−04 |
| GO:1901659 | glycosyl compound biosynthetic process | 1.71E−04 |
| GO:6448 | regulation of translational elongation | 1.72E−04 |
| GO:30003 | cellular cation homeostasis | 1.75E−04 |
| GO:90092 | regulation of transmembrane receptor protein serine/threonine kinase signaling pathway | 1.78E−04 |
| GO:10810 | regulation of cell-substrate adhesion | 1.79E−04 |
| GO:42176 | regulation of protein catabolic process | 1.83E−04 |
| GO:6936 | muscle contraction | 1.83E−04 |
| GO:75733 | intracellular transport of viral material | 1.83E−04 |
| GO:910 | cytokinesis | 1.89E−04 |

TABLE 2-continued

Gene ontology (biological process, cellular component and molecular function) terms enriched in the engineered VF mucosa proteome.
Enriched ontology terms were identified using the BINGO algorithm. The term list shown here corresponds to the functional
enrichment map presented in FIG. 3E. Terms are listed in order of ascending Benjamini Hochberg-adjusted P-value.

| Gene ontology term | Description | Adjusted P-value |
|---|---|---|
| GO:1900026 | positive regulation of substrate adhesion-dependent cell spreading | 1.90E−04 |
| GO:9063 | cellular amino acid catabolic process | 1.90E−04 |
| GO:50764 | regulation of phagocytosis | 1.92E−04 |
| GO:6641 | triglyceride metabolic process | 1.94E−04 |
| GO:48878 | chemical homeostasis | 1.94E−04 |
| GO:16229 | steroid dehydrogenase activity | 1.99E−04 |
| GO:6839 | mitochondrial transport | 2.00E−04 |
| GO:2252 | immune effector process | 2.01E−04 |
| GO:5544 | calcium-dependent phospholipid binding | 2.07E−04 |
| GO:42327 | positive regulation of phosphorylation | 2.08E−04 |
| GO:9167 | purine ribonucleoside monophosphate metabolic process | 2.10E−04 |
| GO:6635 | fatty acid beta-oxidation | 2.10E−04 |
| GO:31253 | cell projection membrane | 2.11E−04 |
| GO:44463 | cell projection part | 2.15E−04 |
| GO:19321 | pentose metabolic process | 2.25E−04 |
| GO:5844 | polysome | 2.30E−04 |
| GO:9126 | purine nucleoside monophosphate metabolic process | 2.35E−04 |
| GO:30054 | cell junction | 2.37E−04 |
| GO:34728 | nucleosome organization | 2.39E−04 |
| GO:16836 | hydro-lyase activity | 2.41E−04 |
| GO:30162 | regulation of proteolysis | 2.41E−04 |
| GO:30117 | membrane coat | 2.42E−04 |
| GO:48475 | coated membrane | 2.42E−04 |
| GO:16453 | C-acetyltransferase activity | 2.47E−04 |
| GO:70934 | CRD-mediated mRNA stabilization | 2.47E−04 |
| GO:10649 | regulation of cell communication by electrical coupling | 2.47E−04 |
| GO:71692 | protein localization to extracellular region | 2.47E−04 |
| GO:71694 | maintenance of protein location in extracellular region | 2.47E−04 |
| GO:48027 | mRNA 5′-UTR binding | 2.47E−04 |
| GO:2000425 | regulation of apoptotic cell clearance | 2.47E−04 |
| GO:3724 | RNA helicase activity | 2.62E−04 |
| GO:19371 | cyclooxygenase pathway | 2.62E−04 |
| GO:42178 | xenobiotic catabolic process | 2.62E−04 |
| GO:30207 | chondroitin sulfate catabolic process | 2.62E−04 |
| GO:5606 | laminin-1 complex | 2.62E−04 |
| GO:10466 | negative regulation of peptidase activity | 2.62E−04 |
| GO:8016 | regulation of heart contraction | 2.70E−04 |
| GO:6405 | RNA export from nucleus | 2.70E−04 |
| GO:30838 | positive regulation of actin filament polymerization | 2.70E−04 |
| GO:10882 | regulation of cardiac muscle contraction by calcium ion signaling | 2.71E−04 |
| GO:5753 | mitochondrial proton-transporting ATP synthase complex | 2.71E−04 |
| GO:42623 | ATPase activity, coupled | 2.71E−04 |
| GO:43280 | positive regulation of cysteine-type endopeptidase activity involved in apoptotic process | 2.83E−04 |
| GO:9967 | positive regulation of signal transduction | 2.83E−04 |
| GO:1101 | response to acid | 2.83E−04 |
| GO:18149 | peptide cross-linking | 2.87E−04 |
| GO:90407 | organophosphate biosynthetic process | 2.88E−04 |
| GO:51651 | maintenance of location in cell | 2.94E−04 |
| GO:9206 | purine ribonucleoside triphosphate biosynthetic process | 2.96E−04 |
| GO:16765 | transferase activity, transferring alkyl or aryl (other than methyl) groups | 3.00E−04 |
| GO:6639 | acylglycerol metabolic process | 3.00E−04 |
| GO:9145 | purine nucleoside triphosphate biosynthetic process | 3.18E−04 |
| GO:6873 | cellular ion homeostasis | 3.21E−04 |
| GO:6638 | neutral lipid metabolic process | 3.42E−04 |
| GO:9062 | fatty acid catabolic process | 3.49E−04 |
| GO:71451 | cellular response to superoxide | 3.53E−04 |
| GO:32964 | collagen biosynthetic process | 3.53E−04 |
| GO:19430 | removal of superoxide radicals | 3.53E−04 |
| GO:3857 | 3-hydroxyacyl-CoA dehydrogenase activity | 3.53E−04 |
| GO:8106 | alcohol dehydrogenase (NADP+) activity | 3.53E−04 |
| GO:30934 | anchoring collagen | 3.53E−04 |
| GO:5694 | chromosome | 3.65E−04 |
| GO:6879 | cellular iron ion homeostasis | 3.66E−04 |
| GO:45185 | maintenance of protein location | 3.66E−04 |
| GO:86 | G2/M transition of mitotic cell cycle | 3.85E−04 |
| GO:16504 | peptidase activator activity | 3.87E−04 |
| GO:6754 | ATP biosynthetic process | 3.89E−04 |
| GO:33118 | endoplasmic reticulum-Golgi intermediate compartment membrane | 3.90E−04 |
| GO:19773 | proteasome core complex, alpha-subunit complex | 3.90E−04 |
| GO:5741 | mitochondrial outer membrane | 3.99E−04 |
| GO:9101 | glycoprotein biosynthetic process | 4.15E−04 |
| GO:48646 | anatomical structure formation involved in morphogenesis | 4.26E−04 |
| GO:97367 | carbohydrate derivative binding | 4.28E−04 |
| GO:6399 | tRNA metabolic process | 4.34E−04 |

TABLE 2-continued

Gene ontology (biological process, cellular component and molecular function) terms enriched in the engineered VF mucosa proteome.
Enriched ontology terms were identified using the BINGO algorithm. The term list shown here corresponds to the functional
enrichment map presented in FIG. 3E. Terms are listed in order of ascending Benjamini Hochberg-adjusted P-value.

| Gene ontology term | Description | Adjusted P-value |
| --- | --- | --- |
| GO:6662 | glycerol ether metabolic process | 4.39E−04 |
| GO:6333 | chromatin assembly or disassembly | 4.43E−04 |
| GO:23056 | positive regulation of signaling | 4.48E−04 |
| GO:22898 | regulation of transmembrane transporter activity | 4.49E−04 |
| GO:51495 | positive regulation of cytoskeleton organization | 4.52E−04 |
| GO:34470 | ncRNA processing | 4.63E−04 |
| GO:50690 | regulation of defense response to virus by virus | 4.63E−04 |
| GO:35581 | sequestering of extracellular ligand from receptor | 4.63E−04 |
| GO:71437 | invadopodium | 4.63E−04 |
| GO:16508 | long-chain-enoyl-CoA hydratase activity | 4.63E−04 |
| GO:70937 | CRD-mediated mRNA stability complex | 4.63E−04 |
| GO:30235 | nitric-oxide synthase regulator activity | 4.63E−04 |
| GO:31581 | hemidesmosome assembly | 4.63E−04 |
| GO:2001258 | negative regulation of cation channel activity | 4.63E−04 |
| GO:46185 | aldehyde catabolic process | 4.63E−04 |
| GO:70003 | threonine-type peptidase activity | 4.68E−04 |
| GO:4298 | threonine-type endopeptidase activity | 4.68E−04 |
| GO:10647 | positive regulation of cell communication | 4.73E−04 |
| GO:9201 | ribonucleoside triphosphate biosynthetic process | 4.75E−04 |
| GO:6888 | ER to Golgi vesicle-mediated transport | 4.75E−04 |
| GO:139 | Golgi membrane | 4.84E−04 |
| GO:6631 | fatty acid metabolic process | 4.86E−04 |
| GO:32411 | positive regulation of transporter activity | 4.89E−04 |
| GO:5774 | vacuolar membrane | 4.94E−04 |
| GO:8283 | cell proliferation | 4.94E−04 |
| GO:65004 | protein-DNA complex assembly | 4.97E−04 |
| GO:5819 | spindle | 5.04E−04 |
| GO:55037 | recycling endosome | 5.10E−04 |
| GO:51272 | positive regulation of cellular component movement | 5.20E−04 |
| GO:51674 | localization of cell | 5.21E−04 |
| GO:50801 | ion homeostasis | 5.21E−04 |
| GO:48870 | cell motility | 5.21E−04 |
| GO:30203 | glycosaminoglycan metabolic process | 5.21E−04 |
| GO:97190 | apoptotic signaling pathway | 5.24E−04 |
| GO:43200 | response to amino acid stimulus | 5.37E−04 |
| GO:43531 | ADP binding | 5.38E−04 |
| GO:33144 | negative regulation of intracellular steroid hormone receptor signaling pathway | 5.38E−04 |
| GO:9897 | external side of plasma membrane | 5.43E−04 |
| GO:97193 | intrinsic apoptotic signaling pathway | 5.46E−04 |
| GO:1900117 | regulation of execution phase of apoptosis | 5.63E−04 |
| GO:30658 | transport vesicle membrane | 5.75E−04 |
| GO:8290 | F-actin capping protein complex | 5.93E−04 |
| GO:8250 | oligosaccharyltransferase complex | 5.93E−04 |
| GO:1900024 | regulation of substrate adhesion-dependent cell spreading | 5.93E−04 |
| GO:1901020 | negative regulation of calcium ion transmembrane transporter activity | 5.93E−04 |
| GO:51131 | chaperone-mediated protein complex assembly | 5.93E−04 |
| GO:42288 | MHC class I protein binding | 5.93E−04 |
| GO:7051 | spindle organization | 6.10E−04 |
| GO:9725 | response to hormone stimulus | 6.14E−04 |
| GO:44766 | multi-organism transport | 6.28E−04 |
| GO:72512 | trivalent inorganic cation transport | 6.28E−04 |
| GO:33572 | transferrin transport | 6.28E−04 |
| GO:15682 | ferric iron transport | 6.28E−04 |
| GO:16655 | oxidoreductase activity, acting on NAD(P)H, quinone or similar compound as acceptor | 6.34E−04 |
| GO:16829 | lyase activity | 6.38E−04 |
| GO:6308 | DNA catabolic process | 6.84E−04 |
| GO:43022 | ribosome binding | 6.86E−04 |
| GO:50776 | regulation of immune response | 7.10E−04 |
| GO:10639 | negative regulation of organelle organization | 7.12E−04 |
| GO:43413 | macromolecule glycosylation | 7.19E−04 |
| GO:6466 | protein glycosylation | 7.19E−04 |
| GO:5839 | proteasome core complex | 7.27E−04 |
| GO:5852 | eukaryotic translation initiation factor 3 complex | 7.27E−04 |
| GO:30866 | cortical actin cytoskeleton organization | 7.31E−04 |
| GO:786 | nucleosome | 7.32E−04 |
| GO:2161 | aminoacyl-tRNA editing activity | 7.53E−04 |
| GO:70419 | nonhomologous end joining complex | 7.61E−04 |
| GO:8429 | phosphatidylethanolamine binding | 7.61E−04 |
| GO:5589 | collagen type VI | 7.61E−04 |
| GO:6101 | citrate metabolic process | 7.61E−04 |
| GO:15037 | peptide disulfide oxidoreductase activity | 7.61E−04 |
| GO:43488 | regulation of mRNA stability | 7.62E−04 |
| GO:9142 | nucleoside triphosphate biosynthetic process | 7.77E−04 |
| GO:32273 | positive regulation of protein polymerization | 7.84E−04 |

TABLE 2-continued

Gene ontology (biological process, cellular component and molecular function) terms enriched in the engineered VF mucosa proteome. Enriched ontology terms were identified using the BINGO algorithm. The term list shown here corresponds to the functional enrichment map presented in FIG. 3E. Terms are listed in order of ascending Benjamini Hochberg-adjusted P-value.

| Gene ontology term | Description | Adjusted P-value |
| --- | --- | --- |
| GO:2684 | positive regulation of immune system process | 7.87E−04 |
| GO:10008 | endosome membrane | 8.26E−04 |
| GO:45807 | positive regulation of endocytosis | 8.26E−04 |
| GO:1937 | negative regulation of endothelial cell proliferation | 8.44E−04 |
| GO:42339 | keratan sulfate metabolic process | 8.44E−04 |
| GO:45121 | membrane raft | 8.48E−04 |
| GO:10563 | negative regulation of phosphorus metabolic process | 8.73E−04 |
| GO:45936 | negative regulation of phosphate metabolic process | 8.73E−04 |
| GO:32409 | regulation of transposer activity | 8.76E−04 |
| GO:9108 | coenzyme biosynthetic process | 8.76E−04 |
| GO:2253 | activation of immune response | 8.78E−04 |
| GO:30336 | negative regulation of cell migration | 8.79E−04 |
| GO:6875 | cellular metal ion homeostasis | 9.08E−04 |
| GO:40013 | negative regulation of locomotion | 9.14E−04 |
| GO:33673 | negative regulation of kinase activity | 9.18E−04 |
| GO:51924 | regulation of calcium ion transport | 9.20E−04 |
| GO:30705 | cytoskeleton-dependent intracellular transport | 9.26E−04 |
| GO:43256 | laminin complex | 9.32E−04 |
| GO:19471 | 4-hydroxyproline metabolic process | 9.32E−04 |
| GO:1901021 | positive regulation of calcium ion transmembrane transporter activity | 9.32E−04 |
| GO:42273 | ribosomal large subunit biogenesis | 9.32E−04 |
| GO:6103 | 2-oxoglutarate metabolic process | 9.32E−04 |
| GO:7009 | plasma membrane organization | 9.57E−04 |
| GO:51099 | positive regulation of binding | 9.80E−04 |
| GO:2000146 | negative regulation of cell motility | 1.01E−03 |
| GO:44325 | ion channel binding | 1.01E−03 |
| GO:1901605 | alpha-amino acid metabolic process | 1.03E−03 |
| GO:44070 | regulation of anion transport | 1.04E−03 |
| GO:70085 | glycosylation | 1.06E−03 |
| GO:6022 | aminoglycan metabolic process | 1.08E−03 |
| GO:5884 | actin filament | 1.09E−03 |
| GO:10740 | positive regulation of intracellular protein kinase cascade | 1.10E−03 |
| GO:70206 | protein trimerization | 1.11E−03 |
| GO:31418 | L-ascorbic acid binding | 1.11E−03 |
| GO:30865 | cortical cytoskeleton organization | 1.11E−03 |
| GO:5911 | cell-cell junction | 1.13E−03 |
| GO:42493 | response to drug | 1.13E−03 |
| GO:18904 | ether metabolic process | 1.14E−03 |
| GO:45022 | early endosome to late endosome transport | 1.15E−03 |
| GO:5836 | proteasome regulatory particle | 1.15E−03 |
| GO:5853 | eukaryotic translation elongation factor 1 complex | 1.15E−03 |
| GO:43024 | ribosomal small subunit binding | 1.15E−03 |
| GO:44597 | daunorubicin metabolic process | 1.15E−03 |
| GO:44598 | doxorubicin metabolic process | 1.15E−03 |
| GO:44183 | protein binding involved in protein folding | 1.15E−03 |
| GO:51016 | barbed-end actin filament capping | 1.15E−03 |
| GO:30647 | aminoglycoside antibiotic metabolic process | 1.15E−03 |
| GO:4300 | enoyl-CoA hydratase activity | 1.15E−03 |
| GO:75713 | establishment of integrated proviral latency | 1.15E−03 |
| GO:15266 | porin activity | 1.15E−03 |
| GO:46487 | glyoxylate metabolic process | 1.15E−03 |
| GO:51015 | actin filament binding | 1.16E−03 |
| GO:43484 | regulation of RNA splicing | 1.17E−03 |
| GO:4866 | endopeptidase inhibitor activity | 1.20E−03 |
| GO:71824 | protein-DNA complex subunit organization | 1.20E−03 |
| GO:10975 | regulation of neuron projection development | 1.21E−03 |
| GO:19897 | extrinsic to plasma membrane | 1.22E−03 |
| GO:35637 | multicellular organsimal signaling | 1.22E−03 |
| GO:61136 | regulation of proteasomal protein catabolic process | 1.23E−03 |
| GO:19903 | protein phosphatase binding | 1.23E−03 |
| GO:8144 | drug binding | 1.23E−03 |
| GO:61383 | trabecula morphogenesis | 1.24E−03 |
| GO:33017 | sarcoplasmic reticulum membrane | 1.25E−03 |
| GO:5605 | basal lamina | 1.25E−03 |
| GO:50688 | regulation of defense response to virus | 1.25E−03 |
| GO:42058 | regulation of epidermal growth factor receptor signaling pathway | 1.25E−03 |
| GO:16705 | oxidoreductase activity, acting on paired donors, with incorporation of reduction of molecular oxygen | 1.27E−03 |
| GO:31344 | regulation of cell projection organization | 1.28E−03 |
| GO:52632 | citrate hydro-lyase (cis-aconitate-forming) activity | 1.30E−03 |
| GO:52633 | isocitrate hydro-lyase (cis-aconitate-forming) activity | 1.30E−03 |
| GO:70288 | ferritin complex | 1.30E−03 |
| GO:461 | endonucleolytic cleavage to generate mature 3'-end of SSU-rRNA from (SSU-rRNA, 5.8S rRNA, LSU-rRNA) | 1.30E−03 |

TABLE 2-continued

Gene ontology (biological process, cellular component and molecular function) terms enriched in the engineered VF mucosa proteome. Enriched ontology terms were identified using the BINGO algorithm. The term list shown here corresponds to the functional enrichment map presented in FIG. 3E. Terms are listed in order of ascending Benjamini Hochberg-adjusted P-value.

| Gene ontology term | Description | Adjusted P-value |
|---|---|---|
| GO:35613 | RNA stem-loop binding | 1.30E−03 |
| GO:17098 | sulfonylurea receptor binding | 1.30E−03 |
| GO:2135 | CTP binding | 1.30E−03 |
| GO:2580 | regulation of antigen processing and presentation of peptide or polysaccharide antigen via MHC class II | 1.30E−03 |
| GO:10501 | RNA secondary structure unwinding | 1.30E−03 |
| GO:1901844 | regulation of cell communication by electrical coupling involved in cardiac conduction | 1.30E−03 |
| GO:5584 | collagen type I | 1.30E−03 |
| GO:5999 | xylulose biosynthetic process | 1.30E−03 |
| GO:6097 | glyoxylate cycle | 1.30E−03 |
| GO:5642 | annulate lamellae | 1.30E−03 |
| GO:6880 | intracellular sequestering of iron ion | 1.30E−03 |
| GO:2001135 | regulation of endocytic recycling | 1.30E−03 |
| GO:2001137 | positive regulation of endocytic recycling | 1.30E−03 |
| GO:31372 | UBC13-MMS2 complex | 1.30E−03 |
| GO:8043 | intracellular ferritin complex | 1.30E−03 |
| GO:43524 | negative regulation of neuron apoptotic process | 1.32E−03 |
| GO:1901184 | regulation of ERBB signaling pathway | 1.33E−03 |
| GO:50778 | positive regulation of immune response | 1.35E−03 |
| GO:43487 | regulation of RNA stability | 1.35E−03 |
| GO:9063 | branched-chain amino acid catabolic process | 1.36E−03 |
| GO:4033 | aldo-keto reductase (NADP) activity | 1.36E−03 |
| GO:44297 | cell body | 1.36E−03 |
| GO:61135 | endopeptidase regulator activity | 1.37E−03 |
| GO:43588 | skin development | 1.44E−03 |
| GO:31674 | I band | 1.45E−03 |
| GO:5765 | lysosomal membrane | 1.45E−03 |
| GO:8202 | steroid metabolic process | 1.46E−03 |
| GO:6469 | negative regulation of protein kinase activity | 1.46E−03 |
| GO:2831 | regulation of response to biotic stimulus | 1.46E−03 |
| GO:15662 | ATPase activity, coupled to transmembrane movement of ions, phosphorylative mechanism | 1.47E−03 |
| GO:6323 | DNA packaging | 1.51E−03 |
| GO:7229 | integrin-mediated signaling pathway | 1.51E−03 |
| GO:55065 | metal ion homeostasis | 1.54E−03 |
| GO:32412 | regulation of ion transmembrane transporter activity | 1.55E−03 |
| GO:30027 | lamellipodium | 1.57E−03 |
| GO:9890 | negative regulation of biosynthetic process | 1.59E−03 |
| GO:43171 | peptide catabolic process | 1.63E−03 |
| GO:33018 | sarcoplasmic reticulum lumen | 1.63E−03 |
| GO:50786 | RAGE receptor binding | 1.63E−03 |
| GO:303 | response to superoxide | 1.63E−03 |
| GO:1516 | prostaglandin biosynthetic process | 1.63E−03 |
| GO:46457 | prostanoid biosynthetic process | 1.63E−03 |
| GO:97202 | activation of cysteine-type endopeptidase activity | 1.65E−03 |
| GO:32508 | DNA duplex unwinding | 1.65E−03 |
| GO:16620 | oxidoreductase activity, acting on the aldehyde or oxo group of donors, NAD or NADP as acceptor | 1.65E−03 |
| GO:6767 | water-soluble vitamin metabolic process | 1.65E−03 |
| GO:70161 | anchoring junction | 1.66E−03 |
| GO:45595 | regulation of cell differentiation | 1.66E−03 |
| GO:51348 | negative regulation of transferase activity | 1.68E−03 |
| GO:9615 | response to virus | 1.68E−03 |
| GO:30414 | peptidase inhibitor activity | 1.69E−03 |
| GO:34097 | response to cytokine stimulus | 1.72E−03 |
| GO:785 | chromatin | 1.73E−03 |
| GO:31256 | leading edge membrane | 1.74E−03 |
| GO:32414 | positive regulation of ion transmembrane transporter activity | 1.76E−03 |
| GO:45259 | proton-transporting ATP synthase complex | 1.76E−03 |
| GO:71705 | nitrogen compound transport | 1.77E−03 |
| GO:19395 | fatty acid oxdation | 1.77E−03 |
| GO:31547 | regulation of protein stability | 1.81E−03 |
| GO:32392 | DNA geometric change | 1.85E−03 |
| GO:7162 | negative regulation of cell adhesion | 1.85E−03 |
| GO:34440 | lipid oxidation | 1.90E−03 |
| GO:8015 | blood circulation | 1.91E−03 |
| GO:30506 | ankyrin binding | 1.93E−03 |
| GO:7517 | muscle organ development | 1.96E−03 |
| GO:30262 | apoptotic nuclear changes | 1.97E−03 |
| GO:7568 | aging | 2.02E−03 |
| GO:10959 | regulation of metal ion transport | 2.05E−03 |
| GO:1901215 | negative regulation of neuron death | 2.07E−03 |
| GO:3013 | circulatory system process | 2.07E−03 |
| GO:16903 | oxidoreductase activity, acting on the aldehyde or oxo group of donors | 2.07E−03 |
| GO:33293 | monocarboxylic acid binding | 2.08E−03 |

TABLE 2-continued

Gene ontology (biological process, cellular component and molecular function) terms enriched in the engineered VF mucosa proteome.
Enriched ontology terms were identified using the BINGO algorithm. The term list shown here corresponds to the functional
enrichment map presented in FIG. 3E. Terms are listed in order of ascending Benjamini Hochberg-adjusted P-value.

| Gene ontology term | Description | Adjusted P-value |
|---|---|---|
| GO:16597 | amino acid binding | 2.16E−03 |
| GO:42277 | peptide binding | 2.17E−03 |
| GO:38127 | ERBB signaling pathway | 2.17E−03 |
| GO:34332 | adherens junction organization | 2.18E−03 |
| GO:8233 | peptidase activity | 2.18E−03 |
| GO:8289 | lipid binding | 2.18E−03 |
| GO:34333 | adherens junction assembly | 2.20E−03 |
| GO:48024 | regulation of mRNA splicing, via spliceosome | 2.20E−03 |
| GO:15985 | energy coupled proton transport, down electrochemical gradient | 2.20E−03 |
| GO:15986 | ATP synthesis coupled proton transport | 2.20E−03 |
| GO:16417 | S-acyltransferase activity | 2.21E−03 |
| GO:10592 | positive regulation of lamellipodium assembly | 2.21E−03 |
| GO:19043 | establishment of viral latency | 2.21E−03 |
| GO:6011 | UDP-glucose metabolic process | 2.21E−03 |
| GO:5652 | nuclear lamina | 2.21E−03 |
| GO:8091 | spectrin | 2.21E−03 |
| GO:50684 | regulation of mRNA processing | 2.25E−03 |
| GO:34080 | CENP-A containing nucleosome assembly at centromere | 2.26E−03 |
| GO:34724 | DNA replication-independent nucleosome organization | 2.26E−03 |
| GO:34308 | primary alcohol metabolic process | 2.26E−03 |
| GO:6336 | DNA replication-independent nucleosome assembly | 2.26E−03 |
| GO:32413 | negative regulation of ion transmembrane transporter activity | 2.26E−03 |
| GO:18208 | peptidyl-proline modification | 2.30E−03 |
| GO:19898 | extrinsic to membrane | 2.32E−03 |
| GO:61061 | muscle structure development | 2.33E−03 |
| GO:2433 | immune response-regulating cell surface receptor signaling pathway involved in phagocytosis | 2.41E−03 |
| GO:38094 | Fc-gamma receptor signaling pathway | 2.41E−03 |
| GO:38096 | Fc-gamma receptor signaling pathway involved in phagocytosis | 2.41E−03 |
| GO:30018 | Z disc | 2.42E−03 |
| GO:47485 | protein N-terminus bindng | 2.43E−03 |
| GO:6766 | vitamin metabolic process | 2.43E−03 |
| GO:16363 | nuclear matrix | 2.43E−03 |
| GO:6090 | pyruvate metabolic process | 2.43E−03 |
| GO:5912 | adherens junction | 2.43E−03 |
| GO:30335 | positive regulation of cell migration | 2.51E−03 |
| GO:51494 | negative regulation of cytoskeleton organization | 2.57E−03 |
| GO:33218 | amide binding | 2.60E−03 |
| GO:2431 | Fc receptor mediated stimulatory signaling pathway | 2.60E−03 |
| GO:4003 | ATP-dependent DNA helicase activity | 2.63E−03 |
| GO:2001259 | positive regulation of cation channel activity | 2.64E−03 |
| GO:42326 | negative regulation of phosphorylation | 2.65E−03 |
| GO:45806 | negative regulation of endocytosis | 2.70E−03 |
| GO:10769 | regulation of cell morphogenesis involved in differentiation | 2.72E−03 |
| GO:10720 | positive regulation of cell development | 2.72E−03 |
| GO:70011 | peptidase activity, acting on L-amino acid peptides | 2.76E−03 |
| GO:19226 | transmission of nerve impulse | 2.77E−03 |
| GO:9161 | ribonucleoside monophosphate metabolic process | 2.79E−03 |
| GO:71229 | cellular response to acid | 2.79E−03 |
| GO:48678 | response to axon injury | 2.79E−03 |
| GO:32434 | regulation of proteasomal ubiquitin-dependent protein catabolic process | 2.79E−03 |
| GO:43523 | regulation of neuron apoptotic process | 2.80E−03 |
| GO:71230 | cellular response to amino acid stimulus | 2.84E−03 |
| GO:38093 | Fc receptor signaling pathway | 2.90E−03 |
| GO:43295 | glutathione binding | 2.90E−03 |
| GO:51409 | response to nitrosative stress | 2.90E−03 |
| GO:1846 | complement binding | 2.90E−03 |
| GO:17166 | vinculin binding | 2.90E−03 |
| GO:1900750 | oligopeptide binding | 2.90E−03 |
| GO:33483 | gas homeostasis | 2.90E−03 |
| GO:19042 | viral latency | 2.90E−03 |
| GO:6102 | isocitrate metabolic process | 2.90E−03 |
| GO:6069 | ethanol oxidation | 2.90E−03 |
| GO:6610 | ribosomal protein import into nucleus | 2.90E−03 |
| GO:6189 | 'de novo' IMP biosynthetic process | 2.90E−03 |
| GO:31904 | endosome lumen | 2.90E−03 |
| GO:2000147 | positive regulation of cell motility | 2.93E−03 |
| GO:51017 | actin filament bundle assembly | 2.95E−03 |
| GO:43034 | costamere | 3.03E−03 |
| GO:42162 | telomeric DNA binding | 3.03E−03 |
| GO:8285 | negative regulation of cell proliferation | 3.09E−03 |
| GO:1901699 | cellular response to nitrogen compound | 3.10E−03 |
| GO:7163 | establishment of maintenance of cell polarity | 3.10E−03 |
| GO:6826 | iron ion transport | 3.14E−03 |
| GO:30234 | enzyme regulator activity | 3.14E−03 |

TABLE 2-continued

Gene ontology (biological process, cellular component and molecular function) terms enriched in the engineered VF mucosa proteome. Enriched ontology terms were identified using the BINGO algorithm. The term list shown here corresponds to the functional enrichment map presented in FIG. 3E. Terms are listed in order of ascending Benjamini Hochberg-adjusted P-value.

| Gene ontology term | Description | Adjusted P-value |
| --- | --- | --- |
| GO:71248 | cellular response to metal ion | 3.14E−03 |
| GO:45335 | phagocytic vesicle | 3.14E−03 |
| GO:30674 | protein binding, bridging | 3.22E−03 |
| GO:51346 | negative regulation of hydrolase activity | 3.23E−03 |
| GO:1556 | regulation of cell growth | 3.26E−03 |
| GO:71277 | cellular response to calcium ion | 3.27E−03 |
| GO:44455 | mitochondrial membrane part | 3.33E−03 |
| GO:51020 | GTPase binding | 3.41E−03 |
| GO:70458 | cellular detoxification of nitrogen compound | 3.41E−03 |
| GO:9169 | purine ribonucleoside monophosphate catabolic process | 3.41E−03 |
| GO:9158 | ribonucleoside monophosphate catabolic process | 3.41E−03 |
| GO:43200 | laminin-11 complex | 3.41E−03 |
| GO:71438 | invadopodium membrane | 3.41E−03 |
| GO:16672 | oxidoreductase activity, acting on a sulfur group of donors, quinone or similar compound as acceptor | 3.41E−03 |
| GO:1884 | pyrimidine nucleoside binding | 3.41E−03 |
| GO:2134 | UTP binding | 3.41E−03 |
| GO:19797 | procollagen-proline 3-dioxygenase activity | 3.41E−03 |
| GO:10716 | negative regulation of extracellular matrix disassembly | 3.41E−03 |
| GO:33484 | nitric oxide homeostasis | 3.41E−03 |
| GO:18636 | phenanthrene 9,10-monooxygenase activity | 3.41E−03 |
| GO:18916 | nitrobenzene metabolic process | 3.41E−03 |
| GO:1901741 | positive regulation of myoblast fusion | 3.41E−03 |
| GO:3994 | aconitate hydratase activity | 3.41E−03 |
| GO:47718 | indanol dehydrogenase activity | 3.41E−03 |
| GO:6106 | fumarate metabolic process | 3.41E−03 |
| GO:6065 | UDP-glucuronate biosynthetic process | 3.41E−03 |
| GO:32557 | pyrimidine ribonucleotide binding | 3.41E−03 |
| GO:32551 | pyrimidine ribonucleoside binding | 3.41E−03 |
| GO:31838 | haptoglobin-hemoglobin complex | 3.41E−03 |
| GO:31544 | peptidyl-proline 3-dioxygenase activity | 3.41E−03 |
| GO:47086 | ketosteroid monooxygenase activity | 3.41E−03 |
| GO:15853 | adenine transport | 3.41E−03 |
| GO:31125 | rRNA 3'-end processing | 3.41E−03 |
| GO:43277 | apoptotic cell clearance | 3.43E−03 |
| GO:17134 | fibroblast growth factor binding | 3.43E−03 |
| GO:5523 | tropomyosin binding | 3.43E−03 |
| GO:6188 | IMP biosynthetic process | 3.43E−03 |
| GO:31055 | chromatin remodeling at centromere | 3.43E−03 |
| GO:1523 | retinoid metabolic process | 3.47E−03 |
| GO:16706 | oxidoreductase activity, acting on paired donors, with incorporation or reduction of molecular oxygen, 2-oxoglutarate as one donor, and incorporation of one atom each of oxygen into both donors | 3.47E−03 |
| GO:3678 | DNA helicase activity | 3.47E−03 |
| GO:8308 | voltage-gated anion channel activity | 3.53E−03 |
| GO:36296 | response to increased oxygen levels | 3.53E−03 |
| GO:35872 | nucleotide-binding domain, leucine rich repeat containing receptor signaling pathway | 3.53E−03 |
| GO:55093 | response to hyperoxia | 3.53E−03 |
| GO:19902 | phosphatase binding | 3.54E−03 |
| GO:1901681 | sulfur compound binding | 3.56E−03 |
| GO:8536 | Ran GTPase binding | 3.65E−03 |
| GO:16461 | unconventional myosin complex | 3.65E−03 |
| GO:19652 | L-ascorbic acid metabolic process | 3.65E−03 |
| GO:34310 | primary alcohol catabolic process | 3.65E−03 |
| GO:32456 | endocytic recycling | 3.65E−03 |
| GO:31996 | thioesterase binding | 3.65E−03 |
| GO:43169 | cation binding | 3.66E−03 |
| GO:6687 | glycosphingolipid metabolic process | 3.66E−03 |
| GO:71417 | cellular response to organic nitrogen | 3.72E−03 |
| GO:42625 | ATPase activity, coupled to transmembrane movement of ions | 3.84E−03 |
| GO:7167 | enzyme linked receptor protein signaling pathway | 3.90E−03 |
| GO:43489 | RNA stabilization | 3.91E−03 |
| GO:51764 | actin crosslink formation | 3.91E−03 |
| GO:2102 | podosome | 3.91E−03 |
| GO:30127 | COPII vesicle coat | 3.91E−03 |
| GO:48255 | mRNA stabilization | 3.91E−03 |
| GO:46040 | IMP metabolic process | 3.91E−03 |
| GO:40017 | positive regulation of locomotion | 3.93E−03 |
| GO:9991 | response to extracellular stimulus | 3.96E−03 |
| GO:42445 | hormone metabolic process | 4.02E−03 |
| GO:71241 | cellular response to inorganic substance | 4.16E−03 |
| GO:33993 | response to lipid | 4.17E−03 |
| GO:90382 | phagosome maturation | 4.24E−03 |
| GO:723 | telomere maintenance | 4.28E−03 |

TABLE 2-continued

Gene ontology (biological process, cellular component and molecular function) terms enriched in the engineered VF mucosa proteome. Enriched ontology terms were identified using the BINGO algorithm. The term list shown here corresponds to the functional enrichment map presented in FIG. 3E. Terms are listed in order of ascending Benjamini Hochberg-adjusted P-value.

| Gene ontology term | Description | Adjusted P-value |
| --- | --- | --- |
| GO:5977 | glycogen metabolic process | 4.28E-03 |
| GO:31123 | RNA 3'-end processing | 4.37E-03 |
| GO:31345 | negative regulation of cell projection organization | 4.39E-03 |
| GO:43269 | regulation of ion transport | 4.39E-03 |
| GO:1901214 | regulation of neuron death | 4.44E-03 |
| GO:51059 | NF-kappaB binding | 4.45E-03 |
| GO:34314 | Arp2/3 complex-mediated actin nucleation | 4.45E-03 |
| GO:45182 | translation regulator activity | 4.45E-03 |
| GO:60284 | regulation of cell development | 4.53E-03 |
| GO:44042 | glucan metabolic process | 4.57E-03 |
| GO:72341 | modified amino acid binding | 4.57E-03 |
| GO:30048 | actin filament-based movement | 4.57E-03 |
| GO:6073 | cellular glucan metabolic process | 4.57E-03 |
| GO:32200 | telomere organization | 4.57E-03 |
| GO:51094 | positive regulation of developmental process | 4.57E-03 |
| GO:36295 | cellular response to increased oxygen levels | 4.57E-03 |
| GO:71455 | cellular response to hyperoxia | 4.57E-03 |
| GO:60346 | bone trabecula formation | 4.57E-03 |
| GO:50765 | negative regulation of phagocytosis | 4.57E-03 |
| GO:30214 | hyaluronan catabolic process | 4.57E-03 |
| GO:7268 | synaptic transmission | 4.69E-03 |
| GO:51188 | cofactor biosynthetic process | 4.69E-03 |
| GO:5539 | glycosaminoglycan binding | 4.69E-03 |
| GO:31346 | positive regulation of cell projection organization | 4.69E-03 |
| GO:51092 | positive regulation of NF-kappaB transcription factor activity | 4.77E-03 |
| GO:44264 | cellular polysaccharide metabolic process | 4.85E-03 |
| GO:16101 | diterpenoid metabolic process | 4.85E-03 |
| GO:1676 | long-chain fatty acid metabolic process | 5.01E-03 |
| GO:45010 | actin nucleation | 5.01E-03 |
| GO:51881 | regulation of mitochondrial membrane potential | 5.01E-03 |
| GO:5916 | fascia adherens | 5.01E-03 |
| GO:9168 | purine ribonucleoside monophosphate biosynthetic process | 5.01E-03 |
| GO:9127 | purine nucleoside monophosphate biosynthetic process | 5.01E-03 |
| GO:19432 | triglyceride biosynthetic process | 5.01E-03 |
| GO:3684 | damaged DNA binding | 5.24E-03 |
| GO:51174 | regulation of phosphorus metabolic process | 5.28E-03 |
| GO:45111 | intermediate filament cytoskeleton | 5.30E-03 |
| GO:6919 | activation of cysteine-type endopeptidase activity involved in apoptotic process | 5.41E-03 |
| GO:6944 | cellular membrane fusion | 5.41E-03 |
| GO:43900 | regulation of multi-organism process | 5.47E-03 |
| GO:7040 | lysosome organization | 5.47E-03 |
| GO:16469 | proton-transporting two-sector ATPase complex | 5.48E-03 |
| GO:90316 | positive regulation of intracellular protein transport | 5.48E-03 |
| GO:10558 | negative regulation of macromolecule biosynthetic process | 5.56E-03 |
| GO:8360 | regulation of cell shape | 5.57E-03 |
| GO:1901615 | organic hydroxy compound metabolic process | 5.58E-03 |
| GO:18401 | peptidyl-proline hydroxylation to 4-hydroxy-L-proline | 5.63E-03 |
| GO:90136 | epithelial cell-cell adhesion | 5.63E-03 |
| GO:5719 | nuclear euchromatin | 5.63E-03 |
| GO:16137 | glycoside metabolic process | 5.63E-03 |
| GO:31258 | lamellipodium membrane | 5.63E-03 |
| GO:9081 | branched-chain amino acid metabolic process | 5.63E-03 |
| GO:43466 | histone exchange | 5.63E-03 |
| GO:48365 | Rac GTPase binding | 5.63E-03 |
| GO:32410 | negative regulation of transporter activity | 5.63E-03 |
| GO:4197 | cysteine-type endopeptidase activity | 5.69E-03 |
| GO:44769 | ATPase activity, coupled to transmembrane movement of ions, rotational mechanism | 5.91E-03 |
| GO:46463 | acylglycerol biosynthetic process | 5.91E-03 |
| GO:46460 | neutral lipid biosynthetic process | 5.91E-03 |
| GO:45216 | cell-cell junction organization | 5.94E-03 |
| GO:31327 | negative regulation of cellular biosynthetic process | 6.05E-03 |
| GO:44389 | small conjugating protein ligase binding | 6.12E-03 |
| GO:31625 | uibiquitin protein ligase binding | 6.12E-03 |
| GO:71345 | cellular response to cytokine stimulus | 6.15E-03 |
| GO:34754 | cellular hormone metabolic process | 6.19E-03 |
| GO:447 | endonucleolytic cleavage in ITS1 to separate SSU-rRNA from 5.8S rRNA and LSU-rRNA from tricistronic rRNA transcript (SSU-rRNA, 5.8S rRNA, LSU-rRNA) | 6.19E-03 |
| GO:478 | endonucleolytic cleavage involved in rRNA processing | 6.19E-03 |
| GO:479 | endonucleolytic cleavage of tricistronic rRNA transcript (SSU-rRNA, 5.8S rRNA, LSU-rRNA) | 6.19E-03 |
| GO:469 | cleavage involved in rRNA processing | 6.19E-03 |
| GO:9128 | purine nucleoside monophosphate catabolic process | 6.19E-03 |
| GO:70061 | fructose binding | 6.19E-03 |
| GO:8426 | protein kinase C inhibitor activity | 6.19E-03 |
| GO:9753 | response to jasmonic acid stimulus | 6.19E-03 |

TABLE 2-continued

Gene ontology (biological process, cellular component and molecular function) terms enriched in the engineered VF mucosa proteome. Enriched ontology terms were identified using the BINGO algorithm. The term list shown here corresponds to the functional enrichment map presented in FIG. 3E. Terms are listed in order of ascending Benjamini Hochberg-adjusted P-value.

| Gene ontology term | Description | Adjusted P-value |
| --- | --- | --- |
| GO:45040 | protein import into mitochondrial outer membrane | 6.19E−03 |
| GO:51683 | establishment of Golgi localization | 6.19E−03 |
| GO:51208 | sequestering of calcium ion | 6.19E−03 |
| GO:36021 | endolysosome lumen | 6.19E−03 |
| GO:71395 | cellular response to jasmonic acid stimulus | 6.19E−03 |
| GO:34205 | beta-amyloid formation | 6.19E−03 |
| GO:1901739 | regulation of myoblast fusion | 6.19E−03 |
| GO:47115 | trans-1,2-dihydrobenzene-1,2-diol dehydrogenase activity | 6.19E−03 |
| GO:90502 | RNA phosphodiester bond hydrolysis, endonucleolytic | 6.19E−03 |
| GO:5997 | xylulose metabolic process | 6.19E−03 |
| GO:5862 | muscle thin filament tropomyosin | 6.19E−03 |
| GO:7161 | calcium-independent cell-matrix adhesion | 6.19E−03 |
| GO:45252 | oxoglutarate dehydrogenase complex | 6.19E−03 |
| GO:7008 | outer mitochondrial membrane organization | 6.19E−03 |
| GO:47023 | androsterone dehydrogenase activity | 6.19E−03 |
| GO:46294 | formaldehyde catabolic process | 6.19E−03 |
| GO:46398 | UDP-glucuronate metabolic process | 6.19E−03 |
| GO:17025 | TBP-class protein binding | 6.23E−03 |
| GO:6309 | apoptotic DNA fragmentation | 6.23E−03 |
| GO:6906 | vesicle fusion | 6.23E−03 |
| GO:60090 | binding, bridging | 6.23E−03 |
| GO:7173 | epidermal growth factor receptor signaling pathway | 6.46E−03 |
| GO:61025 | membrane fusion | 6.54E−03 |
| GO:2757 | immune response-activating signal transduction | 6.65E−03 |
| GO:8565 | protein transporter activity | 6.65E−03 |
| GO:16801 | hydrolase activity, acting on ether bonds | 6.71E−03 |
| GO:51196 | regulation of coenzyme metabolic process | 6.71E−03 |
| GO:51193 | regulation of cofactor metabolic process | 6.71E−03 |
| GO:97066 | response to thyroid hormone stimulus | 6.71E−03 |
| GO:42136 | neurotransmitter biosynthetic process | 6.71E−03 |
| GO:4656 | procollagen-proline 4-dioxygenase activity | 6.71E−03 |
| GO:14912 | negative regulation of smooth muscle cell migration | 6.71E−03 |
| GO:10770 | positive regulation of cell morphogenesis involved in differentiation | 6.82E−03 |
| GO:737 | DNA catabolic process, endonucleolytic | 6.94E−03 |
| GO:34508 | centromere complex assembly | 6.94E−03 |
| GO:6693 | prostaglandin metabolic process | 6.94E−03 |
| GO:6692 | prostanoid metabolic process | 6.94E−03 |
| GO:8186 | RNA-dependent ATPase activity | 6.94E−03 |
| GO:46209 | nitric oxide metabolic process | 6.94E−03 |
| GO:5901 | caveola | 6.98E−03 |
| GO:9607 | response to biotic stimulus | 7.01E−03 |
| GO:30055 | cell-substrate junction | 7.04E−03 |
| GO:15078 | hydrogen ion transmembrane transporter activity | 7.04E−03 |
| GO:30216 | keratinocyte differentiation | 7.20E−03 |
| GO:1901606 | alpha-amino acid catabolic process | 7.30E−03 |
| GO:16324 | apical plasma membrane | 7.49E−03 |
| GO:70469 | respiratory chain | 7.58E−03 |
| GO:5976 | polysaccharide metabolic process | 7.58E−03 |
| GO:51707 | response to other organism | 7.59E−03 |
| GO:2000113 | negative regulation of cellular macromolecule biosynthetic process | 7.60E−03 |
| GO:60351 | cartilage development involved in endochondral bone morphogenesis | 7.72E−03 |
| GO:44275 | cellular carbohydrate catabolic process | 7.72E−03 |
| GO:48041 | focal adhesion assembly | 7.72E−03 |
| GO:30212 | hyaluronan metabolic process | 7.72E−03 |
| GO:7017 | microtubule-based process | 7.94E−03 |
| GO:30145 | manganese ion binding | 7.94E−03 |
| GO:5882 | intermediate filament | 7.99E−03 |
| GO:31667 | response to nutrient levels | 7.99E−03 |
| GO:9113 | purine nucleobase biosynthetic process | 7.99E−03 |
| GO:19511 | peptidyl-proline hydroxylation | 7.99E−03 |
| GO:90075 | relaxation of muscle | 7.99E−03 |
| GO:51156 | glucose 6-phosphate metabolic process | 7.99E−03 |
| GO:2000811 | negative regulation of anoikis | 7.99E−03 |
| GO:5527 | macrolide binding | 7.99E−03 |
| GO:5528 | FK506 binding | 7.99E−03 |
| GO:51172 | negative regulation of nitrogen compound metabolic process | 8.06E−03 |
| GO:10817 | regulation of hormone levels | 8.19E−03 |
| GO:9123 | nucleoside monophosphate metabolic process | 8.31E−03 |
| GO:2764 | immune response-regulating signaling pathway | 8.52E−03 |
| GO:32436 | positive regulation of proteasomal ubiquitin-dependent protein catabolic process | 8.52E−03 |
| GO:43236 | laminin binding | 8.53E−03 |
| GO:4602 | glutathione peroxidase activity | 8.53E−03 |
| GO:5504 | fatty acid binding | 8.53E−03 |
| GO:55038 | recycling endosome membrane | 8.53E−03 |

TABLE 2-continued

Gene ontology (biological process, cellular component and molecular function) terms enriched in the engineered VF mucosa proteome.
Enriched ontology terms were identified using the BINGO algorithm. The term list shown here corresponds to the functional
enrichment map presented in FIG. 3E. Terms are listed in order of ascending Benjamini Hochberg-adjusted P-value.

| Gene ontology term | Description | Adjusted P-value |
| --- | --- | --- |
| GO:790 | nuclear chromatin | 8.68E−03 |
| GO:6029 | proteoglycan metabolic process | 8.71E−03 |
| GO:60491 | regulation of cell projection assembly | 8.79E−03 |
| GO:50821 | protein stabilization | 8.79E−03 |
| GO:6626 | protein targeting to mitochondrion | 8.79E−03 |
| GO:8610 | lipid biosynthetic process | 8.90E−03 |
| GO:3743 | translation initiation factor activity | 8.94E−03 |
| GO:2429 | immune response-activating cell surface receptor signaling pathway | 9.02E−03 |
| GO:19674 | NAD metabolic process | 9.12E−03 |
| GO:50766 | positive regulation of phagocytosis | 9.12E−03 |
| GO:1901570 | fatty acid derivative biosynthetic process | 9.12E−03 |
| GO:5791 | rough endoplasmic reticulum | 9.12E−03 |
| GO:7266 | Rho protein signal transduction | 9.12E−03 |
| GO:46456 | icosanoid biosynthetic process | 9.12E−03 |
| GO:17016 | Ras GTPase binding | 9.16E−03 |
| GO:33157 | regulation of intracellular protein transport | 9.16E−03 |
| GO:46683 | response to organophosphorus | 9.29E−03 |
| GO:32101 | regulation of response to external stimulus | 9.38E−03 |
| GO:62 | fatty-acyl-CoA binding | 9.38E−03 |
| GO:43124 | negative regulation of I-kappaB kinase/NF-kappaB cascade | 9.38E−03 |
| GO:42287 | MHC protein binding | 9.38E−03 |
| GO:46961 | proton-transporting ATPase activity, rotational mechanism | 9.38E−03 |
| GO:35304 | regulation of protein dephosphorylation | 9.38E−03 |
| GO:791 | euchromatin | 9.38E−03 |
| GO:10591 | regulation of lamellipodium assembly | 9.38E−03 |
| GO:6067 | ethanol metabolic process | 9.38E−03 |
| GO:19829 | cation-transporting ATPase activity | 9.46E−03 |
| GO:18119 | peptidyl-cysteine S-nitrosylation | 9.52E−03 |
| GO:16418 | S-acetyltransferase activity | 9.52E−03 |
| GO:36125 | fatty acid beta-oxidation multienzyme complex | 9.52E−03 |
| GO:16507 | mitochondrial fatty acid beta-oxidation multienzyme complex | 9.52E−03 |
| GO:16509 | long-chain-3-hydroxyacyl-CoA dehydrogenase activity | 9.52E−03 |
| GO:60143 | positive regulation of syncytium formation by plasma membrane fusion | 9.52E−03 |
| GO:51410 | detoxification of nitrogen compound | 9.52E−03 |
| GO:16744 | transferase activity, transferring aldehyde or ketonic groups | 9.52E−03 |
| GO:17070 | U6 snRNA binding | 9.52E−03 |
| GO:1765 | membrane raft assembly | 9.52E−03 |
| GO:17014 | protein nitrosylation | 9.52E−03 |
| GO:1849 | complement component C1q binding | 9.52E−03 |
| GO:70836 | caveola assembly | 9.52E−03 |
| GO:1901163 | regulation of trophoblast cell migration | 9.52E−03 |
| GO:71682 | endocytic vesicle lumen | 9.52E−03 |
| GO:34112 | positive regulation of homotypic cell-cell adhesion | 9.52E−03 |
| GO:4301 | epoxide hydrolase activity | 9.52E−03 |
| GO:4822 | isoleucine-tRNA ligase activity | 9.52E−03 |
| GO:90501 | RNA phosphodiester bond hydrolysis | 9.52E−03 |
| GO:6428 | isoleucyl-tRNA aminoacylation | 9.52E−03 |
| GO:32437 | cuticular plate | 9.52E−03 |
| GO:14809 | regulation of skeletal muscle contraction by regulation of release of sequestered calcium ion | 9.52E−03 |
| GO:38069 | positive regulation of cell migration by vascular endothelial growth factor signaling pathway | 9.52E−03 |
| GO:46790 | virion binding | 9.52E−03 |
| GO:31340 | positive regulation of vesicle fusion | 9.52E−03 |
| GO:46292 | formaldehyde metabolic process | 9.52E−03 |
| GO:30911 | TPR domain binding | 9.52E−03 |
| GO:72330 | monocarboxylic acid biosynthetic process | 9.53E−03 |
| GO:1901800 | positive regulation of proteasomal protein catabolic process | 9.60E−03 |
| GO:2020 | protease binding | 9.61E−03 |
| GO:72655 | establishment of protein localization to mitochondrion | 9.61E−03 |
| GO:32479 | regulation of type I interferon production | 9.61E−03 |
| GO:6259 | DNA metabolic process | 9.73E−03 |
| GO:71453 | cellular response to oxygen levels | 9.78E−03 |
| GO:71559 | response to transforming growth factor beta stimulus | 9.79E−03 |
| GO:6694 | steroid biosynthetic process | 9.85E−03 |
| GO:31965 | nuclear membrane | 9.91E−03 |

TABLE 3

Lists of ECM and organogenesis/morphogenesis proteins identified in both engineered and native VF mucosae. Identifications were based on a 1% false discovery rate. Corresponding heatmaps are presented in FIG. 3F. Proteins are listed in order of descending fold change (native VF mucosa compared to engineered VF mucosa).

| Gene symbol | Protein name | Fold change |
|---|---|---|
| ECM proteins | | |
| ALB | Serum albumin | 28.43 |
| TNXB | Tenascin-X | 17.07 |
| COL5A1 | Collagen: alpha-1(V) chain | 14.10 |
| DPYSL3 | Dihydropyrimidinase-related protein 3 | 9.79 |
| FBLN1 | Fibulin-1 | 7.39 |
| FBN1 | Fibrillin-1 | 6.16 |
| SERPINB1 | Leukocyte elastase inhibitor | 5.57 |
| CLU | Clusterin | 4.82 |
| BGN | Biglycan | 4.77 |
| HSPG2 | Basement membrane-specific heparan sulfate proteoglycan care protein | 3.25 |
| TGFBI | Transforming growth factor-beta-induced protein ig-h3 | 3.25 |
| CD109 | CD109 antigen | 3.22 |
| B2M | Beta-2-microglobulin | 3.07 |
| HMGB1 | High mobility group protein B1 | 2.53 |
| COL18A1 | Collagen alpha-1(XVIII) chain | 2.35 |
| LUM | Lumican | 2.27 |
| COL6A2 | Collagen alpha-2(VI) chain | 2.12 |
| DCN | Decorin | 1.88 |
| COL6A1 | Collagen alpha-1(VI) chain | 1.65 |
| LGALS3 | Galectin-3 | 1.63 |
| MYH9 | Myosin-9 | 1.62 |
| STOM | Erythrocyte band 7 integral membrane protein | 1.60 |
| ANXA1 | Annexin A1 | 1.59 |
| PCYOX1 | Prenylcysteine oxidase 1 | 1.51 |
| ACTN4 | Alpha-actinin-4 | 1.50 |
| HSPD1 | 60 kDa heat shock protein, mitochondrial | 1.49 |
| CTSD | Cathepsin D | 1.47 |
| CLTC | Clathrin heavy chain 1 | 1.36 |
| COL6A3 | Collagen alpha-3(VI) chain | 1.35 |
| GSN | Gelsolin | 1.26 |
| GPI | Glucose-6-phosphate isomerase | 1.21 |
| SOD1 | Superoxide dismutase [Cu-Zn] | 1.15 |
| ALDOA | Fructose-bisphosphate aldolase A | 1.11 |
| ANXA5 | Annexin A5 | 1.10 |
| LAMA5 | Laminin subunit alpha-5 | 1.08 |
| ANXA2 | Annexin A2 | 1.00 |
| ENO1 | Alpha-enclase | 0.99 |
| FBLN2 | Fibulin-2 | 0.99 |
| TUBB | Tubulin beta chain | 0.97 |
| GAPDH | Glyceraldehyde-3-phosphate dehydrogenase | 0.96 |
| HSPA8 | Heat shock cognate 71 kDa protein | 0.95 |
| CALR | Calreticulin | 0.95 |
| CTSB | Cathepsin B | 0.91 |
| ACTN1 | Alpha-actinin-1 | 0.91 |
| VIM | Vimentin | 0.82 |
| COL3A1 | Collagen alpha-1(III) chain | 0.81 |
| MSN | Mossin | 0.81 |
| PRDX4 | Peroxiredoxin-4 | 0.71 |
| MVP | Major vault protein | 0.71 |
| PKM | Pyruvate kinase isozymes M1/M2 | 0.70 |
| ANXA6 | Annexin A6 | 0.69 |
| DYNC1H1 | Cytoplasmic dynein 1 heavy chain 1 | 0.65 |
| AKR1B1 | Aldose reductase | 0.64 |
| AHSG | Alpha-2-HS-glycoprotein | 0.63 |
| COPA | Coatomer subunit alpha | 0.61 |
| FN1 | Fibronectin | 0.55 |
| FLNA | Filamin-A | 0.51 |
| RNH1 | Ribonuclease inhibitor | 0.50 |
| RBMX | RNA-bad motif protein, X chromosome | 0.50 |
| ITGB1 | Integrin beta-1 | 0.50 |
| MYOF | Myoferlin | 0.47 |
| LGALS3BP | Galectin-3-binding protein | 0.45 |
| LGALS1 | Gatectin-1 | 0.44 |
| MYO1C | Unconventional myosin-1c | 0.41 |
| THBS1 | Thrombospondin-1 | 0.35 |
| LAMC1 | Laminin subunit gamma-1 | 0.34 |
| HDGF | Hepatoma-derived growth factor | 0.31 |
| EMILIN1 | EMILIN-1 | 0.31 |
| SERPINF1 | Pigment epithelium-derived factor | 0.26 |
| TLN1 | Talin-1 | 0.25 |
| NT5E | 5'-nucleotidase | 0.20 |
| COL12A1 | Collagen alpha-1(XII) chain | 0.19 |
| PSAP | Proactivator polypeptide | 0.19 |
| HDLBP | Vigilin | 0.16 |
| COL1A2 | Collagen alpha-2(I) chain | 0.09 |
| COL1A1 | Collagen alpha-1(I) chain | 0.07 |
| Organogenesis/morphogenesis proteins | | |
| JUP | Junction plakoglobin | 84.57 |
| KRT5 | Keratin, type II cytoskeletal 5 | 32.13 |
| PPL | Periplakin | 23.40 |
| KRT14 | Keratin, type I cytoskeletal 14 | 22.50 |
| KRT6B | Keratin, type II cytoskeletal 6B | 16.64 |
| COL5A1 | Collagen alpha-1(V) chain | 10.13 |
| STEAP4 | Metalioreductase STEAP4 | 8.06 |
| DPYSL3 | Dihydropyrimidinase-elated protein 3 | 6.97 |
| FBLN1 | Fibulin-1 | 5.27 |
| OGDH | 2-oxoglutarate dehydrogenase, mitochondrial | 5.26 |
| FBN1 | Fibrillin-1 | 4.36 |
| DLD | Dihydrolipoyl dehydrogenase, mitochondrial | 3.47 |
| ATP2A2 | Sarcoplasmic/endoplasmic reticulum calcium ATPase 2 | 3.45 |
| SOD2 | Superoxide dismutase [Mn], mitochondrial | 2.95 |
| PRDX3 | Thioredoxin-dependant peroxide reductase, mitochondrial | 2.48 |
| ASAH1 | Acid ceramidase | 2.44 |
| RAB11A | Ras-related protein Rab-11A | 2.41 |
| HSPGA | Basement membrane-specific heparan sulfate proteoglycan core protein | 2.31 |
| ADD1 | Alpha-adducin | 2.29 |
| TGFBI | Transforming growth factor-beta-induced protein ig-h3 | 2.29 |
| B2M | Beta-2-microglobulin | 2.19 |
| KRT10 | Keratin, type I cytoskeletal 10 | 1.85 |
| HMGB1 | High mobility group protein B1 | 1.79 |
| COL18A1 | Collagen alpha-1(XVIII) chain | 1.65 |
| NPM1 | Nucleophosmin | 1.65 |
| LUM | Lumican | 1.61 |
| AP2A2 | AP-2 complex subunit alpha-2 | 1.60 |
| PHB2 | Prohibition-2 | 1.53 |
| COL6A2 | Collagen alpha-2(VI) chain | 1.49 |
| FERMT2 | Fermitin family homolog 2 | 1.48 |
| ATP5A1 | ATP synthase subunit alpha, mitochondrial | 1.34 |
| DCN | Decorin | 1.33 |
| XRCC5 | X-ray repair cross-complementing protein 5 | 1.29 |
| SPTAN1 | Spectrin alpha chain, non-erthrocyclic 1 | 1.26 |
| SPTBN1 | Spectrin beta chain, non-erthrocyclic 1 | 1.25 |
| COL6A1 | Collagen alpha-1(VI) chain | 1.16 |
| TPP1 | Tripeptidyl-peptidase 1 | 1.16 |
| LGALS3 | Galetin-3 | 1.15 |
| MYH9 | Myosin-9 | 1.15 |
| RPS14 | 40S ribosomal protein S14 | 1.14 |
| ANXA1 | Annexin A1 | 1.12 |
| SRI | Sorcin | 1.10 |
| NDRG1 | Protein NDRG1 | 1.10 |
| ATP5B | ATP synthase subunit beta, mitochondrial | 1.08 |
| HSPD1 | 60 kDa shock protein, mitochondrial | 1.06 |
| CANX | Calnexin | 1.02 |
| RPS4X | 40S ribosomal protein S4, X isoform | 1.00 |
| APEX1 | DNA-(apurinic or apyrimidinic site) lyase | 0.99 |
| COL6A3 | Collagen alpha-3(VI) chain | 0.95 |
| RPN2 | Dolichyl-diphosphooligosaccharide-protein glycosyltransferase subunit 2 | 0.92 |
| CDC42 | Cell division control protein 42 homolog | 0.91 |
| ACAT1 | Acetyl-CoA acetyltransferase, mitochondrial | 0.90 |
| DYNLL1 | Dynein light chain 1, cytoplasmic | 0.90 |

TABLE 3-continued

Lists of ECM and organogenesis/morphogenesis proteins identified in both engineered and native VF mucosae. Identifications were based on a 1% false discovery rate. Corresponding heatmaps are presented in FIG. 3F. Proteins are listed in order of descending fold change (native VF mucosa compared to engineered VF mucosa).

| Gene symbol | Protein name | Fold change |
|---|---|---|
| GSN | Gelsolin | 0.89 |
| IQGAP1 | Ras GTPase-activating-like protein IQGAP1 | 0.88 |
| GPI | Glucose-6-phosphate isomerase | 0.86 |
| RPL22 | 60S ribosomal protein L22 | 0.83 |
| SOD1 | Superoxide dismutase [Cu-Zn] | 0.82 |
| PRDX1 | Peroxiredoxin-1 | 0.80 |
| TAGLN2 | Transgelin-2 | 0.78 |
| LAMA5 | Laminin subunit alpha-5 | 0.76 |
| ANXA2 | Annexin A2 | 0.70 |
| RTCB | tRNA-splicing ligase RtcB homolog | 0.70 |
| GSTP1 | Glutathione S-transferase P | 0.70 |
| YWHAG | 14-3-3 protein gamma | 0.69 |
| MYL6 | Myosin light polypeptide 6 | 0.69 |
| RAB14 | Ras-related protein Rab-14 | 0.68 |
| CALR | Calreticulin | 0.67 |
| LMNA | Prelamin-A/C | 0.64 |
| NAPA | Alpha-soluble NSF attachment protein | 0.64 |
| NCL | Nucleolin | 0.64 |
| ARF4 | ADP-ribosylation factor 4 | 0.64 |
| TPI1 | Triosephosphate isomerase | 0.63 |
| KRT1 | Keratin, type II cytoskeletal 1 | 0.62 |
| ALDOC | Fructose-bisphosphate aldolase C | 0.61 |
| CFL1 | Cofilin-1 | 0.61 |
| S100A4 | Protein S100-A4 | 0.59 |
| AP2B1 | AP-2 complex subunit beta | 0.58 |
| VIM | Vimentin | 0.58 |
| COL3A1 | Collagen alpha-1(III) chain | 0.57 |
| YWHAB | 14-3-3 protein beta/alpha | 0.57 |
| TGM2 | Protein-glutamine gamma-glutamyltransferase 2 | 0.57 |
| HSP90AA1 | Heat shock protein HSP 90-alpha | 0.56 |
| KRT9 | Keratin, type I cytoskeletal 9 | 0.56 |
| TMED10 | Transmembrane emp24 domain-containing protein 10 | 0.56 |
| FLOT1 | Flotillin-1 | 0.56 |
| RPL10A | 60S ribosomal protein L10a | 0.56 |
| GNB2L1 | Guanine nucleotide-binding protein subunit beta-2-like 1 | 0.56 |
| HSPA5 | 78 kDa glucose-regulated protein | 0.55 |
| RPS3A | 40S ribosomal protein S3a | 0.54 |
| RPS19 | 40S ribosomal protein S19 | 0.53 |
| RHOC | Rho-related GTP-binding protein RhoC | 0.52 |
| DPYSL2 | Dihydropyrimidinase-related protein 2 | 0.51 |
| SF3B1 | Splicing factor 3B subunit 1 | 0.50 |
| CD44 | CD44 antigen | 0.49 |
| 41889 | Septin-7 | 0.49 |
| CAPN2 | Calpain-2 catalytic subunit | 0.48 |
| CAV1 | Caveolin-1 | 0.47 |
| RTN4 | Reticulon-4 | 0.46 |
| AHSG | Alpha-2-HS-glycoprotein | 0.44 |
| ACTR3 | Actin-related protein 3 | 0.44 |
| AHNAK | Neuroblast differentiation-associated protein AHNAK | 0.42 |
| HSP90AB1 | Heat shock protein HSP 90-beta | 0.42 |
| CAP1 | Adenylyl cyclase-associated protein 1 | 0.40 |
| XRCC6 | X-ray repair cross-complementing protein 6 | 0.40 |
| AP2M1 | AP-2 complex subunit mu | 0.40 |
| FN1 | Fibronectin | 0.39 |
| MGST1 | Microsomal glutathione S-transferase 1 | 0.38 |
| VCL | Vinculin | 0.38 |
| PFN1 | Profilin-1 | 0.38 |
| FLNA | Filamin-A | 0.36 |
| NACA | Nascent polypeptide-associated complex subunit alpha | 0.35 |
| ITGB1 | Integrin beta-1 | 0.35 |
| FLNC | Filamin-C | 0.35 |
| DBI | Acyl-CoA-binding protein | 0.35 |
| IDH1 | Isocitrate dehydrogenase [NADP] cytoplasmic | 0.34 |
| LGALS1 | Galectin-1 | 0.31 |
| NMNT | Nicotinamide N-methyltransferase | 0.30 |
| ASPH | Aspartyl/asparaginyl beta-hydroxylase | 0.30 |
| VAPA | Vesicle-associated membrane protein-associated protein A | 0.29 |
| 41884 | Septin-2 | 0.28 |
| ARHGDIA | Rho GDP-dissociation inhibitor 1 | 0.26 |
| BSG | Basigin | 0.26 |
| THBS1 | Thrombospondin-1 | 0.25 |
| LAMC1 | Laminin subunit gamma-1 | 0.24 |
| PRKDC | DNA-dependent protein kinase catalytic subunit | 0.22 |
| S100A6 | Protein S100-A6 | 0.20 |
| SERPINF1 | Pigment epithelium-derived factor | 0.19 |
| DDX1 | ATP-dependent RNA helicase DDX1 | 0.18 |
| TLN1 | Talin-1 | 0.18 |
| PRKCSH | Glucosidase 2 subunit beta | 0.18 |
| NDUFV2 | NADH dehydrogenase [ubiquinone] flavoprotein 2, mitochondrial | 0.18 |
| STAT1 | Signal transducer and activator of transcription 1-alpha/beta | 0.17 |
| RCN1 | Reticulocalbin-1 | 0.17 |
| ADH5 | Alcohol dehydrogenase class-3 | 0.16 |
| ARF6 | ADP-ribosylation factor 6 | 0.15 |
| COL12A1 | Collagen alpha-1(XII) chain | 0.14 |
| PSAP | Proactivator polypeptide | 0.13 |
| LRP1 | Prolow-density lipoprotein receptor-related protein 1 | 0.12 |
| CAT | Catalase | 0.12 |
| ANPEP | Aminopeptidase N | 0.07 |
| COL1A2 | Collagen alpha-2(I) chain | 0.07 |
| UGDH | UDP-glucose 6-dehydrogenase | 0.06 |
| COL1A1 | Collagen alpha-1(I) chain | 0.05 |
| HEXB | Beta-hexosaminidase subunit beta | 0.03 |

TABLE 4

Lists of proteins significantly overrepresented in engineered VF mucosa compared to VFE on scaffold, VFE on scaffold compared to engineered VF mucosa, engineered VF mucosa compared to VFF in scaffold, and VFF in scaffold compared to engineered VF mucosa. The cutoff criteria for quantitative protein overrepresentation were fold change > 4 and Benjamini Hochberg-adjusted P < 0.01. Corresponding Volcano plots and heatmaps are presented in FIG. 7. Proteins are listed in order of descending fold change.

| Uniprot accession number | Protein name | Gene symbol | Fold change | Adjusted P-value |
|---|---|---|---|---|
| Overrepresented in engineered VF mucosa compared to VFE on scaffold | | | | |
| Q92928 | Putative Ras-related protein Rab-1C | RAB1C | 136.29 | 1.79E−05 |
| P05141 | ADP/ATP translocase 2 | SLC25A5 | 127.20 | 2.44E−05 |

TABLE 4-continued

Lists of proteins significantly overrepresented in engineered VF mucosa compared to VFE on scaffold, VFE on scaffold compared to engineered VF mucosa, engineered VF mucosa compared to VFF in scaffold, and VFF in scaffold compared to engineered VF mucosa. The cutoff criteria for quantitative protein overrepresentation were fold change > 4 and Benjamini Hochberg-adjusted P < 0.01. Corresponding Volcano plots and heatmaps are presented in FIG. 7. Proteins are listed in order of descending fold change.

| Uniprot accession number | Protein name | Gene symbol | Fold change | Adjusted P-value |
|---|---|---|---|---|
| P10909 | Clusterin | CLU | 90.45 | 1.06E−04 |
| P08134 | Rho-related GTP-binding protein RhoC | RHOC | 86.81 | 1.11E−04 |
| Q92688 | Acidic leucine-rich nuclear phosphoprotein 32 family member B | ANP32B | 72.09 | 6.66E−05 |
| Q9UB16 | Guanine nucleotide-binding protein G(I)/G(S)/G(O) subunit gamma-12 | GNG12 | 56.71 | 6.69E−05 |
| P46776 | 60S ribosomal protein L27a | RPL27A | 55.58 | 3.36E−04 |
| P84103 | Serine/arginine-rich splicing factor 3 | SRSF3 | 50.11 | 5.32E−04 |
| P62280 | 40S ribosomal protein S11 | RPS11 | 48.83 | 7.13E−05 |
| P10619 | Lysosomal protective protein | CTSA | 47.59 | 2.94E−04 |
| P13987 | CD59 glycoprotein | CD59 | 44.45 | 3.95E−01 |
| O94973 | AP-2 complex subunit alpha-2 | AP2A2 | 43.47 | 3.37E−03 |
| P45974 | Ubiquitin carboxyl-terminal hydrolase 5 | USP5 | 43.18 | 5.22E−04 |
| P62266 | 40S ribosomal protein S23 | RPS23 | 37.52 | 1.90E−04 |
| O43143 | Putative pre-mRNA-splicing factor ATP-dependent RNA helicase DHX15 | DHX15 | 35.96 | 1.11E−04 |
| O75533 | Splicing factor 3B subunit 1 | SF3B1 | 30.75 | 9.95E−03 |
| Q9UKK3 | Poly [ADP-ribose] polymerase 4 | PARP4 | 27.01 | 9.73E−05 |
| P61254 | 60S ribosomal protein L26 | RPL26 | 26.69 | 3.15E−04 |
| P01026 | Complement C3 [Cleaved into: Complement C3 beta chain; Complement C3 alpha chain] | C3 | 24.97 | 6.50E−04 |
| P30046 | D-dopachrome decarboxylase | DDT | 24.82 | 3.71E−04 |
| P30740 | Leukocyte elastase inhibitor | SERPINB1 | 23.87 | 4.39E−03 |
| Q6IBS0 | Twinfilin-2 | TWF2 | 23.87 | 4.46E−03 |
| O75351 | Vacuolar protein sorting-associated protein 4B | VPS4B | 22.45 | 2.97E−04 |
| Q9UEY8 | Gamma-adducin | ADD3 | 19.93 | 1.08E−03 |
| P20073 | Annexin A7 | ANXA7 | 19.78 | 6.89E−04 |
| Q9NYL9 | Tropomodulin-3 | TMOD3 | 17.74 | 1.91E−04 |
| O94855 | Protein transport protein Sec24D | SEC24D | 15.70 | 8.45E−04 |
| P36405 | ADP-ribosylation factor-like protein 3 | ARL3 | 15.70 | 8.65E−04 |
| P55036 | 26S proteasome non-ATPase regulatory subunit 4 | PSMD4 | 43.48 | 9.95E−03 |
| P08648 | Integrin alpha-5 | ITGA5 | 11.31 | 8.87E−03 |
| Q9P0L0 | Vesicle-associated membrane protein-assoctated protein A | VAPA | 10.99 | 2.97E−03 |
| P21291 | Cysteine and glycine-rich protein 1 | CSRP1 | 8.79 | 5.01E−03 |
| P62491 | Ras-related protein Rab-11A | RAB11A | 6.75 | 3.33E−04 |
| Overrepresented in VFE on scaffold compared to engineered mucosa | | | | |
| P05539 | Collagen alpha-1(II) chain | COL2A1 | 416.83 | 1.06E−04 |
| P62820 | Ras-related protein rab-1A | RAB1A | 127.00 | 4.58E−05 |
| P06962 | CD63 antigen | CD63 | 51.40 | 3.73E−04 |
| P02770 | Serum albumin | ALB | 49.99 | 1.62E−05 |
| P43235 | Cathepsin K | CTSK | 49.08 | 1.27E−03 |
| P35754 | Glutaredoxin-1 | GLRX | 44.94 | 1.02E−04 |
| P13693 | Translationally-controlled tumor protein | TPT1 | 44.56 | 1.85E−04 |
| P01889 | HLA class I histocompatibility antigen, B-7 alpha chain | HLA-B | 42.11 | 1.15E−05 |
| P20340 | Ras-related protein Rab-6A | RAB6A | 37.88 | 9.66E−05 |
| P62753 | 40S ribosomal protein S6 | RPS6 | 35.28 | 5.16E−03 |
| P02795 | Metaliothionein-2 | MT2A | 31.19 | 9.90E−03 |
| P37235 | Hippocalcin-like protein 1 | HPCAL1 | 30.97 | 1.65E−05 |
| P23141 | Liver carboxylesterase 1 | CES1 | 28.75 | 2.32E−05 |
| P63173 | 60S ribosomal protein L38 | RPL38 | 28.37 | 1.99E−04 |
| P48681 | Nestin | NES | 27.71 | 7.33E−04 |
| Q92945 | Far upstream element-binding protein 2 | KHSRP | 27.27 | 3.28E−03 |
| P62899 | 60S ribosomal protein L31 | RPL31 | 25.86 | 4.10E−03 |
| P62847 | 40S ribosomal protein S24 | RPS24 | 25.55 | 6.95E−03 |
| P61163 | Alpha-centractin | ACTR1A | 24.13 | 1.53E−03 |
| O95292 | Vesicle-associated membrane protein-associated protein B/C | VAPB | 23.47 | 1.76E−04 |
| P02640 | Apolipoprotein E | APOE | 23.25 | 5.35E−04 |
| Q9Y5X1 | Sorting nexin-9 | SNX9 | 21.84 | 1.35E−03 |
| P14406 | Cytochrome c oxidase subunit 7A2, mitachondrial | CO7A2 | 21.84 | 1.33E−03 |
| Q9Y646 | Carboxypeptidase Q | CPQ | 20.21 | 9.72E−03 |
| P22307 | Non-specific lipid-transfer protein | SCP2 | 19.24 | 1.92E−05 |
| P28799 | Granulins | GRN | 19.02 | 1.26E−03 |
| Q1KMD3 | Heterogeneous nuclear ribonucleoprotein U-like protein 2 | HNRNPUL2 | 17.23 | 1.26E−03 |
| P27706 | CAD protein [Includes: Glutamin-dependent carbamoyl-phosphate synthase | CAD | 15.75 | 6.95E−03 |
| P62913 | 60S ribosomal protein L11 | RPL11 | 13.37 | 9.90E−05 |
| Q16718 | NADH dehydrogenase [ubiquinone] 1 alpha subcomplex subunit 5 | NDUFA5 | 13.37 | 1.07E−04 |
| P67812 | Signal peptidase complex catalytic subunit SEC11A | SEC11A | 11.75 | 3.26E−04 |
| P49821 | NADH dehydrogenase [ubiquinone] flavoprotein 1, mitochondrial | NDUFV1 | 11.74 | 3.07E−04 |
| Q15063 | Periostin | POSTN | 11.74 | 3.16E−04 |
| Q9BTV4 | Transmembrane protein 43 | TMEM43 | 11.14 | 7.27E−03 |

TABLE 4-continued

Lists of proteins significantly overrepresented in engineered VF mucosa compared to VFE on scaffold, VFE on scaffold compared to engineered VF mucosa, engineered VF mucosa compared to VFF in scaffold, and VFF in scaffold compared to engineered VF mucosa. The cutoff criteria for quantitative protein overrepresentation were fold change > 4 and Benjamini Hochberg-adjusted P < 0.01. Corresponding Volcano plots and heatmaps are presented in FIG. 7. Proteins are listed in order of descending fold change.

| Uniprot accession number | Protein name | Gene symbol | Fold change | Adjusted P-value |
|---|---|---|---|---|
| O60740 | Sorting nexin-2 | SNX2 | 9.51 | 3.33E-03 |
| O00754 | Lysosomal alpha-mannosidase | MAN2B1 | 5.87 | 8.48E-04 |
| Overpresented in engineered VFF mucosa compared to VFF in scaffold | | | | |
| P42330 | Aldo-keto reductase family 1 member C3 | AKR1C3 | 228.80 | 9.75E-05 |
| P35556 | Fibrillin-2 | FBN2 | 213.61 | 2.29E-04 |
| P98095 | Fibulin-2 | FBLN2 | 176.02 | 6.98E-05 |
| P39687 | Acidic leucine-rich nuclear phosphoprotein 32 family member A | ANP32A | 94.87 | 1.37E-04 |
| P27105 | Erythrocyte band7 integral membrane protein | STOM | 93.36 | 1.59E-04 |
| Q9Y6C2 | EMILIN-1 | EMILIN1 | 92.41 | 2.15E-04 |
| P61586 | Transforming protein RhoA | RHOA | 89.42 | 1.18E-04 |
| P06753 | Tropomyosin alpha-3 chain | TPM3 | 84.67 | 1.10E-04 |
| P13674 | Prolyl 4-hydroxytase subunit alpha-1 | P4HA1 | 82.35 | 9.22E-05 |
| P42785 | Lysosomal Pro-X carboxypeptidase | PRCP | 72.67 | 8.12E-05 |
| P00325 | Alcohol dehydrogenase 1B | ADH1B | 69.66 | 5.62E-03 |
| P20700 | Lamin-B1 | LMNB1 | 61.16 | 1.60E-04 |
| P60866 | 40S ribosomal protein S20 | RPS20 | 58.85 | 8.84E-05 |
| P62750 | 60S ribosomal protein L23a | RPL23A | 58.69 | 1.21E-04 |
| P51688 | N-sulphoglucosamine sulphohydrolase | SGSH | 57.39 | 3.73E-04 |
| P46926 | Glucosamine-6-phosphate isomerase 1 | GNPDA1 | 56.55 | 9.99E-05 |
| P01893 | Putative HLA class I histocompatibility antigen, alpha chain H | HLA-H | 55.40 | 2.01E-04 |
| P00966 | Argininosuccinate synthase | ASS1 | 53.74 | 2.19E-04 |
| P55795 | Heterogeneous nuclear ribonucleoprotein H2 | HNRNPH2 | 53.42 | 1.10E-04 |
| Q8NHP8 | Putative phospholipase B-like 2 | PLBD2 | 52.95 | 7.91E-04 |
| P27635 | 60S ribosomal protein L10 | RPL10 | 52.12 | 1.50E-04 |
| P24752 | Acetyl-CoA acetyltransferase, mitochondrial | ACAT1 | 47.33 | 3.09E-03 |
| P23142 | Fibulin-1 | FBLN1 | 47.16 | 7.94E-03 |
| P13987 | CD59 glycoprotein | CD59 | 46.53 | 2.86E-04 |
| Q16363 | Laminin subunit alpha-4 | LAMA4 | 46.51 | 1.41E-04 |
| Q9BS26 | Endoplasmic reticulum resident protein 44 | ERP44 | 46.01 | 4.15E-04 |
| O14773 | Tripeptidyl-peptidase 1 | TPP1 | 45.53 | 1.23E-03 |
| O94973 | AP-2 complex subunit alpha-2 | AP2A2 | 45.52 | 1.82E-03 |
| P45974 | Ubiquitin carboxyl-terminal hydrolase 5 | USP5 | 45.21 | 3.60E-04 |
| Q9Y3I0 | tRNA-splicing ligase RtcB homolog | C22orf28 | 44.55 | 1.26E-04 |
| P42224 | Signal transducer and activator of transcription 1-alpha/beta | STAT1 | 43.88 | 3.65E-04 |
| P25789 | Proteasome subunit alpha type-4 | PSMA4 | 42.59 | 7.01E-04 |
| P30084 | Enoyl-CoA hydratase, mitochondrial | ECHS1 | 42.57 | 2.27E-04 |
| P19623 | Spermidine synthase | SRM | 40.58 | 5.78E-03 |
| Q14258 | E3 ubiquitin/ISG15 ligase TRIM25 | TRIM25 | 40.28 | 1.94E-04 |
| P20618 | Proteasome subunit beta type-1 | PSMB1 | 39.78 | 2.17E-04 |
| P62266 | 40S ribosomal protein S23 | RPS23 | 39.28 | 1.63E-04 |
| Q9UBQ7 | Glyoxylate reductase/hydroxypyruvate reductase | GRHPR | 39.12 | 3.17E-04 |
| P36543 | V-type proton ATPase subunit E 1 | ATP6V1E1 | 37.82 | 3.71E-04 |
| Q9Y3U8 | 60S ribosomal protein L36 | RPL36 | 37.80 | 5.88E-04 |
| P40261 | Nicotinamide N-methyltransferase | NNMT | 37.66 | 1.69E-03 |
| Q43143 | Putative pre-mRNA-splicing factor-ATP-dependent RNA helicase DHX15 | DHX15 | 37.64 | 1.16E-04 |
| Q6NUM9 | All-trans-retinol 13,14-reductase | RETSAT | 36.81 | 8.06E-04 |
| P13473 | Lysosome-associated membrane glycoprotein 2 | LAMP2 | 35.68 | 4.10E-04 |
| P07711 | Cathepsin L1 | CTSL1 | 35.18 | 2.14E-04 |
| P19404 | NADH dehydrogenase [ubiquinone] flavoprotein 2, mitochondrial | NDUFV2 | 33.55 | 7.09E-04 |
| Q9NR45 | Sialic acid synthase | NANS | 33.38 | 1.35E-03 |
| Q15075 | Early endosome antigen I | EEA1 | 32.53 | 1.15E-03 |
| Q92597 | Protein NDRG1 | NDRG1 | 32.39 | 1.16E-03 |
| Q08360 | Galectin-3-binding protein | LGALS3BP | 32.37 | 4.41E-04 |
| O75533 | Splicing factor 3B subunit 1 | SF3B1 | 32.20 | 5.45E-03 |
| P46439 | Glutathione S-transferase Mu 5 | GSTM5 | 32.20 | 5.40E-03 |
| P04062 | Glucosylceramidase | GBA | 31.91 | 8.42E-03 |
| Q12906 | Interleukin enhancer-binding factor 3 | ILF3 | 31.59 | 7.21E-03 |
| Q8IZP2 | Putative protein FAM10A4 | ST13P4 | 30.91 | 2.97E-04 |
| P04179 | Superoxide dismutase, [Mn] mitochondrial | SOD2 | 30.89 | 6.68E-03 |
| Q5T9L3 | Protein wntless homolog | WLS | 30.57 | 1.51E-04 |
| P07954 | Fumarate hydratase, mitochondrial | FH | 30.57 | 1.57E-04 |
| P27487 | Dipeptidyl peptidase 4 | DPP4 | 30.41 | 8.97E-05 |
| Q9UIJ7 | GTP:AMP phosphotransferase AK3, mitochondrial | AK3 | 30.41 | 8.37E-05 |
| O14880 | Microsomal glutathione S-transferase 3 | MGST3 | 29.42 | 3.18E-04 |
| P35555 | Fibrillin-1 | FBN1 | 28.46 | 7.93E-03 |
| P10768 | S-formylglutathione hydrolase | ESD | 28.44 | 7.00E-04 |
| Q9UKK3 | Poly [ADP-ribose] polymerase 4 | PARP4 | 28.28 | 1.01E-04 |

TABLE 4-continued

Lists of proteins significantly overrepresented in engineered VF mucosa compared to VFE on scaffold, VFE on scaffold compared to engineered VF mucosa, engineered VF mucosa compared to VFF in scaffold, and VFF in scaffold compared to engineered VF mucosa. The cutoff criteria for quantitative protein overrepresentation were fold change > 4 and Benjamini Hochberg-adjusted P < 0.01. Corresponding Volcano plots and heatmaps are presented in FIG. 7. Proteins are listed in order of descending fold change.

| Uniprot accession number | Protein name | Gene symbol | Fold change | Adjusted P-value |
|---|---|---|---|---|
| O95741 | Serine/threonine-protein kinase OSR1 | OXSR1 | 28.28 | 9.63E−05 |
| P61254 | 60S ribosomal protein L26 | RPL26 | 27.94 | 2.27E−04 |
| O43491 | Band 4.1-like protein 2 | EPB41L2 | 27.78 | 1.51E−04 |
| O15145 | Actin-related protein 2/3 complex subunit 3 | ARPC3 | 27.78 | 1.56E−04 |
| O43615 | Mitochondrial import inner membrane translocase subunit TIM44 | TIMM44 | 26.48 | 1.47E−03 |
| Q9Y371 | Endophilin-B1 | SH3GLB1 | 25.64 | 6.99E−05 |
| Q32P28 | Prolyl 3-hydroxylase 1 | LEPRE1 | 25.64 | 7.38E−05 |
| P22087 | rRNA 2'-O-methyltransferase fibrillarin | FBL | 25.64 | 7.81E−05 |
| P07942 | Laminin subunit beta-1 | LAMB1 | 25.30 | 1.46E−03 |
| P00403 | Cytochrome c oxidase subunit 2 | MT-CO2 | 24.98 | 2.46E−03 |
| P30740 | Leukocyte elastase inhibitor | SERPINB1 | 24.98 | 2.48E−03 |
| P28161 | Glutathione S-transferase Mu 2 | GSTM2 | 24.34 | 5.12E−03 |
| P49589 | Cysteine--tRNA ligase, cytoplasmic | CARS | 23.84 | 5.53E−04 |
| Q16643 | Drebrin | DBN1 | 23.50 | 2.19E−04 |
| Q13263 | Transcription intermediary factor 1-beta | TRIM28 | 23.50 | 2.24E−04 |
| O75351 | Vacuolar protein sorting-associated protein 4B | VPS4B | 23.50 | 2.34E−04 |
| P14868 | Asparate--tRNA ligase, cytoplasmic | DARS | 23.50 | 2.29E−04 |
| Q02543 | 60S ribosomal protein L18 | RPL18A | 23.34 | 1.18E−04 |
| P38606 | V-type proton ATPase catalytic subunit A | ATP6V1A | 23.01 | 7.46E−04 |
| O00151 | PDZ and LIM domain protein 1 | PDLIM1 | 22.85 | 1.23E−03 |
| P06756 | Integrin alpha-V | ITGAV | 22.85 | 1.25E−03 |
| Q13228 | Selenium-binding protest 1 | SELENBP1 | 22.04 | 7.51E−03 |
| Q13561 | Dynactin subunit 2 | DCTN2 | 21.70 | 2.75E−03 |
| P43490 | Nicotinamide phosphoribosyltransferase | NAMPT | 21.54 | 2.15E−03 |
| P62714 | Serine/threonine-protein phosphatase 2A catalytic subunit beta isoform | PPP2CB | 21.21 | 1.21E−03 |
| O95336 | 6-phosphogluconolactonase | PGLS | 21.05 | 1.16E−03 |
| Q14112 | Nidogen-2 | NID2 | 20.87 | 7.16E−04 |
| Q9Y4L1 | Hypoxia up-regulated protein 1 | HYOU1 | 19.41 | 4.46E−03 |
| P80303 | Nucleobindin-2 | NUCB2 | 18.91 | 6.94E−04 |
| P0CW22 | 40S ribosomal protein S77-like | RPSI7L | 18.57 | 1.82E−04 |
| Q02818 | Nucleobindin-1 | NUCB1 | 18.07 | 8.85E−03 |
| P02461 | Collagen alpha-1(III) chain | COL3A1 | 17.57 | 4.94E−03 |
| P53007 | Tricarboxylate transport protein, mitochondrial | SLC25A1 | 16.77 | 1.45E−03 |
| P05091 | Aldehyde dehydrogenase, mitochondrial | ALDH2 | 16.44 | 5.95E−04 |
| Q9HC38 | Glyoxalase domain-containing protein 4 | GLOD4 | 16.44 | 5.86E−04 |
| P36405 | ADP-ribosylation factor-like protein 3 | ARL3 | 15.44 | 6.04E−04 |
| P99999 | Cytochrome c | CYCS | 16.28 | 2.54E−04 |
| P46063 | ATP-dependent DNA helicase Q1 | RECQL | 16.28 | 2.59E−04 |
| P42765 | 3-ketoacyl-CoA thiolase, mitochondrial | ACAA2 | 16.28 | 2.64E−04 |
| P54727 | UV excision repair protein RAD23 homolog B | RAD23B | 15.94 | 6.16E−03 |
| O75955 | Flotillin-1 | FLOT1 | 15.78 | 8.61E−03 |
| Q16891 | Mitochondrial inner membrane protein | IMMT | 14.14 | 1.53E−04 |
| Q9P2J5 | Leucine--tRNA ligase, cytoplasmic | LARS | 14.14 | 1.58E−04 |
| P10515 | Dihydrolipoyllysine-residue acetyltransferase component of pyruvate dehydrogenase complex, mitochondrial | DLAT | 13.80 | 5.37E−03 |
| P55735 | Protein SEC13 homolog | SEC13 | 13.80 | 5.41E−03 |
| Q02218 | 2-oxoglutarate dehydrogenase, mitochondrial | OGDH | 13.80 | 5.45E−03 |
| P55036 | 26S proteasome non-ATPase regulatory subunit 4 | PSMD4 | 13.80 | 5.50E−03 |
| P54578 | Ubiquitin carboxyl-terminal hydrolase 14 | USP14 | 11.84 | 4.97E−03 |
| Q12884 | Seprase | FAP | 11.84 | 4.93E−03 |
| Q9P0L0 | Vesicle-associated membrane protein-associated protein A | VAPA | 11.50 | 1.66E−03 |
| O15230 | Laminin subunit alpha-5 | LAMA5 | 9.70 | 9.44E−03 |
| Q6IAA8 | Ragulator complex protein LAMTOR1 | LAMTOR1 | 9.70 | 9.51E−03 |
| Q96FQ6 | Protein S100-A16 | S100A16 | 9.70 | 9.57E−03 |
| P27701 | CD82 antigen | CD82 | 9.70 | 9.63E−03 |
| P63220 | 40S ribosomal protein S21 | RPS21 | 9.37 | 5.15E−03 |
| Q6P2Q9 | Pre-mRNA-processing-splicing factor 8 | PRPF8 | 9.21 | 2.93E−03 |
| Q9ULZ3 | Apoptosis-associated speck-like protein containing a CARD | PYCARD | 9.21 | 2.90E−03 |
| P62491 | Ras-related protein Rab-11A | RAB11A | 7.07 | 3.20E−04 |
| Overrepresented in VFF in scaffold compared to engineered VF mucosa | | | | |
| P05530 | Collagen alpha-1(II) chain | COL2A1 | 333.66 | 1.19E−04 |
| P02770 | Serum albumin | ALB | 68.56 | 2.08E−04 |
| P60903 | Protein S100-A10 | S100A10 | 49.96 | 4.11E−04 |
| P01024 | Complement C3 | C3 | 45.51 | 3.10E−03 |
| P02774 | Vitamin D-binding protein | GC | 42.27 | 2.93E−06 |
| P62857 | 40S ribosomal protein S28 | RPS28 | 41.71 | 8.10E−04 |
| P02788 | Lactotransferrin | LTF | 40.99 | 6.76E−04 |
| P13693 | Translationally-controlled tumor protein | TPT1 | 39.35 | 3.21E−04 |

TABLE 4-continued

Lists of proteins significantly overrepresented in engineered VF mucosa compared to VFE on scaffold, VFE on scaffold compared to engineered VF mucosa, engineered VF mucosa compared to VFF in scaffold, and VFF in scaffold compared to engineered VF mucosa. The cutoff criteria for quantitative protein overrepresentation were fold change > 4 and Benjamini Hochberg-adjusted P < 0.01. Corresponding Volcano plots and heatmaps are presented in FIG. 7. Proteins are listed in order of descending fold change.

| Uniprot accession number | Protein name | Gene symbol | Fold change | Adjusted P-value |
|---|---|---|---|---|
| P01008 | Antithrombin-III | SERPINC1 | 22.39 | 5.52E−03 |
| P30493 | HLA class I histocompatibility antigen, B-55 alpha chain | HLA-B | 21.48 | 1.76E−03 |
| P62753 | 40S ribosomal protein S6 | RPS6 | 21.05 | 9.25E−04 |
| P62917 | 60S ribosomal protein L8 | RPL8 | 13.95 | 6.92E−03 |
| P35637 | RNA-binding protein FUS | FUS | 13.65 | 3.67E−03 |
| P49458 | Signal recognition particle 9 kDa protein | SRP9 | 13.06 | 7.08E−03 |
| O15143 | Actin-related protein 2/3 complex subunit 1B | ARPC1B | 7.40 | 5.74E−03 |
| P67809 | Nuclease-sensitive element-binding protein 1 | YBX1 | 7.40 | 5.79E−03 |
| Q9BR76 | Coronin-1B | CORO1B | 7.40 | 5.83E−03 |

TABLE 5

Gene ontology biological process terms enriched in the protein set exclusive to engineered VF mucosa or overrepresented in engineered mucosa compared to both VFF in scaffold and VFE on scaffold. The cutoff criteria for quantitative protein enrichment overrepresentation were fold change > 4 and Benjamini Hochberg-adjusted P < 0.01. Enriched ontology terms were identified using the BiNGO enrichment and REViGO term redundancy algorithms. A subset of these biological process terms are presented in FIG. 6D. Terms are listed in order of ascending Benjamini Hochberg-adjusted P-value.

| Biological process term | Description | Adjusted P-value |
|---|---|---|
| GO:0044265 | cellular macromolecule catabolic process | 1.36E−05 |
| GO:0008104 | protein localization | 2.30E−05 |
| GO:0071840 | cellular component organization or biogenesis | 3.97F−05 |
| GO:0016071 | mRNA metabolic process | 1.29E−04 |
| GO:0034641 | cellular nitrogen compound metabolic process | 2.53E−04 |
| GO:0006807 | nitrogen compound metabolic process | 4.12E−04 |
| GO:0022411 | cellular component disassembly | 7.32E−04 |
| GO:0086004 | regulation of cardiac muscle cell contraction | 8.91E−04 |
| GO:0006413 | translational initiation | 1.41E−03 |
| GO:0044281 | small molecule metabolic process | 1.47E−03 |
| GO:1901360 | organic cyclic compound metabolic process | 1.56E−03 |
| GO:0007044 | cell-substrate junction assembly | 3.03E−03 |
| GO:0044710 | single-organism metabolic process | 3.31E−03 |
| GO:0046483 | heterocycle metabolic process | 5.18E−03 |
| GO:0008544 | epidermis development | 5.27E−03 |
| GO:0006725 | cellular aromatic compound metabolic process | 5.27E−03 |
| GO:0034332 | adheres junction organization | 7.35E−03 |
| GO:0071704 | organic substance metabolic process | 7.55E−03 |
| GO:0006577 | amino-acid betainemetabolic process | 8.58E−03 |
| GO:0034329 | cell junction assembly | 8.72F−03 |
| GO:0044349 | DNA excision | 9.22E−03 |
| GO:0030162 | regulation of proteolysis | 9.35E−03 |

TABLE 6

Antibodies and isotype controls used for flow cytometry.

| Item | Clone | Fluorochrome | Dilution | Manufacturer | Catalog number |
|---|---|---|---|---|---|
| Antibodies | | | | | |
| rabbt anti-human P4H-β | polyclonal | FITC | 1:50 | Bioss | bs-5090R |
| mouse anti-human CD90 | 5E10 | PE-Cy7 | 1:20 | BD Biosciences | 561556 |
| mouse anti-human keratin | LL002 | FITC | 1:10 | Abcam | ab77684 |
| mouse anti-human pan-keratin | C11 | Alexa 647 | 1:50 | Cell Signaling Technology | 4528 |
| mouse anti-human CD227 | 16A | PE | 1:20 | BioLegend | 355603 |
| mouse anti-human keratin 19 | RCK108 | PerCP | 1:5 | Santa CRUZ Biotechnology | sc-53003 |

TABLE 6-continued

Antibodies and isotype controls used for flow cytometry.

| Item | Clone | Fluoro-chrome | Dilution | Manufacturer | Catalog number |
|---|---|---|---|---|---|
| mouse anti-human HLA-ABC | W6/32 | Alexa 488 | 1:20 | BioLengend | 311415 |
| mouse anti-human HLA-DR | LN3 | PE | 1:20 | eBioscience | 12-9956 |
| mouse anti-human PD-L1 (CD274) | 29E.2A3 | APC | 1:20 | BioLegend | 329706 |
| mouse anti-human PD-L2 (CD273) | MIH18 | APC | 1:20 | BioLegend | 345507 |
| mouse anti-human CD80 | L307.4 | FITC | 1:20 | BD Biosciences | 557226 |
| mouse anti-human CD86 | IT2.2 | PE | 1:20 | BioLegend | 305406 |
| mouse anti-human pan-CD45 | HI30 | APC | 1:20 | BD Biosciences | 555485 |
| rat anti-mouse pan-CD45 | 30F11 | FITC | 1:20 | BD Biosciences | 553080 |
| isotype controls | | | | | |
| rabbit IgG | EPR25A | none | 1:100 | Abcam | ab172730 |
| mouse IgG1 | ICIGG1 | none | 1:200 | Abcam | ab91353 |
| | MOPC-21 | APC | 1:20 | BD Biosciences | 400121 |
| | MOPC-21 | FITC | 1:20 | BD Biosciences | 400107 |
| | MOPC-21 | PE | 1:20 | BD Biosciences | 400111 |
| mouse IgG2b | MPC-11 | APC | 1:20 | BioLegend | 400321 |
| | MPC-11 | PE | 1:20 | BioLegend | 400314 |
| rat IgG2b | A95-1 | FITC | 1:20 | BD Biosciences | 553988 |

TABLE 7

Antibodies used for immunocytochemistry and immunohistochemistry.

| Item | Clone | Dilution | Manufacturer | Catalog number | Positive control |
|---|---|---|---|---|---|
| Primary antibodies | | | | | |
| rabbit anti-human e-cadherin | polyclonal | 1:100 | Santa Cruz Biotechnology | sc-7870 | vocal fold |
| mouse anti-human P4H-β | 3-2B12 | 1:250 | Chemicon | MAB2701 | vocal fold |
| goat anti-human α-actin 2 | polyclonal | 1:100 | Thermo Scientific | PA5-18292 | vocal fold |
| mouse anti-human collagen, type IV | COL-94 | 1:100 | Sigma-Aldrich | C1926 | vocal fold |
| rabbit anti-human laminin 5 | polyclonal | 1:200 | Abcam | ab14509 | vocal fold |
| mouse anti-human keratin 5 | XM26 | 1:100 | Santa Cruz Biotechnology | se-58732 | vocal fold |
| mouse anti-human junction plakoglobin | 4C12 | 1:200 | Abcam | ab119908 | vocal fold |
| mouse anti-human mitochondria | 113-1 | 1:200 | Milipore | MAB1273 | thymus |
| rabbit anti-human forkhead box P3 | polyclonal | 1:300 | Abcam | ab10563 | thymus |
| rabbit anti-human CD8 | SP16 | 1:100 | Biocare Medical | CRM311 | thymus |
| rabbit anti-human CD4 | EPR6855 | 1:200 | Abcam | ab133616 | thymus |
| mouse anti-human CD45 | 2B11; PD7/26 | 1:100 | Innovex | MAB321C | thymus |
| Secondary antibodies[a] | | | | | |
| Alexa 488-conjugated donkey anti-mouse IgG | | 1:200 | Life Technolooies | A-21202 | |
| Alexa 594-conjugated donkey anti-mouse IgG | | 1:200 | Life Technologies | A-21203 | |
| Alexa 488-conjugated donkey anti-rabbit IgG | | 1:200 | Life Technologies | A-21206 | |
| Alexa 594-conjugated donkey anti-rabbit IgG | | 1:200 | Life Technologies | A-21207 | |
| Alexa 594-conjugated donkey anti-goat IgG | | 1:200 | Life Technologies | A-11058 | |

[a]Secondary antibodies used for fluorescent detection are listed here; HRP-based detection is described in the Example Materials and Methods.

We claim:

1. A method of making an engineered vocal fold mucosa, comprising:
   (a) culturing a plurality of human vocal fold fibroblasts (VFFs) within a scaffold comprising polymerized collagen to form an engineered non-vascularized lamina propria; and
   (b) culturing a plurality of human vocal fold epithelial cells (VFEs) on a surface of the scaffold to form an engineered stratified squamous epithelium that is in contact with the engineered non-vascularized lamina propria;
   thereby forming an engineered vocal fold mucosa, wherein the plurality of human VFFs and the plurality of human VFEs are primary cells from a single human donor.

2. The method of claim 1, wherein the polymerized collagen is polymerized collagen, type I.

3. The method of claim 1, wherein the step of culturing the plurality of human VFEs on the scaffold surface is first performed within an epithelial cell-oriented medium in which the human VFEs are immersed.

4. The method of claim 3, further comprising culturing the plurality of human VFEs on the scaffold surface at an air-liquid interface on the scaffold surface, wherein the scaffold comprises a composition comprising both a fibroblast-oriented medium and an epithelial cell-oriented medium, and whereby the human VFEs stratify to form a squamous epithelium layer.

5. The method of claim 4, wherein the human VFEs are cultured for 1 to 3 days within the epithelial cell-oriented medium in which the human VFEs are immersed prior to the culturing at the air-liquid interface.

6. The method of claim 4, wherein the human VFEs are cultured for 5 to 50 days at the air-liquid interface on the scaffold surface.

7. The method of claim 1, wherein the step of culturing the plurality of human VFFs within the scaffold is performed when the scaffold comprises a fibroblast-oriented medium, and the step (b) of culturing is performed when the scaffold comprises a composition comprising both a fibroblast-oriented medium and an epithelial cell-oriented medium.

8. The method of claim 1, wherein prior to the culturing the human VFFs within the scaffold, the human VFFs are seeded into the scaffold at a density of between $5 \times 10^4$ and $1 \times 10^6$ VFF/mL.

9. The method of claim 1, wherein the human VFFs for use in the step (a) are obtained by:
(a) seeding human vocal fold mucosa (HVFM) cells onto an extracellular matrix (ECM)-coated surface, whereby some of the HVFM cells adhere to the ECM-coated surface and some of the HVFM cells remain free-floating and non-adherent to generate HVFM adherent cells and HVFM non-adherent cells; and
(b) culturing the HVFM adherent cells in a fibroblast-oriented medium, resulting in a subpopulation of human VFFs.

10. The method of claim 9, wherein human VFEs for use in the step (b) are obtained by the further steps of:
(c) separately culturing the HVFM non-adherent cells in an epithelial cell-oriented medium, whereby the non-adherent cells become adherent cells;
and (d) incubating the adherent cells in a composition comprising 0.05% trypsin to detach one or more of the adherent cells;
and removing one or more of the detached cells to select the remaining adherent cells which are epithelial cells.

11. The method of claim 10, further comprising a passaging the epithelial cells, wherein the passaging comprises detaching the epithelial cells and further culturing the epithelial cells in a separate epithelial cell-oriented medium to constitute a first passage of the epithelial cells.

12. The method of claim 11, further comprising incubating the first passaged epithelial cells in a composition comprising 0.05% trypsin to detach one or more of the epithelial cells, and removing one or more of the detached epithelial cells to select the remaining adherent epithelial cells which are a subpopulation of human VFEs.

13. The method of claim 11, further comprising passaging the epithelial cells at least a second time to constitute at least a second passage.

14. The method of claim 13, wherein the human VFFs, the human VFEs, or both are obtained from the second passage, a third passage, a fourth passage, a fifth passage, a sixth passage, or any combination thereof.

15. The method of claim 9, wherein the HVFM cells are obtained from the human vocal fold mucosa by:
(a) mincing the human vocal fold mucosa;
and (b) enzymatically digesting the minced mucosa to release the HVFM cells from the extracellular matrix (ECM).

* * * * *

UNITED STATES PATENT AND TRADEMARK OFFICE
CERTIFICATE OF CORRECTION

PATENT NO. : 11,896,480 B2
APPLICATION NO. : 16/218667
DATED : February 13, 2024
INVENTOR(S) : Nathan Welham et al.

It is certified that error appears in the above-identified patent and that said Letters Patent is hereby corrected as shown below:

In the Specification

Column 19, Line 27, "iminunoprivleged" should be --immunoprivileged--.

Column 26, Line 65, "Benjamin-Hochberg" should be --Benjamini-Hochberg--.

Signed and Sealed this
Sixteenth Day of April, 2024

Katherine Kelly Vidal
*Director of the United States Patent and Trademark Office*